United States Patent
Li et al.

(10) Patent No.: US 12,370,245 B2
(45) Date of Patent: Jul. 29, 2025

(54) ALK POLYPEPTIDES AND METHODS OF USE THEREOF

(71) Applicant: Elicio Therapeutics, Inc., Boston, MA (US)

(72) Inventors: Adrienne Li, Cambridge, MA (US); Jackson Eby, Arlington, MA (US); Peter C. Demuth, Medford, MA (US)

(73) Assignee: Elicio Therapeutics, Inc., Boston, MA (US)

( * ) Notice: Subject to any disclaimer, the term of this patent is extended or adjusted under 35 U.S.C. 154(b) by 0 days.

(21) Appl. No.: 18/176,013

(22) Filed: Feb. 28, 2023

(65) Prior Publication Data

US 2023/0302108 A1 Sep. 28, 2023

Related U.S. Application Data

(62) Division of application No. 16/072,699, filed as application No. PCT/US2017/015422 on Jan. 27, 2017, now Pat. No. 11,623,002.

(60) Provisional application No. 62/288,972, filed on Jan. 29, 2016.

(51) Int. Cl.

| | | |
|---|---|---|
| A61K 39/00 | (2006.01) | |
| A61K 31/4545 | (2006.01) | |
| A61K 31/506 | (2006.01) | |
| A61K 31/5377 | (2006.01) | |
| A61K 31/675 | (2006.01) | |
| A61K 38/00 | (2006.01) | |
| A61K 38/45 | (2006.01) | |
| A61K 47/10 | (2017.01) | |
| A61K 47/54 | (2017.01) | |
| A61K 47/69 | (2017.01) | |
| A61P 37/04 | (2006.01) | |
| C07K 14/00 | (2006.01) | |
| C07K 14/705 | (2006.01) | |
| C12N 9/00 | (2006.01) | |
| C12N 9/12 | (2006.01) | |

(52) U.S. Cl.
CPC .. *A61K 39/001162* (2018.08); *A61K 31/4545* (2013.01); *A61K 31/506* (2013.01); *A61K 31/5377* (2013.01); *A61K 31/675* (2013.01); *A61K 38/45* (2013.01); *A61K 47/10* (2013.01); *A61K 47/543* (2017.08); *A61K 47/6911* (2017.08); *A61P 37/04* (2018.01); *C07K 14/00* (2013.01); *C07K 14/705* (2013.01); *C12N 9/00* (2013.01); *C12N 9/1205* (2013.01); *A61K 38/00* (2013.01); *A61K 2039/55555* (2013.01); *A61K 2039/6031* (2013.01); *A61K 2039/627* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 4,485,045 A | 11/1984 | Regen | |
| 8,980,287 B2 | 3/2015 | Chiarle et al. | |
| 9,650,614 B2 | 5/2017 | Chiarle et al. | |
| 11,623,002 B2 * | 4/2023 | Li | A61K 47/543 530/324 |
| 2003/0157101 A1 * | 8/2003 | Gambacorti-Passerini | A61P 35/00 530/388.22 |
| 2007/0128633 A1 | 6/2007 | Zozulya et al. | |
| 2009/0118216 A1 | 5/2009 | Chiarle et al. | |
| 2013/0295129 A1 * | 11/2013 | Irvine | A61K 47/6455 424/283.1 |

FOREIGN PATENT DOCUMENTS

| | | | |
|---|---|---|---|
| WO | WO-2016/115480 A1 | 7/2016 | |
| WO | WO-2016160166 A1 * | 10/2016 | A61K 39/12 |
| WO | WO-2021/055580 A2 | 3/2021 | |

OTHER PUBLICATIONS

Aubry et al., "Peptides derived from the dependence receptor ALK are proapoptotic for ALK-positive tumors," Cell Death Dis. 6(5):e1736 (2015) (11 pages).
Blasco, "Abstract A021: Development of an ALK vaccines to treat ALK-rearranged non-small cell lung cancers," <http://cancerimmunolres.aacrjournals.org/content/4/11_Supplement/A021>, retrieved on Jul. 30, 2019 (5 pages).
Dennis et al., "Albumin binding as a general strategy for improving the pharmacokinetics of proteins," J Biol Chem. 277(38):35035-43 (2002).
Extended European Search Report for European Patent Application No. 17745002.0 dated Nov. 18, 2019 (10 pages).
International Preliminary Report on Patentability for International Patent Application No. PCT/US17/15422, issued Jul. 30, 2018 (10 pages).
International Search Report and Written Opinion for International Application No. PCT/US17/15422, mailed Jul. 3, 2017 (21 pages).
Office Action for Canadian Patent Application No. 3,012,764 dated Feb. 21, 2023 (4 pages).
Passoni et al., "In vivo T-cell immune response against anaplastic lymphoma kinase in patients with anaplastic large cell lymphomas," Haematologica. 91(1):48-55 (2006).

(Continued)

*Primary Examiner* — Sergio Coffa

(74) *Attorney, Agent, or Firm* — Clark & Elbing LLP

(57) ABSTRACT

The invention features immunogenic compositions containing anaplastic lymphoma kinase (ALK) polypeptides and methods of use thereof. The immunogenic compositions and methods of the invention may be used to treat a disease associated with ALK in a subject, such as cancer (e.g., a solid tumor cancer or an ALK+ cancer).

9 Claims, 9 Drawing Sheets

Specification includes a Sequence Listing.

(56) References Cited

OTHER PUBLICATIONS

Voena et al., "Efficacy of a Cancer Vaccine against ALK-Rearranged Lung Tumors," Cancer Immunol Res. 3(12):1333-1343 (2015).

* cited by examiner

FIG. 4-1

SEQ ID NO: 67

```
            10         20         30         40         50
     MGAIGLLWLL PLLLSTAAVG SGMGTGQRAG SPAAGPPLQP REPLSYSRLQ
            60         70         80         90        100
     RKSLAVDFVV PSLFRVYARD LLLPPSSSEL KAGRPEARGS LALDCAPLLR
           110        120        130        140        150
     LLGPAPGVSW TAGSPAPAEA RTLSRVLKGG SVRKLRRAKQ LVLELGEEAI
           160        170        180        190        200
     LEGCVGPPGE AAVGLLQFNL SELFSWWIRQ GEGRLRIRLM PEKKASEVGR
           210        220        230        240        250
     EGRLSAATRA SQPRLLFQIF GTGESSLESP TNMPSPSPDY FTWNLTWIMK
           260        270        280        290        300
     DSFPFLSHRS RYGLECSFDF PCELEYSPPL HDLRNQSWSW RRIPSEEASQ
           310        320        330        340        350
     MDLLDGPGAE RSKEMPRGSF LLLNTSADSK HTILSPWMRS SSEHCTLAVS
           360        370        380        390        400
     VHRHLQPSGR YIAQLLPHNE AAREILLMPT PGKHGWTVLQ GRIGRPDNPF
           410        420        430        440        450
     RVALEYISSG NRSLSAVDFF ALKNCSEGTS PGSKMALQSS FTCWNGTVLQ
           460        470        480        490        500
     LGQACDFHQD CAQGEDESQM CRKLPVGFYC NFEDGFCGWT QGTLSPHTPQ
           510        520        530        540        550
     WQVRTLKDAR FQDEQDHALL LSTTDVPASE SATVTSATFP APIKSSPCEL
           560        570        580        590        600
     RMSWLIRGVL RGNVSLVLVE NKTGKEQGRM VWHVAAYEGL SLWQWMVLPL
           610        620        630        640        650
     LDVSDRFWLQ MVAWWGQGSR AIVAFDNISI SLDCYLTISG EDKILQNTAP
           660        670        680        690        700
     KSRNLFERNP NKELKPGENS PRQTPIFDPT VEWLFTTCGA SGPHGPTQAQ
           710        720        730        740        750
     CNNAYQNSNL SVEVGSEGPL KGIQIWKVPA TDTYSISGYG AAGGKGGKNT
           760        770        780        790        800
     MMRSHGVSVL GIFNLEKDDM LYILVGQQGE DACPSTNQLI QKVCIGENNV
           810        820        830        840        850
     IEEEIRVNRS VHHWAGGGGG GGGATYVFKM KDGVPVPLII AAGGGGRAYG
           860        870        880        890        900
     AKTDTFRPER LENNSSVLGL NGNSGAAGGG GGWNDNTSLL WAGKSLQEGA
           910        920        930        940        950
     TGGHSCPQAM KKWGWETRGG FGGGGGGCSS GGGGGGYIGG NAASNNDPEM
           960        970        980        990       1000
     DGEDGVSFIS PLGILYTPAL KVMEGHGEVN IKHYLNCSHC EVDECHMDPE
          1010       1020       1030       1040       1050
     SHKVICFCDH GTVLAEDGVS CIVSPTPEPH LPLSLILSVV TSALVAALVL
          1060       1070       1080       1090       1100
     AFSGIMIVYR RKHQELQAMQ MELQSPEYKL SKLRTSIIMT DYNPNYCFAG
          1110       1120       1130       1140       1150
     KTSSISDLKE VPRKNITLIR GLGHGAFGEV YEGQVSGMPN DPSPLQVAVK
          1160       1170       1180       1190       1200
     TLPEVCSEQD ELDFLMEALI ISKFNHQNIV RCIGVSLQSL PRFILLELMA
          1210       1220       1230       1240       1250
     GGDLKSFLRE TRPRPSQPSS LAMLDLLHVA RDIACGCQYL EENHFIHRDI
          1260       1270       1280       1290       1300
     AARNCLLTCP GPGRVAKIGD FGMARDIYRA SYYRKGGCAM LPVKWMPPEA
          1310       1320       1330       1340       1350
     FMEGIFTSKT DTWSFGVLLW EIFSLGYMPY PSKSNQEVLE FVTSGGRMDP
          1360       1370       1380       1390       1400
     PKNCPGPVYR IMTQCWQHQP EDRPNFAIIL ERIEYCTQDP DVINTALPIE
          1410       1420       1430       1440       1450
     YGPLVEEEEK VPVRPKDPSG VPPLLVSQQA KREEERSPAA PPPLPTTSSG
          1460       1470       1480       1490       1500
     KAAKKPTAAE ISVRVPRGPA VEGGHVNMAF SQSNPPSELH KVHGSRNKPT
          1510       1520       1530       1540       1550
     SLWNPTYGSW FTEKPTKKNN PIAKKEPHDR GNLGLEGSCT VPPNVATGRL
          1560       1570       1580       1590       1600
     PGASLLLEPS SLTANMKEVP LFRLRHFPCG NVNYGYQQQG LPLEAATAPG
          1610       1620
     AGHYEDTILK SKNSMNQPGP
```

FIG. 4-2

SEQ ID NO: 68

```
         10         20         30         40         50
 MGAIGLLWLL PLLLSTAAVG SGMGTGQRAG SPAAGPPLQP REPLSYSRLQ
         60         70         80         90        100
 RKSLAVDFVV PSLFRVYARD LLLPPSSSEL KAGRPEARGS LALDCAPLLR
        110        120        130        140        150
 LLGPAPGVSW TAGSPAPAEA RTLSRVLKGG SVRKLRRAKQ LVLELGEEAI
        160        170        180        190        200
 LEGCVGPPGE AAVGLLQFNL SELFSWWIRQ GEGRLRIRLM PEKKASEVGR
        210        220        230        240        250
 EGRLSAAIRA SQPRLLFQIF GTGESSLESP TNMPSPSPDY FTWNLTWIMK
        260        270        280        290        300
 DSFPFLSHRS RYGLECSFDF PCELEYSPPL HDLRNQSWSW RRIPSEEASQ
        310        320        330        340        350
 MDLLDGPGAE RSKEMPRGSF LLLNTSADSK HTILSPWMRS SSEHCTLAVS
        360        370        380        390        400
 VERELQPSGR YIAQLLPHNE AAREILLMPT PGKHGWTVLQ GRIGRPDNPF
        410        420        430        440        450
 RVALEYISSG NRSLSAVDFF ALKNCSEGTS PGSKMALQSS FTCWNGTVLQ
        460        470        480        490        500
 LGQACDFRQD CAQGEDESQM CRKLPVGFYC NFEDGFCGWT QGTLSPHTPQ
        510        520        530        540        550
 WQVRTLKDAR FQDHQDHALL LSTTDVPASE SATVTSATFP APIKSSPCEL
        560        570        580        590        600
 RMSWLIRGVL RGNVSLVLVE NKTGKEQGRM VWHVAAYEGL SLWQWMVLPL
        610        620        630        640        650
 LDVSDRFWLQ MVAWWGQGSR AIVAFDNISI SLDCYLTISG EDKILQNTAP
        660        670        680        690        700
 KSRNLFERNP NKELKPGENS PRQTPIFDPT VEWLFTTCGA SGPHGPTQAQ
        710        720        730        740        750
 CNNAYQNSNL SVEVGSEGPL KGIQIWKVPA TDTYSISGYG AAGGKGGKNT
        760        770        780        790        800
 MMRSHGVSVL GIFNLEKDDM LYILVGQQGE DACPSTNQLI QKVCIGENNV
        810        820        830        840        850
 IEEEIRVNRS VHEWAGGGGG GGGATYVFKM KDGVPVPLII AAGGGGRAYG
        860        870        880        890        900
 AKTDTFRPER LENNSSVLGL NGNSGAAGGG GGWNDNTSLL WAGKSLQEGA
        910        920        930        940        950
 TGGHSCPQAM KKWGWETRGG FGGGGGGCSS GGGGGGYIGG NAASNNDPEM
        960        970        980        990       1000
 DGEDGVSFIS PLGILYTPAL KVMEGHGEVN IKHYLNCSHC EVDECHMDPE
       1010       1020       1030       1040       1050
 SHKVICFCDH GTVLAEDGVS CIVSPTPEPH LPLSLILSVV TSALVAALVL
       1060       1070       1080       1090       1100
 AFSGIMIVYR RKHQELQAMQ MELQSPEYKL SKLRTSIIMT DYNPNYCFAG
       1110       1120       1130       1140       1150
 KTSSISDLKE VPRKNITLIR GLGHGAFGEV YEGQVSGMPN DPSPLQVAVR
       1160       1170       1180       1190       1200
 TLPEVCSEQD ELDFLMEALI ISKFNHQNIV RCIGVSLQSL PRFILLELMA
       1210       1220       1230       1240       1250
 GGDLKSFLRE TRPRPSQPSS LAMLDLLHVA RDIACGCQYL EENHFIHRDI
       1260       1270       1280       1290       1300
 AARNCLLTCP GPGRVAKIGD FGMARDIYRA SYYRKGGCAM LPVKWMPPEA
       1310       1320       1330       1340       1350
 FMEGIFTSKT DTWSFGVLLW EIFSLGYMPY PSKSNQEVLE FVTSGGRMDP
       1360       1370       1380       1390       1400
 PKNCPGPVYR IMTQCWQHQP EDRPNFAIIL ERIEYCTQDP DVINTALPIE
       1410       1420       1430       1440       1450
 YGPLVEEEEK VPVRPKDPEG VPPLLVSQQA KREEERSPAA PPPLPTTSSG
       1460       1470       1480       1490       1500
 KAAKKPTAAE TSVRVPRGPA VEGGHVNMAF SQSNPPSELH KVHGSRNKPT
       1510       1520       1530       1540       1550
 SLWNPTYGSW FTEKPTKKNN PIAKKEPHDR GNLGLEGSCT VPPNVATGRL
       1560       1570       1580       1590       1600
 PGASLLLEPS SLTANMKEVP LFRLRHFPCG NVNYGYQQQG LPLEAATAPG
       1610       1620
 AGHYEDTILK SKNSMNQPGP
```

FIG. 4-3

SEQ ID NO: 69

```
  1 VYRPSHQELQ ASQMELQSPE YKLSKLRTST IMTDYNPNYC FAGKTSSISD LKEVPRKNIT
 61 LIRGLGHGAF GEVYEGQVSG MPNDPSPLQV AVKTLPEVCS EQDELDFLME ALIISKFNHQ
121 NIVRCIGVSL QSLPRFILLE LMAGGDLKSF LRETRPRPSQ PSSLAMLDLL HVARDIACGC
181 QYLEENHFIH RDIAARNCLL TCPGPGRVAK IGDFGMARDI YRASYYRKGG CAMLPVKWMP
241 PEAFMEGIFT SKTDTWSFGV LLWEIFSLGY MPYPSKSNQE VLEFVTSGGR MDPPKNCPGP
301 VYRIMTQCWQ HQPEDRPNFA IILERIEYCT QDPDVINTAL PIEYGPLVEE EKVPVRPKD
361 PEGVPPLLVS QQAKREEERS PAAPPPLPTT SSGKAAKKPT AAEVSVRVPR SPAVEGGHVN
421 MAFSQSNPPS ELHRVHGSRN KPTSLWNPTY GSWFTEKPTK KNNPIAKKEP HERGNLGLEG
481 SCTVPPNVAT GRLPGASLLL EPSSLTANMK EVPLFRLRHF PCGNVNYGYQ QQGLPLEAAT
541 APGAGHYEDT ILKSKNSMNQ PGP
```

SEQ ID NO: 70

```
  1 VYRPSHQELQ ASQMELQSPE YKLSKLRTST IMTDYNPNYC FAGKTSSISD LKEVPRKNIT
 61 LIRGLGHGAF GEVYEGQVSG MPNDPSPLQV AVKTLPEVCS EQDELDFLME ALIISKFNHQ
121 NIVRCIGVSL QSLPRFILLE LMAGGDLKSF LRETRPRPSQ PSSLAMLDLL HVARDIACGC
181 QYLEENHFIH RDIAARNCLL TCPGPGRVAK IGDFGMARDI YRASYYRKGG CAMLPVKWMP
241 PEAFMEGIFT SKTDTWSFGV LLWEIFSLGY MPYPSKSNQE VLEFVTSGGR MDPPKNCPGP
301 VYRIMTQCWQ HQPEDRPNFA IILERIEYCT QDPDVINTAL PIEYGPLVEE EKVPVRPKD
361 PEGVPPLLVS QQAKREEERS PAAPPPLPTT SSGKAAKKPT AAEVSVRVPR SPAVEGGHVN
421 MAFSQSNPPS ELHRVHGSRN KPTSLWNPTY GSWFTEKPTK KNNPIAKKEP HERGNLGLEG
481 SCTVPPNVAT GRLPGASLLL EPSSLTANMK EVPLFRLRHF PCGNVNYGYQ QQGLPLEAAT
541 APGAGHYEDT ILKSKNSMNQ PGP
```

ALK POLYPEPTIDES AND METHODS OF USE THEREOF

BACKGROUND OF THE INVENTION

Anaplastic lymphoma kinase (ALK) is a receptor tyrosine kinase first identified in a chromosomal translocation associated with anaplastic large cell lymphomas (ALCL), a subset of T-cell non-Hodgkin lymphomas. Within ALCLs, nearly 70% of the cases carry the t(2;5)(p23;q35) chromosomal translocation that juxtaposes the ALK locus to the nucleophosmin (NPM) gene locus, generating a fusion protein of NPM and the cytoplasmic domain of ALK. Other ALK fusion proteins have been identified, including tropomyosin (TMP3), 5-Aminoimidazole-4-carboxamide ribonucleotide formyltransferase/IMP cyclohydrolase (ATIC), transforming growth factor (TGF), and echinoderm microtubule-associated protein-like 4 (EML4), in different types of solid tumors, such as non-small-cell lung cancers, neuroblastoma, rhabdomyosarcoma, neuroectodermal tumors, and glioblastomas. Data from human patients carrying ALK-positive ALCL show that the ALK protein is immunogenic. The ALK-elicited immune response involves $CD8^+$ CTL cells, $CD4^+$ T helper cells, and the production of anti-ALK antibodies, and influences the outcome of the disease. There exists a need for novel and effective immunotherapies against cancers, such as immunotherapies using an ALK protein or a portion thereof.

SEQUENCE LISTING

The instant application contains a Sequence Listing which has been submitted electronically in XML format and is hereby incorporated by reference in its entirety. Said XML copy, created on Feb. 17, 2023, is named 51026-014003_Sequence_Listing_2_17_23 and is 132,178 bytes in size.

SUMMARY OF THE INVENTION

The invention features immunogenic compositions and constructs containing anaplastic lymphoma kinase (ALK) polypeptides and methods of use thereof. The immunogenic compositions and methods of the invention may be used to treat a disease associated with ALK in a subject, such as cancer (e.g., a solid tumor cancer or a cancer that expresses ALK or a portion thereof (e.g., an $ALK^+$ cancer)).

In a first aspect, the invention features an immunogenic composition including an anaplastic lymphoma kinase (ALK) polypeptide, wherein the ALK polypeptide includes at least 6 contiguous amino acids from a sequence of any one of SEQ ID NOs: 1-66 and 93-139 and wherein the ALK polypeptide does not consist of a sequence of any one of SEQ ID NOs: 67-70 and 140-145. In some embodiments, the ALK polypeptide does not include a sequence of any one of SEQ ID NOs: 67-70 and 140-145.

In some embodiments, the ALK polypeptide is 8 to 230 amino acids in length. In some embodiments, the ALK polypeptide is 8 to 60 amino acids in length. In some embodiments, the ALK polypeptide is 8 to 30 amino acids in length. In some embodiments, the ALK polypeptide is 8 to 15 amino acids in length. In some embodiments, the ALK polypeptide is 8 to 11 amino acids in length.

In some embodiments, the ALK polypeptide includes at least 9 contiguous amino acids from a sequence of any one of SEQ ID NOs: 1-66 and 93-139. In some embodiments, the ALK polypeptide is 9 to 40 amino acids in length. In some embodiments, the ALK polypeptide is 15 to 40 amino acids in length. In some embodiments, the ALK polypeptide is 20 to 40 amino acids in length. In some embodiments, the ALK polypeptide is 25 to 40 amino acids in length. In some embodiments, the ALK polypeptide is 30 to 40 amino acids in length.

In some embodiments, the ALK polypeptide includes at least 11 contiguous amino acids from a sequence of any one of SEQ ID NOs: 1-59 and 93-139.

In some embodiments, the ALK polypeptide includes a sequence of any one of SEQ ID NOs: 1-66 and 93-139.

In some embodiments, the ALK polypeptide includes 9 contiguous amino acids from a sequence of any one of SEQ ID NOs: 1-66 and 93-139 and wherein the ALK polypeptide is 9 amino acids in length. In some embodiments, the ALK polypeptide includes 11 contiguous amino acids from a sequence of any one of SEQ ID NOs: 1-59 and 93-139 and wherein the ALK polypeptide is 11 amino acids in length.

In some embodiments of the first aspect of the invention, the sequence is selected from any one of SEQ ID NOs: 93, 96, 100, 106, 111-116, and 121-139. In some embodiments, the sequence is SEQ ID NO: 93. In some embodiments, the sequence is SEQ ID NO: 96. In some embodiments, the sequence is SEQ ID NO: 100. In some embodiments, the sequence is SEQ ID NO: 106. In some embodiments, the sequence is SEQ ID NO: 111. In some embodiments, the sequence is SEQ ID NO: 112. In some embodiments, the sequence is SEQ ID NO: 113. In some embodiments, the sequence is SEQ ID NO: 114. In some embodiments, the sequence is SEQ ID NO: 115. In some embodiments, the sequence is SEQ ID NO: 116. In some embodiments, the sequence is SEQ ID NO: 121. In some embodiments, the sequence is SEQ ID NO: 122. In some embodiments, the sequence is SEQ ID NO: 123. In some embodiments, the sequence is SEQ ID NO: 124. In some embodiments, the sequence is SEQ ID NO: 125. In some embodiments, the sequence is SEQ ID NO: 126. In some embodiments, the sequence is SEQ ID NO: 127. In some embodiments, the sequence is SEQ ID NO: 128. In some embodiments, the sequence is SEQ ID NO: 129. In some embodiments, the sequence is SEQ ID NO: 130. In some embodiments, the sequence is SEQ ID NO: 131. In some embodiments, the sequence is SEQ ID NO: 132. In some embodiments, the sequence is SEQ ID NO: 133. In some embodiments, the sequence is SEQ ID NO: 134. In some embodiments, the sequence is SEQ ID NO: 135. In some embodiments, the sequence is SEQ ID NO: 136. In some embodiments, the sequence is SEQ ID NO: 137. In some embodiments, the sequence is SEQ ID NO: 138. In some embodiments, the sequence is SEQ ID NO: 139.

In some embodiments of the first aspect of the invention, the sequence is selected from any one of SEQ ID NOs: 10, 14, 17, 22, 33, 52, and 53. In some embodiments, the sequence is SEQ ID NO: 10. In some embodiments, the sequence is SEQ ID NO: 14. In some embodiments, the sequence is SEQ ID NO: 17. In some embodiments, the sequence is SEQ ID NO: 22. In some embodiments, the sequence is SEQ ID NO: 33. In some embodiments, the sequence is SEQ ID NO: 52. In some embodiments, the sequence is SEQ ID NO: 53.

In some embodiments of the first aspect of the invention, the immunogenic composition is formulated for administration as a vaccine or an immunotherapy. A "vaccine" refers to an agent (i.e., a biological agent) that provides immunity to a particular disease or pathogen. A vaccine can be a prophylactic vaccine (i.e., a vaccine used to prevent or ameliorate the effects of a future infection by a pathogen) or a therapeutic vaccine (i.e., a vaccine use for treatment of, e.g., an infection). An "immunotherapy" refers to a type of treatment designed to boost the body's immune system to fight against one or more diseases and/or to suppress the body's negative reactions towards one or more diseases and/or drugs used in the treatment of one or more diseases. An immunotherapy can improve, target, and/or restore functions of the immune system.

In some embodiments, the immunogenic composition further includes an adjuvant. In some embodiments, the immunogenic composition is in a unit dosage form.

In a second aspect, the invention features an immunogenic composition including an ALK polypeptide, wherein the ALK polypeptide includes a first sequence including at least 6 contiguous amino acids from a sequence selected from any one of SEQ ID NOs: 1-66 (e.g., SEQ ID NOs: 10, 14, 17, 22, 33, 52, and 53) and a second sequence including at least 6 contiguous amino acids from a sequence selected from any one of SEQ ID NOs: 1-66 (e.g., SEQ ID NOs: 10, 14, 17, 22, 33, 52, and 53), wherein the first and second sequences are different, wherein the first and second sequences include a pair of sequences of SEQ ID NOs recited in Table 2A, and wherein the ALK polypeptide does not include a sequence of any one of SEQ ID NOs: 67-70 and 140-145.

In some embodiments of the second aspect of the invention, the first and second sequences include one of the following pairs of sequences: SEQ ID NOs: 10 and 14, SEQ ID NOs: 10 and 17, SEQ ID NOs: 10 and 22, SEQ ID NOs: 10 and 33, SEQ ID NOs: 10 and 52, SEQ ID NOs: 10 and 53, SEQ ID NOs: 14 and 17, SEQ ID NOs: 14 and 22, SEQ ID NOs: 14 and 33, SEQ ID NOs: 14 and 52, SEQ ID NOs: 14 and 53, SEQ ID NOs: 17 and 22, SEQ ID NOs: 17 and 33, SEQ ID NOs: 17 and 52, SEQ ID NOs: 17 and 53, SEQ ID NOs: 22 and 33, SEQ ID NOs: 22 and 52, SEQ ID NOs: 22 and 53, SEQ ID NOs: 33 and 52, SEQ ID NOs: 33 and 53, and SEQ ID NOs: 52 and 53.

In a third aspect, the invention features an immunogenic composition including an ALK polypeptide, wherein the ALK polypeptide includes a first sequence including at least 6 contiguous amino acids from a sequence selected from any one of SEQ ID NOs: 93, 96, 100, 106, 111-116, and 121-139 and a second sequence including at least 6 contiguous amino acids from a sequence selected from any one of SEQ ID NOs: 93, 96, 100, 106, 111-116, and 121-139, wherein the first and second sequences are different, wherein the first and second sequences include a pair of sequences of SEQ ID NOs recited in Table 2B, and wherein the ALK polypeptide does not include a sequence of any one of SEQ ID NOs: 67-70 and 140-145.

In some embodiments of the second and third aspects of the invention, the first and/or second sequence in the ALK polypeptide is 8 to 230 amino acids in length (e.g., 8 to 230 amino acids in length, 8 to 60 amino acids in length, 8 to 30 amino acids in length, 8 to 15 amino acids in length, or 8 to 11 amino acids in length). In some embodiments of the second and third aspects of the invention, the first and/or second sequence in the ALK polypeptide includes at least 9 contiguous amino acids from a sequence of any one of SEQ ID NOs: 1-66 and 93-139. In some embodiments of the second and third aspects of the invention, the first and/or second sequence in the ALK polypeptide includes at least 11 contiguous amino acids from a sequence of any one of SEQ ID NOs: 1-59 and 93-139. In some embodiments of the second and third aspects of the invention, the first and/or second sequence in the ALK polypeptide includes a sequence of any one of SEQ ID NOs: 1-58 and 93-139. In some embodiments of the second and third aspects of the invention, the first and/or second sequence in the ALK polypeptide includes 9 contiguous amino acids from a sequence of any one of SEQ ID NOs: 1-66 and 93-139 and wherein the first and/or second sequence in the ALK polypeptide is 9 amino acids in length. In some embodiments, the first and/or second sequence in the ALK polypeptide includes 11 contiguous amino acids from a sequence of any one of SEQ ID NOs: 1-59 and 93-139 and wherein the first and/or second sequence in the ALK polypeptide is 11 amino acids in length. In some embodiments, the first and/or second sequence in the ALK polypeptide includes 15 contiguous amino acids from a sequence of any one of SEQ ID NOs: 1-58 and 93-139 and wherein the first and/or second sequence in the ALK polypeptide is 11 amino acids in length.

In some embodiments of the second and third aspects of the invention, the first and/or second sequence in the ALK polypeptide is 9 to 40 amino acids in length (e.g., 9 to 40 amino acids in length, 15 to 40 amino acids in length, 20 to 40 amino acids in length, 25 to 40 amino acids in length, or 30 to 40 amino acids in length). In some embodiments of the second and third aspects of the invention, the first and/or second sequence in the ALK polypeptide includes at least 9 contiguous amino acids from a sequence of any one of SEQ ID NOs: 93, 96, 100, 106, 111-116, and 121-139. In some embodiments of the second and third aspects of the invention, the first and/or second sequence in the ALK polypeptide includes at least 11 contiguous amino acids from a sequence of any one of SEQ ID NOs: 93, 96, 100, 106, 111-116, and 121-139. In some embodiments of the second and third aspects of the invention, the first and/or second sequence in the ALK polypeptide includes a sequence of any one of SEQ ID NOs: 93, 96, 100, 106, 111-116, and 121-139. In some embodiments of the second and third aspects of the invention, the first and/or second sequence in the ALK polypeptide includes 9 contiguous amino acids from a sequence of any one of SEQ ID NOs: 93, 96, 100, 106, 111-116, and 121-139 and wherein the first and/or second sequence in the ALK polypeptide is 9 amino acids in length. In some embodiments, the first and/or second sequence in the ALK polypeptide includes 11 contiguous amino acids from a sequence of any one of SEQ ID NOs: 93, 96, 100, 106, 111-116, and 121-139 and wherein the first and/or second sequence in the ALK polypeptide is 11 amino acids in length. In some embodiments, the first and/or second sequence in the ALK polypeptide includes 15 contiguous amino acids from a sequence of any one of SEQ ID NOs: 93, 96, 100, 106, 111-116, and 121-139 and wherein the first and/or second sequence in the ALK polypeptide is 15 amino acids in length.

In a fourth aspect, the invention features an immunogenic composition including an ALK polypeptide, wherein the ALK polypeptide includes a first sequence including at least 6 contiguous amino acids from a sequence selected from any one of SEQ ID NOs: 1-66 (e.g., SEQ ID NOs: 10, 14, 17, 22, 33, 52, and 53), a second sequence including at least 6 contiguous amino acids from a sequence selected from any one of SEQ ID NOs: 1-66 (e.g., SEQ ID NOs: 10, 14, 17, 22, 33, 52, and 53), and a third sequence including at least 6 contiguous amino acids from a sequence selected from any one of SEQ ID NOs: 1-66 (e.g., SEQ ID NOs: 10, 14, 17, 22, 33, 52, and 53), wherein the first, second, and third sequences are different, wherein the first, second, and third sequences include a set of sequences of SEQ ID NOs recited in Table 3A, and wherein the ALK polypeptide does not include a sequence of any one of SEQ ID NOs: 67-70 and 140-145.

In some embodiments of the fourth aspect of the invention, the first, second, and third sequences include one of the following sets of sequences: SEQ ID NOs: 10, 14, and 17, SEQ ID NOs; 10, 14, and 22, SEQ ID NOs: 10, 14, and 33, SEQ ID NOs:10, 14, and 52, SEQ ID NOs:10, 14, and 53, SEQ ID NOs:10, 17, and 22, SEQ ID NOs:10, 17, and 33, SEQ ID NOs:10, 17, and 52, SEQ ID NOs:10, 17, and 53, SEQ ID NOs:10, 22, and 33, SEQ ID NOs:10, 22, and 52, SEQ ID NOs:10, 22, and 53, SEQ ID NOs:10, 33, and 52, SEQ ID NOs:10, 33, and 53, SEQ ID NOs:10, 52, and 53, SEQ ID NOs:14, 17, and 22, SEQ ID NOs:14, 17, and 33, SEQ ID NOs:14, 17, and 52, SEQ ID NOs:14, 17, and 53, SEQ ID NOs:14, 22, and 33, SEQ ID NOs:14, 22, and 52, SEQ ID NOs:14, 22, and 53, SEQ ID NOs:14, 33, and 52, SEQ ID NOs:14, 33, and 53, SEQ ID NOs:14, 52, and 53, SEQ ID NOs:17, 22, and 33, SEQ ID NOs:17, 22, and 52, SEQ ID NOs:17, 22, and 53, SEQ ID NOs:17, 33, and 52, SEQ ID NOs:17, 33, and 53, SEQ ID NOs:17, 52, and 53, SEQ ID NOs:22, 33, and 52, SEQ ID NOs:22, 33, and 53, SEQ ID NOs:22, 52, and 53, and SEQ ID NOs: 33, 52, and 53.

In a fifth aspect, the invention features an immunogenic composition including an ALK polypeptide, wherein the ALK polypeptide includes a first sequence including at least 6 contiguous amino acids from a sequence selected from any one of SEQ ID NOs: 93, 96, 100, 106, 111-116, and 121-139, a second sequence including at least 6 contiguous amino acids from a sequence selected from any one of SEQ ID NOs: 93, 96, 100, 106, 111-116, and 121-139, and a third sequence including at least 6 contiguous amino acids from a sequence selected from any one of SEQ ID NOs: 93, 96, 100, 106, 111-116, and 121-139, wherein the first, second, and third sequences are different, wherein the first, second, and third sequences include a set of sequences of SEQ ID NOs recited in Table 3B, and wherein the ALK polypeptide does not include a sequence of any one of SEQ ID NOs: 67-70 and 140-145.

In some embodiments of the fourth and fifth aspects of the invention, the first, second, and/or third sequence in the ALK polypeptide is 8 to 230 amino acids in length (e.g., 8 to 230 amino acids in length, 8 to 60 amino acids in length, 8 to 30 amino acids in length, 8 to 15 amino acids in length, or 8 to 11 amino acids in length). In some embodiments of the fourth and fifth aspects of the invention, the first, second, and/or third sequence in the ALK polypeptide includes at least 9 contiguous amino acids from a sequence of any one of SEQ ID NOs: 1-66 and 93-139. In some embodiments of the fourth and fifth aspects of the invention, the first, second, and/or third sequence in the ALK polypeptide includes at least 11 contiguous amino acids from a sequence of any one of SEQ ID NOs: 1-59 and 93-139. In some embodiments of the fourth and fifth aspects of the invention, the first, second, and/or third sequence in the ALK polypeptide includes a sequence of any one of SEQ ID NOs: 1-58 and 93-139. In some embodiments of the fourth and fifth aspects of the invention, the first, second, and/or third sequence in the ALK polypeptide includes 9 contiguous amino acids from a sequence of any one of SEQ ID NOs: 1-66 and 93-139 and wherein the first, second, and/or third sequence in the ALK polypeptide is 9 amino acids in length. In some embodiments, the first, second, and/or third sequence in the ALK polypeptide includes 11 contiguous amino acids from a sequence of any one of SEQ ID NOs: 1-59 and 93-139 and wherein the first, second, and/or third sequence in the ALK polypeptide is 11 amino acids in length. In some embodiments, the first, second, and/or third sequence in the ALK polypeptide includes 15 contiguous amino acids from a sequence of any one of SEQ ID NOs: 1-58 and 93-139 and wherein the first, second, and/or third sequence in the ALK polypeptide is 15 amino acids in length.

In some embodiments of the fourth and fifth aspects of the invention, the first, second, and/or third sequence in the ALK polypeptide is 9 to 40 amino acids in length (e.g., 9 to 40 amino acids in length, 15 to 40 amino acids in length, 20 to 40 amino acids in length, 25 to 40 amino acids in length, or 30 to 40 amino acids in length). In some embodiments of the fourth and fifth aspects of the invention, the first, second, and/or third sequence in the ALK polypeptide includes at least 9 contiguous amino acids from a sequence of any one of SEQ ID NOs: 93, 96, 100, 106, 111-116, and 121-139. In some embodiments of the fourth and fifth aspects of the invention, the first, second, and/or third sequence in the ALK polypeptide includes at least 11 contiguous amino acids from a sequence of any one of SEQ ID NOs: 93, 96, 100, 106, 111-116, and 121-139. In some embodiments of the fourth and fifth aspects of the invention, the first, second, and/or third sequence in the ALK polypeptide includes a sequence of any one of SEQ ID NOs: 93, 96, 100, 106, 111-116, and 121-139. In some embodiments of the fourth and fifth aspects of the invention, the first, second, and/or third sequence in the ALK polypeptide includes 9 contiguous amino acids from a sequence of any one of SEQ ID NOs: 93, 96, 100, 106, 111-116, and 121-139 and wherein the first, second, and/or third sequence in the ALK polypeptide is 9 amino acids in length. In some embodiments, the first, second, and/or third sequence in the ALK polypeptide includes 11 contiguous amino acids from a sequence of any one of SEQ ID NOs: 93, 96, 100, 106, 111-116, and 121-139 and wherein the first, second, and/or third sequence in the ALK polypeptide is 11 amino acids in length. In some embodiments, the first, second, and/or third sequence in the ALK polypeptide includes 15 contiguous amino acids from a sequence of any one of SEQ ID NOs: 93, 96, 100, 106, 111-116, and 121-139 and wherein the first, second, and/or third sequence in the ALK polypeptide is 15 amino acids in length.

In a sixth aspect, the invention features an immunogenic composition including an ALK polypeptide, wherein the ALK polypeptide consists of a sequence selected from any one of SEQ ID NOs: 1-66 and 93-139.

In a seventh aspect, the invention features an immunogenic composition including an ALK polypeptide, wherein the ALK polypeptide consists of a sequence selected from any one of SEQ ID NOs: 93, 96, 100, 106, 111-116, and 121-139.

In some embodiments of the first to the seventh aspects of the invention, a partner protein or a fragment thereof is fused to a N- or C-terminus of the ALK polypeptide. In some embodiments, the partner protein is selected from the group consisting of a nucleophosmin (NPM) protein, a tropomyosin 3 (TPM3) protein, a tropomyosin 4 (TPM4) protein, a TRK-fused gene (TFG) protein, a 5-Aminoimidazole-4-carboxamide ribonucleotide formyltransferase/IMP cyclohydrolase (ATIC) protein, a clathrin heavy chain-like 1 (CLTC1) protein, a moesin (MSN) protein, an ALK lymphoma oligomerization partner on chromosome 17 (ALO17) protein, a RAN binding protein 2 (RANBP2), a non-muscle myosin heavy chain (MYH9) protein, a cysteinyl-tRNA synthetase (CARS) protein, a SEC31 homologue A (SEC31 L1) protein, a transforming growth factor (TGF) protein, and an echinoderm microtubule-associated protein-like 4 (EML4) protein. In some embodiments, the fragment is an extracellular domain of the partner protein or a fragment of such extracellular domain.

In an eighth aspect, the invention features an immunogenic composition including a first ALK polypeptide including a first sequence including at least 6 contiguous amino acids from a sequence of any one of SEQ ID NOs: 1-66 (e.g., SEQ ID NOs: 10, 14, 17, 22, 33, 52, and 53) and a second ALK polypeptide including a second sequence including at least 6 contiguous amino acids from a sequence of any one of SEQ ID NOs: 1-66 (e.g., SEQ ID NOs: 10, 14, 17, 22, 33, 52, and 53), wherein the first and second sequences are different, wherein the first and second sequences include a pair of sequences of SEQ ID NOs recited in Table 2A, and wherein neither the first ALK polypeptide nor the second ALK polypeptide includes a sequence of any one of SEQ ID NOs: 67-70 and 140-145.

In some embodiments of the eighth aspect of the invention, the first and second sequences include one of the following pairs of sequences: SEQ ID NOs: 10 and 14, SEQ ID NOs: 10 and 17, SEQ ID NOs: 10 and 22, SEQ ID NOs: 10 and 33, SEQ ID NOs: 10 and 52, SEQ ID NOs: 10 and 53, SEQ ID NOs: 14 and 17, SEQ ID NOs: 14 and 22, SEQ ID NOs: 14 and 33, SEQ ID NOs: 14 and 52, SEQ ID NOs: 14 and 53, SEQ ID NOs: 17 and 22, SEQ ID NOs: 17 and 33, SEQ ID NOs: 17 and 52, SEQ ID NOs: 17 and 53, SEQ ID NOs: 22 and 33, SEQ ID NOs: 22 and 52, SEQ ID NOs: 22 and 53, SEQ ID NOs: 33 and 52, SEQ ID NOs: 33 and 53, and SEQ ID NOs: 52 and 53.

In a ninth aspect, the invention features an immunogenic composition including a first ALK polypeptide including a first sequence including at least 6 contiguous amino acids from a sequence of any one of SEQ ID NOs: 93, 96, 100, 106, 111-116, and 121-139 and a second ALK polypeptide including a second sequence including at least 6 contiguous amino acids from a sequence of any one of SEQ ID NOs: 93, 96, 100, 106, 111-116, and 121-139, wherein the first and second sequences are different, wherein the first and second sequences include a pair of sequences of SEQ ID NOs recited in Table 2B, and wherein neither the first ALK polypeptide nor the second ALK polypeptide includes a sequence of any one of SEQ ID NOs: 67-70 and 140-145.

In some embodiments of the eight and ninth aspects of the invention, the first and/or second sequence is 8 to 230 amino acids in length (e.g., 8 to 230 amino acids in length, 8 to 60 amino acids in length, 8 to 30 amino acids in length, 8 to 15 amino acids in length, or 8 to 11 amino acids in length). In some embodiments of the eighth and ninth aspects of the invention, the first and/or second sequence includes at least 9 contiguous amino acids from a sequence of any one of SEQ ID NOs: 1-66 and 93-139. In some embodiments of the eighth and ninth aspects of the invention, the first and/or second sequence includes at least 11 contiguous amino acids from a sequence of any one of SEQ ID NOs: 1-59 and 93-139. In some embodiments of the eighth and ninth aspects of the invention, the first and/or second sequence includes a sequence of any one of SEQ ID NOs: 1-58 and 93-139. In some embodiments of the eighth and ninth aspects of the invention, the first and/or second sequence includes 9 contiguous amino acids from a sequence of any one of SEQ ID NOs: 1-66 and 93-139 and wherein the first and/or second sequence is 9 amino acids in length. In some embodiments, the first and/or second sequence includes 11 contiguous amino acids from a sequence of any one of SEQ ID NOs: 1-59 and 93-139 and wherein the first and/or second sequence is 11 amino acids in length. In some embodiments, the first and/or second sequence includes 15 contiguous amino acids from a sequence of any one of SEQ ID NOs: 1-58 and 93-139 and wherein the first and/or second sequence is 15 amino acids in length.

In some embodiments of the eighth and ninth aspects of the invention, the first and/or second sequence is 9 to 40 amino acids in length (e.g., 9 to 40 amino acids in length, 15 to 40 amino acids in length, 20 to 40 amino acids in length, 25 to 40 amino acids in length, or 30 to 40 amino acids in length). In some embodiments of the eighth and ninth aspects of the invention, the first and/or second sequence includes at least 9 contiguous amino acids from a sequence of any one of SEQ ID NOs: 93, 96, 100, 106, 111-116, and 121-139. In some embodiments of the eighth and ninth aspects of the invention, the first and/or second sequence includes at least 11 contiguous amino acids from a sequence of any one of SEQ ID NOs: 93, 96, 100, 106, 111-116, and 121-139. In some embodiments of the eighth and ninth aspects of the invention, the first and/or second sequence includes a sequence of any one of SEQ ID NOs: 93, 96, 100, 106, 111-116, and 121-139. In some embodiments of the eighth and ninth aspects of the invention, the first and/or second sequence includes 9 contiguous amino acids from a sequence of any one of SEQ ID NOs: 93, 96, 100, 106, 111-116, and 121-139 and wherein the first and/or second sequence is 9 amino acids in length. In some embodiments, the first and/or second sequence includes 11 contiguous amino acids from a sequence of any one of SEQ ID NOs: 93, 96, 100, 106, 111-116, and 121-139 and wherein the first and/or second sequence is 11 amino acids in length. In some embodiments, the first and/or second sequence includes 15 contiguous amino acids from a sequence of any one of SEQ ID NOs: 93, 96, 100, 106, 111-116, and 121-139 and wherein the first and/or second sequence is 15 amino acids in length.

In some embodiments of the eighth and ninth aspects of the invention, a first partner protein or a fragment thereof is fused to a N- or C-terminus of the first ALK polypeptide, and/or wherein a second partner protein or a fragment thereof is fused to a N- or C-terminus of the second ALK polypeptide. In some embodiments, the first or second partner protein is selected from the group consisting of a nucleophosmin (NPM) protein, a tropomyosin 3 (TPM3) protein, a tropomyosin 4 (TPM4) protein, a TRK-fused gene (TFG) protein, a 5-Aminoimidazole-4-carboxamide ribonucleotide formyltransferase/IMP cyclohydrolase (ATIC) protein, a clathrin heavy chain-like 1 (CLTC1) protein, a moesin (MSN) protein, an ALK lymphoma oligomerization partner on chromosome 17 (ALO17) protein, a RAN binding protein 2 (RANBP2), a non-muscle myosin heavy chain (MYH9) protein, a cysteinyl-tRNA synthetase (CARS) protein, a SEC31 homologue A (SEC31 L1) protein, a transforming growth factor (TGF) protein, and an echinoderm microtubule-associated protein-like 4 (EML4) protein. In some embodiments the fragment is an extracellular domain of the first and/or second partner protein or a fragment of the extracellular domain of the first and/or second partner protein.

In a tenth aspect, the invention features an immunogenic composition including a first ALK polypeptide including a first sequence including at least 6 contiguous amino acids from a sequence of any one of SEQ ID NOs: 1-66 (e.g., SEQ ID NOs: 10, 14, 17, 22, 33, 52, and 53), a second ALK polypeptide including a second sequence including at least 6 contiguous amino acids from a sequence of any one of SEQ ID NOs: 1-66 (e.g., SEQ ID NOs: 10, 14, 17, 22, 33, 52, and 53), and a third ALK polypeptide including a third sequence including at least 6 contiguous amino acids from a sequence of any one of SEQ ID NOs: 1-66 (e.g., SEQ ID NOs: 10, 14, 17, 22, 33, 52, and 53), wherein the first, second, and third sequences are different, wherein the first, second, and third sequences include a set of sequences of SEQ ID NOs recited in Table 3A, and wherein none of the first, second, and third ALK polypeptides includes a sequence of any one of SEQ ID NOs: 67-70 and 140-145.

In some embodiments of the tenth aspect of the invention, the first, second, and third sequences include one of the following sets of sequences: SEQ ID NOs: 10, 14, and 17, SEQ ID NOs; 10, 14, and 22, SEQ ID NOs: 10, 14, and 33, SEQ ID NOs:10, 14, and 52, SEQ ID NOs:10, 14, and 53, SEQ ID NOs:10, 17, and 22, SEQ ID NOs:10, 17, and 33, SEQ ID NOs:10, 17, and 52, SEQ ID NOs:10, 17, and 53, SEQ ID NOs:10, 22, and 33, SEQ ID NOs:10, 22, and 52, SEQ ID NOs:10, 22, and 53, SEQ ID NOs:10, 33, and 52, SEQ ID NOs:10, 33, and 53, SEQ ID NOs:10, 52, and 53, SEQ ID NOs:14, 17, and 22, SEQ ID NOs:14, 17, and 33, SEQ ID NOs:14, 17, and 52, SEQ ID NOs:14, 17, and 53, SEQ ID NOs:14, 22, and 33, SEQ ID NOs:14, 22, and 52, SEQ ID NOs:14, 22, and 53, SEQ ID NOs:14, 33, and 52, SEQ ID NOs:14, 33, and 53, SEQ ID NOs:14, 52, and 53, SEQ ID NOs:17, 22, and 33, SEQ ID NOs:17, 22, and 52, SEQ ID NOs:17, 22, and 53, SEQ ID NOs:17, 33, and 52, SEQ ID NOs:17, 33, and 53, SEQ ID NOs:17, 52, and 53, SEQ ID NOs:22, 33, and 52, SEQ ID NOs:22, 33, and 53, SEQ ID NOs:22, 52, and 53, and SEQ ID NOs: 33, 52, and 53.

In an eleventh aspect, the invention features an immunogenic composition including a first ALK polypeptide including a first sequence including at least 6 contiguous amino acids from a sequence of any one of SEQ ID NOs: 93, 96, 100, 106, 111-116, and 121-139, a second ALK polypeptide including a second sequence including at least 6 contiguous amino acids from a sequence of any one of SEQ ID NOs: 93, 96, 100, 106, 111-116, and 121-139, and a third ALK polypeptide including a third sequence including at least 6 contiguous amino acids from a sequence of any one of SEQ ID NOs: 93, 96, 100, 106, 111-116, and 121-139, wherein the first, second, and third sequences are different, wherein the first, second, and third sequences include a set of sequences of SEQ ID NOs recited in Table 3B, and wherein none of the first, second, and third ALK polypeptides includes a sequence of any one of SEQ ID NOs: 67-70 and 140-145.

In some embodiments of the tenth and eleventh aspects of the invention, the first, second, and/or third sequence is 8 to 230 amino acids in length (e.g., 8 to 230 amino acids in length, 8 to 60 amino acids in length, 8 to 30 amino acids in length, 8 to 15 amino acids in length, or 8 to 11 amino acids in length). In some embodiments of the tenth and eleventh aspects of the invention, the first, second, and/or third sequence includes at least 9 contiguous amino acids from a sequence of any one of SEQ ID NOs: 1-66 and 93-139. In some embodiments of the tenth and eleventh aspects of the invention, the first, second, and/or third sequence includes at least 11 contiguous amino acids from a sequence of any one of SEQ ID NOs: 1-59 and 93-139. In some embodiments of the tenth and eleventh aspects of the invention, the first, second, and/or third sequence includes a sequence of any one of SEQ ID NOs: 1-58 and 93-139. In some embodiments of the tenth and eleventh aspects of the invention, the first, second, and/or third sequence includes 9 contiguous amino acids from a sequence of any one of SEQ ID NOs: 1-66 and 93-139 and wherein the first, second, and/or third sequence is 9 amino acids in length. In some embodiments, the first, second, and/or third sequence includes 11 contiguous amino acids from a sequence of any one of SEQ ID NOs: 1-59 and 93-139 and wherein the first, second, and/or third sequence is 11 amino acids in length. In some embodiments, the first, second, and/or third sequence includes 15 contiguous amino acids from a sequence of any one of SEQ ID NOs: 1-58 and 93-139 and wherein the first, second, and/or third sequence is 15 amino acids in length.

In some embodiments of the tenth and eleventh aspects of the invention, the first, second, and/or third sequence is 9 to 40 amino acids in length (e.g., 9 to 40 amino acids in length, 15 to 40 amino acids in length, 20 to 40 amino acids in length, 25 to 40 amino acids in length, or 30 to 40 amino acids in length). In some embodiments of the tenth and eleventh aspects of the invention, the first, second, and/or third sequence includes at least 9 contiguous amino acids from a sequence of any one of SEQ ID NOs: 93, 96, 100, 106, 111-116, and 121-139. In some embodiments of the tenth and eleventh aspects of the invention, the first, second, and/or third sequence includes at least 11 contiguous amino acids from a sequence of any one of SEQ ID NOs: 93, 96, 100, 106, 111-116, and 121-139. In some embodiments of the tenth and eleventh aspects of the invention, the first, second, and/or third sequence includes a sequence of any one of SEQ ID NOs: 93, 96, 100, 106, 111-116, and 121-139. In some embodiments of the tenth and eleventh aspects of the invention, the first, second, and/or third sequence includes 9 contiguous amino acids from a sequence of any one of SEQ ID NOs: 93, 96, 100, 106, 111-116, and 121-139 and wherein the first, second, and/or third sequence is 9 amino acids in length. In some embodiments, the first, second, and/or third sequence includes 11 contiguous amino acids from a sequence of any one of SEQ ID NOs: 93, 96, 100, 106, 111-116, and 121-139 and wherein the first, second, and/or third sequence is 11 amino acids in length. In some embodiments, the first, second, and/or third sequence includes 15 contiguous amino acids from a sequence of any one of SEQ ID NOs: 93, 96, 100, 106, 111-116, and 121-139 and wherein the first, second, and/or third sequence is 15 amino acids in length.

In some embodiments of the tenth and eleventh aspects of the invention, a first partner protein or a fragment thereof is fused to a N- or C-terminus of the first ALK polypeptide, and/or wherein a second partner protein or a fragment thereof is fused to a N- or C-terminus of the second ALK polypeptide, and/or wherein a third partner protein or a fragment thereof is fused to a N- or C-terminus of the third ALK polypeptide. In some embodiments of the tenth and eleventh aspects of the invention, the first, second, or third partner protein is selected from the group consisting of a nucleophosmin (NPM) protein, a tropomyosin 3 (TPM3) protein, a tropomyosin 4 (TPM4) protein, a TRK-fused gene (TFG) protein, a 5-Aminoimidazole-4-carboxamide ribonucleotide formyltransferase/IMP cyclohydrolase (ATIC) protein, a clathrin heavy chain-like 1 (CLTC1) protein, a moesin (MSN) protein, an ALK lymphoma oligomerization partner on chromosome 17 (ALO17) protein, a RAN binding protein 2 (RANBP2), a non-muscle myosin heavy chain (MYH9) protein, a cysteinyl-tRNA synthetase (CARS) protein, a SEC31 homologue A (SEC31 L1) protein, a transforming growth factor (TGF) protein, and an echinoderm microtubule-associated protein-like 4 (EML4) protein. In some embodiments, the fragment is an extracellular domain of the first, second, and/or third partner protein or a fragment of the extracellular domain of the first, second, and/or third partner protein.

In a thirteenth aspect, the invention features an immunogenic composition including: (a) a multilamellar lipid vesicle having crosslinks between lipid bilayers; and (b) at least one ALK polypeptide, wherein the ALK polypeptide includes at least 6 contiguous amino acids from a sequence of any one of SEQ ID NOs: 1-66 and 93-139 and wherein the ALK polypeptide does not include a sequence of any one of SEQ ID NOs: 67-70 and 140-145.

In a fourteenth aspect, the invention features an immunogenic composition including: (a) a multilamellar lipid vesicle having crosslinks between lipid bilayers; and (b) at least one ALK polypeptide, wherein the ALK polypeptide includes at least 6 contiguous amino acids from a sequence of any one of SEQ ID NOs: 93, 96, 100, 106, 111-116, and 121-139 and wherein the ALK polypeptide does not include a sequence of any one of SEQ ID NOs: 67-70 and 140-145.

In a fifteenth aspect, the invention features an immunogenic composition including: (a) a multilamellar lipid vesicle having crosslinks between lipid bilayers; and (b) an ALK polypeptide, wherein the ALK polypeptide includes a first sequence including at least 6 contiguous amino acids from a sequence selected from any one of SEQ ID NOs: 1-66 and a second sequence including at least 6 contiguous amino acids from a sequence selected from any one of SEQ ID NOs: 1-66, wherein the first and second sequences are different, wherein the first and second sequences include a pair of sequences of SEQ ID NOs recited in Table 2A, and wherein the ALK polypeptide does not include a sequence of any one of SEQ ID NOs: 67-70 and 140-145.

In a sixteenth aspect, the invention features an immunogenic composition including: (a) a multilamellar lipid vesicle having crosslinks between lipid bilayers; and (b) an ALK polypeptide, wherein the ALK polypeptide includes a first sequence including at least 6 contiguous amino acids from a sequence selected from any one of SEQ ID NOs: 93, 96, 100, 106, 111-116, and 121-139 and a second sequence including at least 6 contiguous amino acids from a sequence selected from any one of SEQ ID NOs: 93, 96, 100, 106, 111-116, and 121-139, wherein the first and second sequences are different, wherein the first and second sequences include a pair of sequences of SEQ ID NOs recited in Table 2B, and wherein the ALK polypeptide does not include a sequence of any one of SEQ ID NOs: 67-70 and 140-145.

In some embodiments of the fifteenth and sixteenth aspects of the invention, the first and/or second sequence is 8 to 230 amino acids in length (e.g., 8 to 230 amino acids in length, 8 to 60 amino acids in length, 8 to 30 amino acids in length, 8 to 15 amino acids in length, or 8 to 11 amino acids in length). In some embodiments of the fifteenth and sixteenth aspects of the invention, the first and/or second sequence includes at least 9 contiguous amino acids from a sequence of any one of SEQ ID NOs: 1-66 and 93-139. In some embodiments of the fifteenth and sixteenth aspects of the invention, the first and/or second sequence includes at least 11 contiguous amino acids from a sequence of any one of SEQ ID NOs: 1-59 and 93-139. In some embodiments of the fifteenth and sixteenth aspects of the invention, the first and/or second sequence includes a sequence of any one of SEQ ID NOs: 1-58 and 93-139. In some embodiments of the fifteenth and sixteenth aspects of the invention, the first and/or second sequence includes 9 contiguous amino acids from a sequence of any one of SEQ ID NOs: 1-66 and 93-139 and wherein the first and/or second sequence is 9 amino acids in length. In some embodiments, the first and/or second sequence includes 11 contiguous amino acids from a sequence of any one of SEQ ID NOs: 1-59 and 93-139 and wherein the first and/or second sequence is 11 amino acids in length. In some embodiments, the first and/or second sequence includes 15 contiguous amino acids from a sequence of any one of SEQ ID NOs: 1-58 and 93-139 and wherein the first and/or second sequence is 15 amino acids in length.

In some embodiments of the fifteenth and sixteenth aspects of the invention, the first and/or second sequence is 9 to 40 amino acids in length (e.g., 9 to 40 amino acids in length, 15 to 40 amino acids in length, 20 to 40 amino acids in length, 25 to 40 amino acids in length, or 30 to 40 amino acids in length). In some embodiments of the fifteenth and sixteenth aspects of the invention, the first and/or second sequence includes at least 9 contiguous amino acids from a sequence of any one of SEQ ID NOs: 93, 96, 100, 106, 111-116, and 121-139. In some embodiments of the fifteenth and sixteenth aspects of the invention, the first and/or second sequence includes at least 11 contiguous amino acids from a sequence of any one of SEQ ID NOs: 93, 96, 100, 106, 111-116, and 121-139. In some embodiments of the fifteenth and sixteenth aspects of the invention, the first and/or second sequence includes a sequence of any one of SEQ ID NOs: 93, 96, 100, 106, 111-116, and 121-139. In some embodiments of the fifteenth and sixteenth aspects of the invention, the first and/or second sequence includes 9 contiguous amino acids from a sequence of any one of SEQ ID NOs: 93, 96, 100, 106, 111-116, and 121-139 and wherein the first and/or second sequence is 9 amino acids in length. In some embodiments, the first and/or second sequence includes 11 contiguous amino acids from a sequence of any one of SEQ ID NOs: 93, 96, 100, 106, 111-116, and 121-139 and wherein the first and/or second sequence is 11 amino acids in length. In some embodiments, the first and/or second sequence includes 15 contiguous amino acids from a sequence of any one of SEQ ID NOs: 93, 96, 100, 106, 111-116, and 121-139 and wherein the first and/or second sequence is 15 amino acids in length.

In a seventeenth aspect, the invention features an immunogenic composition including: (a) a multilamellar lipid vesicle having crosslinks between lipid bilayers; and (b) an ALK polypeptide, wherein the ALK polypeptide includes a first sequence including at least 6 contiguous amino acids from a sequence selected from any one of SEQ ID NOs: 1-66, a second sequence including at least 6 contiguous amino acids from a sequence selected from any one of SEQ ID NOs: 1-66, and a third sequence including at least 6 contiguous amino acids from a sequence selected from any one of SEQ ID NOs: 1-66, wherein the first, second, and third sequences are different, wherein the first, second, and third sequences include a set of sequences of SEQ ID NOs recited in Table 3A, and wherein the ALK polypeptide does not include a sequence of any one of SEQ ID NOs: 67-70 and 140-145.

In an eighteenth aspect, the invention features an immunogenic composition including: (a) a multilamellar lipid vesicle having crosslinks between lipid bilayers; and (b) an ALK polypeptide, wherein the ALK polypeptide includes a first sequence including at least 6 contiguous amino acids from a sequence selected from any one of SEQ ID NOs: 93, 96, 100, 106, 111-116, and 121-139, a second sequence including at least 6 contiguous amino acids from a sequence selected from any one of SEQ ID NOs: 93, 96, 100, 106, 111-116, and 121-139, and a third sequence including at least 6 contiguous amino acids from a sequence selected from any one of SEQ ID NOs: 93, 96, 100, 106, 111-116, and 121-139, wherein the first, second, and third sequences are different, wherein the first, second, and third sequences include a set of sequences of SEQ ID NOs recited in Table 3B, and wherein the ALK polypeptide does not include a sequence of any one of SEQ ID NOs: 67-70 and 140-145.

In some embodiments of the seventeenth and eighteenth aspects of the invention, the first, second, and/or third sequence is 8 to 230 amino acids in length (e.g., 8 to 230 amino acids in length, 8 to 60 amino acids in length, 8 to 30 amino acids in length, 8 to 15 amino acids in length, or 8 to 11 amino acids in length). In some embodiments of the seventeenth and eighteenth aspects of the invention, the first, second, and/or third sequence includes at least 9 contiguous amino acids from a sequence of any one of SEQ ID NOs: 1-66 and 93-139. In some embodiments of the seventeenth and eighteenth aspects of the invention, the first, second, and/or third sequence includes at least 11 contiguous amino acids from a sequence of any one of SEQ ID NOs: 1-59 and 93-139. In some embodiments of the seventeenth and eighteenth aspects of the invention, the first, second, and/or third sequence includes a sequence of any one of SEQ ID NOs: 1-58 and 93-139. In some embodiments of the seventeenth and eighteenth aspects of the invention, the first, second, and/or third sequence includes 9 contiguous amino acids from a sequence of any one of SEQ ID NOs: 1-66 and 93-139 and wherein the first, second, and/or third sequence is 9 amino acids in length. In some embodiments, the first, second, and/or third sequence includes 11 contiguous amino acids from a sequence of any one of SEQ ID NOs: 1-59 and 93-139 and wherein the first, second, and/or third sequence is 11 amino acids in length. In some embodiments, the first, second, and/or third sequence includes 15 contiguous amino acids from a sequence of any one of SEQ ID NOs: 1-58 and 93-139 and wherein the first, second, and/or third sequence is 15 amino acids in length.

In some embodiments of the seventeenth and eighteenth aspects of the invention, the first, second, and/or third sequence is 9 to 40 amino acids in length (e.g., 9 to 40 amino acids in length, 15 to 40 amino acids in length, 20 to 40 amino acids in length, 25 to 40 amino acids in length, or 30 to 40 amino acids in length). In some embodiments of the seventeenth and eighteenth aspects of the invention, the first, second, and/or third sequence includes at least 9 contiguous amino acids from a sequence of any one of SEQ ID NOs: 93, 96, 100, 106, 111-116, and 121-139. In some embodiments of the seventeenth and eighteenth aspects of the invention, the first, second, and/or third sequence includes at least 11 contiguous amino acids from a sequence of any one of SEQ ID NOs: 93, 96, 100, 106, 111-116, and 121-139. In some embodiments of the seventeenth and eighteenth aspects of the invention, the first, second, and/or third sequence includes a sequence of any one of SEQ ID NOs: 93, 96, 100, 106, 111-116, and 121-139. In some embodiments of the seventeenth and eighteenth aspects of the invention, the first, second, and/or third sequence includes 9 contiguous amino acids from a sequence of any one of SEQ ID NOs: 93, 96, 100, 106, 111-116, and 121-139 and wherein the first, second, and/or third sequence is 9 amino acids in length. In some embodiments, the first, second, and/or third sequence includes 11 contiguous amino acids from a sequence of any one of SEQ ID NOs: 93, 96, 100, 106, 111-116, and 121-139 and wherein the first, second, and/or third sequence is 11 amino acids in length. In some embodiments, the first, second, and/or third sequence includes 15 contiguous amino acids from a sequence of any one of SEQ ID NOs: 93, 96, 100, 106, 111-116, and 121-139 and wherein the first, second, and/or third sequence is 15 amino acids in length.

In a nineteenth aspect, the invention features an immunogenic composition including: (a) a multilamellar lipid vesicle having crosslinks between lipid bilayers; and (b) an ALK polypeptide, wherein the ALK polypeptide consists of a sequence selected from any one of SEQ ID NOs: 1-66 and 93-139.

In a twentieth aspect, the invention features an immunogenic composition including: (a) a multilamellar lipid vesicle having crosslinks between lipid bilayers; and (b) an ALK polypeptide, wherein the ALK polypeptide consists of a sequence selected from any one of SEQ ID NOs: 93, 96, 100, 106, 111-116, and 121-139.

In some embodiments of the thirteenth to the twentieth aspects of the invention, the ALK polypeptide is covalently conjugated to a lipid in the multilamellar lipid vesicle. In some embodiments, the ALK polypeptide and/or the multilamellar lipid vesicle is functionalized with a reactive group. In some embodiments, the multilamellar lipid vesicle is functionalized with a maleimide reactive group, which reacts with a cysteine in the ALK polypeptide to form a covalent attachment between the ALK polypeptide and the multilamellar lipid vesicle. In some embodiments, the cysteine in the ALK polypeptide is a naturally occurring cysteine or a non-naturally occurring cysteine. In some embodiments, the cysteine in the ALK polypeptide is a terminal-cysteine. In some embodiments, the ALK polypeptide is functionalized with a thiol reactive group and the multilamellar lipid vesicle is functionalized with a maleimide reactive group, and the thiol reactive group reacts with the maleimide reactive group to form a covalent attachment between the ALK polypeptide and the multilamellar lipid vesicle.

In a twenty-first aspect, the invention features an immunogenic composition including: (a) a multilamellar lipid vesicle having crosslinks between lipid bilayers; (b) a first ALK polypeptide including a first sequence including at least 6 contiguous amino acids from a sequence of any one of SEQ ID NOs: 1-66; and (c) a second ALK polypeptide including a second sequence including at least 6 contiguous amino acids from a sequence of any one of SEQ ID NOs: 1-66, wherein the first and second sequences are different, wherein the first and second sequences include a pair of sequences of SEQ ID NOs recited in Table 2A, and wherein neither the first ALK polypeptide nor the second ALK polypeptide includes a sequence of any one of SEQ ID NOs: 67-70 and 140-145.

In a twenty-second aspect, the invention features an immunogenic composition including: (a) a multilamellar lipid vesicle having crosslinks between lipid bilayers; (b) a first ALK polypeptide including a first sequence including at least 6 contiguous amino acids from a sequence of any one of SEQ ID NOs: 93, 96, 100, 106, 111-116, and 121-139; and (c) a second ALK polypeptide including a second sequence including at least 6 contiguous amino acids from a sequence of any one of SEQ ID NOs: 93, 96, 100, 106, 111-116, and 121-139, wherein the first and second sequences are different, wherein the first and second sequences include a pair of sequences of SEQ ID NOs recited in Table 2B, and wherein neither the first ALK polypeptide nor the second ALK polypeptide includes a sequence of any one of SEQ ID NOs: 67-70 and 140-145.

In some embodiments of the twenty-first and twenty-second aspects of the invention, the first and/or second sequence is 8 to 230 amino acids in length (e.g., 8 to 230 amino acids in length, 8 to 60 amino acids in length, 8 to 30 amino acids in length, 8 to 15 amino acids in length, or 8 to 11 amino acids in length). In some embodiments of the twenty-first and twenty-second aspects of the invention, the first and/or second sequence includes at least 9 contiguous amino acids from a sequence of any one of SEQ ID NOs:

1-66 and 93-139. In some embodiments of the twenty-first and twenty-second aspects of the invention, the first and/or second sequence includes at least 11 contiguous amino acids from a sequence of any one of SEQ ID NOs: 1-59 and 93-139. In some embodiments of the twenty-first and twenty-second aspects of the invention, the first and/or second sequence includes a sequence of any one of SEQ ID NOs: 1-58 and 93-139. In some embodiments of the twenty-first and twenty-second aspects of the invention, the first and/or second sequence includes 9 contiguous amino acids from a sequence of any one of SEQ ID NOs: 1-66 and 93-139 and wherein the first and/or second sequence is 9 amino acids in length. In some embodiments, the first and/or second sequence includes 11 contiguous amino acids from a sequence of any one of SEQ ID NOs: 1-59 and 93-139 and wherein the first and/or second sequence is 11 amino acids in length. In some embodiments, the first and/or second sequence includes 15 contiguous amino acids from a sequence of any one of SEQ ID NOs: 1-58 and 93-139 and wherein the first and/or second sequence is 15 amino acids in length.

In some embodiments of the twenty-first and twenty-second aspects of the invention, the first and/or second sequence is 9 to 40 amino acids in length (e.g., 9 to 40 amino acids in length, 15 to 40 amino acids in length, 20 to 40 amino acids in length, 25 to 40 amino acids in length, or 30 to 40 amino acids in length).

In some embodiments of the twenty-first and twenty-second aspects of the invention, the first and/or second sequence includes at least 9 contiguous amino acids from a sequence of any one of SEQ ID NOs: 93, 96, 100, 106, 111-116, and 121-139. In some embodiments of the twenty-first and twenty-second aspects of the invention, the first and/or second sequence includes at least 11 contiguous amino acids from a sequence of any one of SEQ ID NOs: 93, 96, 100, 106, 111-116, and 121-139. In some embodiments of the twenty-first and twenty-second aspects of the invention, the first and/or second sequence includes a sequence of any one of SEQ ID NOs: 93, 96, 100, 106, 111-116, and 121-139. In some embodiments of the twenty-first and twenty-second aspects of the invention, the first and/or second sequence includes 9 contiguous amino acids from a sequence of any one of SEQ ID NOs: 93, 96, 100, 106, 111-116, and 121-139 and wherein the first and/or second sequence is 9 amino acids in length. In some embodiments, the first and/or second sequence includes 11 contiguous amino acids from a sequence of any one of SEQ ID NOs: 93, 96, 100, 106, 111-116, and 121-139 and wherein the first and/or second sequence is 11 amino acids in length. In some embodiments, the first and/or second sequence includes 15 contiguous amino acids from a sequence of any one of SEQ ID NOs: 93, 96, 100, 106, 111-116, and 121-139 and wherein the first and/or second sequence is 15 amino acids in length.

In some embodiments of the twenty-first and twenty-second aspects of the invention, each of the first and second ALK polypeptides is covalently conjugated to a lipid in the multilamellar lipid vesicle. In some embodiments, each of the first and second ALK polypeptides is functionalized with a reactive group and/or the multilamellar lipid vesicle is functionalized with a reactive group. In some embodiments, the multilamellar lipid vesicle is functionalized with a maleimide reactive group, which reacts with a cysteine in each of the first and second ALK polypeptides to form covalent attachments between the ALK polypeptides and the multilamellar lipid vesicle. In some embodiments, the cysteine in the first or second ALK polypeptide is a naturally occurring cysteine or a non-naturally occurring cysteine. In some embodiments, the cysteine in the first or second ALK polypeptide is a terminal-cysteine. In some embodiments, each of the first and second ALK polypeptides is functionalized with a thiol reactive group and the multilamellar lipid vesicle is functionalized with a maleimide reactive group, and the thiol reactive group in each of the first and second ALK polypeptides reacts with the maleimide reactive group to form covalent attachments between the ALK polypeptides and the multilamellar lipid vesicle.

In a twenty-third aspect, the invention features an immunogenic composition including: (a) a multilamellar lipid vesicle having crosslinks between lipid bilayers; (b) a first ALK polypeptide including a first sequence including at least 6 contiguous amino acids from a sequence of any one of SEQ ID NOs: 1-66; (c) a second ALK polypeptide including a second sequence including at least 6 contiguous amino acids from a sequence of any one of SEQ ID NOs: 1-66; and (d) a third ALK polypeptide including a third sequence including at least 6 contiguous amino acids from a sequence of any one of SEQ ID NOs: 1-66, wherein the first, second, and third sequences are different, wherein the first, second, and third sequences include a set of sequences of SEQ ID NOs recited in Table 3A, and wherein none of the first, second, and third ALK polypeptides includes a sequence of any one of SEQ ID NOs: 67-70 and 140-145.

In a twenty-fourth aspect, the invention features an immunogenic composition including: (a) a multilamellar lipid vesicle having crosslinks between lipid bilayers; (b) a first ALK polypeptide including a first sequence including at least 6 contiguous amino acids from a sequence of any one of SEQ ID NOs: 93, 96, 100, 106, 111-116, and 121-139; (c) a second ALK polypeptide including a second sequence including at least 6 contiguous amino acids from a sequence of any one of SEQ ID NOs: 93, 96, 100, 106, 111-116, and 121-139; and (d) a third ALK polypeptide including a third sequence including at least 6 contiguous amino acids from a sequence of any one of SEQ ID NOs: 93, 96, 100, 106, 111-116, and 121-139, wherein the first, second, and third sequences are different, wherein the first, second, and third sequences include a set of sequences of SEQ ID NOs recited in Table 3B, and wherein none of the first, second, and third ALK polypeptides includes a sequence of any one of SEQ ID NOs: 67-70 and 140-145.

In some embodiments of the twenty-third and twenty-fourth aspects of the invention, the first, second, and/or third sequence is 8 to 230 amino acids in length (e.g., 8 to 230 amino acids in length, 8 to 60 amino acids in length, 8 to 30 amino acids in length, 8 to 15 amino acids in length, or 8 to 11 amino acids in length). In some embodiments of the twenty-third and twenty-fourth aspects of the invention, the first, second, and/or third sequence includes at least 9 contiguous amino acids from a sequence of any one of SEQ ID NOs: 1-66 and 93-139. In some embodiments of the twenty-third and twenty-fourth aspects of the invention, the first, second, and/or third sequence includes at least 11 contiguous amino acids from a sequence of any one of SEQ ID NOs: 1-59 and 93-139. In some embodiments of the twenty-third and twenty-fourth aspects of the invention, the first, second, and/or third sequence includes a sequence of any one of SEQ ID NOs: 1-58 and 93-139. In some embodiments of the twenty-third and twenty-fourth aspects of the invention, the first, second, and/or third sequence includes 9 contiguous amino acids from a sequence of any one of SEQ ID NOs: 1-66 and 93-139 and wherein the first, second, and/or third sequence is 9 amino acids in length. In some embodiments, the first, second, and/or third sequence includes 11 contiguous amino acids from a sequence of any one of SEQ ID NOs: 1-59 and 93-139 and wherein the first, second, and/or third sequence is 11 amino acids in length. In some embodiments, the first, second, and/or third sequence includes 15 contiguous amino acids from a sequence of any one of SEQ ID NOs: 1-58 and 93-139 and wherein the first, second, and/or third sequence is 15 amino acids in length.

In some embodiments of the twenty-third and twenty-fourth aspects of the invention, the first, second, and/or third sequence is 9 to 40 amino acids in length (e.g., 9 to 40 amino acids in length, 15 to 40 amino acids in length, 20 to 40 amino acids in length, 25 to 40 amino acids in length, or 30 to 40 amino acids in length). In some embodiments of the twenty-third and twenty-fourth aspects of the invention, the first, second, and/or third sequence includes at least 9 contiguous amino acids from a sequence of any one of SEQ ID NOs: 93, 96, 100, 106, 111-116, and 121-139. In some embodiments of the twenty-third and twenty-fourth aspects of the invention, the first, second, and/or third sequence includes at least 11 contiguous amino acids from a sequence of any one of SEQ ID NOs: 93, 96, 100, 106, 111-116, and 121-139. In some embodiments of the twenty-third and twenty-fourth aspects of the invention, the first, second, and/or third sequence includes a sequence of any one of SEQ ID NOs: 93, 96, 100, 106, 111-116, and 121-139. In some embodiments of the twenty-third and twenty-fourth aspects of the invention, the first, second, and/or third sequence includes 9 contiguous amino acids from a sequence of any one of SEQ ID NOs: 93, 96, 100, 106, 111-116, and 121-139 and wherein the first, second, and/or third sequence is 9 amino acids in length. In some embodiments, the first, second, and/or third sequence includes 11 contiguous amino acids from a sequence of any one of SEQ ID NOs: 93, 96, 100, 106, 111-116, and 121-139 and wherein the first, second, and/or third sequence is 11 amino acids in length. In some embodiments, the first, second, and/or third sequence includes 15 contiguous amino acids from a sequence of any one of SEQ ID NOs: 93, 96, 100, 106, 111-116, and 121-139 and wherein the first, second, and/or third sequence is 15 amino acids in length.

In some embodiments of the twenty-third and twenty-fourth aspects of the invention, each of the first, second, and third ALK polypeptides is covalently conjugated to a lipid in the multilamellar lipid vesicle. In some embodiments, the each of the first, second, and third ALK polypeptides is functionalized with a reactive group and/or the multilamellar lipid vesicle is functionalized with a reactive group. In some embodiments, the multilamellar lipid vesicle is functionalized with a maleimide reactive group, which reacts with a cysteine in each of the first, second, and third ALK polypeptides to form covalent attachments between the ALK polypeptides and the multilamellar lipid vesicle. In some embodiments, the cysteine in the first, second, or third ALK polypeptide is a naturally occurring cysteine or a non-naturally occurring cysteine. In some embodiments, the cysteine in the first, second, or third ALK polypeptide is a terminal-cysteine. In some embodiments, each of the first, second, and third ALK polypeptides is functionalized with a thiol reactive group and the multilamellar lipid vesicle is functionalized with a maleimide reactive group, and the thiol reactive group in each of the first, second, and third ALK polypeptides reacts with the maleimide reactive group to form covalent attachments between the ALK polypeptides and the multilamellar lipid vesicle.

In some embodiments of the first to the twenty-fourth aspects of the invention, the immunogenic composition described therein further includes an immunomodulator. In some embodiments, the immunogenic composition further includes an adjuvant. In some embodiments, the immunogenic composition further includes an anti-cancer agent. In some embodiments, the anti-cancer agent is a tyrosine kinase inhibitor. In some embodiments, the tyrosine kinase inhibitor is Crizotinib. In some embodiments, the tyrosine kinase inhibitor is Ceritinib. In some embodiments, the tyrosine kinase inhibitor is Alectinib. In some embodiments, the tyrosine kinase inhibitor is Brigatinib.

In a twenty-fifth aspect, the invention features an amphiphilic conjugate including: (a) an albumin-binding domain; (b) an ALK polypeptide; and (c) an optional linker, wherein the ALK polypeptide includes at least 6 contiguous amino acids from a sequence of any one of SEQ ID NOs: 1-66 and 93-139 and does not include a sequence of any one of SEQ ID NOs: 67-70 and 140-145, and wherein the ALK polypeptide is conjugated directly to the albumin-binding domain or is conjugated to the albumin-binding domain through the linker.

In a twenty-fifth aspect, the invention features an amphiphilic conjugate including: (a) an albumin-binding domain; (b) an ALK polypeptide; and (c) an optional linker, wherein the ALK polypeptide includes at least 6 contiguous amino acids from a sequence of any one of SEQ ID NOs: 93, 96, 100, 106, 111-116, and 121-139 and does not include a sequence of any one of SEQ ID NOs: 67-70 and 140-145, and wherein the ALK polypeptide is conjugated directly to the albumin-binding domain or is conjugated to the albumin-binding domain through the linker.

In a twenty-sixth aspect, the invention features an amphiphilic conjugate including: (a) an albumin-binding domain; (b) an ALK polypeptide; and (c) an optional linker, wherein the ALK polypeptide includes a first sequence including at least 6 contiguous amino acids from a sequence selected from any one of SEQ ID NOs: 1-66 and a second sequence including at least 6 contiguous amino acids from a sequence selected from any one of SEQ ID NOs: 1-66, wherein the first and second sequences are different, wherein the first and second sequences include a pair of sequences of SEQ ID NOs recited in Table 2A, wherein the ALK polypeptide does not include a sequence of any one of SEQ ID NOs: 67-70 and 140-145, and wherein the ALK polypeptide is conjugated directly to the albumin-binding domain or is conjugated to the albumin-binding domain through the linker.

In a twenty-seventh aspect, the invention features an amphiphilic conjugate including: (a) an albumin-binding domain; (b) an ALK polypeptide; and (c) an optional linker, wherein the ALK polypeptide includes a first sequence including at least 6 contiguous amino acids from a sequence selected from any one of SEQ ID NOs: 93, 96, 100, 106, 111-116, and 121-139 and a second sequence including at least 6 contiguous amino acids from a sequence selected from any one of SEQ ID NOs: 93, 96, 100, 106, 111-116, and 121-139, wherein the first and second sequences are different, wherein the first and second sequences include a pair of sequences of SEQ ID NOs recited in Table 2B, wherein the ALK polypeptide does not include a sequence of any one of SEQ ID NOs: 67-70 and 140-145, and wherein the ALK polypeptide is conjugated directly to the albumin-binding domain or is conjugated to the albumin-binding domain through the linker.

In some embodiments of the twenty-sixth and twenty-seventh aspects of the invention, the first and/or second sequence is 8 to 230 amino acids in length (e.g., 8 to 230 amino acids in length, 8 to 60 amino acids in length, 8 to 30 amino acids in length, 8 to 15 amino acids in length, or 8 to 11 amino acids in length). In some embodiments of the twenty-sixth and twenty-seventh aspects of the invention, the first and/or second sequence includes at least 9 contiguous amino acids from a sequence of any one of SEQ ID NOs: 1-66 and 93-139. In some embodiments of the twenty-sixth and twenty-seventh aspects of the invention, the first and/or second sequence includes at least 11 contiguous amino acids from a sequence of any one of SEQ ID NOs: 1-59 and 93-139. In some embodiments of the twenty-sixth and twenty-seventh aspects of the invention, the first and/or second sequence includes a sequence of any one of SEQ ID NOs: 1-58 and 93-139. In some embodiments of the twenty-sixth and twenty-seventh aspects of the invention, the first and/or second sequence includes 9 contiguous amino acids from a sequence of any one of SEQ ID NOs: 1-66 and 93-139 and wherein the first and/or second sequence is 9 amino acids in length. In some embodiments, the first and/or second sequence includes 11 contiguous amino acids from a sequence of any one of SEQ ID NOs: 1-59 and 93-139 and wherein the first and/or second sequence is 11 amino acids in length. In some embodiments, the first and/or second sequence includes 15 contiguous amino acids from a sequence of any one of SEQ ID NOs: 1-58 and 93-139 and wherein the first and/or second sequence is 15 amino acids in length.

In some embodiments of the twenty-sixth and twenty-seventh aspects of the invention, the first and/or second sequence is 9 to 40 amino acids in length (e.g., 9 to 40 amino acids in length, 15 to 40 amino acids in length, 20 to 40 amino acids in length, 25 to 40 amino acids in length, or 30 to 40 amino acids in length). In some embodiments of the twenty-sixth and twenty-seventh aspects of the invention, the first and/or second sequence includes at least 9 contiguous amino acids from a sequence of any one of SEQ ID NOs: 93, 96, 100, 106, 111-116, and 121-139. In some embodiments of the twenty-sixth and twenty-seventh aspects of the invention, the first and/or second sequence includes at least 11 contiguous amino acids from a sequence of any one of SEQ ID NOs: 93, 96, 100, 106, 111-116, and 121-139. In some embodiments of the twenty-sixth and twenty-seventh aspects of the invention, the first and/or second sequence includes a sequence of any one of SEQ ID NOs: 93, 96, 100, 106, 111-116, and 121-139. In some embodiments of the twenty-sixth and twenty-seventh aspects of the invention, the first and/or second sequence includes 9 contiguous amino acids from a sequence of any one of SEQ ID NOs: 93, 96, 100, 106, 111-116, and 121-139 and wherein the first and/or second sequence is 9 amino acids in length. In some embodiments, the first and/or second sequence includes 11 contiguous amino acids from a sequence of any one of SEQ ID NOs: 93, 96, 100, 106, 111-116, and 121-139 and wherein the first and/or second sequence is 11 amino acids in length. In some embodiments, the first and/or second sequence includes 15 contiguous amino acids from a sequence of any one of SEQ ID NOs: 93, 96, 100, 106, 111-116, and 121-139 and wherein the first and/or second sequence is 15 amino acids in length.

In a twenty-eighth aspect, the invention features an amphiphilic conjugate including: (a) an albumin-binding domain; (b) an ALK polypeptide; and (c) an optional linker, wherein the ALK polypeptide includes a first sequence including at least 6 contiguous amino acids from a sequence selected from any one of SEQ ID NOs: 1-66, a second sequence including at least 6 contiguous amino acids from a sequence selected from any one of SEQ ID NOs: 1-66, and a third sequence including at least 6 contiguous amino acids from a sequence selected from any one of SEQ ID NOs: 1-66, wherein the first, second, and third sequences are different, wherein the first, second, and third sequences include a set of sequences of SEQ ID NOs recited in Table 3A, wherein the ALK polypeptide does not include a sequence of any one of SEQ ID NOs: 67-70 and 140-145, and wherein the ALK polypeptide is conjugated directly to the albumin-binding domain or is conjugated to the albumin-binding domain through the linker.

In a twenty-ninth aspect, the invention features an amphiphilic conjugate including: (a) an albumin-binding domain; (b) an ALK polypeptide; and (c) an optional linker, wherein the ALK polypeptide includes a first sequence including at least 6 contiguous amino acids from a sequence selected from any one of SEQ ID NOs: 93, 96, 100, 106, 111-116, and 121-139, a second sequence including at least 6 contiguous amino acids from a sequence selected from any one of SEQ ID NOs: 93, 96, 100, 106, 111-116, and 121-139, and a third sequence including at least 6 contiguous amino acids from a sequence selected from any one of SEQ ID NOs: 93, 96, 100, 106, 111-116, and 121-139, wherein the first, second, and third sequences are different, wherein the first, second, and third sequences include a set of sequences of SEQ ID NOs recited in Table 3B, wherein the ALK polypeptide does not include a sequence of any one of SEQ ID NOs: 67-70 and 140-145, and wherein the ALK polypeptide conjugated directly to the albumin-binding domain or is conjugated to the albumin-binding domain through the linker.

In some embodiments of the twenty-eighth and twenty-ninth aspects of the invention, the first, second, and/or third sequence is 8 to 230 amino acids in length (e.g., 8 to 230 amino acids in length, 8 to 60 amino acids in length, 8 to 30 amino acids in length, 8 to 15 amino acids in length, or 8 to 11 amino acids in length). In some embodiments of the twenty-eighth and twenty-ninth aspects of the invention, the first, second, and/or third sequence includes at least 9 contiguous amino acids from a sequence of any one of SEQ ID NOs: 1-66 and 93-139. In some embodiments of the twenty-eighth and twenty-ninth aspects of the invention, the first, second, and/or third sequence includes at least 11 contiguous amino acids from a sequence of any one of SEQ ID NOs: 1-59 and 93-139. In some embodiments of the twenty-eighth and twenty-ninth aspects of the invention, the first, second, and/or third sequence includes a sequence of any one of SEQ ID NOs: 1-58 and 93-139. In some embodiments of the twenty-eighth and twenty-ninth aspects of the invention, the first, second, and/or third sequence includes 9 contiguous amino acids from a sequence of any one of SEQ ID NOs: 1-66 and 93-139 and wherein the first, second, and/or third sequence is 9 amino acids in length. In some embodiments, the first, second, and/or third sequence includes 11 contiguous amino acids from a sequence of any one of SEQ ID NOs: 1-59 and 93-139 and wherein the first, second, and/or third sequence is 11 amino acids in length. In some embodiments, the first, second, and/or third sequence includes 15 contiguous amino acids from a sequence of any one of SEQ ID NOs: 1-58 and 93-139 and wherein the first, second, and/or third sequence is 15 amino acids in length.

In some embodiments of the twenty-eighth and twenty-ninth aspects of the invention, the first, second, and/or third sequence is 9 to 40 amino acids in length (e.g., 9 to 40 amino acids in length, 15 to 40 amino acids in length, 20 to 40 amino acids in length, 25 to 40 amino acids in length, or 30 to 40 amino acids in length). In some embodiments of the twenty-eighth and twenty-ninth aspects of the invention, the first, second, and/or third sequence includes at least 9 contiguous amino acids from a sequence of any one of SEQ ID NOs: 93, 96, 100, 106, 111-116, and 121-139. In some embodiments of the twenty-eighth and twenty-ninth aspects of the invention, the first, second, and/or third sequence includes at least 11 contiguous amino acids from a sequence of any one of SEQ ID NOs: 93, 96, 100, 106, 111-116, and 121-139. In some embodiments of the twenty-eighth and twenty-ninth aspects of the invention, the first, second, and/or third sequence includes a sequence of any one of SEQ ID NOs: 93, 96, 100, 106, 111-116, and 121-139. In some embodiments of the twenty-eighth and twenty-ninth aspects of the invention, the first, second, and/or third sequence includes 9 contiguous amino acids from a sequence of any one of SEQ ID NOs: 93, 96, 100, 106, 111-116, and 121-139 and wherein the first, second, and/or third sequence is 9 amino acids in length. In some embodiments, the first, second, and/or third sequence includes 11 contiguous amino acids from a sequence of any one of SEQ ID NOs: 93, 96, 100, 106, 111-116, and 121-139 and wherein the first, second, and/or third sequence is 11 amino acids in length. In some embodiments, the first, second, and/or third sequence includes 15 contiguous amino acids from a sequence of any one of SEQ ID NOs: 93, 96, 100, 106, 111-116, and 121-139 and wherein the first, second, and/or third sequence is 15 amino acids in length.

In some embodiments of the twenty-fifth to the twenty-ninth aspects of the invention, the albumin-binding domain is a lipid.

In some embodiments of the twenty-fifth to the twenty-ninth aspects of the invention, the linker is selected from the group consisting of polymers, a string of amino acids, nucleic acids, polysaccharides, or a combination thereof. In some embodiments, the linker includes consecutive polyethylene glycol units. In some embodiments, the linker includes "N" consecutive polyethylene glycol units, wherein N is between 20 and 80. In some embodiments, the linker includes "N" consecutive polyethylene glycol units, wherein N is between 30 and 80. In some embodiments, the linker includes "N" consecutive polyethylene glycol units, wherein N is between 40 and 60. In some embodiments, the linker includes "N" consecutive polyethylene glycol units, wherein N is between 45 and 55. In some embodiments, the linker includes 48 consecutive polyethylene glycol units.

In some embodiments of the twenty-fifth to the twenty-ninth aspects of the invention, the conjugate spontaneously inserts itself into lipid bilayers of a multilamellar lipid vesicle having crosslinks between lipid bilayers.

In a thirtieth aspect, the invention features an immunogenic composition including an amphiphilic conjugate described in any one of twenty-fifth to the twenty-ninth aspects of the invention.

In some embodiments of the thirtieth aspect of the invention, the immunogenic composition described therein further includes an immunomodulator. In some embodiments, the immunogenic composition further includes an adjuvant. In some embodiments, the immunogenic composition further includes an anti-cancer agent. In some embodiments, the anti-cancer agent is a tyrosine kinase inhibitor. In some embodiments, the tyrosine kinase inhibitor is Crizotinib. In some embodiments, the tyrosine kinase inhibitor is Ceritinib. In some embodiments, the tyrosine kinase inhibitor is Alectinib. In some embodiments, the tyrosine kinase inhibitor is Brigatinib.

In a thirty-first aspect, the invention features a pharmaceutical composition including a therapeutically effective amount of an immunogenic composition described in any one of the first to twenty-third and thirtieth aspects of the invention and one or more pharmaceutically acceptable carriers or excipients.

In a thirty-second aspect, the invention features a method of treating a disease associated with ALK in a subject, wherein the method includes administering to the subject a therapeutically effective amount of an immunogenic composition described in any one of the first to twenty-third and thirtieth aspects of the invention or the pharmaceutical composition described in the thirty-first aspect of the invention.

In some embodiments of the thirty-second aspect of the invention, the pharmaceutical composition is administered without an immunomodulator, an adjuvant, and/or an anti-cancer agent.

In a thirty-third aspect, the invention features a method of treating a disease associated with ALK in a subject, wherein the method includes administering to the subject 1) a therapeutically effective amount of an immunogenic composition described in any one of the first to twenty-third and thirtieth aspects of the invention or the pharmaceutical composition described in the thirty-first aspect of the invention, and 2) at least one immunomodulator.

In a thirty-fourth aspect, the invention features method of treating a disease associated with ALK in a subject, wherein the method includes administering to the subject 1) a therapeutically effective amount of an immunogenic composition described in any one of the first to twenty-third and thirtieth aspects of the invention or the pharmaceutical composition described in the thirty-first aspect of the invention, and 2) at least one tyrosine kinase inhibitor.

In some embodiments of the thirty-third and thirty-fourth aspects of the invention, 1) and 2) are administered substantially simultaneously. In some embodiments, 1) and 2) are administered separately. In some embodiments, 1) is administered first, followed by administering of 2). In some embodiments, 2) is administered first, followed by administering of 1).

In some embodiments of the thirty-third aspect of the invention, the immunomodulator is selected from the group consisting of a PD-1 inhibitor, an anti-PD-L1 antibody, an anti-CTLA-4 antibody, an anti-CD40 antibody, a cyclophosphamide (CPM), an AMD3100, an anti-LAG-3/CD223 antibody, an anti-B7-H5 antibody, an anti-OX40 antibody, an anti-CD28 antibody, an anti-GITR antibody, an anti-4-1BB/CD137 antibody, a 4-1 BB ligand, an anti-BTLA antibody, an anti-TIM-3/HAVCR2 antibody, an anti-KIR antibody, an anti-Flt3/CD135 antibody, an anti-FasL antibody, an anti-CD25 antibody, an GM-CSF, an anti-GM-CSF-receptor (R) antibody, an IL-2, an anti-IL-2-R antibody, an IL-7, an anti-IL-7-R antibody, an IL-21, an anti-IL-21-R antibody, an IL-12, an anti-IL-12-R antibody, an IL-15, an anti-IL-15-R antibody, an IL-18, an anti-IL-18-R antibody, an anti-IDO antibody, an ipilimumab, a crizotinib, a ceritinib, an alectinib, a brigatinib, a celecoxib, a SOCS-1 inhibitor, a heat shock protein (HSP), a HSP inhibitor, a polyinosinic:polycytidylic acid (poly I:C), and an anti-galectin-1 antibody.

In some embodiments of the thirty-fourth aspect of the invention, the tyrosine kinase inhibitor is Crizotinib. In some embodiments, the tyrosine kinase inhibitor is Ceritinib. In some embodiments, the tyrosine kinase inhibitor is Alectinib. In some embodiments, the tyrosine kinase inhibitor is Brigatinib.

In some embodiments, the disease is cancer. In some embodiments, the cancer is a solid tumor cancer. In some embodiments, the cancer is an ALK$^+$ cancer (i.e., a cancer that expresses ALK). In some embodiments, the cancer is anaplastic large cell lymphoma, non-small-cell lung cancer, neuroblastoma, rhabdomyosarcoma, neuroectodermal cancer, glioblastoma, breast carcinoma, melanoma, inflammatory myofibroblastic tumor, soft tissue tumor, ALK expressing lymphoma, or ALK expressing lung, colon, or prostate carcinoma.

In some embodiments, the cancer is selected from the group consisting of bladder cancer, pancreatic cancer, lung cancer, liver cancer, ovarian cancer, colon cancer, stomach cancer, breast cancer, prostate cancer, renal cancer, testicular cancer, thyroid cancer, uterine cancer, rectal cancer, a cancer of the respiratory system, a cancer of the urinary system, oral cavity cancer, skin cancer, leukemia, sarcoma, carcinoma, basal cell carcinoma, non-Hodgkin's lymphoma, acute myeloid leukemia (AML), chronic lymphocytic leukemia (CLL), B-cells chronic lymphocytic leukemia (B-CLL), multiple myeloma (MM), erythroleukemia, renal cell carcinoma, astrocytoma, oligoastrocytoma, biliary tract cancer, choriocarcinoma, CNS cancer, larynx cancer, small cell lung cancer, adenocarcinoma, giant (or oat) cell carcinoma, and squamous cell carcinoma.

In some embodiments, the immunogenic composition is administered before or after surgery to remove at least some of a solid tumor in the solid tumor cancer.

In some embodiments, the subject is a mammal (e.g., a human).

DESCRIPTION OF THE DRAWINGS

FIGS. 4-1 to 4-3 show the sequence of wild-type, full-length ALK (SEQ ID NO: 67; UniProt ID NO: B6D4Y2), the sequence of full-length ALK having K1150R substitution (SEQ ID No: 68), the sequence of wild-type, cytoplasmic domain of ALK (SEQ ID NO: 69), and the sequence of cytoplasmic domain of ALK having K93R substitution (SEQ ID NO: 70).

DETAILED DESCRIPTION OF THE INVENTION

The present invention features immunogenic compositions containing anaplastic lymphoma kinase (ALK) polypeptides and methods of use thereof. In some embodiments, the immunogenic compositions may include one or more ALK polypeptides. The immunogenic compositions and methods of the invention may be used to treat a disease associated with ALK in a subject, such as cancer (e.g., a solid tumor cancer or a cancer that expresses ALK or a portion thereof (e.g., an ALK+ cancer)).

Anaplastic Lymphoma Kinase (ALK) Polypeptides and Immunogenic Compositions

Figure 1:
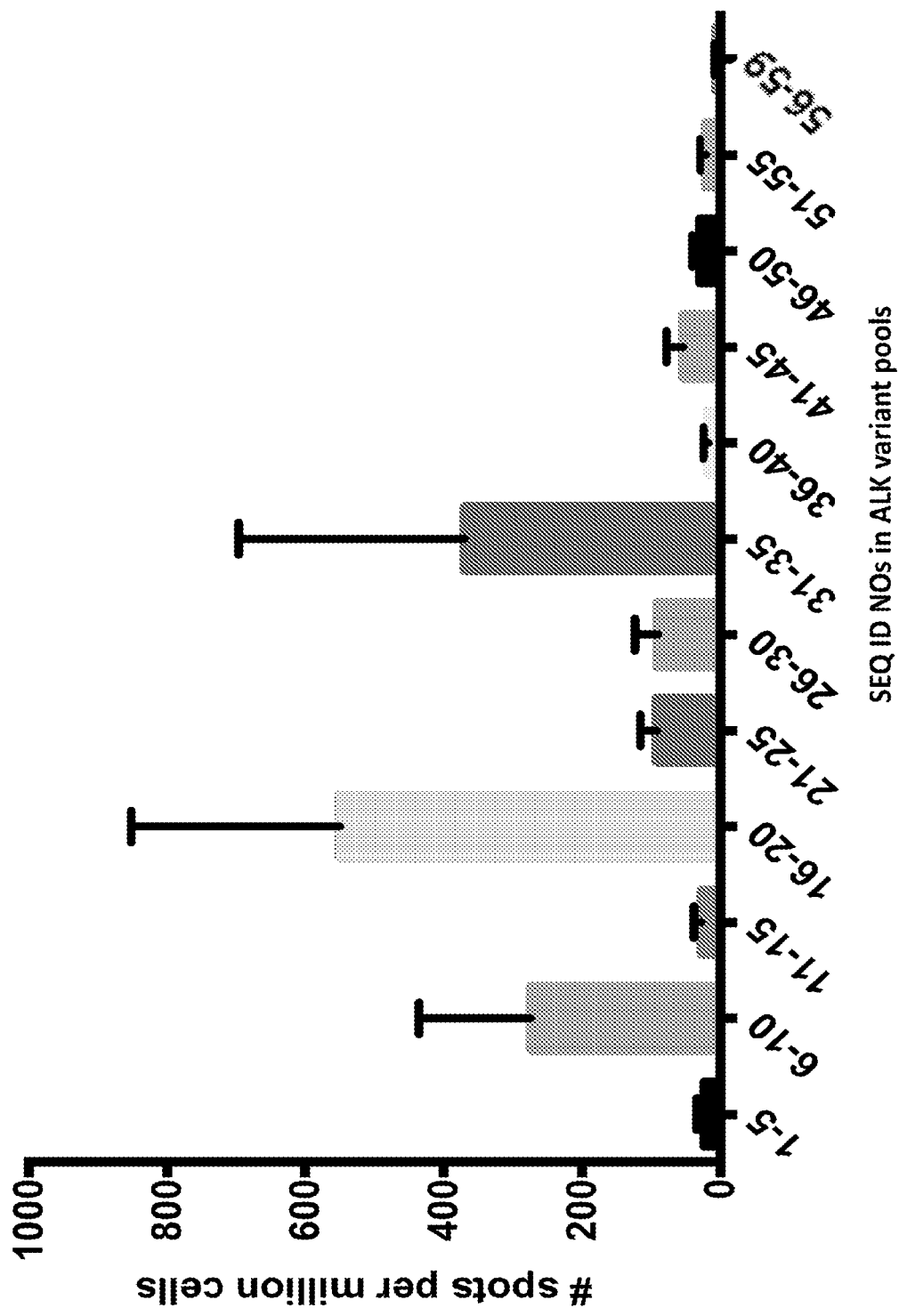
FIG. 1 shows the overall T-cell response stimulated by various ALK polypeptide pools each containing 5 ALK polypeptides having the sequences of SEQ ID NOs listed in Table 1A.
Figure 3:
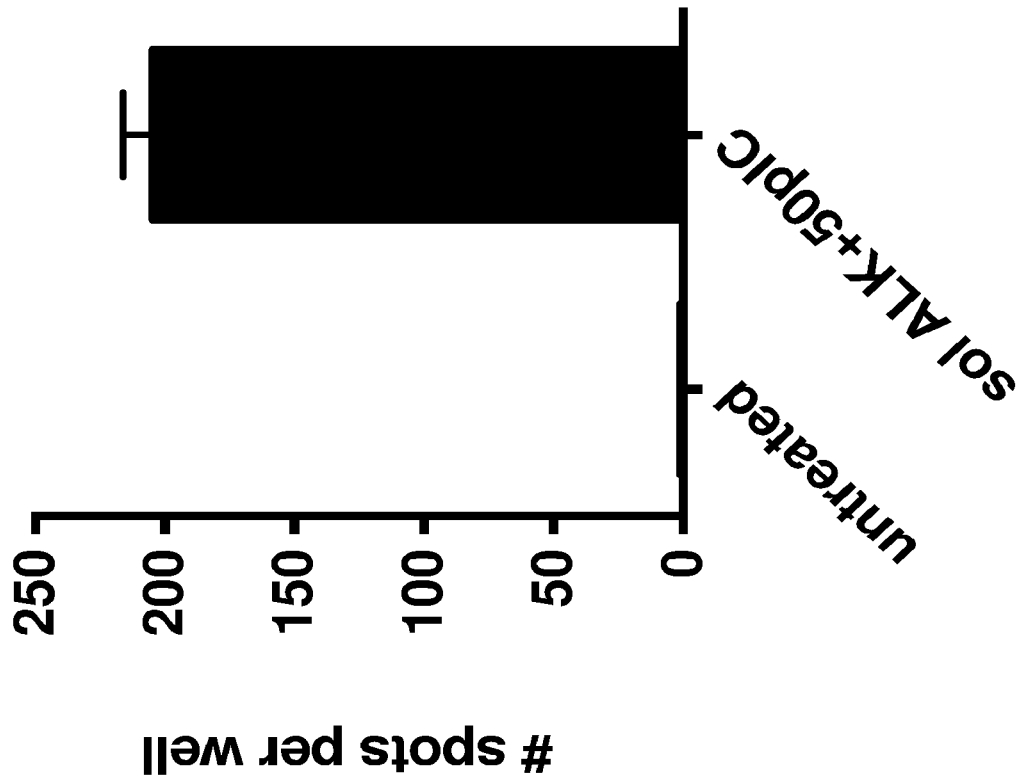
FIG. 3 shows the overall T-cell response stimulated by an ALK polypeptide pool containing 7 ALK polypeptides having the sequences of SEQ ID NOs: 60-66 listed in Table 1A.

An ALK polypeptide is a mutant or fragment of the cytoplasmic domain of ALK. FIGS. 4-1 to 4-3 show the sequence of wild-type, full-length ALK (SEQ ID NO: 67; UniProt ID NO: B6D4Y2), the sequence of full-length ALK having K1150R substitution (SEQ ID No: 68), the sequence of wild-type, cytoplasmic domain of ALK (SEQ ID NO: 69), and the sequence of cytoplasmic domain of ALK having K93R substitution (SEQ ID NO: 70). The amino acid substitution K1150R in SEQ ID NO: 68 and the amino acid substitution K93R in SEQ ID NO: 70 render the tyrosine kinase domain of ALK inactive and the resulting ALK non-oncogenic. ALK polypeptides that are specifically excluded from the claimed invention are: PSSLAMLDLLH-VARDIACGCQYLE (SEQ ID NO: 140), KFNHQNIVR-CIGVSLQSLPRFILL (SEQ ID NO: 141), PKNCPGPVYRIMTQCWQHQPEDRP (SEQ ID NO: 142), SLAMLDLLHV (SEQ ID NO: 143), AMLDLLHVA (SEQ ID NO: 144), and CIGVSLQSL (SEQ ID NO: 145).

In some embodiments, an ALK polypeptide includes at least 6 contiguous amino acids (e.g., 6, 7, 8, 9, 10, 11, 12, 13, 14, 15, 16, 17, 18, 19, 20, 21, 22, 23, 24, 25, 26, 27, 28, 29, 30, or 31 amino acids) from a sequence of any one of SEQ ID NOs: 1-66 (e.g., SEQ ID NOs: 10, 14, 17, 22, 33, 52, and 53 (e.g., SEQ ID NO: 33)) and 93-139 (see Tables 1A and 1B). In particular, an ALK polypeptide includes at least 6 contiguous amino acids (e.g., 6, 7, 8, 9, 10, 11, 12, 13, 14, 15, 16, 17, 18, 19, 20, 21, 22, 23, 24, 25, 26, 27, 28, 29, 30, or 31 amino acids) from a sequence of any one of SEQ ID NOs: 93, 96, 100, 106, 111-116, and 121-139 (see Table 1C). An ALK polypeptide described herein does not include a sequence of any one of SEQ ID NOs: 67-70 and 140-145. In some embodiments, an ALK polypeptide is 8 to 230 amino acids in length (e.g., 8 to 200, 8 to 170, 8 to 140, 8 to 110, 8 to 70, 8 to 60, 8 to 30, or 8 to 15 amino acids in length, e.g., 8, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, or 230 amino acids in length), 8 to 60 amino acids in length, 8 to 30 amino acids in length, 8 to 15 amino acids in length, or 8 to 11 amino acids in length. In some embodiments, an ALK polypeptide is at least 9 amino acids in length, e.g., 9 to 40 amino acids in length (e.g., 15 to 40, 20 to 40, 25 to 40, or 30 to 40 amino acids in length, e.g., 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids in length).

In particular embodiments, an ALK polypeptide is 31 amino acids in length and consists of a sequence of any one of SEQ ID NOs: 93, 96, 100, 106, 111-116, and 121-139 (Table 10).

In some embodiments, an ALK polypeptide includes at least 9 contiguous amino acids (e.g., 9, 10, 11, 12, 13, 14, or 15 amino acids) from a sequence of any one of SEQ ID NOs: 1-66 (e.g., SEQ ID NOs: 10, 14, 17, 22, 33, 52, and 53 (e.g., SEQ ID NO: 33)) and 93-139. In some embodiments, an ALK polypeptide includes at least 11 contiguous amino acids (e.g., 11, 12, 13, 14, or 15 amino acids) from a sequence of any one of SEQ ID NOs: 1-59 (e.g., SEQ ID NOs: 10, 14, 17, 22, 33, 52, and 53 (e.g., SEQ ID NO: 33)) and 93-139. In some embodiments, an ALK polypeptide includes a sequence of any one of SEQ ID NOs: 1-66 (e.g., SEQ ID NOs: 10, 14, 17, 22, 33, 52, and 53 (e.g., SEQ ID NO: 33)) and 93-139.

In some embodiments, an ALK polypeptide includes at least 9 contiguous amino acids (e.g., 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 amino acids) from a sequence of any one of SEQ ID NOs: 93, 96, 100, 106, 111-116, and 121-139.

In some embodiments, an ALK polypeptide is 9 amino acids in length and includes 9 contiguous amino acids from a sequence of any one of SEQ ID NOs: 1-66 (e.g., SEQ ID NOs: 10, 14, 17, 22, 33, 52, and 53 (e.g., SEQ ID NO: 33)) and 93-139. In some embodiments, an ALK polypeptide is 11 amino acids in length and includes 11 contiguous amino acids from a sequence of any one of SEQ ID NOs: 1-59 (e.g., SEQ ID NOs: 10, 14, 17, 22, 33, 52, and 53 (e.g., SEQ ID NO: 33)) and 93-139. In some embodiments, an ALK polypeptide includes at least 6 contiguous amino acids (e.g., 6, 7, 8, or 9 amino acids) from a sequence of any one of SEQ ID NOs: 60-66.

In some embodiments, an ALK polypeptide is 9 amino acids in length and includes 9 contiguous amino acids from a sequence of any one of SEQ ID NOs: 93, 96, 100, 106, 111-116, and 121-139. In some embodiments, an ALK polypeptide is 11 amino acids in length and includes 11 contiguous amino acids from a sequence of any one of SEQ ID NOs: 93, 96, 100, 106, 111-116, and 121-139.

In some embodiments, an ALK polypeptide consists of a sequence selected from any one of SEQ ID NOs: 1-66 and 93-139. In some embodiments, an ALK polypeptide consists of a sequence selected from any one of SEQ ID NOs: 93, 96, 100, 106, 111-116, and 121-139. In some embodiments, an ALK polypeptide consists of a sequence selected from any one of SEQ ID NOs: 60-66. In some embodiments, an ALK polypeptide consists of a sequence selected from any one of SEQ ID NOs: 10, 14, 17, 22, 33, 52, and 53. In some embodiments, an ALK polypeptide consists of the sequence of SEQ ID NO: 10. In some embodiments, an ALK polypeptide consists of the sequence of SEQ ID NO: 14. In some embodiments, an ALK polypeptide consists of the sequence of SEQ ID NO: 17. In some embodiments, an ALK polypeptide consists of the sequence of SEQ ID NO: 22. In some embodiments, an ALK polypeptide consists of the sequence of SEQ ID NO: 33. In some embodiments, an ALK polypeptide consists of the sequence of SEQ ID NO: 52. In some embodiments, an ALK polypeptide consists of the sequence of SEQ ID NO: 53.

In some embodiments, one or more amino acid substitutions in an ALK polypeptide may improve its immunogenic property. In some embodiments, an amino acid in a wild-type ALK may be replaced by a different amino acid (e.g., a naturally occurring amino acid (e.g., Ala, Arg, Asn, Asp, Cys, Gln, Glu, Gly, His, Ile, Leu, Lys, Met, Phe, Pro, Ser, Thr, Trp, Tyr, or Val) or a non-naturally occurring amino acid). Examples of non-naturally occurring amino acids are described in detail further herein. In some embodiments, a Cys in an ALK polypeptide described herein (e.g., any one of the ALK polypeptides in Tables 1A and 1B) may be replaced by an Ala.

An ALK polypeptide described herein does not include a sequence of any one of SEQ ID NOs: 67-70 and 140-145.

In some embodiments, ALK polypeptides of the invention are shown in Tables 1A and 1B. Table 1A shows ALK polypeptides having 9-15 amino acids. Table 1B shows ALK polypeptides having 31 amino acids.

TABLE 1A

| SEQ ID NO | Sequence of an ALK Polypeptide | Length |
|---|---|---|
| 1 | CFAGKTSSISDLKEV | 15-mer |
| 2 | TSSISDLKEVPRKNI | 15-mer |
| 3 | DLKEVPRKNITLIRG | 15-mer |
| 4 | PRKNITLIRGLGHGA | 15-mer |

TABLE 1A-continued

| SEQ ID NO | Sequence of an ALK Polypeptide | Length |
|---|---|---|
| 5 | TLIRGLGHGAFGEVY | 15-mer |
| 6 | LGHGAFGEVYEGQVS | 15-mer |
| 7 | FGEVYEGQVSGMPND | 15-mer |
| 8 | EGQVSGMPNDPSPLQ | 15-mer |
| 9 | GMPNDPSPLQVAVRT | 15-mer |
| 10 | PSPLQVAVRTLPEVC | 15-mer |
| 11 | VAVRTLPEVCSEQDE | 15-mer |
| 12 | LPEVCSEQDELDFLM | 15-mer |
| 13 | SEQDELDFLMEALII | 15-mer |
| 14 | LDFLMEALIISKFNH | 15-mer |
| 15 | EALIISKFNHQNIVR | 15-mer |
| 16 | SKFNHQNIVRCIGVS | 15-mer |
| 17 | QNIVRCIGVSLQSLP | 15-mer |
| 18 | CIGVSLQSLPRFILL | 15-mer |
| 19 | LQSLPRFILLELMAG | 15-mer |
| 20 | RFILLELMAGGDLKS | 15-mer |
| 21 | ELMAGGDLKSFLRET | 15-mer |
| 22 | GDLKSFLRETRPRPS | 15-mer |
| 23 | FLRETRPRPSQPSSL | 15-mer |
| 24 | RPRPSQPSSLAMLDL | 15-mer |
| 25 | QPSSLAMLDLLHVAR | 15-mer |
| 26 | AMLDLLHVARDIACG | 15-mer |
| 27 | LHVARDIACGCQYLE | 15-mer |
| 28 | DIACGCQYLEENHFI | 15-mer |
| 29 | CQYLEENHFIHRDIA | 15-mer |
| 30 | ENHFIHRDIAARNCL | 15-mer |
| 31 | HRDIAARNCLLTCPG | 15-mer |
| 32 | ARNCLLTCPGPGRVA | 15-mer |
| 33 | LTCPGPGRVAKIGDF | 15-mer |
| 34 | PGRVAKIGDFGMARD | 15-mer |
| 35 | KIGDFGMARDIYRAS | 15-mer |
| 36 | GMARDIYRASYYRKG | 15-mer |
| 37 | IYRASYYRKGGCAML | 15-mer |
| 38 | YYRKGGCAMLPVKWM | 15-mer |
| 39 | GCAMLPVKWMPPEAF | 15-mer |
| 40 | PVKWMPPEAFMEGIF | 15-mer |
| 41 | PPEAFMEGIFTSKTD | 15-mer |
| 42 | MEGIFTSKTDTWSFG | 15-mer |
| 43 | TSKTDTWSFGVLLWE | 15-mer |

TABLE 1A-continued

| SEQ ID NO | Sequence of an ALK Polypeptide | Length |
|---|---|---|
| 44 | TWSFGVLLWEIFSLG | 15-mer |
| 45 | VLLWEIFSLGYMPYP | 15-mer |
| 46 | IFSLGYMPYPSKSNQ | 15-mer |
| 47 | YMPYPSKSNQEVLEF | 15-mer |
| 48 | SKSNQEVLEFVTSGG | 15-mer |
| 49 | EVLEFVTSGGRMDPP | 15-mer |
| 50 | VTSGGRMDPPKNCPG | 15-mer |
| 51 | RMDPPKNCPGPVYRI | 15-mer |
| 52 | KNCPGPVYRIMTQCW | 15-mer |
| 53 | PVYRIMTQCWQHQPE | 15-mer |
| 54 | MTQCWQHQPEDRPNF | 15-mer |
| 55 | QHQPEDRPNFAIILE | 15-mer |
| 56 | DRPNFAIILERIEYC | 15-mer |
| 57 | AIILERIEYCTQDPD | 15-mer |
| 58 | RIEYCTQDPDVINTA | 15-mer |
| 59 | TQDPDVINTALP | 12-mer |
| 60 | LTCPGPGRV | 9-mer |
| 61 | TCPGPGRVA | 9-mer |
| 62 | CPGPGRVAK | 9-mer |
| 63 | PGPGRVAKI | 9-mer |
| 64 | GPGRVAKIG | 9-mer |
| 65 | PGRVAKIGD | 9-mer |
| 66 | GRVAKIGDF | 9-mer |

TABLE 1B

| SEQ ID NO | Sequence of an ALK Polypeptide | Length |
|---|---|---|
| 93 | VYRRKHQELQAMQMELQSPEYKLSKLRTSTI | 31-mer |
| 94 | EYKLSKLRTSTIMTDYNPNYCFAGKTSSISD | 31-mer |
| 95 | YCFAGKTSSISDLKEVPRKNITLIRGLGHGA | 31-mer |
| 96 | NITLIRGLGHGAFGEVYEGQVSGMPNDPSPL | 31-mer |
| 97 | QVSGMPNDPSPLQVAVKTLPEVCSEQDELDF | 31-mer |
| 98 | PEVCSEQDELDFLMEALIISKFNHQNIVRCI | 31-mer |
| 99 | SKFNHQNIVRCIGVSLQSLPRFILLELMAGG | 31-mer |
| 100 | PRFILLELMAGGDLKSFLRETRPRPSQPSSL | 31-mer |
| 101 | ETRPRPSQPSSLAMLDLLHVARDIACGCQYL | 31-mer |
| 102 | VARDIACGCQYLEENHFIHRDIAARNCLLTC | 31-mer |
| 103 | RDIAARNCLLTCPGPGRVAKIGDFGMARDIY | 31-mer |
| 104 | KIGDFGMARDIYRASYYRKGGCAMLPVKWMP | 31-mer |
| 105 | GGCAMLPVKWMPPEAFMEGIFTSKTDTWSFG | 31-mer |
| 106 | IFTSKTDTWSFGVLLWEIFSLGYMPYPSKSN | 31-mer |
| 107 | SLGYMPYPSKSNQEVLEFVTSGGRMDPPKNC | 31-mer |
| 108 | TSGGRMDPPKNCPGPVYRIMTQCWQHQPEDR | 31-mer |
| 109 | MTQCWQHQPEDRPNFAIILERIEYCTQDPDV | 31-mer |
| 110 | ERIEYCTQDPDVINTALPIEYGPLVEEEEKV | 31-mer |
| 111 | EYGPLVEEEEKVPVRPKDPEGVPPLLVSQQA | 31-mer |
| 112 | EGVPPLLVSQQAKREEERSPAAPPPLPTTSS | 31-mer |
| 113 | PAAPPPLPTTSSGKAAKKPTAAEISVRVPRG | 31-mer |
| 114 | TAAEISVRVPRGPAVEGGHVNMAFSQSNPPS | 31-mer |
| 115 | VNMAFSQSNPPSELHKVHGSRNKPTSLWNPT | 31-mer |
| 116 | SRNKPTSLWNPTYGSWFTEKPTKKNNPIAKK | 31-mer |
| 117 | KPTKKNNPIAKKEPHDRGNLGLEGSCTVPPN | 31-mer |
| 118 | LGLEGSCTVPPNVATGRLPGASLLLEPSSLT | 31-mer |
| 119 | GASLLLEPSSLTANMKEVPLFRLRHFPCGNV | 31-mer |
| 120 | LFRLRHFPCGNVNYGYQQQGLPLEAATAPGA | 31-mer |
| 121 | GLPLEAATAPGAGHYEDTILKSKNSMNQPGP | 31-mer |

In some embodiments, a Cys in an ALK polypeptide described herein (e.g., any one of the ALK polypeptides in Tables 1A and 1B) may be replaced by an Ala. In some embodiments, a Cys in an ALK polypeptide of any one of SEQ ID NOs: 94, 95, 97-99, 101-105, 107-110, and 117-120 may be replaced with an Ala, generating the ALK polypeptides of SEQ ID NOs: 122-139 in Table 10.

TABLE 1C

| SEQ ID NO | Sequence of an ALK Polypeptide | Length |
|---|---|---|
| 122 | EYKLSKLRTSTIMTDYNPNYAF AGKTSSISD | 31-mer |
| 123 | YAFAGKTSSISDLKEVPRKNIT LIRGLGHGA | 31-mer |
| 124 | QVSGMPNDPSPLQVAVKTLPEV ASEQDELDF | 31-mer |
| 125 | PEVASEQDELDFLMEALIISKF NHQNIVRAI | 31-mer |
| 126 | SKFNHQNIVRAIGVSLQSLPRF ILLELMAGG | 31-mer |
| 127 | ETRPRPSQPSSLAMLDLLHVA RDIAAGAQYL | 31-mer |
| 128 | VARDIAAGAQYLEENHFIHRD IAARNALLTA | 31-mer |
| 129 | RDIAARNALLTAPGPGRVAKI GDFGMARDIY | 31-mer |
| 130 | KIGDFGMARDIYRASYYRKGG AAMLPVKWMP | 31-mer |
| 131 | GGAAMLPVKWMPPEAFMEGIF TSKTDTWSFG | 31-mer |
| 132 | SLGYMPYPSKSNQEVLEFVTS GGRMDPPKNA | 31-mer |
| 133 | TSGGRMDPPKNAPGPVYRIMT QAWQHQPEDR | 31-mer |
| 134 | MTQAWQHQPEDRPNFAIILER IEYATQDPDV | 31-mer |
| 135 | ERIEYATQDPDVINTALPIEY GPLVEEEEKV | 31-mer |
| 136 | KPTKKNNPIAKKEPHDRGNLG LEGSATVPPN | 31-mer |
| 137 | LGLEGSATVPPNVATGRLPGA SLLLEPSSLT | 31-mer |
| 138 | GASLLLEPSSLTANMKEVPLF RLRHFPAGNV | 31-mer |
| 139 | LFRLRHFPAGNVNYGYQQQGL PLEAATAPGA | 31-mer |

In some embodiments, an ALK polypeptide used in an aspect of the invention described herein may be selected from any of the polypeptides listed in Tables 1A, 1B, and 1C.

In some embodiments, when two ALK polypeptides are used in an aspect of the invention described herein, one ALK polypeptide may be selected from the polypeptides listed in Table 1A and the other ALK polypeptide may be selected from the polypeptides listed in Tables 1B and 1C (e.g., ALK polypeptides having the sequences of SEQ ID NOs: 93, 96, 100, 106, 111-116, and 121-139).

In some embodiments, when an ALK polypeptide includes a first sequence and a second sequence in an aspect of the invention described herein, the first sequence may be selected from the polypeptides listed in Table 1A and the second sequence may be selected from the polypeptides listed in Tables 1B and 1C (e.g., ALK polypeptides having the sequences of SEQ ID NOs: 93, 96, 100, 106, 111-116, and 121-139).

In some embodiments, when three ALK polypeptides are used in an aspect of the invention described herein, one or two ALK polypeptides may be selected from the polypeptides listed in Table 1A and the remaining ALK polypeptide(s) may be selected from the polypeptides listed in Tables 1B and 1C (e.g., ALK polypeptides having the sequences of SEQ ID NOs: 93, 96, 100, 106, 111-116, and 121-139).

In some embodiments, when an ALK polypeptide includes three sequences (e.g., a first sequence, a second sequence, and a third sequence) in an aspect of the invention described herein, one or two sequences may be selected from the polypeptides listed in Table 1A and the remaining sequence(s) may be selected from the polypeptides listed in Tables 1B and 1C (e.g., ALK polypeptides having the sequences of SEQ ID NOs: 93, 96, 100, 106, 111-116, and 121-139).

In particular embodiments, an ALK polypeptide includes a sequence selected from any one of SEQ ID NOs: 93, 96, 100, 106, 111-116, and 121-139. In particular embodiments, an ALK polypeptide consists of a sequence selected from any one of SEQ ID NOs: 93, 96, 100, 106, 111-116, and 121-139.

In some embodiments, an ALK polypeptide includes a first sequence selected from any one of SEQ ID NOs: 1-66 (e.g., SEQ ID NOs: 10, 14, 17, 22, 33, 52, and 53) and a second sequence selected from any one of SEQ ID NOs: 1-66 (e.g., SEQ ID NOs: 10, 14, 17, 22, 33, 52, and 53), in which the first and second sequences are different and include a pair of sequences of SEQ ID NOs recited in Table 2A, and in which the ALK polypeptide does not include a sequence of any one of SEQ ID NOs: 67-70 and 140-145. In some embodiments, the first and second sequences in the ALK polypeptide include one of the following pairs of sequences: SEQ ID NOs: 10 and 14, SEQ ID NOs: 10 and 17, SEQ ID NOs: 10 and 22, SEQ ID NOs: 10 and 33, SEQ ID NOs: 10 and 52, SEQ ID NOs: 10 and 53, SEQ ID NOs: 14 and 17, SEQ ID NOs: 14 and 22, SEQ ID NOs: 14 and 33, SEQ ID NOs: 14 and 52, SEQ ID NOs: 14 and 53, SEQ ID NOs: 17 and 22, SEQ ID NOs: 17 and 33, SEQ ID NOs: 17 and 52, SEQ ID NOs: 17 and 53, SEQ ID NOs: 22 and 33, SEQ ID NOs: 22 and 52, SEQ ID NOs: 22 and 53, SEQ ID NOs: 33 and 52, SEQ ID NOs: 33 and 53, and SEQ ID NOs: 52 and 53.

In some embodiments, an ALK polypeptide includes a first sequence selected from any one of SEQ ID NOs: 60-66 and a second sequence selected from any one of SEQ ID NOs: 60-66, in which the first and second sequences are different and include one of the following pairs of sequences: SEQ ID NOs: 60 and 61, SEQ ID NOs: 60 and 62, SEQ ID NOs: 60 and 63, SEQ ID NOs: 60 and 64, SEQ ID NOs: 60 and 65, SEQ ID NOs: 60 and 66, SEQ ID NOs: 61 and 62, SEQ ID NOs: 61 and 63, SEQ ID NOs: 61 and 64, SEQ ID NOs: 61 and 65, SEQ ID NOs: 61 and 66, SEQ ID NOs: 62 and 63, SEQ ID NOs: 62 and 64, SEQ ID NOs: 62 and 65, SEQ ID NOs: 62 and 66, SEQ ID NOs: 63 and 64, SEQ ID NOs: 63 and 65, SEQ ID NOs: 63 and 66, SEQ ID NOs: 64 and 65, SEQ ID NOs: 64 and 66, and SEQ ID NOs: 65 and 66, and in which the ALK polypeptide does not include a sequence of any one of SEQ ID NOs: 67-70 and 140-145.

In some embodiments, an ALK polypeptide includes a first sequence selected from any one of SEQ ID NOs: 93, 96, 100, 106, 111-116, and 121-139 and a second sequence selected from any one of SEQ ID NOs: 93, 96, 100, 106, 111-116, and 121-139, in which the first and second sequences are different and include a pair of sequences of SEQ ID NOs recited in Table 2B, and in which the ALK polypeptide does not include a sequence of any one of SEQ ID NOs: 67-70 and 140-145.

In the case that an ALK polypeptide includes a first sequence and a second sequence, each bracket listed in Tables 2A and 2B contains two SEQ ID NOs representing the first and second sequences in the ALK polypeptide. For example, {1,2} represents {a first sequence of SEQ ID NO: 1, a second sequence of SEQ ID NO: 2}.

An immunogenic composition may include at least one ALK polypeptide described herein. In some embodiments, an immunogenic composition includes an ALK polypeptide consisting of a sequence selected from any one of SEQ ID NOs: 1-66 and 93-139. In particular embodiments, an immunogenic composition includes an ALK polypeptide consisting of a sequence selected from any one of SEQ ID NOs: 93, 96, 100, 106, 111-116, and 121-139.

In some embodiments, an immunogenic composition includes two ALK polypeptides, a first ALK polypeptide including a first sequence of any one of SEQ ID NOs: 1-66 (e.g., SEQ ID NOs: 10, 14, 17, 22, 33, 52, and 53) and a second ALK polypeptide including a second sequence of any one of SEQ ID NOs: 1-66 (e.g., SEQ ID NOs: 10, 14, 17, 22, 33, 52, and 53), in which the first and second sequences are different and include a pair of sequences of SEQ ID NOs recited in Table 2A, and in which neither the first ALK polypeptide nor the second ALK polypeptide includes a sequence of any one of SEQ ID NOs: 67-70 and 140-145. In some embodiments, the first sequence in the first ALK polypeptide and second sequence in the second ALK polypeptide include one of the following pairs of sequences: SEQ ID NOs: 10 and 14, SEQ ID NOs: 10 and 17, SEQ ID NOs: 10 and 22, SEQ ID NOs: 10 and 33, SEQ ID NOs: 10 and 52, SEQ ID NOs: 10 and 53, SEQ ID NOs: 14 and 17, SEQ ID NOs: 14 and 22, SEQ ID NOs: 14 and 33, SEQ ID NOs: 14 and 52, SEQ ID NOs: 14 and 53, SEQ ID NOs: 17 and 22, SEQ ID NOs: 17 and 33, SEQ ID NOs: 17 and 52, SEQ ID NOs: 17 and 53, SEQ ID NOs: 22 and 33, SEQ ID NOs: 22 and 52, SEQ ID NOs: 22 and 53, SEQ ID NOs: 33 and 52, SEQ ID NOs: 33 and 53, and SEQ ID NOs: 52 and 53.

In some embodiments, an immunogenic composition includes two ALK polypeptides, a first ALK polypeptide including a first sequence of any one of SEQ ID NOs: 60-66 and a second ALK polypeptide including a second sequence of any one of SEQ ID NOs: 60-66, in which the first and second sequences are different and include one of the following pairs of sequences: SEQ ID NOs: 60 and 61, SEQ ID NOs: 60 and 62, SEQ ID NOs: 60 and 63, SEQ ID NOs: 60 and 64, SEQ ID NOs: 60 and 65, SEQ ID NOs: 60 and 66, SEQ ID NOs: 61 and 62, SEQ ID NOs: 61 and 63, SEQ ID NOs: 61 and 64, SEQ ID NOs: 61 and 65, SEQ ID NOs: 61 and 66, SEQ ID NOs: 62 and 63, SEQ ID NOs: 62 and 64, SEQ ID NOs: 62 and 65, SEQ ID NOs: 62 and 66, SEQ ID NOs: 63 and 64, SEQ ID NOs: 63 and 65, SEQ ID NOs: 63 and 66, SEQ ID NOs: 64 and 65, SEQ ID NOs: 64 and 66, and SEQ ID NOs: 65 and 66, and in which neither the first ALK polypeptide nor the second ALK polypeptide includes a sequence of any one of SEQ ID NOs: 67-70 and 140-145.

In some embodiments, an immunogenic composition includes two ALK polypeptides, a first ALK polypeptide including a first sequence of any one of SEQ ID NOs: 93, 96, 100, 106, 111-116, and 121-139 and a second ALK polypeptide including a second sequence of any one of SEQ ID NOs: 93, 96, 100, 106, 111-116, and 121-139, in which the first and second sequences are different and include a pair of sequences of SEQ ID NOs recited in Table 2B, and in which neither the first ALK polypeptide nor the second ALK polypeptide includes a sequence of any one of SEQ ID NOs: 67-70 and 140-145.

In the case for two ALK polypeptides in one immunogenic composition, a first ALK polypeptide including a first sequence and a second ALK polypeptide including a second sequence, each bracket listed in Tables 2A and 2B contains two SEQ ID NOs representing the first sequence in the first ALK polypeptide and the second sequence in the second ALK polypeptide. For example, {1,2} represents {the first sequence of SEQ ID NO: 1 in the first ALK polypeptide, the second sequence of SEQ ID NO: 2 in the second ALK polypeptide}.

TABLE 2A

{1,2} {1,3} {1,4} {1,5} {1,6} {1,7} {1,8} {1,9} {1,10} {1,11} {1,12} {1,13} {1,14} {1,15} {1,16} {1,17} {1,18}
{1,19} {1,20} {1,21} {1,22} {1,23} {1,24} {1,25} {1,26} {1,27} {1,28} {1,29} {1,30} {1,31} {1,32} {1,33} {1,34}
{1,35} {1,36} {1,37} {1,38} {1,39} {1,40} {1,41} {1,42} {1,43} {1,44} {1,45} {1,46} {1,47} {1,48} {1,49} {1,50}
{1,51} {1,52} {1,53} {1,54} {1,55} {1,56} {1,57} {1,58} {1,59} {1,60} {1,61} {1,62} {1,63} {1,64} {1,65} {1,66}
{2,3} {2,4} {2,5} {2,6} {2,7} {2,8} {2,9} {2,10} {2,11} {2,12} {2,13} {2,14} {2,15} {2,16} {2,17} {2,18} {2,19}
{2,20} {2,21} {2,22} {2,23} {2,24} {2,25} {2,26} {2,27} {2,28} {2,29} {2,30} {2,31} {2,32} {2,33} {2,34} {2,35}
{2,36} {2,37} {2,38} {2,39} {2,40} {2,41} {2,42} {2,43} {2,44} {2,45} {2,46} {2,47} {2,48} {2,49} {2,50} {2,51}
{2,52} {2,53} {2,54} {2,55} {2,56} {2,57} {2,58} {2,59} {2,60} {2,61} {2,62} {2,63} {2,64} {2,65} {2,66} {3,4}
{3,5} {3,6} {3,7} {3,8} {3,9} {3,10} {3,11} {3,12} {3,13} {3,14} {3,15} {3,16} {3,17} {3,18} {3,19} {3,20} {3,21}
{3,22} {3,23} {3,24} {3,25} {3,26} {3,27} {3,28} {3,29} {3,30} {3,31} {3,32} {3,33} {3,34} {3,35} {3,36} {3,37}
{3,38} {3,39} {3,40} {3,41} {3,42} {3,43} {3,44} {3,45} {3,46} {3,47} {3,48} {3,49} {3,50} {3,51} {3,52} {3,53}
{3,54} {3,55} {3,56} {3,57} {3,58} {3,59} {3,60} {3,61} {3,62} {3,63} {3,64} {3,65} {3,66} {4,5} {4,6} {4,7} {4,8}
{4,9} {4,10} {4,11} {4,12} {4,13} {4,14} {4,15} {4,16} {4,17} {4,18} {4,19} {4,20} {4,21} {4,22} {4,23} {4,24}
{4,25} {4,26} {4,27} {4,28} {4,29} {4,30} {4,31} {4,32} {4,33} {4,34} {4,35} {4,36} {4,37} {4,38} {4,39} {4,40}
{4,41} {4,42} {4,43} {4,44} {4,45} {4,46} {4,47} {4,48} {4,49} {4,50} {4,51} {4,52} {4,53} {4,54} {4,55} {4,56}
{4,57} {4,58} {4,59} {4,60} {4,61} {4,62} {4,63} {4,64} {4,65} {4,66} {5,6} {5,7} {5,8} {5,9} {5,10} {5,11} {5,12}
{5,13} {5,14} {5,15} {5,16} {5,17} {5,18} {5,19} {5,20} {5,21} {5,22} {5,23} {5,24} {5,25} {5,26} {5,27} {5,28}
{5,29} {5,30} {5,31} {5,32} {5,33} {5,34} {5,35} {5,36} {5,37} {5,38} {5,39} {5,40} {5,41} {5,42} {5,43} {5,44}
{5,45} {5,46} {5,47} {5,48} {5,49} {5,50} {5,51} {5,52} {5,53} {5,54} {5,55} {5,56} {5,57} {5,58} {5,59} {5,60}
{5,61} {5,62} {5,63} {5,64} {5,65} {5,66} {6,7} {6,8} {6,9} {6,10} {6,11} {6,12} {6,13} {6,14} {6,15} {6,16}
{6,17} {6,18} {6,19} {6,20} {6,21} {6,22} {6,23} {6,24} {6,25} {6,26} {6,27} {6,28} {6,29} {6,30} {6,31} {6,32}
{6,33} {6,34} {6,35} {6,36} {6,37} {6,38} {6,39} {6,40} {6,41} {6,42} {6,43} {6,44} {6,45} {6,46} {6,47} {6,48}
{6,49} {6,50} {6,51} {6,52} {6,53} {6,54} {6,55} {6,56} {6,57} {6,58} {6,59} {6,60} {6,61} {6,62} {6,63} {6,64}
{6,65} {6,66} {7,8} {7,9} {7,10} {7,11} {7,12} {7,13} {7,14} {7,15} {7,16} {7,17} {7,18} {7,19} {7,20} {7,21}
{7,22} {7,23} {7,24} {7,25} {7,26} {7,27} {7,28} {7,29} {7,30} {7,31} {7,32} {7,33} {7,34} {7,35} {7,36} {7,37}
{7,38} {7,39} {7,40} {7,41} {7,42} {7,43} {7,44} {7,45} {7,46} {7,47} {7,48} {7,49} {7,50} {7,51} {7,52} {7,53}
{7,54} {7,55} {7,56} {7,57} {7,58} {7,59} {7,60} {7,61} {7,62} {7,63} {7,64} {7,65} {7,66} {8,9} {8,10} {8,11}
{8,12} {8,13} {8,14} {8,15} {8,16} {8,17} {8,18} {8,19} {8,20} {8,21} {8,22} {8,23} {8,24} {8,25} {8,26} {8,27}

TABLE 2A-continued

{8,28} {8,29} {8,30} {8,31} {8,32} {8,33} {8,34} {8,35} {8,36} {8,37} {8,38} {8,39} {8,40} {8,41} {8,42} {8,43}
{8,44} {8,45} {8,46} {8,47} {8,48} {8,49} {8,50} {8,51} {8,52} {8,53} {8,54} {8,55} {8,56} {8,57} {8,58} {8,59}
{8,60} {8,61} {8,62} {8,63} {8,64} {8,65} {8,66} {9,10} {9,11} {9,12} {9,13} {9,14} {9,15} {9,16} {9,17} {9,18}
{9,19} {9,20} {9,21} {9,22} {9,23} {9,24} {9,25} {9,26} {9,27} {9,28} {9,29} {9,30} {9,31} {9,32} {9,33} {9,34}
{9,35} {9,36} {9,37} {9,38} {9,39} {9,40} {9,41} {9,42} {9,43} {9,44} {9,45} {9,46} {9,47} {9,48} {9,49} {9,50}
{9,51} {9,52} {9,53} {9,54} {9,55} {9,56} {9,57} {9,58} {9,59} {9,60} {9,61} {9,62} {9,63} {9,64} {9,65} {9,66}
{10,11} {10,12} {10,13} {10,14} {10,15} {10,16} {10,17} {10,18} {10,19} {10,20} {10,21} {10,22} {10,23}
{10,24} {10,25} {10,26} {10,27} {10,28} {10,29} {10,30} {10,31} {10,32} {10,33} {10,34} {10,35} {10,36}
{10,37} {10,38} {10,39} {10,40} {10,41} {10,42} {10,43} {10,44} {10,45} {10,46} {10,47} {10,48} {10,49}
{10,50} {10,51} {10,52} {10,53} {10,54} {10,55} {10,56} {10,57} {10,58} {10,59} {10,60} {10,61} {10,62}
{10,63} {10,64} {10,65} {10,66} {11,12} {11,13} {11,14} {11,15} {11,16} {11,17} {11,18} {11,19} {11,20}
{11,21} {11,22} {11,23} {11,24} {11,25} {11,26} {11,27} {11,28} {11,29} {11,30} {11,31} {11,32} {11,33}
{11,34} {11,35} {11,36} {11,37} {11,38} {11,39} {11,40} {11,41} {11,42} {11,43} {11,44} {11,45} {11,46}
{11,47} {11,48} {11,49} {11,50} {11,51} {11,52} {11,53} {11,54} {11,55} {11,56} {11,57} {11,58} {11,59}
{11,60} {11,61} {11,62} {11,63} {11,64} {11,65} {11,66} {12,13} {12,14} {12,15} {12,16} {12,17} {12,18}
{12,19} {12,20} {12,21} {12,22} {12,23} {12,24} {12,25} {12,26} {12,27} {12,28} {12,29} {12,30} {12,31}
{12,32} {12,33} {12,34} {12,35} {12,36} {12,37} {12,38} {12,39} {12,40} {12,41} {12,42} {12,43} {12,44}
{12,45} {12,46} {12,47} {12,48} {12,49} {12,50} {12,51} {12,52} {12,53} {12,54} {12,55} {12,56} {12,57}
{12,58} {12,59} {12,60} {12,61} {12,62} {12,63} {12,64} {12,65} {12,66} {13,14} {13,15} {13,16} {13,17}
{13,18} {13,19} {13,20} {13,21} {13,22} {13,23} {13,24} {13,25} {13,26} {13,27} {13,28} {13,29} {13,30}
{13,31} {13,32} {13,33} {13,34} {13,35} {13,36} {13,37} {13,38} {13,39} {13,40} {13,41} {13,42} {13,43}
{13,44} {13,45} {13,46} {13,47} {13,48} {13,49} {13,50} {13,51} {13,52} {13,53} {13,54} {13,55} {13,56}
{13,57} {13,58} {13,59} {13,60} {13,61} {13,62} {13,63} {13,64} {13,65} {13,66} {14,15} {14,16} {14,17}
{14,18} {14,19} {14,20} {14,21} {14,22} {14,23} {14,24} {14,25} {14,26} {14,27} {14,28} {14,29} {14,30}
{14,31} {14,32} {14,33} {14,34} {14,35} {14,36} {14,37} {14,38} {14,39} {14,40} {14,41} {14,42} {14,43}
{14,44} {14,45} {14,46} {14,47} {14,48} {14,49} {14,50} {14,51} {14,52} {14,53} {14,54} {14,55} {14,56}
{14,57} {14,58} {14,59} {14,60} {14,61} {14,62} {14,63} {14,64} {14,65} {14,66} {15,16} {15,17} {15,18}
{15,19} {15,20} {15,21} {15,22} {15,23} {15,24} {15,25} {15,26} {15,27} {15,28} {15,29} {15,30} {15,31}
{15,32} {15,33} {15,34} {15,35} {15,36} {15,37} {15,38} {15,39} {15,40} {15,41} {15,42} {15,43} {15,44}
{15,45} {15,46} {15,47} {15,48} {15,49} {15,50} {15,51} {15,52} {15,53} {15,54} {15,55} {15,56} {15,57}
{15,58} {15,59} {15,60} {15,61} {15,62} {15,63} {15,64} {15,65} {15,66} {16,17} {16,18} {16,19} {16,20}
{16,21} {16,22} {16,23} {16,24} {16,25} {16,26} {16,27} {16,28} {16,29} {16,30} {16,31} {16,32} {16,33}
{16,34} {16,35} {16,36} {16,37} {16,38} {16,39} {16,40} {16,41} {16,42} {16,43} {16,44} {16,45} {16,46}
{16,47} {16,48} {16,49} {16,50} {16,51} {16,52} {16,53} {16,54} {16,55} {16,56} {16,57} {16,58} {16,59}
{16,60} {16,61} {16,62} {16,63} {16,64} {16,65} {16,66} {17,18} {17,19} {17,20} {17,21} {17,22} {17,23}
{17,24} {17,25} {17,26} {17,27} {17,28} {17,29} {17,30} {17,31} {17,32} {17,33} {17,34} {17,35} {17,36}
{17,37} {17,38} {17,39} {17,40} {17,41} {17,42} {17,43} {17,44} {17,45} {17,46} {17,47} {17,48} {17,49}
{17,50} {17,51} {17,52} {17,53} {17,54} {17,55} {17,56} {17,57} {17,58} {17,59} {17,60} {17,61} {17,62}
{17,63} {17,64} {17,65} {17,66} {18,19} {18,20} {18,21} {18,22} {18,23} {18,24} {18,25} {18,26} {18,27}
{18,28} {18,29} {18,30} {18,31} {18,32} {18,33} {18,34} {18,35} {18,36} {18,37} {18,38} {18,39} {18,40}
{18,41} {18,42} {18,43} {18,44} {18,45} {18,46} {18,47} {18,48} {18,49} {18,50} {18,51} {18,52} {18,53}
{18,54} {18,55} {18,56} {18,57} {18,58} {18,59} {18,60} {18,61} {18,62} {18,63} {18,64} {18,65} {18,66}
{19,20} {19,21} {19,22} {19,23} {19,24} {19,25} {19,26} {19,27} {19,28} {19,29} {19,30} {19,31} {19,32}
{19,33} {19,34} {19,35} {19,36} {19,37} {19,38} {19,39} {19,40} {19,41} {19,42} {19,43} {19,44} {19,45}
{19,46} {19,47} {19,48} {19,49} {19,50} {19,51} {19,52} {19,53} {19,54} {19,55} {19,56} {19,57} {19,58}
{19,59} {19,60} {19,61} {19,62} {19,63} {19,64} {19,65} {19,66} {20,21} {20,22} {20,23} {20,24} {20,25}
{20,26} {20,27} {20,28} {20,29} {20,30} {20,31} {20,32} {20,33} {20,34} {20,35} {20,36} {20,37} {20,38}
{20,39} {20,40} {20,41} {20,42} {20,43} {20,44} {20,45} {20,46} {20,47} {20,48} {20,49} {20,50} {20,51}
{20,52} {20,53} {20,54} {20,55} {20,56} {20,57} {20,58} {20,59} {20,60} {20,61} {20,62} {20,63} {20,64}
{20,65} {20,66} {21,22} {21,23} {21,24} {21,25} {21,26} {21,27} {21,28} {21,29} {21,30} {21,31} {21,32}
{21,33} {21,34} {21,35} {21,36} {21,37} {21,38} {21,39} {21,40} {21,41} {21,42} {21,43} {21,44} {21,45}
{21,46} {21,47} {21,48} {21,49} {21,50} {21,51} {21,52} {21,53} {21,54} {21,55} {21,56} {21,57} {21,58}
{21,59} {21,60} {21,61} {21,62} {21,63} {21,64} {21,65} {21,66} {22,23} {22,24} {22,25} {22,26} {22,27}
{22,28} {22,29} {22,30} {22,31} {22,32} {22,33} {22,34} {22,35} {22,36} {22,37} {22,38} {22,39} {22,40}
{22,41} {22,42} {22,43} {22,44} {22,45} {22,46} {22,47} {22,48} {22,49} {22,50} {22,51} {22,52} {22,53}
{22,54} {22,55} {22,56} {22,57} {22,58} {22,59} {22,60} {22,61} {22,62} {22,63} {22,64} {22,65} {22,66}
{23,24} {23,25} {23,26} {23,27} {23,28} {23,29} {23,30} {23,31} {23,32} {23,33} {23,34} {23,35} {23,36}
{23,37} {23,38} {23,39} {23,40} {23,41} {23,42} {23,43} {23,44} {23,45} {23,46} {23,47} {23,48} {23,49}
{23,50} {23,51} {23,52} {23,53} {23,54} {23,55} {23,56} {23,57} {23,58} {23,59} {23,60} {23,61} {23,62}
{23,63} {23,64} {23,65} {23,66} {24,25} {24,26} {24,27} {24,28} {24,29} {24,30} {24,31} {24,32} {24,33}
{24,34} {24,35} {24,36} {24,37} {24,38} {24,39} {24,40} {24,41} {24,42} {24,43} {24,44} {24,45} {24,46}
{24,47} {24,48} {24,49} {24,50} {24,51} {24,52} {24,53} {24,54} {24,55} {24,56} {24,57} {24,58} {24,59}
{24,60} {24,61} {24,62} {24,63} {24,64} {24,65} {24,66} {25,26} {25,27} {25,28} {25,29} {25,30} {25,31}
{25,32} {25,33} {25,34} {25,35} {25,36} {25,37} {25,38} {25,39} {25,40} {25,41} {25,42} {25,43} {25,44}
{25,45} {25,46} {25,47} {25,48} {25,49} {25,50} {25,51} {25,52} {25,53} {25,54} {25,55} {25,56} {25,57}
{25,58} {25,59} {25,60} {25,61} {25,62} {25,63} {25,64} {25,65} {25,66} {26,27} {26,28} {26,29} {26,30}
{26,31} {26,32} {26,33} {26,34} {26,35} {26,36} {26,37} {26,38} {26,39} {26,40} {26,41} {26,42} {26,43}
{26,44} {26,45} {26,46} {26,47} {26,48} {26,49} {26,50} {26,51} {26,52} {26,53} {26,54} {26,55} {26,56}
{26,57} {26,58} {26,59} {26,60} {26,61} {26,62} {26,63} {26,64} {26,65} {26,66} {27,28} {27,29} {27,30}
{27,31} {27,32} {27,33} {27,34} {27,35} {27,36} {27,37} {27,38} {27,39} {27,40} {27,41} {27,42} {27,43}
{27,44} {27,45} {27,46} {27,47} {27,48} {27,49} {27,50} {27,51} {27,52} {27,53} {27,54} {27,55} {27,56}
{27,57} {27,58} {27,59} {27,60} {27,61} {27,62} {27,63} {27,64} {27,65} {27,66} {28,29} {28,30} {28,31}
{28,32} {28,33} {28,34} {28,35} {28,36} {28,37} {28,38} {28,39} {28,40} {28,41} {28,42} {28,43} {28,44}
{28,45} {28,46} {28,47} {28,48} {28,49} {28,50} {28,51} {28,52} {28,53} {28,54} {28,55} {28,56} {28,57}
{28,58} {28,59} {28,60} {28,61} {28,62} {28,63} {28,64} {28,65} {28,66} {29,30} {29,31} {29,32} {29,33}
{29,34} {29,35} {29,36} {29,37} {29,38} {29,39} {29,40} {29,41} {29,42} {29,43} {29,44} {29,45} {29,46}
{29,47} {29,48} {29,49} {29,50} {29,51} {29,52} {29,53} {29,54} {29,55} {29,56} {29,57} {29,58} {29,59}
{29,60} {29,61} {29,62} {29,63} {29,64} {29,65} {29,66} {30,31} {30,32} {30,33} {30,34} {30,35} {30,36}
{30,37} {30,38} {30,39} {30,40} {30,41} {30,42} {30,43} {30,44} {30,45} {30,46} {30,47} {30,48} {30,49}
{30,50} {30,51} {30,52} {30,53} {30,54} {30,55} {30,56} {30,57} {30,58} {30,59} {30,60} {30,61} {30,62}

TABLE 2A-continued

{30,63} {30,64} {30,65} {30,66} {31,32} {31,33} {31,34} {31,35} {31,36} {31,37} {31,38} {31,39} {31,40}
{31,41} {31,42} {31,43} {31,44} {31,45} {31,46} {31,47} {31,48} {31,49} {31,50} {31,51} {31,52} {31,53}
{31,54} {31,55} {31,56} {31,57} {31,58} {31,59} {31,60} {31,61} {31,62} {31,63} {31,64} {31,65} {31,66}
{32,33} {32,34} {32,35} {32,36} {32,37} {32,38} {32,39} {32,40} {32,41} {32,42} {32,43} {32,44} {32,45}
{32,46} {32,47} {32,48} {32,49} {32,50} {32,51} {32,52} {32,53} {32,54} {32,55} {32,56} {32,57} {32,58}
{32,59} {32,60} {32,61} {32,62} {32,63} {32,64} {32,65} {32,66} {33,34} {33,35} {33,36} {33,37} {33,38}
{33,39} {33,40} {33,41} {33,42} {33,43} {33,44} {33,45} {33,46} {33,47} {33,48} {33,49} {33,50} {33,51}
{33,52} {33,53} {33,54} {33,55} {33,56} {33,57} {33,58} {33,59} {33,60} {33,61} {33,62} {33,63} {33,64}
{33,65} {33,66} {34,35} {34,36} {34,37} {34,38} {34,39} {34,40} {34,41} {34,42} {34,43} {34,44} {34,45}
{34,46} {34,47} {34,48} {34,49} {34,50} {34,51} {34,52} {34,53} {34,54} {34,55} {34,56} {34,57} {34,58}
{34,59} {34,60} {34,61} {34,62} {34,63} {34,64} {34,65} {34,66} {35,36} {35,37} {35,38} {35,39} {35,40}
{35,41} {35,42} {35,43} {35,44} {35,45} {35,46} {35,47} {35,48} {35,49} {35,50} {35,51} {35,52} {35,53}
{35,54} {35,55} {35,56} {35,57} {35,58} {35,59} {35,60} {35,61} {35,62} {35,63} {35,64} {35,65} {35,66}
{36,37} {36,38} {36,39} {36,40} {36,41} {36,42} {36,43} {36,44} {36,45} {36,46} {36,47} {36,48} {36,49}
{36,50} {36,51} {36,52} {36,53} {36,54} {36,55} {36,56} {36,57} {36,58} {36,59} {36,60} {36,61} {36,62}
{36,63} {36,64} {36,65} {36,66} {37,38} {37,39} {37,40} {37,41} {37,42} {37,43} {37,44} {37,45} {37,46}
{37,47} {37,48} {37,49} {37,50} {37,51} {37,52} {37,53} {37,54} {37,55} {37,56} {37,57} {37,58} {37,59}
{37,60} {37,61} {37,62} {37,63} {37,64} {37,65} {37,66} {38,39} {38,40} {38,41} {38,42} {38,43} {38,44}
{38,45} {38,46} {38,47} {38,48} {38,49} {38,50} {38,51} {38,52} {38,53} {38,54} {38,55} {38,56} {38,57}
{38,58} {38,59} {38,60} {38,61} {38,62} {38,63} {38,64} {38,65} {38,66} {39,40} {39,41} {39,42} {39,43}
{39,44} {39,45} {39,46} {39,47} {39,48} {39,49} {39,50} {39,51} {39,52} {39,53} {39,54} {39,55} {39,56}
{39,57} {39,58} {39,59} {39,60} {39,61} {39,62} {39,63} {39,64} {39,65} {39,66} {40,41} {40,42} {40,43}
{40,44} {40,45} {40,46} {40,47} {40,48} {40,49} {40,50} {40,51} {40,52} {40,53} {40,54} {40,55} {40,56}
{40,57} {40,58} {40,59} {40,60} {40,61} {40,62} {40,63} {40,64} {40,65} {40,66} {41,42} {41,43} {41,44}
{41,45} {41,46} {41,47} {41,48} {41,49} {41,50} {41,51} {41,52} {41,53} {41,54} {41,55} {41,56} {41,57}
{41,58} {41,59} {41,60} {41,61} {41,62} {41,63} {41,64} {41,65} {41,66} {42,43} {42,44} {42,45} {42,46}
{42,47} {42,48} {42,49} {42,50} {42,51} {42,52} {42,53} {42,54} {42,55} {42,56} {42,57} {42,58} {42,59}
{42,60} {42,61} {42,62} {42,63} {42,64} {42,65} {42,66} {43,44} {43,45} {43,46} {43,47} {43,48} {43,49}
{43,50} {43,51} {43,52} {43,53} {43,54} {43,55} {43,56} {43,57} {43,58} {43,59} {43,60} {43,61} {43,62}
{43,63} {43,64} {43,65} {43,66} {44,45} {44,46} {44,47} {44,48} {44,49} {44,50} {44,51} {44,52} {44,53}
{44,54} {44,55} {44,56} {44,57} {44,58} {44,59} {44,60} {44,61} {44,62} {44,63} {44,64} {44,65} {44,66}
{45,46} {45,47} {45,48} {45,49} {45,50} {45,51} {45,52} {45,53} {45,54} {45,55} {45,56} {45,57} {45,58}
{45,59} {45,60} {45,61} {45,62} {45,63} {45,64} {45,65} {45,66} {46,47} {46,48} {46,49} {46,50} {46,51}
{46,52} {46,53} {46,54} {46,55} {46,56} {46,57} {46,58} {46,59} {46,60} {46,61} {46,62} {46,63} {46,64}
{46,65} {46,66} {47,48} {47,49} {47,50} {47,51} {47,52} {47,53} {47,54} {47,55} {47,56} {47,57} {47,58}
{47,59} {47,60} {47,61} {47,62} {47,63} {47,64} {47,65} {47,66} {48,49} {48,50} {48,51} {48,52} {48,53}
{48,54} {48,55} {48,56} {48,57} {48,58} {48,59} {48,60} {48,61} {48,62} {48,63} {48,64} {48,65} {48,66}
{49,50} {49,51} {49,52} {49,53} {49,54} {49,55} {49,56} {49,57} {49,58} {49,59} {49,60} {49,61} {49,62}
{49,63} {49,64} {49,65} {49,66} {50,51} {50,52} {50,53} {50,54} {50,55} {50,56} {50,57} {50,58} {50,59}
{50,60} {50,61} {50,62} {50,63} {50,64} {50,65} {50,66} {51,52} {51,53} {51,54} {51,55} {51,56} {51,57}
{51,58} {51,59} {51,60} {51,61} {51,62} {51,63} {51,64} {51,65} {51,66} {52,53} {52,54} {52,55} {52,56}
{52,57} {52,58} {52,59} {52,60} {52,61} {52,62} {52,63} {52,64} {52,65} {52,66} {53,54} {53,55} {53,56}
{53,57} {53,58} {53,59} {53,60} {53,61} {53,62} {53,63} {53,64} {53,65} {53,66} {54,55} {54,56} {54,57}
{54,58} {54,59} {54,60} {54,61} {54,62} {54,63} {54,64} {54,65} {54,66} {55,56} {55,57} {55,58} {55,59}
{55,60} {55,61} {55,62} {55,63} {55,64} {55,65} {55,66} {56,57} {56,58} {56,59} {56,60} {56,61} {56,62}
{56,63} {56,64} {56,65} {56,66} {57,58} {57,59} {57,60} {57,61} {57,62} {57,63} {57,64} {57,65} {57,66}
{58,59} {58,60} {58,61} {58,62} {58,63} {58,64} {58,65} {58,66} {59,60} {59,61} {59,62} {59,63} {59,64}
{59,65} {59,66} {60,61} {60,62} {60,63} {60,64} {60,65} {60,66} {61,62} {61,63} {61,64} {61,65} {61,66}
{62,63} {62,64} {62,65} {62,66} {63,64} {63,65} {63,66} {64,65} {64,66} {65,66}

TABLE 2B

{93,96} {93,100} {93,106} {93,111} {93,112} {93,113} {93,114} {93,115} {93,116} {93,121} {93,122} {93,123}
{93,124} {93,125} {93,126} {93,127} {93,128} {93,129} {93,130} {93,131} {93,132} {93,133} {93,134} {93,135}
{93,136} {93,137} {93,138} {93,139} {96,100} {96,106} {96,111} {96,112} {96,113} {96,114} {96,115} {96,116}
{96,121} {96,122} {96,123} {96,124} {96,125} {96,126} {96,127} {96,128} {96,129} {96,130} {96,131} {96,132}
{96,133} {96,134} {96,135} {96,136} {96,137} {96,138} {96,139} {100,106} {100,111} {100,112} {100,113}
{100,114} {100,115} {100,116} {100,121} {100,122} {100,123} {100,124} {100,125} {100,126} {100,127}
{100,128} {100,129} {100,130} {100,131} {100,132} {100,133} {100,134} {100,135} {100,136} {100,137}
{100,138} {100,139} {106,111} {106,112} {106,113} {106,114} {106,115} {106,116} {106,121} {106,122}
{106,123} {106,124} {106,125} {106,126} {106,127} {106,128} {106,129} {106,130} {106,131} {106,132}
{106,133} {106,134} {106,135} {106,136} {106,137} {106,138} {106,139} {111,112} {111,113} {111,114}
{111,115} {111,116} {111,121} {111,122} {111,123} {111,124} {111,125} {111,126} {111,127} {111,128}
{111,129} {111,130} {111,131} {111,132} {111,133} {111,134} {111,135} {111,136} {111,137} {111,138}
{111,139} {112,113} {112,114} {112,115} {112,116} {112,121} {112,122} {112,123} {112,124} {112,125}
{112,126} {112,127} {112,128} {112,129} {112,130} {112,131} {112,132} {112,133} {112,134} {112,135}
{112,136} {112,137} {112,138} {112,139} {113,114} {113,115} {113,116} {113,121} {113,122} {113,123}
{113,124} {113,125} {113,126} {113,127} {113,128} {113,129} {113,130} {113,131} {113,132} {113,133}
{113,134} {113,135} {113,136} {113,137} {113,138} {113,139} {114,115} {114,116} {114,121} {114,122}
{114,123} {114,124} {114,125} {114,126} {114,127} {114,128} {114,129} {114,130} {114,131} {114,132}
{114,133} {114,134} {114,135} {114,136} {114,137} {114,138} {114,139} {115,116} {115,121} {115,122}
{115,123} {115,124} {115,125} {115,126} {115,127} {115,128} {115,129} {115,130} {115,131} {115,132}
{115,133} {115,134} {115,135} {115,136} {115,137} {115,138} {115,139} {116,121} {116,122} {116,123}
{116,124} {116,125} {116,126} {116,127} {116,128} {116,129} {116,130} {116,131} {116,132} {116,133}
{116,134} {116,135} {116,136} {116,137} {116,138} {116,139} {121,122} {121,123} {121,124} {121,125}
{121,126} {121,127} {121,128} {121,129} {121,130} {121,131} {121,132} {121,133} {121,134} {121,135}

TABLE 2B-continued

{121,136} {121,137} {121,138} {121,139} {122,123} {122,124} {122,125} {122,126} {122,127} {122,128}
{122,129} {122,130} {122,131} {122,132} {122,133} {122,134} {122,135} {122,136} {122,137} {122,138}
{122,139} {123,124} {123,125} {123,126} {123,127} {123,128} {123,129} {123,130} {123,131} {123,132}
{123,133} {123,134} {123,135} {123,136} {123,137} {123,138} {123,139} {124,125} {124,126} {124,127}
{124,128} {124,129} {124,130} {124,131} {124,132} {124,133} {124,134} {124,135} {124,136} {124,137}
{124,138} {124,139} {125,126} {125,127} {125,128} {125,129} {125,130} {125,131} {125,132} {125,133}
{125,134} {125,135} {125,136} {125,137} {125,138} {125,139} {126,127} {126,128} {126,129} {126,130}
{126,131} {126,132} {126,133} {126,134} {126,135} {126,136} {126,137} {126,138} {126,139} {127,128}
{127,129} {127,130} {127,131} {127,132} {127,133} {127,134} {127,135} {127,136} {127,137} {127,138}
{127,139} {128,129} {128,130} {128,131} {128,132} {128,133} {128,134} {128,135} {128,136} {128,137}
{128,138} {128,139} {129,130} {129,131} {129,132} {129,133} {129,134} {129,135} {129,136} {129,137}
{129,138} {129,139} {130,131} {130,132} {130,133} {130,134} {130,135} {130,136} {130,137} {130,138}
{130,139} {131,132} {131,133} {131,134} {131,135} {131,136} {131,137} {131,138} {131,139} {132,133}
{132,134} {132,135} {132,136} {132,137} {132,138} {132,139} {133,134} {133,135} {133,136} {133,137}
{133,138} {133,139} {134,135} {134,136} {134,137} {134,138} {134,139} {135,136} {135,137} {135,138}
{135,139} {136,137} {136,138} {136,139} {137,138} {137,139} {138,139}

In some embodiments, an ALK polypeptide includes a first sequence selected from any one of SEQ ID NOs: 1-66 (e.g., SEQ ID NOs: 10, 14, 17, 22, 33, 52, and 53), a second sequence selected from any one of SEQ ID NOs: 1-66 (e.g., SEQ ID NOs: 10, 14, 17, 22, 33, 52, and 53), and a third sequence selected from any one of SEQ ID NOs: 1-66 (e.g., SEQ ID NOs: 10, 14, 17, 22, 33, 52, and 53), in which the first, second, and third sequences are different and include a set of sequences of SEQ ID NOs recited in Table 3A, and in which the ALK polypeptide does not include a sequence of any one of SEQ ID NOs: 67-70 and 140-145. In some embodiments, the first, second, and third sequences in the ALK polypeptide include one of the following sets of sequences: SEQ ID NOs: 10, 14, and 17, SEQ ID NOs; 10, 14, and 22, SEQ ID NOs: 10, 14, and 33, SEQ ID NOs:10, 14, and 52, SEQ ID NOs:10, 14, and 53, SEQ ID NOs:10, 17, and 22, SEQ ID NOs:10, 17, and 33, SEQ ID NOs:10, 17, and 52, SEQ ID NOs:10, 17, and 53, SEQ ID NOs:10, 22, and 33, SEQ ID NOs:10, 22, and 52, SEQ ID NOs:10, 22, and 53, SEQ ID NOs:10, 33, and 52, SEQ ID NOs:10, 33, and 53, SEQ ID NOs:10, 52, and 53, SEQ ID NOs:14, 17, and 22, SEQ ID NOs:14, 17, and 33, SEQ ID NOs:14, 17, and 52, SEQ ID NOs:14, 17, and 53, SEQ ID NOs:14, 22, and 33, SEQ ID NOs:14, 22, and 52, SEQ ID NOs:14, 22, and 53, SEQ ID NOs:14, 33, and 52, SEQ ID NOs:14, 33, and 53, SEQ ID NOs:14, 52, and 53, SEQ ID NOs:17, 22, and 33, SEQ ID NOs:17, 22, and 52, SEQ ID NOs:17, 22, and 53, SEQ ID NOs:17, 33, and 52, SEQ ID NOs:17, 33, and 53, SEQ ID NOs:17, 52, and 53, SEQ ID NOs:22, 33, and 52, SEQ ID NOs:22, 33, and 53, SEQ ID NOs:22, 52, and 53, and SEQ ID NOs: 33, 52, and 53.

In some embodiments, an ALK polypeptide includes a first sequence selected from any one of SEQ ID NOs: 60-66, a second sequence selected from any one of SEQ ID NOs: 60-66, and a third sequence selected from any one of SEQ ID NOs: 60-66, in which the first and second sequences are different and include one of the following pairs of sequences: SEQ ID NOs: 60, 61, and 62; SEQ ID NOs: 60, 61, and 63; SEQ ID NOs: 60, 61, and 64; SEQ ID NOs: 60, 61, and 65; SEQ ID NOs: 60, 61, and 66; SEQ ID NOs: 60, 62, and 63; SEQ ID NOs: 60, 62, and 64; SEQ ID NOs: 60, 62, and 65; SEQ ID NOs: 60, 62, and 66; SEQ ID NOs: 60, 63, and 64; SEQ ID NOs: 60, 63, and 65; SEQ ID NOs: 60, 63, and 66; SEQ ID NOs: 60, 64, and 65; SEQ ID NOs: 60, 64, and 66; SEQ ID NOs: 60, 65, and 66; SEQ ID NOs: 61, 62, and 63; SEQ ID NOs: 61, 62, and 64; SEQ ID NOs: 61, 62, and 65; SEQ ID NOs: 61, 62, and 66; SEQ ID NOs: 61, 63, and 64; SEQ ID NOs: 61, 63, and 65; SEQ ID NOs: 61, 63, and 66; SEQ ID NOs: 61, 64, and 65; SEQ ID NOs: 61, 64, and 66; SEQ ID NOs: 61, 65, and 66; SEQ ID NOs: 62, 63, and 64; SEQ ID NOs: 62, 63, and 65; SEQ ID NOs: 62, 63, and 66; SEQ ID NOs: 62, 64, and 65; SEQ ID NOs: 62, 64, and 66; SEQ ID NOs: 62, 65, and 66; SEQ ID NOs: 63, 64, and 65; SEQ ID NOs: 63, 64, and 66; SEQ ID NOs: 63, 65, and 66; SEQ ID NOs: 64, 65, and 66, and in which the ALK polypeptide does not include a sequence of any one of SEQ ID NOs: 67-70 and 140-145.

In some embodiments, an ALK polypeptide includes a first sequence selected from any one of SEQ ID NOs: 93, 96, 100, 106, 111-116, and 121-139, a second sequence selected from any one of SEQ ID NOs: 93, 96, 100, 106, 111-116, and 121-139, and a third sequence selected from any one of SEQ ID NOs: 93, 96, 100, 106, 111-116, and 121-139, in which the first, second, and third sequences are different and include a set of sequences of SEQ ID NOs recited in Table 3B, and in which the ALK polypeptide does not include a sequence of any one of SEQ ID NOs: 67-70 and 140-145.

In the case that an ALK polypeptide includes a first sequence, a second sequence, and a third sequence, each bracket listed in Tables 3A and 3B contains three SEQ ID NOs representing the first, second, and third sequences in the ALK polypeptide. For example, {1,2,3} represents {a first sequence of SEQ ID NO: 1, a second sequence of SEQ ID NO: 2, a third sequence of SEQ ID NO: 3}.

In some embodiments, an immunogenic composition includes three ALK polypeptides, a first ALK polypeptide including a first sequence of any one of SEQ ID NOs: 1-66 (e.g., SEQ ID NOs: 10, 14, 17, 22, 33, 52, and 53), a second ALK polypeptide including a second sequence of any one of SEQ ID NOs: 1-66 (e.g., SEQ ID NOs: 10, 14, 17, 22, 33, 52, and 53), and a third ALK polypeptide including a third sequence of any one of SEQ ID NOs: 1-66 (e.g., SEQ ID NOs: 10, 14, 17, 22, 33, 52, and 53), in which the first, second, and third sequences are different and include a set of sequences of SEQ ID NOs recited in Table 3A, and in which none of the first, second, and third ALK polypeptides includes a sequence of any one of SEQ ID NOs: 67-70 and 140-145. In some embodiments, the first sequence in the first ALK polypeptide, the second sequence in the second ALK polypeptide, and the third sequence in the third ALK polypeptide include one of the following sets of sequences: SEQ ID NOs: 10, 14, and 17, SEQ ID NOs; 10, 14, and 22, SEQ ID NOs: 10, 14, and 33, SEQ ID NOs:10, 14, and 52, SEQ ID NOs:10, 14, and 53, SEQ ID NOs:10, 17, and 22, SEQ ID NOs:10, 17, and 33, SEQ ID NOs:10, 17, and 52, SEQ ID NOs:10, 17, and 53, SEQ ID NOs:10, 22, and 33, SEQ ID NOs:10, 22, and 52, SEQ ID NOs:10, 22, and 53, SEQ ID NOs:10, 33, and 52, SEQ ID NOs:10, 33, and 53, SEQ ID NOs:10, 52, and 53, SEQ ID NOs:14, 17, and 22, SEQ ID NOs:14, 17, and 33, SEQ ID NOs:14, 17, and 52, SEQ ID NOs:14, 17, and 53, SEQ ID NOs:14, 22, and 33, SEQ ID NOs:14, 22, and 52, SEQ ID NOs:14, 22, and 53, SEQ ID NOs:14, 33, and 52, SEQ ID NOs:14, 33, and 53, SEQ ID NOs:14, 52, and 53, SEQ ID NOs:17, 22, and 33, SEQ ID NOs:17, 22, and 52, SEQ ID NOs:17, 22, and 53, SEQ ID NOs:17, 33, and 52, SEQ ID NOs:17, 33, and 53, SEQ ID NOs:17, 52, and 53, SEQ ID NOs:22, 33, and 52, SEQ ID NOs:22, 33, and 53, SEQ ID NOs:22, 52, and 53, and SEQ ID NOs: 33, 52, and 53.

In some embodiments, an immunogenic composition includes three ALK polypeptides, a first ALK polypeptide including a first sequence selected from any one of SEQ ID NOs: 60-66, a second ALK polypeptide including a second sequence selected from any one of SEQ ID NOs: 60-66, and a third ALK polypeptide including a third sequence selected from any one of SEQ ID NOs: 60-66, in which the first, second, and third sequences are different and include one of the following sets of sequences: SEQ ID NOs: 60, 61, and 62; SEQ ID NOs: 60, 61, and 63; SEQ ID NOs: 60, 61, and 64; SEQ ID NOs: 60, 61, and 65; SEQ ID NOs: 60, 61, and 66; SEQ ID NOs: 60, 62, and 63; SEQ ID NOs: 60, 62, and 64; SEQ ID NOs: 60, 62, and 65; SEQ ID NOs: 60, 62, and 66; SEQ ID NOs: 60, 63, and 64; SEQ ID NOs: 60, 63, and 65; SEQ ID NOs: 60, 63, and 66; SEQ ID NOs: 60, 64, and 65; SEQ ID NOs: 60, 64, and 66; SEQ ID NOs: 60, 65, and 66; SEQ ID NOs: 61, 62, and 63; SEQ ID NOs: 61, 62, and 64; SEQ ID NOs: 61, 62, and 65; SEQ ID NOs: 61, 62, and 66; SEQ ID NOs: 61, 63, and 64; SEQ ID NOs: 61, 63, and 65; SEQ ID NOs: 61, 63, and 66; SEQ ID NOs: 61, 64, and 65; SEQ ID NOs: 61, 64, and 66; SEQ ID NOs: 61, 65, and 66; SEQ ID NOs: 62, 63, and 64; SEQ ID NOs: 62, 63, and 65; SEQ ID NOs: 62, 63, and 66; SEQ ID NOs: 62, 64, and 65; SEQ ID NOs: 62, 64, and 66; SEQ ID NOs: 62, 65, and 66; SEQ ID NOs: 63, 64, and 65; SEQ ID NOs: 63, 64, and 66; SEQ ID NOs: 63, 65, and 66; SEQ ID NOs: 64, 65, and 66, and which none of the first, second, and third ALK polypeptides includes a sequence of any one of SEQ ID NOs: 67-70 and 140-145.

In some embodiments, an immunogenic composition includes three ALK polypeptides, a first ALK polypeptide including a first sequence of any one of SEQ ID NOs: 93, 96, 100, 106, 111-116, and 121-139, a second ALK polypeptide including a second sequence of any one of SEQ ID NOs: 93, 96, 100, 106, 111-116, and 121-139, and a third ALK polypeptide including a third sequence of any one of SEQ ID NOs: 93, 96, 100, 106, 111-116, and 121-139, in which the first, second, and third sequences are different and include a set of sequences of SEQ ID NOs recited in Table 3B, and in which none of the first, second, and third ALK polypeptides includes a sequence of any one of SEQ ID NOs: 67-70 and 140-145

In the case for three ALK polypeptides in one immunogenic composition, a first ALK polypeptide including a first sequence, a second ALK polypeptide including a second sequence, and a third ALK polypeptide including a third sequence, each bracket listed in Tables 3A and 3B contains three SEQ ID NOs representing the first sequence in the first ALK polypeptide, the second sequence in the second ALK polypeptide, and the third sequence in the third ALK polypeptide. For example, {1,2,3} represents {the first sequence of SEQ ID NO: 1 in the first ALK polypeptide, the second sequence of SEQ ID NO: 2 in the second ALK polypeptide, the third sequence of SEQ ID NO: 3 in the third ALK polypeptide}.

TABLE 3A

{1,2,3} {1,2,4} {1,2,5} {1,2,6} {1,2,7} {1,2,8} {1,2,9} {1,2,10} {1,2,11} {1,2,12} {1,2,13} {1,2,14} {1,2,15}
{1,2,16} {1,2,17} {1,2,18} {1,2,19} {1,2,20} {1,2,21} {1,2,22} {1,2,23} {1,2,24} {1,2,25} {1,2,26} {1,2,27}
{1,2,28} {1,2,29} {1,2,30} {1,2,31} {1,2,32} {1,2,33} {1,2,34} {1,2,35} {1,2,36} {1,2,37} {1,2,38} {1,2,39}
{1,2,40} {1,2,41} {1,2,42} {1,2,43} {1,2,44} {1,2,45} {1,2,46} {1,2,47} {1,2,48} {1,2,49} {1,2,50} {1,2,51}
{1,2,52} {1,2,53} {1,2,54} {1,2,55} {1,2,56} {1,2,57} {1,2,58} {1,2,59} {1,2,60} {1,2,61} {1,2,62} {1,2,63}
{1,2,64} {1,2,65} {1,2,66} {1,3,4} {1,3,5} {1,3,6} {1,3,7} {1,3,8} {1,3,9} {1,3,10} {1,3,11} {1,3,12} {1,3,13}
{1,3,14} {1,3,15} {1,3,16} {1,3,17} {1,3,18} {1,3,19} {1,3,20} {1,3,21} {1,3,22} {1,3,23} {1,3,24} {1,3,25}
{1,3,26} {1,3,27} {1,3,28} {1,3,29} {1,3,30} {1,3,31} {1,3,32} {1,3,33} {1,3,34} {1,3,35} {1,3,36} {1,3,37}
{1,3,38} {1,3,39} {1,3,40} {1,3,41} {1,3,42} {1,3,43} {1,3,44} {1,3,45} {1,3,46} {1,3,47} {1,3,48} {1,3,49}
{1,3,50} {1,3,51} {1,3,52} {1,3,53} {1,3,54} {1,3,55} {1,3,56} {1,3,57} {1,3,58} {1,3,59} {1,3,60} {1,3,61}
{1,3,62} {1,3,63} {1,3,64} {1,3,65} {1,3,66} {1,4,5} {1,4,6} {1,4,7} {1,4,8} {1,4,9} {1,4,10} {1,4,11} {1,4,12}
{1,4,13} {1,4,14} {1,4,15} {1,4,16} {1,4,17} {1,4,18} {1,4,19} {1,4,20} {1,4,21} {1,4,22} {1,4,23} {1,4,24}
{1,4,25} {1,4,26} {1,4,27} {1,4,28} {1,4,29} {1,4,30} {1,4,31} {1,4,32} {1,4,33} {1,4,34} {1,4,35} {1,4,36}
{1,4,37} {1,4,38} {1,4,39} {1,4,40} {1,4,41} {1,4,42} {1,4,43} {1 ,4,44} {1,4,45} {1,4,46} {1,4,47} {1,4,48}
{1,4,49} {1,4,50} {1,4,51} {1,4,52} {1,4,53} {1,4,54} {1,4,55} {1,4,56} {1,4,57} {1,4,58} {1,4,59} {1,4,60}
{1,4,61} {1,4,62} {1,4,63} {1,4,64} {1,4,65} {1,4,66} {1,5,6} {1,5,7} {1,5,8} {1,5,9} {1,5,10} {1,5,11} {1,5,12}
{1,5,13} {1,5,14} {1,5,15} {1,5,16} {1,5,17} {1,5,18} {1,5,19} {1,5,20} {1,5,21} {1,5,22} {1,5,23} {1,5,24}
{1,5,25} {1,5,26} {1,5,27} {1,5,28} {1,5,29} {1,5,30} {1,5,31} {1,5,32} {1,5,33} {1,5,34} {1,5,35} {1,5,36}
{1,5,37} {1,5,38} {1,5,39} {1,5,40} {1,5,41} {1,5,42} {1,5,43} {1,5,44} {1,5,45} {1,5,46} {1,5,47} {1,5,48}
{1,5,49} {1,5,50} {1,5,51} {1,5,52} {1,5,53} {1,5,54} {1,5,55} {1,5,56} {1,5,57} {1,5,58} {1,5,59} {1,5,60}
{1,5,61} {1,5,62} {1,5,63} {1,5,64} {1,5,65} {1,5,66} {1,6,7} {1,6,8} {1,6,9} {1,6,10} {1,6,11} {1,6,12} {1,6,13}
{1,6,14} {1,6,15} {1,6,16} {1,6,17} {1,6,18} {1,6,19} {1,6,20} {1,6,21} {1,6,22} {1,6,23} {1,6,24} {1,6,25}
{1,6,26} {1,6,27} {1,6,28} {1,6,29} {1,6,30} {1,6,31} {1,6,32} {1,6,33} {1,6,34} {1,6,35} {1,6,36} {1,6,37}
{1,6,38} {1,6,39} {1,6,40} {1,6,41} {1,6,42} {1,6,43} {1,6,44} {1,6,45} {1,6,46} {1,6,47} {1,6,48} {1,6,49}
{1,6,50} {1,6,51} {1,6,52} {1,6,53} {1,6,54} {1,6,55} {1,6,56} {1,6,57} {1,6,58} {1,6,59} {1,6,60} {1,6,61}
{1,6,62} {1,6,63} {1,6,64} {1,6,65} {1,6,66} {1,7,8} {1,7,9} {1,7,10} {1,7,11} {1,7,12} {1,7,13} {1,7,14}
{1,7,15} {1,7,16} {1,7,17} {1,7,18} {1,7,19} {1,7,20} {1,7,21} {1,7,22} {1,7,23} {1,7,24} {1,7,25} {1,7,26}
{1,7,27} {1,7,28} {1,7,29} {1,7,30} {1,7,31} {1,7,32} {1,7,33} {1,7,34} {1,7,35} {1,7,36} {1,7,37} {1,7,38}
{1,7,39} {1,7,40} {1,7,41} {1,7,42} {1,7,43} {1,7,44} {1,7,45} {1,7,46} {1,7,47} {1,7,48} {1,7,49} {1,7,50}
{1,7,51} {1,7,52} {1,7,53} {1,7,54} {1,7,55} {1,7,56} {1,7,57} {1,7,58} {1,7,59} {1,7,60} {1,7,61} {1,7,62}
{1,7,63} {1,7,64} {1,7,65} {1,7,66} {1,8,9} {1,8,10} {1,8,11} {1,8,12} {1,8,13} {1,8,14} {1,8,15} {1,8,16}
{1,8,17} {1,8,18} {1,8,19} {1,8,20} {1,8,21} {1,8,22} {1,8,23} {1,8,24} {1,8,25} {1,8,26} {1,8,27} {1,8,28}
{1,8,29} {1,8,30} {1,8,31} {1,8,32} {1,8,33} {1,8,34} {1,8,35} {1,8,36} {1,8,37} {1,8,38} {1,8,39} {1,8,40}
{1,8,41} {1,8,42} {1,8,43} {1,8,44} {1,8,45} {1,8,46} {1,8,47} {1,8,48} {1,8,49} {1,8,50} {1,8,51} {1,8,52}
{1,8,53} {1,8,54} {1,8,55} {1,8,56} {1,8,57} {1,8,58} {1,8,59} {1,8,60} {1,8,61} {1,8,62} {1,8,63} {1,8,64}
{1,8,65} {1,8,66} {1,9,10} {1,9,11} {1,9,12} {1,9,13} {1,9,14} {1,9,15} {1,9,16} {1,9,17} {1,9,18} {1,9,19}
{1,9,20} {1,9,21} {1,9,22} {1,9,23} {1,9,24} {1,9,25} {1,9,26} {1,9,27} {1,9,28} {1,9,29} {1,9,30} {1,9,31}
{1,9,32} {1,9,33} {1,9,34} {1,9,35} {1,9,36} {1,9,37} {1,9,38} {1,9,39} {1,9,40} {1,9,41} {1,9,42} {1,9,43}
{1,9,44} {1,9,45} {1,9,46} {1,9,47} {1,9,48} {1,9,49} {1,9,50} {1,9,51} {1,9,52} {1,9,53} {1,9,54} {1,9,55}

TABLE 3A-continued

{1,9,56} {1,9,57} {1,9,58} {1,9,59} {1,9,60} {1,9,61} {1,9,62} {1,9,63} {1,9,64} {1,9,65} {1,9,66} {1,10,11}
{1,10,12} {1,10,13} {1,10,14} {1,10,15} {1,10,16} {1,10,17} {1,10,18} {1,10,19} {1,10,20} {1,10,21}
{1,10,22} {1,10,23} {1,10,24} {1,10,25} {1,10,26} {1,10,27} {1,10,28} {1,10,29} {1,10,30} {1,10,31}
{1,10,32} {1,10,33} {1,10,34} {1,10,35} {1,10,36} {1,10,37} {1,10,38} {1,10,39} {1,10,40} {1,10,41}
{1,10,42} {1,10,43} {1,10,44} {1,10,45} {1,10,46} {1,10,47} {1,10,48} {1,10,49} {1,10,50} {1,10,51}
{1,10,52} {1,10,53} {1,10,54} {1,10,55} {1,10,56} {1,10,57} {1,10,58} {1,10,59} {1,10,60} {1,10,61}
{1,10,62} {1,10,63} {1,10,64} {1,10,65} {1,10,66} {1,11,12} {1,11,13} {1,11,14} {1,11,15} {1,11,16}
{1,11,17} {1,11,18} {1,11,19} {1,11,20} {1,11,21} {1,11,22} {1,11,23} {1,11,24} {1,11,25} {1,11,26}
{1,11,27} {1,11,28} {1,11,29} {1,11,30} {1,11,31} {1,11,32} {1,11,33} {1,11,34} {1,11,35} {1,11,36}
{1,11,37} {1,11,38} {1,11,39} {1,11,40} {1,11,41} {1,11,42} {1,11,43} {1,11,44} {1,11,45} {1,11,46}
{1,11,47} {1,11,48} {1,11,49} {1,11,50} {1,11,51} {1,11,52} {1,11,53} {1,11,54} {1,11,55} {1,11,56}
{1,11,57} {1,11,58} {1,11,59} {1,11,60} {1,11,61} {1,11,62} {1,11,63} {1,11,64} {1,11,65} {1,11,66}
{1,12,13} {1,12,14} {1,12,15} {1,12,16} {1,12,17} {1,12,18} {1,12,19} {1,12,20} {1,12,21} {1,12,22}
{1,12,23} {1,12,24} {1,12,25} {1,12,26} {1,12,27} {1,12,28} {1,12,29} {1,12,30} {1,12,31} {1,12,32}
{1,12,33} {1,12,34} {1,12,35} {1,12,36} {1,12,37} {1,12,38} {1,12,39} {1,12,40} {1,12,41} {1,12,42}
{1,12,43} {1,12,44} {1,12,45} {1,12,46} {1,12,47} {1,12,48} {1,12,49} {1,12,50} {1,12,51} {1,12,52}
{1,12,53} {1,12,54} {1,12,55} {1,12,56} {1,12,57} {1,12,58} {1,12,59} {1,12,60} {1,12,61} {1,12,62}
{1,12,63} {1,12,64} {1,12,65} {1,12,66} {1,13,14} {1,13,15} {1,13,16} {1,13,17} {1,13,18} {1,13,19}
{1,13,20} {1,13,21} {1,13,22} {1,13,23} {1,13,24} {1,13,25} {1,13,26} {1,13,27} {1,13,28} {1,13,29}
{1,13,30} {1,13,31} {1,13,32} {1,13,33} {1,13,34} {1,13,35} {1,13,36} {1,13,37} {1,13,38} {1,13,39}
{1,13,40} {1,13,41} {1,13,42} {1,13,43} {1,13,44} {1,13,45} {1,13,46} {1,13,47} {1,13,48} {1,13,49}
{1,13,50} {1,13,51} {1,13,52} {1,13,53} {1,13,54} {1,13,55} {1,13,56} {1,13,57} {1,13,58} {1,13,59}
{1,13,60} {1,13,61} {1,13,62} {1,13,63} {1,13,64} {1,13,65} {1,13,66} {1,14,15} {1,14,16} {1,14,17}
{1,14,18} {1,14,19} {1,14,20} {1,14,21} {1,14,22} {1,14,23} {1,14,24} {1,14,25} {1,14,26} {1,14,27}
{1,14,28} {1,14,29} {1,14,30} {1,14,31} {1,14,32} {1,14,33} {1,14,34} {1,14,35} {1,14,36} {1,14,37}
{1,14,38} {1,14,39} {1,14,40} {1,14,41} {1,14,42} {1,14,43} {1,14,44} {1,14,45} {1,14,46} {1,14,47}
{1,14,48} {1,14,49} {1,14,50} {1,14,51} {1,14,52} {1,14,53} {1,14,54} {1,14,55} {1,14,56} {1,14,57}
{1,14,58} {1,14,59} {1,14,60} {1,14,61} {1,14,62} {1,14,63} {1,14,64} {1,14,65} {1,14,66} {1,15,16}
{1,15,17} {1,15,18} {1,15,19} {1,15,20} {1,15,21} {1,15,22} {1,15,23} {1,15,24} {1,15,25} {1,15,26}
{1,15,27} {1,15,28} {1,15,29} {1,15,30} {1,15,31} {1,15,32} {1,15,33} {1,15,34} {1,15,35} {1,15,36}
{1,15,37} {1,15,38} {1,15,39} {1,15,40} {1,15,41} {1,15,42} {1,15,43} {1,15,44} {1,15,45} {1,15,46}
{1,15,47} {1,15,48} {1,15,49} {1,15,50} {1,15,51} {1,15,52} {1,15,53} {1,15,54} {1,15,55} {1,15,56}
{1,15,57} {1,15,58} {1,15,59} {1,15,60} {1,15,61} {1,15,62} {1,15,63} {1,15,64} {1,15,65} {1,15,66}
{1,16,17} {1,16,18} {1,16,19} {1,16,20} {1,16,21} {1,16,22} {1,16,23} {1,16,24} {1,16,25} {1,16,26}
{1,16,27} {1,16,28} {1,16,29} {1,16,30} {1,16,31} {1,16,32} {1,16,33} {1,16,34} {1,16,35} {1,16,36}
{1,16,37} {1,16,38} {1,16,39} {1,16,40} {1,16,41} {1,16,42} {1,16,43} {1,16,44} {1,16,45} {1,16,46}
{1,16,47} {1,16,48} {1,16,49} {1,16,50} {1,16,51} {1,16,52} {1,16,53} {1,16,54} {1,16,55} {1,16,56}
{1,16,57} {1,16,58} {1,16,59} {1,16,60} {1,16,61} {1,16,62} {1,16,63} {1,16,64} {1,16,65} {1,16,66}
{1,17,18} {1,17,19} {1,17,20} {1,17,21} {1,17,22} {1,17,23} {1,17,24} {1,17,25} {1,17,26} {1,17,27}
{1,17,28} {1,17,29} {1,17,30} {1,17,31} {1,17,32} {1,17,33} {1,17,34} {1,17,35} {1,17,36} {1,17,37}
{1,17,38} {1,17,39} {1,17,40} {1,17,41} {1,17,42} {1,17,43} {1,17,44} {1,17,45} {1,17,46} {1,17,47}
{1,17,48} {1,17,49} {1,17,50} {1,17,51} {1,17,52} {1,17,53} {1,17,54} {1,17,55} {1,17,56} {1,17,57}
{1,17,58} {1,17,59} {1,17,60} {1,17,61} {1,17,62} {1,17,63} {1,17,64} {1,17,65} {1,17,66} {1,18,19}
{1,18,20} {1,18,21} {1,18,22} {1,18,23} {1,18,24} {1,18,25} {1,18,26} {1,18,27} {1,18,28} {1,18,29}
{1,18,30} {1,18,31} {1,18,32} {1,18,33} {1,18,34} {1,18,35} {1,18,36} {1,18,37} {1,18,38} {1,18,39}
{1,18,40} {1,18,41} {1,18,42} {1,18,43} {1,18,44} {1,18,45} {1,18,46} {1,18,47} {1,18,48} {1,18,49}
{1,18,50} {1,18,51} {1,18,52} {1,18,53} {1,18,54} {1,18,55} {1,18,56} {1,18,57} {1,18,58} {1,18,59}
{1,18,60} {1,18,61} {1,18,62} {1,18,63} {1,18,64} {1,18,65} {1,18,66} {1,19,20} {1,19,21} {1,19,22}
{1,19,23} {1,19,24} {1,19,25} {1,19,26} {1,19,27} {1,19,28} {1,19,29} {1,19,30} {1,19,31} {1,19,32}
{1,19,33} {1,19,34} {1,19,35} {1,19,36} {1,19,37} {1,19,38} {1,19,39} {1,19,40} {1,19,41} {1,19,42}
{1,19,43} {1,19,44} {1,19,45} {1,19,46} {1,19,47} {1,19,48} {1,19,49} {1,19,50} {1,19,51} {1,19,52}
{1,19,53} {1,19,54} {1,19,55} {1,19,56} {1,19,57} {1,19,58} {1,19,59} {1,19,60} {1,19,61} {1,19,62}
{1,19,63} {1,19,64} {1,19,65} {1,19,66} {1,20,21} {1,20,22} {1,20,23} {1,20,24} {1,20,25} {1,20,26}
{1,20,27} {1,20,28} {1,20,29} {1,20,30} {1,20,31} {1,20,32} {1,20,33} {1,20,34} {1,20,35} {1,20,36}
{1,20,37} {1,20,38} {1,20,39} {1,20,40} {1,20,41} {1,20,42} {1,20,43} {1,20,44} {1,20,45} {1,20,46}
{1,20,47} {1,20,48} {1,20,49} {1,20,50} {1,20,51} {1,20,52} {1,20,53} {1,20,54} {1,20,55} {1,20,56}
{1,20,57} {1,20,58} {1,20,59} {1,20,60} {1,20,61} {1,20,62} {1,20,63} {1,20,64} {1,20,65} {1,20,66}
{1,21,22} {1,21,23} {1,21,24} {1,21,25} {1,21,26} {1,21,27} {1,21,28} {1,21,29} {1,21,30} {1,21,31}
{1,21,32} {1,21,33} {1,21,34} {1,21,35} {1,21,36} {1,21,37} {1,21,38} {1,21,39} {1,21,40} {1,21,41}
{1,21,42} {1,21,43} {1,21,44} {1,21,45} {1,21,46} {1,21,47} {1,21,48} {1,21,49} {1,21,50} {1,21,51}
{1,21,52} {1,21,53} {1,21,54} {1,21,55} {1,21,56} {1,21,57} {1,21,58} {1,21,59} {1,21,60} {1,21,61}
{1,21,62} {1,21,63} {1,21,64} {1,21,65} {1,21,66} {1,22,23} {1,22,24} {1,22,25} {1,22,26} {1,22,27}
{1,22,28} {1,22,29} {1,22,30} {1,22,31} {1,22,32} {1,22,33} {1,22,34} {1,22,35} {1,22,36} {1,22,37}
{1,22,38} {1,22,39} {1,22,40} {1,22,41} {1,22,42} {1,22,43} {1,22,44} {1,22,45} {1,22,46} {1,22,47}
{1,22,48} {1,22,49} {1,22,50} {1,22,51} {1,22,52} {1,22,53} {1,22,54} {1,22,55} {1,22,56} {1,22,57}
{1,22,58} {1,22,59} {1,22,60} {1,22,61} {1,22,62} {1,22,63} {1,22,64} {1,22,65} {1,22,66} {1,23,24}
{1,23,25} {1,23,26} {1,23,27} {1,23,28} {1,23,29} {1,23,30} {1,23,31} {1,23,32} {1,23,33} {1,23,34}
{1,23,35} {1,23,36} {1,23,37} {1,23,38} {1,23,39} {1,23,40} {1,23,41} {1,23,42} {1,23,43} {1,23,44}
{1,23,45} {1,23,46} {1,23,47} {1,23,48} {1,23,49} {1,23,50} {1,23,51} {1,23,52} {1,23,53} {1,23,54}
{1,23,55} {1,23,56} {1,23,57} {1,23,58} {1,23,59} {1,23,60} {1,23,61} {1,23,62} {1,23,63} {1,23,64}
{1,23,65} {1,23,66} {1,24,25} {1,24,26} {1,24,27} {1,24,28} {1,24,29} {1,24,30} {1,24,31} {1,24,32}
{1,24,33} {1,24,34} {1,24,35} {1,24,36} {1,24,37} {1,24,38} {1,24,39} {1,24,40} {1,24,41} {1,24,42}
{1,24,43} {1,24,44} {1,24,45} {1,24,46} {1,24,47} {1,24,48} {1,24,49} {1,24,50} {1,24,51} {1,24,52}
{1,24,53} {1,24,54} {1,24,55} {1,24,56} {1,24,57} {1,24,58} {1,24,59} {1,24,60} {1,24,61} {1,24,62}
{1,24,63} {1,24,64} {1,24,65} {1,24,66} {1,25,26} {1,25,27} {1,25,28} {1,25,29} {1,25,30} {1,25,31}
{1,25,32} {1,25,33} {1,25,34} {1,25,35} {1,25,36} {1,25,37} {1,25,38} {1,25,39} {1,25,40} {1,25,41}
{1,25,42} {1,25,43} {1,25,44} {1,25,45} {1,25,46} {1,25,47} {1,25,48} {1,25,49} {1,25,50} {1,25,51}
{1,25,52} {1,25,53} {1,25,54} {1,25,55} {1,25,56} {1,25,57} {1,25,58} {1,25,59} {1,25,60} {1,25,61}
{1,25,62} {1,25,63} {1,25,64} {1,25,65} {1,25,66} {1,26,27} {1,26,28} {1,26,29} {1,26,30} {1,26,31}
{1,26,32} {1,26,33} {1,26,34} {1,26,35} {1,26,36} {1,26,37} {1,26,38} {1,26,39} {1,26,40} {1,26,41}

TABLE 3A-continued

{1,26,42} {1,26,43} {1,26,44} {1,26,45} {1,26,46} {1,26,47} {1,26,48} {1,26,49} {1,26,50} {1,26,51}
{1,26,52} {1,26,53} {1,26,54} {1,26,55} {1,26,56} {1,26,57} {1,26,58} {1,26,59} {1,26,60} {1,26,61}
{1,26,62} {1,26,63} {1,26,64} {1,26,65} {1,26,66} {1,27,28} {1,27,29} {1,27,30} {1,27,31} {1,27,32}
{1,27,33} {1,27,34} {1,27,35} {1,27,36} {1,27,37} {1,27,38} {1,27,39} {1,27,40} {1,27,41} {1,27,42}
{1,27,43} {1,27,44} {1,27,45} {1,27,46} {1,27,47} {1,27,48} {1,27,49} {1,27,50} {1,27,51} {1,27,52}
{1,27,53} {1,27,54} {1,27,55} {1,27,56} {1,27,57} {1,27,58} {1,27,59} {1,27,60} {1,27,61} {1,27,62}
{1,27,63} {1,27,64} {1,27,65} {1,27,66} {1,28,29} {1,28,30} {1,28,31} {1,28,32} {1,28,33} {1,28,34}
{1,28,35} {1,28,36} {1,28,37} {1,28,38} {1,28,39} {1,28,40} {1,28,41} {1,28,42} {1,28,43} {1,28,44}
{1,28,45} {1,28,46} {1,28,47} {1,28,48} {1,28,49} {1,28,50} {1,28,51} {1,28,52} {1,28,53} {1,28,54}
{1,28,55} {1,28,56} {1,28,57} {1,28,58} {1,28,59} {1,28,60} {1,28,61} {1,28,62} {1,28,63} {1,28,64}
{1,28,65} {1,28,66} {1,29,30} {1,29,31} {1,29,32} {1,29,33} {1,29,34} {1,29,35} {1,29,36} {1,29,37}
{1,29,38} {1,29,39} {1,29,40} {1,29,41} {1,29,42} {1,29,43} {1,29,44} {1,29,45} {1,29,46} {1,29,47}
{1,29,48} {1,29,49} {1,29,50} {1,29,51} {1,29,52} {1,29,53} {1,29,54} {1,29,55} {1,29,56} {1,29,57}
{1,29,58} {1,29,59} {1,29,60} {1,29,61} {1,29,62} {1,29,63} {1,29,64} {1,29,65} {1,29,66} {1,30,31}
{1,30,32} {1,30,33} {1,30,34} {1,30,35} {1,30,36} {1,30,37} {1,30,38} {1,30,39} {1,30,40} {1,30,41}
{1,30,42} {1,30,43} {1,30,44} {1,30,45} {1,30,46} {1,30,47} {1,30,48} {1,30,49} {1,30,50} {1,30,51}
{1,30,52} {1,30,53} {1,30,54} {1,30,55} {1,30,56} {1,30,57} {1,30,58} {1,30,59} {1,30,60} {1,30,61}
{1,30,62} {1,30,63} {1,30,64} {1,30,65} {1,30,66} {1,31,32} {1,31,33} {1,31,34} {1,31,35} {1,31,36}
{1,31,37} {1,31,38} {1,31,39} {1,31,40} {1,31,41} {1,31,42} {1,31,43} {1,31,44} {1,31,45} {1,31,46}
{1,31,47} {1,31,48} {1,31,49} {1,31,50} {1,31,51} {1,31,52} {1,31,53} {1,31,54} {1,31,55} {1,31,56}
{1,31,57} {1,31,58} {1,31,59} {1,31,60} {1,31,61} {1,31,62} {1,31,63} {1,31,64} {1,31,65} {1,31,66}
{1,32,33} {1,32,34} {1,32,35} {1,32,36} {1,32,37} {1,32,38} {1,32,39} {1,32,40} {1,32,41} {1,32,42}
{1,32,43} {1,32,44} {1,32,45} {1,32,46} {1,32,47} {1,32,48} {1,32,49} {1,32,50} {1,32,51} {1,32,52}
{1,32,53} {1,32,54} {1,32,55} {1,32,56} {1,32,57} {1,32,58} {1,32,59} {1,32,60} {1,32,61} {1,32,62}
{1,32,63} {1,32,64} {1,32,65} {1,32,66} {1,33,34} {1,33,35} {1,33,36} {1,33,37} {1,33,38} {1,33,39}
{1,33,40} {1,33,41} {1,33,42} {1,33,43} {1,33,44} {1,33,45} {1,33,46} {1,33,47} {1,33,48} {1,33,49}
{1,33,50} {1,33,51} {1,33,52} {1,33,53} {1,33,54} {1,33,55} {1,33,56} {1,33,57} {1,33,58} {1,33,59}
{1,33,60} {1,33,61} {1,33,62} {1,33,63} {1,33,64} {1,33,65} {1,33,66} {1,34,35} {1,34,36} {1,34,37}
{1,34,38} {1,34,39} {1,34,40} {1,34,41} {1,34,42} {1,34,43} {1,34,44} {1,34,45} {1,34,46} {1,34,47}
{1,34,48} {1,34,49} {1,34,50} {1,34,51} {1,34,52} {1,34,53} {1,34,54} {1,34,55} {1,34,56} {1,34,57}
{1,34,58} {1,34,59} {1,34,60} {1,34,61} {1,34,62} {1,34,63} {1,34,64} {1,34,65} {1,34,66} {1,35,36}
{1,35,37} {1,35,38} {1,35,39} {1,35,40} {1,35,41} {1,35,42} {1,35,43} {1,35,44} {1,35,45} {1,35,46}
{1,35,47} {1,35,48} {1,35,49} {1,35,50} {1,35,51} {1,35,52} {1,35,53} {1,35,54} {1,35,55} {1,35,56}
{1,35,57} {1,35,58} {1,35,59} {1,35,60} {1,35,61} {1,35,62} {1,35,63} {1,35,64} {1,35,65} {1,35,66}
{1,36,37} {1,36,38} {1,36,39} {1,36,40} {1,36,41} {1,36,42} {1,36,43} {1,36,44} {1,36,45} {1,36,46}
{1,36,47} {1,36,48} {1,36,49} {1,36,50} {1,36,51} {1,36,52} {1,36,53} {1,36,54} {1,36,55} {1,36,56}
{1,36,57} {1,36,58} {1,36,59} {1,36,60} {1,36,61} {1,36,62} {1,36,63} {1,36,64} {1,36,65} {1,36,66}
{1,37,38} {1,37,39} {1,37,40} {1,37,41} {1,37,42} {1,37,43} {1,37,44} {1,37,45} {1,37,46} {1,37,47}
{1,37,48} {1,37,49} {1,37,50} {1,37,51} {1,37,52} {1,37,53} {1,37,54} {1,37,55} {1,37,56} {1,37,57}
{1,37,58} {1,37,59} {1,37,60} {1,37,61} {1,37,62} {1,37,63} {1,37,64} {1,37,65} {1,37,66} {1,38,39}
{1,38,40} {1,38,41} {1,38,42} {1,38,43} {1,38,44} {1,38,45} {1,38,46} {1,38,47} {1,38,48} {1,38,49}
{1,38,50} {1,38,51} {1,38,52} {1,38,53} {1,38,54} {1,38,55} {1,38,56} {1,38,57} {1,38,58} {1,38,59}
{1,38,60} {1,38,61} {1,38,62} {1,38,63} {1,38,64} {1,38,65} {1,38,66} {1,39,40} {1,39,41} {1,39,42}
{1,39,43} {1,39,44} {1,39,45} {1,39,46} {1,39,47} {1,39,48} {1,39,49} {1,39,50} {1,39,51} {1,39,52}
{1,39,53} {1,39,54} {1,39,55} {1,39,56} {1,39,57} {1,39,58} {1,39,59} {1,39,60} {1,39,61} {1,39,62}
{1,39,63} {1,39,64} {1,39,65} {1,39,66} {1,40,41} {1,40,42} {1,40,43} {1,40,44} {1,40,45} {1,40,46}
{1,40,47} {1,40,48} {1,40,49} {1,40,50} {1,40,51} {1,40,52} {1,40,53} {1,40,54} {1,40,55} {1,40,56}
{1,40,57} {1,40,58} {1,40,59} {1,40,60} {1,40,61} {1,40,62} {1,40,63} {1,40,64} {1,40,65} {1,40,66}
{1,41,42} {1,41,43} {1,41,44} {1,41,45} {1,41,46} {1,41,47} {1,41,48} {1,41,49} {1,41,50} {1,41,51}
{1,41,52} {1,41,53} {1,41,54} {1,41,55} {1,41,56} {1,41,57} {1,41,58} {1,41,59} {1,41,60} {1,41,61}
{1,41,62} {1,41,63} {1,41,64} {1,41,65} {1,41,66} {1,42,43} {1,42,44} {1,42,45} {1,42,46} {1,42,47}
{1,42,48} {1,42,49} {1,42,50} {1,42,51} {1,42,52} {1,42,53} {1,42,54} {1,42,55} {1,42,56} {1,42,57}
{1,42,58} {1,42,59} {1,42,60} {1,42,61} {1,42,62} {1,42,63} {1,42,64} {1,42,65} {1,42,66} {1,43,44}
{1,43,45} {1,43,46} {1,43,47} {1,43,48} {1,43,49} {1,43,50} {1,43,51} {1,43,52} {1,43,53} {1,43,54}
{1,43,55} {1,43,56} {1,43,57} {1,43,58} {1,43,59} {1,43,60} {1,43,61} {1,43,62} {1,43,63} {1,43,64}
{1,43,65} {1,43,66} {1,44,45} {1,44,46} {1,44,47} {1,44,48} {1,44,49} {1,44,50} {1,44,51} {1,44,52}
{1,44,53} {1,44,54} {1,44,55} {1,44,56} {1,44,57} {1,44,58} {1,44,59} {1,44,60} {1,44,61} {1,44,62}
{1,44,63} {1,44,64} {1,44,65} {1,44,66} {1,45,46} {1,45,47} {1,45,48} {1,45,49} {1,45,50} {1,45,51}
{1,45,52} {1,45,53} {1,45,54} {1,45,55} {1,45,56} {1,45,57} {1,45,58} {1,45,59} {1,45,60} {1,45,61}
{1,45,62} {1,45,63} {1,45,64} {1,45,65} {1,45,66} {1,46,47} {1,46,48} {1,46,49} {1,46,50} {1,46,51}
{1,46,52} {1,46,53} {1,46,54} {1,46,55} {1,46,56} {1,46,57} {1,46,58} {1,46,59} {1,46,60} {1,46,61}
{1,46,62} {1,46,63} {1,46,64} {1,46,65} {1,46,66} {1,47,48} {1,47,49} {1,47,50} {1,47,51} {1,47,52}
{1,47,53} {1,47,54} {1,47,55} {1,47,56} {1,47,57} {1,47,58} {1,47,59} {1,47,60} {1,47,61} {1,47,62}
{1,47,63} {1,47,64} {1,47,65} {1,47,66} {1,48,49} {1,48,50} {1,48,51} {1,48,52} {1,48,53} {1,48,54}
{1,48,55} {1,48,56} {1,48,57} {1,48,58} {1,48,59} {1,48,60} {1,48,61} {1,48,62} {1,48,63} {1,48,64}
{1,48,65} {1,48,66} {1,49,50} {1,49,51} {1,49,52} {1,49,53} {1,49,54} {1,49,55} {1,49,56} {1,49,57}
{1,49,58} {1,49,59} {1,49,60} {1,49,61} {1,49,62} {1,49,63} {1,49,64} {1,49,65} {1,49,66} {1,50,51}
{1,50,52} {1,50,53} {1,50,54} {1,50,55} {1,50,56} {1,50,57} {1,50,58} {1,50,59} {1,50,60} {1,50,61}
{1,50,62} {1,50,63} {1,50,64} {1,50,65} {1,50,66} {1,51,52} {1,51,53} {1,51,54} {1,51,55} {1,51,56}
{1,51,57} {1,51,58} {1,51,59} {1,51,60} {1,51,61} {1,51,62} {1,51,63} {1,51,64} {1,51,65} {1,51,66}
{1,52,53} {1,52,54} {1,52,55} {1,52,56} {1,52,57} {1,52,58} {1,52,59} {1,52,60} {1,52,61} {1,52,62}
{1,52,63} {1,52,64} {1,52,65} {1,52,66} {1,53,54} {1,53,55} {1,53,56} {1,53,57} {1,53,58} {1,53,59}
{1,53,60} {1,53,61} {1,53,62} {1,53,63} {1,53,64} {1,53,65} {1,53,66} {1,54,55} {1,54,56} {1,54,57}
{1,54,58} {1,54,59} {1,54,60} {1,54,61} {1,54,62} {1,54,63} {1,54,64} {1,54,65} {1,54,66} {1,55,56}
{1,55,57} {1,55,58} {1,55,59} {1,55,60} {1,55,61} {1,55,62} {1,55,63} {1,55,64} {1,55,65} {1,55,66}
{1,56,57} {1,56,58} {1,56,59} {1,56,60} {1,56,61} {1,56,62} {1,56,63} {1,56,64} {1,56,65} {1,56,66}
{1,57,58} {1,57,59} {1,57,60} {1,57,61} {1,57,62} {1,57,63} {1,57,64} {1,57,65} {1,57,66} {1,58,59}
{1,58,60} {1,58,61} {1,58,62} {1,58,63} {1,58,64} {1,58,65} {1,58,66} {1,59,60} {1,59,61} {1,59,62}
{1,59,63} {1,59,64} {1,59,65} {1,59,66} {1,60,61} {1,60,62} {1,60,63} {1,60,64} {1,60,65} {1,60,66}
{1,61,62} {1,61,63} {1,61,64} {1,61,65} {1,61,66} {1,62,63} {1,62,64} {1,62,65} {1,62,66} {1,63,64}

TABLE 3A-continued

{1,63,65} {1,63,66} {1,64,65} {1,64,66} {1,65,66} {2,3,4} {2,3,5} {2,3,6} {2,3,7} {2,3,8} {2,3,9} {2,3,10}
{2,3,11} {2,3,12} {2,3,13} {2,3,14} {2,3,15} {2,3,16} {2,3,17} {2,3,18} {2,3,19} {2,3,20} {2,3,21} {2,3,22}
{2,3,23} {2,3,24} {2,3,25} {2,3,26} {2,3,27} {2,3,28} {2,3,29} {2,3,30} {2,3,31} {2,3,32} {2,3,33} {2,3,34}
{2,3,35} {2,3,36} {2,3,37} {2,3,38} {2,3,39} {2,3,40} {2,3,41} {2,3,42} {2,3,43} {2,3,44} {2,3,45} {2,3,46}
{2,3,47} {2,3,48} {2,3,49} {2,3,50} {2,3,51} {2,3,52} {2,3,53} {2,3,54} {2,3,55} {2,3,56} {2,3,57} {2,3,58}
{2,3,59} {2,3,60} {2,3,61} {2,3,62} {2,3,63} {2,3,64} {2,3,65} {2,3,66} {2,4,5} {2,4,6} {2,4,7} {2,4,8} {2,4,9}
{2,4,10} {2,4,11} {2,4,12} {2,4,13} {2,4,14} {2,4,15} {2,4,16} {2,4,17} {2,4,18} {2,4,19} {2,4,20} {2,4,21}
{2,4,22} {2,4,23} {2,4,24} {2,4,25} {2,4,26} {2,4,27} {2,4,28} {2,4,29} {2,4,30} {2,4,31} {2,4,32} {2,4,33}
{2,4,34} {2,4,35} {2,4,36} {2,4,37} {2,4,38} {2,4,39} {2,4,40} {2,4,41} {2,4,42} {2,4,43} {2,4,44} {2,4,45}
{2,4,46} {2,4,47} {2,4,48} {2,4,49} {2,4,50} {2,4,51} {2,4,52} {2,4,53} {2,4,54} {2,4,55} {2,4,56} {2,4,57}
{2,4,58} {2,4,59} {2,4,60} {2,4,61} {2,4,62} {2,4,63} {2,4,64} {2,4,65} {2,4,66} {2,5,6} {2,5,7} {2,5,8} {2,5,9}
{2,5,10} {2,5,11} {2,5,12} {2,5,13} {2,5,14} {2,5,15} {2,5,16} {2,5,17} {2,5,18} {2,5,19} {2,5,20} {2,5,21}
{2,5,22} {2,5,23} {2,5,24} {2,5,25} {2,5,26} {2,5,27} {2,5,28} {2,5,29} {2,5,30} {2,5,31} {2,5,32} {2,5,33}
{2,5,34} {2,5,35} {2,5,36} {2,5,37} {2,5,38} {2,5,39} {2,5,40} {2,5,41} {2,5,42} {2,5,43} {2,5,44} {2,5,45}
{2,5,46} {2,5,47} {2,5,48} {2,5,49} {2,5,50} {2,5,51} {2,5,52} {2,5,53} {2,5,54} {2,5,55} {2,5,56} {2,5,57}
{2,5,58} {2,5,59} {2,5,60} {2,5,61} {2,5,62} {2,5,63} {2,5,64} {2,5,65} {2,5,66} {2,6,7} {2,6,8} {2,6,9} {2,6,10}
{2,6,11} {2,6,12} {2,6,13} {2,6,14} {2,6,15} {2,6,16} {2,6,17} {2,6,18} {2,6,19} {2,6,20} {2,6,21} {2,6,22}
{2,6,23} {2,6,24} {2,6,25} {2,6,26} {2,6,27} {2,6,28} {2,6,29} {2,6,30} {2,6,31} {2,6,32} {2,6,33} {2,6,34}
{2,6,35} {2,6,36} {2,6,37} {2,6,38} {2,6,39} {2,6,40} {2,6,41} {2,6,42} {2,6,43} {2,6,44} {2,6,45} {2,6,46}
{2,6,47} {2,6,48} {2,6,49} {2,6,50} {2,6,51} {2,6,52} {2,6,53} {2,6,54} {2,6,55} {2,6,56} {2,6,57} {2,6,58}
{2,6,59} {2,6,60} {2,6,61} {2,6,62} {2,6,63} {2,6,64} {2,6,65} {2,6,66} {2,7,8} {2,7,9} {2,7,10} {2,7,11}
{2,7,12} {2,7,13} {2,7,14} {2,7,15} {2,7,16} {2,7,17} {2,7,18} {2,7,19} {2,7,20} {2,7,21} {2,7,22} {2,7,23}
{2,7,24} {2,7,25} {2,7,26} {2,7,27} {2,7,28} {2,7,29} {2,7,30} {2,7,31} {2,7,32} {2,7,33} {2,7,34} {2,7,35}
{2,7,36} {2,7,37} {2,7,38} {2,7,39} {2,7,40} {2,7,41} {2,7,42} {2,7,43} {2,7,44} {2,7,45} {2,7,46} {2,7,47}
{2,7,48} {2,7,49} {2,7,50} {2,7,51} {2,7,52} {2,7,53} {2,7,54} {2,7,55} {2,7,56} {2,7,57} {2,7,58} {2,7,59}
{2,7,60} {2,7,61} {2,7,62} {2,7,63} {2,7,64} {2,7,65} {2,7,66} {2,8,9} {2,8,10} {2,8,11} {2,8,12} {2,8,13}
{2,8,14} {2,8,15} {2,8,16} {2,8,17} {2,8,18} {2,8,19} {2,8,20} {2,8,21} {2,8,22} {2,8,23} {2,8,24} {2,8,25}
{2,8,26} {2,8,27} {2,8,28} {2,8,29} {2,8,30} {2,8,31} {2,8,32} {2,8,33} {2,8,34} {2,8,35} {2,8,36} {2,8,37}
{2,8,38} {2,8,39} {2,8,40} {2,8,41} {2,8,42} {2,8,43} {2,8,44} {2,8,45} {2,8,46} {2,8,47} {2,8,48} {2,8,49}
{2,8,50} {2,8,51} {2,8,52} {2,8,53} {2,8,54} {2,8,55} {2,8,56} {2,8,57} {2,8,58} {2,8,59} {2,8,60} {2,8,61}
{2,8,62} {2,8,63} {2,8,64} {2,8,65} {2,8,66} {2,9,10} {2,9,11} {2,9,12} {2,9,13} {2,9,14} {2,9,15} {2,9,16}
{2,9,17} {2,9,18} {2,9,19} {2,9,20} {2,9,21} {2,9,22} {2,9,23} {2,9,24} {2,9,25} {2,9,26} {2,9,27} {2,9,28}
{2,9,29} {2,9,30} {2,9,31} {2,9,32} {2,9,33} {2,9,34} {2,9,35} {2,9,36} {2,9,37} {2,9,38} {2,9,39} {2,9,40}
{2,9,41} {2,9,42} {2,9,43} {2,9,44} {2,9,45} {2,9,46} {2,9,47} {2,9,48} {2,9,49} {2,9,50} {2,9,51} {2,9,52}
{2,9,53} {2,9,54} {2,9,55} {2,9,56} {2,9,57} {2,9,58} {2,9,59} {2,9,60} {2,9,61} {2,9,62} {2,9,63} {2,9,64}
{2,9,65} {2,9,66} {2,10,11} {2,10,12} {2,10,13} {2,10,14} {2,10,15} {2,10,16} {2,10,17} {2,10,18} {2,10,19}
{2,10,20} {2,10,21} {2,10,22} {2,10,23} {2,10,24} {2,10,25} {2,10,26} {2,10,27} {2,10,28} {2,10,29}
{2,10,30} {2,10,31} {2,10,32} {2,10,33} {2,10,34} {2,10,35} {2,10,36} {2,10,37} {2,10,38} {2,10,39}
{2,10,40} {2,10,41} {2,10,42} {2,10,43} {2,10,44} {2,10,45} {2,10,46} {2,10,47} {2,10,48} {2,10,49}
{2,10,50} {2,10,51} {2,10,52} {2,10,53} {2,10,54} {2,10,55} {2,10,56} {2,10,57} {2,10,58} {2,10,59}
{2,10,60} {2,10,61} {2,10,62} {2,10,63} {2,10,64} {2,10,65} {2,10,66} {2,11,12} {2,11,13} {2,11,14}
{2,11,15} {2,11,16} {2,11,17} {2,11,18} {2,11,19} {2,11,20} {2,11,21} {2,11,22} {2,11,23} {2,11,24}
{2,11,25} {2,11,26} {2,11,27} {2,11,28} {2,11,29} {2,11,30} {2,11,31} {2,11,32} {2,11,33} {2,11,34}
{2,11,35} {2,11,36} {2,11,37} {2,11,38} {2,11,39} {2,11,40} {2,11,41} {2,11,42} {2,11,43} {2,11,44}
{2,11,45} {2,11,46} {2,11,47} {2,11,48} {2,11,49} {2,11,50} {2,11,51} {2,11,52} {2,11,53} {2,11,54}
{2,11,55} {2,11,56} {2,11,57} {2,11,58} {2,11,59} {2,11,60} {2,11,61} {2,11,62} {2,11,63} {2,11,64}
{2,11,65} {2,11,66} {2,12,13} {2,12,14} {2,12,15} {2,12,16} {2,12,17} {2,12,18} {2,12,19} {2,12,20}
{2,12,21} {2,12,22} {2,12,23} {2,12,24} {2,12,25} {2,12,26} {2,12,27} {2,12,28} {2,12,29} {2,12,30}
{2,12,31} {2,12,32} {2,12,33} {2,12,34} {2,12,35} {2,12,36} {2,12,37} {2,12,38} {2,12,39} {2,12,40}
{2,12,41} {2,12,42} {2,12,43} {2,12,44} {2,12,45} {2,12,46} {2,12,47} {2,12,48} {2,12,49} {2,12,50}
{2,12,51} {2,12,52} {2,12,53} {2,12,54} {2,12,55} {2,12,56} {2,12,57} {2,12,58} {2,12,59} {2,12,60}
{2,12,61} {2,12,62} {2,12,63} {2,12,64} {2,12,65} {2,12,66} {2,13,14} {2,13,15} {2,13,16} {2,13,17}
{2,13,18} {2,13,19} {2,13,20} {2,13,21} {2,13,22} {2,13,23} {2,13,24} {2,13,25} {2,13,26} {2,13,27}
{2,13,28} {2,13,29} {2,13,30} {2,13,31} {2,13,32} {2,13,33} {2,13,34} {2,13,35} {2,13,36} {2,13,37}
{2,13,38} {2,13,39} {2,13,40} {2,13,41} {2,13,42} {2,13,43} {2,13,44} {2,13,45} {2,13,46} {2,13,47}
{2,13,48} {2,13,49} {2,13,50} {2,13,51} {2,13,52} {2,13,53} {2,13,54} {2,13,55} {2,13,56} {2,13,57}
{2,13,58} {2,13,59} {2,13,60} {2,13,61} {2,13,62} {2,13,63} {2,13,64} {2,13,65} {2,13,66} {2,14,15}
{2,14,16} {2,14,17} {2,14,18} {2,14,19} {2,14,20} {2,14,21} {2,14,22} {2,14,23} {2,14,24} {2,14,25}
{2,14,26} {2,14,27} {2,14,28} {2,14,29} {2,14,30} {2,14,31} {2,14,32} {2,14,33} {2,14,34} {2,14,35}
{2,14,36} {2,14,37} {2,14,38} {2,14,39} {2,14,40} {2,14,41} {2,14,42} {2,14,43} {2,14,44} {2,14,45}
{2,14,46} {2,14,47} {2,14,48} {2,14,49} {2,14,50} {2,14,51} {2,14,52} {2,14,53} {2,14,54} {2,14,55}
{2,14,56} {2,14,57} {2,14,58} {2,14,59} {2,14,60} {2,14,61} {2,14,62} {2,14,63} {2,14,64} {2,14,65}
{2,14,66} {2,15,16} {2,15,17} {2,15,18} {2,15,19} {2,15,20} {2,15,21} {2,15,22} {2,15,23} {2,15,24}
{2,15,25} {2,15,26} {2,15,27} {2,15,28} {2,15,29} {2,15,30} {2,15,31} {2,15,32} {2,15,33} {2,15,34}
{2,15,35} {2,15,36} {2,15,37} {2,15,38} {2,15,39} {2,15,40} {2,15,41} {2,15,42} {2,15,43} {2,15,44}
{2,15,45} {2,15,46} {2,15,47} {2,15,48} {2,15,49} {2,15,50} {2,15,51} {2,15,52} {2,15,53} {2,15,54}
{2,15,55} {2,15,56} {2,15,57} {2,15,58} {2,15,59} {2,15,60} {2,15,61} {2,15,62} {2,15,63} {2,15,64}
{2,15,65} {2,15,66} {2,16,17} {2,16,18} {2,16,19} {2,16,20} {2,16,21} {2,16,22} {2,16,23} {2,16,24}
{2,16,25} {2,16,26} {2,16,27} {2,16,28} {2,16,29} {2,16,30} {2,16,31} {2,16,32} {2,16,33} {2,16,34}
{2,16,35} {2,16,36} {2,16,37} {2,16,38} {2,16,39} {2,16,40} {2,16,41} {2,16,42} {2,16,43} {2,16,44}
{2,16,45} {2,16,46} {2,16,47} {2,16,48} {2,16,49} {2,16,50} {2,16,51} {2,16,52} {2,16,53} {2,16,54}
{2,16,55} {2,16,56} {2,16,57} {2,16,58} {2,16,59} {2,16,60} {2,16,61} {2,16,62} {2,16,63} {2,16,64}
{2,16,65} {2,16,66} {2,17,18} {2,17,19} {2,17,20} {2,17,21} {2,17,22} {2,17,23} {2,17,24} {2,17,25}
{2,17,26} {2,17,27} {2,17,28} {2,17,29} {2,17,30} {2,17,31} {2,17,32} {2,17,33} {2,17,34} {2,17,35}
{2,17,36} {2,17,37} {2,17,38} {2,17,39} {2,17,40} {2,17,41} {2,17,42} {2,17,43} {2,17,44} {2,17,45}
{2,17,46} {2,17,47} {2,17,48} {2,17,49} {2,17,50} {2,17,51} {2,17,52} {2,17,53} {2,17,54} {2,17,55}
{2,17,56} {2,17,57} {2,17,58} {2,17,59} {2,17,60} {2,17,61} {2,17,62} {2,17,63} {2,17,64} {2,17,65}
{2,17,66} {2,18,19} {2,18,20} {2,18,21} {2,18,22} {2,18,23} {2,18,24} {2,18,25} {2,18,26} {2,18,27}
{2,18,28} {2,18,29} {2,18,30} {2,18,31} {2,18,32} {2,18,33} {2,18,34} {2,18,35} {2,18,36} {2,18,37}
{2,18,38} {2,18,39} {2,18,40} {2,18,41} {2,18,42} {2,18,43} {2,18,44} {2,18,45} {2,18,46} {2,18,47}

TABLE 3A-continued

| | | | | | | | | |
|---|---|---|---|---|---|---|---|---|
| {2,18,48} | {2,18,49} | {2,18,50} | {2,18,51} | {2,18,52} | {2,18,53} | {2,18,54} | {2,18,55} | {2,18,56} | {2,18,57} |
| {2,18,58} | {2,18,59} | {2,18,60} | {2,18,61} | {2,18,62} | {2,18,63} | {2,18,64} | {2,18,65} | {2,18,66} | {2,19,20} |
| {2,19,21} | {2,19,22} | {2,19,23} | {2,19,24} | {2,19,25} | {2,19,26} | {2,19,27} | {2,19,28} | {2,19,29} | {2,19,30} |
| {2,19,31} | {2,19,32} | {2,19,33} | {2,19,34} | {2,19,35} | {2,19,36} | {2,19,37} | {2,19,38} | {2,19,39} | {2,19,40} |
| {2,19,41} | {2,19,42} | {2,19,43} | {2,19,44} | {2,19,45} | {2,19,46} | {2,19,47} | {2,19,48} | {2,19,49} | {2,19,50} |
| {2,19,51} | {2,19,52} | {2,19,53} | {2,19,54} | {2,19,55} | {2,19,56} | {2,19,57} | {2,19,58} | {2,19,59} | {2,19,60} |
| {2,19,61} | {2,19,62} | {2,19,63} | {2,19,64} | {2,19,65} | {2,19,66} | {2,20,21} | {2,20,22} | {2,20,23} | {2,20,24} |
| {2,20,25} | {2,20,26} | {2,20,27} | {2,20,28} | {2,20,29} | {2,20,30} | {2,20,31} | {2,20,32} | {2,20,33} | {2,20,34} |
| {2,20,35} | {2,20,36} | {2,20,37} | {2,20,38} | {2,20,39} | {2,20,40} | {2,20,41} | {2,20,42} | {2,20,43} | {2,20,44} |
| {2,20,45} | {2,20,46} | {2,20,47} | {2,20,48} | {2,20,49} | {2,20,50} | {2,20,51} | {2,20,52} | {2,20,53} | {2,20,54} |
| {2,20,55} | {2,20,56} | {2,20,57} | {2,20,58} | {2,20,59} | {2,20,60} | {2,20,61} | {2,20,62} | {2,20,63} | {2,20,64} |
| {2,20,65} | {2,20,66} | {2,21,22} | {2,21,23} | {2,21,24} | {2,21,25} | {2,21,26} | {2,21,27} | {2,21,28} | {2,21,29} |
| {2,21,30} | {2,21,31} | {2,21,32} | {2,21,33} | {2,21,34} | {2,21,35} | {2,21,36} | {2,21,37} | {2,21,38} | {2,21,39} |
| {2,21,40} | {2,21,41} | {2,21,42} | {2,21,43} | {2,21,44} | {2,21,45} | {2,21,46} | {2,21,47} | {2,21,48} | {2,21,49} |
| {2,21,50} | {2,21,51} | {2,21,52} | {2,21,53} | {2,21,54} | {2,21,55} | {2,21,56} | {2,21,57} | {2,21,58} | {2,21,59} |
| {2,21,60} | {2,21,61} | {2,21,62} | {2,21,63} | {2,21,64} | {2,21,65} | {2,21,66} | {2,22,23} | {2,22,24} | {2,22,25} |
| {2,22,26} | {2,22,27} | {2,22,28} | {2,22,29} | {2,22,30} | {2,22,31} | {2,22,32} | {2,22,33} | {2,22,34} | {2,22,35} |
| {2,22,36} | {2,22,37} | {2,22,38} | {2,22,39} | {2,22,40} | {2,22,41} | {2,22,42} | {2,22,43} | {2,22,44} | {2,22,45} |
| {2,22,46} | {2,22,47} | {2,22,48} | {2,22,49} | {2,22,50} | {2,22,51} | {2,22,52} | {2,22,53} | {2,22,54} | {2,22,55} |
| {2,22,56} | {2,22,57} | {2,22,58} | {2,22,59} | {2,22,60} | {2,22,61} | {2,22,62} | {2,22,63} | {2,22,64} | {2,22,65} |
| {2,22,66} | {2,23,24} | {2,23,25} | {2,23,26} | {2,23,27} | {2,23,28} | {2,23,29} | {2,23,30} | {2,23,31} | {2,23,32} |
| {2,23,33} | {2,23,34} | {2,23,35} | {2,23,36} | {2,23,37} | {2,23,38} | {2,23,39} | {2,23,40} | {2,23,41} | {2,23,42} |
| {2,23,43} | {2,23,44} | {2,23,45} | {2,23,46} | {2,23,47} | {2,23,48} | {2,23,49} | {2,23,50} | {2,23,51} | {2,23,52} |
| {2,23,53} | {2,23,54} | {2,23,55} | {2,23,56} | {2,23,57} | {2,23,58} | {2,23,59} | {2,23,60} | {2,23,61} | {2,23,62} |
| {2,23,63} | {2,23,64} | {2,23,65} | {2,23,66} | {2,24,25} | {2,24,26} | {2,24,27} | {2,24,28} | {2,24,29} | {2,24,30} |
| {2,24,31} | {2,24,32} | {2,24,33} | {2,24,34} | {2,24,35} | {2,24,36} | {2,24,37} | {2,24,38} | {2,24,39} | {2,24,40} |
| {2,24,41} | {2,24,42} | {2,24,43} | {2,24,44} | {2,24,45} | {2,24,46} | {2,24,47} | {2,24,48} | {2,24,49} | {2,24,50} |
| {2,24,51} | {2,24,52} | {2,24,53} | {2,24,54} | {2,24,55} | {2,24,56} | {2,24,57} | {2,24,58} | {2,24,59} | {2,24,60} |
| {2,24,61} | {2,24,62} | {2,24,63} | {2,24,64} | {2,24,65} | {2,24,66} | {2,25,26} | {2,25,27} | {2,25,28} | {2,25,29} |
| {2,25,30} | {2,25,31} | {2,25,32} | {2,25,33} | {2,25,34} | {2,25,35} | {2,25,36} | {2,25,37} | {2,25,38} | {2,25,39} |
| {2,25,40} | {2,25,41} | {2,25,42} | {2,25,43} | {2,25,44} | {2,25,45} | {2,25,46} | {2,25,47} | {2,25,48} | {2,25,49} |
| {2,25,50} | {2,25,51} | {2,25,52} | {2,25,53} | {2,25,54} | {2,25,55} | {2,25,56} | {2,25,57} | {2,25,58} | {2,25,59} |
| {2,25,60} | {2,25,61} | {2,25,62} | {2,25,63} | {2,25,64} | {2,25,65} | {2,25,66} | {2,26,27} | {2,26,28} | {2,26,29} |
| {2,26,30} | {2,26,31} | {2,26,32} | {2,26,33} | {2,26,34} | {2,26,35} | {2,26,36} | {2,26,37} | {2,26,38} | {2,26,39} |
| {2,26,40} | {2,26,41} | {2,26,42} | {2,26,43} | {2,26,44} | {2,26,45} | {2,26,46} | {2,26,47} | {2,26,48} | {2,26,49} |
| {2,26,50} | {2,26,51} | {2,26,52} | {2,26,53} | {2,26,54} | {2,26,55} | {2,26,56} | {2,26,57} | {2,26,58} | {2,26,59} |
| {2,26,60} | {2,26,61} | {2,26,62} | {2,26,63} | {2,26,64} | {2,26,65} | {2,26,66} | {2,27,28} | {2,27,29} | {2,27,30} |
| {2,27,31} | {2,27,32} | {2,27,33} | {2,27,34} | {2,27,35} | {2,27,36} | {2,27,37} | {2,27,38} | {2,27,39} | {2,27,40} |
| {2,27,41} | {2,27,42} | {2,27,43} | {2,27,44} | {2,27,45} | {2,27,46} | {2,27,47} | {2,27,48} | {2,27,49} | {2,27,50} |
| {2,27,51} | {2,27,52} | {2,27,53} | {2,27,54} | {2,27,55} | {2,27,56} | {2,27,57} | {2,27,58} | {2,27,59} | {2,27,60} |
| {2,27,61} | {2,27,62} | {2,27,63} | {2,27,64} | {2,27,65} | {2,27,66} | {2,28,29} | {2,28,30} | {2,28,31} | {2,28,32} |
| {2,28,33} | {2,28,34} | {2,28,35} | {2,28,36} | {2,28,37} | {2,28,38} | {2,28,39} | {2,28,40} | {2,28,41} | {2,28,42} |
| {2,28,43} | {2,28,44} | {2,28,45} | {2,28,46} | {2,28,47} | {2,28,48} | {2,28,49} | {2,28,50} | {2,28,51} | {2,28,52} |
| {2,28,53} | {2,28,54} | {2,28,55} | {2,28,56} | {2,28,57} | {2,28,58} | {2,28,59} | {2,28,60} | {2,28,61} | {2,28,62} |
| {2,28,63} | {2,28,64} | {2,28,65} | {2,28,66} | {2,29,30} | {2,29,31} | {2,29,32} | {2,29,33} | {2,29,34} | {2,29,35} |
| {2,29,36} | {2,29,37} | {2,29,38} | {2,29,39} | {2,29,40} | {2,29,41} | {2,29,42} | {2,29,43} | {2,29,44} | {2,29,45} |
| {2,29,46} | {2,29,47} | {2,29,48} | {2,29,49} | {2,29,50} | {2,29,51} | {2,29,52} | {2,29,53} | {2,29,54} | {2,29,55} |
| {2,29,56} | {2,29,57} | {2,29,58} | {2,29,59} | {2,29,60} | {2,29,61} | {2,29,62} | {2,29,63} | {2,29,64} | {2,29,65} |
| {2,29,66} | {2,30,31} | {2,30,32} | {2,30,33} | {2,30,34} | {2,30,35} | {2,30,36} | {2,30,37} | {2,30,38} | {2,30,39} |
| {2,30,40} | {2,30,41} | {2,30,42} | {2,30,43} | {2,30,44} | {2,30,45} | {2,30,46} | {2,30,47} | {2,30,48} | {2,30,49} |
| {2,30,50} | {2,30,51} | {2,30,52} | {2,30,53} | {2,30,54} | {2,30,55} | {2,30,56} | {2,30,57} | {2,30,58} | {2,30,59} |
| {2,30,60} | {2,30,61} | {2,30,62} | {2,30,63} | {2,30,64} | {2,30,65} | {2,30,66} | {2,31,32} | {2,31,33} | {2,31,34} |
| {2,31,35} | {2,31,36} | {2,31,37} | {2,31,38} | {2,31,39} | {2,31,40} | {2,31,41} | {2,31,42} | {2,31,43} | {2,31,44} |
| {2,31,45} | {2,31,46} | {2,31,47} | {2,31,48} | {2,31,49} | {2,31,50} | {2,31,51} | {2,31,52} | {2,31,53} | {2,31,54} |
| {2,31,55} | {2,31,56} | {2,31,57} | {2,31,58} | {2,31,59} | {2,31,60} | {2,31,61} | {2,31,62} | {2,31,63} | {2,31,64} |
| {2,31,65} | {2,31,66} | {2,32,33} | {2,32,34} | {2,32,35} | {2,32,36} | {2,32,37} | {2,32,38} | {2,32,39} | {2,32,40} |
| {2,32,41} | {2,32,42} | {2,32,43} | {2,32,44} | {2,32,45} | {2,32,46} | {2,32,47} | {2,32,48} | {2,32,49} | {2,32,50} |
| {2,32,51} | {2,32,52} | {2,32,53} | {2,32,54} | {2,32,55} | {2,32,56} | {2,32,57} | {2,32,58} | {2,32,59} | {2,32,60} |
| {2,32,61} | {2,32,62} | {2,32,63} | {2,32,64} | {2,32,65} | {2,32,66} | {2,33,34} | {2,33,35} | {2,33,36} | {2,33,37} |
| {2,33,38} | {2,33,39} | {2,33,40} | {2,33,41} | {2,33,42} | {2,33,43} | {2,33,44} | {2,33,45} | {2,33,46} | {2,33,47} |
| {2,33,48} | {2,33,49} | {2,33,50} | {2,33,51} | {2,33,52} | {2,33,53} | {2,33,54} | {2,33,55} | {2,33,56} | {2,33,57} |
| {2,33,58} | {2,33,59} | {2,33,60} | {2,33,61} | {2,33,62} | {2,33,63} | {2,33,64} | {2,33,65} | {2,33,66} | {2,34,35} |
| {2,34,36} | {2,34,37} | {2,34,38} | {2,34,39} | {2,34,40} | {2,34,41} | {2,34,42} | {2,34,43} | {2,34,44} | {2,34,45} |
| {2,34,46} | {2,34,47} | {2,34,48} | {2,34,49} | {2,34,50} | {2,34,51} | {2,34,52} | {2,34,53} | {2,34,54} | {2,34,55} |
| {2,34,56} | {2,34,57} | {2,34,58} | {2,34,59} | {2,34,60} | {2,34,61} | {2,34,62} | {2,34,63} | {2,34,64} | {2,34,65} |
| {2,34,66} | {2,35,36} | {2,35,37} | {2,35,38} | {2,35,39} | {2,35,40} | {2,35,41} | {2,35,42} | {2,35,43} | {2,35,44} |
| {2,35,45} | {2,35,46} | {2,35,47} | {2,35,48} | {2,35,49} | {2,35,50} | {2,35,51} | {2,35,52} | {2,35,53} | {2,35,54} |
| {2,35,55} | {2,35,56} | {2,35,57} | {2,35,58} | {2,35,59} | {2,35,60} | {2,35,61 | {2,35,62} | {2,35,63} | {2,35,64} |
| {2,35,65} | {2,35,66} | {2,36,37} | {2,36,38} | {2,36,39} | {2,36,40} | {2,36,41} | {2,36,42} | {2,36,43} | {2,36,44} |
| {2,36,45} | {2,36,46} | {2,36,47} | {2,36,48} | {2,36,49} | {2,36,50} | {2,36,51} | {2,36,52} | {2,36,53} | {2,36,54} |
| {2,36,55} | {2,36,56} | {2,36,57} | {2,36,58} | {2,36,59} | {2,36,60} | {2,36,61} | {2,36,62} | {2,36,63} | {2,36,64} |
| {2,36,65} | {2,36,66} | {2,37,38} | {2,37,39} | {2,37,40} | {2,37,41} | {2,37,42} | {2,37,43} | {2,37,44} | {2,37,45} |
| {2,37,46} | {2,37,47} | {2,37,48} | {2,37,49} | {2,37,50} | {2,37,51} | {2,37,52} | {2,37,53} | {2,37,54} | {2,37,55} |
| {2,37,56} | {2,37,57} | {2,37,58} | {2,37,59} | {2,37,60} | {2,37,61} | {2,37,62} | {2,37,63} | {2,37,64} | {2,37,65} |
| {2,37,66} | {2,38,39} | {2,38,40} | {2,38,41} | {2,38,42} | {2,38,43} | {2,38,44} | {2,38,45} | {2,38,46} | {2,38,47} |
| {2,38,48} | {2,38,49} | {2,38,50} | {2,38,51} | {2,38,52} | {2,38,53} | {2,38,54} | {2,38,55} | {2,38,56} | {2,38,57} |
| {2,38,58} | {2,38,59} | {2,38,60} | {2,38,61} | {2,38,62} | {2,38,63} | {2,38,64} | {2,38,65} | {2,38,66} | {2,39,40} |
| {2,39,41} | {2,39,42} | {2,39,43} | {2,39,44} | {2,39,45} | {2,39,46} | {2,39,47} | {2,39,48} | {2,39,49} | {2,39,50} |
| {2,39,51} | {2,39,52} | {2,39,53} | {2,39,54} | {2,39,55} | {2,39,56} | {2,39,57} | {2,39,58} | {2,39,59} | {2,39,60} |
| {2,39,61} | {2,39,62} | {2,39,63} | {2,39,64} | {2,39,65} | {2,39,66} | {2,40,41} | {2,40,42} | {2,40,43} | {2,40,44} |

TABLE 3A-continued

{2,40,45} {2,40,46} {2,40,47} {2,40,48} {2,40,49} {2,40,50} {2,40,51} {2,40,52} {2,40,53} {2,40,54}
{2,40,55} {2,40,56} {2,40,57} {2,40,58} {2,40,59} {2,40,60} {2,40,61} {2,40,62} {2,40,63} {2,40,64}
{2,40,65} {2,40,66} {2,41,42} {2,41,43} {2,41,44} {2,41,45} {2,41,46} {2,41,47} {2,41,48} {2,41,49}
{2,41,50} {2,41,51} {2,41,52} {2,41,53} {2,41,54} {2,41,55} {2,41,56} {2,41,57} {2,41,58} {2,41,59}
{2,41,60} {2,41,61} {2,41,62} {2,41,63} {2,41,64} {2,41,65} {2,41,66} {2,42,43} {2,42,44} {2,42,45}
{2,42,46} {2,42,47} {2,42,48} {2,42,49} {2,42,50} {2,42,51} {2,42,52} {2,42,53} {2,42,54} {2,42,55}
{2,42,56} {2,42,57} {2,42,58} {2,42,59} {2,42,60} {2,42,61} {2,42,62} {2,42,63} {2,42,64} {2,42,65}
{2,42,66} {2,43,44} {2,43,45} {2,43,46} {2,43,47} {2,43,48} {2,43,49} {2,43,50} {2,43,51} {2,43,52}
{2,43,53} {2,43,54} {2,43,55} {2,43,56} {2,43,57} {2,43,58} {2,43,59} {2,43,60} {2,43,61} {2,43,62}
{2,43,63} {2,43,64} {2,43,65} {2,43,66} {2,44,45} {2,44,46} {2,44,47} {2,44,48} {2,44,49} {2,44,50}
{2,44,51} {2,44,52} {2,44,53} {2,44,54} {2,44,55} {2,44,56} {2,44,57} {2,44,58} {2,44,59} {2,44,60}
{2,44,61} {2,44,62} {2,44,63} {2,44,64} {2,44,65} {2,44,66} {2,45,46} {2,45,47} {2,45,48} {2,45,49}
{2,45,50} {2,45,51} {2,45,52} {2,45,53} {2,45,54} {2,45,55} {2,45,56} {2,45,57} {2,45,58} {2,45,59}
{2,45,60} {2,45,61} {2,45,62} {2,45,63} {2,45,64} {2,45,65} {2,45,66} {2,46,47} {2,46,48} {2,46,49}
{2,46,50} {2,46,51} {2,46,52} {2,46,53} {2,46,54} {2,46,55} {2,46,56} {2,46,57} {2,46,58} {2,46,59}
{2,46,60} {2,46,61} {2,46,62} {2,46,63} {2,46,64} {2,46,65} {2,46,66} {2,47,48} {2,47,49} {2,47,50}
{2,47,51} {2,47,52} {2,47,53} {2,47,54} {2,47,55} {2,47,56} {2,47,57} {2,47,58} {2,47,59} {2,47,60}
{2,47,61} {2,47,62} {2,47,63} {2,47,64} {2,47,65} {2,47,66} {2,48,49} {2,48,50} {2,48,51} {2,48,52}
{2,48,53} {2,48,54} {2,48,55} {2,48,56} {2,48,57} {2,48,58} {2,48,59} {2,48,60} {2,48,61} {2,48,62}
{2,48,63} {2,48,64} {2,48,65} {2,48,66} {2,49,50} {2,49,51} {2,49,52} {2,49,53} {2,49,54} {2,49,55}
{2,49,56} {2,49,57} {2,49,58} {2,49,59} {2,49,60} {2,49,61} {2,49,62} {2,49,63} {2,49,64} {2,49,65}
{2,49,66} {2,50,51} {2,50,52} {2,50,53} {2,50,54} {2,50,55} {2,50,56} {2,50,57} {2,50,58} {2,50,59}
{2,50,60} {2,50,61} {2,50,62} {2,50,63} {2,50,64} {2,50,65} {2,50,66} {2,51,52} {2,51,53} {2,51,54}
{2,51,55} {2,51,56} {2,51,57} {2,51,58} {2,51,59} {2,51,60} {2,51,61} {2,51,62} {2,51,63} {2,51,64}
{2,51,65} {2,51,66} {2,52,53} {2,52,54} {2,52,55} {2,52,56} {2,52,57} {2,52,58} {2,52,59} {2,52,60}
{2,52,61} {2,52,62} {2,52,63} {2,52,64} {2,52,65} {2,52,66} {2,53,54} {2,53,55} {2,53,56} {2,53,57}
{2,53,58} {2,53,59} {2,53,60} {2,53,61} {2,53,62} {2,53,63} {2,53,64} {2,53,65} {2,53,66} {2,54,55}
{2,54,56} {2,54,57} {2,54,58} {2,54,59} {2,54,60} {2,54,61} {2,54,62} {2,54,63} {2,54,64} {2,54,65}
{2,54,66} {2,55,56} {2,55,57} {2,55,58} {2,55,59} {2,55,60} {2,55,61} {2,55,62} {2,55,63} {2,55,64}
{2,55,65} {2,55,66} {2,56,57} {2,56,58} {2,56,59} {2,56,60} {2,56,61} {2,56,62} {2,56,63} {2,56,64}
{2,56,65} {2,56,66} {2,57,58} {2,57,59} {2,57,60} {2,57,61} {2,57,62} {2,57,63} {2,57,64} {2,57,65}
{2,57,66} {2,58,59} {2,58,60} {2,58,61} {2,58,62} {2,58,63} {2,58,64} {2,58,65} {2,58,66} {2,59,60}
{2,59,61} {2,59,62} {2,59,63} {2,59,64} {2,59,65} {2,59,66} {2,60,61} {2,60,62} {2,60,63} {2,60,64}
{2,60,65} {2,60,66} {2,61,62} {2,61,63} {2,61,64} {2,61,65} {2,61,66} {2,62,63} {2,62,64} {2,62,65}
{2,62,66} {2,63,64} {2,63,65} {2,63,66} {2,64,65} {2,64,66} {2,65,66} {3,4,5} {3,4,6} {3,4,7} {3,4,8} {3,4,9}
{3,4,10} {3,4,11} {3,4,12} {3,4,13} {3,4,14} {3,4,15} {3,4,16} {3,4,17} {3,4,18} {3,4,19} {3,4,20} {3,4,21}
{3,4,22} {3,4,23} {3,4,24} {3,4,25} {3,4,26} {3,4,27} {3,4,28} {3,4,29} {3,4,30} {3,4,31} {3,4,32} {3,4,33}
{3,4,34} {3,4,35} {3,4,36} {3,4,37} {3,4,38} {3,4,39} {3,4,40} {3,4,41} {3,4,42} {3,4,43} {3,4,44} {3,4,45}
{3,4,46} {3,4,47} {3,4,48} {3,4,49} {3,4,50} {3,4,51} {3,4,52} {3,4,53} {3,4,54} {3,4,55} {3,4,56} {3,4,57}
{3,4,58} {3,4,59} {3,4,60} {3,4,61} {3,4,62} {3,4,63} {3,4,64} {3,4,65} {3,4,66} {3,5,6} {3,5,7} {3,5,8} {3,5,9}
{3,5,10} {3,5,11} {3,5,12} {3,5,13} {3,5,14} {3,5,15} {3,5,16} {3,5,17} {3,5,18} {3,5,19} {3,5,20} {3,5,21}
{3,5,22} {3,5,23} {3,5,24} {3,5,25} {3,5,26} {3,5,27} {3,5,28} {3,5,29} {3,5,30} {3,5,31} {3,5,32} {3,5,33}
{3,5,34} {3,5,35} {3,5,36} {3,5,37} {3,5,38} {3,5,39} {3,5,40} {3,5,41} {3,5,42} {3,5,43} {3,5,44} {3,5,45}
{3,5,46} {3,5,47} {3,5,48} {3,5,49} {3,5,50} {3,5,51} {3,5,52} {3,5,53} {3,5,54} {3,5,55} {3,5,56} {3,5,57}
{3,5,58} {3,5,59} {3,5,60} {3,5,61} {3,5,62} {3,5,63} {3,5,64} {3,5,65} {3,5,66} {3,6,7} {3,6,8} {3,6,9} {3,6,10}
{3,6,11} {3,6,12} {3,6,13} {3,6,14} {3,6,15} {3,6,16} {3,6,17} {3,6,18} {3,6,19} {3,6,20} {3,6,21} {3,6,22}
{3,6,23} {3,6,24} {3,6,25} {3,6,26} {3,6,27} {3,6,28} {3,6,29} {3,6,30} {3,6,31} {3,6,32} {3,6,33} {3,6,34}
{3,6,35} {3,6,36} {3,6,37} {3,6,38} {3,6,39} {3,6,40} {3,6,41} {3,6,42} {3,6,43} {3,6,44} {3,6,45} {3,6,46}
{3,6,47} {3,6,48} {3,6,49} {3,6,50} {3,6,51} {3,6,52} {3,6,53} {3,6,54} {3,6,55} {3,6,56} {3,6,57} {3,6,58}
{3,6,59} {3,6,60} {3,6,61} {3,6,62} {3,6,63} {3,6,64} {3,6,65} {3,6,66} {3,7,8} {3,7,9} {3,7,10} {3,7,11}
{3,7,12} {3,7,13} {3,7,14} {3,7,15} {3,7,16} {3,7,17} {3,7,18} {3,7,19} {3,7,20} {3,7,21} {3,7,22} {3,7,23}
{3,7,24} {3,7,25} {3,7,26} {3,7,27} {3,7,28} {3,7,29} {3,7,30} {3,7,31} {3,7,32} {3,7,33} {3,7,34} {3,7,35}
{3,7,36} {3,7,37} {3,7,38} {3,7,39} {3,7,40} {3,7,41} {3,7,42} {3,7,43} {3,7,44} {3,7,45} {3,7,46} {3,7,47}
{3,7,48} {3,7,49} {3,7,50} {3,7,51} {3,7,52} {3,7,53} {3,7,54} {3,7,55} {3,7,56} {3,7,57} {3,7,58} {3,7,59}
{3,7,60} {3,7,61} {3,7,62} {3,7,63} {3,7,64} {3,7,65} {3,7,66} {3,8,9} {3,8,10} {3,8,11} {3,8,12} {3,8,13}
{3,8,14} {3,8,15} {3,8,16} {3,8,17} {3,8,18} {3,8,19} {3,8,20} {3,8,21} {3,8,22} {3,8,23} {3,8,24} {3,8,25}
{3,8,26} {3,8,27} {3,8,28} {3,8,29} {3,8,30} {3,8,31} {3,8,32} {3,8,33} {3,8,34} {3,8,35} {3,8,36} {3,8,37}
{3,8,38} {3,8,39} {3,8,40} {3,8,41} {3,8,42} {3,8,43} {3,8,44} {3,8,45} {3,8,46} {3,8,47} {3,8,48} {3,8,49}
{3,8,50} {3,8,51} {3,8,52} {3,8,53} {3,8,54} {3,8,55} {3,8,56} {3,8,57} {3,8,58} {3,8,59} {3,8,60} {3,8,61}
{3,8,62} {3,8,63} {3,8,64} {3,8,65} {3,8,66} {3,9,10} {3,9,11} {3,9,12} {3,9,13} {3,9,14} {3,9,15} {3,9,16}
{3,9,17} {3,9,18} {3,9,19} {3,9,20} {3,9,21} {3,9,22} {3,9,23} {3,9,24} {3,9,25} {3,9,26} {3,9,27} {3,9,28}
{3,9,29} {3,9,30} {3,9,31} {3,9,32} {3,9,33} {3,9,34} {3,9,35} {3,9,36} {3,9,37} {3,9,38} {3,9,39} {3,9,40}
{3,9,41} {3,9,42} {3,9,43} {3,9,44} {3,9,45} {3,9,46} {3,9,47} {3,9,48} {3,9,49} {3,9,50} {3,9,51} {3,9,52}
{3,9,53} {3,9,54} {3,9,55} {3,9,56} {3,9,57} {3,9,58} {3,9,59} {3,9,60} {3,9,61} {3,9,62} {3,9,63} {3,9,64}
{3,9,65} {3,9,66} {3,10,11} {3,10,12} {3,10,13} {3,10,14} {3,10,15} {3,10,16} {3,10,17} {3,10,18} {3,10,19}
{3,10,20} {3,10,21} {3,10,22} {3,10,23} {3,10,24} {3,10,25} {3,10,26} {3,10,27} {3,10,28} {3,10,29}
{3,10,30} {3,10,31} {3,10,32} {3,10,33} {3,10,34} {3,10,35} {3,10,36} {3,10,37} {3,10,38} {3,10,39}
{3,10,40} {3,10,41} {3,10,42} {3,10,43} {3,10,44} {3,10,45} {3,10,46} {3,10,47} {3,10,48} {3,10,49}
{3,10,50} {3,10,51} {3,10,52} {3,10,53} {3,10,54} {3,10,55} {3,10,56} {3,10,57} {3,10,58} {3,10,59}
{3,10,60} {3,10,61} {3,10,62} {3,10,63} {3,10,64} {3,10,65} {3,10,66} {3,11,12} {3,11,13} {3,11,14}
{3,11,15} {3,11,16} {3,11,17} {3,11,18} {3,11,19} {3,11,20} {3,11,21} {3,11,22} {3,11,23} {3,11,24}
{3,11,25} {3,11,26} {3,11,27} {3,11,28} {3,11,29} {3,11,30} {3,11,31} {3,11,32} {3,11,33} {3,11,34}
{3,11,35} {3,11,36} {3,11,37} {3,11,38} {3,11,39} {3,11,40} {3,11,41} {3,11,42} {3,11,43} {3,11,44}
{3,11,45} {3,11,46} {3,11,47} {3,11,48} {3,11,49} {3,11,50} {3,11,51} {3,11,52} {3,11,53} {3,11,54}
{3,11,55} {3,11,56} {3,11,57} {3,11,58} {3,11,59} {3,11,60} {3,11,61} {3,11,62} {3,11,63} {3,11,64}
{3,11,65} {3,11,66} {3,12,13} {3,12,14} {3,12,15} {3,12,16} {3,12,17} {3,12,18} {3,12,19} {3,12,20}
{3,12,21} {3,12,22} {3,12,23} {3,12,24} {3,12,25} {3,12,26} {3,12,27} {3,12,28} {3,12,29} {3,12,30}
{3,12,31} {3,12,32} {3,12,33} {3,12,34} {3,12,35} {3,12,36} {3,12,37} {3,12,38} {3,12,39} {3,12,40}
{3,12,41} {3,12,42} {3,12,43} {3,12,44} {3,12,45} {3,12,46} {3,12,47} {3,12,48} {3,12,49} {3,12,50}
{3,12,51} {3,12,52} {3,12,53} {3,12,54} {3,12,55} {3,12,56} {3,12,57} {3,12,58} {3,12,59} {3,12,60}

TABLE 3A-continued

{3,12,61} {3,12,62} {3,12,63} {3,12,64} {3,12,65} {3,12,66} {3,13,14} {3,13,15} {3,13,16} {3,13,17}
{3,13,18} {3,13,19} {3,13,20} {3,13,21} {3,13,22} {3,13,23} {3,13,24} {3,13,25} {3,13,26} {3,13,27}
{3,13,28} {3,13,29} {3,13,30} {3,13,31} {3,13,32} {3,13,33} {3,13,34} {3,13,35} {3,13,36} {3,13,37}
{3,13,38} {3,13,39} {3,13,40} {3,13,41} {3,13,42} {3,13,43} {3,13,44} {3,13,45} {3,13,46} {3,13,47}
{3,13,48} {3,13,49} {3,13,50} {3,13,51} {3,13,52} {3,13,53} {3,13,54} {3,13,55} {3,13,56} {3,13,57}
{3,13,58} {3,13,59} {3,13,60} {3,13,61} {3,13,62} {3,13,63} {3,13,64} {3,13,65} {3,13,66} {3,14,15}
{3,14,16} {3,14,17} {3,14,18} {3,14,19} {3,14,20} {3,14,21} {3,14,22} {3,14,23} {3,14,24} {3,14,25}
{3,14,26} {3,14,27} {3,14,28} {3,14,29} {3,14,30} {3,14,31} {3,14,32} {3,14,33} {3,14,34} {3,14,35}
{3,14,36} {3,14,37} {3,14,38} {3,14,39} {3,14,40} {3,14,41} {3,14,42} {3,14,43} {3,14,44} {3,14,45}
{3,14,46} {3,14,47} {3,14,48} {3,14,49} {3,14,50} {3,14,51} {3,14,52} {3,14,53} {3,14,54} {3,14,55}
{3,14,56} {3,14,57} {3,14,58} {3,14,59} {3,14,60} {3,14,61} {3,14,62} {3,14,63} {3,14,64} {3,14,65}
{3,14,66} {3,15,16} {3,15,17} {3,15,18} {3,15,19} {3,15,20} {3,15,21} {3,15,22} {3,15,23} {3,15,24}
{3,15,25} {3,15,26} {3,15,27} {3,15,28} {3,15,29} {3,15,30} {3,15,31} {3,15,32} {3,15,33} {3,15,34}
{3,15,35} {3,15,36} {3,15,37} {3,15,38} {3,15,39} {3,15,40} {3,15,41} {3,15,42} {3,15,43} {3,15,44}
{3,15,45} {3,15,46} {3,15,47} {3,15,48} {3,15,49} {3,15,50} {3,15,51} {3,15,52} {3,15,53} {3,15,54}
{3,15,55} {3,15,56} {3,15,57} {3,15,58} {3,15,59} {3,15,60} {3,15,61} {3,15,62} {3,15,63} {3,15,64}
{3,15,65} {3,15,66} {3,16,17} {3,16,18} {3,16,19} {3,16,20} {3,16,21} {3,16,22} {3,16,23} {3,16,24}
{3,16,25} {3,16,26} {3,16,27} {3,16,28} {3,16,29} {3,16,30} {3,16,31} {3,16,32} {3,16,33} {3,16,34}
{3,16,35} {3,16,36} {3,16,37} {3,16,38} {3,16,39} {3,16,40} {3,16,41} {3,16,42} {3,16,43} {3,16,44}
{3,16,45} {3,16,46} {3,16,47} {3,16,48} {3,16,49} {3,16,50} {3,16,51} {3,16,52} {3,16,53} {3,16,54}
{3,16,55} {3,16,56} {3,16,57} {3,16,58} {3,16,59} {3,16,60} {3,16,61} {3,16,62} {3,16,63} {3,16,64}
{3,16,65} {3,16,66} {3,17,18} {3,17,19} {3,17,20} {3,17,21} {3,17,22} {3,17,23} {3,17,24} {3,17,25}
{3,17,26} {3,17,27} {3,17,28} {3,17,29} {3,17,30} {3,17,31} {3,17,32} {3,17,33} {3,17,34} {3,17,35}
{3,17,36} {3,17,37} {3,17,38} {3,17,39} {3,17,40} {3,17,41} {3,17,42} {3,17,43} {3,17,44} {3,17,45}
{3,17,46} {3,17,47} {3,17,48} {3,17,49} {3,17,50} {3,17,51} {3,17,52} {3,17,53} {3,17,54} {3,17,55}
{3,17,56} {3,17,57} {3,17,58} {3,17,59} {3,17,60} {3,17,61} {3,17,62} {3,17,63} {3,17,64} {3,17,65}
{3,17,66} {3,18,19} {3,18,20} {3,18,21} {3,18,22} {3,18,23} {3,18,24} {3,18,25} {3,18,26} {3,18,27}
{3,18,28} {3,18,29} {3,18,30} {3,18,31} {3,18,32} {3,18,33} {3,18,34} {3,18,35} {3,18,36} {3,18,37}
{3,18,38} {3,18,39} {3,18,40} {3,18,41} {3,18,42} {3,18,43} {3,18,44} {3,18,45} {3,18,46} {3,18,47}
{3,18,48} {3,18,49} {3,18,50} {3,18,51} {3,18,52} {3,18,53} {3,18,54} {3,18,55} {3,18,56} {3,18,57}
{3,18,58} {3,18,59} {3,18,60} {3,18,61} {3,18,62} {3,18,63} {3,18,64} {3,18,65} {3,18,66} {3,19,20}
{3,19,21} {3,19,22} {3,19,23} {3,19,24} {3,19,25} {3,19,26} {3,19,27} {3,19,28} {3,19,29} {3,19,30}
{3,19,31} {3,19,32} {3,19,33} {3,19,34} {3,19,35} {3,19,36} {3,19,37} {3,19,38} {3,19,39} {3,19,40}
{3,19,41} {3,19,42} {3,19,43} {3,19,44} {3,19,45} {3,19,46} {3,19,47} {3,19,48} {3,19,49} {3,19,50}
{3,19,51} {3,19,52} {3,19,53} {3,19,54} {3,19,55} {3,19,56} {3,19,57} {3,19,58} {3,19,59} {3,19,60}
{3,19,61} {3,19,62} {3,19,63} {3,19,64} {3,19,65} {3,19,66} {3,20,21} {3,20,22} {3,20,23} {3,20,24}
{3,20,25} {3,20,26} {3,20,27} {3,20,28} {3,20,29} {3,20,30} {3,20,31} {3,20,32} {3,20,33} {3,20,34}
{3,20,35} {3,20,36} {3,20,37} {3,20,38} {3,20,39} {3,20,40} {3,20,41} {3,20,42} {3,20,43} {3,20,44}
{3,20,45} {3,20,46} {3,20,47} {3,20,48} {3,20,49} {3,20,50} {3,20,51} {3,20,52} {3,20,53} {3,20,54}
{3,20,55} {3,20,56} {3,20,57} {3,20,58} {3,20,59} {3,20,60} {3,20,61} {3,20,62} {3,20,63} {3,20,64}
{3,20,65} {3,20,66} {3,21,22} {3,21,23} {3,21,24} {3,21,25} {3,21,26} {3,21,27} {3,21,28} {3,21,29}
{3,21,30} {3,21,31} {3,21,32} {3,21,33} {3,21,34} {3,21,35} {3,21,36} {3,21,37} {3,21,38} {3,21,39}
{3,21,40} {3,21,41} {3,21,42} {3,21,43} {3,21,44} {3,21,45} {3,21,46} {3,21,47} {3,21,48} {3,21,49}
{3,21,50} {3,21,51} {3,21,52} {3,21,53} {3,21,54} {3,21,55} {3,21,56} {3,21,57} {3,21,58} {3,21,59}
{3,21,60} {3,21,61} {3,21,62} {3,21,63} {3,21,64} {3,21,65} {3,21,66} {3,22,23} {3,22,24} {3,22,25}
{3,22,26} {3,22,27} {3,22,28} {3,22,29} {3,22,30} {3,22,31} {3,22,32} {3,22,33} {3,22,34} {3,22,35}
{3,22,36} {3,22,37} {3,22,38} {3,22,39} {3,22,40} {3,22,41} {3,22,42} {3,22,43} {3,22,44} {3,22,45}
{3,22,46} {3,22,47} {3,22,48} {3,22,49} {3,22,50} {3,22,51} {3,22,52} {3,22,53} {3,22,54} {3,22,55}
{3,22,56} {3,22,57} {3,22,58} {3,22,59} {3,22,60} {3,22,61} {3,22,62} {3,22,63} {3,22,64} {3,22,65}
{3,22,66} {3,23,24} {3,23,25} {3,23,26} {3,23,27} {3,23,28} {3,23,29} {3,23,30} {3,23,31} {3,23,32}
{3,23,33} {3,23,34} {3,23,35} {3,23,36} {3,23,37} {3,23,38} {3,23,39} {3,23,40} {3,23,41} {3,23,42}
{3,23,43} {3,23,44} {3,23,45} {3,23,46} {3,23,47} {3,23,48} {3,23,49} {3,23,50} {3,23,51} {3,23,52}
{3,23,53} {3,23,54} {3,23,55} {3,23,56} {3,23,57} {3,23,58} {3,23,59} {3,23,60} {3,23,61} {3,23,62}
{3,23,63} {3,23,64} {3,23,65} {3,23,66} {3,24,25} {3,24,26} {3,24,27} {3,24,28} {3,24,29} {3,24,30}
{3,24,31} {3,24,32} {3,24,33} {3,24,34} {3,24,35} {3,24,36} {3,24,37} {3,24,38} {3,24,39} {3,24,40}
{3,24,41} {3,24,42} {3,24,43} {3,24,44} {3,24,45} {3,24,46} {3,24,47} {3,24,48} {3,24,49} {3,24,50}
{3,24,51} {3,24,52} {3,24,53} {3,24,54} {3,24,55} {3,24,56} {3,24,57} {3,24,58} {3,24,59} {3,24,60}
{3,24,61} {3,24,62} {3,24,63} {3,24,64} {3,24,65} {3,24,66} {3,25,26} {3,25,27} {3,25,28} {3,25,29}
{3,25,30} {3,25,31} {3,25,32} {3,25,33} {3,25,34} {3,25,35} {3,25,36} {3,25,37} {3,25,38} {3,25,39}
{3,25,40} {3,25,41} {3,25,42} {3,25,43} {3,25,44} {3,25,45} {3,25,46} {3,25,47} {3,25,48} {3,25,49}
{3,25,50} {3,25,51} {3,25,52} {3,25,53} {3,25,54} {3,25,55} {3,25,56} {3,25,57} {3,25,58} {3,25,59}
{3,25,60} {3,25,61} {3,25,62} {3,25,63} {3,25,64} {3,25,65} {3,25,66} {3,26,27} {3,26,28} {3,26,29}
{3,26,30} {3,26,31} {3,26,32} {3,26,33} {3,26,34} {3,26,35} {3,26,36} {3,26,37} {3,26,38} {3,26,39}
{3,26,40} {3,26,41} {3,26,42} {3,26,43} {3,26,44} {3,26,45} {3,26,46} {3,26,47} {3,26,48} {3,26,49}
{3,26,50} {3,26,51} {3,26,52} {3,26,53} {3,26,54} {3,26,55} {3,26,56} {3,26,57} {3,26,58} {3,26,59}
{3,26,60} {3,26,61} {3,26,62} {3,26,63} {3,26,64} {3,26,65} {3,26,66} {3,27,28} {3,27,29} {3,27,30}
{3,27,31} {3,27,32} {3,27,33} {3,27,34} {3,27,35} {3,27,36} {3,27,37} {3,27,38} {3,27,39} {3,27,40}
{3,27,41} {3,27,42} {3,27,43} {3,27,44} {3,27,45} {3,27,46} {3,27,47} {3,27,48} {3,27,49} {3,27,50}
{3,27,51} {3,27,52} {3,27,53} {3,27,54} {3,27,55} {3,27,56} {3,27,57} {3,27,58} {3,27,59} {3,27,60}
{3,27,61} {3,27,62} {3,27,63} {3,27,64} {3,27,65} {3,27,66} {3,28,29} {3,28,30} {3,28,31} {3,28,32}
{3,28,33} {3,28,34} {3,28,35} {3,28,36} {3,28,37} {3,28,38} {3,28,39} {3,28,40} {3,28,41} {3,28,42}
{3,28,43} {3,28,44} {3,28,45} {3,28,46} {3,28,47} {3,28,48} {3,28,49} {3,28,50} {3,28,51} {3,28,52}
{3,28,53} {3,28,54} {3,28,55} {3,28,56} {3,28,57} {3,28,58} {3,28,59} {3,28,60} {3,28,61} {3,28,62}
{3,28,63} {3,28,64} {3,28,65} {3,28,66} {3,29,30} {3,29,31} {3,29,32} {3,29,33} {3,29,34} {3,29,35}
{3,29,36} {3,29,37} {3,29,38} {3,29,39} {3,29,40} {3,29,41} {3,29,42} {3,29,43} {3,29,44} {3,29,45}
{3,29,46} {3,29,47} {3,29,48} {3,29,49} {3,29,50} {3,29,51} {3,29,52} {3,29,53} {3,29,54} {3,29,55}
{3,29,56} {3,29,57} {3,29,58} {3,29,59} {3,29,60} {3,29,61} {3,29,62} {3,29,63} {3,29,64} {3,29,65}
{3,29,66} {3,30,31} {3,30,32} {3,30,33} {3,30,34} {3,30,35} {3,30,36} {3,30,37} {3,30,38} {3,30,39}
{3,30,40} {3,30,41} {3,30,42} {3,30,43} {3,30,44} {3,30,45} {3,30,46} {3,30,47} {3,30,48} {3,30,49}
{3,30,50} {3,30,51} {3,30,52} {3,30,53} {3,30,54} {3,30,55} {3,30,56} {3,30,57} {3,30,58} {3,30,59}

TABLE 3A-continued

{3,30,60} {3,30,61} {3,30,62} {3,30,63} {3,30,64} {3,30,65} {3,30,66} {3,31,32} {3,31,33} {3,31,34}
{3,31,35} {3,31,36} {3,31,37} {3,31,38} {3,31,39} {3,31,40} {3,31,41} {3,31,42} {3,31,43} {3,31,44}
{3,31,45} {3,31,46} {3,31,47} {3,31,48} {3,31,49} {3,31,50} {3,31,51} {3,31,52} {3,31,53} {3,31,54}
{3,31,55} {3,31,56} {3,31,57} {3,31,58} {3,31,59} {3,31,60} {3,31,61} {3,31,62} {3,31,63} {3,31,64}
{3,31,65} {3,31,66} {3,32,33} {3,32,34} {3,32,35} {3,32,36} {3,32,37} {3,32,38} {3,32,39} {3,32,40}
{3,32,41} {3,32,42} {3,32,43} {3,32,44} {3,32,45} {3,32,46} {3,32,47} {3,32,48} {3,32,49} {3,32,50}
{3,32,51} {3,32,52} {3,32,53} {3,32,54} {3,32,55} {3,32,56} {3,32,57} {3,32,58} {3,32,59} {3,32,60}
{3,32,61} {3,32,62} {3,32,63} {3,32,64} {3,32,65} {3,32,66} {3,33,34} {3,33,35} {3,33,36} {3,33,37}
{3,33,38} {3,33,39} {3,33,40} {3,33,41} {3,33,42} {3,33,43} {3,33,44} {3,33,45} {3,33,46} {3,33,47}
{3,33,48} {3,33,49} {3,33,50} {3,33,51} {3,33,52} {3,33,53} {3,33,54} {3,33,55} {3,33,56} {3,33,57}
{3,33,58} {3,33,59} {3,33,60} {3,33,61} {3,33,62} {3,33,63} {3,33,64} {3,33,65} {3,33,66} {3,34,35}
{3,34,36} {3,34,37} {3,34,38} {3,34,39} {3,34,40} {3,34,41} {3,34,42} {3,34,43} {3,34,44} {3,34,45}
{3,34,46} {3,34,47} {3,34,48} {3,34,49} {3,34,50} {3,34,51} {3,34,52} {3,34,53} {3,34,54} {3,34,55}
{3,34,56} {3,34,57} {3,34,58} {3,34,59} {3,34,60} {3,34,61} {3,34,62} {3,34,63} {3,34,64} {3,34,65}
{3,34,66} {3,35,36} {3,35,37} {3,35,38} {3,35,39} {3,35,40} {3,35,41} {3,35,42} {3,35,43} {3,35,44}
{3,35,45} {3,35,46} {3,35,47} {3,35,48} {3,35,49} {3,35,50} {3,35,51} {3,35,52} {3,35,53} {3,35,54}
{3,35,55} {3,35,56} {3,35,57} {3,35,58} {3,35,59} {3,35,60} {3,35,61} {3,35,62} {3,35,63} {3,35,64}
{3,35,65} {3,35,66} {3,36,37} {3,36,38} {3,36,39} {3,36,40} {3,36,41} {3,36,42} {3,36,43} {3,36,44}
{3,36,45} {3,36,46} {3,36,47} {3,36,48} {3,36,49} {3,36,50} {3,36,51} {3,36,52} {3,36,53} {3,36,54}
{3,36,55} {3,36,56} {3,36,57} {3,36,58} {3,36,59} {3,36,60} {3,36,61} {3,36,62} {3,36,63} {3,36,64}
{3,36,65} {3,36,66} {3,37,38} {3,37,39} {3,37,40} {3,37,41} {3,37,42} {3,37,43} {3,37,44} {3,37,45}
{3,37,46} {3,37,47} {3,37,48} {3,37,49} {3,37,50} {3,37,51} {3,37,52} {3,37,53} {3,37,54} {3,37,55}
{3,37,56} {3,37,57} {3,37,58} {3,37,59} {3,37,60} {3,37,61} {3,37,62} {3,37,63} {3,37,64} {3,37,65}
{3,37,66} {3,38,39} {3,38,40} {3,38,41} {3,38,42} {3,38,43} {3,38,44} {3,38,45} {3,38,46} {3,38,47}
{3,38,48} {3,38,49} {3,38,50} {3,38,51} {3,38,52} {3,38,53} {3,38,54} {3,38,55} {3,38,56} {3,38,57}
{3,38,58} {3,38,59} {3,38,60} {3,38,61} {3,38,62} {3,38,63} {3,38,64} {3,38,65} {3,38,66} {3,39,40}
{3,39,41} {3,39,42} {3,39,43} {3,39,44} {3,39,45} {3,39,46} {3,39,47} {3,39,48} {3,39,49} {3,39,50}
{3,39,51} {3,39,52} {3,39,53} {3,39,54} {3,39,55} {3,39,56} {3,39,57} {3,39,58} {3,39,59} {3,39,60}
{3,39,61} {3,39,62} {3,39,63} {3,39,64} {3,39,65} {3,39,66} {3,40,41} {3,40,42} {3,40,43} {3,40,44}
{3,40,45} {3,40,46} {3,40,47} {3,40,48} {3,40,49} {3,40,50} {3,40,51} {3,40,52} {3,40,53} {3,40,54}
{3,40,55} {3,40,56} {3,40,57} {3,40,58} {3,40,59} {3,40,60} {3,40,61} {3,40,62} {3,40,63} {3,40,64}
{3,40,65} {3,40,66} {3,41,42} {3,41,43} {3,41,44} {3,41,45} {3,41,46} {3,41,47} {3,41,48} {3,41,49}
{3,41,50} {3,41,51} {3,41,52} {3,41,53} {3,41,54} {3,41,55} {3,41,56} {3,41,57} {3,41,58} {3,41,59}
{3,41,60} {3,41,61} {3,41,62} {3,41,63} {3,41,64} {3,41,65} {3,41,66} {3,42,43} {3,42,44} {3,42,45}
{3,42,46} {3,42,47} {3,42,48} {3,42,49} {3,42,50} {3,42,51} {3,42,52} {3,42,53} {3,42,54} {3,42,55}
{3,42,56} {3,42,57} {3,42,58} {3,42,59} {3,42,60} {3,42,61} {3,42,62} {3,42,63} {3,42,64} {3,42,65}
{3,42,66} {3,43,44} {3,43,45} {3,43,46} {3,43,47} {3,43,48} {3,43,49} {3,43,50} {3,43,51} {3,43,52}
{3,43,53} {3,43,54} {3,43,55} {3,43,56} {3,43,57} {3,43,58} {3,43,59} {3,43,60} {3,43,61} {3,43,62}
{3,43,63} {3,43,64} {3,43,65} {3,43,66} {3,44,45} {3,44,46} {3,44,47} {3,44,48} {3,44,49} {3,44,50}
{3,44,51} {3,44,52} {3,44,53} {3,44,54} {3,44,55} {3,44,56} {3,44,57} {3,44,58} {3,44,59} {3,44,60}
{3,44,61} {3,44,62} {3,44,63} {3,44,64} {3,44,65} {3,44,66} {3,45,46} {3,45,47} {3,45,48} {3,45,49}
{3,45,50} {3,45,51} {3,45,52} {3,45,53} {3,45,54} {3,45,55} {3,45,56} {3,45,57} {3,45,58} {3,45,59}
{3,45,60} {3,45,61} {3,45,62} {3,45,63} {3,45,64} {3,45,65} {3,45,66} {3,46,47} {3,46,48} {3,46,49}
{3,46,50} {3,46,51} {3,46,52} {3,46,53} {3,46,54} {3,46,55} {3,46,56} {3,46,57} {3,46,58} {3,46,59}
{3,46,60} {3,46,61} {3,46,62} {3,46,63} {3,46,64} {3,46,65} {3,46,66} {3,47,48} {3,47,49} {3,47,50}
{3,47,51} {3,47,52} {3,47,53} {3,47,54} {3,47,55} {3,47,56} {3,47,57} {3,47,58} {3,47,59} {3,47,60}
{3,47,61} {3,47,62} {3,47,63} {3,47,64} {3,47,65} {3,47,66} {3,48,49} {3,48,50} {3,48,51} {3,48,52}
{3,48,53} {3,48,54} {3,48,55} {3,48,56} {3,48,57} {3,48,58} {3,48,59} {3,48,60} {3,48,61} {3,48,62}
{3,48,63} {3,48,64} {3,48,65} {3,48,66} {3,49,50} {3,49,51} {3,49,52} {3,49,53} {3,49,54} {3,49,55}
{3,49,56} {3,49,57} {3,49,58} {3,49,59} {3,49,60} {3,49,61} {3,49,62} {3,49,63} {3,49,64} {3,49,65}
{3,49,66} {3,50,51} {3,50,52} {3,50,53} {3,50,54} {3,50,55} {3,50,56} {3,50,57} {3,50,58} {3,50,59}
{3,50,60} {3,50,61} {3,50,62} {3,50,63} {3,50,64} {3,50,65} {3,50,66} {3,51,52} {3,51,53} {3,51,54}
{3,51,55} {3,51,56} {3,51,57} {3,51,58} {3,51,59} {3,51,60} {3,51,61} {3,51,62} {3,51,63} {3,51,64}
{3,51,65} {3,51,66} {3,52,53} {3,52,54} {3,52,55} {3,52,56} {3,52,57} {3,52,58} {3,52,59} {3,52,60}
{3,52,61} {3,52,62} {3,52,63} {3,52,64} {3,52,65} {3,52,66} {3,53,54} {3,53,55} {3,53,56} {3,53,57}
{3,53,58} {3,53,59} {3,53,60} {3,53,61} {3,53,62} {3,53,63} {3,53,64} {3,53,65} {3,53,66} {3,54,55}
{3,54,56} {3,54,57} {3,54,58} {3,54,59} {3,54,60} {3,54,61} {3,54,62} {3,54,63} {3,54,64} {3,54,65}
{3,54,66} {3,55,56} {3,55,57} {3,55,58} {3,55,59} {3,55,60} {3,55,61} {3,55,62} {3,55,63} {3,55,64}
{3,55,65} {3,55,66} {3,56,57} {3,56,58} {3,56,59} {3,56,60} {3,56,61} {3,56,62} {3,56,63} {3,56,64}
{3,56,65} {3,56,66} {3,57,58} {3,57,59} {3,57,60} {3,57,61} {3,57,62} {3,57,63} {3,57,64} {3,57,65}
{3,57,66} {3,58,59} {3,58,60} {3,58,61} {3,58,62} {3,58,63} {3,58,64} {3,58,65} {3,58,66} {3,59,60}
{3,59,61} {3,59,62} {3,59,63} {3,59,64} {3,59,65} {3,59,66} {3,60,61} {3,60,62} {3,60,63} {3,60,64}
{3,60,65} {3,60,66} {3,61,62} {3,61,63} {3,61,64} {3,61,65} {3,61,66} {3,62,63} {3,62,64} {3,62,65}
{3,62,66} {3,63,64} {3,63,65} {3,63,66} {3,64,65} {3,64,66} {3,65,66} {4,5,6} {4,5,7} {4,5,8} {4,5,9} {4,5,10}
{4,5,11} {4,5,12} {4,5,13} {4,5,14} {4,5,15} {4,5,16} {4,5,17} {4,5,18} {4,5,19} {4,5,20} {4,5,21} {4,5,22}
{4,5,23} {4,5,24} {4,5,25} {4,5,26} {4,5,27} {4,5,28} {4,5,29} {4,5,30} {4,5,31} {4,5,32} {4,5,33} {4,5,34}
{4,5,35} {4,5,36} {4,5,37} {4,5,38} {4,5,39} {4,5,40} {4,5,41} {4,5,42} {4,5,43} {4,5,44} {4,5,45} {4,5,46}
{4,5,47} {4,5,48} {4,5,49} {4,5,50} {4,5,51} {4,5,52} {4,5,53} {4,5,54} {4,5,55} {4,5,56} {4,5,57} {4,5,58}
{4,5,59} {4,5,60} {4,5,61} {4,5,62} {4,5,63} {4,5,64} {4,5,65} {4,5,66} {4,6,7} {4,6,8} {4,6,9} {4,6,10} {4,6,11}
{4,6,12} {4,6,13} {4,6,14} {4,6,15} {4,6,16} {4,6,17} {4,6,18} {4,6,19} {4,6,20} {4,6,21} {4,6,22} {4,6,23}
{4,6,24} {4,6,25} {4,6,26} {4,6,27} {4,6,28} {4,6,29} {4,6,30} {4,6,31} {4,6,32} {4,6,33} {4,6,34} {4,6,35}
{4,6,36} {4,6,37} {4,6,38} {4,6,39} {4,6,40} {4,6,41} {4,6,42} {4,6,43} {4,6,44} {4,6,45} {4,6,46} {4,6,47}
{4,6,48} {4,6,49} {4,6,50} {4,6,51} {4,6,52} {4,6,53} {4,6,54} {4,6,55} {4,6,56} {4,6,57} {4,6,58} {4,6,59}
{4,6,60} {4,6,61} {4,6,62} {4,6,63} {4,6,64} {4,6,65} {4,6,66} {4,7,8} {4,7,9} {4,7,10} {4,7,11} {4,7,12}
{4,7,13} {4,7,14} {4,7,15} {4,7,16} {4,7,17} {4,7,18} {4,7,19} {4,7,20} {4,7,21} {4,7,22} {4,7,23} {4,7,24}
{4,7,25} {4,7,26} {4,7,27} {4,7,28} {4,7,29} {4,7,30} {4,7,31} {4,7,32} {4,7,33} {4,7,34} {4,7,35} {4,7,36}
{4,7,37} {4,7,38} {4,7,39} {4,7,40} {4,7,41} {4,7,42} {4,7,43} {4,7,44} {4,7,45} {4,7,46} {4,7,47} {4,7,48}
{4,7,49} {4,7,50} {4,7,51} {4,7,52} {4,7,53} {4,7,54} {4,7,55} {4,7,56} {4,7,57} {4,7,58} {4,7,59} {4,7,60}
{4,7,61} {4,7,62} {4,7,63} {4,7,64} {4,7,65} {4,7,66} {4,8,9} {4,8,10} {4,8,11} {4,8,12} {4,8,13} {4,8,14}
{4,8,15} {4,8,16} {4,8,17} {4,8,18} {4,8,19} {4,8,20} {4,8,21} {4,8,22} {4,8,23} {4,8,24} {4,8,25} {4,8,26}

TABLE 3A-continued

{4,8,27} {4,8,28} {4,8,29} {4,8,30} {4,8,31} {4,8,32} {4,8,33} {4,8,34} {4,8,35} {4,8,36} {4,8,37} {4,8,38}
{4,8,39} {4,8,40} {4,8,41} {4,8,42} {4,8,43} {4,8,44} {4,8,45} {4,8,46} {4,8,47} {4,8,48} {4,8,49} {4,8,50}
{4,8,51} {4,8,52} {4,8,53} {4,8,54} {4,8,55} {4,8,56} {4,8,57} {4,8,58} {4,8,59} {4,8,60} {4,8,61} {4,8,62}
{4,8,63} {4,8,64} {4,8,65} {4,8,66} {4,9,10} {4,9,11} {4,9,12} {4,9,13} {4,9,14} {4,9,15} {4,9,16} {4,9,17}
{4,9,18} {4,9,19} {4,9,20} {4,9,21} {4,9,22} {4,9,23} {4,9,24} {4,9,25} {4,9,26} {4,9,27} {4,9,28} {4,9,29}
{4,9,30} {4,9,31} {4,9,32} {4,9,33} {4,9,34} {4,9,35} {4,9,36} {4,9,37} {4,9,38} {4,9,39} {4,9,40} {4,9,41}
{4,9,42} {4,9,43} {4,9,44} {4,9,45} {4,9,46} {4,9,47} {4,9,48} {4,9,49} {4,9,50} {4,9,51} {4,9,52} {4,9,53}
{4,9,54} {4,9,55} {4,9,56} {4,9,57} {4,9,58} {4,9,59} {4,9,60} {4,9,61} {4,9,62} {4,9,63} {4,9,64} {4,9,65}
{4,9,66} {4,10,11} {4,10,12} {4,10,13} {4,10,14} {4,10,15} {4,10,16} {4,10,17} {4,10,18} {4,10,19} {4,10,20}
{4,10,21} {4,10,22} {4,10,23} {4,10,24} {4,10,25} {4,10,26} {4,10,27} {4,10,28} {4,10,29} {4,10,30}
{4,10,31} {4,10,32} {4,10,33} {4,10,34} {4,10,35} {4,10,36} {4,10,37} {4,10,38} {4,10,39} {4,10,40}
{4,10,41} {4,10,42} {4,10,43} {4,10,44} {4,10,45} {4,10,46} {4,10,47} {4,10,48} {4,10,49} {4,10,50}
{4,10,51} {4,10,52} {4,10,53} {4,10,54} {4,10,55} {4,10,56} {4,10,57} {4,10,58} {4,10,59} {4,10,60}
{4,10,61} {4,10,62} {4,10,63} {4,10,64} {4,10,65} {4,10,66} {4,11,12} {4,11,13} {4,11,14} {4,11,15}
{4,11,16} {4,11,17} {4,11,18} {4,11,19} {4,11,20} {4,11,21} {4,11,22} {4,11,23} {4,11,24} {4,11,25}
{4,11,26} {4,11,27} {4,11,28} {4,11,29} {4,11,30} {4,11,31} {4,11,32} {4,11,33} {4,11,34} {4,11,35}
{4,11,36} {4,11,37} {4,11,38} {4,11,39} {4,11,40} {4,11,41} {4,11,42} {4,11,43} {4,11,44} {4,11,45}
{4,11,46} {4,11,47} {4,11,48} {4,11,49} {4,11,50} {4,11,51} {4,11,52} {4,11,53} {4,11,54} {4,11,55}
{4,11,56} {4,11,57} {4,11,58} {4,11,59} {4,11,60} {4,11,61} {4,11,62} {4,11,63} {4,11,64} {4,11,65}
{4,11,66} {4,12,13} {4,12,14} {4,12,15} {4,12,16} {4,12,17} {4,12,18} {4,12,19} {4,12,20} {4,12,21}
{4,12,22} {4,12,23} {4,12,24} {4,12,25} {4,12,26} {4,12,27} {4,12,28} {4,12,29} {4,12,30} {4,12,31}
{4,12,32} {4,12,33} {4,12,34} {4,12,35} {4,12,36} {4,12,37} {4,12,38} {4,12,39} {4,12,40} {4,12,41}
{4,12,42} {4,12,43} {4,12,44} {4,12,45} {4,12,46} {4,12,47} {4,12,48} {4,12,49} {4,12,50} {4,12,51}
{4,12,52} {4,12,53} {4,12,54} {4,12,55} {4,12,56} {4,12,57} {4,12,58} {4,12,59} {4,12,60} {4,12,61}
{4,12,62} {4,12,63} {4,12,64} {4,12,65} {4,12,66} {4,13,14} {4,13,15} {4,13,16} {4,13,17} {4,13,18}
{4,13,19} {4,13,20} {4,13,21} {4,13,22} {4,13,23} {4,13,24} {4,13,25} {4,13,26} {4,13,27} {4,13,28}
{4,13,29} {4,13,30} {4,13,31} {4,13,32} {4,13,33} {4,13,34} {4,13,35} {4,13,36} {4,13,37} {4,13,38}
{4,13,39} {4,13,40} {4,13,41} {4,13,42} {4,13,43} {4,13,44} {4,13,45} {4,13,46} {4,13,47} {4,13,48}
{4,13,49} {4,13,50} {4,13,51} {4,13,52} {4,13,53} {4,13,54} {4,13,55} {4,13,56} {4,13,57} {4,13,58}
{4,13,59} {4,13,60} {4,13,61} {4,13,62} {4,13,63} {4,13,64} {4,13,65} {4,13,66} {4,14,15} {4,14,16}
{4,14,17} {4,14,18} {4,14,19} {4,14,20} {4,14,21} {4,14,22} {4,14,23} {4,14,24} {4,14,25} {4,14,26}
{4,14,27} {4,14,28} {4,14,29} {4,14,30} {4,14,31} {4,14,32} {4,14,33} {4,14,34} {4,14,35} {4,14,36}
{4,14,37} {4,14,38} {4,14,39} {4,14,40} {4,14,41} {4,14,42} {4,14,43} {4,14,44} {4,14,45} {4,14,46}
{4,14,47} {4,14,48} {4,14,49} {4,14,50} {4,14,51} {4,14,52} {4,14,53} {4,14,54} {4,14,55} {4,14,56}
{4,14,57} {4,14,58} {4,14,59} {4,14,60} {4,14,61} {4,14,62} {4,14,63} {4,14,64} {4,14,65} {4,14,66}
{4,15,16} {4,15,17} {4,15,18} {4,15,19} {4,15,20} {4,15,21} {4,15,22} {4,15,23} {4,15,24} {4,15,25}
{4,15,26} {4,15,27} {4,15,28} {4,15,29} {4,15,30} {4,15,31} {4,15,32} {4,15,33} {4,15,34} {4,15,35}
{4,15,36} {4,15,37} {4,15,38} {4,15,39} {4,15,40} {4,15,41} {4,15,42} {4,15,43} {4,15,44} {4,15,45}
{4,15,46} {4,15,47} {4,15,48} {4,15,49} {4,15,50} {4,15,51} {4,15,52} {4,15,53} {4,15,54} {4,15,55}
{4,15,56} {4,15,57} {4,15,58} {4,15,59} {4,15,60} {4,15,61} {4,15,62} {4,15,63} {4,15,64} {4,15,65}
{4,15,66} {4,16,17} {4,16,18} {4,16,19} {4,16,20} {4,16,21} {4,16,22} {4,16,23} {4,16,24} {4,16,25}
{4,16,26} {4,16,27} {4,16,28} {4,16,29} {4,16,30} {4,16,31} {4,16,32} {4,16,33} {4,16,34} {4,16,35}
{4,16,36} {4,16,37} {4,16,38} {4,16,39} {4,16,40} {4,16,41} {4,16,42} {4,16,43} {4,16,44} {4,16,45}
{4,16,46} {4,16,47} {4,16,48} {4,16,49} {4,16,50} {4,16,51} {4,16,52} {4,16,53} {4,16,54} {4,16,55}
{4,16,56} {4,16,57} {4,16,58} {4,16,59} {4,16,60} {4,16,61} {4,16,62} {4,16,63} {4,16,64} {4,16,65}
{4,16,66} {4,17,18} {4,17,19} {4,17,20} {4,17,21} {4,17,22} {4,17,23} {4,17,24} {4,17,25} {4,17,26}
{4,17,27} {4,17,28} {4,17,29} {4,17,30} {4,17,31} {4,17,32} {4,17,33} {4,17,34} {4,17,35} {4,17,36}
{4,17,37} {4,17,38} {4,17,39} {4,17,40} {4,17,41} {4,17,42} {4,17,43} {4,17,44} {4,17,45} {4,17,46}
{4,17,47} {4,17,48} {4,17,49} {4,17,50} {4,17,51} {4,17,52} {4,17,53} {4,17,54} {4,17,55} {4,17,56}
{4,17,57} {4,17,58} {4,17,59} {4,17,60} {4,17,61} {4,17,62} {4,17,63} {4,17,64} {4,17,65} {4,17,66}
{4,18,19} {4,18,20} {4,18,21} {4,18,22} {4,18,23} {4,18,24} {4,18,25} {4,18,26} {4,18,27} {4,18,28}
{4,18,29} {4,18,30} {4,18,31} {4,18,32} {4,18,33} {4,18,34} {4,18,35} {4,18,36} {4,18,37} {4,18,38}
{4,18,39} {4,18,40} {4,18,41} {4,18,42} {4,18,43} {4,18,44} {4,18,45} {4,18,46} {4,18,47} {4,18,48}
{4,18,49} {4,18,50} {4,18,51} {4,18,52} {4,18,53} {4,18,54} {4,18,55} {4,18,56} {4,18,57} {4,18,58}
{4,18,59} {4,18,60} {4,18,61} {4,18,62} {4,18,63} {4,18,64} {4,18,65} {4,18,66} {4,19,20} {4,19,21}
{4,19,22} {4,19,23} {4,19,24} {4,19,25} {4,19,26} {4,19,27} {4,19,28} {4,19,29} {4,19,30} {4,19,31}
{4,19,32} {4,19,33} {4,19,34} {4,19,35} {4,19,36} {4,19,37} {4,19,38} {4,19,39} {4,19,40} {4,19,41}
{4,19,42} {4,19,43} {4,19,44} {4,19,45} {4,19,46} {4,19,47} {4,19,48} {4,19,49} {4,19,50} {4,19,51}
{4,19,52} {4,19,53} {4,19,54} {4,19,55} {4,19,56} {4,19,57} {4,19,58} {4,19,59} {4,19,60} {4,19,61}
{4,19,62} {4,19,63} {4,19,64} {4,19,65} {4,19,66} {4,20,21} {4,20,22} {4,20,23} {4,20,24} {4,20,25}
{4,20,26} {4,20,27} {4,20,28} {4,20,29} {4,20,30} {4,20,31} {4,20,32} {4,20,33} {4,20,34} {4,20,35}
{4,20,36} {4,20,37} {4,20,38} {4,20,39} {4,20,40} {4,20,41} {4,20,42} {4,20,43} {4,20,44} {4,20,45}
{4,20,46} {4,20,47} {4,20,48} {4,20,49} {4,20,50} {4,20,51} {4,20,52} {4,20,53} {4,20,54} {4,20,55}
{4,20,56} {4,20,57} {4,20,58} {4,20,59} {4,20,60} {4,20,61} {4,20,62} {4,20,63} {4,20,64} {4,20,65}
{4,20,66} {4,21,22} {4,21,23} {4,21,24} {4,21,25} {4,21,26} {4,21,27} {4,21,28} {4,21,29} {4,21,30}
{4,21,31} {4,21,32} {4,21,33} {4,21,34} {4,21,35} {4,21,36} {4,21,37} {4,21,38} {4,21,39} {4,21,40}
{4,21,41} {4,21,42} {4,21,43} {4,21,44} {4,21,45} {4,21,46} {4,21,47} {4,21,48} {4,21,49} {4,21,50}
{4,21,51} {4,21,52} {4,21,53} {4,21,54} {4,21,55} {4,21,56} {4,21,57} {4,21,58} {4,21,59} {4,21,60}
{4,21,61} {4,21,62} {4,21,63} {4,21,64} {4,21,65} {4,21,66} {4,22,23} {4,22,24} {4,22,25} {4,22,26}
{4,22,27} {4,22,28} {4,22,29} {4,22,30} {4,22,31} {4,22,32} {4,22,33} {4,22,34} {4,22,35} {4,22,36}
{4,22,37} {4,22,38} {4,22,39} {4,22,40} {4,22,41} {4,22,42} {4,22,43} {4,22,44} {4,22,45} {4,22,46}
{4,22,47} {4,22,48} {4,22,49} {4,22,50} {4,22,51} {4,22,52} {4,22,53} {4,22,54} {4,22,55} {4,22,56}
{4,22,57} {4,22,58} {4,22,59} {4,22,60} {4,22,61} {4,22,62} {4,22,63} {4,22,64} {4,22,65} {4,22,66}
{4,23,24} {4,23,25} {4,23,26} {4,23,27} {4,23,28} {4,23,29} {4,23,30} {4,23,31} {4,23,32} {4,23,33}
{4,23,34} {4,23,35} {4,23,36} {4,23,37} {4,23,38} {4,23,39} {4,23,40} {4,23,41} {4,23,42} {4,23,43}
{4,23,44} {4,23,45} {4,23,46} {4,23,47} {4,23,48} {4,23,49} {4,23,50} {4,23,51} {4,23,52} {4,23,53}
{4,23,54} {4,23,55} {4,23,56} {4,23,57} {4,23,58} {4,23,59} {4,23,60} {4,23,61} {4,23,62} {4,23,63}
{4,23,64} {4,23,65} {4,23,66} {4,24,25} {4,24,26} {4,24,27} {4,24,28} {4,24,29} {4,24,30} {4,24,31}
{4,24,32} {4,24,33} {4,24,34} {4,24,35} {4,24,36} {4,24,37} {4,24,38} {4,24,39} {4,24,40} {4,24,41}
{4,24,42} {4,24,43} {4,24,44} {4,24,45} {4,24,46} {4,24,47} {4,24,48} {4,24,49} {4,24,50} {4,24,51}

TABLE 3A-continued

| | | | | | | | | |
|---|---|---|---|---|---|---|---|---|
| {4,24,52} | {4,24,53} | {4,24,54} | {4,24,55} | {4,24,56} | {4,24,57} | {4,24,58} | {4,24,59} | {4,24,60} | {4,24,61} |
| {4,24,62} | {4,24,63} | {4,24,64} | {4,24,65} | {4,24,66} | {4,25,26} | {4,25,27} | {4,25,28} | {4,25,29} | {4,25,30} |
| {4,25,31} | {4,25,32} | {4,25,33} | {4,25,34} | {4,25,35} | {4,25,36} | {4,25,37} | {4,25,38} | {4,25,39} | {4,25,40} |
| {4,25,41} | {4,25,42} | {4,25,43} | {4,25,44} | {4,25,45} | {4,25,46} | {4,25,47} | {4,25,48} | {4,25,49} | {4,25,50} |
| {4,25,51} | {4,25,52} | {4,25,53} | {4,25,54} | {4,25,55} | {4,25,56} | {4,25,57} | {4,25,58} | {4,25,59} | {4,25,60} |
| {4,25,61} | {4,25,62} | {4,25,63} | {4,25,64} | {4,25,65} | {4,25,66} | {4,26,27} | {4,26,28} | {4,26,29} | {4,26,30} |
| {4,26,31} | {4,26,32} | {4,26,33} | {4,26,34} | {4,26,35} | {4,26,36} | {4,26,37} | {4,26,38} | {4,26,39} | {4,26,40} |
| {4,26,41} | {4,26,42} | {4,26,43} | {4,26,44} | {4,26,45} | {4,26,46} | {4,26,47} | {4,26,48} | {4,26,49} | {4,26,50} |
| {4,26,51} | {4,26,52} | {4,26,53} | {4,26,54} | {4,26,55} | {4,26,56} | {4,26,57} | {4,26,58} | {4,26,59} | {4,26,60} |
| {4,26,61} | {4,26,62} | {4,26,63} | {4,26,64} | {4,26,65} | {4,26,66} | {4,27,28} | {4,27,29} | {4,27,30} | {4,27,31} |
| {4,27,32} | {4,27,33} | {4,27,34} | {4,27,35} | {4,27,36} | {4,27,37} | {4,27,38} | {4,27,39} | {4,27,40} | {4,27,41} |
| {4,27,42} | {4,27,43} | {4,27,44} | {4,27,45} | {4,27,46} | {4,27,47} | {4,27,48} | {4,27,49} | {4,27,50} | {4,27,51} |
| {4,27,52} | {4,27,53} | {4,27,54} | {4,27,55} | {4,27,56} | {4,27,57} | {4,27,58} | {4,27,59} | {4,27,60} | {4,27,61} |
| {4,27,62} | {4,27,63} | {4,27,64} | {4,27,65} | {4,27,66} | {4,28,29} | {4,28,30} | {4,28,31} | {4,28,32} | {4,28,33} |
| {4,28,34} | {4,28,35} | {4,28,36} | {4,28,37} | {4,28,38} | {4,28,39} | {4,28,40} | {4,28,41} | {4,28,42} | {4,28,43} |
| {4,28,44} | {4,28,45} | {4,28,46} | {4,28,47} | {4,28,48} | {4,28,49} | {4,28,50} | {4,28,51} | {4,28,52} | {4,28,53} |
| {4,28,54} | {4,28,55} | {4,28,56} | {4,28,57} | {4,28,58} | {4,28,59} | {4,28,60} | {4,28,61} | {4,28,62} | {4,28,63} |
| {4,28,64} | {4,28,65} | {4,28,66} | {4,29,30} | {4,29,31} | {4,29,32} | {4,29,33} | {4,29,34} | {4,29,35} | {4,29,36} |
| {4,29,37} | {4,29,38} | {4,29,39} | {4,29,40} | {4,29,41} | {4,29,42} | {4,29,43} | {4,29,44} | {4,29,45} | {4,29,46} |
| {4,29,47} | {4,29,48} | {4,29,49} | {4,29,50} | {4,29,51} | {4,29,52} | {4,29,53} | {4,29,54} | {4,29,55} | {4,29,56} |
| {4,29,57} | {4,29,58} | {4,29,59} | {4,29,60} | {4,29,61} | {4,29,62} | {4,29,63} | {4,29,64} | {4,29,65} | {4,29,66} |
| {4,30,31} | {4,30,32} | {4,30,33} | {4,30,34} | {4,30,35} | {4,30,36} | {4,30,37} | {4,30,38} | {4,30,39} | {4,30,40} |
| {4,30,41} | {4,30,42} | {4,30,43} | {4,30,44} | {4,30,45} | {4,30,46} | {4,30,47} | {4,30,48} | {4,30,49} | {4,30,50} |
| {4,30,51} | {4,30,52} | {4,30,53} | {4,30,54} | {4,30,55} | {4,30,56} | {4,30,57} | {4,30,58} | {4,30,59} | {4,30,60} |
| {4,30,61} | {4,30,62} | {4,30,63} | {4,30,64} | {4,30,65} | {4,30,66} | {4,31,32} | {4,31,33} | {4,31,34} | {4,31,35} |
| {4,31,36} | {4,31,37} | {4,31,38} | {4,31,39} | {4,31,40} | {4,31,41} | {4,31,42} | {4,31,43} | {4,31,44} | {4,31,45} |
| {4,31,46} | {4,31,47} | {4,31,48} | {4,31,49} | {4,31,50} | {4,31,51} | {4,31,52} | {4,31,53} | {4,31,54} | {4,31,55} |
| {4,31,56} | {4,31,57} | {4,31,58} | {4,31,59} | {4,31,60} | {4,31,61} | {4,31,62} | {4,31,63} | {4,31,64} | {4,31,65} |
| {4,31,66} | {4,32,33} | {4,32,34} | {4,32,35} | {4,32,36} | {4,32,37} | {4,32,38} | {4,32,39} | {4,32,40} | {4,32,41} |
| {4,32,42} | {4,32,43} | {4,32,44} | {4,32,45} | {4,32,46} | {4,32,47} | {4,32,48} | {4,32,49} | {4,32,50} | {4,32,51} |
| {4,32,52} | {4,32,53} | {4,32,54} | {4,32,55} | {4,32,56} | {4,32,57} | {4,32,58} | {4,32,59} | {4,32,60} | {4,32,61} |
| {4,32,62} | {4,32,63} | {4,32,64} | {4,32,65} | {4,32,66} | {4,33,34} | {4,33,35} | {4,33,36} | {4,33,37} | {4,33,38} |
| {4,33,39} | {4,33,40} | {4,33,41} | {4,33,42} | {4,33,43} | {4,33,44} | {4,33,45} | {4,33,46} | {4,33,47} | {4,33,48} |
| {4,33,49} | {4,33,50} | {4,33,51} | {4,33,52} | {4,33,53} | {4,33,54} | {4,33,55} | {4,33,56} | {4,33,57} | {4,33,58} |
| {4,33,59} | {4,33,60} | {4,33,61} | {4,33,62} | {4,33,63} | {4,33,64} | {4,33,65} | {4,33,66} | {4,34,35} | {4,34,36} |
| {4,34,37} | {4,34,38} | {4,34,39} | {4,34,40} | {4,34,41} | {4,34,42} | {4,34,43} | {4,34,44} | {4,34,45} | {4,34,46} |
| {4,34,47} | {4,34,48} | {4,34,49} | {4,34,50} | {4,34,51} | {4,34,52} | {4,34,53} | {4,34,54} | {4,34,55} | {4,34,56} |
| {4,34,57} | {4,34,58} | {4,34,59} | {4,34,60} | {4,34,61} | {4,34,62} | {4,34,63} | {4,34,64} | {4,34,65} | {4,34,66} |
| {4,35,36} | {4,35,37} | {4,35,38} | {4,35,39} | {4,35,40} | {4,35,41} | {4,35,42} | {4,35,43} | {4,35,44} | {4,35,45} |
| {4,35,46} | {4,35,47} | {4,35,48} | {4,35,49} | {4,35,50} | {4,35,51} | {4,35,52} | {4,35,53} | {4,35,54} | {4,35,55} |
| {4,35,56} | {4,35,57} | {4,35,58} | {4,35,59} | {4,35,60} | {4,35,61} | {4,35,62} | {4,35,63} | {4,35,64} | {4,35,65} |
| {4,35,66} | {4,36,37} | {4,36,38} | {4,36,39} | {4,36,40} | {4,36,41} | {4,36,42} | {4,36,43} | {4,36,44} | {4,36,45} |
| {4,36,46} | {4,36,47} | {4,36,48} | {4,36,49} | {4,36,50} | {4,36,51} | {4,36,52} | {4,36,53} | {4,36,54} | {4,36,55} |
| {4,36,56} | {4,36,57} | {4,36,58} | {4,36,59} | {4,36,60} | {4,36,61} | {4,36,62} | {4,36,63} | {4,36,64} | {4,36,65} |
| {4,36,66} | {4,37,38} | {4,37,39} | {4,37,40} | {4,37,41} | {4,37,42} | {4,37,43} | {4,37,44} | {4,37,45} | {4,37,46} |
| {4,37,47} | {4,37,48} | {4,37,49} | {4,37,50} | {4,37,51} | {4,37,52} | {4,37,53} | {4,37,54} | {4,37,55} | {4,37,56} |
| {4,37,57} | {4,37,58} | {4,37,59} | {4,37,60} | {4,37,61} | {4,37,62} | {4,37,63} | {4,37,64} | {4,37,65} | {4,37,66} |
| {4,38,39} | {4,38,40} | {4,38,41} | {4,38,42} | {4,38,43} | {4,38,44} | {4,38,45} | {4,38,46} | {4,38,47} | {4,38,48} |
| {4,38,49} | {4,38,50} | {4,38,51} | {4,38,52} | {4,38,53} | {4,38,54} | {4,38,55} | {4,38,56} | {4,38,57} | {4,38,58} |
| {4,38,59} | {4,38,60} | {4,38,61} | {4,38,62} | {4,38,63} | {4,38,64} | {4,38,65} | {4,38,66} | {4,39,40} | {4,39,41} |
| {4,39,42} | {4,39,43} | {4,39,44} | {4,39,45} | {4,39,46} | {4,39,47} | {4,39,48} | {4,39,49} | {4,39,50} | {4,39,51} |
| {4,39,52} | {4,39,53} | {4,39,54} | {4,39,55} | {4,39,56} | {4,39,57} | {4,39,58} | {4,39,59} | {4,39,60} | {4,39,61} |
| {4,39,62} | {4,39,63} | {4,39,64} | {4,39,65} | {4,39,66} | {4,40,41} | {4,40,42} | {4,40,43} | {4,40,44} | {4,40,45} |
| {4,40,46} | {4,40,47} | {4,40,48} | {4,40,49} | {4,40,50} | {4,40,51} | {4,40,52} | {4,40,53} | {4,40,54} | {4,40,55} |
| {4,40,56} | {4,40,57} | {4,40,58} | {4,40,59} | {4,40,60} | {4,40,61} | {4,40,62} | {4,40,63} | {4,40,64} | {4,40,65} |
| {4,40,66} | {4,41,42} | {4,41,43} | {4,41,44} | {4,41,45} | {4,41,46} | {4,41,47} | {4,41,48} | {4,41,49} | {4,41,50} |
| {4,41,51} | {4,41,52} | {4,41,53} | {4,41,54} | {4,41,55} | {4,41,56} | {4,41,57} | {4,41,58} | {4,41,59} | {4,41,60} |
| {4,41,61} | {4,41,62} | {4,41,63} | {4,41,64} | {4,41,65} | {4,41,66} | {4,42,43} | {4,42,44} | {4,42,45} | {4,42,46} |
| {4,42,47} | {4,42,48} | {4,42,49} | {4,42,50} | {4,42,51} | {4,42,52} | {4,42,53} | {4,42,54} | {4,42,55} | {4,42,56} |
| {4,42,57} | {4,42,58} | {4,42,59} | {4,42,60} | {4,42,61} | {4,42,62} | {4,42,63} | {4,42,64} | {4,42,65} | {4,42,66} |
| {4,43,44} | {4,43,45} | {4,43,46} | {4,43,47} | {4,43,48} | {4,43,49} | {4,43,50} | {4,43,51} | {4,43,52} | {4,43,53} |
| {4,43,54} | {4,43,55} | {4,43,56} | {4,43,57} | {4,43,58} | {4,43,59} | {4,43,60} | {4,43,61} | {4,43,62} | {4,43,63} |
| {4,43,64} | {4,43,65} | {4,43,66} | {4,44,45} | {4,44,46} | {4,44,47} | {4,44,48} | {4,44,49} | {4,44,50} | {4,44,51} |
| {4,44,52} | {4,44,53} | {4,44,54} | {4,44,55} | {4,44,56} | {4,44,57} | {4,44,58} | {4,44,59} | {4,44,60} | {4,44,61} |
| {4,44,62} | {4,44,63} | {4,44,64} | {4,44,65} | {4,44,66} | {4,45,46} | {4,45,47} | {4,45,48} | {4,45,49} | {4,45,50} |
| {4,45,51} | {4,45,52} | {4,45,53} | {4,45,54} | {4,45,55} | {4,45,56} | {4,45,57} | {4,45,58} | {4,45,59} | {4,45,60} |
| {4,45,61} | {4,45,62} | {4,45,63} | {4,45,64} | {4,45,65} | {4,45,66} | {4,46,47} | {4,46,48} | {4,46,49} | {4,46,50} |
| {4,46,51} | {4,46,52} | {4,46,53} | {4,46,54} | {4,46,55} | {4,46,56} | {4,46,57} | {4,46,58} | {4,46,59} | {4,46,60} |
| {4,46,61} | {4,46,62} | {4,46,63} | {4,46,64} | {4,46,65} | {4,46,66} | {4,47,48} | {4,47,49} | {4,47,50} | {4,47,51} |
| {4,47,52} | {4,47,53} | {4,47,54} | {4,47,55} | {4,47,56} | {4,47,57} | {4,47,58} | {4,47,59} | {4,47,60} | {4,47,61} |
| {4,47,62} | {4,47,63} | {4,47,64} | {4,47,65} | {4,47,66} | {4,48,49} | {4,48,50} | {4,48,51} | {4,48,52} | {4,48,53} |
| {4,48,54} | {4,48,55} | {4,48,56} | {4,48,57} | {4,48,58} | {4,48,59} | {4,48,60} | {4,48,61} | {4,48,62} | {4,48,63} |
| {4,48,64} | {4,48,65} | {4,48,66} | {4,49,50} | {4,49,51} | {4,49,52} | {4,49,53} | {4,49,54} | {4,49,55} | {4,49,56} |
| {4,49,57} | {4,49,58} | {4,49,59} | {4,49,60} | {4,49,61} | {4,49,62} | {4,49,63} | {4,49,64} | {4,49,65} | {4,49,66} |
| {4,50,51} | {4,50,52} | {4,50,53} | {4,50,54} | {4,50,55} | {4,50,56} | {4,50,57} | {4,50,58} | {4,50,59} | {4,50,60} |
| {4,50,61} | {4,50,62} | {4,50,63} | {4,50,64} | {4,50,65} | {4,50,66} | {4,51,52} | {4,51,53} | {4,51,54} | {4,51,55} |
| {4,51,56} | {4,51,57} | {4,51,58} | {4,51,59} | {4,51,60} | {4,51,61} | {4,51,62} | {4,51,63} | {4,51,64} | {4,51,65} |
| {4,51,66} | {4,52,53} | {4,52,54} | {4,52,55} | {4,52,56} | {4,52,57} | {4,52,58} | {4,52,59} | {4,52,60} | {4,52,61} |
| {4,52,62} | {4,52,63} | {4,52,64} | {4,52,65} | {4,52,66} | {4,53,54} | {4,53,55} | {4,53,56} | {4,53,57} | {4,53,58} |
| {4,53,59} | {4,53,60} | {4,53,61} | {4,53,62} | {4,53,63} | {4,53,64} | {4,53,65} | {4,53,66} | {4,54,55} | {4,54,56} |

TABLE 3A-continued

{4,54,57} {4,54,58} {4,54,59} {4,54,60} {4,54,61} {4,54,62} {4,54,63} {4,54,64} {4,54,65} {4,54,66}
{4,55,56} {4,55,57} {4,55,58} {4,55,59} {4,55,60} {4,55,61} {4,55,62} {4,55,63} {4,55,64} {4,55,65}
{4,55,66} {4,56,57} {4,56,58} {4,56,59} {4,56,60} {4,56,61} {4,56,62} {4,56,63} {4,56,64} {4,56,65}
{4,56,66} {4,57,58} {4,57,59} {4,57,60} {4,57,61} {4,57,62} {4,57,63} {4,57,64} {4,57,65} {4,57,66}
{4,58,59} {4,58,60} {4,58,61} {4,58,62} {4,58,63} {4,58,64} {4,58,65} {4,58,66} {4,59,60} {4,59,61}
{4,59,62} {4,59,63} {4,59,64} {4,59,65} {4,59,66} {4,60,61} {4,60,62} {4,60,63} {4,60,64} {4,60,65}
{4,60,66} {4,61,62} {4,61,63} {4,61,64} {4,61,65} {4,61,66} {4,62,63} {4,62,64} {4,62,65} {4,62,66}
{4,63,64} {4,63,65} {4,63,66} {4,64,65} {4,64,66} {4,65,66} {5,6,7} {5,6,8} {5,6,9} {5,6,10} {5,6,11} {5,6,12}
{5,6,13} {5,6,14} {5,6,15} {5,6,16} {5,6,17} {5,6,18} {5,6,19} {5,6,20} {5,6,21} {5,6,22} {5,6,23} {5,6,24}
{5,6,25} {5,6,26} {5,6,27} {5,6,28} {5,6,29} {5,6,30} {5,6,31} {5,6,32} {5,6,33} {5,6,34} {5,6,35} {5,6,36}
{5,6,37} {5,6,38} {5,6,39} {5,6,40} {5,6,41} {5,6,42} {5,6,43} {5,6,44} {5,6,45} {5,6,46} {5,6,47} {5,6,48}
{5,6,49} {5,6,50} {5,6,51} {5,6,52} {5,6,53} {5,6,54} {5,6,55} {5,6,56} {5,6,57} {5,6,58} {5,6,59} {5,6,60}
{5,6,61} {5,6,62} {5,6,63} {5,6,64} {5,6,65} {5,6,66} {5,7,8} {5,7,9} {5,7,10} {5,7,11} {5,7,12} {5,7,13}
{5,7,14} {5,7,15} {5,7,16} {5,7,17} {5,7,18} {5,7,19} {5,7,20} {5,7,21} {5,7,22} {5,7,23} {5,7,24} {5,7,25}
{5,7,26} {5,7,27} {5,7,28} {5,7,29} {5,7,30} {5,7,31} {5,7,32} {5,7,33} {5,7,34} {5,7,35} {5,7,36} {5,7,37}
{5,7,38} {5,7,39} {5,7,40} {5,7,41} {5,7,42} {5,7,43} {5,7,44} {5,7,45} {5,7,46} {5,7,47} {5,7,48} {5,7,49}
{5,7,50} {5,7,51} {5,7,52} {5,7,53} {5,7,54} {5,7,55} {5,7,56} {5,7,57} {5,7,58} {5,7,59} {5,7,60} {5,7,61}
{5,7,62} {5,7,63} {5,7,64} {5,7,65} {5,7,66} {5,8,9} {5,8,10} {5,8,11} {5,8,12} {5,8,13} {5,8,14} {5,8,15}
{5,8,16} {5,8,17} {5,8,18} {5,8,19} {5,8,20} {5,8,21} {5,8,22} {5,8,23} {5,8,24} {5,8,25} {5,8,26} {5,8,27}
{5,8,28} {5,8,29} {5,8,30} {5,8,31} {5,8,32} {5,8,33} {5,8,34} {5,8,35} {5,8,36} {5,8,37} {5,8,38} {5,8,39}
{5,8,40} {5,8,41} {5,8,42} {5,8,43} {5,8,44} {5,8,45} {5,8,46} {5,8,47} {5,8,48} {5,8,49} {5,8,50} {5,8,51}
{5,8,52} {5,8,53} {5,8,54} {5,8,55} {5,8,56} {5,8,57} {5,8,58} {5,8,59} {5,8,60} {5,8,61} {5,8,62} {5,8,63}
{5,8,64} {5,8,65} {5,8,66} {5,9,10} {5,9,11} {5,9,12} {5,9,13} {5,9,14} {5,9,15} {5,9,16} {5,9,17} {5,9,18}
{5,9,19} {5,9,20} {5,9,21} {5,9,22} {5,9,23} {5,9,24} {5,9,25} {5,9,26} {5,9,27} {5,9,28} {5,9,29} {5,9,30}
{5,9,31} {5,9,32} {5,9,33} {5,9,34} {5,9,35} {5,9,36} {5,9,37} {5,9,38} {5,9,39} {5,9,40} {5,9,41} {5,9,42}
{5,9,43} {5,9,44} {5,9,45} {5,9,46} {5,9,47} {5,9,48} {5,9,49} {5,9,50} {5,9,51} {5,9,52} {5,9,53} {5,9,54}
{5,9,55} {5,9,56} {5,9,57} {5,9,58} {5,9,59} {5,9,60} {5,9,61} {5,9,62} {5,9,63} {5,9,64} {5,9,65} {5,9,66}
{5,10,11} {5,10,12} {5,10,13} {5,10,14} {5,10,15} {5,10,16} {5,10,17} {5,10,18} {5,10,19} {5,10,20}
{5,10,21} {5,10,22} {5,10,23} {5,10,24} {5,10,25} {5,10,26} {5,10,27} {5,10,28} {5,10,29} {5,10,30}
{5,10,31} {5,10,32} {5,10,33} {5,10,34} {5,10,35} {5,10,36} {5,10,37} {5,10,38} {5,10,39} {5,10,40}
{5,10,41} {5,10,42} {5,10,43} {5,10,44} {5,10,45} {5,10,46} {5,10,47} {5,10,48} {5,10,49} {5,10,50}
{5,10,51} {5,10,52} {5,10,53} {5,10,54} {5,10,55} {5,10,56} {5,10,57} {5,10,58} {5,10,59} {5,10,60}
{5,10,61} {5,10,62} {5,10,63} {5,10,64} {5,10,65} {5,10,66} {5,11,12} {5,11,13} {5,11,14} {5,11,15}
{5,11,16} {5,11,17} {5,11,18} {5,11,19} {5,11,20} {5,11,21} {5,11,22} {5,11,23} {5,11,24} {5,11,25}
{5,11,26} {5,11,27} {5,11,28} {5,11,29} {5,11,30} {5,11,31} {5,11,32} {5,11,33} {5,11,34} {5,11,35}
{5,11,36} {5,11,37} {5,11,38} {5,11,39} {5,11,40} {5,11,41} {5,11,42} {5,11,43} {5,11,44} {5,11,45}
{5,11,46} {5,11,47} {5,11,48} {5,11,49} {5,11,50} {5,11,51} {5,11,52} {5,11,53} {5,11,54} {5,11,55}
{5,11,56} {5,11,57} {5,11,58} {5,11,59} {5,11,60} {5,11,61} {5,11,62} {5,11,63} {5,11,64} {5,11,65}
{5,11,66} {5,12,13} {5,12,14} {5,12,15} {5,12,16} {5,12,17} {5,12,18} {5,12,19} {5,12,20} {5,12,21}
{5,12,22} {5,12,23} {5,12,24} {5,12,25} {5,12,26} {5,12,27} {5,12,28} {5,12,29} {5,12,30} {5,12,31}
{5,12,32} {5,12,33} {5,12,34} {5,12,35} {5,12,36} {5,12,37} {5,12,38} {5,12,39} {5,12,40} {5,12,41}
{5,12,42} {5,12,43} {5,12,44} {5,12,45} {5,12,46} {5,12,47} {5,12,48} {5,12,49} {5,12,50} {5,12,51}
{5,12,52} {5,12,53} {5,12,54} {5,12,55} {5,12,56} {5,12,57} {5,12,58} {5,12,59} {5,12,60} {5,12,61}
{5,12,62} {5,12,63} {5,12,64} {5,12,65} {5,12,66} {5,13,14} {5,13,15} {5,13,16} {5,13,17} {5,13,18}
{5,13,19} {5,13,20} {5,13,21} {5,13,22} {5,13,23} {5,13,24} {5,13,25} {5,13,26} {5,13,27} {5,13,28}
{5,13,29} {5,13,30} {5,13,31} {5,13,32} {5,13,33} {5,13,34} {5,13,35} {5,13,36} {5,13,37} {5,13,38}
{5,13,39} {5,13,40} {5,13,41} {5,13,42} {5,13,43} {5,13,44} {5,13,45} {5,13,46} {5,13,47} {5,13,48}
{5,13,49} {5,13,50} {5,13,51} {5,13,52} {5,13,53} {5,13,54} {5,13,55} {5,13,56} {5,13,57} {5,13,58}
{5,13,59} {5,13,60} {5,13,61} {5,13,62} {5,13,63} {5,13,64} {5,13,65} {5,13,66} {5,14,15} {5,14,16}
{5,14,17} {5,14,18} {5,14,19} {5,14,20} {5,14,21} {5,14,22} {5,14,23} {5,14,24} {5,14,25} {5,14,26}
{5,14,27} {5,14,28} {5,14,29} {5,14,30} {5,14,31} {5,14,32} {5,14,33} {5,14,34} {5,14,35} {5,14,36}
{5,14,37} {5,14,38} {5,14,39} {5,14,40} {5,14,41} {5,14,42} {5,14,43} {5,14,44} {5,14,45} {5,14,46}
{5,14,47} {5,14,48} {5,14,49} {5,14,50} {5,14,51} {5,14,52} {5,14,53} {5,14,54} {5,14,55} {5,14,56}
{5,14,57} {5,14,58} {5,14,59} {5,14,60} {5,14,61} {5,14,62} {5,14,63} {5,14,64} {5,14,65} {5,14,66}
{5,15,16} {5,15,17} {5,15,18} {5,15,19} {5,15,20} {5,15,21} {5,15,22} {5,15,23} {5,15,24} {5,15,25}
{5,15,26} {5,15,27} {5,15,28} {5,15,29} {5,15,30} {5,15,31} {5,15,32} {5,15,33} {5,15,34} {5,15,35}
{5,15,36} {5,15,37} {5,15,38} {5,15,39} {5,15,40} {5,15,41} {5,15,42} {5,15,43} {5,15,44} {5,15,45}
{5,15,46} {5,15,47} {5,15,48} {5,15,49} {5,15,50} {5,15,51} {5,15,52} {5,15,53} {5,15,54} {5,15,55}
{5,15,56} {5,15,57} {5,15,58} {5,15,59} {5,15,60} {5,15,61} {5,15,62} {5,15,63} {5,15,64} {5,15,65}
{5,15,66} {5,16,17} {5,16,18} {5,16,19} {5,16,20} {5,16,21} {5,16,22} {5,16,23} {5,16,24} {5,16,25}
{5,16,26} {5,16,27} {5,16,28} {5,16,29} {5,16,30} {5,16,31} {5,16,32} {5,16,33} {5,16,34} {5,16,35}
{5,16,36} {5,16,37} {5,16,38} {5,16,39} {5,16,40} {5,16,41} {5,16,42} {5,16,43} {5,16,44} {5,16,45}
{5,16,46} {5,16,47} {5,16,48} {5,16,49} {5,16,50} {5,16,51} {5,16,52} {5,16,53} {5,16,54} {5,16,55}
{5,16,56} {5,16,57} {5,16,58} {5,16,59} {5,16,60} {5,16,61} {5,16,62} {5,16,63} {5,16,64} {5,16,65}
{5,16,66} {5,17,18} {5,17,19} {5,17,20} {5,17,21} {5,17,22} {5,17,23} {5,17,24} {5,17,25} {5,17,26}
{5,17,27} {5,17,28} {5,17,29} {5,17,30} {5,17,31} {5,17,32} {5,17,33} {5,17,34} {5,17,35} {5,17,36}
{5,17,37} {5,17,38} {5,17,39} {5,17,40} {5,17,41} {5,17,42} {5,17,43} {5,17,44} {5,17,45} {5,17,46}
{5,17,47} {5,17,48} {5,17,49} {5,17,50} {5,17,51} {5,17,52} {5,17,53} {5,17,54} {5,17,55} {5,17,56}
{5,17,57} {5,17,58} {5,17,59} {5,17,60} {5,17,61} {5,17,62} {5,17,63} {5,17,64} {5,17,65} {5,17,66}
{5,18,19} {5,18,20} {5,18,21} {5,18,22} {5,18,23} {5,18,24} {5,18,25} {5,18,26} {5,18,27} {5,18,28}
{5,18,29} {5,18,30} {5,18,31} {5,18,32} {5,18,33} {5,18,34} {5,18,35} {5,18,36} {5,18,37} {5,18,38}
{5,18,39} {5,18,40} {5,18,41} {5,18,42} {5,18,43} {5,18,44} {5,18,45} {5,18,46} {5,18,47} {5,18,48}
{5,18,49} {5,18,50} {5,18,51} {5,18,52} {5,18,53} {5,18,54} {5,18,55} {5,18,56} {5,18,57} {5,18,58}
{5,18,59} {5,18,60} {5,18,61} {5,18,62} {5,18,63} {5,18,64} {5,18,65} {5,18,66} {5,19,20} {5,19,21}
{5,19,22} {5,19,23} {5,19,24} {5,19,25} {5,19,26} {5,19,27} {5,19,28} {5,19,29} {5,19,30} {5,19,31}
{5,19,32} {5,19,33} {5,19,34} {5,19,35} {5,19,36} {5,19,37} {5,19,38} {5,19,39} {5,19,40} {5,19,41}
{5,19,42} {5,19,43} {5,19,44} {5,19,45} {5,19,46} {5,19,47} {5,19,48} {5,19,49} {5,19,50} {5,19,51}
{5,19,52} {5,19,53} {5,19,54} {5,19,55} {5,19,56} {5,19,57} {5,19,58} {5,19,59} {5,19,60} {5,19,61}
{5,19,62} {5,19,63} {5,19,64} {5,19,65} {5,19,66} {5,20,21} {5,20,22} {5,20,23} {5,20,24} {5,20,25}
{5,20,26} {5,20,27} {5,20,28} {5,20,29} {5,20,30} {5,20,31} {5,20,32} {5,20,33} {5,20,34} {5,20,35}

TABLE 3A-continued

| | | | | | | | | |
|---|---|---|---|---|---|---|---|---|
| {5,20,36} | {5,20,37} | {5,20,38} | {5,20,39} | {5,20,40} | {5,20,41} | {5,20,42} | {5,20,43} | {5,20,44} | {5,20,45} |
| {5,20,46} | {5,20,47} | {5,20,48} | {5,20,49} | {5,20,50} | {5,20,51} | {5,20,52} | {5,20,53} | {5,20,54} | {5,20,55} |
| {5,20,56} | {5,20,57} | {5,20,58} | {5,20,59} | {5,20,60} | {5,20,61} | {5,20,62} | {5,20,63} | {5,20,64} | {5,20,65} |
| {5,20,66} | {5,21,22} | {5,21,23} | {5,21,24} | {5,21,25} | {5,21,26} | {5,21,27} | {5,21,28} | {5,21,29} | {5,21,30} |
| {5,21,31} | {5,21,32} | {5,21,33} | {5,21,34} | {5,21,35} | {5,21,36} | {5,21,37} | {5,21,38} | {5,21,39} | {5,21,40} |
| {5,21,41} | {5,21,42} | {5,21,43} | {5,21,44} | {5,21,45} | {5,21,46} | {5,21,47} | {5,21,48} | {5,21,49} | {5,21,50} |
| {5,21,51} | {5,21,52} | {5,21,53} | {5,21,54} | {5,21,55} | {5,21,56} | {5,21,57} | {5,21,58} | {5,21,59} | {5,21,60} |
| {5,21,61} | {5,21,62} | {5,21,63} | {5,21,64} | {5,21,65} | {5,21,66} | {5,22,23} | {5,22,24} | {5,22,25} | {5,22,26} |
| {5,22,27} | {5,22,28} | {5,22,29} | {5,22,30} | {5,22,31} | {5,22,32} | {5,22,33} | {5,22,34} | {5,22,35} | {5,22,36} |
| {5,22,37} | {5,22,38} | {5,22,39} | {5,22,40} | {5,22,41} | {5,22,42} | {5,22,43} | {5,22,44} | {5,22,45} | {5,22,46} |
| {5,22,47} | {5,22,48} | {5,22,49} | {5,22,50} | {5,22,51} | {5,22,52} | {5,22,53} | {5,22,54} | {5,22,55} | {5,22,56} |
| {5,22,57} | {5,22,58} | {5,22,59} | {5,22,60} | {5,22,61} | {5,22,62} | {5,22,63} | {5,22,64} | {5,22,65} | {5,22,66} |
| {5,23,24} | {5,23,25} | {5,23,26} | {5,23,27} | {5,23,28} | {5,23,29} | {5,23,30} | {5,23,31} | {5,23,32} | {5,23,33} |
| {5,23,34} | {5,23,35} | {5,23,36} | {5,23,37} | {5,23,38} | {5,23,39} | {5,23,40} | {5,23,41} | {5,23,42} | {5,23,43} |
| {5,23,44} | {5,23,45} | {5,23,46} | {5,23,47} | {5,23,48} | {5,23,49} | {5,23,50} | {5,23,51} | {5,23,52} | {5,23,53} |
| {5,23,54} | {5,23,55} | {5,23,56} | {5,23,57} | {5,23,58} | {5,23,59} | {5,23,60} | {5,23,61} | {5,23,62} | {5,23,63} |
| {5,23,64} | {5,23,65} | {5,23,66} | {5,24,25} | {5,24,26} | {5,24,27} | {5,24,28} | {5,24,29} | {5,24,30} | {5,24,31} |
| {5,24,32} | {5,24,33} | {5,24,34} | {5,24,35} | {5,24,36} | {5,24,37} | {5,24,38} | {5,24,39} | {5,24,40} | {5,24,41} |
| {5,24,42} | {5,24,43} | {5,24,44} | {5,24,45} | {5,24,46} | {5,24,47} | {5,24,48} | {5,24,49} | {5,24,50} | {5,24,51} |
| {5,24,52} | {5,24,53} | {5,24,54} | {5,24,55} | {5,24,56} | {5,24,57} | {5,24,58} | {5,24,59} | {5,24,60} | {5,24,61} |
| {5,24,62} | {5,24,63} | {5,24,64} | {5,24,65} | {5,24,66} | {5,25,26} | {5,25,27} | {5,25,28} | {5,25,29} | {5,25,30} |
| {5,25,31} | {5,25,32} | {5,25,33} | {5,25,34} | {5,25,35} | {5,25,36} | {5,25,37} | {5,25,38} | {5,25,39} | {5,25,40} |
| {5,25,41} | {5,25,42} | {5,25,43} | {5,25,44} | {5,25,45} | {5,25,46} | {5,25,47} | {5,25,48} | {5,25,49} | {5,25,50} |
| {5,25,51} | {5,25,52} | {5,25,53} | {5,25,54} | {5,25,55} | {5,25,56} | {5,25,57} | {5,25,58} | {5,25,59} | {5,25,60} |
| {5,25,61} | {5,25,62} | {5,25,63} | {5,25,64} | {5,25,65} | {5,25,66} | {5,26,27} | {5,26,28} | {5,26,29} | {5,26,30} |
| {5,26,31} | {5,26,32} | {5,26,33} | {5,26,34} | {5,26,35} | {5,26,36} | {5,26,37} | {5,26,38} | {5,26,39} | {5,26,40} |
| {5,26,41} | {5,26,42} | {5,26,43} | {5,26,44} | {5,26,45} | {5,26,46} | {5,26,47} | {5,26,48} | {5,26,49} | {5,26,50} |
| {5,26,51} | {5,26,52} | {5,26,53} | {5,26,54} | {5,26,55} | {5,26,56} | {5,26,57} | {5,26,58} | {5,26,59} | {5,26,60} |
| {5,26,61} | {5,26,62} | {5,26,63} | {5,26,64} | {5,26,65} | {5,26,66} | {5,27,28} | {5,27,29} | {5,27,30} | {5,27,31} |
| {5,27,32} | {5,27,33} | {5,27,34} | {5,27,35} | {5,27,36} | {5,27,37} | {5,27,38} | {5,27,39} | {5,27,40} | {5,27,41} |
| {5,27,42} | {5,27,43} | {5,27,44} | {5,27,45} | {5,27,46} | {5,27,47} | {5,27,48} | {5,27,49} | {5,27,50} | {5,27,51} |
| {5,27,52} | {5,27,53} | {5,27,54} | {5,27,55} | {5,27,56} | {5,27,57} | {5,27,58} | {5,27,59} | {5,27,60} | {5,27,61} |
| {5,27,62} | {5,27,63} | {5,27,64} | {5,27,65} | {5,27,66} | {5,28,29} | {5,28,30} | {5,28,31} | {5,28,32} | {5,28,33} |
| {5,28,34} | {5,28,35} | {5,28,36} | {5,28,37} | {5,28,38} | {5,28,39} | {5,28,40} | {5,28,41} | {5,28,42} | {5,28,43} |
| {5,28,44} | {5,28,45} | {5,28,46} | {5,28,47} | {5,28,48} | {5,28,49} | {5,28,50} | {5,28,51} | {5,28,52} | {5,28,53} |
| {5,28,54} | {5,28,55} | {5,28,56} | {5,28,57} | {5,28,58} | {5,28,59} | {5,28,60} | {5,28,61} | {5,28,62} | {5,28,63} |
| {5,28,64} | {5,28,65} | {5,28,66} | {5,29,30} | {5,29,31} | {5,29,32} | {5,29,33} | {5,29,34} | {5,29,35} | {5,29,36} |
| {5,29,37} | {5,29,38} | {5,29,39} | {5,29,40} | {5,29,41} | {5,29,42} | {5,29,43} | {5,29,44} | {5,29,45} | {5,29,46} |
| {5,29,47} | {5,29,48} | {5,29,49} | {5,29,50} | {5,29,51} | {5,29,52} | {5,29,53} | {5,29,54} | {5,29,55} | {5,29,56} |
| {5,29,57} | {5,29,58} | {5,29,59} | {5,29,60} | {5,29,61} | {5,29,62} | {5,29,63} | {5,29,64} | {5,29,65} | {5,29,66} |
| {5,30,31} | {5,30,32} | {5,30,33} | {5,30,34} | {5,30,35} | {5,30,36} | {5,30,37} | {5,30,38} | {5,30,39} | {5,30,40} |
| {5,30,41} | {5,30,42} | {5,30,43} | {5,30,44} | {5,30,45} | {5,30,46} | {5,30,47} | {5,30,48} | {5,30,49} | {5,30,50} |
| {5,30,51} | {5,30,52} | {5,30,53} | {5,30,54} | {5,30,55} | {5,30,56} | {5,30,57} | {5,30,58} | {5,30,59} | {5,30,60} |
| {5,30,61} | {5,30,62} | {5,30,63} | {5,30,64} | {5,30,65} | {5,30,66} | {5,31,32} | {5,31,33} | {5,31,34} | {5,31,35} |
| {5,31,36} | {5,31,37} | {5,31,38} | {5,31,39} | {5,31,40} | {5,31,41} | {5,31,42} | {5,31,43} | {5,31,44} | {5,31,45} |
| {5,31,46} | {5,31,47} | {5,31,48} | {5,31,49} | {5,31,50} | {5,31,51} | {5,31,52} | {5,31,53} | {5,31,54} | {5,31,55} |
| {5,31,56} | {5,31,57} | {5,31,58} | {5,31,59} | {5,31,60} | {5,31,61} | {5,31,62} | {5,31,63} | {5,31,64} | {5,31,65} |
| {5,31,66} | {5,32,33} | {5,32,34} | {5,32,35} | {5,32,36} | {5,32,37} | {5,32,38} | {5,32,39} | {5,32,40} | {5,32,41} |
| {5,32,42} | {5,32,43} | {5,32,44} | {5,32,45} | {5,32,46} | {5,32,47} | {5,32,48} | {5,32,49} | {5,32,50} | {5,32,51} |
| {5,32,52} | {5,32,53} | {5,32,54} | {5,32,55} | {5,32,56} | {5,32,57} | {5,32,58} | {5,32,59} | {5,32,60} | {5,32,61} |
| {5,32,62} | {5,32,63} | {5,32,64} | {5,32,65} | {5,32,66} | {5,33,34} | {5,33,35} | {5,33,36} | {5,33,37} | {5,33,38} |
| {5,33,39} | {5,33,40} | {5,33,41} | {5,33,42} | {5,33,43} | {5,33,44} | {5,33,45} | {5,33,46} | {5,33,47} | {5,33,48} |
| {5,33,49} | {5,33,50} | {5,33,51} | {5,33,52} | {5,33,53} | {5,33,54} | {5,33,55} | {5,33,56} | {5,33,57} | {5,33,58} |
| {5,33,59} | {5,33,60} | {5,33,61} | {5,33,62} | {5,33,63} | {5,33,64} | {5,33,65} | {5,33,66} | {5,34,35} | {5,34,36} |
| {5,34,37} | {5,34,38} | {5,34,39} | {5,34,40} | {5,34,41} | {5,34,42} | {5,34,43} | {5,34,44} | {5,34,45} | {5,34,46} |
| {5,34,47} | {5,34,48} | {5,34,49} | {5,34,50} | {5,34,51} | {5,34,52} | {5,34,53} | {5,34,54} | {5,34,55} | {5,34,56} |
| {5,34,57} | {5,34,58} | {5,34,59} | {5,34,60} | {5,34,61} | {5,34,62} | {5,34,63} | {5,34,64} | {5,34,65} | {5,34,66} |
| {5,35,36} | {5,35,37} | {5,35,38} | {5,35,39} | {5,35,40} | {5,35,41} | {5,35,42} | {5,35,43} | {5,35,44} | {5,35,45} |
| {5,35,46} | {5,35,47} | {5,35,48} | {5,35,49} | {5,35,50} | {5,35,51} | {5,35,52} | {5,35,53} | {5,35,54} | {5,35,55} |
| {5,35,56} | {5,35,57} | {5,35,58} | {5,35,59} | {5,35,60} | {5,35,61} | {5,35,62} | {5,35,63} | {5,35,64} | {5,35,65} |
| {5,35,66} | {5,36,37} | {5,36,38} | {5,36,39} | {5,36,40} | {5,36,41} | {5,36,42} | {5,36,43} | {5,36,44} | {5,36,45} |
| {5,36,46} | {5,36,47} | {5,36,48} | {5,36,49} | {5,36,50} | {5,36,51} | {5,36,52} | {5,36,53} | {5,36,54} | {5,36,55} |
| {5,36,56} | {5,36,57} | {5,36,58} | {5,36,59} | {5,36,60} | {5,36,61} | {5,36,62} | {5,36,63} | {5,36,64} | {5,36,65} |
| {5,36,66} | {5,37,38} | {5,37,39} | {5,37,40} | {5,37,41} | {5,37,42} | {5,37,43} | {5,37,44} | {5,37,45} | {5,37,46} |
| {5,37,47} | {5,37,48} | {5,37,49} | {5,37,50} | {5,37,51} | {5,37,52} | {5,37,53} | {5,37,54} | {5,37,55} | {5,37,56} |
| {5,37,57} | {5,37,58} | {5,37,59} | {5,37,60} | {5,37,61} | {5,37,62} | {5,37,63} | {5,37,64} | {5,37,65} | {5,37,66} |
| {5,38,39} | {5,38,40} | {5,38,41} | {5,38,42} | {5,38,43} | {5,38,44} | {5,38,45} | {5,38,46} | {5,38,47} | {5,38,48} |
| {5,38,49} | {5,38,50} | {5,38,51} | {5,38,52} | {5,38,53} | {5,38,54} | {5,38,55} | {5,38,56} | {5,38,57} | {5,38,58} |
| {5,38,59} | {5,38,60} | {5,38,61} | {5,38,62} | {5,38,63} | {5,38,64} | {5,38,65} | {5,38,66} | {5,39,40} | {5,39,41} |
| {5,39,42} | {5,39,43} | {5,39,44} | {5,39,45} | {5,39,46} | {5,39,47} | {5,39,48} | {5,39,49} | {5,39,50} | {5,39,51} |
| {5,39,52} | {5,39,53} | {5,39,54} | {5,39,55} | {5,39,56} | {5,39,57} | {5,39,58} | {5,39,59} | {5,39,60} | {5,39,61} |
| {5,39,62} | {5,39,63} | {5,39,64} | {5,39,65} | {5,39,66} | {5,40,41} | {5,40,42} | {5,40,43} | {5,40,44} | {5,40,45} |
| {5,40,46} | {5,40,47} | {5,40,48} | {5,40,49} | {5,40,50} | {5,40,51} | {5,40,52} | {5,40,53} | {5,40,54} | {5,40,55} |
| {5,40,56} | {5,40,57} | {5,40,58} | {5,40,59} | {5,40,60} | {5,40,61} | {5,40,62} | {5,40,63} | {5,40,64} | {5,40,65} |
| {5,40,66} | {5,41,42} | {5,41,43} | {5,41,44} | {5,41,45} | {5,41,46} | {5,41,47} | {5,41,48} | {5,41,49} | {5,41,50} |
| {5,41,51} | {5,41,52} | {5,41,53} | {5,41,54} | {5,41,55} | {5,41,56} | {5,41,57} | {5,41,58} | {5,41,59} | {5,41,60} |
| {5,41,61} | {5,41,62} | {5,41,63} | {5,41,64} | {5,41,65} | {5,41,66} | {5,42,43} | {5,42,44} | {5,42,45} | {5,42,46} |
| {5,42,47} | {5,42,48} | {5,42,49} | {5,42,50} | {5,42,51} | {5,42,52} | {5,42,53} | {5,42,54} | {5,42,55} | {5,42,56} |
| {5,42,57} | {5,42,58} | {5,42,59} | {5,42,60} | {5,42,61} | {5,42,62} | {5,42,63} | {5,42,64} | {5,42,65} | {5,42,66} |
| {5,43,44} | {5,43,45} | {5,43,46} | {5,43,47} | {5,43,48} | {5,43,49} | {5,43,50} | {5,43,51} | {5,43,52} | {5,43,53} |

TABLE 3A-continued

{5,43,54} {5,43,55} {5,43,56} {5,43,57} {5,43,58} {5,43,59} {5,43,60} {5,43,61} {5,43,62} {5,43,63}
{5,43,64} {5,43,65} {5,43,66} {5,44,45} {5,44,46} {5,44,47} {5,44,48} {5,44,49} {5,44,50} {5,44,51}
{5,44,52} {5,44,53} {5,44,54} {5,44,55} {5,44,56} {5,44,57} {5,44,58} {5,44,59} {5,44,60} {5,44,61}
{5,44,62} {5,44,63} {5,44,64} {5,44,65} {5,44,66} {5,45,46} {5,45,47} {5,45,48} {5,45,49} {5,45,50}
{5,45,51} {5,45,52} {5,45,53} {5,45,54} {5,45,55} {5,45,56} {5,45,57} {5,45,58} {5,45,59} {5,45,60}
{5,45,61} {5,45,62} {5,45,63} {5,45,64} {5,45,65} {5,45,66} {5,46,47} {5,46,48} {5,46,49} {5,46,50}
{5,46,51} {5,46,52} {5,46,53} {5,46,54} {5,46,55} {5,46,56} {5,46,57} {5,46,58} {5,46,59} {5,46,60}
{5,46,61} {5,46,62} {5,46,63} {5,46,64} {5,46,65} {5,46,66} {5,47,48} {5,47,49} {5,47,50} {5,47,51}
{5,47,52} {5,47,53} {5,47,54} {5,47,55} {5,47,56} {5,47,57} {5,47,58} {5,47,59} {5,47,60} {5,47,61}
{5,47,62} {5,47,63} {5,47,64} {5,47,65} {5,47,66} {5,48,49} {5,48,50} {5,48,51} {5,48,52} {5,48,53}
{5,48,54} {5,48,55} {5,48,56} {5,48,57} {5,48,58} {5,48,59} {5,48,60} {5,48,61} {5,48,62} {5,48,63}
{5,48,64} {5,48,65} {5,48,66} {5,49,50} {5,49,51} {5,49,52} {5,49,53} {5,49,54} {5,49,55} {5,49,56}
{5,49,57} {5,49,58} {5,49,59} {5,49,60} {5,49,61} {5,49,62} {5,49,63} {5,49,64} {5,49,65} {5,49,66}
{5,50,51} {5,50,52} {5,50,53} {5,50,54} {5,50,55} {5,50,56} {5,50,57} {5,50,58} {5,50,59} {5,50,60}
{5,50,61} {5,50,62} {5,50,63} {5,50,64} {5,50,65} {5,50,66} {5,51,52} {5,51,53} {5,51,54} {5,51,55}
{5,51,56} {5,51,57} {5,51,58} {5,51,59} {5,51,60} {5,51,61} {5,51,62} {5,51,63} {5,51,64} {5,51,65}
{5,51,66} {5,52,53} {5,52,54} {5,52,55} {5,52,56} {5,52,57} {5,52,58} {5,52,59} {5,52,60} {5,52,61}
{5,52,62} {5,52,63} {5,52,64} {5,52,65} {5,52,66} {5,53,54} {5,53,55} {5,53,56} {5,53,57} {5,53,58}
{5,53,59} {5,53,60} {5,53,61} {5,53,62} {5,53,63} {5,53,64} {5,53,65} {5,53,66} {5,54,55} {5,54,56}
{5,54,57} {5,54,58} {5,54,59} {5,54,60} {5,54,61} {5,54,62} {5,54,63} {5,54,64} {5,54,65} {5,54,66}
{5,55,56} {5,55,57} {5,55,58} {5,55,59} {5,55,60} {5,55,61} {5,55,62} {5,55,63} {5,55,64} {5,55,65}
{5,55,66} {5,56,57} {5,56,58} {5,56,59} {5,56,60} {5,56,61} {5,56,62} {5,56,63} {5,56,64} {5,56,65}
{5,56,66} {5,57,58} {5,57,59} {5,57,60} {5,57,61} {5,57,62} {5,57,63} {5,57,64} {5,57,65} {5,57,66}
{5,58,59} {5,58,60} {5,58,61} {5,58,62} {5,58,63} {5,58,64} {5,58,65} {5,58,66} {5,59,60} {5,59,61}
{5,59,62} {5,59,63} {5,59,64} {5,59,65} {5,59,66} {5,60,61} {5,60,62} {5,60,63} {5,60,64} {5,60,65}
{5,60,66} {5,61,62} {5,61,63} {5,61,64} {5,61,65} {5,61,66} {5,62,63} {5,62,64} {5,62,65} {5,62,66}
{5,63,64} {5,63,65} {5,63,66} {5,64,65} {5,64,66} {5,65,66} {6,7,8} {6,7,9} {6,7,10} {6,7,11} {6,7,12} {6,7,13}
{6,7,14} {6,7,15} {6,7,16} {6,7,17} {6,7,18} {6,7,19} {6,7,20} {6,7,21} {6,7,22} {6,7,23} {6,7,24} {6,7,25}
{6,7,26} {6,7,27} {6,7,28} {6,7,29} {6,7,30} {6,7,31} {6,7,32} {6,7,33} {6,7,34} {6,7,35} {6,7,36} {6,7,37}
{6,7,38} {6,7,39} {6,7,40} {6,7,41} {6,7,42} {6,7,43} {6,7,44} {6,7,45} {6,7,46} {6,7,47} {6,7,48} {6,7,49}
{6,7,50} {6,7,51} {6,7,52} {6,7,53} {6,7,54} {6,7,55} {6,7,56} {6,7,57} {6,7,58} {6,7,59} {6,7,60} {6,7,61}
{6,7,62} {6,7,63} {6,7,64} {6,7,65} {6,7,66} {6,8,9} {6,8,10} {6,8,11} {6,8,12} {6,8,13} {6,8,14} {6,8,15}
{6,8,16} {6,8,17} {6,8,18} {6,8,19} {6,8,20} {6,8,21} {6,8,22} {6,8,23} {6,8,24} {6,8,25} {6,8,26} {6,8,27}
{6,8,28} {6,8,29} {6,8,30} {6,8,31} {6,8,32} {6,8,33} {6,8,34} {6,8,35} {6,8,36} {6,8,37} {6,8,38} {6,8,39}
{6,8,40} {6,8,41} {6,8,42} {6,8,43} {6,8,44} {6,8,45} {6,8,46} {6,8,47} {6,8,48} {6,8,49} {6,8,50} {6,8,51}
{6,8,52} {6,8,53} {6,8,54} {6,8,55} {6,8,56} {6,8,57} {6,8,58} {6,8,59} {6,8,60} {6,8,61} {6,8,62} {6,8,63}
{6,8,64} {6,8,65} {6,8,66} {6,9,10} {6,9,11} {6,9,12} {6,9,13} {6,9,14} {6,9,15} {6,9,16} {6,9,17} {6,9,18}
{6,9,19} {6,9,20} {6,9,21} {6,9,22} {6,9,23} {6,9,24} {6,9,25} {6,9,26} {6,9,27} {6,9,28} {6,9,29} {6,9,30}
{6,9,31} {6,9,32} {6,9,33} {6,9,34} {6,9,35} {6,9,36} {6,9,37} {6,9,38} {6,9,39} {6,9,40} {6,9,41} {6,9,42}
{6,9,43} {6,9,44} {6,9,45} {6,9,46} {6,9,47} {6,9,48} {6,9,49} {6,9,50} {6,9,51} {6,9,52} {6,9,53} {6,9,54}
{6,9,55} {6,9,56} {6,9,57} {6,9,58} {6,9,59} {6,9,60} {6,9,61} {6,9,62} {6,9,63} {6,9,64} {6,9,65} {6,9,66}
{6,10,11} {6,10,12} {6,10,13} {6,10,14} {6,10,15} {6,10,16} {6,10,17} {6,10,18} {6,10,19} {6,10,20}
{6,10,21} {6,10,22} {6,10,23} {6,10,24} {6,10,25} {6,10,26} {6,10,27} {6,10,28} {6,10,29} {6,10,30}
{6,10,31} {6,10,32} {6,10,33} {6,10,34} {6,10,35} {6,10,36} {6,10,37} {6,10,38} {6,10,39} {6,10,40}
{6,10,41} {6,10,42} {6,10,43} {6,10,44} {6,10,45} {6,10,46} {6,10,47} {6,10,48} {6,10,49} {6,10,50}
{6,10,51} {6,10,52} {6,10,53} {6,10,54} {6,10,55} {6,10,56} {6,10,57} {6,10,58} {6,10,59} {6,10,60}
{6,10,61} {6,10,62} {6,10,63} {6,10,64} {6,10,65} {6,10,66} {6,11,12} {6,11,13} {6,11,14} {6,11,15}
{6,11,16} {6,11,17} {6,11,18} {6,11,19} {6,11,20} {6,11,21} {6,11,22} {6,11,23} {6,11,24} {6,11,25}
{6,11,26} {6,11,27} {6,11,28} {6,11,29} {6,11,30} {6,11,31} {6,11,32} {6,11,33} {6,11,34} {6,11,35}
{6,11,36} {6,11,37} {6,11,38} {6,11,39} {6,11,40} {6,11,41} {6,11,42} {6,11,43} {6,11,44} {6,11,45}
{6,11,46} {6,11,47} {6,11,48} {6,11,49} {6,11,50} {6,11,51} {6,11,52} {6,11,53} {6,11,54} {6,11,55}
{6,11,56} {6,11,57} {6,11,58} {6,11,59} {6,11,60} {6,11,61} {6,11,62} {6,11,63} {6,11,64} {6,11,65}
{6,11,66} {6,12,13} {6,12,14} {6,12,15} {6,12,16} {6,12,17} {6,12,18} {6,12,19} {6,12,20} {6,12,21}
{6,12,22} {6,12,23} {6,12,24} {6,12,25} {6,12,26} {6,12,27} {6,12,28} {6,12,29} {6,12,30} {6,12,31}
{6,12,32} {6,12,33} {6,12,34} {6,12,35} {6,12,36} {6,12,37} {6,12,38} {6,12,39} {6,12,40} {6,12,41}
{6,12,42} {6,12,43} {6,12,44} {6,12,45} {6,12,46} {6,12,47} {6,12,48} {6,12,49} {6,12,50} {6,12,51}
{6,12,52} {6,12,53} {6,12,54} {6,12,55} {6,12,56} {6,12,57} {6,12,58} {6,12,59} {6,12,60} {6,12,61}
{6,12,62} {6,12,63} {6,12,64} {6,12,65} {6,12,66} {6,13,14} {6,13,15} {6,13,16} {6,13,17} {6,13,18}
{6,13,19} {6,13,20} {6,13,21} {6,13,22} {6,13,23} {6,13,24} {6,13,25} {6,13,26} {6,13,27} {6,13,28}
{6,13,29} {6,13,30} {6,13,31} {6,13,32} {6,13,33} {6,13,34} {6,13,35} {6,13,36} {6,13,37} {6,13,38}
{6,13,39} {6,13,40} {6,13,41} {6,13,42} {6,13,43} {6,13,44} {6,13,45} {6,13,46} {6,13,47} {6,13,48}
{6,13,49} {6,13,50} {6,13,51} {6,13,52} {6,13,53} {6,13,54} {6,13,55} {6,13,56} {6,13,57} {6,13,58}
{6,13,59} {6,13,60} {6,13,61} {6,13,62} {6,13,63} {6,13,64} {6,13,65} {6,13,66} {6,14,15} {6,14,16}
{6,14,17} {6,14,18} {6,14,19} {6,14,20} {6,14,21} {6,14,22} {6,14,23} {6,14,24} {6,14,25} {6,14,26}
{6,14,27} {6,14,28} {6,14,29} {6,14,30} {6,14,31} {6,14,32} {6,14,33} {6,14,34} {6,14,35} {6,14,36}
{6,14,37} {6,14,38} {6,14,39} {6,14,40} {6,14,41} {6,14,42} {6,14,43} {6,14,44} {6,14,45} {6,14,46}
{6,14,47} {6,14,48} {6,14,49} {6,14,50} {6,14,51} {6,14,52} {6,14,53} {6,14,54} {6,14,55} {6,14,56}
{6,14,57} {6,14,58} {6,14,59} {6,14,60} {6,14,61} {6,14,62} {6,14,63} {6,14,64} {6,14,65} {6,14,66}
{6,15,16} {6,15,17} {6,15,18} {6,15,19} {6,15,20} {6,15,21} {6,15,22} {6,15,23} {6,15,24} {6,15,25}
{6,15,26} {6,15,27} {6,15,28} {6,15,29} {6,15,30} {6,15,31} {6,15,32} {6,15,33} {6,15,34} {6,15,35}
{6,15,36} {6,15,37} {6,15,38} {6,15,39} {6,15,40} {6,15,41} {6,15,42} {6,15,43} {6,15,44} {6,15,45}
{6,15,46} {6,15,47} {6,15,48} {6,15,49} {6,15,50} {6,15,51} {6,15,52} {6,15,53} {6,15,54} {6,15,55}
{6,15,56} {6,15,57} {6,15,58} {6,15,59} {6,15,60} {6,15,61} {6,15,62} {6,15,63} {6,15,64} {6,15,65}
{6,15,66} {6,16,17} {6,16,18} {6,16,19} {6,16,20} {6,16,21} {6,16,22} {6,16,23} {6,16,24} {6,16,25}
{6,16,26} {6,16,27} {6,16,28} {6,16,29} {6,16,30} {6,16,31} {6,16,32} {6,16,33} {6,16,34} {6,16,35}
{6,16,36} {6,16,37} {6,16,38} {6,16,39} {6,16,40} {6,16,41} {6,16,42} {6,16,43} {6,16,44} {6,16,45}
{6,16,46} {6,16,47} {6,16,48} {6,16,49} {6,16,50} {6,16,51} {6,16,52} {6,16,53} {6,16,54} {6,16,55}
{6,16,56} {6,16,57} {6,16,58} {6,16,59} {6,16,60} {6,16,61} {6,16,62} {6,16,63} {6,16,64} {6,16,65}
{6,16,66} {6,17,18} {6,17,19} {6,17,20} {6,17,21} {6,17,22} {6,17,23} {6,17,24} {6,17,25} {6,17,26}
{6,17,27} {6,17,28} {6,17,29} {6,17,30} {6,17,31} {6,17,32} {6,17,33} {6,17,34} {6,17,35} {6,17,36}

TABLE 3A-continued

{6,17,37} {6,17,38} {6,17,39} {6,17,40} {6,17,41} {6,17,42} {6,17,43} {6,17,44} {6,17,45} {6,17,46}
{6,17,47} {6,17,48} {6,17,49} {6,17,50} {6,17,51} {6,17,52} {6,17,53} {6,17,54} {6,17,55} {6,17,56}
{6,17,57} {6,17,58} {6,17,59} {6,17,60} {6,17,61} {6,17,62} {6,17,63} {6,17,64} {6,17,65} {6,17,66}
{6,18,19} {6,18,20} {6,18,21} {6,18,22} {6,18,23} {6,18,24} {6,18,25} {6,18,26} {6,18,27} {6,18,28}
{6,18,29} {6,18,30} {6,18,31} {6,18,32} {6,18,33} {6,18,34} {6,18,35} {6,18,36} {6,18,37} {6,18,38}
{6,18,39} {6,18,40} {6,18,41} {6,18,42} {6,18,43} {6,18,44} {6,18,45} {6,18,46} {6,18,47} {6,18,48}
{6,18,49} {6,18,50} {6,18,51} {6,18,52} {6,18,53} {6,18,54} {6,18,55} {6,18,56} {6,18,57} {6,18,58}
{6,18,59} {6,18,60} {6,18,61} {6,18,62} {6,18,63} {6,18,64} {6,18,65} {6,18,66} {6,19,20} {6,19,21}
{6,19,22} {6,19,23} {6,19,24} {6,19,25} {6,19,26} {6,19,27} {6,19,28} {6,19,29} {6,19,30} {6,19,31}
{6,19,32} {6,19,33} {6,19,34} {6,19,35} {6,19,36} {6,19,37} {6,19,38} {6,19,39} {6,19,40} {6,19,41}
{6,19,42} {6,19,43} {6,19,44} {6,19,45} {6,19,46} {6,19,47} {6,19,48} {6,19,49} {6,19,50} {6,19,51}
{6,19,52} {6,19,53} {6,19,54} {6,19,55} {6,19,56} {6,19,57} {6,19,58} {6,19,59} {6,19,60} {6,19,61}
{6,19,62} {6,19,63} {6,19,64} {6,19,65} {6,19,66} {6,20,21} {6,20,22} {6,20,23} {6,20,24} {6,20,25}
{6,20,26} {6,20,27} {6,20,28} {6,20,29} {6,20,30} {6,20,31} {6,20,32} {6,20,33} {6,20,34} {6,20,35}
{6,20,36} {6,20,37} {6,20,38} {6,20,39} {6,20,40} {6,20,41} {6,20,42} {6,20,43} {6,20,44} {6,20,45}
{6,20,46} {6,20,47} {6,20,48} {6,20,49} {6,20,50} {6,20,51} {6,20,52} {6,20,53} {6,20,54} {6,20,55}
{6,20,56} {6,20,57} {6,20,58} {6,20,59} {6,20,60} {6,20,61} {6,20,62} {6,20,63} {6,20,64} {6,20,65}
{6,20,66} {6,21,22} {6,21,23} {6,21,24} {6,21,25} {6,21,26} {6,21,27} {6,21,28} {6,21,29} {6,21,30}
{6,21,31} {6,21,32} {6,21,33} {6,21,34} {6,21,35} {6,21,36} {6,21,37} {6,21,38} {6,21,39} {6,21,40}
{6,21,41} {6,21,42} {6,21,43} {6,21,44} {6,21,45} {6,21,46} {6,21,47} {6,21,48} {6,21,49} {6,21,50}
{6,21,51} {6,21,52} {6,21,53} {6,21,54} {6,21,55} {6,21,56} {6,21,57} {6,21,58} {6,21,59} {6,21,60}
{6,21,61} {6,21,62} {6,21,63} {6,21,64} {6,21,65} {6,21,66} {6,22,23} {6,22,24} {6,22,25} {6,22,26}
{6,22,27} {6,22,28} {6,22,29} {6,22,30} {6,22,31} {6,22,32} {6,22,33} {6,22,34} {6,22,35} {6,22,36}
{6,22,37} {6,22,38} {6,22,39} {6,22,40} {6,22,41} {6,22,42} {6,22,43} {6,22,44} {6,22,45} {6,22,46}
{6,22,47} {6,22,48} {6,22,49} {6,22,50} {6,22,51} {6,22,52} {6,22,53} {6,22,54} {6,22,55} {6,22,56}
{6,22,57} {6,22,58} {6,22,59} {6,22,60} {6,22,61} {6,22,62} {6,22,63} {6,22,64} {6,22,65} {6,22,66}
{6,23,24} {6,23,25} {6,23,26} {6,23,27} {6,23,28} {6,23,29} {6,23,30} {6,23,31} {6,23,32} {6,23,33}
{6,23,34} {6,23,35} {6,23,36} {6,23,37} {6,23,38} {6,23,39} {6,23,40} {6,23,41} {6,23,42} {6,23,43}
{6,23,44} {6,23,45} {6,23,46} {6,23,47} {6,23,48} {6,23,49} {6,23,50} {6,23,51} {6,23,52} {6,23,53}
{6,23,54} {6,23,55} {6,23,56} {6,23,57} {6,23,58} {6,23,59} {6,23,60} {6,23,61} {6,23,62} {6,23,63}
{6,23,64} {6,23,65} {6,23,66} {6,24,25} {6,24,26} {6,24,27} {6,24,28} {6,24,29} {6,24,30} {6,24,31}
{6,24,32} {6,24,33} {6,24,34} {6,24,35} {6,24,36} {6,24,37} {6,24,38} {6,24,39} {6,24,40} {6,24,41}
{6,24,42} {6,24,43} {6,24,44} {6,24,45} {6,24,46} {6,24,47} {6,24,48} {6,24,49} {6,24,50} {6,24,51}
{6,24,52} {6,24,53} {6,24,54} {6,24,55} {6,24,56} {6,24,57} {6,24,58} {6,24,59} {6,24,60} {6,24,61}
{6,24,62} {6,24,63} {6,24,64} {6,24,65} {6,24,66} {6,25,26} {6,25,27} {6,25,28} {6,25,29} {6,25,30}
{6,25,31} {6,25,32} {6,25,33} {6,25,34} {6,25,35} {6,25,36} {6,25,37} {6,25,38} {6,25,39} {6,25,40}
{6,25,41} {6,25,42} {6,25,43} {6,25,44} {6,25,45} {6,25,46} {6,25,47} {6,25,48} {6,25,49} {6,25,50}
{6,25,51} {6,25,52} {6,25,53} {6,25,54} {6,25,55} {6,25,56} {6,25,57} {6,25,58} {6,25,59} {6,25,60}
{6,25,61} {6,25,62} {6,25,63} {6,25,64} {6,25,65} {6,25,66} {6,26,27} {6,26,28} {6,26,29} {6,26,30}
{6,26,31} {6,26,32} {6,26,33} {6,26,34} {6,26,35} {6,26,36} {6,26,37} {6,26,38} {6,26,39} {6,26,40}
{6,26,41} {6,26,42} {6,26,43} {6,26,44} {6,26,45} {6,26,46} {6,26,47} {6,26,48} {6,26,49} {6,26,50}
{6,26,51} {6,26,52} {6,26,53} {6,26,54} {6,26,55} {6,26,56} {6,26,57} {6,26,58} {6,26,59} {6,26,60}
{6,26,61} {6,26,62} {6,26,63} {6,26,64} {6,26,65} {6,26,66} {6,27,28} {6,27,29} {6,27,30} {6,27,31}
{6,27,32} {6,27,33} {6,27,34} {6,27,35} {6,27,36} {6,27,37} {6,27,38} {6,27,39} {6,27,40} {6,27,41}
{6,27,42} {6,27,43} {6,27,44} {6,27,45} {6,27,46} {6,27,47} {6,27,48} {6,27,49} {6,27,50} {6,27,51}
{6,27,52} {6,27,53} {6,27,54} {6,27,55} {6,27,56} {6,27,57} {6,27,58} {6,27,59} {6,27,60} {6,27,61}
{6,27,62} {6,27,63} {6,27,64} {6,27,65} {6,27,66} {6,28,29} {6,28,30} {6,28,31} {6,28,32} {6,28,33}
{6,28,34} {6,28,35} {6,28,36} {6,28,37} {6,28,38} {6,28,39} {6,28,40} {6,28,41} {6,28,42} {6,28,43}
{6,28,44} {6,28,45} {6,28,46} {6,28,47} {6,28,48} {6,28,49} {6,28,50} {6,28,51} {6,28,52} {6,28,53}
{6,28,54} {6,28,55} {6,28,56} {6,28,57} {6,28,58} {6,28,59} {6,28,60} {6,28,61} {6,28,62} {6,28,63}
{6,28,64} {6,28,65} {6,28,66} {6,29,30} {6,29,31} {6,29,32} {6,29,33} {6,29,34} {6,29,35} {6,29,36}
{6,29,37} {6,29,38} {6,29,39} {6,29,40} {6,29,41} {6,29,42} {6,29,43} {6,29,44} {6,29,45} {6,29,46}
{6,29,47} {6,29,48} {6,29,49} {6,29,50} {6,29,51} {6,29,52} {6,29,53} {6,29,54} {6,29,55} {6,29,56}
{6,29,57} {6,29,58} {6,29,59} {6,29,60} {6,29,61} {6,29,62} {6,29,63} {6,29,64} {6,29,65} {6,29,66}
{6,30,31} {6,30,32} {6,30,33} {6,30,34} {6,30,35} {6,30,36} {6,30,37} {6,30,38} {6,30,39} {6,30,40}
{6,30,41} {6,30,42} {6,30,43} {6,30,44} {6,30,45} {6,30,46} {6,30,47} {6,30,48} {6,30,49} {6,30,50}
{6,30,51} {6,30,52} {6,30,53} {6,30,54} {6,30,55} {6,30,56} {6,30,57} {6,30,58} {6,30,59} {6,30,60}
{6,30,61} {6,30,62} {6,30,63} {6,30,64} {6,30,65} {6,30,66} {6,31,32} {6,31,33} {6,31,34} {6,31,35}
{6,31,36} {6,31,37} {6,31,38} {6,31,39} {6,31,40} {6,31,41} {6,31,42} {6,31,43} {6,31,44} {6,31,45}
{6,31,46} {6,31,47} {6,31,48} {6,31,49} {6,31,50} {6,31,51} {6,31,52} {6,31,53} {6,31,54} {6,31,55}
{6,31,56} {6,31,57} {6,31,58} {6,31,59} {6,31,60} {6,31,61} {6,31,62} {6,31,63} {6,31,64} {6,31,65}
{6,31,66} {6,32,33} {6,32,34} {6,32,35} {6,32,36} {6,32,37} {6,32,38} {6,32,39} {6,32,40} {6,32,41}
{6,32,42} {6,32,43} {6,32,44} {6,32,45} {6,32,46} {6,32,47} {6,32,48} {6,32,49} {6,32,50} {6,32,51}
{6,32,52} {6,32,53} {6,32,54} {6,32,55} {6,32,56} {6,32,57} {6,32,58} {6,32,59} {6,32,60} {6,32,61}
{6,32,62} {6,32,63} {6,32,64} {6,32,65} {6,32,66} {6,33,34} {6,33,35} {6,33,36} {6,33,37} {6,33,38}
{6,33,39} {6,33,40} {6,33,41} {6,33,42} {6,33,43} {6,33,44} {6,33,45} {6,33,46} {6,33,47} {6,33,48}
{6,33,49} {6,33,50} {6,33,51} {6,33,52} {6,33,53} {6,33,54} {6,33,55} {6,33,56} {6,33,57} {6,33,58}
{6,33,59} {6,33,60} {6,33,61} {6,33,62} {6,33,63} {6,33,64} {6,33,65} {6,33,66} {6,34,35} {6,34,36}
{6,34,37} {6,34,38} {6,34,39} {6,34,40} {6,34,41} {6,34,42} {6,34,43} {6,34,44} {6,34,45} {6,34,46}
{6,34,47} {6,34,48} {6,34,49} {6,34,50} {6,34,51} {6,34,52} {6,34,53} {6,34,54} {6,34,55} {6,34,56}
{6,34,57} {6,34,58} {6,34,59} {6,34,60} {6,34,61} {6,34,62} {6,34,63} {6,34,64} {6,34,65} {6,34,66}
{6,35,36} {6,35,37} {6,35,38} {6,35,39} {6,35,40} {6,35,41} {6,35,42} {6,35,43} {6,35,44} {6,35,45}
{6,35,46} {6,35,47} {6,35,48} {6,35,49} {6,35,50} {6,35,51} {6,35,52} {6,35,53} {6,35,54} {6,35,55}
{6,35,56} {6,35,57} {6,35,58} {6,35,59} {6,35,60} {6,35,61} {6,35,62} {6,35,63} {6,35,64} {6,35,65}
{6,35,66} {6,36,37} {6,36,38} {6,36,39} {6,36,40} {6,36,41} {6,36,42} {6,36,43} {6,36,44} {6,36,45}
{6,36,46} {6,36,47} {6,36,48} {6,36,49} {6,36,50} {6,36,51} {6,36,52} {6,36,53} {6,36,54} {6,36,55}
{6,36,56} {6,36,57} {6,36,58} {6,36,59} {6,36,60} {6,36,61} {6,36,62} {6,36,63} {6,36,64} {6,36,65}
{6,36,66} {6,37,38} {6,37,39} {6,37,40} {6,37,41} {6,37,42} {6,37,43} {6,37,44} {6,37,45} {6,37,46}
{6,37,47} {6,37,48} {6,37,49} {6,37,50} {6,37,51} {6,37,52} {6,37,53} {6,37,54} {6,37,55} {6,37,56}
{6,37,57} {6,37,58} {6,37,59} {6,37,60} {6,37,61} {6,37,62} {6,37,63} {6,37,64} {6,37,65} {6,37,66}

TABLE 3A-continued

{6,38,39} {6,38,40} {6,38,41} {6,38,42} {6,38,43} {6,38,44} {6,38,45} {6,38,46} {6,38,47} {6,38,48}
{6,38,49} {6,38,50} {6,38,51} {6,38,52} {6,38,53} {6,38,54} {6,38,55} {6,38,56} {6,38,57} {6,38,58}
{6,38,59} {6,38,60} {6,38,61} {6,38,62} {6,38,63} {6,38,64} {6,38,65} {6,38,66} {6,39,40} {6,39,41}
{6,39,42} {6,39,43} {6,39,44} {6,39,45} {6,39,46} {6,39,47} {6,39,48} {6,39,49} {6,39,50} {6,39,51}
{6,39,52} {6,39,53} {6,39,54} {6,39,55} {6,39,56} {6,39,57} {6,39,58} {6,39,59} {6,39,60} {6,39,61}
{6,39,62} {6,39,63} {6,39,64} {6,39,65} {6,39,66} {6,40,41} {6,40,42} {6,40,43} {6,40,44} {6,40,45}
{6,40,46} {6,40,47} {6,40,48} {6,40,49} {6,40,50} {6,40,51} {6,40,52} {6,40,53} {6,40,54} {6,40,55}
{6,40,56} {6,40,57} {6,40,58} {6,40,59} {6,40,60} {6,40,61} {6,40,62} {6,40,63} {6,40,64} {6,40,65}
{6,40,66} {6,41,42} {6,41,43} {6,41,44} {6,41,45} {6,41,46} {6,41,47} {6,41,48} {6,41,49} {6,41,50}
{6,41,51} {6,41,52} {6,41,53} {6,41,54} {6,41,55} {6,41,56} {6,41,57} {6,41,58} {6,41,59} {6,41,60}
{6,41,61} {6,41,62} {6,41,63} {6,41,64} {6,41,65} {6,41,66} {6,42,43} {6,42,44} {6,42,45} {6,42,46}
{6,42,47} {6,42,48} {6,42,49} {6,42,50} {6,42,51} {6,42,52} {6,42,53} {6,42,54} {6,42,55} {6,42,56}
{6,42,57} {6,42,58} {6,42,59} {6,42,60} {6,42,61} {6,42,62} {6,42,63} {6,42,64} {6,42,65} {6,42,66}
{6,43,44} {6,43,45} {6,43,46} {6,43,47} {6,43,48} {6,43,49} {6,43,50} {6,43,51} {6,43,52} {6,43,53}
{6,43,54} {6,43,55} {6,43,56} {6,43,57} {6,43,58} {6,43,59} {6,43,60} {6,43,61} {6,43,62} {6,43,63}
{6,43,64} {6,43,65} {6,43,66} {6,44,45} {6,44,46} {6,44,47} {6,44,48} {6,44,49} {6,44,50} {6,44,51}
{6,44,52} {6,44,53} {6,44,54} {6,44,55} {6,44,56} {6,44,57} {6,44,58} {6,44,59} {6,44,60} {6,44,61}
{6,44,62} {6,44,63} {6,44,64} {6,44,65} {6,44,66} {6,45,46} {6,45,47} {6,45,48} {6,45,49} {6,45,50}
{6,45,51} {6,45,52} {6,45,53} {6,45,54} {6,45,55} {6,45,56} {6,45,57} {6,45,58} {6,45,59} {6,45,60}
{6,45,61} {6,45,62} {6,45,63} {6,45,64} {6,45,65} {6,45,66} {6,46,47} {6,46,48} {6,46,49} {6,46,50}
{6,46,51} {6,46,52} {6,46,53} {6,46,54} {6,46,55} {6,46,56} {6,46,57} {6,46,58} {6,46,59} {6,46,60}
{6,46,61} {6,46,62} {6,46,63} {6,46,64} {6,46,65} {6,46,66} {6,47,48} {6,47,49} {6,47,50} {6,47,51}
{6,47,52} {6,47,53} {6,47,54} {6,47,55} {6,47,56} {6,47,57} {6,47,58} {6,47,59} {6,47,60} {6,47,61}
{6,47,62} {6,47,63} {6,47,64} {6,47,65} {6,47,66} {6,48,49} {6,48,50} {6,48,51} {6,48,52} {6,48,53}
{6,48,54} {6,48,55} {6,48,56} {6,48,57} {6,48,58} {6,48,59} {6,48,60} {6,48,61} {6,48,62} {6,48,63}
{6,48,64} {6,48,65} {6,48,66} {6,49,50} {6,49,51} {6,49,52} {6,49,53} {6,49,54} {6,49,55} {6,49,56}
{6,49,57} {6,49,58} {6,49,59} {6,49,60} {6,49,61} {6,49,62} {6,49,63} {6,49,64} {6,49,65} {6,49,66}
{6,50,51} {6,50,52} {6,50,53} {6,50,54} {6,50,55} {6,50,56} {6,50,57} {6,50,58} {6,50,59} {6,50,60}
{6,50,61} {6,50,62} {6,50,63} {6,50,64} {6,50,65} {6,50,66} {6,51,52} {6,51,53} {6,51,54} {6,51,55}
{6,51,56} {6,51,57} {6,51,58} {6,51,59} {6,51,60} {6,51,61} {6,51,62} {6,51,63} {6,51,64} {6,51,65}
{6,51,66} {6,52,53} {6,52,54} {6,52,55} {6,52,56} {6,52,57} {6,52,58} {6,52,59} {6,52,60} {6,52,61}
{6,52,62} {6,52,63} {6,52,64} {6,52,65} {6,52,66} {6,53,54} {6,53,55} {6,53,56} {6,53,57} {6,53,58}
{6,53,59} {6,53,60} {6,53,61} {6,53,62} {6,53,63} {6,53,64} {6,53,65} {6,53,66} {6,54,55} {6,54,56}
{6,54,57} {6,54,58} {6,54,59} {6,54,60} {6,54,61} {6,54,62} {6,54,63} {6,54,64} {6,54,65} {6,54,66}
{6,55,56} {6,55,57} {6,55,58} {6,55,59} {6,55,60} {6,55,61} {6,55,62} {6,55,63} {6,55,64} {6,55,65}
{6,55,66} {6,56,57} {6,56,58} {6,56,59} {6,56,60} {6,56,61} {6,56,62} {6,56,63} {6,56,64} {6,56,65}
{6,56,66} {6,57,58} {6,57,59} {6,57,60} {6,57,61} {6,57,62} {6,57,63} {6,57,64} {6,57,65} {6,57,66}
{6,58,59} {6,58,60} {6,58,61} {6,58,62} {6,58,63} {6,58,64} {6,58,65} {6,58,66} {6,59,60} {6,59,61}
{6,59,62} {6,59,63} {6,59,64} {6,59,65} {6,59,66} {6,60,61} {6,60,62} {6,60,63} {6,60,64} {6,60,65}
{6,60,66} {6,61,62} {6,61,63} {6,61,64} {6,61,65} {6,61,66} {6,62,63} {6,62,64} {6,62,65} {6,62,66}
{6,63,64} {6,63,65} {6,63,66} {6,64,65} {6,64,66} {6,65,66} {7,8,9} {7,8,10} {7,8,11} {7,8,12} {7,8,13}
{7,8,14} {7,8,15} {7,8,16} {7,8,17} {7,8,18} {7,8,19} {7,8,20} {7,8,21} {7,8,22} {7,8,23} {7,8,24} {7,8,25}
{7,8,26} {7,8,27} {7,8,28} {7,8,29} {7,8,30} {7,8,31} {7,8,32} {7,8,33} {7,8,34} {7,8,35} {7,8,36} {7,8,37}
{7,8,38} {7,8,39} {7,8,40} {7,8,41} {7,8,42} {7,8,43} {7,8,44} {7,8,45} {7,8,46} {7,8,47} {7,8,48} {7,8,49}
{7,8,50} {7,8,51} {7,8,52} {7,8,53} {7,8,54} {7,8,55} {7,8,56} {7,8,57} {7,8,58} {7,8,59} {7,8,60} {7,8,61}
{7,8,62} {7,8,63} {7,8,64} {7,8,65} {7,8,66} {7,9,10} {7,9,11} {7,9,12} {7,9,13} {7,9,14} {7,9,15} {7,9,16}
{7,9,17} {7,9,18} {7,9,19} {7,9,20} {7,9,21} {7,9,22} {7,9,23} {7,9,24} {7,9,25} {7,9,26} {7,9,27} {7,9,28}
{7,9,29} {7,9,30} {7,9,31} {7,9,32} {7,9,33} {7,9,34} {7,9,35} {7,9,36} {7,9,37} {7,9,38} {7,9,39} {7,9,40}
{7,9,41} {7,9,42} {7,9,43} {7,9,44} {7,9,45} {7,9,46} {7,9,47} {7,9,48} {7,9,49} {7,9,50} {7,9,51} {7,9,52}
{7,9,53} {7,9,54} {7,9,55} {7,9,56} {7,9,57} {7,9,58} {7,9,59} {7,9,60} {7,9,61} {7,9,62} {7,9,63} {7,9,64}
{7,9,65} {7,9,66} {7,10,11} {7,10,12} {7,10,13} {7,10,14} {7,10,15} {7,10,16} {7,10,17} {7,10,18} {7,10,19}
{7,10,20} {7,10,21} {7,10,22} {7,10,23} {7,10,24} {7,10,25} {7,10,26} {7,10,27} {7,10,28} {7,10,29}
{7,10,30} {7,10,31} {7,10,32} {7,10,33} {7,10,34} {7,10,35} {7,10,36} {7,10,37} {7,10,38} {7,10,39}
{7,10,40} {7,10,41} {7,10,42} {7,10,43} {7,10,44} {7,10,45} {7,10,46} {7,10,47} {7,10,48} {7,10,49}
{7,10,50} {7,10,51} {7,10,52} {7,10,53} {7,10,54} {7,10,55} {7,10,56} {7,10,57} {7,10,58} {7,10,59}
{7,10,60} {7,10,61} {7,10,62} {7,10,63} {7,10,64} {7,10,65} {7,10,66} {7,11,12} {7,11,13} {7,11,14}
{7,11,15} {7,11,16} {7,11,17} {7,11,18} {7,11,19} {7,11,20} {7,11,21} {7,11,22} {7,11,23} {7,11,24}
{7,11,25} {7,11,26} {7,11,27} {7,11,28} {7,11,29} {7,11,30} {7,11,31} {7,11,32} {7,11,33} {7,11,34}
{7,11,35} {7,11,36} {7,11,37} {7,11,38} {7,11,39} {7,11,40} {7,11,41} {7,11,42} {7,11,43} {7,11,44}
{7,11,45} {7,11,46} {7,11,47} {7,11,48} {7,11,49} {7,11,50} {7,11,51} {7,11,52} {7,11,53} {7,11,54}
{7,11,55} {7,11,56} {7,11,57} {7,11,58} {7,11,59} {7,11,60} {7,11,61} {7,11,62} {7,11,63} {7,11,64}
{7,11,65} {7,11,66} {7,12,13} {7,12,14} {7,12,15} {7,12,16} {7,12,17} {7,12,18} {7,12,19} {7,12,20}
{7,12,21} {7,12,22} {7,12,23} {7,12,24} {7,12,25} {7,12,26} {7,12,27} {7,12,28} {7,12,29} {7,12,30}
{7,12,31} {7,12,32} {7,12,33} {7,12,34} {7,12,35} {7,12,36} {7,12,37} {7,12,38} {7,12,39} {7,12,40}
{7,12,41} {7,12,42} {7,12,43} {7,12,44} {7,12,45} {7,12,46} {7,12,47} {7,12,48} {7,12,49} {7,12,50}
{7,12,51} {7,12,52} {7,12,53} {7,12,54} {7,12,55} {7,12,56} {7,12,57} {7,12,58} {7,12,59} {7,12,60}
{7,12,61} {7,12,62} {7,12,63} {7,12,64} {7,12,65} {7,12,66} {7,13,14} {7,13,15} {7,13,16} {7,13,17}
{7,13,18} {7,13,19} {7,13,20} {7,13,21} {7,13,22} {7,13,23} {7,13,24} {7,13,25} {7,13,26} {7,13,27}
{7,13,28} {7,13,29} {7,13,30} {7,13,31} {7,13,32} {7,13,33} {7,13,34} {7,13,35} {7,13,36} {7,13,37}
{7,13,38} {7,13,39} {7,13,40} {7,13,41} {7,13,42} {7,13,43} {7,13,44} {7,13,45} {7,13,46} {7,13,47}
{7,13,48} {7,13,49} {7,13,50} {7,13,51} {7,13,52} {7,13,53} {7,13,54} {7,13,55} {7,13,56} {7,13,57}
{7,13,58} {7,13,59} {7,13,60} {7,13,61} {7,13,62} {7,13,63} {7,13,64} {7,13,65} {7,13,66} {7,14,15}
{7,14,16} {7,14,17} {7,14,18} {7,14,19} {7,14,20} {7,14,21} {7,14,22} {7,14,23} {7,14,24} {7,14,25}
{7,14,26} {7,14,27} {7,14,28} {7,14,29} {7,14,30} {7,14,31} {7,14,32} {7,14,33} {7,14,34} {7,14,35}
{7,14,36} {7,14,37} {7,14,38} {7,14,39} {7,14,40} {7,14,41} {7,14,42} {7,14,43} {7,14,44} {7,14,45}
{7,14,46} {7,14,47} {7,14,48} {7,14,49} {7,14,50} {7,14,51} {7,14,52} {7,14,53} {7,14,54} {7,14,55}
{7,14,56} {7,14,57} {7,14,58} {7,14,59} {7,14,60} {7,14,61} {7,14,62} {7,14,63} {7,14,64} {7,14,65}
{7,14,66} {7,15,16} {7,15,17} {7,15,18} {7,15,19} {7,15,20} {7,15,21} {7,15,22} {7,15,23} {7,15,24}
{7,15,25} {7,15,26} {7,15,27} {7,15,28} {7,15,29} {7,15,30} {7,15,31} {7,15,32} {7,15,33} {7,15,34}
{7,15,35} {7,15,36} {7,15,37} {7,15,38} {7,15,39} {7,15,40} {7,15,41} {7,15,42} {7,15,43} {7,15,44}

TABLE 3A-continued

{7,15,45} {7,15,46} {7,15,47} {7,15,48} {7,15,49} {7,15,50} {7,15,51} {7,15,52} {7,15,53} {7,15,54}
{7,15,55} {7,15,56} {7,15,57} {7,15,58} {7,15,59} {7,15,60} {7,15,61} {7,15,62} {7,15,63} {7,15,64}
{7,15,65} {7,15,66} {7,16,17} {7,16,18} {7,16,19} {7,16,20} {7,16,21} {7,16,22} {7,16,23} {7,16,24}
{7,16,25} {7,16,26} {7,16,27} {7,16,28} {7,16,29} {7,16,30} {7,16,31} {7,16,32} {7,16,33} {7,16,34}
{7,16,35} {7,16,36} {7,16,37} {7,16,38} {7,16,39} {7,16,40} {7,16,41} {7,16,42} {7,16,43} {7,16,44}
{7,16,45} {7,16,46} {7,16,47} {7,16,48} {7,16,49} {7,16,50} {7,16,51} {7,16,52} {7,16,53} {7,16,54}
{7,16,55} {7,16,56} {7,16,57} {7,16,58} {7,16,59} {7,16,60} {7,16,61} {7,16,62} {7,16,63} {7,16,64}
{7,16,65} {7,16,66} {7,17,18} {7,17,19} {7,17,20} {7,17,21} {7,17,22} {7,17,23} {7,17,24} {7,17,25}
{7,17,26} {7,17,27} {7,17,28} {7,17,29} {7,17,30} {7,17,31} {7,17,32} {7,17,33} {7,17,34} {7,17,35}
{7,17,36} {7,17,37} {7,17,38} {7,17,39} {7,17,40} {7,17,41} {7,17,42} {7,17,43} {7,17,44} {7,17,45}
{7,17,46} {7,17,47} {7,17,48} {7,17,49} {7,17,50} {7,17,51} {7,17,52} {7,17,53} {7,17,54} {7,17,55}
{7,17,56} {7,17,57} {7,17,58} {7,17,59} {7,17,60} {7,17,61} {7,17,62} {7,17,63} {7,17,64} {7,17,65}
{7,17,66} {7,18,19} {7,18,20} {7,18,21} {7,18,22} {7,18,23} {7,18,24} {7,18,25} {7,18,26} {7,18,27}
{7,18,28} {7,18,29} {7,18,30} {7,18,31} {7,18,32} {7,18,33} {7,18,34} {7,18,35} {7,18,36} {7,18,37}
{7,18,38} {7,18,39} {7,18,40} {7,18,41} {7,18,42} {7,18,43} {7,18,44} {7,18,45} {7,18,46} {7,18,47}
{7,18,48} {7,18,49} {7,18,50} {7,18,51} {7,18,52} {7,18,53} {7,18,54} {7,18,55} {7,18,56} {7,18,57}
{7,18,58} {7,18,59} {7,18,60} {7,18,61} {7,18,62} {7,18,63} {7,18,64} {7,18,65} {7,18,66} {7,19,20}
{7,19,21} {7,19,22} {7,19,23} {7,19,24} {7,19,25} {7,19,26} {7,19,27} {7,19,28} {7,19,29} {7,19,30}
{7,19,31} {7,19,32} {7,19,33} {7,19,34} {7,19,35} {7,19,36} {7,19,37} {7,19,38} {7,19,39} {7,19,40}
{7,19,41} {7,19,42} {7,19,43} {7,19,44} {7,19,45} {7,19,46} {7,19,47} {7,19,48} {7,19,49} {7,19,50}
{7,19,51} {7,19,52} {7,19,53} {7,19,54} {7,19,55} {7,19,56} {7,19,57} {7,19,58} {7,19,59} {7,19,60}
{7,19,61} {7,19,62} {7,19,63} {7,19,64} {7,19,65} {7,19,66} {7,20,21} {7,20,22} {7,20,23} {7,20,24}
{7,20,25} {7,20,26} {7,20,27} {7,20,28} {7,20,29} {7,20,30} {7,20,31} {7,20,32} {7,20,33} {7,20,34}
{7,20,35} {7,20,36} {7,20,37} {7,20,38} {7,20,39} {7,20,40} {7,20,41} {7,20,42} {7,20,43} {7,20,44}
{7,20,45} {7,20,46} {7,20,47} {7,20,48} {7,20,49} {7,20,50} {7,20,51} {7,20,52} {7,20,53} {7,20,54}
{7,20,55} {7,20,56} {7,20,57} {7,20,58} {7,20,59} {7,20,60} {7,20,61} {7,20,62} {7,20,63} {7,20,64}
{7,20,65} {7,20,66} {7,21,22} {7,21,23} {7,21,24} {7,21,25} {7,21,26} {7,21,27} {7,21,28} {7,21,29}
{7,21,30} {7,21,31} {7,21,32} {7,21,33} {7,21,34} {7,21,35} {7,21,36} {7,21,37} {7,21,38} {7,21,39}
{7,21,40} {7,21,41} {7,21,42} {7,21,43} {7,21,44} {7,21,45} {7,21,46} {7,21,47} {7,21,48} {7,21,49}
{7,21,50} {7,21,51} {7,21,52} {7,21,53} {7,21,54} {7,21,55} {7,21,56} {7,21,57} {7,21,58} {7,21,59}
{7,21,60} {7,21,61} {7,21,62} {7,21,63} {7,21,64} {7,21,65} {7,21,66} {7,22,23} {7,22,24} {7,22,25}
{7,22,26} {7,22,27} {7,22,28} {7,22,29} {7,22,30} {7,22,31} {7,22,32} {7,22,33} {7,22,34} {7,22,35}
{7,22,36} {7,22,37} {7,22,38} {7,22,39} {7,22,40} {7,22,41} {7,22,42} {7,22,43} {7,22,44} {7,22,45}
{7,22,46} {7,22,47} {7,22,48} {7,22,49} {7,22,50} {7,22,51} {7,22,52} {7,22,53} {7,22,54} {7,22,55}
{7,22,56} {7,22,57} {7,22,58} {7,22,59} {7,22,60} {7,22,61} {7,22,62} {7,22,63} {7,22,64} {7,22,65}
{7,22,66} {7,23,24} {7,23,25} {7,23,26} {7,23,27} {7,23,28} {7,23,29} {7,23,30} {7,23,31} {7,23,32}
{7,23,33} {7,23,34} {7,23,35} {7,23,36} {7,23,37} {7,23,38} {7,23,39} {7,23,40} {7,23,41} {7,23,42}
{7,23,43} {7,23,44} {7,23,45} {7,23,46} {7,23,47} {7,23,48} {7,23,49} {7,23,50} {7,23,51} {7,23,52}
{7,23,53} {7,23,54} {7,23,55} {7,23,56} {7,23,57} {7,23,58} {7,23,59} {7,23,60} {7,23,61} {7,23,62}
{7,23,63} {7,23,64} {7,23,65} {7,23,66} {7,24,25} {7,24,26} {7,24,27} {7,24,28} {7,24,29} {7,24,30}
{7,24,31} {7,24,32} {7,24,33} {7,24,34} {7,24,35} {7,24,36} {7,24,37} {7,24,38} {7,24,39} {7,24,40}
{7,24,41} {7,24,42} {7,24,43} {7,24,44} {7,24,45} {7,24,46} {7,24,47} {7,24,48} {7,24,49} {7,24,50}
{7,24,51} {7,24,52} {7,24,53} {7,24,54} {7,24,55} {7,24,56} {7,24,57} {7,24,58} {7,24,59} {7,24,60}
{7,24,61} {7,24,62} {7,24,63} {7,24,64} {7,24,65} {7,24,66} {7,25,26} {7,25,27} {7,25,28} {7,25,29}
{7,25,30} {7,25,31} {7,25,32} {7,25,33} {7,25,34} {7,25,35} {7,25,36} {7,25,37} {7,25,38} {7,25,39}
{7,25,40} {7,25,41} {7,25,42} {7,25,43} {7,25,44} {7,25,45} {7,25,46} {7,25,47} {7,25,48} {7,25,49}
{7,25,50} {7,25,51} {7,25,52} {7,25,53} {7,25,54} {7,25,55} {7,25,56} {7,25,57} {7,25,58} {7,25,59}
{7,25,60} {7,25,61} {7,25,62} {7,25,63} {7,25,64} {7,25,65} {7,25,66} {7,26,27} {7,26,28} {7,26,29}
{7,26,30} {7,26,31} {7,26,32} {7,26,33} {7,26,34} {7,26,35} {7,26,36} {7,26,37} {7,26,38} {7,26,39}
{7,26,40} {7,26,41} {7,26,42} {7,26,43} {7,26,44} {7,26,45} {7,26,46} {7,26,47} {7,26,48} {7,26,49}
{7,26,50} {7,26,51} {7,26,52} {7,26,53} {7,26,54} {7,26,55} {7,26,56} {7,26,57} {7,26,58} {7,26,59}
{7,26,60} {7,26,61} {7,26,62} {7,26,63} {7,26,64} {7,26,65} {7,26,66} {7,27,28} {7,27,29} {7,27,30}
{7,27,31} {7,27,32} {7,27,33} {7,27,34} {7,27,35} {7,27,36} {7,27,37} {7,27,38} {7,27,39} {7,27,40}
{7,27,41} {7,27,42} {7,27,43} {7,27,44} {7,27,45} {7,27,46} {7,27,47} {7,27,48} {7,27,49} {7,27,50}
{7,27,51} {7,27,52} {7,27,53} {7,27,54} {7,27,55} {7,27,56} {7,27,57} {7,27,58} {7,27,59} {7,27,60}
{7,27,61} {7,27,62} {7,27,63} {7,27,64} {7,27,65} {7,27,66} {7,28,29} {7,28,30} {7,28,31} {7,28,32}
{7,28,33} {7,28,34} {7,28,35} {7,28,36} {7,28,37} {7,28,38} {7,28,39} {7,28,40} {7,28,41} {7,28,42}
{7,28,43} {7,28,44} {7,28,45} {7,28,46} {7,28,47} {7,28,48} {7,28,49} {7,28,50} {7,28,51} {7,28,52}
{7,28,53} {7,28,54} {7,28,55} {7,28,56} {7,28,57} {7,28,58} {7,28,59} {7,28,60} {7,28,61} {7,28,62}
{7,28,63} {7,28,64} {7,28,65} {7,28,66} {7,29,30} {7,29,31} {7,29,32} {7,29,33} {7,29,34} {7,29,35}
{7,29,36} {7,29,37} {7,29,38} {7,29,39} {7,29,40} {7,29,41} {7,29,42} {7,29,43} {7,29,44} {7,29,45}
{7,29,46} {7,29,47} {7,29,48} {7,29,49} {7,29,50} {7,29,51} {7,29,52} {7,29,53} {7,29,54} {7,29,55}
{7,29,56} {7,29,57} {7,29,58} {7,29,59} {7,29,60} {7,29,61} {7,29,62} {7,29,63} {7,29,64} {7,29,65}
{7,29,66} {7,30,31} {7,30,32} {7,30,33} {7,30,34} {7,30,35} {7,30,36} {7,30,37} {7,30,38} {7,30,39}
{7,30,40} {7,30,41} {7,30,42} {7,30,43} {7,30,44} {7,30,45} {7,30,46} {7,30,47} {7,30,48} {7,30,49}
{7,30,50} {7,30,51} {7,30,52} {7,30,53} {7,30,54} {7,30,55} {7,30,56} {7,30,57} {7,30,58} {7,30,59}
{7,30,60} {7,30,61} {7,30,62} {7,30,63} {7,30,64} {7,30,65} {7,30,66} {7,31,32} {7,31,33} {7,31,34}
{7,31,35} {7,31,36} {7,31,37} {7,31,38} {7,31,39} {7,31,40} {7,31,41} {7,31,42} {7,31,43} {7,31,44}
{7,31,45} {7,31,46} {7,31,47} {7,31,48} {7,31,49} {7,31,50} {7,31,51} {7,31,52} {7,31,53} {7,31,54}
{7,31,55} {7,31,56} {7,31,57} {7,31,58} {7,31,59} {7,31,60} {7,31,61} {7,31,62} {7,31,63} {7,31,64}
{7,31,65} {7,31,66} {7,32,33} {7,32,34} {7,32,35} {7,32,36} {7,32,37} {7,32,38} {7,32,39} {7,32,40}
{7,32,41} {7,32,42} {7,32,43} {7,32,44} {7,32,45} {7,32,46} {7,32,47} {7,32,48} {7,32,49} {7,32,50}
{7,32,51} {7,32,52} {7,32,53} {7,32,54} {7,32,55} {7,32,56} {7,32,57} {7,32,58} {7,32,59} {7,32,60}
{7,32,61} {7,32,62} {7,32,63} {7,32,64} {7,32,65} {7,32,66} {7,33,34} {7,33,35} {7,33,36} {7,33,37}
{7,33,38} {7,33,39} {7,33,40} {7,33,41} {7,33,42} {7,33,43} {7,33,44} {7,33,45} {7,33,46} {7,33,47}
{7,33,48} {7,33,49} {7,33,50} {7,33,51} {7,33,52} {7,33,53} {7,33,54} {7,33,55} {7,33,56} {7,33,57}
{7,33,58} {7,33,59} {7,33,60} {7,33,61} {7,33,62} {7,33,63} {7,33,64} {7,33,65} {7,33,66} {7,34,35}
{7,34,36} {7,34,37} {7,34,38} {7,34,39} {7,34,40} {7,34,41} {7,34,42} {7,34,43} {7,34,44} {7,34,45}
{7,34,46} {7,34,47} {7,34,48} {7,34,49} {7,34,50} {7,34,51} {7,34,52} {7,34,53} {7,34,54} {7,34,55}
{7,34,56} {7,34,57} {7,34,58} {7,34,59} {7,34,60} {7,34,61} {7,34,62} {7,34,63} {7,34,64} {7,34,65}

TABLE 3A-continued

{7,34,66} {7,35,36} {7,35,37} {7,35,38} {7,35,39} {7,35,40} {7,35,41} {7,35,42} {7,35,43} {7,35,44}
{7,35,45} {7,35,46} {7,35,47} {7,35,48} {7,35,49} {7,35,50} {7,35,51} {7,35,52} {7,35,53} {7,35,54}
{7,35,55} {7,35,56} {7,35,57} {7,35,58} {7,35,59} {7,35,60} {7,35,61} {7,35,62} {7,35,63} {7,35,64}
{7,35,65} {7,35,66} {7,36,37} {7,36,38} {7,36,39} {7,36,40} {7,36,41} {7,36,42} {7,36,43} {7,36,44}
{7,36,45} {7,36,46} {7,36,47} {7,36,48} {7,36,49} {7,36,50} {7,36,51} {7,36,52} {7,36,53} {7,36,54}
{7,36,55} {7,36,56} {7,36,57} {7,36,58} {7,36,59} {7,36,60} {7,36,61} {7,36,62} {7,36,63} {7,36,64}
{7,36,65} {7,36,66} {7,37,38} {7,37,39} {7,37,40} {7,37,41} {7,37,42} {7,37,43} {7,37,44} {7,37,45}
{7,37,46} {7,37,47} {7,37,48} {7,37,49} {7,37,50} {7,37,51} {7,37,52} {7,37,53} {7,37,54} {7,37,55}
{7,37,56} {7,37,57} {7,37,58} {7,37,59} {7,37,60} {7,37,61} {7,37,62} {7,37,63} {7,37,64} {7,37,65}
{7,37,66} {7,38,39} {7,38,40} {7,38,41} {7,38,42} {7,38,43} {7,38,44} {7,38,45} {7,38,46} {7,38,47}
{7,38,48} {7,38,49} {7,38,50} {7,38,51} {7,38,52} {7,38,53} {7,38,54} {7,38,55} {7,38,56} {7,38,57}
{7,38,58} {7,38,59} {7,38,60} {7,38,61} {7,38,62} {7,38,63} {7,38,64} {7,38,65} {7,38,66} {7,39,40}
{7,39,41} {7,39,42} {7,39,43} {7,39,44} {7,39,45} {7,39,46} {7,39,47} {7,39,48} {7,39,49} {7,39,50}
{7,39,51} {7,39,52} {7,39,53} {7,39,54} {7,39,55} {7,39,56} {7,39,57} {7,39,58} {7,39,59} {7,39,60}
{7,39,61} {7,39,62} {7,39,63} {7,39,64} {7,39,65} {7,39,66} {7,40,41} {7,40,42} {7,40,43} {7,40,44}
{7,40,45} {7,40,46} {7,40,47} {7,40,48} {7,40,49} {7,40,50} {7,40,51} {7,40,52} {7,40,53} {7,40,54}
{7,40,55} {7,40,56} {7,40,57} {7,40,58} {7,40,59} {7,40,60} {7,40,61} {7,40,62} {7,40,63} {7,40,64}
{7,40,65} {7,40,66} {7,41,42} {7,41,43} {7,41,44} {7,41,45} {7,41,46} {7,41,47} {7,41,48} {7,41,49}
{7,41,50} {7,41,51} {7,41,52} {7,41,53} {7,41,54} {7,41,55} {7,41,56} {7,41,57} {7,41,58} {7,41,59}
{7,41,60} {7,41,61} {7,41,62} {7,41,63} {7,41,64} {7,41,65} {7,41,66} {7,42,43} {7,42,44} {7,42,45}
{7,42,46} {7,42,47} {7,42,48} {7,42,49} {7,42,50} {7,42,51} {7,42,52} {7,42,53} {7,42,54} {7,42,55}
{7,42,56} {7,42,57} {7,42,58} {7,42,59} {7,42,60} {7,42,61} {7,42,62} {7,42,63} {7,42,64} {7,42,65}
{7,42,66} {7,43,44} {7,43,45} {7,43,46} {7,43,47} {7,43,48} {7,43,49} {7,43,50} {7,43,51} {7,43,52}
{7,43,53} {7,43,54} {7,43,55} {7,43,56} {7,43,57} {7,43,58} {7,43,59} {7,43,60} {7,43,61} {7,43,62}
{7,43,63} {7,43,64} {7,43,65} {7,43,66} {7,44,45} {7,44,46} {7,44,47} {7,44,48} {7,44,49} {7,44,50}
{7,44,51} {7,44,52} {7,44,53} {7,44,54} {7,44,55} {7,44,56} {7,44,57} {7,44,58} {7,44,59} {7,44,60}
{7,44,61} {7,44,62} {7,44,63} {7,44,64} {7,44,65} {7,44,66} {7,45,46} {7,45,47} {7,45,48} {7,45,49}
{7,45,50} {7,45,51} {7,45,52} {7,45,53} {7,45,54} {7,45,55} {7,45,56} {7,45,57} {7,45,58} {7,45,59}
{7,45,60} {7,45,61} {7,45,62} {7,45,63} {7,45,64} {7,45,65} {7,45,66} {7,46,47} {7,46,48} {7,46,49}
{7,46,50} {7,46,51} {7,46,52} {7,46,53} {7,46,54} {7,46,55} {7,46,56} {7,46,57} {7,46,58} {7,46,59}
{7,46,60} {7,46,61} {7,46,62} {7,46,63} {7,46,64} {7,46,65} {7,46,66} {7,47,48} {7,47,49} {7,47,50}
{7,47,51} {7,47,52} {7,47,53} {7,47,54} {7,47,55} {7,47,56} {7,47,57} {7,47,58} {7,47,59} {7,47,60}
{7,47,61} {7,47,62} {7,47,63} {7,47,64} {7,47,65} {7,47,66} {7,48,49} {7,48,50} {7,48,51} {7,48,52}
{7,48,53} {7,48,54} {7,48,55} {7,48,56} {7,48,57} {7,48,58} {7,48,59} {7,48,60} {7,48,61} {7,48,62}
{7,48,63} {7,48,64} {7,48,65} {7,48,66} {7,49,50} {7,49,51} {7,49,52} {7,49,53} {7,49,54} {7,49,55}
{7,49,56} {7,49,57} {7,49,58} {7,49,59} {7,49,60} {7,49,61} {7,49,62} {7,49,63} {7,49,64} {7,49,65}
{7,49,66} {7,50,51} {7,50,52} {7,50,53} {7,50,54} {7,50,55} {7,50,56} {7,50,57} {7,50,58} {7,50,59}
{7,50,60} {7,50,61} {7,50,62} {7,50,63} {7,50,64} {7,50,65} {7,50,66} {7,51,52} {7,51,53} {7,51,54}
{7,51,55} {7,51,56} {7,51,57} {7,51,58} {7,51,59} {7,51,60} {7,51,61} {7,51,62} {7,51,63} {7,51,64}
{7,51,65} {7,51,66} {7,52,53} {7,52,54} {7,52,55} {7,52,56} {7,52,57} {7,52,58} {7,52,59} {7,52,60}
{7,52,61} {7,52,62} {7,52,63} {7,52,64} {7,52,65} {7,52,66} {7,53,54} {7,53,55} {7,53,56} {7,53,57}
{7,53,58} {7,53,59} {7,53,60} {7,53,61} {7,53,62} {7,53,63} {7,53,64} {7,53,65} {7,53,66} {7,54,55}
{7,54,56} {7,54,57} {7,54,58} {7,54,59} {7,54,60} {7,54,61} {7,54,62} {7,54,63} {7,54,64} {7,54,65}
{7,54,66} {7,55,56} {7,55,57} {7,55,58} {7,55,59} {7,55,60} {7,55,61} {7,55,62} {7,55,63} {7,55,64}
{7,55,65} {7,55,66} {7,56,57} {7,56,58} {7,56,59} {7,56,60} {7,56,61} {7,56,62} {7,56,63} {7,56,64}
{7,56,65} {7,56,66} {7,57,58} {7,57,59} {7,57,60} {7,57,61} {7,57,62} {7,57,63} {7,57,64} {7,57,65}
{7,57,66} {7,58,59} {7,58,60} {7,58,61} {7,58,62} {7,58,63} {7,58,64} {7,58,65} {7,58,66} {7,59,60}
{7,59,61} {7,59,62} {7,59,63} {7,59,64} {7,59,65} {7,59,66} {7,60,61} {7,60,62} {7,60,63} {7,60,64}
{7,60,65} {7,60,66} {7,61,62} {7,61,63} {7,61,64} {7,61,65} {7,61,66} {7,62,63} {7,62,64} {7,62,65}
{7,62,66} {7,63,64} {7,63,65} {7,63,66} {7,64,65} {7,64,66} {7,65,66} {8,9,10} {8,9,11} {8,9,12} {8,9,13}
{8,9,14} {8,9,15} {8,9,16} {8,9,17} {8,9,18} {8,9,19} {8,9,20} {8,9,21} {8,9,22} {8,9,23} {8,9,24} {8,9,25}
{8,9,26} {8,9,27} {8,9,28} {8,9,29} {8,9,30} {8,9,31} {8,9,32} {8,9,33} {8,9,34} {8,9,35} {8,9,36} {8,9,37}
{8,9,38} {8,9,39} {8,9,40} {8,9,41} {8,9,42} {8,9,43} {8,9,44} {8,9,45} {8,9,46} {8,9,47} {8,9,48} {8,9,49}
{8,9,50} {8,9,51} {8,9,52} {8,9,53} {8,9,54} {8,9,55} {8,9,56} {8,9,57} {8,9,58} {8,9,59} {8,9,60} {8,9,61}
{8,9,62} {8,9,63} {8,9,64} {8,9,65} {8,9,66} {8,10,11} {8,10,12} {8,10,13} {8,10,14} {8,10,15} {8,10,16}
{8,10,17} {8,10,18} {8,10,19} {8,10,20} {8,10,21} {8,10,22} {8,10,23} {8,10,24} {8,10,25} {8,10,26}
{8,10,27} {8,10,28} {8,10,29} {8,10,30} {8,10,31} {8,10,32} {8,10,33} {8,10,34} {8,10,35} {8,10,36}
{8,10,37} {8,10,38} {8,10,39} {8,10,40} {8,10,41} {8,10,42} {8,10,43} {8,10,44} {8,10,45} {8,10,46}
{8,10,47} {8,10,48} {8,10,49} {8,10,50} {8,10,51} {8,10,52} {8,10,53} {8,10,54} {8,10,55} {8,10,56}
{8,10,57} {8,10,58} {8,10,59} {8,10,60} {8,10,61} {8,10,62} {8,10,63} {8,10,64} {8,10,65} {8,10,66}
{8,11,12} {8,11,13} {8,11,14} {8,11,15} {8,11,16} {8,11,17} {8,11,18} {8,11,19} {8,11,20} {8,11,21}
{8,11,22} {8,11,23} {8,11,24} {8,11,25} {8,11,26} {8,11,27} {8,11,28} {8,11,29} {8,11,30} {8,11,31}
{8,11,32} {8,11,33} {8,11,34} {8,11,35} {8,11,36} {8,11,37} {8,11,38} {8,11,39} {8,11,40} {8,11,41}
{8,11,42} {8,11,43} {8,11,44} {8,11,45} {8,11,46} {8,11,47} {8,11,48} {8,11,49} {8,11,50} {8,11,51}
{8,11,52} {8,11,53} {8,11,54} {8,11,55} {8,11,56} {8,11,57} {8,11,58} {8,11,59} {8,11,60} {8,11,61}
{8,11,62} {8,11,63} {8,11,64} {8,11,65} {8,11,66} {8,12,13} {8,12,14} {8,12,15} {8,12,16} {8,12,17}
{8,12,18} {8,12,19} {8,12,20} {8,12,21} {8,12,22} {8,12,23} {8,12,24} {8,12,25} {8,12,26} {8,12,27}
{8,12,28} {8,12,29} {8,12,30} {8,12,31} {8,12,32} {8,12,33} {8,12,34} {8,12,35} {8,12,36} {8,12,37}
{8,12,38} {8,12,39} {8,12,40} {8,12,41} {8,12,42} {8,12,43} {8,12,44} {8,12,45} {8,12,46} {8,12,47}
{8,12,48} {8,12,49} {8,12,50} {8,12,51} {8,12,52} {8,12,53} {8,12,54} {8,12,55} {8,12,56} {8,12,57}
{8,12,58} {8,12,59} {8,12,60} {8,12,61} {8,12,62} {8,12,63} {8,12,64} {8,12,65} {8,12,66} {8,13,14}
{8,13,15} {8,13,16} {8,13,17} {8,13,18} {8,13,19} {8,13,20} {8,13,21} {8,13,22} {8,13,23} {8,13,24}
{8,13,25} {8,13,26} {8,13,27} {8,13,28} {8,13,29} {8,13,30} {8,13,31} {8,13,32} {8,13,33} {8,13,34}
{8,13,35} {8,13,36} {8,13,37} {8,13,38} {8,13,39} {8,13,40} {8,13,41} {8,13,42} {8,13,43} {8,13,44}
{8,13,45} {8,13,46} {8,13,47} {8,13,48} {8,13,49} {8,13,50} {8,13,51} {8,13,52} {8,13,53} {8,13,54}
{8,13,55} {8,13,56} {8,13,57} {8,13,58} {8,13,59} {8,13,60} {8,13,61} {8,13,62} {8,13,63} {8,13,64}
{8,13,65} {8,13,66} {8,14,15} {8,14,16} {8,14,17} {8,14,18} {8,14,19} {8,14,20} {8,14,21} {8,14,22}
{8,14,23} {8,14,24} {8,14,25} {8,14,26} {8,14,27} {8,14,28} {8,14,29} {8,14,30} {8,14,31} {8,14,32}
{8,14,33} {8,14,34} {8,14,35} {8,14,36} {8,14,37} {8,14,38} {8,14,39} {8,14,40} {8,14,41} {8,14,42}
{8,14,43} {8,14,44} {8,14,45} {8,14,46} {8,14,47} {8,14,48} {8,14,49} {8,14,50} {8,14,51} {8,14,52}

TABLE 3A-continued

{8,14,53} {8,14,54} {8,14,55} {8,14,56} {8,14,57} {8,14,58} {8,14,59} {8,14,60} {8,14,61} {8,14,62}
{8,14,63} {8,14,64} {8,14,65} {8,14,66} {8,15,16} {8,15,17} {8,15,18} {8,15,19} {8,15,20} {8,15,21}
{8,15,22} {8,15,23} {8,15,24} {8,15,25} {8,15,26} {8,15,27} {8,15,28} {8,15,29} {8,15,30} {8,15,31}
{8,15,32} {8,15,33} {8,15,34} {8,15,35} {8,15,36} {8,15,37} {8,15,38} {8,15,39} {8,15,40} {8,15,41}
{8,15,42} {8,15,43} {8,15,44} {8,15,45} {8,15,46} {8,15,47} {8,15,48} {8,15,49} {8,15,50} {8,15,51}
{8,15,52} {8,15,53} {8,15,54} {8,15,55} {8,15,56} {8,15,57} {8,15,58} {8,15,59} {8,15,60} {8,15,61}
{8,15,62} {8,15,63} {8,15,64} {8,15,65} {8,15,66} {8,16,17} {8,16,18} {8,16,19} {8,16,20} {8,16,21}
{8,16,22} {8,16,23} {8,16,24} {8,16,25} {8,16,26} {8,16,27} {8,16,28} {8,16,29} {8,16,30} {8,16,31}
{8,16,32} {8,16,33} {8,16,34} {8,16,35} {8,16,36} {8,16,37} {8,16,38} {8,16,39} {8,16,40} {8,16,41}
{8,16,42} {8,16,43} {8,16,44} {8,16,45} {8,16,46} {8,16,47} {8,16,48} {8,16,49} {8,16,50} {8,16,51}
{8,16,52} {8,16,53} {8,16,54} {8,16,55} {8,16,56} {8,16,57} {8,16,58} {8,16,59} {8,16,60} {8,16,61}
{8,16,62} {8,16,63} {8,16,64} {8,16,65} {8,16,66} {8,17,18} {8,17,19} {8,17,20} {8,17,21} {8,17,22}
{8,17,23} {8,17,24} {8,17,25} {8,17,26} {8,17,27} {8,17,28} {8,17,29} {8,17,30} {8,17,31} {8,17,32}
{8,17,33} {8,17,34} {8,17,35} {8,17,36} {8,17,37} {8,17,38} {8,17,39} {8,17,40} {8,17,41} {8,17,42}
{8,17,43} {8,17,44} {8,17,45} {8,17,46} {8,17,47} {8,17,48} {8,17,49} {8,17,50} {8,17,51} {8,17,52}
{8,17,53} {8,17,54} {8,17,55} {8,17,56} {8,17,57} {8,17,58} {8,17,59} {8,17,60} {8,17,61} {8,17,62}
{8,17,63} {8,17,64} {8,17,65} {8,17,66} {8,18,19} {8,18,20} {8,18,21} {8,18,22} {8,18,23} {8,18,24}
{8,18,25} {8,18,26} {8,18,27} {8,18,28} {8,18,29} {8,18,30} {8,18,31} {8,18,32} {8,18,33} {8,18,34}
{8,18,35} {8,18,36} {8,18,37} {8,18,38} {8,18,39} {8,18,40} {8,18,41} {8,18,42} {8,18,43} {8,18,44}
{8,18,45} {8,18,46} {8,18,47} {8,18,48} {8,18,49} {8,18,50} {8,18,51} {8,18,52} {8,18,53} {8,18,54}
{8,18,55} {8,18,56} {8,18,57} {8,18,58} {8,18,59} {8,18,60} {8,18,61} {8,18,62} {8,18,63} {8,18,64}
{8,18,65} {8,18,66} {8,19,20} {8,19,21} {8,19,22} {8,19,23} {8,19,24} {8,19,25} {8,19,26} {8,19,27}
{8,19,28} {8,19,29} {8,19,30} {8,19,31} {8,19,32} {8,19,33} {8,19,34} {8,19,35} {8,19,36} {8,19,37}
{8,19,38} {8,19,39} {8,19,40} {8,19,41} {8,19,42} {8,19,43} {8,19,44} {8,19,45} {8,19,46} {8,19,47}
{8,19,48} {8,19,49} {8,19,50} {8,19,51} {8,19,52} {8,19,53} {8,19,54} {8,19,55} {8,19,56} {8,19,57}
{8,19,58} {8,19,59} {8,19,60} {8,19,61} {8,19,62} {8,19,63} {8,19,64} {8,19,65} {8,19,66} {8,20,21}
{8,20,22} {8,20,23} {8,20,24} {8,20,25} {8,20,26} {8,20,27} {8,20,28} {8,20,29} {8,20,30} {8,20,31}
{8,20,32} {8,20,33} {8,20,34} {8,20,35} {8,20,36} {8,20,37} {8,20,38} {8,20,39} {8,20,40} {8,20,41}
{8,20,42} {8,20,43} {8,20,44} {8,20,45} {8,20,46} {8,20,47} {8,20,48} {8,20,49} {8,20,50} {8,20,51}
{8,20,52} {8,20,53} {8,20,54} {8,20,55} {8,20,56} {8,20,57} {8,20,58} {8,20,59} {8,20,60} {8,20,61}
{8,20,62} {8,20,63} {8,20,64} {8,20,65} {8,20,66} {8,21,22} {8,21,23} {8,21,24} {8,21,25} {8,21,26}
{8,21,27} {8,21,28} {8,21,29} {8,21,30} {8,21,31} {8,21,32} {8,21,33} {8,21,34} {8,21,35} {8,21,36}
{8,21,37} {8,21,38} {8,21,39} {8,21,40} {8,21,41} {8,21,42} {8,21,43} {8,21,44} {8,21,45} {8,21,46}
{8,21,47} {8,21,48} {8,21,49} {8,21,50} {8,21,51} {8,21,52} {8,21,53} {8,21,54} {8,21,55} {8,21,56}
{8,21,57} {8,21,58} {8,21,59} {8,21,60} {8,21,61} {8,21,62} {8,21,63} {8,21,64} {8,21,65} {8,21,66}
{8,22,23} {8,22,24} {8,22,25} {8,22,26} {8,22,27} {8,22,28} {8,22,29} {8,22,30} {8,22,31} {8,22,32}
{8,22,33} {8,22,34} {8,22,35} {8,22,36} {8,22,37} {8,22,38} {8,22,39} {8,22,40} {8,22,41} {8,22,42}
{8,22,43} {8,22,44} {8,22,45} {8,22,46} {8,22,47} {8,22,48} {8,22,49} {8,22,50} {8,22,51} {8,22,52}
{8,22,53} {8,22,54} {8,22,55} {8,22,56} {8,22,57} {8,22,58} {8,22,59} {8,22,60} {8,22,61} {8,22,62}
{8,22,63} {8,22,64} {8,22,65} {8,22,66} {8,23,24} {8,23,25} {8,23,26} {8,23,27} {8,23,28} {8,23,29}
{8,23,30} {8,23,31} {8,23,32} {8,23,33} {8,23,34} {8,23,35} {8,23,36} {8,23,37} {8,23,38} {8,23,39}
{8,23,40} {8,23,41} {8,23,42} {8,23,43} {8,23,44} {8,23,45} {8,23,46} {8,23,47} {8,23,48} {8,23,49}
{8,23,50} {8,23,51} {8,23,52} {8,23,53} {8,23,54} {8,23,55} {8,23,56} {8,23,57} {8,23,58} {8,23,59}
{8,23,60} {8,23,61} {8,23,62} {8,23,63} {8,23,64} {8,23,65} {8,23,66} {8,24,25} {8,24,26} {8,24,27}
{8,24,28} {8,24,29} {8,24,30} {8,24,31} {8,24,32} {8,24,33} {8,24,34} {8,24,35} {8,24,36} {8,24,37}
{8,24,38} {8,24,39} {8,24,40} {8,24,41} {8,24,42} {8,24,43} {8,24,44} {8,24,45} {8,24,46} {8,24,47}
{8,24,48} {8,24,49} {8,24,50} {8,24,51} {8,24,52} {8,24,53} {8,24,54} {8,24,55} {8,24,56} {8,24,57}
{8,24,58} {8,24,59} {8,24,60} {8,24,61} {8,24,62} {8,24,63} {8,24,64} {8,24,65} {8,24,66} {8,25,26}
{8,25,27} {8,25,28} {8,25,29} {8,25,30} {8,25,31} {8,25,32} {8,25,33} {8,25,34} {8,25,35} {8,25,36}
{8,25,37} {8,25,38} {8,25,39} {8,25,40} {8,25,41} {8,25,42} {8,25,43} {8,25,44} {8,25,45} {8,25,46}
{8,25,47} {8,25,48} {8,25,49} {8,25,50} {8,25,51} {8,25,52} {8,25,53} {8,25,54} {8,25,55} {8,25,56}
{8,25,57} {8,25,58} {8,25,59} {8,25,60} {8,25,61} {8,25,62} {8,25,63} {8,25,64} {8,25,65} {8,25,66}
{8,26,27} {8,26,28} {8,26,29} {8,26,30} {8,26,31} {8,26,32} {8,26,33} {8,26,34} {8,26,35} {8,26,36}
{8,26,37} {8,26,38} {8,26,39} {8,26,40} {8,26,41} {8,26,42} {8,26,43} {8,26,44} {8,26,45} {8,26,46}
{8,26,47} {8,26,48} {8,26,49} {8,26,50} {8,26,51} {8,26,52} {8,26,53} {8,26,54} {8,26,55} {8,26,56}
{8,26,57} {8,26,58} {8,26,59} {8,26,60} {8,26,61} {8,26,62} {8,26,63} {8,26,64} {8,26,65} {8,26,66}
{8,27,28} {8,27,29} {8,27,30} {8,27,31} {8,27,32} {8,27,33} {8,27,34} {8,27,35} {8,27,36} {8,27,37}
{8,27,38} {8,27,39} {8,27,40} {8,27,41} {8,27,42} {8,27,43} {8,27,44} {8,27,45} {8,27,46} {8,27,47}
{8,27,48} {8,27,49} {8,27,50} {8,27,51} {8,27,52} {8,27,53} {8,27,54} {8,27,55} {8,27,56} {8,27,57}
{8,27,58} {8,27,59} {8,27,60} {8,27,61} {8,27,62} {8,27,63} {8,27,64} {8,27,65} {8,27,66} {8,28,29}
{8,28,30} {8,28,31} {8,28,32} {8,28,33} {8,28,34} {8,28,35} {8,28,36} {8,28,37} {8,28,38} {8,28,39}
{8,28,40} {8,28,41} {8,28,42} {8,28,43} {8,28,44} {8,28,45} {8,28,46} {8,28,47} {8,28,48} {8,28,49}
{8,28,50} {8,28,51} {8,28,52} {8,28,53} {8,28,54} {8,28,55} {8,28,56} {8,28,57} {8,28,58} {8,28,59}
{8,28,60} {8,28,61} {8,28,62} {8,28,63} {8,28,64} {8,28,65} {8,28,66} {8,29,30} {8,29,31} {8,29,32}
{8,29,33} {8,29,34} {8,29,35} {8,29,36} {8,29,37} {8,29,38} {8,29,39} {8,29,40} {8,29,41} {8,29,42}
{8,29,43} {8,29,44} {8,29,45} {8,29,46} {8,29,47} {8,29,48} {8,29,49} {8,29,50} {8,29,51} {8,29,52}
{8,29,53} {8,29,54} {8,29,55} {8,29,56} {8,29,57} {8,29,58} {8,29,59} {8,29,60} {8,29,61} {8,29,62}
{8,29,63} {8,29,64} {8,29,65} {8,29,66} {8,30,31} {8,30,32} {8,30,33} {8,30,34} {8,30,35} {8,30,36}
{8,30,37} {8,30,38} {8,30,39} {8,30,40} {8,30,41} {8,30,42} {8,30,43} {8,30,44} {8,30,45} {8,30,46}
{8,30,47} {8,30,48} {8,30,49} {8,30,50} {8,30,51} {8,30,52} {8,30,53} {8,30,54} {8,30,55} {8,30,56}
{8,30,57} {8,30,58} {8,30,59} {8,30,60} {8,30,61} {8,30,62} {8,30,63} {8,30,64} {8,30,65} {8,30,66}
{8,31,32} {8,31,33} {8,31,34} {8,31,35} {8,31,36} {8,31,37} {8,31,38} {8,31,39} {8,31,40} {8,31,41}
{8,31,42} {8,31,43} {8,31,44} {8,31,45} {8,31,46} {8,31,47} {8,31,48} {8,31,49} {8,31,50} {8,31,51}
{8,31,52} {8,31,53} {8,31,54} {8,31,55} {8,31,56} {8,31,57} {8,31,58} {8,31,59} {8,31,60} {8,31,61}
{8,31,62} {8,31,63} {8,31,64} {8,31,65} {8,31,66} {8,32,33} {8,32,34} {8,32,35} {8,32,36} {8,32,37}
{8,32,38} {8,32,39} {8,32,40} {8,32,41} {8,32,42} {8,32,43} {8,32,44} {8,32,45} {8,32,46} {8,32,47}
{8,32,48} {8,32,49} {8,32,50} {8,32,51} {8,32,52} {8,32,53} {8,32,54} {8,32,55} {8,32,56} {8,32,57}
{8,32,58} {8,32,59} {8,32,60} {8,32,61} {8,32,62} {8,32,63} {8,32,64} {8,32,65} {8,32,66} {8,33,34}
{8,33,35} {8,33,36} {8,33,37} {8,33,38} {8,33,39} {8,33,40} {8,33,41} {8,33,42} {8,33,43} {8,33,44}
{8,33,45} {8,33,46} {8,33,47} {8,33,48} {8,33,49} {8,33,50} {8,33,51} {8,33,52} {8,33,53} {8,33,54}

TABLE 3A-continued

| | | | | | | | | |
|---|---|---|---|---|---|---|---|---|
| {8,33,55} | {8,33,56} | {8,33,57} | {8,33,58} | {8,33,59} | {8,33,60} | {8,33,61} | {8,33,62} | {8,33,63} | {8,33,64} |
| {8,33,65} | {8,33,66} | {8,34,35} | {8,34,36} | {8,34,37} | {8,34,38} | {8,34,39} | {8,34,40} | {8,34,41} | {8,34,42} |
| {8,34,43} | {8,34,44} | {8,34,45} | {8,34,46} | {8,34,47} | {8,34,48} | {8,34,49} | {8,34,50} | {8,34,51} | {8,34,52} |
| {8,34,53} | {8,34,54} | {8,34,55} | {8,34,56} | {8,34,57} | {8,34,58} | {8,34,59} | {8,34,60} | {8,34,61} | {8,34,62} |
| {8,34,63} | {8,34,64} | {8,34,65} | {8,34,66} | {8,35,36} | {8,35,37} | {8,35,38} | {8,35,39} | {8,35,40} | {8,35,41} |
| {8,35,42} | {8,35,43} | {8,35,44} | {8,35,45} | {8,35,46} | {8,35,47} | {8,35,48} | {8,35,49} | {8,35,50} | {8,35,51} |
| {8,35,52} | {8,35,53} | {8,35,54} | {8,35,55} | {8,35,56} | {8,35,57} | {8,35,58} | {8,35,59} | {8,35,60} | {8,35,61} |
| {8,35,62} | {8,35,63} | {8,35,64} | {8,35,65} | {8,35,66} | {8,36,37} | {8,36,38} | {8,36,39} | {8,36,40} | {8,36,41} |
| {8,36,42} | {8,36,43} | {8,36,44} | {8,36,45} | {8,36,46} | {8,36,47} | {8,36,48} | {8,36,49} | {8,36,50} | {8,36,51} |
| {8,36,52} | {8,36,53} | {8,36,54} | {8,36,55} | {8,36,56} | {8,36,57} | {8,36,58} | {8,36,59} | {8,36,60} | {8,36,61} |
| {8,36,62} | {8,36,63} | {8,36,64} | {8,36,65} | {8,36,66} | {8,37,38} | {8,37,39} | {8,37,40} | {8,37,41} | {8,37,42} |
| {8,37,43} | {8,37,44} | {8,37,45} | {8,37,46} | {8,37,47} | {8,37,48} | {8,37,49} | {8,37,50} | {8,37,51} | {8,37,52} |
| {8,37,53} | {8,37,54} | {8,37,55} | {8,37,56} | {8,37,57} | {8,37,58} | {8,37,59} | {8,37,60} | {8,37,61} | {8,37,62} |
| {8,37,63} | {8,37,64} | {8,37,65} | {8,37,66} | {8,38,39} | {8,38,40} | {8,38,41} | {8,38,42} | {8,38,43} | {8,38,44} |
| {8,38,45} | {8,38,46} | {8,38,47} | {8,38,48} | {8,38,49} | {8,38,50} | {8,38,51} | {8,38,52} | {8,38,53} | {8,38,54} |
| {8,38,55} | {8,38,56} | {8,38,57} | {8,38,58} | {8,38,59} | {8,38,60} | {8,38,61} | {8,38,62} | {8,38,63} | {8,38,64} |
| {8,38,65} | {8,38,66} | {8,39,40} | {8,39,41} | {8,39,42} | {8,39,43} | {8,39,44} | {8,39,45} | {8,39,46} | {8,39,47} |
| {8,39,48} | {8,39,49} | {8,39,50} | {8,39,51} | {8,39,52} | {8,39,53} | {8,39,54} | {8,39,55} | {8,39,56} | {8,39,57} |
| {8,39,58} | {8,39,59} | {8,39,60} | {8,39,61} | {8,39,62} | {8,39,63} | {8,39,64} | {8,39,65} | {8,39,66} | {8,40,41} |
| {8,40,42} | {8,40,43} | {8,40,44} | {8,40,45} | {8,40,46} | {8,40,47} | {8,40,48} | {8,40,49} | {8,40,50} | {8,40,51} |
| {8,40,52} | {8,40,53} | {8,40,54} | {8,40,55} | {8,40,56} | {8,40,57} | {8,40,58} | {8,40,59} | {8,40,60} | {8,40,61} |
| {8,40,62} | {8,40,63} | {8,40,64} | {8,40,65} | {8,40,66} | {8,41,42} | {8,41,43} | {8,41,44} | {8,41,45} | {8,41,46} |
| {8,41,47} | {8,41,48} | {8,41,49} | {8,41,50} | {8,41,51} | {8,41,52} | {8,41,53} | {8,41,54} | {8,41,55} | {8,41,56} |
| {8,41,57} | {8,41,58} | {8,41,59} | {8,41,60} | {8,41,61} | {8,41,62} | {8,41,63} | {8,41,64} | {8,41,65} | {8,41,66} |
| {8,42,43} | {8,42,44} | {8,42,45} | {8,42,46} | {8,42,47} | {8,42,48} | {8,42,49} | {8,42,50} | {8,42,51} | {8,42,52} |
| {8,42,53} | {8,42,54} | {8,42,55} | {8,42,56} | {8,42,57} | {8,42,58} | {8,42,59} | {8,42,60} | {8,42,61} | {8,42,62} |
| {8,42,63} | {8,42,64} | {8,42,65} | {8,42,66} | {8,43,44} | {8,43,45} | {8,43,46} | {8,43,47} | {8,43,48} | {8,43,49} |
| {8,43,50} | {8,43,51} | {8,43,52} | {8,43,53} | {8,43,54} | {8,43,55} | {8,43,56} | {8,43,57} | {8,43,58} | {8,43,59} |
| {8,43,60} | {8,43,61} | {8,43,62} | {8,43,63} | {8,43,64} | {8,43,65} | {8,43,66} | {8,44,45} | {8,44,46} | {8,44,47} |
| {8,44,48} | {8,44,49} | {8,44,50} | {8,44,51} | {8,44,52} | {8,44,53} | {8,44,54} | {8,44,55} | {8,44,56} | {8,44,57} |
| {8,44,58} | {8,44,59} | {8,44,60} | {8,44,61} | {8,44,62} | {8,44,63} | {8,44,64} | {8,44,65} | {8,44,66} | {8,45,46} |
| {8,45,47} | {8,45,48} | {8,45,49} | {8,45,50} | {8,45,51} | {8,45,52} | {8,45,53} | {8,45,54} | {8,45,55} | {8,45,56} |
| {8,45,57} | {8,45,58} | {8,45,59} | {8,45,60} | {8,45,61} | {8,45,62} | {8,45,63} | {8,45,64} | {8,45,65} | {8,45,66} |
| {8,46,47} | {8,46,48} | {8,46,49} | {8,46,50} | {8,46,51} | {8,46,52} | {8,46,53} | {8,46,54} | {8,46,55} | {8,46,56} |
| {8,46,57} | {8,46,58} | {8,46,59} | {8,46,60} | {8,46,61} | {8,46,62} | {8,46,63} | {8,46,64} | {8,46,65} | {8,46,66} |
| {8,47,48} | {8,47,49} | {8,47,50} | {8,47,51} | {8,47,52} | {8,47,53} | {8,47,54} | {8,47,55} | {8,47,56} | {8,47,57} |
| {8,47,58} | {8,47,59} | {8,47,60} | {8,47,61} | {8,47,62} | {8,47,63} | {8,47,64} | {8,47,65} | {8,47,66} | {8,48,49} |
| {8,48,50} | {8,48,51} | {8,48,52} | {8,48,53} | {8,48,54} | {8,48,55} | {8,48,56} | {8,48,57} | {8,48,58} | {8,48,59} |
| {8,48,60} | {8,48,61} | {8,48,62} | {8,48,63} | {8,48,64} | {8,48,65} | {8,48,66} | {8,49,50} | {8,49,51} | {8,49,52} |
| {8,49,53} | {8,49,54} | {8,49,55} | {8,49,56} | {8,49,57} | {8,49,58} | {8,49,59} | {8,49,60} | {8,49,61} | {8,49,62} |
| {8,49,63} | {8,49,64} | {8,49,65} | {8,49,66} | {8,50,51} | {8,50,52} | {8,50,53} | {8,50,54} | {8,50,55} | {8,50,56} |
| {8,50,57} | {8,50,58} | {8,50,59} | {8,50,60} | {8,50,61} | {8,50,62} | {8,50,63} | {8,50,64} | {8,50,65} | {8,50,66} |
| {8,51,52} | {8,51,53} | {8,51,54} | {8,51,55} | {8,51,56} | {8,51,57} | {8,51,58} | {8,51,59} | {8,51,60} | {8,51,61} |
| {8,51,62} | {8,51,63} | {8,51,64} | {8,51,65} | {8,51,66} | {8,52,53} | {8,52,54} | {8,52,55} | {8,52,56} | {8,52,57} |
| {8,52,58} | {8,52,59} | {8,52,60} | {8,52,61} | {8,52,62} | {8,52,63} | {8,52,64} | {8,52,65} | {8,52,66} | {8,53,54} |
| {8,53,55} | {8,53,56} | {8,53,57} | {8,53,58} | {8,53,59} | {8,53,60} | {8,53,61} | {8,53,62} | {8,53,63} | {8,53,64} |
| {8,53,65} | {8,53,66} | {8,54,55} | {8,54,56} | {8,54,57} | {8,54,58} | {8,54,59} | {8,54,60} | {8,54,61} | {8,54,62} |
| {8,54,63} | {8,54,64} | {8,54,65} | {8,54,66} | {8,55,56} | {8,55,57} | {8,55,58} | {8,55,59} | {8,55,60} | {8,55,61} |
| {8,55,62} | {8,55,63} | {8,55,64} | {8,55,65} | {8,55,66} | {8,56,57} | {8,56,58} | {8,56,59} | {8,56,60} | {8,56,61} |
| {8,56,62} | {8,56,63} | {8,56,64} | {8,56,65} | {8,56,66} | {8,57,58} | {8,57,59} | {8,57,60} | {8,57,61} | {8,57,62} |
| {8,57,63} | {8,57,64} | {8,57,65} | {8,57,66} | {8,58,59} | {8,58,60} | {8,58,61} | {8,58,62} | {8,58,63} | {8,58,64} |
| {8,58,65} | {8,58,66} | {8,59,60} | {8,59,61} | {8,59,62} | {8,59,63} | {8,59,64} | {8,59,65} | {8,59,66} | {8,60,61} |
| {8,60,62} | {8,60,63} | {8,60,64} | {8,60,65} | {8,60,66} | {8,61,62} | {8,61,63} | {8,61,64} | {8,61,65} | {8,61,66} |
| {8,62,63} | {8,62,64} | {8,62,65} | {8,62,66} | {8,63,64} | {8,63,65} | {8,63,66} | {8,64,65} | {8,64,66} | {8,65,66} |
| {9,10,11} | {9,10,12} | {9,10,13} | {9,10,14} | {9,10,15} | {9,10,16} | {9,10,17} | {9,10,18} | {9,10,19} | {9,10,20} |
| {9,10,21} | {9,10,22} | {9,10,23} | {9,10,24} | {9,10,25} | {9,10,26} | {9,10,27} | {9,10,28} | {9,10,29} | {9,10,30} |
| {9,10,31} | {9,10,32} | {9,10,33} | {9,10,34} | {9,10,35} | {9,10,36} | {9,10,37} | {9,10,38} | {9,10,39} | {9,10,40} |
| {9,10,41} | {9,10,42} | {9,10,43} | {9,10,44} | {9,10,45} | {9,10,46} | {9,10,47} | {9,10,48} | {9,10,49} | {9,10,50} |
| {9,10,51} | {9,10,52} | {9,10,53} | {9,10,54} | {9,10,55} | {9,10,56} | {9,10,57} | {9,10,58} | {9,10,59} | {9,10,60} |
| {9,10,61} | {9,10,62} | {9,10,63} | {9,10,64} | {9,10,65} | {9,10,66} | {9,11,12} | {9,11,13} | {9,11,14} | {9,11,15} |
| {9,11,16} | {9,11,17} | {9,11,18} | {9,11,19} | {9,11,20} | {9,11,21} | {9,11,22} | {9,11,23} | {9,11,24} | {9,11,25} |
| {9,11,26} | {9,11,27} | {9,11,28} | {9,11,29} | {9,11,30} | {9,11,31} | {9,11,32} | {9,11,33} | {9,11,34} | {9,11,35} |
| {9,11,36} | {9,11,37} | {9,11,38} | {9,11,39} | {9,11,40} | {9,11,41} | {9,11,42} | {9,11,43} | {9,11,44} | {9,11,45} |
| {9,11,46} | {9,11,47} | {9,11,48} | {9,11,49} | {9,11,50} | {9,11,51} | {9,11,52} | {9,11,53} | {9,11,54} | {9,11,55} |
| {9,11,56} | {9,11,57} | {9,11,58} | {9,11,59} | {9,11,60} | {9,11,61} | {9,11,62} | {9,11,63} | {9,11,64} | {9,11,65} |
| {9,11,66} | {9,12,13} | {9,12,14} | {9,12,15} | {9,12,16} | {9,12,17} | {9,12,18} | {9,12,19} | {9,12,20} | {9,12,21} |
| {9,12,22} | {9,12,23} | {9,12,24} | {9,12,25} | {9,12,26} | {9,12,27} | {9,12,28} | {9,12,29} | {9,12,30} | {9,12,31} |
| {9,12,32} | {9,12,33} | {9,12,34} | {9,12,35} | {9,12,36} | {9,12,37} | {9,12,38} | {9,12,39} | {9,12,40} | {9,12,41} |
| {9,12,42} | {9,12,43} | {9,12,44} | {9,12,45} | {9,12,46} | {9,12,47} | {9,12,48} | {9,12,49} | {9,12,50} | {9,12,51} |
| {9,12,52} | {9,12,53} | {9,12,54} | {9,12,55} | {9,12,56} | {9,12,57} | {9,12,58} | {9,12,59} | {9,12,60} | {9,12,61} |
| {9,12,62} | {9,12,63} | {9,12,64} | {9,12,65} | {9,12,66} | {9,13,14} | {9,13,15} | {9,13,16} | {9,13,17} | {9,13,18} |
| {9,13,19} | {9,13,20} | {9,13,21} | {9,13,22} | {9,13,23} | {9,13,24} | {9,13,25} | {9,13,26} | {9,13,27} | {9,13,28} |
| {9,13,29} | {9,13,30} | {9,13,31} | {9,13,32} | {9,13,33} | {9,13,34} | {9,13,35} | {9,13,36} | {9,13,37} | {9,13,38} |
| {9,13,39} | {9,13,40} | {9,13,41} | {9,13,42} | {9,13,43} | {9,13,44} | {9,13,45} | {9,13,46} | {9,13,47} | {9,13,48} |
| {9,13,49} | {9,13,50} | {9,13,51} | {9,13,52} | {9,13,53} | {9,13,54} | {9,13,55} | {9,13,56} | {9,13,57} | {9,13,58} |
| {9,13,59} | {9,13,60} | {9,13,61} | {9,13,62} | {9,13,63} | {9,13,64} | {9,13,65} | {9,13,66} | {9,14,15} | {9,14,16} |
| {9,14,17} | {9,14,18} | {9,14,19} | {9,14,20} | {9,14,21} | {9,14,22} | {9,14,23} | {9,14,24} | {9,14,25} | {9,14,26} |
| {9,14,27} | {9,14,28} | {9,14,29} | {9,14,30} | {9,14,31} | {9,14,32} | {9,14,33} | {9,14,34} | {9,14,35} | {9,14,36} |
| {9,14,37} | {9,14,38} | {9,14,39} | {9,14,40} | {9,14,41} | {9,14,42} | {9,14,43} | {9,14,44} | {9,14,45} | {9,14,46} |
| {9,14,47} | {9,14,48} | {9,14,49} | {9,14,50} | {9,14,51} | {9,14,52} | {9,14,53} | {9,14,54} | {9,14,55} | {9,14,56} |

TABLE 3A-continued

| | | | | | | | | |
|---|---|---|---|---|---|---|---|---|
| {9,14,57} | {9,14,58} | {9,14,59} | {9,14,60} | {9,14,61} | {9,14,62} | {9,14,63} | {9,14,64} | {9,14,65} | {9,14,66} |
| {9,15,16} | {9,15,17} | {9,15,18} | {9,15,19} | {9,15,20} | {9,15,21} | {9,15,22} | {9,15,23} | {9,15,24} | {9,15,25} |
| {9,15,26} | {9,15,27} | {9,15,28} | {9,15,29} | {9,15,30} | {9,15,31} | {9,15,32} | {9,15,33} | {9,15,34} | {9,15,35} |
| {9,15,36} | {9,15,37} | {9,15,38} | {9,15,39} | {9,15,40} | {9,15,41} | {9,15,42} | {9,15,43} | {9,15,44} | {9,15,45} |
| {9,15,46} | {9,15,47} | {9,15,48} | {9,15,49} | {9,15,50} | {9,15,51} | {9,15,52} | {9,15,53} | {9,15,54} | {9,15,55} |
| {9,15,56} | {9,15,57} | {9,15,58} | {9,15,59} | {9,15,60} | {9,15,61} | {9,15,62} | {9,15,63} | {9,15,64} | {9,15,65} |
| {9,15,66} | {9,16,17} | {9,16,18} | {9,16,19} | {9,16,20} | {9,16,21} | {9,16,22} | {9,16,23} | {9,16,24} | {9,16,25} |
| {9,16,26} | {9,16,27} | {9,16,28} | {9,16,29} | {9,16,30} | {9,16,31} | {9,16,32} | {9,16,33} | {9,16,34} | {9,16,35} |
| {9,16,36} | {9,16,37} | {9,16,38} | {9,16,39} | {9,16,40} | {9,16,41} | {9,16,42} | {9,16,43} | {9,16,44} | {9,16,45} |
| {9,16,46} | {9,16,47} | {9,16,48} | {9,16,49} | {9,16,50} | {9,16,51} | {9,16,52} | {9,16,53} | {9,16,54} | {9,16,55} |
| {9,16,56} | {9,16,57} | {9,16,58} | {9,16,59} | {9,16,60} | {9,16,61} | {9,16,62} | {9,16,63} | {9,16,64} | {9,16,65} |
| {9,16,66} | {9,17,18} | {9,17,19} | {9,17,20} | {9,17,21} | {9,17,22} | {9,17,23} | {9,17,24} | {9,17,25} | {9,17,26} |
| {9,17,27} | {9,17,28} | {9,17,29} | {9,17,30} | {9,17,31} | {9,17,32} | {9,17,33} | {9,17,34} | {9,17,35} | {9,17,36} |
| {9,17,37} | {9,17,38} | {9,17,39} | {9,17,40} | {9,17,41} | {9,17,42} | {9,17,43} | {9,17,44} | {9,17,45} | {9,17,46} |
| {9,17,47} | {9,17,48} | {9,17,49} | {9,17,50} | {9,17,51} | {9,17,52} | {9,17,53} | {9,17,54} | {9,17,55} | {9,17,56} |
| {9,17,57} | {9,17,58} | {9,17,59} | {9,17,60} | {9,17,61} | {9,17,62} | {9,17,63} | {9,17,64} | {9,17,65} | {9,17,66} |
| {9,18,19} | {9,18,20} | {9,18,21} | {9,18,22} | {9,18,23} | {9,18,24} | {9,18,25} | {9,18,26} | {9,18,27} | {9,18,28} |
| {9,18,29} | {9,18,30} | {9,18,31} | {9,18,32} | {9,18,33} | {9,18,34} | {9,18,35} | {9,18,36} | {9,18,37} | {9,18,38} |
| {9,18,39} | {9,18,40} | {9,18,41} | {9,18,42} | {9,18,43} | {9,18,44} | {9,18,45} | {9,18,46} | {9,18,47} | {9,18,48} |
| {9,18,49} | {9,18,50} | {9,18,51} | {9,18,52} | {9,18,53} | {9,18,54} | {9,18,55} | {9,18,56} | {9,18,57} | {9,18,58} |
| {9,18,59} | {9,18,60} | {9,18,61} | {9,18,62} | {9,18,63} | {9,18,64} | {9,18,65} | {9,18,66} | {9,19,20} | {9,19,21} |
| {9,19,22} | {9,19,23} | {9,19,24} | {9,19,25} | {9,19,26} | {9,19,27} | {9,19,28} | {9,19,29} | {9,19,30} | {9,19,31} |
| {9,19,32} | {9,19,33} | {9,19,34} | {9,19,35} | {9,19,36} | {9,19,37} | {9,19,38} | {9,19,39} | {9,19,40} | {9,19,41} |
| {9,19,42} | {9,19,43} | {9,19,44} | {9,19,45} | {9,19,46} | {9,19,47} | {9,19,48} | {9,19,49} | {9,19,50} | {9,19,51} |
| {9,19,52} | {9,19,53} | {9,19,54} | {9,19,55} | {9,19,56} | {9,19,57} | {9,19,58} | {9,19,59} | {9,19,60} | {9,19,61} |
| {9,19,62} | {9,19,63} | {9,19,64} | {9,19,65} | {9,19,66} | {9,20,21} | {9,20,22} | {9,20,23} | {9,20,24} | {9,20,25} |
| {9,20,26} | {9,20,27} | {9,20,28} | {9,20,29} | {9,20,30} | {9,20,31} | {9,20,32} | {9,20,33} | {9,20,34} | {9,20,35} |
| {9,20,36} | {9,20,37} | {9,20,38} | {9,20,39} | {9,20,40} | {9,20,41} | {9,20,42} | {9,20,43} | {9,20,44} | {9,20,45} |
| {9,20,46} | {9,20,47} | {9,20,48} | {9,20,49} | {9,20,50} | {9,20,51} | {9,20,52} | {9,20,53} | {9,20,54} | {9,20,55} |
| {9,20,56} | {9,20,57} | {9,20,58} | {9,20,59} | {9,20,60} | {9,20,61} | {9,20,62} | {9,20,63} | {9,20,64} | {9,20,65} |
| {9,20,66} | {9,21,22} | {9,21,23} | {9,21,24} | {9,21,25} | {9,21,26} | {9,21,27} | {9,21,28} | {9,21,29} | {9,21,30} |
| {9,21,31} | {9,21,32} | {9,21,33} | {9,21,34} | {9,21,35} | {9,21,36} | {9,21,37} | {9,21,38} | {9,21,39} | {9,21,40} |
| {9,21,41} | {9,21,42} | {9,21,43} | {9,21,44} | {9,21,45} | {9,21,46} | {9,21,47} | {9,21,48} | {9,21,49} | {9,21,50} |
| {9,21,51} | {9,21,52} | {9,21,53} | {9,21,54} | {9,21,55} | {9,21,56} | {9,21,57} | {9,21,58} | {9,21,59} | {9,21,60} |
| {9,21,61} | {9,21,62} | {9,21,63} | {9,21,64} | {9,21,65} | {9,21,66} | {9,22,23} | {9,22,24} | {9,22,25} | {9,22,26} |
| {9,22,27} | {9,22,28} | {9,22,29} | {9,22,30} | {9,22,31} | {9,22,32} | {9,22,33} | {9,22,34} | {9,22,35} | {9,22,36} |
| {9,22,37} | {9,22,38} | {9,22,39} | {9,22,40} | {9,22,41} | {9,22,42} | {9,22,43} | {9,22,44} | {9,22,45} | {9,22,46} |
| {9,22,47} | {9,22,48} | {9,22,49} | {9,22,50} | {9,22,51} | {9,22,52} | {9,22,53} | {9,22,54} | {9,22,55} | {9,22,56} |
| {9,22,57} | {9,22,58} | {9,22,59} | {9,22,60} | {9,22,61} | {9,22,62} | {9,22,63} | {9,22,64} | {9,22,65} | {9,22,66} |
| {9,23,24} | {9,23,25} | {9,23,26} | {9,23,27} | {9,23,28} | {9,23,29} | {9,23,30} | {9,23,31} | {9,23,32} | {9,23,33} |
| {9,23,34} | {9,23,35} | {9,23,36} | {9,23,37} | {9,23,38} | {9,23,39} | {9,23,40} | {9,23,41} | {9,23,42} | {9,23,43} |
| {9,23,44} | {9,23,45} | {9,23,46} | {9,23,47} | {9,23,48} | {9,23,49} | {9,23,50} | {9,23,51} | {9,23,52} | {9,23,53} |
| {9,23,54} | {9,23,55} | {9,23,56} | {9,23,57} | {9,23,58} | {9,23,59} | {9,23,60} | {9,23,61} | {9,23,62} | {9,23,63} |
| {9,23,64} | {9,23,65} | {9,23,66} | {9,24,25} | {9,24,26} | {9,24,27} | {9,24,28} | {9,24,29} | {9,24,30} | {9,24,31} |
| {9,24,32} | {9,24,33} | {9,24,34} | {9,24,35} | {9,24,36} | {9,24,37} | {9,24,38} | {9,24,39} | {9,24,40} | {9,24,41} |
| {9,24,42} | {9,24,43} | {9,24,44} | {9,24,45} | {9,24,46} | {9,24,47} | {9,24,48} | {9,24,49} | {9,24,50} | {9,24,51} |
| {9,24,52} | {9,24,53} | {9,24,54} | {9,24,55} | {9,24,56} | {9,24,57} | {9,24,58} | {9,24,59} | {9,24,60} | {9,24,61} |
| {9,24,62} | {9,24,63} | {9,24,64} | {9,24,65} | {9,24,66} | {9,25,26} | {9,25,27} | {9,25,28} | {9,25,29} | {9,25,30} |
| {9,25,31} | {9,25,32} | {9,25,33} | {9,25,34} | {9,25,35} | {9,25,36} | {9,25,37} | {9,25,38} | {9,25,39} | {9,25,40} |
| {9,25,41} | {9,25,42} | {9,25,43} | {9,25,44} | {9,25,45} | {9,25,46} | {9,25,47} | {9,25,48} | {9,25,49} | {9,25,50} |
| {9,25,51} | {9,25,52} | {9,25,53} | {9,25,54} | {9,25,55} | {9,25,56} | {9,25,57} | {9,25,58} | {9,25,59} | {9,25,60} |
| {9,25,61} | {9,25,62} | {9,25,63} | {9,25,64} | {9,25,65} | {9,25,66} | {9,26,27} | {9,26,28} | {9,26,29} | {9,26,30} |
| {9,26,31} | {9,26,32} | {9,26,33} | {9,26,34} | {9,26,35} | {9,26,36} | {9,26,37} | {9,26,38} | {9,26,39} | {9,26,40} |
| {9,26,41} | {9,26,42} | {9,26,43} | {9,26,44} | {9,26,45} | {9,26,46} | {9,26,47} | {9,26,48} | {9,26,49} | {9,26,50} |
| {9,26,51} | {9,26,52} | {9,26,53} | {9,26,54} | {9,26,55} | {9,26,56} | {9,26,57} | {9,26,58} | {9,26,59} | {9,26,60} |
| {9,26,61} | {9,26,62} | {9,26,63} | {9,26,64} | {9,26,65} | {9,26,66} | {9,27,28} | {9,27,29} | {9,27,30} | {9,27,31} |
| {9,27,32} | {9,27,33} | {9,27,34} | {9,27,35} | {9,27,36} | {9,27,37} | {9,27,38} | {9,27,39} | {9,27,40} | {9,27,41} |
| {9,27,42} | {9,27,43} | {9,27,44} | {9,27,45} | {9,27,46} | {9,27,47} | {9,27,48} | {9,27,49} | {9,27,50} | {9,27,51} |
| {9,27,52} | {9,27,53} | {9,27,54} | {9,27,55} | {9,27,56} | {9,27,57} | {9,27,58} | {9,27,59} | {9,27,60} | {9,27,61} |
| {9,27,62} | {9,27,63} | {9,27,64} | {9,27,65} | {9,27,66} | {9,28,29} | {9,28,30} | {9,28,31} | {9,28,32} | {9,28,33} |
| {9,28,34} | {9,28,35} | {9,28,36} | {9,28,37} | {9,28,38} | {9,28,39} | {9,28,40} | {9,28,41} | {9,28,42} | {9,28,43} |
| {9,28,44} | {9,28,45} | {9,28,46} | {9,28,47} | {9,28,48} | {9,28,49} | {9,28,50} | {9,28,51} | {9,28,52} | {9,28,53} |
| {9,28,54} | {9,28,55} | {9,28,56} | {9,28,57} | {9,28,58} | {9,28,59} | {9,28,60} | {9,28,61} | {9,28,62} | {9,28,63} |
| {9,28,64} | {9,28,65} | {9,28,66} | {9,29,30} | {9,29,31} | {9,29,32} | {9,29,33} | {9,29,34} | {9,29,35} | {9,29,36} |
| {9,29,37} | {9,29,38} | {9,29,39} | {9,29,40} | {9,29,41} | {9,29,42} | {9,29,43} | {9,29,44} | {9,29,45} | {9,29,46} |
| {9,29,47} | {9,29,48} | {9,29,49} | {9,29,50} | {9,29,51} | {9,29,52} | {9,29,53} | {9,29,54} | {9,29,55} | {9,29,56} |
| {9,29,57} | {9,29,58} | {9,29,59} | {9,29,60} | {9,29,61} | {9,29,62} | {9,29,63} | {9,29,64} | {9,29,65} | {9,29,66} |
| {9,30,31} | {9,30,32} | {9,30,33} | {9,30,34} | {9,30,35} | {9,30,36} | {9,30,37} | {9,30,38} | {9,30,39} | {9,30,40} |
| {9,30,41} | {9,30,42} | {9,30,43} | {9,30,44} | {9,30,45} | {9,30,46} | {9,30,47} | {9,30,48} | {9,30,49} | {9,30,50} |
| {9,30,51} | {9,30,52} | {9,30,53} | {9,30,54} | {9,30,55} | {9,30,56} | {9,30,57} | {9,30,58} | {9,30,59} | {9,30,60} |
| {9,30,61} | {9,30,62} | {9,30,63} | {9,30,64} | {9,30,65} | {9,30,66} | {9,31,32} | {9,31,33} | {9,31,34} | {9,31,35} |
| {9,31,36} | {9,31,37} | {9,31,38} | {9,31,39} | {9,31,40} | {9,31,41} | {9,31,42} | {9,31,43} | {9,31,44} | {9,31,45} |
| {9,31,46} | {9,31,47} | {9,31,48} | {9,31,49} | {9,31,50} | {9,31,51} | {9,31,52} | {9,31,53} | {9,31,54} | {9,31,55} |
| {9,31,56} | {9,31,57} | {9,31,58} | {9,31,59} | {9,31,60} | {9,31,61} | {9,31,62} | {9,31,63} | {9,31,64} | {9,31,65} |
| {9,31,66} | {9,32,33} | {9,32,34} | {9,32,35} | {9,32,36} | {9,32,37} | {9,32,38} | {9,32,39} | {9,32,40} | {9,32,41} |
| {9,32,42} | {9,32,43} | {9,32,44} | {9,32,45} | {9,32,46} | {9,32,47} | {9,32,48} | {9,32,49} | {9,32,50} | {9,32,51} |
| {9,32,52} | {9,32,53} | {9,32,54} | {9,32,55} | {9,32,56} | {9,32,57} | {9,32,58} | {9,32,59} | {9,32,60} | {9,32,61} |
| {9,32,62} | {9,32,63} | {9,32,64} | {9,32,65} | {9,32,66} | {9,33,34} | {9,33,35} | {9,33,36} | {9,33,37} | {9,33,38} |
| {9,33,39} | {9,33,40} | {9,33,41} | {9,33,42} | {9,33,43} | {9,33,44} | {9,33,45} | {9,33,46} | {9,33,47} | {9,33,48} |
| {9,33,49} | {9,33,50} | {9,33,51} | {9,33,52} | {9,33,53} | {9,33,54} | {9,33,55} | {9,33,56} | {9,33,57} | {9,33,58} |

TABLE 3A-continued

{9,33,59} {9,33,60} {9,33,61} {9,33,62} {9,33,63} {9,33,64} {9,33,65} {9,33,66} {9,34,35} {9,34,36}
{9,34,37} {9,34,38} {9,34,39} {9,34,40} {9,34,41} {9,34,42} {9,34,43} {9,34,44} {9,34,45} {9,34,46}
{9,34,47} {9,34,48} {9,34,49} {9,34,50} {9,34,51} {9,34,52} {9,34,53} {9,34,54} {9,34,55} {9,34,56}
{9,34,57} {9,34,58} {9,34,59} {9,34,60} {9,34,61} {9,34,62} {9,34,63} {9,34,64} {9,34,65} {9,34,66}
{9,35,36} {9,35,37} {9,35,38} {9,35,39} {9,35,40} {9,35,41} {9,35,42} {9,35,43} {9,35,44} {9,35,45}
{9,35,46} {9,35,47} {9,35,48} {9,35,49} {9,35,50} {9,35,51} {9,35,52} {9,35,53} {9,35,54} {9,35,55}
{9,35,56} {9,35,57} {9,35,58} {9,35,59} {9,35,60} {9,35,61} {9,35,62} {9,35,63} {9,35,64} {9,35,65}
{9,35,66} {9,36,37} {9,36,38} {9,36,39} {9,36,40} {9,36,41} {9,36,42} {9,36,43} {9,36,44} {9,36,45}
{9,36,46} {9,36,47} {9,36,48} {9,36,49} {9,36,50} {9,36,51} {9,36,52} {9,36,53} {9,36,54} {9,36,55}
{9,36,56} {9,36,57} {9,36,58} {9,36,59} {9,36,60} {9,36,61} {9,36,62} {9,36,63} {9,36,64} {9,36,65}
{9,36,66} {9,37,38} {9,37,39} {9,37,40} {9,37,41} {9,37,42} {9,37,43} {9,37,44} {9,37,45} {9,37,46}
{9,37,47} {9,37,48} {9,37,49} {9,37,50} {9,37,51} {9,37,52} {9,37,53} {9,37,54} {9,37,55} {9,37,56}
{9,37,57} {9,37,58} {9,37,59} {9,37,60} {9,37,61} {9,37,62} {9,37,63} {9,37,64} {9,37,65} {9,37,66}
{9,38,39} {9,38,40} {9,38,41} {9,38,42} {9,38,43} {9,38,44} {9,38,45} {9,38,46} {9,38,47} {9,38,48}
{9,38,49} {9,38,50} {9,38,51} {9,38,52} {9,38,53} {9,38,54} {9,38,55} {9,38,56} {9,38,57} {9,38,58}
{9,38,59} {9,38,60} {9,38,61} {9,38,62} {9,38,63} {9,38,64} {9,38,65} {9,38,66} {9,39,40} {9,39,41}
{9,39,42} {9,39,43} {9,39,44} {9,39,45} {9,39,46} {9,39,47} {9,39,48} {9,39,49} {9,39,50} {9,39,51}
{9,39,52} {9,39,53} {9,39,54} {9,39,55} {9,39,56} {9,39,57} {9,39,58} {9,39,59} {9,39,60} {9,39,61}
{9,39,62} {9,39,63} {9,39,64} {9,39,65} {9,39,66} {9,40,41} {9,40,42} {9,40,43} {9,40,44} {9,40,45}
{9,40,46} {9,40,47} {9,40,48} {9,40,49} {9,40,50} {9,40,51} {9,40,52} {9,40,53} {9,40,54} {9,40,55}
{9,40,56} {9,40,57} {9,40,58} {9,40,59} {9,40,60} {9,40,61} {9,40,62} {9,40,63} {9,40,64} {9,40,65}
{9,40,66} {9,41,42} {9,41,43} {9,41,44} {9,41,45} {9,41,46} {9,41,47} {9,41,48} {9,41,49} {9,41,50}
{9,41,51} {9,41,52} {9,41,53} {9,41,54} {9,41,55} {9,41,56} {9,41,57} {9,41,58} {9,41,59} {9,41,60}
{9,41,61} {9,41,62} {9,41,63} {9,41,64} {9,41,65} {9,41,66} {9,42,43} {9,42,44} {9,42,45} {9,42,46}
{9,42,47} {9,42,48} {9,42,49} {9,42,50} {9,42,51} {9,42,52} {9,42,53} {9,42,54} {9,42,55} {9,42,56}
{9,42,57} {9,42,58} {9,42,59} {9,42,60} {9,42,61} {9,42,62} {9,42,63} {9,42,64} {9,42,65} {9,42,66}
{9,43,44} {9,43,45} {9,43,46} {9,43,47} {9,43,48} {9,43,49} {9,43,50} {9,43,51} {9,43,52} {9,43,53}
{9,43,54} {9,43,55} {9,43,56} {9,43,57} {9,43,58} {9,43,59} {9,43,60} {9,43,61} {9,43,62} {9,43,63}
{9,43,64} {9,43,65} {9,43,66} {9,44,45} {9,44,46} {9,44,47} {9,44,48} {9,44,49} {9,44,50} {9,44,51}
{9,44,52} {9,44,53} {9,44,54} {9,44,55} {9,44,56} {9,44,57} {9,44,58} {9,44,59} {9,44,60} {9,44,61}
{9,44,62} {9,44,63} {9,44,64} {9,44,65} {9,44,66} {9,45,46} {9,45,47} {9,45,48} {9,45,49} {9,45,50}
{9,45,51} {9,45,52} {9,45,53} {9,45,54} {9,45,55} {9,45,56} {9,45,57} {9,45,58} {9,45,59} {9,45,60}
{9,45,61} {9,45,62} {9,45,63} {9,45,64} {9,45,65} {9,45,66} {9,46,47} {9,46,48} {9,46,49} {9,46,50}
{9,46,51} {9,46,52} {9,46,53} {9,46,54} {9,46,55} {9,46,56} {9,46,57} {9,46,58} {9,46,59} {9,46,60}
{9,46,61} {9,46,62} {9,46,63} {9,46,64} {9,46,65} {9,46,66} {9,47,48} {9,47,49} {9,47,50} {9,47,51}
{9,47,52} {9,47,53} {9,47,54} {9,47,55} {9,47,56} {9,47,57} {9,47,58} {9,47,59} {9,47,60} {9,47,61}
{9,47,62} {9,47,63} {9,47,64} {9,47,65} {9,47,66} {9,48,49} {9,48,50} {9,48,51} {9,48,52} {9,48,53}
{9,48,54} {9,48,55} {9,48,56} {9,48,57} {9,48,58} {9,48,59} {9,48,60} {9,48,61} {9,48,62} {9,48,63}
{9,48,64} {9,48,65} {9,48,66} {9,49,50} {9,49,51} {9,49,52} {9,49,53} {9,49,54} {9,49,55} {9,49,56}
{9,49,57} {9,49,58} {9,49,59} {9,49,60} {9,49,61} {9,49,62} {9,49,63} {9,49,64} {9,49,65} {9,49,66}
{9,50,51} {9,50,52} {9,50,53} {9,50,54} {9,50,55} {9,50,56} {9,50,57} {9,50,58} {9,50,59} {9,50,60}
{9,50,61} {9,50,62} {9,50,63} {9,50,64} {9,50,65} {9,50,66} {9,51,52} {9,51,53} {9,51,54} {9,51,55}
{9,51,56} {9,51,57} {9,51,58} {9,51,59} {9,51,60} {9,51,61} {9,51,62} {9,51,63} {9,51,64} {9,51,65}
{9,51,66} {9,52,53} {9,52,54} {9,52,55} {9,52,56} {9,52,57} {9,52,58} {9,52,59} {9,52,60} {9,52,61}
{9,52,62} {9,52,63} {9,52,64} {9,52,65} {9,52,66} {9,53,54} {9,53,55} {9,53,56} {9,53,57} {9,53,58}
{9,53,59} {9,53,60} {9,53,61} {9,53,62} {9,53,63} {9,53,64} {9,53,65} {9,53,66} {9,54,55} {9,54,56}
{9,54,57} {9,54,58} {9,54,59} {9,54,60} {9,54,61} {9,54,62} {9,54,63} {9,54,64} {9,54,65} {9,54,66}
{9,55,56} {9,55,57} {9,55,58} {9,55,59} {9,55,60} {9,55,61} {9,55,62} {9,55,63} {9,55,64} {9,55,65}
{9,55,66} {9,56,57} {9,56,58} {9,56,59} {9,56,60} {9,56,61} {9,56,62} {9,56,63} {9,56,64} {9,56,65}
{9,56,66} {9,57,58} {9,57,59} {9,57,60} {9,57,61} {9,57,62} {9,57,63} {9,57,64} {9,57,65} {9,57,66}
{9,58,59} {9,58,60} {9,58,61} {9,58,62} {9,58,63} {9,58,64} {9,58,65} {9,58,66} {9,59,60} {9,59,61}
{9,59,62} {9,59,63} {9,59,64} {9,59,65} {9,59,66} {9,60,61} {9,60,62} {9,60,63} {9,60,64} {9,60,65}
{9,60,66} {9,61,62} {9,61,63} {9,61,64} {9,61,65} {9,61,66} {9,62,63} {9,62,64} {9,62,65} {9,62,66}
{9,63,64} {9,63,65} {9,63,66} {9,64,65} {9,64,66} {9,65,66} {10,11,12} {10,11,13} {10,11,14} {10,11,15}
{10,11,16} {10,11,17} {10,11,18} {10,11,19} {10,11,20} {10,11,21} {10,11,22} {10,11,23} {10,11,24}
{10,11,25} {10,11,26} {10,11,27} {10,11,28} {10,11,29} {10,11,30} {10,11,31} {10,11,32} {10,11,33}
{10,11,34} {10,11,35} {10,11,36} {10,11,37} {10,11,38} {10,11,39} {10,11,40} {10,11,41} {10,11,42}
{10,11,43} {10,11,44} {10,11,45} {10,11,46} {10,11,47} {10,11,48} {10,11,49} {10,11,50} {10,11,51}
{10,11,52} {10,11,53} {10,11,54} {10,11,55} {10,11,56} {10,11,57} {10,11,58} {10,11,59} {10,11,60}
{10,11,61} {10,11,62} {10,11,63} {10,11,64} {10,11,65} {10,11,66} {10,12,13} {10,12,14} {10,12,15}
{10,12,16} {10,12,17} {10,12,18} {10,12,19} {10,12,20} {10,12,21} {10,12,22} {10,12,23} {10,12,24}
{10,12,25} {10,12,26} {10,12,27} {10,12,28} {10,12,29} {10,12,30} {10,12,31} {10,12,32} {10,12,33}
{10,12,34} {10,12,35} {10,12,36} {10,12,37} {10,12,38} {10,12,39} {10,12,40} {10,12,41} {10,12,42}
{10,12,43} {10,12,44} {10,12,45} {10,12,46} {10,12,47} {10,12,48} {10,12,49} {10,12,50} {10,12,51}
{10,12,52} {10,12,53} {10,12,54} {10,12,55} {10,12,56} {10,12,57} {10,12,58} {10,12,59} {10,12,60}
{10,12,61} {10,12,62} {10,12,63} {10,12,64} {10,12,65} {10,12,66} {10,13,14} {10,13,15} {10,13,16}
{10,13,17} {10,13,18} {10,13,19} {10,13,20} {10,13,21} {10,13,22} {10,13,23} {10,13,24} {10,13,25}
{10,13,26} {10,13,27} {10,13,28} {10,13,29} {10,13,30} {10,13,31} {10,13,32} {10,13,33} {10,13,34}
{10,13,35} {10,13,36} {10,13,37} {10,13,38} {10,13,39} {10,13,40} {10,13,41} {10,13,42} {10,13,43}
{10,13,44} {10,13,45} {10,13,46} {10,13,47} {10,13,48} {10,13,49} {10,13,50} {10,13,51} {10,13,52}
{10,13,53} {10,13,54} {10,13,55} {10,13,56} {10,13,57} {10,13,58} {10,13,59} {10,13,60} {10,13,61}
{10,13,62} {10,13,63} {10,13,64} {10,13,65} {10,13,66} {10,14,15} {10,14,16} {10,14,17} {10,14,18}
{10,14,19} {10,14,20} {10,14,21} {10,14,22} {10,14,23} {10,14,24} {10,14,25} {10,14,26} {10,14,27}
{10,14,28} {10,14,29} {10,14,30} {10,14,31} {10,14,32} {10,14,33} {10,14,34} {10,14,35} {10,14,36}
{10,14,37} {10,14,38} {10,14,39} {10,14,40} {10,14,41} {10,14,42} {10,14,43} {10,14,44} {10,14,45}
{10,14,46} {10,14,47} {10,14,48} {10,14,49} {10,14,50} {10,14,51} {10,14,52} {10,14,53} {10,14,54}
{10,14,55} {10,14,56} {10,14,57} {10,14,58} {10,14,59} {10,14,60} {10,14,61} {10,14,62} {10,14,63}
{10,14,64} {10,14,65} {10,14,66} {10,15,16} {10,15,17} {10,15,18} {10,15,19} {10,15,20} {10,15,21}
{10,15,22} {10,15,23} {10,15,24} {10,15,25} {10,15,26} {10,15,27} {10,15,28} {10,15,29} {10,15,30}
{10,15,31} {10,15,32} {10,15,33} {10,15,34} {10,15,35} {10,15,36} {10,15,37} {10,15,38} {10,15,39}

TABLE 3A-continued

{10,15,40} {10,15,41} {10,15,42} {10,15,43} {10,15,44} {10,15,45} {10,15,46} {10,15,47} {10,15,48}
{10,15,49} {10,15,50} {10,15,51} {10,15,52} {10,15,53} {10,15,54} {10,15,55} {10,15,56} {10,15,57}
{10,15,58} {10,15,59} {10,15,60} {10,15,61} {10,15,62} {10,15,63} {10,15,64} {10,15,65} {10,15,66}
{10,16,17} {10,16,18} {10,16,19} {10,16,20} {10,16,21} {10,16,22} {10,16,23} {10,16,24} {10,16,25}
{10,16,26} {10,16,27} {10,16,28} {10,16,29} {10,16,30} {10,16,31} {10,16,32} {10,16,33} {10,16,34}
{10,16,35} {10,16,36} {10,16,37} {10,16,38} {10,16,39} {10,16,40} {10,16,41} {10,16,42} {10,16,43}
{10,16,44} {10,16,45} {10,16,46} {10,16,47} {10,16,48} {10,16,49} {10,16,50} {10,16,51} {10,16,52}
{10,16,53} {10,16,54} {10,16,55} {10,16,56} {10,16,57} {10,16,58} {10,16,59} {10,16,60} {10,16,61}
{10,16,62} {10,16,63} {10,16,64} {10,16,65} {10,16,66} {10,17,18} {10,17,19} {10,17,20} {10,17,21}
{10,17,22} {10,17,23} {10,17,24} {10,17,25} {10,17,26} {10,17,27} {10,17,28} {10,17,29} {10,17,30}
{10,17,31} {10,17,32} {10,17,33} {10,17,34} {10,17,35} {10,17,36} {10,17,37} {10,17,38} {10,17,39}
{10,17,40} {10,17,41} {10,17,42} {10,17,43} {10,17,44} {10,17,45} {10,17,46} {10,17,47} {10,17,48}
{10,17,49} {10,17,50} {10,17,51} {10,17,52} {10,17,53} {10,17,54} {10,17,55} {10,17,56} {10,17,57}
{10,17,58} {10,17,59} {10,17,60} {10,17,61} {10,17,62} {10,17,63} {10,17,64} {10,17,65} {10,17,66}
{10,18,19} {10,18,20} {10,18,21} {10,18,22} {10,18,23} {10,18,24} {10,18,25} {10,18,26} {10,18,27}
{10,18,28} {10,18,29} {10,18,30} {10,18,31} {10,18,32} {10,18,33} {10,18,34} {10,18,35} {10,18,36}
{10,18,37} {10,18,38} {10,18,39} {10,18,40} {10,18,41} {10,18,42} {10,18,43} {10,18,44} {10,18,45}
{10,18,46} {10,18,47} {10,18,48} {10,18,49} {10,18,50} {10,18,51} {10,18,52} {10,18,53} {10,18,54}
{10,18,55} {10,18,56} {10,18,57} {10,18,58} {10,18,59} {10,18,60} {10,18,61} {10,18,62} {10,18,63}
{10,18,64} {10,18,65} {10,18,66} {10,19,20} {10,19,21} {10,19,22} {10,19,23} {10,19,24} {10,19,25}
{10,19,26} {10,19,27} {10,19,28} {10,19,29} {10,19,30} {10,19,31} {10,19,32} {10,19,33} {10,19,34}
{10,19,35} {10,19,36} {10,19,37} {10,19,38} {10,19,39} {10,19,40} {10,19,41} {10,19,42} {10,19,43}
{10,19,44} {10,19,45} {10,19,46} {10,19,47} {10,19,48} {10,19,49} {10,19,50} {10,19,51} {10,19,52}
{10,19,53} {10,19,54} {10,19,55} {10,19,56} {10,19,57} {10,19,58} {10,19,59} {10,19,60} {10,19,61}
{10,19,62} {10,19,63} {10,19,64} {10,19,65} {10,19,66} {10,20,21} {10,20,22} {10,20,23} {10,20,24}
{10,20,25} {10,20,26} {10,20,27} {10,20,28} {10,20,29} {10,20,30} {10,20,31} {10,20,32} {10,20,33}
{10,20,34} {10,20,35} {10,20,36} {10,20,37} {10,20,38} {10,20,39} {10,20,40} {10,20,41} {10,20,42}
{10,20,43} {10,20,44} {10,20,45} {10,20,46} {10,20,47} {10,20,48} {10,20,49} {10,20,50} {10,20,51}
{10,20,52} {10,20,53} {10,20,54} {10,20,55} {10,20,56} {10,20,57} {10,20,58} {10,20,59} {10,20,60}
{10,20,61} {10,20,62} {10,20,63} {10,20,64} {10,20,65} {10,20,66} {10,21,22} {10,21,23} {10,21,24}
{10,21,25} {10,21,26} {10,21,27} {10,21,28} {10,21,29} {10,21,30} {10,21,31} {10,21,32} {10,21,33}
{10,21,34} {10,21,35} {10,21,36} {10,21,37} {10,21,38} {10,21,39} {10,21,40} {10,21,41} {10,21,42}
{10,21,43} {10,21,44} {10,21,45} {10,21,46} {10,21,47} {10,21,48} {10,21,49} {10,21,50} {10,21,51}
{10,21,52} {10,21,53} {10,21,54} {10,21,55} {10,21,56} {10,21,57} {10,21,58} {10,21,59} {10,21,60}
{10,21,61} {10,21,62} {10,21,63} {10,21,64} {10,21,65} {10,21,66} {10,22,23} {10,22,24} {10,22,25}
{10,22,26} {10,22,27} {10,22,28} {10,22,29} {10,22,30} {10,22,31} {10,22,32} {10,22,33} {10,22,34}
{10,22,35} {10,22,36} {10,22,37} {10,22,38} {10,22,39} {10,22,40} {10,22,41} {10,22,42} {10,22,43}
{10,22,44} {10,22,45} {10,22,46} {10,22,47} {10,22,48} {10,22,49} {10,22,50} {10,22,51} {10,22,52}
{10,22,53} {10,22,54} {10,22,55} {10,22,56} {10,22,57} {10,22,58} {10,22,59} {10,22,60} {10,22,61}
{10,22,62} {10,22,63} {10,22,64} {10,22,65} {10,22,66} {10,23,24} {10,23,25} {10,23,26} {10,23,27}
{10,23,28} {10,23,29} {10,23,30} {10,23,31} {10,23,32} {10,23,33} {10,23,34} {10,23,35} {10,23,36}
{10,23,37} {10,23,38} {10,23,39} {10,23,40} {10,23,41} {10,23,42} {10,23,43} {10,23,44} {10,23,45}
{10,23,46} {10,23,47} {10,23,48} {10,23,49} {10,23,50} {10,23,51} {10,23,52} {10,23,53} {10,23,54}
{10,23,55} {10,23,56} {10,23,57} {10,23,58} {10,23,59} {10,23,60} {10,23,61} {10,23,62} {10,23,63}
{10,23,64} {10,23,65} {10,23,66} {10,24,25} {10,24,26} {10,24,27} {10,24,28} {10,24,29} {10,24,30}
{10,24,31} {10,24,32} {10,24,33} {10,24,34} {10,24,35} {10,24,36} {10,24,37} {10,24,38} {10,24,39}
{10,24,40} {10,24,41} {10,24,42} {10,24,43} {10,24,44} {10,24,45} {10,24,46} {10,24,47} {10,24,48}
{10,24,49} {10,24,50} {10,24,51} {10,24,52} {10,24,53} {10,24,54} {10,24,55} {10,24,56} {10,24,57}
{10,24,58} {10,24,59} {10,24,60} {10,24,61} {10,24,62} {10,24,63} {10,24,64} {10,24,65} {10,24,66}
{10,25,26} {10,25,27} {10,25,28} {10,25,29} {10,25,30} {10,25,31} {10,25,32} {10,25,33} {10,25,34}
{10,25,35} {10,25,36} {10,25,37} {10,25,38} {10,25,39} {10,25,40} {10,25,41} {10,25,42} {10,25,43}
{10,25,44} {10,25,45} {10,25,46} {10,25,47} {10,25,48} {10,25,49} {10,25,50} {10,25,51} {10,25,52}
{10,25,53} {10,25,54} {10,25,55} {10,25,56} {10,25,57} {10,25,58} {10,25,59} {10,25,60} {10,25,61}
{10,25,62} {10,25,63} {10,25,64} {10,25,65} {10,25,66} {10,26,27} {10,26,28} {10,26,29} {10,26,30}
{10,26,31} {10,26,32} {10,26,33} {10,26,34} {10,26,35} {10,26,36} {10,26,37} {10,26,38} {10,26,39}
{10,26,40} {10,26,41} {10,26,42} {10,26,43} {10,26,44} {10,26,45} {10,26,46} {10,26,47} {10,26,48}
{10,26,49} {10,26,50} {10,26,51} {10,26,52} {10,26,53} {10,26,54} {10,26,55} {10,26,56} {10,26,57}
{10,26,58} {10,26,59} {10,26,60} {10,26,61} {10,26,62} {10,26,63} {10,26,64} {10,26,65} {10,26,66}
{10,27,28} {10,27,29} {10,27,30} {10,27,31} {10,27,32} {10,27,33} {10,27,34} {10,27,35} {10,27,36}
{10,27,37} {10,27,38} {10,27,39} {10,27,40} {10,27,41} {10,27,42} {10,27,43} {10,27,44} {10,27,45}
{10,27,46} {10,27,47} {10,27,48} {10,27,49} {10,27,50} {10,27,51} {10,27,52} {10,27,53} {10,27,54}
{10,27,55} {10,27,56} {10,27,57} {10,27,58} {10,27,59} {10,27,60} {10,27,61} {10,27,62} {10,27,63}
{10,27,64} {10,27,65} {10,27,66} {10,28,29} {10,28,30} {10,28,31} {10,28,32} {10,28,33} {10,28,34}
{10,28,35} {10,28,36} {10,28,37} {10,28,38} {10,28,39} {10,28,40} {10,28,41} {10,28,42} {10,28,43}
{10,28,44} {10,28,45} {10,28,46} {10,28,47} {10,28,48} {10,28,49} {10,28,50} {10,28,51} {10,28,52}
{10,28,53} {10,28,54} {10,28,55} {10,28,56} {10,28,57} {10,28,58} {10,28,59} {10,28,60} {10,28,61}
{10,28,62} {10,28,63} {10,28,64} {10,28,65} {10,28,66} {10,29,30} {10,29,31} {10,29,32} {10,29,33}
{10,29,34} {10,29,35} {10,29,36} {10,29,37} {10,29,38} {10,29,39} {10,29,40} {10,29,41} {10,29,42}
{10,29,43} {10,29,44} {10,29,45} {10,29,46} {10,29,47} {10,29,48} {10,29,49} {10,29,50} {10,29,51}
{10,29,52} {10,29,53} {10,29,54} {10,29,55} {10,29,56} {10,29,57} {10,29,58} {10,29,59} {10,29,60}
{10,29,61} {10,29,62} {10,29,63} {10,29,64} {10,29,65} {10,29,66} {10,30,31} {10,30,32} {10,30,33}
{10,30,34} {10,30,35} {10,30,36} {10,30,37} {10,30,38} {10,30,39} {10,30,40} {10,30,41} {10,30,42}
{10,30,43} {10,30,44} {10,30,45} {10,30,46} {10,30,47} {10,30,48} {10,30,49} {10,30,50} {10,30,51}
{10,30,52} {10,30,53} {10,30,54} {10,30,55} {10,30,56} {10,30,57} {10,30,58} {10,30,59} {10,30,60}
{10,30,61} {10,30,62} {10,30,63} {10,30,64} {10,30,65} {10,30,66} {10,31,32} {10,31,33} {10,31,34}
{10,31,35} {10,31,36} {10,31,37} {10,31,38} {10,31,39} {10,31,40} {10,31,41} {10,31,42} {10,31,43}
{10,31,44} {10,31,45} {10,31,46} {10,31,47} {10,31,48} {10,31,49} {10,31,50} {10,31,51} {10,31,52}
{10,31,53} {10,31,54} {10,31,55} {10,31,56} {10,31,57} {10,31,58} {10,31,59} {10,31,60} {10,31,61}
{10,31,62} {10,31,63} {10,31,64} {10,31,65} {10,31,66} {10,32,33} {10,32,34} {10,32,35} {10,32,36}
{10,32,37} {10,32,38} {10,32,39} {10,32,40} {10,32,41} {10,32,42} {10,32,43} {10,32,44} {10,32,45}

TABLE 3A-continued

| | | | | | | | |
|---|---|---|---|---|---|---|---|
| {10,32,46} | {10,32,47} | {10,32,48} | {10,32,49} | {10,32,50} | {10,32,51} | {10,32,52} | {10,32,53} | {10,32,54} |
| {10,32,55} | {10,32,56} | {10,32,57} | {10,32,58} | {10,32,59} | {10,32,60} | {10,32,61} | {10,32,62} | {10,32,63} |
| {10,32,64} | {10,32,65} | {10,32,66} | {10,33,34} | {10,33,35} | {10,33,36} | {10,33,37} | {10,33,38} | {10,33,39} |
| {10,33,40} | {10,33,41} | {10,33,42} | {10,33,43} | {10,33,44} | {10,33,45} | {10,33,46} | {10,33,47} | {10,33,48} |
| {10,33,49} | {10,33,50} | {10,33,51} | {10,33,52} | {10,33,53} | {10,33,54} | {10,33,55} | {10,33,56} | {10,33,57} |
| {10,33,58} | {10,33,59} | {10,33,60} | {10,33,61} | {10,33,62} | {10,33,63} | {10,33,64} | {10,33,65} | {10,33,66} |
| {10,34,35} | {10,34,36} | {10,34,37} | {10,34,38} | {10,34,39} | {10,34,40} | {10,34,41} | {10,34,42} | {10,34,43} |
| {10,34,44} | {10,34,45} | {10,34,46} | {10,34,47} | {10,34,48} | {10,34,49} | {10,34,50} | {10,34,51} | {10,34,52} |
| {10,34,53} | {10,34,54} | {10,34,55} | {10,34,56} | {10,34,57} | {10,34,58} | {10,34,59} | {10,34,60} | {10,34,61} |
| {10,34,62} | {10,34,63} | {10,34,64} | {10,34,65} | {10,34,66} | {10,35,36} | {10,35,37} | {10,35,38} | {10,35,39} |
| {10,35,40} | {10,35,41} | {10,35,42} | {10,35,43} | {10,35,44} | {10,35,45} | {10,35,46} | {10,35,47} | {10,35,48} |
| {10,35,49} | {10,35,50} | {10,35,51} | {10,35,52} | {10,35,53} | {10,35,54} | {10,35,55} | {10,35,56} | {10,35,57} |
| {10,35,58} | {10,35,59} | {10,35,60} | {10,35,61} | {10,35,62} | {10,35,63} | {10,35,64} | {10,35,65} | {10,35,66} |
| {10,36,37} | {10,36,38} | {10,36,39} | {10,36,40} | {10,36,41} | {10,36,42} | {10,36,43} | {10,36,44} | {10,36,45} |
| {10,36,46} | {10,36,47} | {10,36,48} | {10,36,49} | {10,36,50} | {10,36,51} | {10,36,52} | {10,36,53} | {10,36,54} |
| {10,36,55} | {10,36,56} | {10,36,57} | {10,36,58} | {10,36,59} | {10,36,60} | {10,36,61} | {10,36,62} | {10,36,63} |
| {10,36,64} | {10,36,65} | {10,36,66} | {10,37,38} | {10,37,39} | {10,37,40} | {10,37,41} | {10,37,42} | {10,37,43} |
| {10,37,44} | {10,37,45} | {10,37,46} | {10,37,47} | {10,37,48} | {10,37,49} | {10,37,50} | {10,37,51} | {10,37,52} |
| {10,37,53} | {10,37,54} | {10,37,55} | {10,37,56} | {10,37,57} | {10,37,58} | {10,37,59} | {10,37,60} | {10,37,61} |
| {10,37,62} | {10,37,63} | {10,37,64} | {10,37,65} | {10,37,66} | {10,38,39} | {10,38,40} | {10,38,41} | {10,38,42} |
| {10,38,43} | {10,38,44} | {10,38,45} | {10,38,46} | {10,38,47} | {10,38,48} | {10,38,49} | {10,38,50} | {10,38,51} |
| {10,38,52} | {10,38,53} | {10,38,54} | {10,38,55} | {10,38,56} | {10,38,57} | {10,38,58} | {10,38,59} | {10,38,60} |
| {10,38,61} | {10,38,62} | {10,38,63} | {10,38,64} | {10,38,65} | {10,38,66} | {10,39,40} | {10,39,41} | {10,39,42} |
| {10,39,43} | {10,39,44} | {10,39,45} | {10,39,46} | {10,39,47} | {10,39,48} | {10,39,49} | {10,39,50} | {10,39,51} |
| {10,39,52} | {10,39,53} | {10,39,54} | {10,39,55} | {10,39,56} | {10,39,57} | {10,39,58} | {10,39,59} | {10,39,60} |
| {10,39,61} | {10,39,62} | {10,39,63} | {10,39,64} | {10,39,65} | {10,39,66} | {10,40,41} | {10,40,42} | {10,40,43} |
| {10,40,44} | {10,40,45} | {10,40,46} | {10,40,47} | {10,40,48} | {10,40,49} | {10,40,50} | {10,40,51} | {10,40,52} |
| {10,40,53} | {10,40,54} | {10,40,55} | {10,40,56} | {10,40,57} | {10,40,58} | {10,40,59} | {10,40,60} | {10,40,61} |
| {10,40,62} | {10,40,63} | {10,40,64} | {10,40,65} | {10,40,66} | {10,41,42} | {10,41,43} | {10,41,44} | {10,41,45} |
| {10,41,46} | {10,41,47} | {10,41,48} | {10,41,49} | {10,41,50} | {10,41,51} | {10,41,52} | {10,41,53} | {10,41,54} |
| {10,41,55} | {10,41,56} | {10,41,57} | {10,41,58} | {10,41,59} | {10,41,60} | {10,41,61} | {10,41,62} | {10,41,63} |
| {10,41,64} | {10,41,65} | {10,41,66} | {10,42,43} | {10,42,44} | {10,42,45} | {10,42,46} | {10,42,47} | {10,42,48} |
| {10,42,49} | {10,42,50} | {10,42,51} | {10,42,52} | {10,42,53} | {10,42,54} | {10,42,55} | {10,42,56} | {10,42,57} |
| {10,42,58} | {10,42,59} | {10,42,60} | {10,42,61} | {10,42,62} | {10,42,63} | {10,42,64} | {10,42,65} | {10,42,66} |
| {10,43,44} | {10,43,45} | {10,43,46} | {10,43,47} | {10,43,48} | {10,43,49} | {10,43,50} | {10,43,51} | {10,43,52} |
| {10,43,53} | {10,43,54} | {10,43,55} | {10,43,56} | {10,43,57} | {10,43,58} | {10,43,59} | {10,43,60} | {10,43,61} |
| {10,43,62} | {10,43,63} | {10,43,64} | {10,43,65} | {10,43,66} | {10,44,45} | {10,44,46} | {10,44,47} | {10,44,48} |
| {10,44,49} | {10,44,50} | {10,44,51} | {10,44,52} | {10,44,53} | {10,44,54} | {10,44,55} | {10,44,56} | {10,44,57} |
| {10,44,58} | {10,44,59} | {10,44,60} | {10,44,61} | {10,44,62} | {10,44,63} | {10,44,64} | {10,44,65} | {10,44,66} |
| {10,45,46} | {10,45,47} | {10,45,48} | {10,45,49} | {10,45,50} | {10,45,51} | {10,45,52} | {10,45,53} | {10,45,54} |
| {10,45,55} | {10,45,56} | {10,45,57} | {10,45,58} | {10,45,59} | {10,45,60} | {10,45,61} | {10,45,62} | {10,45,63} |
| {10,45,64} | {10,45,65} | {10,45,66} | {10,46,47} | {10,46,48} | {10,46,49} | {10,46,50} | {10,46,51} | {10,46,52} |
| {10,46,53} | {10,46,54} | {10,46,55} | {10,46,56} | {10,46,57} | {10,46,58} | {10,46,59} | {10,46,60} | {10,46,61} |
| {10,46,62} | {10,46,63} | {10,46,64} | {10,46,65} | {10,46,66} | {10,47,48} | {10,47,49} | {10,47,50} | {10,47,51} |
| {10,47,52} | {10,47,53} | {10,47,54} | {10,47,55} | {10,47,56} | {10,47,57} | {10,47,58} | {10,47,59} | {10,47,60} |
| {10,47,61} | {10,47,62} | {10,47,63} | {10,47,64} | {10,47,65} | {10,47,66} | {10,48,49} | {10,48,50} | {10,48,51} |
| {10,48,52} | {10,48,53} | {10,48,54} | {10,48,55} | {10,48,56} | {10,48,57} | {10,48,58} | {10,48,59} | {10,48,60} |
| {10,48,61} | {10,48,62} | {10,48,63} | {10,48,64} | {10,48,65} | {10,48,66} | {10,49,50} | {10,49,51} | {10,49,52} |
| {10,49,53} | {10,49,54} | {10,49,55} | {10,49,56} | {10,49,57} | {10,49,58} | {10,49,59} | {10,49,60} | {10,49,61} |
| {10,49,62} | {10,49,63} | {10,49,64} | {10,49,65} | {10,49,66} | {10,50,51} | {10,50,52} | {10,50,53} | {10,50,54} |
| {10,50,55} | {10,50,56} | {10,50,57} | {10,50,58} | {10,50,59} | {10,50,60} | {10,50,61} | {10,50,62} | {10,50,63} |
| {10,50,64} | {10,50,65} | {10,50,66} | {10,51,52} | {10,51,53} | {10,51,54} | {10,51,55} | {10,51,56} | {10,51,57} |
| {10,51,58} | {10,51,59} | {10,51,60} | {10,51,61} | {10,51,62} | {10,51,63} | {10,51,64} | {10,51,65} | {10,51,66} |
| {10,52,53} | {10,52,54} | {10,52,55} | {10,52,56} | {10,52,57} | {10,52,58} | {10,52,59} | {10,52,60} | {10,52,61} |
| {10,52,62} | {10,52,63} | {10,52,64} | {10,52,65} | {10,52,66} | {10,53,54} | {10,53,55} | {10,53,56} | {10,53,57} |
| {10,53,58} | {10,53,59} | {10,53,60} | {10,53,61} | {10,53,62} | {10,53,63} | {10,53,64} | {10,53,65} | {10,53,66} |
| {10,54,55} | {10,54,56} | {10,54,57} | {10,54,58} | {10,54,59} | {10,54,60} | {10,54,61} | {10,54,62} | {10,54,63} |
| {10,54,64} | {10,54,65} | {10,54,66} | {10,55,56} | {10,55,57} | {10,55,58} | {10,55,59} | {10,55,60} | {10,55,61} |
| {10,55,62} | {10,55,63} | {10,55,64} | {10,55,65} | {10,55,66} | {10,56,57} | {10,56,58} | {10,56,59} | {10,56,60} |
| {10,56,61} | {10,56,62} | {10,56,63} | {10,56,64} | {10,56,65} | {10,56,66} | {10,57,58} | {10,57,59} | {10,57,60} |
| {10,57,61} | {10,57,62} | {10,57,63} | {10,57,64} | {10,57,65} | {10,57,66} | {10,58,59} | {10,58,60} | {10,58,61} |
| {10,58,62} | {10,58,63} | {10,58,64} | {10,58,65} | {10,58,66} | {10,59,60} | {10,59,61} | {10,59,62} | {10,59,63} |
| {10,59,64} | {10,59,65} | {10,59,66} | {10,60,61} | {10,60,62} | {10,60,63} | {10,60,64} | {10,60,65} | {10,60,66} |
| {10,61,62} | {10,61,63} | {10,61,64} | {10,61,65} | {10,61,66} | {10,62,63} | {10,62,64} | {10,62,65} | {10,62,66} |
| {10,63,64} | {10,63,65} | {10,63,66} | {10,64,65} | {10,64,66} | {10,65,66} | {11,12,13} | {11,12,14} | {11,12,15} |
| {11,12,16} | {11,12,17} | {11,12,18} | {11,12,19} | {11,12,20} | {11,12,21} | {11,12,22} | {11,12,23} | {11,12,24} |
| {11,12,25} | {11,12,26} | {11,12,27} | {11,12,28} | {11,12,29} | {11,12,30} | {11,12,31} | {11,12,32} | {11,12,33} |
| {11,12,34} | {11,12,35} | {11,12,36} | {11,12,37} | {11,12,38} | {11,12,39} | {11,12,40} | {11,12,41} | {11,12,42} |
| {11,12,43} | {11,12,44} | {11,12,45} | {11,12,46} | {11,12,47} | {11,12,48} | {11,12,49} | {11,12,50} | {11,12,51} |
| {11,12,52} | {11,12,53} | {11,12,54} | {11,12,55} | {11,12,56} | {11,12,57} | {11,12,58} | {11,12,59} | {11,12,60} |
| {11,12,61} | {11,12,62} | {11,12,63} | {11,12,64} | {11,12,65} | {11,12,66} | {11,13,14} | {11,13,15} | {11,13,16} |
| {11,13,17} | {11,13,18} | {11,13,19} | {11,13,20} | {11,13,21} | {11,13,22} | {11,13,23} | {11,13,24} | {11,13,25} |
| {11,13,26} | {11,13,27} | {11,13,28} | {11,13,29} | {11,13,30} | {11,13,31} | {11,13,32} | {11,13,33} | {11,13,34} |
| {11,13,35} | {11,13,36} | {11,13,37} | {11,13,38} | {11,13,39} | {11,13,40} | {11,13,41} | {11,13,42} | {11,13,43} |
| {11,13,44} | {11,13,45} | {11,13,46} | {11,13,47} | {11,13,48} | {11,13,49} | {11,13,50} | {11,13,51} | {11,13,52} |
| {11,13,53} | {11,13,54} | {11,13,55} | {11,13,56} | {11,13,57} | {11,13,58} | {11,13,59} | {11,13,60} | {11,13,61} |
| {11,13,62} | {11,13,63} | {11,13,64} | {11,13,65} | {11,13,66} | {11,14,15} | {11,14,16} | {11,14,17} | {11,14,18} |
| {11,14,19} | {11,14,20} | {11,14,21} | {11,14,22} | {11,14,23} | {11,14,24} | {11,14,25} | {11,14,26} | {11,14,27} |
| {11,14,28} | {11,14,29} | {11,14,30} | {11,14,31} | {11,14,32} | {11,14,33} | {11,14,34} | {11,14,35} | {11,14,36} |
| {11,14,37} | {11,14,38} | {11,14,39} | {11,14,40} | {11,14,41} | {11,14,42} | {11,14,43} | {11,14,44} | {11,14,45} |

TABLE 3A-continued

| | | | | | | | |
|---|---|---|---|---|---|---|---|
| {11,14,46} | {11,14,47} | {11,14,48} | {11,14,49} | {11,14,50} | {11,14,51} | {11,14,52} | {11,14,53} | {11,14,54} |
| {11,14,55} | {11,14,56} | {11,14,57} | {11,14,58} | {11,14,59} | {11,14,60} | {11,14,61} | {11,14,62} | {11,14,63} |
| {11,14,64} | {11,14,65} | {11,14,66} | {11,15,16} | {11,15,17} | {11,15,18} | {11,15,19} | {11,15,20} | {11,15,21} |
| {11,15,22} | {11,15,23} | {11,15,24} | {11,15,25} | {11,15,26} | {11,15,27} | {11,15,28} | {11,15,29} | {11,15,30} |
| {11,15,31} | {11,15,32} | {11,15,33} | {11,15,34} | {11,15,35} | {11,15,36} | {11,15,37} | {11,15,38} | {11,15,39} |
| {11,15,40} | {11,15,41} | {11,15,42} | {11,15,43} | {11,15,44} | {11,15,45} | {11,15,46} | {11,15,47} | {11,15,48} |
| {11,15,49} | {11,15,50} | {11,15,51} | {11,15,52} | {11,15,53} | {11,15,54} | {11,15,55} | {11,15,56} | {11,15,57} |
| {11,15,58} | {11,15,59} | {11,15,60} | {11,15,61} | {11,15,62} | {11,15,63} | {11,15,64} | {11,15,65} | {11,15,66} |
| {11,16,17} | {11,16,18} | {11,16,19} | {11,16,20} | {11,16,21} | {11,16,22} | {11,16,23} | {11,16,24} | {11,16,25} |
| {11,16,26} | {11,16,27} | {11,16,28} | {11,16,29} | {11,16,30} | {11,16,31} | {11,16,32} | {11,16,33} | {11,16,34} |
| {11,16,35} | {11,16,36} | {11,16,37} | {11,16,38} | {11,16,39} | {11,16,40} | {11,16,41} | {11,16,42} | {11,16,43} |
| {11,16,44} | {11,16,45} | {11,16,46} | {11,16,47} | {11,16,48} | {11,16,49} | {11,16,50} | {11,16,51} | {11,16,52} |
| {11,16,53} | {11,16,54} | {11,16,55} | {11,16,56} | {11,16,57} | {11,16,58} | {11,16,59} | {11,16,60} | {11,16,61} |
| {11,16,62} | {11,16,63} | {11,16,64} | {11,16,65} | {11,16,66} | {11,17,18} | {11,17,19} | {11,17,20} | {11,17,21} |
| {11,17,22} | {11,17,23} | {11,17,24} | {11,17,25} | {11,17,26} | {11,17,27} | {11,17,28} | {11,17,29} | {11,17,30} |
| {11,17,31} | {11,17,32} | {11,17,33} | {11,17,34} | {11,17,35} | {11,17,36} | {11,17,37} | {11,17,38} | {11,17,39} |
| {11,17,40} | {11,17,41} | {11,17,42} | {11,17,43} | {11,17,44} | {11,17,45} | {11,17,46} | {11,17,47} | {11,17,48} |
| {11,17,49} | {11,17,50} | {11,17,51} | {11,17,52} | {11,17,53} | {11,17,54} | {11,17,55} | {11,17,56} | {11,17,57} |
| {11,17,58} | {11,17,59} | {11,17,60} | {11,17,61} | {11,17,62} | {11,17,63} | {11,17,64} | {11,17,65} | {11,17,66} |
| {11,18,19} | {11,18,20} | {11,18,21} | {11,18,22} | {11,18,23} | {11,18,24} | {11,18,25} | {11,18,26} | {11,18,27} |
| {11,18,28} | {11,18,29} | {11,18,30} | {11,18,31} | {11,18,32} | {11,18,33} | {11,18,34} | {11,18,35} | {11,18,36} |
| {11,18,37} | {11,18,38} | {11,18,39} | {11,18,40} | {11,18,41} | {11,18,42} | {11,18,43} | {11,18,44} | {11,18,45} |
| {11,18,46} | {11,18,47} | {11,18,48} | {11,18,49} | {11,18,50} | {11,18,51} | {11,18,52} | {11,18,53} | {11,18,54} |
| {11,18,55} | {11,18,56} | {11,18,57} | {11,18,58} | {11,18,59} | {11,18,60} | {11,18,61} | {11,18,62} | {11,18,63} |
| {11,18,64} | {11,18,65} | {11,18,66} | {11,19,20} | {11,19,21} | {11,19,22} | {11,19,23} | {11,19,24} | {11,19,25} |
| {11,19,26} | {11,19,27} | {11,19,28} | {11,19,29} | {11,19,30} | {11,19,31} | {11,19,32} | {11,19,33} | {11,19,34} |
| {11,19,35} | {11,19,36} | {11,19,37} | {11,19,38} | {11,19,39} | {11,19,40} | {11,19,41} | {11,19,42} | {11,19,43} |
| {11,19,44} | {11,19,45} | {11,19,46} | {11,19,47} | {11,19,48} | {11,19,49} | {11,19,50} | {11,19,51} | {11,19,52} |
| {11,19,53} | {11,19,54} | {11,19,55} | {11,19,56} | {11,19,57} | {11,19,58} | {11,19,59} | {11,19,60} | {11,19,61} |
| {11,19,62} | {11,19,63} | {11,19,64} | {11,19,65} | {11,19,66} | {11,20,21} | {11,20,22} | {11,20,23} | {11,20,24} |
| {11,20,25} | {11,20,26} | {11,20,27} | {11,20,28} | {11,20,29} | {11,20,30} | {11,20,31} | {11,20,32} | {11,20,33} |
| {11,20,34} | {11,20,35} | {11,20,36} | {11,20,37} | {11,20,38} | {11,20,39} | {11,20,40} | {11,20,41} | {11,20,42} |
| {11,20,43} | {11,20,44} | {11,20,45} | {11,20,46} | {11,20,47} | {11,20,48} | {11,20,49} | {11,20,50} | {11,20,51} |
| {11,20,52} | {11,20,53} | {11,20,54} | {11,20,55} | {11,20,56} | {11,20,57} | {11,20,58} | {11,20,59} | {11,20,60} |
| {11,20,61} | {11,20,62} | {11,20,63} | {11,20,64} | {11,20,65} | {11,20,66} | {11,21,22} | {11,21,23} | {11,21,24} |
| {11,21,25} | {11,21,26} | {11,21,27} | {11,21,28} | {11,21,29} | {11,21,30} | {11,21,31} | {11,21,32} | {11,21,33} |
| {11,21,34} | {11,21,35} | {11,21,36} | {11,21,37} | {11,21,38} | {11,21,39} | {11,21,40} | {11,21,41} | {11,21,42} |
| {11,21,43} | {11,21,44} | {11,21,45} | {11,21,46} | {11,21,47} | {11,21,48} | {11,21,49} | {11,21,50} | {11,21,51} |
| {11,21,52} | {11,21,53} | {11,21,54} | {11,21,55} | {11,21,56} | {11,21,57} | {11,21,58} | {11,21,59} | {11,21,60} |
| {11,21,61} | {11,21,62} | {11,21,63} | {11,21,64} | {11,21,65} | {11,21,66} | {11,22,23} | {11,22,24} | {11,22,25} |
| {11,22,26} | {11,22,27} | {11,22,28} | {11,22,29} | {11,22,30} | {11,22,31} | {11,22,32} | {11,22,33} | {11,22,34} |
| {11,22,35} | {11,22,36} | {11,22,37} | {11,22,38} | {11,22,39} | {11,22,40} | {11,22,41} | {11,22,42} | {11,22,43} |
| {11,22,44} | {11,22,45} | {11,22,46} | {11,22,47} | {11,22,48} | {11,22,49} | {11,22,50} | {11,22,51} | {11,22,52} |
| {11,22,53} | {11,22,54} | {11,22,55} | {11,22,56} | {11,22,57} | {11,22,58} | {11,22,59} | {11,22,60} | {11,22,61} |
| {11,22,62} | {11,22,63} | {11,22,64} | {11,22,65} | {11,22,66} | {11,23,24} | {11,23,25} | {11,23,26} | {11,23,27} |
| {11,23,28} | {11,23,29} | {11,23,30} | {11,23,31} | {11,23,32} | {11,23,33} | {11,23,34} | {11,23,35} | {11,23,36} |
| {11,23,37} | {11,23,38} | {11,23,39} | {11,23,40} | {11,23,41} | {11,23,42} | {11,23,43} | {11,23,44} | {11,23,45} |
| {11,23,46} | {11,23,47} | {11,23,48} | {11,23,49} | {11,23,50} | {11,23,51} | {11,23,52} | {11,23,53} | {11,23,54} |
| {11,23,55} | {11,23,56} | {11,23,57} | {11,23,58} | {11,23,59} | {11,23,60} | {11,23,61} | {11,23,62} | {11,23,63} |
| {11,23,64} | {11,23,65} | {11,23,66} | {11,24,25} | {11,24,26} | {11,24,27} | {11,24,28} | {11,24,29} | {11,24,30} |
| {11,24,31} | {11,24,32} | {11,24,33} | {11,24,34} | {11,24,35} | {11,24,36} | {11,24,37} | {11,24,38} | {11,24,39} |
| {11,24,40} | {11,24,41} | {11,24,42} | {11,24,43} | {11,24,44} | {11,24,45} | {11,24,46} | {11,24,47} | {11,24,48} |
| {11,24,49} | {11,24,50} | {11,24,51} | {11,24,52} | {11,24,53} | {11,24,54} | {11,24,55} | {11,24,56} | {11,24,57} |
| {11,24,58} | {11,24,59} | {11,24,60} | {11,24,61} | {11,24,62} | {11,24,63} | {11,24,64} | {11,24,65} | {11,24,66} |
| {11,25,26} | {11,25,27} | {11,25,28} | {11,25,29} | {11,25,30} | {11,25,31} | {11,25,32} | {11,25,33} | {11,25,34} |
| {11,25,35} | {11,25,36} | {11,25,37} | {11,25,38} | {11,25,39} | {11,25,40} | {11,25,41} | {11,25,42} | {11,25,43} |
| {11,25,44} | {11,25,45} | {11,25,46} | {11,25,47} | {11,25,48} | {11,25,49} | {11,25,50} | {11,25,51} | {11,25,52} |
| {11,25,53} | {11,25,54} | {11,25,55} | {11,25,56} | {11,25,57} | {11,25,58} | {11,25,59} | {11,25,60} | {11,25,61} |
| {11,25,62} | {11,25,63} | {11,25,64} | {11,25,65} | {11,25,66} | {11,26,27} | {11,26,28} | {11,26,29} | {11,26,30} |
| {11,26,31} | {11,26,32} | {11,26,33} | {11,26,34} | {11,26,35} | {11,26,36} | {11,26,37} | {11,26,38} | {11,26,39} |
| {11,26,40} | {11,26,41} | {11,26,42} | {11,26,43} | {11,26,44} | {11,26,45} | {11,26,46} | {11,26,47} | {11,26,48} |
| {11,26,49} | {11,26,50} | {11,26,51} | {11,26,52} | {11,26,53} | {11,26,54} | {11,26,55} | {11,26,56} | {11,26,57} |
| {11,26,58} | {11,26,59} | {11,26,60} | {11,26,61} | {11,26,62} | {11,26,63} | {11,26,64} | {11,26,65} | {11,26,66} |
| {11,27,28} | {11,27,29} | {11,27,30} | {11,27,31} | {11,27,32} | {11,27,33} | {11,27,34} | {11,27,35} | {11,27,36} |
| {11,27,37} | {11,27,38} | {11,27,39} | {11,27,40} | {11,27,41} | {11,27,42} | {11,27,43} | {11,27,44} | {11,27,45} |
| {11,27,46} | {11,27,47} | {11,27,48} | {11,27,49} | {11,27,50} | {11,27,51} | {11,27,52} | {11,27,53} | {11,27,54} |
| {11,27,55} | {11,27,56} | {11,27,57} | {11,27,58} | {11,27,59} | {11,27,60} | {11,27,61} | {11,27,62} | {11,27,63} |
| {11,27,64} | {11,27,65} | {11,27,66} | {11,28,29} | {11,28,30} | {11,28,31} | {11,28,32} | {11,28,33} | {11,28,34} |
| {11,28,35} | {11,28,36} | {11,28,37} | {11,28,38} | {11,28,39} | {11,28,40} | {11,28,41} | {11,28,42} | {11,28,43} |
| {11,28,44} | {11,28,45} | {11,28,46} | {11,28,47} | {11,28,48} | {11,28,49} | {11,28,50} | {11,28,51} | {11,28,52} |
| {11,28,53} | {11,28,54} | {11,28,55} | {11,28,56} | {11,28,57} | {11,28,58} | {11,28,59} | {11,28,60} | {11,28,61} |
| {11,28,62} | {11,28,63} | {11,28,64} | {11,28,65} | {11,28,66} | {11,29,30} | {11,29,31} | {11,29,32} | {11,29,33} |
| {11,29,34} | {11,29,35} | {11,29,36} | {11,29,37} | {11,29,38} | {11,29,39} | {11,29,40} | {11,29,41} | {11,29,42} |
| {11,29,43} | {11,29,44} | {11,29,45} | {11,29,46} | {11,29,47} | {11,29,48} | {11,29,49} | {11,29,50} | {11,29,51} |
| {11,29,52} | {11,29,53} | {11,29,54} | {11,29,55} | {11,29,56} | {11,29,57} | {11,29,58} | {11,29,59} | {11,29,60} |
| {11,29,61} | {11,29,62} | {11,29,63} | {11,29,64} | {11,29,65} | {11,29,66} | {11,30,31} | {11,30,32} | {11,30,33} |
| {11,30,34} | {11,30,35} | {11,30,36} | {11,30,37} | {11,30,38} | {11,30,39} | {11,30,40} | {11,30,41} | {11,30,42} |
| {11,30,43} | {11,30,44} | {11,30,45} | {11,30,46} | {11,30,47} | {11,30,48} | {11,30,49} | {11,30,50} | {11,30,51} |
| {11,30,52} | {11,30,53} | {11,30,54} | {11,30,55} | {11,30,56} | {11,30,57} | {11,30,58} | {11,30,59} | {11,30,60} |
| {11,30,61} | {11,30,62} | {11,30,63} | {11,30,64} | {11,30,65} | {11,30,66} | {11,31,32} | {11,31,33} | {11,31,34} |

TABLE 3A-continued

{11,31,35} {11,31,36} {11,31,37} {11,31,38} {11,31,39} {11,31,40} {11,31,41} {11,31,42} {11,31,43}
{11,31,44} {11,31,45} {11,31,46} {11,31,47} {11,31,48} {11,31,49} {11,31,50} {11,31,51} {11,31,52}
{11,31,53} {11,31,54} {11,31,55} {11,31,56} {11,31,57} {11,31,58} {11,31,59} {11,31,60} {11,31,61}
{11,31,62} {11,31,63} {11,31,64} {11,31,65} {11,31,66} {11,32,33} {11,32,34} {11,32,35} {11,32,36}
{11,32,37} {11,32,38} {11,32,39} {11,32,40} {11,32,41} {11,32,42} {11,32,43} {11,32,44} {11,32,45}
{11,32,46} {11,32,47} {11,32,48} {11,32,49} {11,32,50} {11,32,51} {11,32,52} {11,32,53} {11,32,54}
{11,32,55} {11,32,56} {11,32,57} {11,32,58} {11,32,59} {11,32,60} {11,32,61} {11,32,62} {11,32,63}
{11,32,64} {11,32,65} {11,32,66} {11,33,34} {11,33,35} {11,33,36} {11,33,37} {11,33,38} {11,33,39}
{11,33,40} {11,33,41} {11,33,42} {11,33,43} {11,33,44} {11,33,45} {11,33,46} {11,33,47} {11,33,48}
{11,33,49} {11,33,50} {11,33,51} {11,33,52} {11,33,53} {11,33,54} {11,33,55} {11,33,56} {11,33,57}
{11,33,58} {11,33,59} {11,33,60} {11,33,61} {11,33,62} {11,33,63} {11,33,64} {11,33,65} {11,33,66}
{11,34,35} {11,34,36} {11,34,37} {11,34,38} {11,34,39} {11,34,40} {11,34,41} {11,34,42} {11,34,43}
{11,34,44} {11,34,45} {11,34,46} {11,34,47} {11,34,48} {11,34,49} {11,34,50} {11,34,51} {11,34,52}
{11,34,53} {11,34,54} {11,34,55} {11,34,56} {11,34,57} {11,34,58} {11,34,59} {11,34,60} {11,34,61}
{11,34,62} {11,34,63} {11,34,64} {11,34,65} {11,34,66} {11,35,36} {11,35,37} {11,35,38} {11,35,39}
{11,35,40} {11,35,41} {11,35,42} {11,35,43} {11,35,44} {11,35,45} {11,35,46} {11,35,47} {11,35,48}
{11,35,49} {11,35,50} {11,35,51} {11,35,52} {11,35,53} {11,35,54} {11,35,55} {11,35,56} {11,35,57}
{11,35,58} {11,35,59} {11,35,60} {11,35,61} {11,35,62} {11,35,63} {11,35,64} {11,35,65} {11,35,66}
{11,36,37} {11,36,38} {11,36,39} {11,36,40} {11,36,41} {11,36,42} {11,36,43} {11,36,44} {11,36,45}
{11,36,46} {11,36,47} {11,36,48} {11,36,49} {11,36,50} {11,36,51} {11,36,52} {11,36,53} {11,36,54}
{11,36,55} {11,36,56} {11,36,57} {11,36,58} {11,36,59} {11,36,60} {11,36,61} {11,36,62} {11,36,63}
{11,36,64} {11,36,65} {11,36,66} {11,37,38} {11,37,39} {11,37,40} {11,37,41} {11,37,42} {11,37,43}
{11,37,44} {11,37,45} {11,37,46} {11,37,47} {11,37,48} {11,37,49} {11,37,50} {11,37,51} {11,37,52}
{11,37,53} {11,37,54} {11,37,55} {11,37,56} {11,37,57} {11,37,58} {11,37,59} {11,37,60} {11,37,61}
{11,37,62} {11,37,63} {11,37,64} {11,37,65} {11,37,66} {11,38,39} {11,38,40} {11,38,41} {11,38,42}
{11,38,43} {11,38,44} {11,38,45} {11,38,46} {11,38,47} {11,38,48} {11,38,49} {11,38,50} {11,38,51}
{11,38,52} {11,38,53} {11,38,54} {11,38,55} {11,38,56} {11,38,57} {11,38,58} {11,38,59} {11,38,60}
{11,38,61} {11,38,62} {11,38,63} {11,38,64} {11,38,65} {11,38,66} {11,39,40} {11,39,41} {11,39,42}
{11,39,43} {11,39,44} {11,39,45} {11,39,46} {11,39,47} {11,39,48} {11,39,49} {11,39,50} {11,39,51}
{11,39,52} {11,39,53} {11,39,54} {11,39,55} {11,39,56} {11,39,57} {11,39,58} {11,39,59} {11,39,60}
{11,39,61} {11,39,62} {11,39,63} {11,39,64} {11,39,65} {11,39,66} {11,40,41} {11,40,42} {11,40,43}
{11,40,44} {11,40,45} {11,40,46} {11,40,47} {11,40,48} {11,40,49} {11,40,50} {11,40,51} {11,40,52}
{11,40,53} {11,40,54} {11,40,55} {11,40,56} {11,40,57} {11,40,58} {11,40,59} {11,40,60} {11,40,61}
{11,40,62} {11,40,63} {11,40,64} {11,40,65} {11,40,66} {11,41,42} {11,41,43} {11,41,44} {11,41,45}
{11,41,46} {11,41,47} {11,41,48} {11,41,49} {11,41,50} {11,41,51} {11,41,52} {11,41,53} {11,41,54}
{11,41,55} {11,41,56} {11,41,57} {11,41,58} {11,41,59} {11,41,60} {11,41,61} {11,41,62} {11,41,63}
{11,41,64} {11,41,65} {11,41,66} {11,42,43} {11,42,44} {11,42,45} {11,42,46} {11,42,47} {11,42,48}
{11,42,49} {11,42,50} {11,42,51} {11,42,52} {11,42,53} {11,42,54} {11,42,55} {11,42,56} {11,42,57}
{11,42,58} {11,42,59} {11,42,60} {11,42,61} {11,42,62} {11,42,63} {11,42,64} {11,42,65} {11,42,66}
{11,43,44} {11,43,45} {11,43,46} {11,43,47} {11,43,48} {11,43,49} {11,43,50} {11,43,51} {11,43,52}
{11,43,53} {11,43,54} {11,43,55} {11,43,56} {11,43,57} {11,43,58} {11,43,59} {11,43,60} {11,43,61}
{11,43,62} {11,43,63} {11,43,64} {11,43,65} {11,43,66} {11,44,45} {11,44,46} {11,44,47} {11,44,48}
{11,44,49} {11,44,50} {11,44,51} {11,44,52} {11,44,53} {11,44,54} {11,44,55} {11,44,56} {11,44,57}
{11,44,58} {11,44,59} {11,44,60} {11,44,61} {11,44,62} {11,44,63} {11,44,64} {11,44,65} {11,44,66}
{11,45,46} {11,45,47} {11,45,48} {11,45,49} {11,45,50} {11,45,51} {11,45,52} {11,45,53} {11,45,54}
{11,45,55} {11,45,56} {11,45,57} {11,45,58} {11,45,59} {11,45,60} {11,45,61} {11,45,62} {11,45,63}
{11,45,64} {11,45,65} {11,45,66} {11,46,47} {11,46,48} {11,46,49} {11,46,50} {11,46,51} {11,46,52}
{11,46,53} {11,46,54} {11,46,55} {11,46,56} {11,46,57} {11,46,58} {11,46,59} {11,46,60} {11,46,61}
{11,46,62} {11,46,63} {11,46,64} {11,46,65} {11,46,66} {11,47,48} {11,47,49} {11,47,50} {11,47,51}
{11,47,52} {11,47,53} {11,47,54} {11,47,55} {11,47,56} {11,47,57} {11,47,58} {11,47,59} {11,47,60}
{11,47,61} {11,47,62} {11,47,63} {11,47,64} {11,47,65} {11,47,66} {11,48,49} {11,48,50} {11,48,51}
{11,48,52} {11,48,53} {11,48,54} {11,48,55} {11,48,56} {11,48,57} {11,48,58} {11,48,59} {11,48,60}
{11,48,61} {11,48,62} {11,48,63} {11,48,64} {11,48,65} {11,48,66} {11,49,50} {11,49,51} {11,49,52}
{11,49,53} {11,49,54} {11,49,55} {11,49,56} {11,49,57} {11,49,58} {11,49,59} {11,49,60} {11,49,61}
{11,49,62} {11,49,63} {11,49,64} {11,49,65} {11,49,66} {11,50,51} {11,50,52} {11,50,53} {11,50,54}
{11,50,55} {11,50,56} {11,50,57} {11,50,58} {11,50,59} {11,50,60} {11,50,61} {11,50,62} {11,50,63}
{11,50,64} {11,50,65} {11,50,66} {11,51,52} {11,51,53} {11,51,54} {11,51,55} {11,51,56} {11,51,57}
{11,51,58} {11,51,59} {11,51,60} {11,51,61} {11,51,62} {11,51,63} {11,51,64} {11,51,65} {11,51,66}
{11,52,53} {11,52,54} {11,52,55} {11,52,56} {11,52,57} {11,52,58} {11,52,59} {11,52,60} {11,52,61}
{11,52,62} {11,52,63} {11,52,64} {11,52,65} {11,52,66} {11,53,54} {11,53,55} {11,53,56} {11,53,57}
{11,53,58} {11,53,59} {11,53,60} {11,53,61} {11,53,62} {11,53,63} {11,53,64} {11,53,65} {11,53,66}
{11,54,55} {11,54,56} {11,54,57} {11,54,58} {11,54,59} {11,54,60} {11,54,61} {11,54,62} {11,54,63}
{11,54,64} {11,54,65} {11,54,66} {11,55,56} {11,55,57} {11,55,58} {11,55,59} {11,55,60} {11,55,61}
{11,55,62} {11,55,63} {11,55,64} {11,55,65} {11,55,66} {11,56,57} {11,56,58} {11,56,59} {11,56,60}
{11,56,61} {11,56,62} {11,56,63} {11,56,64} {11,56,65} {11,56,66} {11,57,58} {11,57,59} {11,57,60}
{11,57,61} {11,57,62} {11,57,63} {11,57,64} {11,57,65} {11,57,66} {11,58,59} {11,58,60} {11,58,61}
{11,58,62} {11,58,63} {11,58,64} {11,58,65} {11,58,66} {11,59,60} {11,59,61} {11,59,62} {11,59,63}
{11,59,64} {11,59,65} {11,59,66} {11,60,61} {11,60,62} {11,60,63} {11,60,64} {11,60,65} {11,60,66}
{11,61,62} {11,61,63} {11,61,64} {11,61,65} {11,61,66} {11,62,63} {11,62,64} {11,62,65} {11,62,66}
{11,63,64} {11,63,65} {11,63,66} {11,64,65} {11,64,66} {11,65,66} {12,13,14} {12,13,15} {12,13,16}
{12,13,17} {12,13,18} {12,13,19} {12,13,20} {12,13,21} {12,13,22} {12,13,23} {12,13,24} {12,13,25}
{12,13,26} {12,13,27} {12,13,28} {12,13,29} {12,13,30} {12,13,31} {12,13,32} {12,13,33} {12,13,34}
{12,13,35} {12,13,36} {12,13,37} {12,13,38} {12,13,39} {12,13,40} {12,13,41} {12,13,42} {12,13,43}
{12,13,44} {12,13,45} {12,13,46} {12,13,47} {12,13,48} {12,13,49} {12,13,50} {12,13,51} {12,13,52}
{12,13,53} {12,13,54} {12,13,55} {12,13,56} {12,13,57} {12,13,58} {12,13,59} {12,13,60} {12,13,61}
{12,13,62} {12,13,63} {12,13,64} {12,13,65} {12,13,66} {12,14,15} {12,14,16} {12,14,17} {12,14,18}
{12,14,19} {12,14,20} {12,14,21} {12,14,22} {12,14,23} {12,14,24} {12,14,25} {12,14,26} {12,14,27}
{12,14,28} {12,14,29} {12,14,30} {12,14,31} {12,14,32} {12,14,33} {12,14,34} {12,14,35} {12,14,36}
{12,14,37} {12,14,38} {12,14,39} {12,14,40} {12,14,41} {12,14,42} {12,14,43} {12,14,44} {12,14,45}
{12,14,46} {12,14,47} {12,14,48} {12,14,49} {12,14,50} {12,14,51} {12,14,52} {12,14,53} {12,14,54}

TABLE 3A-continued

| | | | | | | | | |
|---|---|---|---|---|---|---|---|---|
| {12,14,55} | {12,14,56} | {12,14,57} | {12,14,58} | {12,14,59} | {12,14,60} | {12,14,61} | {12,14,62} | {12,14,63} |
| {12,14,64} | {12,14,65} | {12,14,66} | {12,15,16} | {12,15,17} | {12,15,18} | {12,15,19} | {12,15,20} | {12,15,21} |
| {12,15,22} | {12,15,23} | {12,15,24} | {12,15,25} | {12,15,26} | {12,15,27} | {12,15,28} | {12,15,29} | {12,15,30} |
| {12,15,31} | {12,15,32} | {12,15,33} | {12,15,34} | {12,15,35} | {12,15,36} | {12,15,37} | {12,15,38} | {12,15,39} |
| {12,15,40} | {12,15,41} | {12,15,42} | {12,15,43} | {12,15,44} | {12,15,45} | {12,15,46} | {12,15,47} | {12,15,48} |
| {12,15,49} | {12,15,50} | {12,15,51} | {12,15,52} | {12,15,53} | {12,15,54} | {12,15,55} | {12,15,56} | {12,15,57} |
| {12,15,58} | {12,15,59} | {12,15,60} | {12,15,61} | {12,15,62} | {12,15,63} | {12,15,64} | {12,15,65} | {12,15,66} |
| {12,16,17} | {12,16,18} | {12,16,19} | {12,16,20} | {12,16,21} | {12,16,22} | {12,16,23} | {12,16,24} | {12,16,25} |
| {12,16,26} | {12,16,27} | {12,16,28} | {12,16,29} | {12,16,30} | {12,16,31} | {12,16,32} | {12,16,33} | {12,16,34} |
| {12,16,35} | {12,16,36} | {12,16,37} | {12,16,38} | {12,16,39} | {12,16,40} | {12,16,41} | {12,16,42} | {12,16,43} |
| {12,16,44} | {12,16,45} | {12,16,46} | {12,16,47} | {12,16,48} | {12,16,49} | {12,16,50} | {12,16,51} | {12,16,52} |
| {12,16,53} | {12,16,54} | {12,16,55} | {12,16,56} | {12,16,57} | {12,16,58} | {12,16,59} | {12,16,60} | {12,16,61} |
| {12,16,62} | {12,16,63} | {12,16,64} | {12,16,65} | {12,16,66} | {12,17,18} | {12,17,19} | {12,17,20} | {12,17,21} |
| {12,17,22} | {12,17,23} | {12,17,24} | {12,17,25} | {12,17,26} | {12,17,27} | {12,17,28} | {12,17,29} | {12,17,30} |
| {12,17,31} | {12,17,32} | {12,17,33} | {12,17,34} | {12,17,35} | {12,17,36} | {12,17,37} | {12,17,38} | {12,17,39} |
| {12,17,40} | {12,17,41} | {12,17,42} | {12,17,43} | {12,17,44} | {12,17,45} | {12,17,46} | {12,17,47} | {12,17,48} |
| {12,17,49} | {12,17,50} | {12,17,51} | {12,17,52} | {12,17,53} | {12,17,54} | {12,17,55} | {12,17,56} | {12,17,57} |
| {12,17,58} | {12,17,59} | {12,17,60} | {12,17,61} | {12,17,62} | {12,17,63} | {12,17,64} | {12,17,65} | {12,17,66} |
| {12,18,19} | {12,18,20} | {12,18,21} | {12,18,22} | {12,18,23} | {12,18,24} | {12,18,25} | {12,18,26} | {12,18,27} |
| {12,18,28} | {12,18,29} | {12,18,30} | {12,18,31} | {12,18,32} | {12,18,33} | {12,18,34} | {12,18,35} | {12,18,36} |
| {12,18,37} | {12,18,38} | {12,18,39} | {12,18,40} | {12,18,41} | {12,18,42} | {12,18,43} | {12,18,44} | {12,18,45} |
| {12,18,46} | {12,18,47} | {12,18,48} | {12,18,49} | {12,18,50} | {12,18,51} | {12,18,52} | {12,18,53} | {12,18,54} |
| {12,18,55} | {12,18,56} | {12,18,57} | {12,18,58} | {12,18,59} | {12,18,60} | {12,18,61} | {12,18,62} | {12,18,63} |
| {12,18,64} | {12,18,65} | {12,18,66} | {12,19,20} | {12,19,21} | {12,19,22} | {12,19,23} | {12,19,24} | {12,19,25} |
| {12,19,26} | {12,19,27} | {12,19,28} | {12,19,29} | {12,19,30} | {12,19,31} | {12,19,32} | {12,19,33} | {12,19,34} |
| {12,19,35} | {12,19,36} | {12,19,37} | {12,19,38} | {12,19,39} | {12,19,40} | {12,19,41} | {12,19,42} | {12,19,43} |
| {12,19,44} | {12,19,45} | {12,19,46} | {12,19,47} | {12,19,48} | {12,19,49} | {12,19,50} | {12,19,51} | {12,19,52} |
| {12,19,53} | {12,19,54} | {12,19,55} | {12,19,56} | {12,19,57} | {12,19,58} | {12,19,59} | {12,19,60} | {12,19,61} |
| {12,19,62} | {12,19,63} | {12,19,64} | {12,19,65} | {12,19,66} | {12,20,21} | {12,20,22} | {12,20,23} | {12,20,24} |
| {12,20,25} | {12,20,26} | {12,20,27} | {12,20,28} | {12,20,29} | {12,20,30} | {12,20,31} | {12,20,32} | {12,20,33} |
| {12,20,34} | {12,20,35} | {12,20,36} | {12,20,37} | {12,20,38} | {12,20,39} | {12,20,40} | {12,20,41} | {12,20,42} |
| {12,20,43} | {12,20,44} | {12,20,45} | {12,20,46} | {12,20,47} | {12,20,48} | {12,20,49} | {12,20,50} | {12,20,51} |
| {12,20,52} | {12,20,53} | {12,20,54} | {12,20,55} | {12,20,56} | {12,20,57} | {12,20,58} | {12,20,59} | {12,20,60} |
| {12,20,61} | {12,20,62} | {12,20,63} | {12,20,64} | {12,20,65} | {12,20,66} | {12,21,22} | {12,21,23} | {12,21,24} |
| {12,21,25} | {12,21,26} | {12,21,27} | {12,21,28} | {12,21,29} | {12,21,30} | {12,21,31} | {12,21,32} | {12,21,33} |
| {12,21,34} | {12,21,35} | {12,21,36} | {12,21,37} | {12,21,38} | {12,21,39} | {12,21,40} | {12,21,41} | {12,21,42} |
| {12,21,43} | {12,21,44} | {12,21,45} | {12,21,46} | {12,21,47} | {12,21,48} | {12,21,49} | {12,21,50} | {12,21,51} |
| {12,21,52} | {12,21,53} | {12,21,54} | {12,21,55} | {12,21,56} | {12,21,57} | {12,21,58} | {12,21,59} | {12,21,60} |
| {12,21,61} | {12,21,62} | {12,21,63} | {12,21,64} | {12,21,65} | {12,21,66} | {12,22,23} | {12,22,24} | {12,22,25} |
| {12,22,26} | {12,22,27} | {12,22,28} | {12,22,29} | {12,22,30} | {12,22,31} | {12,22,32} | {12,22,33} | {12,22,34} |
| {12,22,35} | {12,22,36} | {12,22,37} | {12,22,38} | {12,22,39} | {12,22,40} | {12,22,41} | {12,22,42} | {12,22,43} |
| {12,22,44} | {12,22,45} | {12,22,46} | {12,22,47} | {12,22,48} | {12,22,49} | {12,22,50} | {12,22,51} | {12,22,52} |
| {12,22,53} | {12,22,54} | {12,22,55} | {12,22,56} | {12,22,57} | {12,22,58} | {12,22,59} | {12,22,60} | {12,22,61} |
| {12,22,62} | {12,22,63} | {12,22,64} | {12,22,65} | {12,22,66} | {12,23,24} | {12,23,25} | {12,23,26} | {12,23,27} |
| {12,23,28} | {12,23,29} | {12,23,30} | {12,23,31} | {12,23,32} | {12,23,33} | {12,23,34} | {12,23,35} | {12,23,36} |
| {12,23,37} | {12,23,38} | {12,23,39} | {12,23,40} | {12,23,41} | {12,23,42} | {12,23,43} | {12,23,44} | {12,23,45} |
| {12,23,46} | {12,23,47} | {12,23,48} | {12,23,49} | {12,23,50} | {12,23,51} | {12,23,52} | {12,23,53} | {12,23,54} |
| {12,23,55} | {12,23,56} | {12,23,57} | {12,23,58} | {12,23,59} | {12,23,60} | {12,23,61} | {12,23,62} | {12,23,63} |
| {12,23,64} | {12,23,65} | {12,23,66} | {12,24,25} | {12,24,26} | {12,24,27} | {12,24,28} | {12,24,29} | {12,24,30} |
| {12,24,31} | {12,24,32} | {12,24,33} | {12,24,34} | {12,24,35} | {12,24,36} | {12,24,37} | {12,24,38} | {12,24,39} |
| {12,24,40} | {12,24,41} | {12,24,42} | {12,24,43} | {12,24,44} | {12,24,45} | {12,24,46} | {12,24,47} | {12,24,48} |
| {12,24,49} | {12,24,50} | {12,24,51} | {12,24,52} | {12,24,53} | {12,24,54} | {12,24,55} | {12,24,56} | {12,24,57} |
| {12,24,58} | {12,24,59} | {12,24,60} | {12,24,61} | {12,24,62} | {12,24,63} | {12,24,64} | {12,24,65} | {12,24,66} |
| {12,25,26} | {12,25,27} | {12,25,28} | {12,25,29} | {12,25,30} | {12,25,31} | {12,25,32} | {12,25,33} | {12,25,34} |
| {12,25,35} | {12,25,36} | {12,25,37} | {12,25,38} | {12,25,39} | {12,25,40} | {12,25,41} | {12,25,42} | {12,25,43} |
| {12,25,44} | {12,25,45} | {12,25,46} | {12,25,47} | {12,25,48} | {12,25,49} | {12,25,50} | {12,25,51} | {12,25,52} |
| {12,25,53} | {12,25,54} | {12,25,55} | {12,25,56} | {12,25,57} | {12,25,58} | {12,25,59} | {12,25,60} | {12,25,61} |
| {12,25,62} | {12,25,63} | {12,25,64} | {12,25,65} | {12,25,66} | {12,26,27} | {12,26,28} | {12,26,29} | {12,26,30} |
| {12,26,31} | {12,26,32} | {12,26,33} | {12,26,34} | {12,26,35} | {12,26,36} | {12,26,37} | {12,26,38} | {12,26,39} |
| {12,26,40} | {12,26,41} | {12,26,42} | {12,26,43} | {12,26,44} | {12,26,45} | {12,26,46} | {12,26,47} | {12,26,48} |
| {12,26,49} | {12,26,50} | {12,26,51} | {12,26,52} | {12,26,53} | {12,26,54} | {12,26,55} | {12,26,56} | {12,26,57} |
| {12,26,58} | {12,26,59} | {12,26,60} | {12,26,61} | {12,26,62} | {12,26,63} | {12,26,64} | {12,26,65} | {12,26,66} |
| {12,27,28} | {12,27,29} | {12,27,30} | {12,27,31} | {12,27,32} | {12,27,33} | {12,27,34} | {12,27,35} | {12,27,36} |
| {12,27,37} | {12,27,38} | {12,27,39} | {12,27,40} | {12,27,41} | {12,27,42} | {12,27,43} | {12,27,44} | {12,27,45} |
| {12,27,46} | {12,27,47} | {12,27,48} | {12,27,49} | {12,27,50} | {12,27,51} | {12,27,52} | {12,27,53} | {12,27,54} |
| {12,27,55} | {12,27,56} | {12,27,57} | {12,27,58} | {12,27,59} | {12,27,60} | {12,27,61} | {12,27,62} | {12,27,63} |
| {12,27,64} | {12,27,65} | {12,27,66} | {12,28,29} | {12,28,30} | {12,28,31} | {12,28,32} | {12,28,33} | {12,28,34} |
| {12,28,35} | {12,28,36} | {12,28,37} | {12,28,38} | {12,28,39} | {12,28,40} | {12,28,41} | {12,28,42} | {12,28,43} |
| {12,28,44} | {12,28,45} | {12,28,46} | {12,28,47} | {12,28,48} | {12,28,49} | {12,28,50} | {12,28,51} | {12,28,52} |
| {12,28,53} | {12,28,54} | {12,28,55} | {12,28,56} | {12,28,57} | {12,28,58} | {12,28,59} | {12,28,60} | {12,28,61} |
| {12,28,62} | {12,28,63} | {12,28,64} | {12,28,65} | {12,28,66} | {12,29,30} | {12,29,31} | {12,29,32} | {12,29,33} |
| {12,29,34} | {12,29,35} | {12,29,36} | {12,29,37} | {12,29,38} | {12,29,39} | {12,29,40} | {12,29,41} | {12,29,42} |
| {12,29,43} | {12,29,44} | {12,29,45} | {12,29,46} | {12,29,47} | {12,29,48} | {12,29,49} | {12,29,50} | {12,29,51} |
| {12,29,52} | {12,29,53} | {12,29,54} | {12,29,55} | {12,29,56} | {12,29,57} | {12,29,58} | {12,29,59} | {12,29,60} |
| {12,29,61} | {12,29,62} | {12,29,63} | {12,29,64} | {12,29,65} | {12,29,66} | {12,30,31} | {12,30,32} | {12,30,33} |
| {12,30,34} | {12,30,35} | {12,30,36} | {12,30,37} | {12,30,38} | {12,30,39} | {12,30,40} | {12,30,41} | {12,30,42} |
| {12,30,43} | {12,30,44} | {12,30,45} | {12,30,46} | {12,30,47} | {12,30,48} | {12,30,49} | {12,30,50} | {12,30,51} |
| {12,30,52} | {12,30,53} | {12,30,54} | {12,30,55} | {12,30,56} | {12,30,57} | {12,30,58} | {12,30,59} | {12,30,60} |
| {12,30,61} | {12,30,62} | {12,30,63} | {12,30,64} | {12,30,65} | {12,30,66} | {12,31,32} | {12,31,33} | {12,31,34} |
| {12,31,35} | {12,31,36} | {12,31,37} | {12,31,38} | {12,31,39} | {12,31,40} | {12,31,41} | {12,31,42} | {12,31,43} |

TABLE 3A-continued

{12,31,44} {12,31,45} {12,31,46} {12,31,47} {12,31,48} {12,31,49} {12,31,50} {12,31,51} {12,31,52}
{12,31,53} {12,31,54} {12,31,55} {12,31,56} {12,31,57} {12,31,58} {12,31,59} {12,31,60} {12,31,61}
{12,31,62} {12,31,63} {12,31,64} {12,31,65} {12,31,66} {12,32,33} {12,32,34} {12,32,35} {12,32,36}
{12,32,37} {12,32,38} {12,32,39} {12,32,40} {12,32,41} {12,32,42} {12,32,43} {12,32,44} {12,32,45}
{12,32,46} {12,32,47} {12,32,48} {12,32,49} {12,32,50} {12,32,51} {12,32,52} {12,32,53} {12,32,54}
{12,32,55} {12,32,56} {12,32,57} {12,32,58} {12,32,59} {12,32,60} {12,32,61} {12,32,62} {12,32,63}
{12,32,64} {12,32,65} {12,32,66} {12,33,34} {12,33,35} {12,33,36} {12,33,37} {12,33,38} {12,33,39}
{12,33,40} {12,33,41} {12,33,42} {12,33,43} {12,33,44} {12,33,45} {12,33,46} {12,33,47} {12,33,48}
{12,33,49} {12,33,50} {12,33,51} {12,33,52} {12,33,53} {12,33,54} {12,33,55} {12,33,56} {12,33,57}
{12,33,58} {12,33,59} {12,33,60} {12,33,61} {12,33,62} {12,33,63} {12,33,64} {12,33,65} {12,33,66}
{12,34,35} {12,34,36} {12,34,37} {12,34,38} {12,34,39} {12,34,40} {12,34,41} {12,34,42} {12,34,43}
{12,34,44} {12,34,45} {12,34,46} {12,34,47} {12,34,48} {12,34,49} {12,34,50} {12,34,51} {12,34,52}
{12,34,53} {12,34,54} {12,34,55} {12,34,56} {12,34,57} {12,34,58} {12,34,59} {12,34,60} {12,34,61}
{12,34,62} {12,34,63} {12,34,64} {12,34,65} {12,34,66} {12,35,36} {12,35,37} {12,35,38} {12,35,39}
{12,35,40} {12,35,41} {12,35,42} {12,35,43} {12,35,44} {12,35,45} {12,35,46} {12,35,47} {12,35,48}
{12,35,49} {12,35,50} {12,35,51} {12,35,52} {12,35,53} {12,35,54} {12,35,55} {12,35,56} {12,35,57}
{12,35,58} {12,35,59} {12,35,60} {12,35,61} {12,35,62} {12,35,63} {12,35,64} {12,35,65} {12,35,66}
{12,36,37} {12,36,38} {12,36,39} {12,36,40} {12,36,41} {12,36,42} {12,36,43} {12,36,44} {12,36,45}
{12,36,46} {12,36,47} {12,36,48} {12,36,49} {12,36,50} {12,36,51} {12,36,52} {12,36,53} {12,36,54}
{12,36,55} {12,36,56} {12,36,57} {12,36,58} {12,36,59} {12,36,60} {12,36,61} {12,36,62} {12,36,63}
{12,36,64} {12,36,65} {12,36,66} {12,37,38} {12,37,39} {12,37,40} {12,37,41} {12,37,42} {12,37,43}
{12,37,44} {12,37,45} {12,37,46} {12,37,47} {12,37,48} {12,37,49} {12,37,50} {12,37,51} {12,37,52}
{12,37,53} {12,37,54} {12,37,55} {12,37,56} {12,37,57} {12,37,58} {12,37,59} {12,37,60} {12,37,61}
{12,37,62} {12,37,63} {12,37,64} {12,37,65} {12,37,66} {12,38,39} {12,38,40} {12,38,41} {12,38,42}
{12,38,43} {12,38,44} {12,38,45} {12,38,46} {12,38,47} {12,38,48} {12,38,49} {12,38,50} {12,38,51}
{12,38,52} {12,38,53} {12,38,54} {12,38,55} {12,38,56} {12,38,57} {12,38,58} {12,38,59} {12,38,60}
{12,38,61} {12,38,62} {12,38,63} {12,38,64} {12,38,65} {12,38,66} {12,39,40} {12,39,41} {12,39,42}
{12,39,43} {12,39,44} {12,39,45} {12,39,46} {12,39,47} {12,39,48} {12,39,49} {12,39,50} {12,39,51}
{12,39,52} {12,39,53} {12,39,54} {12,39,55} {12,39,56} {12,39,57} {12,39,58} {12,39,59} {12,39,60}
{12,39,61} {12,39,62} {12,39,63} {12,39,64} {12,39,65} {12,39,66} {12,40,41} {12,40,42} {12,40,43}
{12,40,44} {12,40,45} {12,40,46} {12,40,47} {12,40,48} {12,40,49} {12,40,50} {12,40,51} {12,40,52}
{12,40,53} {12,40,54} {12,40,55} {12,40,56} {12,40,57} {12,40,58} {12,40,59} {12,40,60} {12,40,61}
{12,40,62} {12,40,63} {12,40,64} {12,40,65} {12,40,66} {12,41,42} {12,41,43} {12,41,44} {12,41,45}
{12,41,46} {12,41,47} {12,41,48} {12,41,49} {12,41,50} {12,41,51} {12,41,52} {12,41,53} {12,41,54}
{12,41,55} {12,41,56} {12,41,57} {12,41,58} {12,41,59} {12,41,60} {12,41,61} {12,41,62} {12,41,63}
{12,41,64} {12,41,65} {12,41,66} {12,42,43} {12,42,44} {12,42,45} {12,42,46} {12,42,47} {12,42,48}
{12,42,49} {12,42,50} {12,42,51} {12,42,52} {12,42,53} {12,42,54} {12,42,55} {12,42,56} {12,42,57}
{12,42,58} {12,42,59} {12,42,60} {12,42,61} {12,42,62} {12,42,63} {12,42,64} {12,42,65} {12,42,66}
{12,43,44} {12,43,45} {12,43,46} {12,43,47} {12,43,48} {12,43,49} {12,43,50} {12,43,51} {12,43,52}
{12,43,53} {12,43,54} {12,43,55} {12,43,56} {12,43,57} {12,43,58} {12,43,59} {12,43,60} {12,43,61}
{12,43,62} {12,43,63} {12,43,64} {12,43,65} {12,43,66} {12,44,45} {12,44,46} {12,44,47} {12,44,48}
{12,44,49} {12,44,50} {12,44,51} {12,44,52} {12,44,53} {12,44,54} {12,44,55} {12,44,56} {12,44,57}
{12,44,58} {12,44,59} {12,44,60} {12,44,61} {12,44,62} {12,44,63} {12,44,64} {12,44,65} {12,44,66}
{12,45,46} {12,45,47} {12,45,48} {12,45,49} {12,45,50} {12,45,51} {12,45,52} {12,45,53} {12,45,54}
{12,45,55} {12,45,56} {12,45,57} {12,45,58} {12,45,59} {12,45,60} {12,45,61} {12,45,62} {12,45,63}
{12,45,64} {12,45,65} {12,45,66} {12,46,47} {12,46,48} {12,46,49} {12,46,50} {12,46,51} {12,46,52}
{12,46,53} {12,46,54} {12,46,55} {12,46,56} {12,46,57} {12,46,58} {12,46,59} {12,46,60} {12,46,61}
{12,46,62} {12,46,63} {12,46,64} {12,46,65} {12,46,66} {12,47,48} {12,47,49} {12,47,50} {12,47,51}
{12,47,52} {12,47,53} {12,47,54} {12,47,55} {12,47,56} {12,47,57} {12,47,58} {12,47,59} {12,47,60}
{12,47,61} {12,47,62} {12,47,63} {12,47,64} {12,47,65} {12,47,66} {12,48,49} {12,48,50} {12,48,51}
{12,48,52} {12,48,53} {12,48,54} {12,48,55} {12,48,56} {12,48,57} {12,48,58} {12,48,59} {12,48,60}
{12,48,61} {12,48,62} {12,48,63} {12,48,64} {12,48,65} {12,48,66} {12,49,50} {12,49,51} {12,49,52}
{12,49,53} {12,49,54} {12,49,55} {12,49,56} {12,49,57} {12,49,58} {12,49,59} {12,49,60} {12,49,61}
{12,49,62} {12,49,63} {12,49,64} {12,49,65} {12,49,66} {12,50,51} {12,50,52} {12,50,53} {12,50,54}
{12,50,55} {12,50,56} {12,50,57} {12,50,58} {12,50,59} {12,50,60} {12,50,61} {12,50,62} {12,50,63}
{12,50,64} {12,50,65} {12,50,66} {12,51,52} {12,51,53} {12,51,54} {12,51,55} {12,51,56} {12,51,57}
{12,51,58} {12,51,59} {12,51,60} {12,51,61} {12,51,62} {12,51,63} {12,51,64} {12,51,65} {12,51,66}
{12,52,53} {12,52,54} {12,52,55} {12,52,56} {12,52,57} {12,52,58} {12,52,59} {12,52,60} {12,52,61}
{12,52,62} {12,52,63} {12,52,64} {12,52,65} {12,52,66} {12,53,54} {12,53,55} {12,53,56} {12,53,57}
{12,53,58} {12,53,59} {12,53,60} {12,53,61} {12,53,62} {12,53,63} {12,53,64} {12,53,65} {12,53,66}
{12,54,55} {12,54,56} {12,54,57} {12,54,58} {12,54,59} {12,54,60} {12,54,61} {12,54,62} {12,54,63}
{12,54,64} {12,54,65} {12,54,66} {12,55,56} {12,55,57} {12,55,58} {12,55,59} {12,55,60} {12,55,61}
{12,55,62} {12,55,63} {12,55,64} {12,55,65} {12,55,66} {12,56,57} {12,56,58} {12,56,59} {12,56,60}
{12,56,61} {12,56,62} {12,56,63} {12,56,64} {12,56,65} {12,56,66} {12,57,58} {12,57,59} {12,57,60}
{12,57,61} {12,57,62} {12,57,63} {12,57,64} {12,57,65} {12,57,66} {12,58,59} {12,58,60} {12,58,61}
{12,58,62} {12,58,63} {12,58,64} {12,58,65} {12,58,66} {12,59,60} {12,59,61} {12,59,62} {12,59,63}
{12,59,64} {12,59,65} {12,59,66} {12,60,61} {12,60,62} {12,60,63} {12,60,64} {12,60,65} {12,60,66}
{12,61,62} {12,61,63} {12,61,64} {12,61,65} {12,61,66} {12,62,63} {12,62,64} {12,62,65} {12,62,66}
{12,63,64} {12,63,65} {12,63,66} {12,64,65} {12,64,66} {12,65,66} {13,14,15} {13,14,16} {13,14,17}
{13,14,18} {13,14,19} {13,14,20} {13,14,21} {13,14,22} {13,14,23} {13,14,24} {13,14,25} {13,14,26}
{13,14,27} {13,14,28} {13,14,29} {13,14,30} {13,14,31} {13,14,32} {13,14,33} {13,14,34} {13,14,35}
{13,14,36} {13,14,37} {13,14,38} {13,14,39} {13,14,40} {13,14,41} {13,14,42} {13,14,43} {13,14,44}
{13,14,45} {13,14,46} {13,14,47} {13,14,48} {13,14,49} {13,14,50} {13,14,51} {13,14,52} {13,14,53}
{13,14,54} {13,14,55} {13,14,56} {13,14,57} {13,14,58} {13,14,59} {13,14,60} {13,14,61} {13,14,62}
{13,14,63} {13,14,64} {13,14,65} {13,14,66} {13,15,16} {13,15,17} {13,15,18} {13,15,19} {13,15,20}
{13,15,21} {13,15,22} {13,15,23} {13,15,24} {13,15,25} {13,15,26} {13,15,27} {13,15,28} {13,15,29}
{13,15,30} {13,15,31} {13,15,32} {13,15,33} {13,15,34} {13,15,35} {13,15,36} {13,15,37} {13,15,38}
{13,15,39} {13,15,40} {13,15,41} {13,15,42} {13,15,43} {13,15,44} {13,15,45} {13,15,46} {13,15,47}
{13,15,48} {13,15,49} {13,15,50} {13,15,51} {13,15,52} {13,15,53} {13,15,54} {13,15,55} {13,15,56}
{13,15,57} {13,15,58} {13,15,59} {13,15,60} {13,15,61} {13,15,62} {13,15,63} {13,15,64} {13,15,65}

TABLE 3A-continued

| | | | | | | | |
|---|---|---|---|---|---|---|---|
| {13,15,66} | {13,16,17} | {13,16,18} | {13,16,19} | {13,16,20} | {13,16,21} | {13,16,22} | {13,16,23} | {13,16,24} |
| {13,16,25} | {13,16,26} | {13,16,27} | {13,16,28} | {13,16,29} | {13,16,30} | {13,16,31} | {13,16,32} | {13,16,33} |
| {13,16,34} | {13,16,35} | {13,16,36} | {13,16,37} | {13,16,38} | {13,16,39} | {13,16,40} | {13,16,41} | {13,16,42} |
| {13,16,43} | {13,16,44} | {13,16,45} | {13,16,46} | {13,16,47} | {13,16,48} | {13,16,49} | {13,16,50} | {13,16,51} |
| {13,16,52} | {13,16,53} | {13,16,54} | {13,16,55} | {13,16,56} | {13,16,57} | {13,16,58} | {13,16,59} | {13,16,60} |
| {13,16,61} | {13,16,62} | {13,16,63} | {13,16,64} | {13,16,65} | {13,16,66} | {13,17,18} | {13,17,19} | {13,17,20} |
| {13,17,21} | {13,17,22} | {13,17,23} | {13,17,24} | {13,17,25} | {13,17,26} | {13,17,27} | {13,17,28} | {13,17,29} |
| {13,17,30} | {13,17,31} | {13,17,32} | {13,17,33} | {13,17,34} | {13,17,35} | {13,17,36} | {13,17,37} | {13,17,38} |
| {13,17,39} | {13,17,40} | {13,17,41} | {13,17,42} | {13,17,43} | {13,17,44} | {13,17,45} | {13,17,46} | {13,17,47} |
| {13,17,48} | {13,17,49} | {13,17,50} | {13,17,51} | {13,17,52} | {13,17,53} | {13,17,54} | {13,17,55} | {13,17,56} |
| {13,17,57} | {13,17,58} | {13,17,59} | {13,17,60} | {13,17,61} | {13,17,62} | {13,17,63} | {13,17,64} | {13,17,65} |
| {13,17,66} | {13,18,19} | {13,18,20} | {13,18,21} | {13,18,22} | {13,18,23} | {13,18,24} | {13,18,25} | {13,18,26} |
| {13,18,27} | {13,18,28} | {13,18,29} | {13,18,30} | {13,18,31} | {13,18,32} | {13,18,33} | {13,18,34} | {13,18,35} |
| {13,18,36} | {13,18,37} | {13,18,38} | {13,18,39} | {13,18,40} | {13,18,41} | {13,18,42} | {13,18,43} | {13,18,44} |
| {13,18,45} | {13,18,46} | {13,18,47} | {13,18,48} | {13,18,49} | {13,18,50} | {13,18,51} | {13,18,52} | {13,18,53} |
| {13,18,54} | {13,18,55} | {13,18,56} | {13,18,57} | {13,18,58} | {13,18,59} | {13,18,60} | {13,18,61} | {13,18,62} |
| {13,18,63} | {13,18,64} | {13,18,65} | {13,18,66} | {13,19,20} | {13,19,21} | {13,19,22} | {13,19,23} | {13,19,24} |
| {13,19,25} | {13,19,26} | {13,19,27} | {13,19,28} | {13,19,29} | {13,19,30} | {13,19,31} | {13,19,32} | {13,19,33} |
| {13,19,34} | {13,19,35} | {13,19,36} | {13,19,37} | {13,19,38} | {13,19,39} | {13,19,40} | {13,19,41} | {13,19,42} |
| {13,19,43} | {13,19,44} | {13,19,45} | {13,19,46} | {13,19,47} | {13,19,48} | {13,19,49} | {13,19,50} | {13,19,51} |
| {13,19,52} | {13,19,53} | {13,19,54} | {13,19,55} | {13,19,56} | {13,19,57} | {13,19,58} | {13,19,59} | {13,19,60} |
| {13,19,61} | {13,19,62} | {13,19,63} | {13,19,64} | {13,19,65} | {13,19,66} | {13,20,21} | {13,20,22} | {13,20,23} |
| {13,20,24} | {13,20,25} | {13,20,26} | {13,20,27} | {13,20,28} | {13,20,29} | {13,20,30} | {13,20,31} | {13,20,32} |
| {13,20,33} | {13,20,34} | {13,20,35} | {13,20,36} | {13,20,37} | {13,20,38} | {13,20,39} | {13,20,40} | {13,20,41} |
| {13,20,42} | {13,20,43} | {13,20,44} | {13,20,45} | {13,20,46} | {13,20,47} | {13,20,48} | {13,20,49} | {13,20,50} |
| {13,20,51} | {13,20,52} | {13,20,53} | {13,20,54} | {13,20,55} | {13,20,56} | {13,20,57} | {13,20,58} | {13,20,59} |
| {13,20,60} | {13,20,61} | {13,20,62} | {13,20,63} | {13,20,64} | {13,20,65} | {13,20,66} | {13,21,22} | {13,21,23} |
| {13,21,24} | {13,21,25} | {13,21,26} | {13,21,27} | {13,21,28} | {13,21,29} | {13,21,30} | {13,21,31} | {13,21,32} |
| {13,21,33} | {13,21,34} | {13,21,35} | {13,21,36} | {13,21,37} | {13,21,38} | {13,21,39} | {13,21,40} | {13,21,41} |
| {13,21,42} | {13,21,43} | {13,21,44} | {13,21,45} | {13,21,46} | {13,21,47} | {13,21,48} | {13,21,49} | {13,21,50} |
| {13,21,51} | {13,21,52} | {13,21,53} | {13,21,54} | {13,21,55} | {13,21,56} | {13,21,57} | {13,21,58} | {13,21,59} |
| {13,21,60} | {13,21,61} | {13,21,62} | {13,21,63} | {13,21,64} | {13,21,65} | {13,21,66} | {13,22,23} | {13,22,24} |
| {13,22,25} | {13,22,26} | {13,22,27} | {13,22,28} | {13,22,29} | {13,22,30} | {13,22,31} | {13,22,32} | {13,22,33} |
| {13,22,34} | {13,22,35} | {13,22,36} | {13,22,37} | {13,22,38} | {13,22,39} | {13,22,40} | {13,22,41} | {13,22,42} |
| {13,22,43} | {13,22,44} | {13,22,45} | {13,22,46} | {13,22,47} | {13,22,48} | {13,22,49} | {13,22,50} | {13,22,51} |
| {13,22,52} | {13,22,53} | {13,22,54} | {13,22,55} | {13,22,56} | {13,22,57} | {13,22,58} | {13,22,59} | {13,22,60} |
| {13,22,61} | {13,22,62} | {13,22,63} | {13,22,64} | {13,22,65} | {13,22,66} | {13,23,24} | {13,23,25} | {13,23,26} |
| {13,23,27} | {13,23,28} | {13,23,29} | {13,23,30} | {13,23,31} | {13,23,32} | {13,23,33} | {13,23,34} | {13,23,35} |
| {13,23,36} | {13,23,37} | {13,23,38} | {13,23,39} | {13,23,40} | {13,23,41} | {13,23,42} | {13,23,43} | {13,23,44} |
| {13,23,45} | {13,23,46} | {13,23,47} | {13,23,48} | {13,23,49} | {13,23,50} | {13,23,51} | {13,23,52} | {13,23,53} |
| {13,23,54} | {13,23,55} | {13,23,56} | {13,23,57} | {13,23,58} | {13,23,59} | {13,23,60} | {13,23,61} | {13,23,62} |
| {13,23,63} | {13,23,64} | {13,23,65} | {13,23,66} | {13,24,25} | {13,24,26} | {13,24,27} | {13,24,28} | {13,24,29} |
| {13,24,30} | {13,24,31} | {13,24,32} | {13,24,33} | {13,24,34} | {13,24,35} | {13,24,36} | {13,24,37} | {13,24,38} |
| {13,24,39} | {13,24,40} | {13,24,41} | {13,24,42} | {13,24,43} | {13,24,44} | {13,24,45} | {13,24,46} | {13,24,47} |
| {13,24,48} | {13,24,49} | {13,24,50} | {13,24,51} | {13,24,52} | {13,24,53} | {13,24,54} | {13,24,55} | {13,24,56} |
| {13,24,57} | {13,24,58} | {13,24,59} | {13,24,60} | {13,24,61} | {13,24,62} | {13,24,63} | {13,24,64} | {13,24,65} |
| {13,24,66} | {13,25,26} | {13,25,27} | {13,25,28} | {13,25,29} | {13,25,30} | {13,25,31} | {13,25,32} | {13,25,33} |
| {13,25,34} | {13,25,35} | {13,25,36} | {13,25,37} | {13,25,38} | {13,25,39} | {13,25,40} | {13,25,41} | {13,25,42} |
| {13,25,43} | {13,25,44} | {13,25,45} | {13,25,46} | {13,25,47} | {13,25,48} | {13,25,49} | {13,25,50} | {13,25,51} |
| {13,25,52} | {13,25,53} | {13,25,54} | {13,25,55} | {13,25,56} | {13,25,57} | {13,25,58} | {13,25,59} | {13,25,60} |
| {13,25,61} | {13,25,62} | {13,25,63} | {13,25,64} | {13,25,65} | {13,25,66} | {13,26,27} | {13,26,28} | {13,26,29} |
| {13,26,30} | {13,26,31} | {13,26,32} | {13,26,33} | {13,26,34} | {13,26,35} | {13,26,36} | {13,26,37} | {13,26,38} |
| {13,26,39} | {13,26,40} | {13,26,41} | {13,26,42} | {13,26,43} | {13,26,44} | {13,26,45} | {13,26,46} | {13,26,47} |
| {13,26,48} | {13,26,49} | {13,26,50} | {13,26,51} | {13,26,52} | {13,26,53} | {13,26,54} | {13,26,55} | {13,26,56} |
| {13,26,57} | {13,26,58} | {13,26,59} | {13,26,60} | {13,26,61} | {13,26,62} | {13,26,63} | {13,26,64} | {13,26,65} |
| {13,26,66} | {13,27,28} | {13,27,29} | {13,27,30} | {13,27,31} | {13,27,32} | {13,27,33} | {13,27,34} | {13,27,35} |
| {13,27,36} | {13,27,37} | {13,27,38} | {13,27,39} | {13,27,40} | {13,27,41} | {13,27,42} | {13,27,43} | {13,27,44} |
| {13,27,45} | {13,27,46} | {13,27,47} | {13,27,48} | {13,27,49} | {13,27,50} | {13,27,51} | {13,27,52} | {13,27,53} |
| {13,27,54} | {13,27,55} | {13,27,56} | {13,27,57} | {13,27,58} | {13,27,59} | {13,27,60} | {13,27,61} | {13,27,62} |
| {13,27,63} | {13,27,64} | {13,27,65} | {13,27,66} | {13,28,29} | {13,28,30} | {13,28,31} | {13,28,32} | {13,28,33} |
| {13,28,34} | {13,28,35} | {13,28,36} | {13,28,37} | {13,28,38} | {13,28,39} | {13,28,40} | {13,28,41} | {13,28,42} |
| {13,28,43} | {13,28,44} | {13,28,45} | {13,28,46} | {13,28,47} | {13,28,48} | {13,28,49} | {13,28,50} | {13,28,51} |
| {13,28,52} | {13,28,53} | {13,28,54} | {13,28,55} | {13,28,56} | {13,28,57} | {13,28,58} | {13,28,59} | {13,28,60} |
| {13,28,61} | {13,28,62} | {13,28,63} | {13,28,64} | {13,28,65} | {13,28,66} | {13,29,30} | {13,29,31} | {13,29,32} |
| {13,29,33} | {13,29,34} | {13,29,35} | {13,29,36} | {13,29,37} | {13,29,38} | {13,29,39} | {13,29,40} | {13,29,41} |
| {13,29,42} | {13,29,43} | {13,29,44} | {13,29,45} | {13,29,46} | {13,29,47} | {13,29,48} | {13,29,49} | {13,29,50} |
| {13,29,51} | {13,29,52} | {13,29,53} | {13,29,54} | {13,29,55} | {13,29,56} | {13,29,57} | {13,29,58} | {13,29,59} |
| {13,29,60} | {13,29,61} | {13,29,62} | {13,29,63} | {13,29,64} | {13,29,65} | {13,29,66} | {13,30,31} | {13,30,32} |
| {13,30,33} | {13,30,34} | {13,30,35} | {13,30,36} | {13,30,37} | {13,30,38} | {13,30,39} | {13,30,40} | {13,30,41} |
| {13,30,42} | {13,30,43} | {13,30,44} | {13,30,45} | {13,30,46} | {13,30,47} | {13,30,48} | {13,30,49} | {13,30,50} |
| {13,30,51} | {13,30,52} | {13,30,53} | {13,30,54} | {13,30,55} | {13,30,56} | {13,30,57} | {13,30,58} | {13,30,59} |
| {13,30,60} | {13,30,61} | {13,30,62} | {13,30,63} | {13,30,64} | {13,30,65} | {13,30,66} | {13,31,32} | {13,31,33} |
| {13,31,34} | {13,31,35} | {13,31,36} | {13,31,37} | {13,31,38} | {13,31,39} | {13,31,40} | {13,31,41} | {13,31,42} |
| {13,31,43} | {13,31,44} | {13,31,45} | {13,31,46} | {13,31,47} | {13,31,48} | {13,31,49} | {13,31,50} | {13,31,51} |
| {13,31,52} | {13,31,53} | {13,31,54} | {13,31,55} | {13,31,56} | {13,31,57} | {13,31,58} | {13,31,59} | {13,31,60} |
| {13,31,61} | {13,31,62} | {13,31,63} | {13,31,64} | {13,31,65} | {13,31,66} | {13,32,33} | {13,32,34} | {13,32,35} |
| {13,32,36} | {13,32,37} | {13,32,38} | {13,32,39} | {13,32,40} | {13,32,41} | {13,32,42} | {13,32,43} | {13,32,44} |
| {13,32,45} | {13,32,46} | {13,32,47} | {13,32,48} | {13,32,49} | {13,32,50} | {13,32,51} | {13,32,52} | {13,32,53} |
| {13,32,54} | {13,32,55} | {13,32,56} | {13,32,57} | {13,32,58} | {13,32,59} | {13,32,60} | {13,32,61} | {13,32,62} |
| {13,32,63} | {13,32,64} | {13,32,65} | {13,32,66} | {13,33,34} | {13,33,35} | {13,33,36} | {13,33,37} | {13,33,38} |

TABLE 3A-continued

{13,33,39} {13,33,40} {13,33,41} {13,33,42} {13,33,43} {13,33,44} {13,33,45} {13,33,46} {13,33,47}
{13,33,48} {13,33,49} {13,33,50} {13,33,51} {13,33,52} {13,33,53} {13,33,54} {13,33,55} {13,33,56}
{13,33,57} {13,33,58} {13,33,59} {13,33,60} {13,33,61} {13,33,62} {13,33,63} {13,33,64} {13,33,65}
{13,33,66} {13,34,35} {13,34,36} {13,34,37} {13,34,38} {13,34,39} {13,34,40} {13,34,41} {13,34,42}
{13,34,43} {13,34,44} {13,34,45} {13,34,46} {13,34,47} {13,34,48} {13,34,49} {13,34,50} {13,34,51}
{13,34,52} {13,34,53} {13,34,54} {13,34,55} {13,34,56} {13,34,57} {13,34,58} {13,34,59} {13,34,60}
{13,34,61} {13,34,62} {13,34,63} {13,34,64} {13,34,65} {13,34,66} {13,35,36} {13,35,37} {13,35,38}
{13,35,39} {13,35,40} {13,35,41} {13,35,42} {13,35,43} {13,35,44} {13,35,45} {13,35,46} {13,35,47}
{13,35,48} {13,35,49} {13,35,50} {13,35,51} {13,35,52} {13,35,53} {13,35,54} {13,35,55} {13,35,56}
{13,35,57} {13,35,58} {13,35,59} {13,35,60} {13,35,61} {13,35,62} {13,35,63} {13,35,64} {13,35,65}
{13,35,66} {13,36,37} {13,36,38} {13,36,39} {13,36,40} {13,36,41} {13,36,42} {13,36,43} {13,36,44}
{13,36,45} {13,36,46} {13,36,47} {13,36,48} {13,36,49} {13,36,50} {13,36,51} {13,36,52} {13,36,53}
{13,36,54} {13,36,55} {13,36,56} {13,36,57} {13,36,58} {13,36,59} {13,36,60} {13,36,61} {13,36,62}
{13,36,63} {13,36,64} {13,36,65} {13,36,66} {13,37,38} {13,37,39} {13,37,40} {13,37,41} {13,37,42}
{13,37,43} {13,37,44} {13,37,45} {13,37,46} {13,37,47} {13,37,48} {13,37,49} {13,37,50} {13,37,51}
{13,37,52} {13,37,53} {13,37,54} {13,37,55} {13,37,56} {13,37,57} {13,37,58} {13,37,59} {13,37,60}
{13,37,61} {13,37,62} {13,37,63} {13,37,64} {13,37,65} {13,37,66} {13,38,39} {13,38,40} {13,38,41}
{13,38,42} {13,38,43} {13,38,44} {13,38,45} {13,38,46} {13,38,47} {13,38,48} {13,38,49} {13,38,50}
{13,38,51} {13,38,52} {13,38,53} {13,38,54} {13,38,55} {13,38,56} {13,38,57} {13,38,58} {13,38,59}
{13,38,60} {13,38,61} {13,38,62} {13,38,63} {13,38,64} {13,38,65} {13,38,66} {13,39,40} {13,39,41}
{13,39,42} {13,39,43} {13,39,44} {13,39,45} {13,39,46} {13,39,47} {13,39,48} {13,39,49} {13,39,50}
{13,39,51} {13,39,52} {13,39,53} {13,39,54} {13,39,55} {13,39,56} {13,39,57} {13,39,58} {13,39,59}
{13,39,60} {13,39,61} {13,39,62} {13,39,63} {13,39,64} {13,39,65} {13,39,66} {13,40,41} {13,40,42}
{13,40,43} {13,40,44} {13,40,45} {13,40,46} {13,40,47} {13,40,48} {13,40,49} {13,40,50} {13,40,51}
{13,40,52} {13,40,53} {13,40,54} {13,40,55} {13,40,56} {13,40,57} {13,40,58} {13,40,59} {13,40,60}
{13,40,61} {13,40,62} {13,40,63} {13,40,64} {13,40,65} {13,40,66} {13,41,42} {13,41,43} {13,41,44}
{13,41,45} {13,41,46} {13,41,47} {13,41,48} {13,41,49} {13,41,50} {13,41,51} {13,41,52} {13,41,53}
{13,41,54} {13,41,55} {13,41,56} {13,41,57} {13,41,58} {13,41,59} {13,41,60} {13,41,61} {13,41,62}
{13,41,63} {13,41,64} {13,41,65} {13,41,66} {13,42,43} {13,42,44} {13,42,45} {13,42,46} {13,42,47}
{13,42,48} {13,42,49} {13,42,50} {13,42,51} {13,42,52} {13,42,53} {13,42,54} {13,42,55} {13,42,56}
{13,42,57} {13,42,58} {13,42,59} {13,42,60} {13,42,61} {13,42,62} {13,42,63} {13,42,64} {13,42,65}
{13,42,66} {13,43,44} {13,43,45} {13,43,46} {13,43,47} {13,43,48} {13,43,49} {13,43,50} {13,43,51}
{13,43,52} {13,43,53} {13,43,54} {13,43,55} {13,43,56} {13,43,57} {13,43,58} {13,43,59} {13,43,60}
{13,43,61} {13,43,62} {13,43,63} {13,43,64} {13,43,65} {13,43,66} {13,44,45} {13,44,46} {13,44,47}
{13,44,48} {13,44,49} {13,44,50} {13,44,51} {13,44,52} {13,44,53} {13,44,54} {13,44,55} {13,44,56}
{13,44,57} {13,44,58} {13,44,59} {13,44,60} {13,44,61} {13,44,62} {13,44,63} {13,44,64} {13,44,65}
{13,44,66} {13,45,46} {13,45,47} {13,45,48} {13,45,49} {13,45,50} {13,45,51} {13,45,52} {13,45,53}
{13,45,54} {13,45,55} {13,45,56} {13,45,57} {13,45,58} {13,45,59} {13,45,60} {13,45,61} {13,45,62}
{13,45,63} {13,45,64} {13,45,65} {13,45,66} {13,46,47} {13,46,48} {13,46,49} {13,46,50} {13,46,51}
{13,46,52} {13,46,53} {13,46,54} {13,46,55} {13,46,56} {13,46,57} {13,46,58} {13,46,59} {13,46,60}
{13,46,61} {13,46,62} {13,46,63} {13,46,64} {13,46,65} {13,46,66} {13,47,48} {13,47,49} {13,47,50}
{13,47,51} {13,47,52} {13,47,53} {13,47,54} {13,47,55} {13,47,56} {13,47,57} {13,47,58} {13,47,59}
{13,47,60} {13,47,61} {13,47,62} {13,47,63} {13,47,64} {13,47,65} {13,47,66} {13,48,49} {13,48,50}
{13,48,51} {13,48,52} {13,48,53} {13,48,54} {13,48,55} {13,48,56} {13,48,57} {13,48,58} {13,48,59}
{13,48,60} {13,48,61} {13,48,62} {13,48,63} {13,48,64} {13,48,65} {13,48,66} {13,49,50} {13,49,51}
{13,49,52} {13,49,53} {13,49,54} {13,49,55} {13,49,56} {13,49,57} {13,49,58} {13,49,59} {13,49,60}
{13,49,61} {13,49,62} {13,49,63} {13,49,64} {13,49,65} {13,49,66} {13,50,51} {13,50,52} {13,50,53}
{13,50,54} {13,50,55} {13,50,56} {13,50,57} {13,50,58} {13,50,59} {13,50,60} {13,50,61} {13,50,62}
{13,50,63} {13,50,64} {13,50,65} {13,50,66} {13,51,52} {13,51,53} {13,51,54} {13,51,55} {13,51,56}
{13,51,57} {13,51,58} {13,51,59} {13,51,60} {13,51,61} {13,51,62} {13,51,63} {13,51,64} {13,51,65}
{13,51,66} {13,52,53} {13,52,54} {13,52,55} {13,52,56} {13,52,57} {13,52,58} {13,52,59} {13,52,60}
{13,52,61} {13,52,62} {13,52,63} {13,52,64} {13,52,65} {13,52,66} {13,53,54} {13,53,55} {13,53,56}
{13,53,57} {13,53,58} {13,53,59} {13,53,60} {13,53,61} {13,53,62} {13,53,63} {13,53,64} {13,53,65}
{13,53,66} {13,54,55} {13,54,56} {13,54,57} {13,54,58} {13,54,59} {13,54,60} {13,54,61} {13,54,62}
{13,54,63} {13,54,64} {13,54,65} {13,54,66} {13,55,56} {13,55,57} {13,55,58} {13,55,59} {13,55,60}
{13,55,61} {13,55,62} {13,55,63} {13,55,64} {13,55,65} {13,55,66} {13,56,57} {13,56,58} {13,56,59}
{13,56,60} {13,56,61} {13,56,62} {13,56,63} {13,56,64} {13,56,65} {13,56,66} {13,57,58} {13,57,59}
{13,57,60} {13,57,61} {13,57,62} {13,57,63} {13,57,64} {13,57,65} {13,57,66} {13,58,59} {13,58,60}
{13,58,61} {13,58,62} {13,58,63} {13,58,64} {13,58,65} {13,58,66} {13,59,60} {13,59,61} {13,59,62}
{13,59,63} {13,59,64} {13,59,65} {13,59,66} {13,60,61} {13,60,62} {13,60,63} {13,60,64} {13,60,65}
{13,60,66} {13,61,62} {13,61,63} {13,61,64} {13,61,65} {13,61,66} {13,62,63} {13,62,64} {13,62,65}
{13,62,66} {13,63,64} {13,63,65} {13,63,66} {13,64,65} {13,64,66} {13,65,66} {14,15,16} {14,15,17}
{14,15,18} {14,15,19} {14,15,20} {14,15,21} {14,15,22} {14,15,23} {14,15,24} {14,15,25} {14,15,26}
{14,15,27} {14,15,28} {14,15,29} {14,15,30} {14,15,31} {14,15,32} {14,15,33} {14,15,34} {14,15,35}
{14,15,36} {14,15,37} {14,15,38} {14,15,39} {14,15,40} {14,15,41} {14,15,42} {14,15,43} {14,15,44}
{14,15,45} {14,15,46} {14,15,47} {14,15,48} {14,15,49} {14,15,50} {14,15,51} {14,15,52} {14,15,53}
{14,15,54} {14,15,55} {14,15,56} {14,15,57} {14,15,58} {14,15,59} {14,15,60} {14,15,61} {14,15,62}
{14,15,63} {14,15,64} {14,15,65} {14,15,66} {14,16,17} {14,16,18} {14,16,19} {14,16,20} {14,16,21}
{14,16,22} {14,16,23} {14,16,24} {14,16,25} {14,16,26} {14,16,27} {14,16,28} {14,16,29} {14,16,30}
{14,16,31} {14,16,32} {14,16,33} {14,16,34} {14,16,35} {14,16,36} {14,16,37} {14,16,38} {14,16,39}
{14,16,40} {14,16,41} {14,16,42} {14,16,43} {14,16,44} {14,16,45} {14,16,46} {14,16,47} {14,16,48}
{14,16,49} {14,16,50} {14,16,51} {14,16,52} {14,16,53} {14,16,54} {14,16,55} {14,16,56} {14,16,57}
{14,16,58} {14,16,59} {14,16,60} {14,16,61} {14,16,62} {14,16,63} {14,16,64} {14,16,65} {14,16,66}
{14,17,18} {14,17,19} {14,17,20} {14,17,21} {14,17,22} {14,17,23} {14,17,24} {14,17,25} {14,17,26}
{14,17,27} {14,17,28} {14,17,29} {14,17,30} {14,17,31} {14,17,32} {14,17,33} {14,17,34} {14,17,35}
{14,17,36} {14,17,37} {14,17,38} {14,17,39} {14,17,40} {14,17,41} {14,17,42} {14,17,43} {14,17,44}
{14,17,45} {14,17,46} {14,17,47} {14,17,48} {14,17,49} {14,17,50} {14,17,51} {14,17,52} {14,17,53}
{14,17,54} {14,17,55} {14,17,56} {14,17,57} {14,17,58} {14,17,59} {14,17,60} {14,17,61} {14,17,62}
{14,17,63} {14,17,64} {14,17,65} {14,17,66} {14,18,19} {14,18,20} {14,18,21} {14,18,22} {14,18,23}
{14,18,24} {14,18,25} {14,18,26} {14,18,27} {14,18,28} {14,18,29} {14,18,30} {14,18,31} {14,18,32}

TABLE 3A-continued

| | | | | | | | |
|---|---|---|---|---|---|---|---|
| {14,18,33} | {14,18,34} | {14,18,35} | {14,18,36} | {14,18,37} | {14,18,38} | {14,18,39} | {14,18,40} | {14,18,41} |
| {14,18,42} | {14,18,43} | {14,18,44} | {14,18,45} | {14,18,46} | {14,18,47} | {14,18,48} | {14,18,49} | {14,18,50} |
| {14,18,51} | {14,18,52} | {14,18,53} | {14,18,54} | {14,18,55} | {14,18,56} | {14,18,57} | {14,18,58} | {14,18,59} |
| {14,18,60} | {14,18,61} | {14,18,62} | {14,18,63} | {14,18,64} | {14,18,65} | {14,18,66} | {14,19,20} | {14,19,21} |
| {14,19,22} | {14,19,23} | {14,19,24} | {14,19,25} | {14,19,26} | {14,19,27} | {14,19,28} | {14,19,29} | {14,19,30} |
| {14,19,31} | {14,19,32} | {14,19,33} | {14,19,34} | {14,19,35} | {14,19,36} | {14,19,37} | {14,19,38} | {14,19,39} |
| {14,19,40} | {14,19,41} | {14,19,42} | {14,19,43} | {14,19,44} | {14,19,45} | {14,19,46} | {14,19,47} | {14,19,48} |
| {14,19,49} | {14,19,50} | {14,19,51} | {14,19,52} | {14,19,53} | {14,19,54} | {14,19,55} | {14,19,56} | {14,19,57} |
| {14,19,58} | {14,19,59} | {14,19,60} | {14,19,61} | {14,19,62} | {14,19,63} | {14,19,64} | {14,19,65} | {14,19,66} |
| {14,20,21} | {14,20,22} | {14,20,23} | {14,20,24} | {14,20,25} | {14,20,26} | {14,20,27} | {14,20,28} | {14,20,29} |
| {14,20,30} | {14,20,31} | {14,20,32} | {14,20,33} | {14,20,34} | {14,20,35} | {14,20,36} | {14,20,37} | {14,20,38} |
| {14,20,39} | {14,20,40} | {14,20,41} | {14,20,42} | {14,20,43} | {14,20,44} | {14,20,45} | {14,20,46} | {14,20,47} |
| {14,20,48} | {14,20,49} | {14,20,50} | {14,20,51} | {14,20,52} | {14,20,53} | {14,20,54} | {14,20,55} | {14,20,56} |
| {14,20,57} | {14,20,58} | {14,20,59} | {14,20,60} | {14,20,61} | {14,20,62} | {14,20,63} | {14,20,64} | {14,20,65} |
| {14,20,66} | {14,21,22} | {14,21,23} | {14,21,24} | {14,21,25} | {14,21,26} | {14,21,27} | {14,21,28} | {14,21,29} |
| {14,21,30} | {14,21,31} | {14,21,32} | {14,21,33} | {14,21,34} | {14,21,35} | {14,21,36} | {14,21,37} | {14,21,38} |
| {14,21,39} | {14,21,40} | {14,21,41} | {14,21,42} | {14,21,43} | {14,21,44} | {14,21,45} | {14,21,46} | {14,21,47} |
| {14,21,48} | {14,21,49} | {14,21,50} | {14,21,51} | {14,21,52} | {14,21,53} | {14,21,54} | {14,21,55} | {14,21,56} |
| {14,21,57} | {14,21,58} | {14,21,59} | {14,21,60} | {14,21,61} | {14,21,62} | {14,21,63} | {14,21,64} | {14,21,65} |
| {14,21,66} | {14,22,23} | {14,22,24} | {14,22,25} | {14,22,26} | {14,22,27} | {14,22,28} | {14,22,29} | {14,22,30} |
| {14,22,31} | {14,22,32} | {14,22,33} | {14,22,34} | {14,22,35} | {14,22,36} | {14,22,37} | {14,22,38} | {14,22,39} |
| {14,22,40} | {14,22,41} | {14,22,42} | {14,22,43} | {14,22,44} | {14,22,45} | {14,22,46} | {14,22,47} | {14,22,48} |
| {14,22,49} | {14,22,50} | {14,22,51} | {14,22,52} | {14,22,53} | {14,22,54} | {14,22,55} | {14,22,56} | {14,22,57} |
| {14,22,58} | {14,22,59} | {14,22,60} | {14,22,61} | {14,22,62} | {14,22,63} | {14,22,64} | {14,22,65} | {14,22,66} |
| {14,23,24} | {14,23,25} | {14,23,26} | {14,23,27} | {14,23,28} | {14,23,29} | {14,23,30} | {14,23,31} | {14,23,32} |
| {14,23,33} | {14,23,34} | {14,23,35} | {14,23,36} | {14,23,37} | {14,23,38} | {14,23,39} | {14,23,40} | {14,23,41} |
| {14,23,42} | {14,23,43} | {14,23,44} | {14,23,45} | {14,23,46} | {14,23,47} | {14,23,48} | {14,23,49} | {14,23,50} |
| {14,23,51} | {14,23,52} | {14,23,53} | {14,23,54} | {14,23,55} | {14,23,56} | {14,23,57} | {14,23,58} | {14,23,59} |
| {14,23,60} | {14,23,61} | {14,23,62} | {14,23,63} | {14,23,64} | {14,23,65} | {14,23,66} | {14,24,25} | {14,24,26} |
| {14,24,27} | {14,24,28} | {14,24,29} | {14,24,30} | {14,24,31} | {14,24,32} | {14,24,33} | {14,24,34} | {14,24,35} |
| {14,24,36} | {14,24,37} | {14,24,38} | {14,24,39} | {14,24,40} | {14,24,41} | {14,24,42} | {14,24,43} | {14,24,44} |
| {14,24,45} | {14,24,46} | {14,24,47} | {14,24,48} | {14,24,49} | {14,24,50} | {14,24,51} | {14,24,52} | {14,24,53} |
| {14,24,54} | {14,24,55} | {14,24,56} | {14,24,57} | {14,24,58} | {14,24,59} | {14,24,60} | {14,24,61} | {14,24,62} |
| {14,24,63} | {14,24,64} | {14,24,65} | {14,24,66} | {14,25,26} | {14,25,27} | {14,25,28} | {14,25,29} | {14,25,30} |
| {14,25,31} | {14,25,32} | {14,25,33} | {14,25,34} | {14,25,35} | {14,25,36} | {14,25,37} | {14,25,38} | {14,25,39} |
| {14,25,40} | {14,25,41} | {14,25,42} | {14,25,43} | {14,25,44} | {14,25,45} | {14,25,46} | {14,25,47} | {14,25,48} |
| {14,25,49} | {14,25,50} | {14,25,51} | {14,25,52} | {14,25,53} | {14,25,54} | {14,25,55} | {14,25,56} | {14,25,57} |
| {14,25,58} | {14,25,59} | {14,25,60} | {14,25,61} | {14,25,62} | {14,25,63} | {14,25,64} | {14,25,65} | {14,25,66} |
| {14,26,27} | {14,26,28} | {14,26,29} | {14,26,30} | {14,26,31} | {14,26,32} | {14,26,33} | {14,26,34} | {14,26,35} |
| {14,26,36} | {14,26,37} | {14,26,38} | {14,26,39} | {14,26,40} | {14,26,41} | {14,26,42} | {14,26,43} | {14,26,44} |
| {14,26,45} | {14,26,46} | {14,26,47} | {14,26,48} | {14,26,49} | {14,26,50} | {14,26,51} | {14,26,52} | {14,26,53} |
| {14,26,54} | {14,26,55} | {14,26,56} | {14,26,57} | {14,26,58} | {14,26,59} | {14,26,60} | {14,26,61} | {14,26,62} |
| {14,26,63} | {14,26,64} | {14,26,65} | {14,26,66} | {14,27,28} | {14,27,29} | {14,27,30} | {14,27,31} | {14,27,32} |
| {14,27,33} | {14,27,34} | {14,27,35} | {14,27,36} | {14,27,37} | {14,27,38} | {14,27,39} | {14,27,40} | {14,27,41} |
| {14,27,42} | {14,27,43} | {14,27,44} | {14,27,45} | {14,27,46} | {14,27,47} | {14,27,48} | {14,27,49} | {14,27,50} |
| {14,27,51} | {14,27,52} | {14,27,53} | {14,27,54} | {14,27,55} | {14,27,56} | {14,27,57} | {14,27,58} | {14,27,59} |
| {14,27,60} | {14,27,61} | {14,27,62} | {14,27,63} | {14,27,64} | {14,27,65} | {14,27,66} | {14,28,29} | {14,28,30} |
| {14,28,31} | {14,28,32} | {14,28,33} | {14,28,34} | {14,28,35} | {14,28,36} | {14,28,37} | {14,28,38} | {14,28,39} |
| {14,28,40} | {14,28,41} | {14,28,42} | {14,28,43} | {14,28,44} | {14,28,45} | {14,28,46} | {14,28,47} | {14,28,48} |
| {14,28,49} | {14,28,50} | {14,28,51} | {14,28,52} | {14,28,53} | {14,28,54} | {14,28,55} | {14,28,56} | {14,28,57} |
| {14,28,58} | {14,28,59} | {14,28,60} | {14,28,61} | {14,28,62} | {14,28,63} | {14,28,64} | {14,28,65} | {14,28,66} |
| {14,29,30} | {14,29,31} | {14,29,32} | {14,29,33} | {14,29,34} | {14,29,35} | {14,29,36} | {14,29,37} | {14,29,38} |
| {14,29,39} | {14,29,40} | {14,29,41} | {14,29,42} | {14,29,43} | {14,29,44} | {14,29,45} | {14,29,46} | {14,29,47} |
| {14,29,48} | {14,29,49} | {14,29,50} | {14,29,51} | {14,29,52} | {14,29,53} | {14,29,54} | {14,29,55} | {14,29,56} |
| {14,29,57} | {14,29,58} | {14,29,59} | {14,29,60} | {14,29,61} | {14,29,62} | {14,29,63} | {14,29,64} | {14,29,65} |
| {14,29,66} | {14,30,31} | {14,30,32} | {14,30,33} | {14,30,34} | {14,30,35} | {14,30,36} | {14,30,37} | {14,30,38} |
| {14,30,39} | {14,30,40} | {14,30,41} | {14,30,42} | {14,30,43} | {14,30,44} | {14,30,45} | {14,30,46} | {14,30,47} |
| {14,30,48} | {14,30,49} | {14,30,50} | {14,30,51} | {14,30,52} | {14,30,53} | {14,30,54} | {14,30,55} | {14,30,56} |
| {14,30,57} | {14,30,58} | {14,30,59} | {14,30,60} | {14,30,61} | {14,30,62} | {14,30,63} | {14,30,64} | {14,30,65} |
| {14,30,66} | {14,31,32} | {14,31,33} | {14,31,34} | {14,31,35} | {14,31,36} | {14,31,37} | {14,31,38} | {14,31,39} |
| {14,31,40} | {14,31,41} | {14,31,42} | {14,31,43} | {14,31,44} | {14,31,45} | {14,31,46} | {14,31,47} | {14,31,48} |
| {14,31,49} | {14,31,50} | {14,31,51} | {14,31,52} | {14,31,53} | {14,31,54} | {14,31,55} | {14,31,56} | {14,31,57} |
| {14,31,58} | {14,31,59} | {14,31,60} | {14,31,61} | {14,31,62} | {14,31,63} | {14,31,64} | {14,31,65} | {14,31,66} |
| {14,32,33} | {14,32,34} | {14,32,35} | {14,32,36} | {14,32,37} | {14,32,38} | {14,32,39} | {14,32,40} | {14,32,41} |
| {14,32,42} | {14,32,43} | {14,32,44} | {14,32,45} | {14,32,46} | {14,32,47} | {14,32,48} | {14,32,49} | {14,32,50} |
| {14,32,51} | {14,32,52} | {14,32,53} | {14,32,54} | {14,32,55} | {14,32,56} | {14,32,57} | {14,32,58} | {14,32,59} |
| {14,32,60} | {14,32,61} | {14,32,62} | {14,32,63} | {14,32,64} | {14,32,65} | {14,32,66} | {14,33,34} | {14,33,35} |
| {14,33,36} | {14,33,37} | {14,33,38} | {14,33,39} | {14,33,40} | {14,33,41} | {14,33,42} | {14,33,43} | {14,33,44} |
| {14,33,45} | {14,33,46} | {14,33,47} | {14,33,48} | {14,33,49} | {14,33,50} | {14,33,51} | {14,33,52} | {14,33,53} |
| {14,33,54} | {14,33,55} | {14,33,56} | {14,33,57} | {14,33,58} | {14,33,59} | {14,33,60} | {14,33,61} | {14,33,62} |
| {14,33,63} | {14,33,64} | {14,33,65} | {14,33,66} | {14,34,35} | {14,34,36} | {14,34,37} | {14,34,38} | {14,34,39} |
| {14,34,40} | {14,34,41} | {14,34,42} | {14,34,43} | {14,34,44} | {14,34,45} | {14,34,46} | {14,34,47} | {14,34,48} |
| {14,34,49} | {14,34,50} | {14,34,51} | {14,34,52} | {14,34,53} | {14,34,54} | {14,34,55} | {14,34,56} | {14,34,57} |
| {14,34,58} | {14,34,59} | {14,34,60} | {14,34,61} | {14,34,62} | {14,34,63} | {14,34,64} | {14,34,65} | {14,34,66} |
| {14,35,36} | {14,35,37} | {14,35,38} | {14,35,39} | {14,35,40} | {14,35,41} | {14,35,42} | {14,35,43} | {14,35,44} |
| {14,35,45} | {14,35,46} | {14,35,47} | {14,35,48} | {14,35,49} | {14,35,50} | {14,35,51} | {14,35,52} | {14,35,53} |
| {14,35,54} | {14,35,55} | {14,35,56} | {14,35,57} | {14,35,58} | {14,35,59} | {14,35,60} | {14,35,61} | {14,35,62} |
| {14,35,63} | {14,35,64} | {14,35,65} | {14,35,66} | {14,36,37} | {14,36,38} | {14,36,39} | {14,36,40} | {14,36,41} |
| {14,36,42} | {14,36,43} | {14,36,44} | {14,36,45} | {14,36,46} | {14,36,47} | {14,36,48} | {14,36,49} | {14,36,50} |
| {14,36,51} | {14,36,52} | {14,36,53} | {14,36,54} | {14,36,55} | {14,36,56} | {14,36,57} | {14,36,58} | {14,36,59} |

TABLE 3A-continued

{14,36,60} {14,36,61} {14,36,62} {14,36,63} {14,36,64} {14,36,65} {14,36,66} {14,37,38} {14,37,39}
{14,37,40} {14,37,41} {14,37,42} {14,37,43} {14,37,44} {14,37,45} {14,37,46} {14,37,47} {14,37,48}
{14,37,49} {14,37,50} {14,37,51} {14,37,52} {14,37,53} {14,37,54} {14,37,55} {14,37,56} {14,37,57}
{14,37,58} {14,37,59} {14,37,60} {14,37,61} {14,37,62} {14,37,63} {14,37,64} {14,37,65} {14,37,66}
{14,38,39} {14,38,40} {14,38,41} {14,38,42} {14,38,43} {14,38,44} {14,38,45} {14,38,46} {14,38,47}
{14,38,48} {14,38,49} {14,38,50} {14,38,51} {14,38,52} {14,38,53} {14,38,54} {14,38,55} {14,38,56}
{14,38,57} {14,38,58} {14,38,59} {14,38,60} {14,38,61} {14,38,62} {14,38,63} {14,38,64} {14,38,65}
{14,38,66} {14,39,40} {14,39,41} {14,39,42} {14,39,43} {14,39,44} {14,39,45} {14,39,46} {14,39,47}
{14,39,48} {14,39,49} {14,39,50} {14,39,51} {14,39,52} {14,39,53} {14,39,54} {14,39,55} {14,39,56}
{14,39,57} {14,39,58} {14,39,59} {14,39,60} {14,39,61} {14,39,62} {14,39,63} {14,39,64} {14,39,65}
{14,39,66} {14,40,41} {14,40,42} {14,40,43} {14,40,44} {14,40,45} {14,40,46} {14,40,47} {14,40,48}
{14,40,49} {14,40,50} {14,40,51} {14,40,52} {14,40,53} {14,40,54} {14,40,55} {14,40,56} {14,40,57}
{14,40,58} {14,40,59} {14,40,60} {14,40,61} {14,40,62} {14,40,63} {14,40,64} {14,40,65} {14,40,66}
{14,41,42} {14,41,43} {14,41,44} {14,41,45} {14,41,46} {14,41,47} {14,41,48} {14,41,49} {14,41,50}
{14,41,51} {14,41,52} {14,41,53} {14,41,54} {14,41,55} {14,41,56} {14,41,57} {14,41,58} {14,41,59}
{14,41,60} {14,41,61} {14,41,62} {14,41,63} {14,41,64} {14,41,65} {14,41,66} {14,42,43} {14,42,44}
{14,42,45} {14,42,46} {14,42,47} {14,42,48} {14,42,49} {14,42,50} {14,42,51} {14,42,52} {14,42,53}
{14,42,54} {14,42,55} {14,42,56} {14,42,57} {14,42,58} {14,42,59} {14,42,60} {14,42,61} {14,42,62}
{14,42,63} {14,42,64} {14,42,65} {14,42,66} {14,43,44} {14,43,45} {14,43,46} {14,43,47} {14,43,48}
{14,43,49} {14,43,50} {14,43,51} {14,43,52} {14,43,53} {14,43,54} {14,43,55} {14,43,56} {14,43,57}
{14,43,58} {14,43,59} {14,43,60} {14,43,61} {14,43,62} {14,43,63} {14,43,64} {14,43,65} {14,43,66}
{14,44,45} {14,44,46} {14,44,47} {14,44,48} {14,44,49} {14,44,50} {14,44,51} {14,44,52} {14,44,53}
{14,44,54} {14,44,55} {14,44,56} {14,44,57} {14,44,58} {14,44,59} {14,44,60} {14,44,61} {14,44,62}
{14,44,63} {14,44,64} {14,44,65} {14,44,66} {14,45,46} {14,45,47} {14,45,48} {14,45,49} {14,45,50}
{14,45,51} {14,45,52} {14,45,53} {14,45,54} {14,45,55} {14,45,56} {14,45,57} {14,45,58} {14,45,59}
{14,45,60} {14,45,61} {14,45,62} {14,45,63} {14,45,64} {14,45,65} {14,45,66} {14,46,47} {14,46,48}
{14,46,49} {14,46,50} {14,46,51} {14,46,52} {14,46,53} {14,46,54} {14,46,55} {14,46,56} {14,46,57}
{14,46,58} {14,46,59} {14,46,60} {14,46,61} {14,46,62} {14,46,63} {14,46,64} {14,46,65} {14,46,66}
{14,47,48} {14,47,49} {14,47,50} {14,47,51} {14,47,52} {14,47,53} {14,47,54} {14,47,55} {14,47,56}
{14,47,57} {14,47,58} {14,47,59} {14,47,60} {14,47,61} {14,47,62} {14,47,63} {14,47,64} {14,47,65}
{14,47,66} {14,48,49} {14,48,50} {14,48,51} {14,48,52} {14,48,53} {14,48,54} {14,48,55} {14,48,56}
{14,48,57} {14,48,58} {14,48,59} {14,48,60} {14,48,61} {14,48,62} {14,48,63} {14,48,64} {14,48,65}
{14,48,66} {14,49,50} {14,49,51} {14,49,52} {14,49,53} {14,49,54} {14,49,55} {14,49,56} {14,49,57}
{14,49,58} {14,49,59} {14,49,60} {14,49,61} {14,49,62} {14,49,63} {14,49,64} {14,49,65} {14,49,66}
{14,50,51} {14,50,52} {14,50,53} {14,50,54} {14,50,55} {14,50,56} {14,50,57} {14,50,58} {14,50,59}
{14,50,60} {14,50,61} {14,50,62} {14,50,63} {14,50,64} {14,50,65} {14,50,66} {14,51,52} {14,51,53}
{14,51,54} {14,51,55} {14,51,56} {14,51,57} {14,51,58} {14,51,59} {14,51,60} {14,51,61} {14,51,62}
{14,51,63} {14,51,64} {14,51,65} {14,51,66} {14,52,53} {14,52,54} {14,52,55} {14,52,56} {14,52,57}
{14,52,58} {14,52,59} {14,52,60} {14,52,61} {14,52,62} {14,52,63} {14,52,64} {14,52,65} {14,52,66}
{14,53,54} {14,53,55} {14,53,56} {14,53,57} {14,53,58} {14,53,59} {14,53,60} {14,53,61} {14,53,62}
{14,53,63} {14,53,64} {14,53,65} {14,53,66} {14,54,55} {14,54,56} {14,54,57} {14,54,58} {14,54,59}
{14,54,60} {14,54,61} {14,54,62} {14,54,63} {14,54,64} {14,54,65} {14,54,66} {14,55,56} {14,55,57}
{14,55,58} {14,55,59} {14,55,60} {14,55,61} {14,55,62} {14,55,63} {14,55,64} {14,55,65} {14,55,66}
{14,56,57} {14,56,58} {14,56,59} {14,56,60} {14,56,61} {14,56,62} {14,56,63} {14,56,64} {14,56,65}
{14,56,66} {14,57,58} {14,57,59} {14,57,60} {14,57,61} {14,57,62} {14,57,63} {14,57,64} {14,57,65}
{14,57,66} {14,58,59} {14,58,60} {14,58,61} {14,58,62} {14,58,63} {14,58,64} {14,58,65} {14,58,66}
{14,59,60} {14,59,61} {14,59,62} {14,59,63} {14,59,64} {14,59,65} {14,59,66} {14,60,61} {14,60,62}
{14,60,63} {14,60,64} {14,60,65} {14,60,66} {14,61,62} {14,61,63} {14,61,64} {14,61,65} {14,61,66}
{14,62,63} {14,62,64} {14,62,65} {14,62,66} {14,63,64} {14,63,65} {14,63,66} {14,64,65} {14,64,66}
{14,65,66} {15,16,17} {15,16,18} {15,16,19} {15,16,20} {15,16,21} {15,16,22} {15,16,23} {15,16,24}
{15,16,25} {15,16,26} {15,16,27} {15,16,28} {15,16,29} {15,16,30} {15,16,31} {15,16,32} {15,16,33}
{15,16,34} {15,16,35} {15,16,36} {15,16,37} {15,16,38} {15,16,39} {15,16,40} {15,16,41} {15,16,42}
{15,16,43} {15,16,44} {15,16,45} {15,16,46} {15,16,47} {15,16,48} {15,16,49} {15,16,50} {15,16,51}
{15,16,52} {15,16,53} {15,16,54} {15,16,55} {15,16,56} {15,16,57} {15,16,58} {15,16,59} {15,16,60}
{15,16,61} {15,16,62} {15,16,63} {15,16,64} {15,16,65} {15,16,66} {15,17,18} {15,17,19} {15,17,20}
{15,17,21} {15,17,22} {15,17,23} {15,17,24} {15,17,25} {15,17,26} {15,17,27} {15,17,28} {15,17,29}
{15,17,30} {15,17,31} {15,17,32} {15,17,33} {15,17,34} {15,17,35} {15,17,36} {15,17,37} {15,17,38}
{15,17,39} {15,17,40} {15,17,41} {15,17,42} {15,17,43} {15,17,44} {15,17,45} {15,17,46} {15,17,47}
{15,17,48} {15,17,49} {15,17,50} {15,17,51} {15,17,52} {15,17,53} {15,17,54} {15,17,55} {15,17,56}
{15,17,57} {15,17,58} {15,17,59} {15,17,60} {15,17,61} {15,17,62} {15,17,63} {15,17,64} {15,17,65}
{15,17,66} {15,18,19} {15,18,20} {15,18,21} {15,18,22} {15,18,23} {15,18,24} {15,18,25} {15,18,26}
{15,18,27} {15,18,28} {15,18,29} {15,18,30} {15,18,31} {15,18,32} {15,18,33} {15,18,34} {15,18,35}
{15,18,36} {15,18,37} {15,18,38} {15,18,39} {15,18,40} {15,18,41} {15,18,42} {15,18,43} {15,18,44}
{15,18,45} {15,18,46} {15,18,47} {15,18,48} {15,18,49} {15,18,50} {15,18,51} {15,18,52} {15,18,53}
{15,18,54} {15,18,55} {15,18,56} {15,18,57} {15,18,58} {15,18,59} {15,18,60} {15,18,61} {15,18,62}
{15,18,63} {15,18,64} {15,18,65} {15,18,66} {15,19,20} {15,19,21} {15,19,22} {15,19,23} {15,19,24}
{15,19,25} {15,19,26} {15,19,27} {15,19,28} {15,19,29} {15,19,30} {15,19,31} {15,19,32} {15,19,33}
{15,19,34} {15,19,35} {15,19,36} {15,19,37} {15,19,38} {15,19,39} {15,19,40} {15,19,41} {15,19,42}
{15,19,43} {15,19,44} {15,19,45} {15,19,46} {15,19,47} {15,19,48} {15,19,49} {15,19,50} {15,19,51}
{15,19,52} {15,19,53} {15,19,54} {15,19,55} {15,19,56} {15,19,57} {15,19,58} {15,19,59} {15,19,60}
{15,19,61} {15,19,62} {15,19,63} {15,19,64} {15,19,65} {15,19,66} {15,20,21} {15,20,22} {15,20,23}
{15,20,24} {15,20,25} {15,20,26} {15,20,27} {15,20,28} {15,20,29} {15,20,30} {15,20,31} {15,20,32}
{15,20,33} {15,20,34} {15,20,35} {15,20,36} {15,20,37} {15,20,38} {15,20,39} {15,20,40} {15,20,41}
{15,20,42} {15,20,43} {15,20,44} {15,20,45} {15,20,46} {15,20,47} {15,20,48} {15,20,49} {15,20,50}
{15,20,51} {15,20,52} {15,20,53} {15,20,54} {15,20,55} {15,20,56} {15,20,57} {15,20,58} {15,20,59}
{15,20,60} {15,20,61} {15,20,62} {15,20,63} {15,20,64} {15,20,65} {15,20,66} {15,21,22} {15,21,23}
{15,21,24} {15,21,25} {15,21,26} {15,21,27} {15,21,28} {15,21,29} {15,21,30} {15,21,31} {15,21,32}
{15,21,33} {15,21,34} {15,21,35} {15,21,36} {15,21,37} {15,21,38} {15,21,39} {15,21,40} {15,21,41}
{15,21,42} {15,21,43} {15,21,44} {15,21,45} {15,21,46} {15,21,47} {15,21,48} {15,21,49} {15,21,50}
{15,21,51} {15,21,52} {15,21,53} {15,21,54} {15,21,55} {15,21,56} {15,21,57} {15,21,58} {15,21,59}

TABLE 3A-continued

| | | | | | | | |
|---|---|---|---|---|---|---|---|
| {15,21,60} | {15,21,61} | {15,21,62} | {15,21,63} | {15,21,64} | {15,21,65} | {15,21,66} | {15,22,23} | {15,22,24} |
| {15,22,25} | {15,22,26} | {15,22,27} | {15,22,28} | {15,22,29} | {15,22,30} | {15,22,31} | {15,22,32} | {15,22,33} |
| {15,22,34} | {15,22,35} | {15,22,36} | {15,22,37} | {15,22,38} | {15,22,39} | {15,22,40} | {15,22,41} | {15,22,42} |
| {15,22,43} | {15,22,44} | {15,22,45} | {15,22,46} | {15,22,47} | {15,22,48} | {15,22,49} | {15,22,50} | {15,22,51} |
| {15,22,52} | {15,22,53} | {15,22,54} | {15,22,55} | {15,22,56} | {15,22,57} | {15,22,58} | {15,22,59} | {15,22,60} |
| {15,22,61} | {15,22,62} | {15,22,63} | {15,22,64} | {15,22,65} | {15,22,66} | {15,23,24} | {15,23,25} | {15,23,26} |
| {15,23,27} | {15,23,28} | {15,23,29} | {15,23,30} | {15,23,31} | {15,23,32} | {15,23,33} | {15,23,34} | {15,23,35} |
| {15,23,36} | {15,23,37} | {15,23,38} | {15,23,39} | {15,23,40} | {15,23,41} | {15,23,42} | {15,23,43} | {15,23,44} |
| {15,23,45} | {15,23,46} | {15,23,47} | {15,23,48} | {15,23,49} | {15,23,50} | {15,23,51} | {15,23,52} | {15,23,53} |
| {15,23,54} | {15,23,55} | {15,23,56} | {15,23,57} | {15,23,58} | {15,23,59} | {15,23,60} | {15,23,61} | {15,23,62} |
| {15,23,63} | {15,23,64} | {15,23,65} | {15,23,66} | {15,24,25} | {15,24,26} | {15,24,27} | {15,24,28} | {15,24,29} |
| {15,24,30} | {15,24,31} | {15,24,32} | {15,24,33} | {15,24,34} | {15,24,35} | {15,24,36} | {15,24,37} | {15,24,38} |
| {15,24,39} | {15,24,40} | {15,24,41} | {15,24,42} | {15,24,43} | {15,24,44} | {15,24,45} | {15,24,46} | {15,24,47} |
| {15,24,48} | {15,24,49} | {15,24,50} | {15,24,51} | {15,24,52} | {15,24,53} | {15,24,54} | {15,24,55} | {15,24,56} |
| {15,24,57} | {15,24,58} | {15,24,59} | {15,24,60} | {15,24,61} | {15,24,62} | {15,24,63} | {15,24,64} | {15,24,65} |
| {15,24,66} | {15,25,26} | {15,25,27} | {15,25,28} | {15,25,29} | {15,25,30} | {15,25,31} | {15,25,32} | {15,25,33} |
| {15,25,34} | {15,25,35} | {15,25,36} | {15,25,37} | {15,25,38} | {15,25,39} | {15,25,40} | {15,25,41} | {15,25,42} |
| {15,25,43} | {15,25,44} | {15,25,45} | {15,25,46} | {15,25,47} | {15,25,48} | {15,25,49} | {15,25,50} | {15,25,51} |
| {15,25,52} | {15,25,53} | {15,25,54} | {15,25,55} | {15,25,56} | {15,25,57} | {15,25,58} | {15,25,59} | {15,25,60} |
| {15,25,61} | {15,25,62} | {15,25,63} | {15,25,64} | {15,25,65} | {15,25,66} | {15,26,27} | {15,26,28} | {15,26,29} |
| {15,26,30} | {15,26,31} | {15,26,32} | {15,26,33} | {15,26,34} | {15,26,35} | {15,26,36} | {15,26,37} | {15,26,38} |
| {15,26,39} | {15,26,40} | {15,26,41} | {15,26,42} | {15,26,43} | {15,26,44} | {15,26,45} | {15,26,46} | {15,26,47} |
| {15,26,48} | {15,26,49} | {15,26,50} | {15,26,51} | {15,26,52} | {15,26,53} | {15,26,54} | {15,26,55} | {15,26,56} |
| {15,26,57} | {15,26,58} | {15,26,59} | {15,26,60} | {15,26,61} | {15,26,62} | {15,26,63} | {15,26,64} | {15,26,65} |
| {15,26,66} | {15,27,28} | {15,27,29} | {15,27,30} | {15,27,31} | {15,27,32} | {15,27,33} | {15,27,34} | {15,27,35} |
| {15,27,36} | {15,27,37} | {15,27,38} | {15,27,39} | {15,27,40} | {15,27,41} | {15,27,42} | {15,27,43} | {15,27,44} |
| {15,27,45} | {15,27,46} | {15,27,47} | {15,27,48} | {15,27,49} | {15,27,50} | {15,27,51} | {15,27,52} | {15,27,53} |
| {15,27,54} | {15,27,55} | {15,27,56} | {15,27,57} | {15,27,58} | {15,27,59} | {15,27,60} | {15,27,61} | {15,27,62} |
| {15,27,63} | {15,27,64} | {15,27,65} | {15,27,66} | {15,28,29} | {15,28,30} | {15,28,31} | {15,28,32} | {15,28,33} |
| {15,28,34} | {15,28,35} | {15,28,36} | {15,28,37} | {15,28,38} | {15,28,39} | {15,28,40} | {15,28,41} | {15,28,42} |
| {15,28,43} | {15,28,44} | {15,28,45} | {15,28,46} | {15,28,47} | {15,28,48} | {15,28,49} | {15,28,50} | {15,28,51} |
| {15,28,52} | {15,28,53} | {15,28,54} | {15,28,55} | {15,28,56} | {15,28,57} | {15,28,58} | {15,28,59} | {15,28,60} |
| {15,28,61} | {15,28,62} | {15,28,63} | {15,28,64} | {15,28,65} | {15,28,66} | {15,29,30} | {15,29,31} | {15,29,32} |
| {15,29,33} | {15,29,34} | {15,29,35} | {15,29,36} | {15,29,37} | {15,29,38} | {15,29,39} | {15,29,40} | {15,29,41} |
| {15,29,42} | {15,29,43} | {15,29,44} | {15,29,45} | {15,29,46} | {15,29,47} | {15,29,48} | {15,29,49} | {15,29,50} |
| {15,29,51} | {15,29,52} | {15,29,53} | {15,29,54} | {15,29,55} | {15,29,56} | {15,29,57} | {15,29,58} | {15,29,59} |
| {15,29,60} | {15,29,61} | {15,29,62} | {15,29,63} | {15,29,64} | {15,29,65} | {15,29,66} | {15,30,31} | {15,30,32} |
| {15,30,33} | {15,30,34} | {15,30,35} | {15,30,36} | {15,30,37} | {15,30,38} | {15,30,39} | {15,30,40} | {15,30,41} |
| {15,30,42} | {15,30,43} | {15,30,44} | {15,30,45} | {15,30,46} | {15,30,47} | {15,30,48} | {15,30,49} | {15,30,50} |
| {15,30,51} | {15,30,52} | {15,30,53} | {15,30,54} | {15,30,55} | {15,30,56} | {15,30,57} | {15,30,58} | {15,30,59} |
| {15,30,60} | {15,30,61} | {15,30,62} | {15,30,63} | {15,30,64} | {15,30,65} | {15,30,66} | {15,31,32} | {15,31,33} |
| {15,31,34} | {15,31,35} | {15,31,36} | {15,31,37} | {15,31,38} | {15,31,39} | {15,31,40} | {15,31,41} | {15,31,42} |
| {15,31,43} | {15,31,44} | {15,31,45} | {15,31,46} | {15,31,47} | {15,31,48} | {15,31,49} | {15,31,50} | {15,31,51} |
| {15,31,52} | {15,31,53} | {15,31,54} | {15,31,55} | {15,31,56} | {15,31,57} | {15,31,58} | {15,31,59} | {15,31,60} |
| {15,31,61} | {15,31,62} | {15,31,63} | {15,31,64} | {15,31,65} | {15,31,66} | {15,32,33} | {15,32,34} | {15,32,35} |
| {15,32,36} | {15,32,37} | {15,32,38} | {15,32,39} | {15,32,40} | {15,32,41} | {15,32,42} | {15,32,43} | {15,32,44} |
| {15,32,45} | {15,32,46} | {15,32,47} | {15,32,48} | {15,32,49} | {15,32,50} | {15,32,51} | {15,32,52} | {15,32,53} |
| {15,32,54} | {15,32,55} | {15,32,56} | {15,32,57} | {15,32,58} | {15,32,59} | {15,32,60} | {15,32,61} | {15,32,62} |
| {15,32,63} | {15,32,64} | {15,32,65} | {15,32,66} | {15,33,34} | {15,33,35} | {15,33,36} | {15,33,37} | {15,33,38} |
| {15,33,39} | {15,33,40} | {15,33,41} | {15,33,42} | {15,33,43} | {15,33,44} | {15,33,45} | {15,33,46} | {15,33,47} |
| {15,33,48} | {15,33,49} | {15,33,50} | {15,33,51} | {15,33,52} | {15,33,53} | {15,33,54} | {15,33,55} | {15,33,56} |
| {15,33,57} | {15,33,58} | {15,33,59} | {15,33,60} | {15,33,61} | {15,33,62} | {15,33,63} | {15,33,64} | {15,33,65} |
| {15,33,66} | {15,34,35} | {15,34,36} | {15,34,37} | {15,34,38} | {15,34,39} | {15,34,40} | {15,34,41} | {15,34,42} |
| {15,34,43} | {15,34,44} | {15,34,45} | {15,34,46} | {15,34,47} | {15,34,48} | {15,34,49} | {15,34,50} | {15,34,51} |
| {15,34,52} | {15,34,53} | {15,34,54} | {15,34,55} | {15,34,56} | {15,34,57} | {15,34,58} | {15,34,59} | {15,34,60} |
| {15,34,61} | {15,34,62} | {15,34,63} | {15,34,64} | {15,34,65} | {15,34,66} | {15,35,36} | {15,35,37} | {15,35,38} |
| {15,35,39} | {15,35,40} | {15,35,41} | {15,35,42} | {15,35,43} | {15,35,44} | {15,35,45} | {15,35,46} | {15,35,47} |
| {15,35,48} | {15,35,49} | {15,35,50} | {15,35,51} | {15,35,52} | {15,35,53} | {15,35,54} | {15,35,55} | {15,35,56} |
| {15,35,57} | {15,35,58} | {15,35,59} | {15,35,60} | {15,35,61} | {15,35,62} | {15,35,63} | {15,35,64} | {15,35,65} |
| {15,35,66} | {15,36,37} | {15,36,38} | {15,36,39} | {15,36,40} | {15,36,41} | {15,36,42} | {15,36,43} | {15,36,44} |
| {15,36,45} | {15,36,46} | {15,36,47} | {15,36,48} | {15,36,49} | {15,36,50} | {15,36,51} | {15,36,52} | {15,36,53} |
| {15,36,54} | {15,36,55} | {15,36,56} | {15,36,57} | {15,36,58} | {15,36,59} | {15,36,60} | {15,36,61} | {15,36,62} |
| {15,36,63} | {15,36,64} | {15,36,65} | {15,36,66} | {15,37,38} | {15,37,39} | {15,37,40} | {15,37,41} | {15,37,42} |
| {15,37,43} | {15,37,44} | {15,37,45} | {15,37,46} | {15,37,47} | {15,37,48} | {15,37,49} | {15,37,50} | {15,37,51} |
| {15,37,52} | {15,37,53} | {15,37,54} | {15,37,55} | {15,37,56} | {15,37,57} | {15,37,58} | {15,37,59} | {15,37,60} |
| {15,37,61} | {15,37,62} | {15,37,63} | {15,37,64} | {15,37,65} | {15,37,66} | {15,38,39} | {15,38,40} | {15,38,41} |
| {15,38,42} | {15,38,43} | {15,38,44} | {15,38,45} | {15,38,46} | {15,38,47} | {15,38,48} | {15,38,49} | {15,38,50} |
| {15,38,51} | {15,38,52} | {15,38,53} | {15,38,54} | {15,38,55} | {15,38,56} | {15,38,57} | {15,38,58} | {15,38,59} |
| {15,38,60} | {15,38,61} | {15,38,62} | {15,38,63} | {15,38,64} | {15,38,65} | {15,38,66} | {15,39,40} | {15,39,41} |
| {15,39,42} | {15,39,43} | {15,39,44} | {15,39,45} | {15,39,46} | {15,39,47} | {15,39,48} | {15,39,49} | {15,39,50} |
| {15,39,51} | {15,39,52} | {15,39,53} | {15,39,54} | {15,39,55} | {15,39,56} | {15,39,57} | {15,39,58} | {15,39,59} |
| {15,39,60} | {15,39,61} | {15,39,62} | {15,39,63} | {15,39,64} | {15,39,65} | {15,39,66} | {15,40,41} | {15,40,42} |
| {15,40,43} | {15,40,44} | {15,40,45} | {15,40,46} | {15,40,47} | {15,40,48} | {15,40,49} | {15,40,50} | {15,40,51} |
| {15,40,52} | {15,40,53} | {15,40,54} | {15,40,55} | {15,40,56} | {15,40,57} | {15,40,58} | {15,40,59} | {15,40,60} |
| {15,40,61} | {15,40,62} | {15,40,63} | {15,40,64} | {15,40,65} | {15,40,66} | {15,41,42} | {15,41,43} | {15,41,44} |
| {15,41,45} | {15,41,46} | {15,41,47} | {15,41,48} | {15,41,49} | {15,41,50} | {15,41,51} | {15,41,52} | {15,41,53} |
| {15,41,54} | {15,41,55} | {15,41,56} | {15,41,57} | {15,41,58} | {15,41,59} | {15,41,60} | {15,41,61} | {15,41,62} |
| {15,41,63} | {15,41,64} | {15,41,65} | {15,41,66} | {15,42,43} | {15,42,44} | {15,42,45} | {15,42,46} | {15,42,47} |
| {15,42,48} | {15,42,49} | {15,42,50} | {15,42,51} | {15,42,52} | {15,42,53} | {15,42,54} | {15,42,55} | {15,42,56} |
| {15,42,57} | {15,42,58} | {15,42,59} | {15,42,60} | {15,42,61} | {15,42,62} | {15,42,63} | {15,42,64} | {15,42,65} |

TABLE 3A-continued

{15,42,66} {15,43,44} {15,43,45} {15,43,46} {15,43,47} {15,43,48} {15,43,49} {15,43,50} {15,43,51}
{15,43,52} {15,43,53} {15,43,54} {15,43,55} {15,43,56} {15,43,57} {15,43,58} {15,43,59} {15,43,60}
{15,43,61} {15,43,62} {15,43,63} {15,43,64} {15,43,65} {15,43,66} {15,44,45} {15,44,46} {15,44,47}
{15,44,48} {15,44,49} {15,44,50} {15,44,51} {15,44,52} {15,44,53} {15,44,54} {15,44,55} {15,44,56}
{15,44,57} {15,44,58} {15,44,59} {15,44,60} {15,44,61} {15,44,62} {15,44,63} {15,44,64} {15,44,65}
{15,44,66} {15,45,46} {15,45,47} {15,45,48} {15,45,49} {15,45,50} {15,45,51} {15,45,52} {15,45,53}
{15,45,54} {15,45,55} {15,45,56} {15,45,57} {15,45,58} {15,45,59} {15,45,60} {15,45,61} {15,45,62}
{15,45,63} {15,45,64} {15,45,65} {15,45,66} {15,46,47} {15,46,48} {15,46,49} {15,46,50} {15,46,51}
{15,46,52} {15,46,53} {15,46,54} {15,46,55} {15,46,56} {15,46,57} {15,46,58} {15,46,59} {15,46,60}
{15,46,61} {15,46,62} {15,46,63} {15,46,64} {15,46,65} {15,46,66} {15,47,48} {15,47,49} {15,47,50}
{15,47,51} {15,47,52} {15,47,53} {15,47,54} {15,47,55} {15,47,56} {15,47,57} {15,47,58} {15,47,59}
{15,47,60} {15,47,61} {15,47,62} {15,47,63} {15,47,64} {15,47,65} {15,47,66} {15,48,49} {15,48,50}
{15,48,51} {15,48,52} {15,48,53} {15,48,54} {15,48,55} {15,48,56} {15,48,57} {15,48,58} {15,48,59}
{15,48,60} {15,48,61} {15,48,62} {15,48,63} {15,48,64} {15,48,65} {15,48,66} {15,49,50} {15,49,51}
{15,49,52} {15,49,53} {15,49,54} {15,49,55} {15,49,56} {15,49,57} {15,49,58} {15,49,59} {15,49,60}
{15,49,61} {15,49,62} {15,49,63} {15,49,64} {15,49,65} {15,49,66} {15,50,51} {15,50,52} {15,50,53}
{15,50,54} {15,50,55} {15,50,56} {15,50,57} {15,50,58} {15,50,59} {15,50,60} {15,50,61} {15,50,62}
{15,50,63} {15,50,64} {15,50,65} {15,50,66} {15,51,52} {15,51,53} {15,51,54} {15,51,55} {15,51,56}
{15,51,57} {15,51,58} {15,51,59} {15,51,60} {15,51,61} {15,51,62} {15,51,63} {15,51,64} {15,51,65}
{15,51,66} {15,52,53} {15,52,54} {15,52,55} {15,52,56} {15,52,57} {15,52,58} {15,52,59} {15,52,60}
{15,52,61} {15,52,62} {15,52,63} {15,52,64} {15,52,65} {15,52,66} {15,53,54} {15,53,55} {15,53,56}
{15,53,57} {15,53,58} {15,53,59} {15,53,60} {15,53,61} {15,53,62} {15,53,63} {15,53,64} {15,53,65}
{15,53,66} {15,54,55} {15,54,56} {15,54,57} {15,54,58} {15,54,59} {15,54,60} {15,54,61} {15,54,62}
{15,54,63} {15,54,64} {15,54,65} {15,54,66} {15,55,56} {15,55,57} {15,55,58} {15,55,59} {15,55,60}
{15,55,61} {15,55,62} {15,55,63} {15,55,64} {15,55,65} {15,55,66} {15,56,57} {15,56,58} {15,56,59}
{15,56,60} {15,56,61} {15,56,62} {15,56,63} {15,56,64} {15,56,65} {15,56,66} {15,57,58} {15,57,59}
{15,57,60} {15,57,61} {15,57,62} {15,57,63} {15,57,64} {15,57,65} {15,57,66} {15,58,59} {15,58,60}
{15,58,61} {15,58,62} {15,58,63} {15,58,64} {15,58,65} {15,58,66} {15,59,60} {15,59,61} {15,59,62}
{15,59,63} {15,59,64} {15,59,65} {15,59,66} {15,60,61} {15,60,62} {15,60,63} {15,60,64} {15,60,65}
{15,60,66} {15,61,62} {15,61,63} {15,61,64} {15,61,65} {15,61,66} {15,62,63} {15,62,64} {15,62,65}
{15,62,66} {15,63,64} {15,63,65} {15,63,66} {15,64,65} {15,64,66} {15,65,66} {16,17,18} {16,17,19}
{16,17,20} {16,17,21} {16,17,22} {16,17,23} {16,17,24} {16,17,25} {16,17,26} {16,17,27} {16,17,28}
{16,17,29} {16,17,30} {16,17,31} {16,17,32} {16,17,33} {16,17,34} {16,17,35} {16,17,36} {16,17,37}
{16,17,38} {16,17,39} {16,17,40} {16,17,41} {16,17,42} {16,17,43} {16,17,44} {16,17,45} {16,17,46}
{16,17,47} {16,17,48} {16,17,49} {16,17,50} {16,17,51} {16,17,52} {16,17,53} {16,17,54} {16,17,55}
{16,17,56} {16,17,57} {16,17,58} {16,17,59} {16,17,60} {16,17,61} {16,17,62} {16,17,63} {16,17,64}
{16,17,65} {16,17,66} {16,18,19} {16,18,20} {16,18,21} {16,18,22} {16,18,23} {16,18,24} {16,18,25}
{16,18,26} {16,18,27} {16,18,28} {16,18,29} {16,18,30} {16,18,31} {16,18,32} {16,18,33} {16,18,34}
{16,18,35} {16,18,36} {16,18,37} {16,18,38} {16,18,39} {16,18,40} {16,18,41} {16,18,42} {16,18,43}
{16,18,44} {16,18,45} {16,18,46} {16,18,47} {16,18,48} {16,18,49} {16,18,50} {16,18,51} {16,18,52}
{16,18,53} {16,18,54} {16,18,55} {16,18,56} {16,18,57} {16,18,58} {16,18,59} {16,18,60} {16,18,61}
{16,18,62} {16,18,63} {16,18,64} {16,18,65} {16,18,66} {16,19,20} {16,19,21} {16,19,22} {16,19,23}
{16,19,24} {16,19,25} {16,19,26} {16,19,27} {16,19,28} {16,19,29} {16,19,30} {16,19,31} {16,19,32}
{16,19,33} {16,19,34} {16,19,35} {16,19,36} {16,19,37} {16,19,38} {16,19,39} {16,19,40} {16,19,41}
{16,19,42} {16,19,43} {16,19,44} {16,19,45} {16,19,46} {16,19,47} {16,19,48} {16,19,49} {16,19,50}
{16,19,51} {16,19,52} {16,19,53} {16,19,54} {16,19,55} {16,19,56} {16,19,57} {16,19,58} {16,19,59}
{16,19,60} {16,19,61} {16,19,62} {16,19,63} {16,19,64} {16,19,65} {16,19,66} {16,20,21} {16,20,22}
{16,20,23} {16,20,24} {16,20,25} {16,20,26} {16,20,27} {16,20,28} {16,20,29} {16,20,30} {16,20,31}
{16,20,32} {16,20,33} {16,20,34} {16,20,35} {16,20,36} {16,20,37} {16,20,38} {16,20,39} {16,20,40}
{16,20,41} {16,20,42} {16,20,43} {16,20,44} {16,20,45} {16,20,46} {16,20,47} {16,20,48} {16,20,49}
{16,20,50} {16,20,51} {16,20,52} {16,20,53} {16,20,54} {16,20,55} {16,20,56} {16,20,57} {16,20,58}
{16,20,59} {16,20,60} {16,20,61} {16,20,62} {16,20,63} {16,20,64} {16,20,65} {16,20,66} {16,21,22}
{16,21,23} {16,21,24} {16,21,25} {16,21,26} {16,21,27} {16,21,28} {16,21,29} {16,21,30} {16,21,31}
{16,21,32} {16,21,33} {16,21,34} {16,21,35} {16,21,36} {16,21,37} {16,21,38} {16,21,39} {16,21,40}
{16,21,41} {16,21,42} {16,21,43} {16,21,44} {16,21,45} {16,21,46} {16,21,47} {16,21,48} {16,21,49}
{16,21,50} {16,21,51} {16,21,52} {16,21,53} {16,21,54} {16,21,55} {16,21,56} {16,21,57} {16,21,58}
{16,21,59} {16,21,60} {16,21,61} {16,21,62} {16,21,63} {16,21,64} {16,21,65} {16,21,66} {16,22,23}
{16,22,24} {16,22,25} {16,22,26} {16,22,27} {16,22,28} {16,22,29} {16,22,30} {16,22,31} {16,22,32}
{16,22,33} {16,22,34} {16,22,35} {16,22,36} {16,22,37} {16,22,38} {16,22,39} {16,22,40} {16,22,41}
{16,22,42} {16,22,43} {16,22,44} {16,22,45} {16,22,46} {16,22,47} {16,22,48} {16,22,49} {16,22,50}
{16,22,51} {16,22,52} {16,22,53} {16,22,54} {16,22,55} {16,22,56} {16,22,57} {16,22,58} {16,22,59}
{16,22,60} {16,22,61} {16,22,62} {16,22,63} {16,22,64} {16,22,65} {16,22,66} {16,23,24} {16,23,25}
{16,23,26} {16,23,27} {16,23,28} {16,23,29} {16,23,30} {16,23,31} {16,23,32} {16,23,33} {16,23,34}
{16,23,35} {16,23,36} {16,23,37} {16,23,38} {16,23,39} {16,23,40} {16,23,41} {16,23,42} {16,23,43}
{16,23,44} {16,23,45} {16,23,46} {16,23,47} {16,23,48} {16,23,49} {16,23,50} {16,23,51} {16,23,52}
{16,23,53} {16,23,54} {16,23,55} {16,23,56} {16,23,57} {16,23,58} {16,23,59} {16,23,60} {16,23,61}
{16,23,62} {16,23,63} {16,23,64} {16,23,65} {16,23,66} {16,24,25} {16,24,26} {16,24,27} {16,24,28}
{16,24,29} {16,24,30} {16,24,31} {16,24,32} {16,24,33} {16,24,34} {16,24,35} {16,24,36} {16,24,37}
{16,24,38} {16,24,39} {16,24,40} {16,24,41} {16,24,42} {16,24,43} {16,24,44} {16,24,45} {16,24,46}
{16,24,47} {16,24,48} {16,24,49} {16,24,50} {16,24,51} {16,24,52} {16,24,53} {16,24,54} {16,24,55}
{16,24,56} {16,24,57} {16,24,58} {16,24,59} {16,24,60} {16,24,61} {16,24,62} {16,24,63} {16,24,64}
{16,24,65} {16,24,66} {16,25,26} {16,25,27} {16,25,28} {16,25,29} {16,25,30} {16,25,31} {16,25,32}
{16,25,33} {16,25,34} {16,25,35} {16,25,36} {16,25,37} {16,25,38} {16,25,39} {16,25,40} {16,25,41}
{16,25,42} {16,25,43} {16,25,44} {16,25,45} {16,25,46} {16,25,47} {16,25,48} {16,25,49} {16,25,50}
{16,25,51} {16,25,52} {16,25,53} {16,25,54} {16,25,55} {16,25,56} {16,25,57} {16,25,58} {16,25,59}
{16,25,60} {16,25,61} {16,25,62} {16,25,63} {16,25,64} {16,25,65} {16,25,66} {16,26,27} {16,26,28}
{16,26,29} {16,26,30} {16,26,31} {16,26,32} {16,26,33} {16,26,34} {16,26,35} {16,26,36} {16,26,37}
{16,26,38} {16,26,39} {16,26,40} {16,26,41} {16,26,42} {16,26,43} {16,26,44} {16,26,45} {16,26,46}
{16,26,47} {16,26,48} {16,26,49} {16,26,50} {16,26,51} {16,26,52} {16,26,53} {16,26,54} {16,26,55}
{16,26,56} {16,26,57} {16,26,58} {16,26,59} {16,26,60} {16,26,61} {16,26,62} {16,26,63} {16,26,64}

TABLE 3A-continued

| | | | | | | | |
|---|---|---|---|---|---|---|---|
| {16,26,65} | {16,26,66} | {16,27,28} | {16,27,29} | {16,27,30} | {16,27,31} | {16,27,32} | {16,27,33} | {16,27,34} |
| {16,27,35} | {16,27,36} | {16,27,37} | {16,27,38} | {16,27,39} | {16,27,40} | {16,27,41} | {16,27,42} | {16,27,43} |
| {16,27,44} | {16,27,45} | {16,27,46} | {16,27,47} | {16,27,48} | {16,27,49} | {16,27,50} | {16,27,51} | {16,27,52} |
| {16,27,53} | {16,27,54} | {16,27,55} | {16,27,56} | {16,27,57} | {16,27,58} | {16,27,59} | {16,27,60} | {16,27,61} |
| {16,27,62} | {16,27,63} | {16,27,64} | {16,27,65} | {16,27,66} | {16,28,29} | {16,28,30} | {16,28,31} | {16,28,32} |
| {16,28,33} | {16,28,34} | {16,28,35} | {16,28,36} | {16,28,37} | {16,28,38} | {16,28,39} | {16,28,40} | {16,28,41} |
| {16,28,42} | {16,28,43} | {16,28,44} | {16,28,45} | {16,28,46} | {16,28,47} | {16,28,48} | {16,28,49} | {16,28,50} |
| {16,28,51} | {16,28,52} | {16,28,53} | {16,28,54} | {16,28,55} | {16,28,56} | {16,28,57} | {16,28,58} | {16,28,59} |
| {16,28,60} | {16,28,61} | {16,28,62} | {16,28,63} | {16,28,64} | {16,28,65} | {16,28,66} | {16,29,30} | {16,29,31} |
| {16,29,32} | {16,29,33} | {16,29,34} | {16,29,35} | {16,29,36} | {16,29,37} | {16,29,38} | {16,29,39} | {16,29,40} |
| {16,29,41} | {16,29,42} | {16,29,43} | {16,29,44} | {16,29,45} | {16,29,46} | {16,29,47} | {16,29,48} | {16,29,49} |
| {16,29,50} | {16,29,51} | {16,29,52} | {16,29,53} | {16,29,54} | {16,29,55} | {16,29,56} | {16,29,57} | {16,29,58} |
| {16,29,59} | {16,29,60} | {16,29,61} | {16,29,62} | {16,29,63} | {16,29,64} | {16,29,65} | {16,29,66} | {16,30,31} |
| {16,30,32} | {16,30,33} | {16,30,34} | {16,30,35} | {16,30,36} | {16,30,37} | {16,30,38} | {16,30,39} | {16,30,40} |
| {16,30,41} | {16,30,42} | {16,30,43} | {16,30,44} | {16,30,45} | {16,30,46} | {16,30,47} | {16,30,48} | {16,30,49} |
| {16,30,50} | {16,30,51} | {16,30,52} | {16,30,53} | {16,30,54} | {16,30,55} | {16,30,56} | {16,30,57} | {16,30,58} |
| {16,30,59} | {16,30,60} | {16,30,61} | {16,30,62} | {16,30,63} | {16,30,64} | {16,30,65} | {16,30,66} | {16,31,32} |
| {16,31,33} | {16,31,34} | {16,31,35} | {16,31,36} | {16,31,37} | {16,31,38} | {16,31,39} | {16,31,40} | {16,31,41} |
| {16,31,42} | {16,31,43} | {16,31,44} | {16,31,45} | {16,31,46} | {16,31,47} | {16,31,48} | {16,31,49} | {16,31,50} |
| {16,31,51} | {16,31,52} | {16,31,53} | {16,31,54} | {16,31,55} | {16,31,56} | {16,31,57} | {16,31,58} | {16,31,59} |
| {16,31,60} | {16,31,61} | {16,31,62} | {16,31,63} | {16,31,64} | {16,31,65} | {16,31,66} | {16,32,33} | {16,32,34} |
| {16,32,35} | {16,32,36} | {16,32,37} | {16,32,38} | {16,32,39} | {16,32,40} | {16,32,41} | {16,32,42} | {16,32,43} |
| {16,32,44} | {16,32,45} | {16,32,46} | {16,32,47} | {16,32,48} | {16,32,49} | {16,32,50} | {16,32,51} | {16,32,52} |
| {16,32,53} | {16,32,54} | {16,32,55} | {16,32,56} | {16,32,57} | {16,32,58} | {16,32,59} | {16,32,60} | {16,32,61} |
| {16,32,62} | {16,32,63} | {16,32,64} | {16,32,65} | {16,32,66} | {16,33,34} | {16,33,35} | {16,33,36} | {16,33,37} |
| {16,33,38} | {16,33,39} | {16,33,40} | {16,33,41} | {16,33,42} | {16,33,43} | {16,33,44} | {16,33,45} | {16,33,46} |
| {16,33,47} | {16,33,48} | {16,33,49} | {16,33,50} | {16,33,51} | {16,33,52} | {16,33,53} | {16,33,54} | {16,33,55} |
| {16,33,56} | {16,33,57} | {16,33,58} | {16,33,59} | {16,33,60} | {16,33,61} | {16,33,62} | {16,33,63} | {16,33,64} |
| {16,33,65} | {16,33,66} | {16,34,35} | {16,34,36} | {16,34,37} | {16,34,38} | {16,34,39} | {16,34,40} | {16,34,41} |
| {16,34,42} | {16,34,43} | {16,34,44} | {16,34,45} | {16,34,46} | {16,34,47} | {16,34,48} | {16,34,49} | {16,34,50} |
| {16,34,51} | {16,34,52} | {16,34,53} | {16,34,54} | {16,34,55} | {16,34,56} | {16,34,57} | {16,34,58} | {16,34,59} |
| {16,34,60} | {16,34,61} | {16,34,62} | {16,34,63} | {16,34,64} | {16,34,65} | {16,34,66} | {16,35,36} | {16,35,37} |
| {16,35,38} | {16,35,39} | {16,35,40} | {16,35,41} | {16,35,42} | {16,35,43} | {16,35,44} | {16,35,45} | {16,35,46} |
| {16,35,47} | {16,35,48} | {16,35,49} | {16,35,50} | {16,35,51} | {16,35,52} | {16,35,53} | {16,35,54} | {16,35,55} |
| {16,35,56} | {16,35,57} | {16,35,58} | {16,35,59} | {16,35,60} | {16,35,61} | {16,35,62} | {16,35,63} | {16,35,64} |
| {16,35,65} | {16,35,66} | {16,36,37} | {16,36,38} | {16,36,39} | {16,36,40} | {16,36,41} | {16,36,42} | {16,36,43} |
| {16,36,44} | {16,36,45} | {16,36,46} | {16,36,47} | {16,36,48} | {16,36,49} | {16,36,50} | {16,36,51} | {16,36,52} |
| {16,36,53} | {16,36,54} | {16,36,55} | {16,36,56} | {16,36,57} | {16,36,58} | {16,36,59} | {16,36,60} | {16,36,61} |
| {16,36,62} | {16,36,63} | {16,36,64} | {16,36,65} | {16,36,66} | {16,37,38} | {16,37,39} | {16,37,40} | {16,37,41} |
| {16,37,42} | {16,37,43} | {16,37,44} | {16,37,45} | {16,37,46} | {16,37,47} | {16,37,48} | {16,37,49} | {16,37,50} |
| {16,37,51} | {16,37,52} | {16,37,53} | {16,37,54} | {16,37,55} | {16,37,56} | {16,37,57} | {16,37,58} | {16,37,59} |
| {16,37,60} | {16,37,61} | {16,37,62} | {16,37,63} | {16,37,64} | {16,37,65} | {16,37,66} | {16,38,39} | {16,38,40} |
| {16,38,41} | {16,38,42} | {16,38,43} | {16,38,44} | {16,38,45} | {16,38,46} | {16,38,47} | {16,38,48} | {16,38,49} |
| {16,38,50} | {16,38,51} | {16,38,52} | {16,38,53} | {16,38,54} | {16,38,55} | {16,38,56} | {16,38,57} | {16,38,58} |
| {16,38,59} | {16,38,60} | {16,38,61} | {16,38,62} | {16,38,63} | {16,38,64} | {16,38,65} | {16,38,66} | {16,39,40} |
| {16,39,41} | {16,39,42} | {16,39,43} | {16,39,44} | {16,39,45} | {16,39,46} | {16,39,47} | {16,39,48} | {16,39,49} |
| {16,39,50} | {16,39,51} | {16,39,52} | {16,39,53} | {16,39,54} | {16,39,55} | {16,39,56} | {16,39,57} | {16,39,58} |
| {16,39,59} | {16,39,60} | {16,39,61} | {16,39,62} | {16,39,63} | {16,39,64} | {16,39,65} | {16,39,66} | {16,40,41} |
| {16,40,42} | {16,40,43} | {16,40,44} | {16,40,45} | {16,40,46} | {16,40,47} | {16,40,48} | {16,40,49} | {16,40,50} |
| {16,40,51} | {16,40,52} | {16,40,53} | {16,40,54} | {16,40,55} | {16,40,56} | {16,40,57} | {16,40,58} | {16,40,59} |
| {16,40,60} | {16,40,61} | {16,40,62} | {16,40,63} | {16,40,64} | {16,40,65} | {16,40,66} | {16,41,42} | {16,41,43} |
| {16,41,44} | {16,41,45} | {16,41,46} | {16,41,47} | {16,41,48} | {16,41,49} | {16,41,50} | {16,41,51} | {16,41,52} |
| {16,41,53} | {16,41,54} | {16,41,55} | {16,41,56} | {16,41,57} | {16,41,58} | {16,41,59} | {16,41,60} | {16,41,61} |
| {16,41,62} | {16,41,63} | {16,41,64} | {16,41,65} | {16,41,66} | {16,42,43} | {16,42,44} | {16,42,45} | {16,42,46} |
| {16,42,47} | {16,42,48} | {16,42,49} | {16,42,50} | {16,42,51} | {16,42,52} | {16,42,53} | {16,42,54} | {16,42,55} |
| {16,42,56} | {16,42,57} | {16,42,58} | {16,42,59} | {16,42,60} | {16,42,61} | {16,42,62} | {16,42,63} | {16,42,64} |
| {16,42,65} | {16,42,66} | {16,43,44} | {16,43,45} | {16,43,46} | {16,43,47} | {16,43,48} | {16,43,49} | {16,43,50} |
| {16,43,51} | {16,43,52} | {16,43,53} | {16,43,54} | {16,43,55} | {16,43,56} | {16,43,57} | {16,43,58} | {16,43,59} |
| {16,43,60} | {16,43,61} | {16,43,62} | {16,43,63} | {16,43,64} | {16,43,65} | {16,43,66} | {16,44,45} | {16,44,46} |
| {16,44,47} | {16,44,48} | {16,44,49} | {16,44,50} | {16,44,51} | {16,44,52} | {16,44,53} | {16,44,54} | {16,44,55} |
| {16,44,56} | {16,44,57} | {16,44,58} | {16,44,59} | {16,44,60} | {16,44,61} | {16,44,62} | {16,44,63} | {16,44,64} |
| {16,44,65} | {16,44,66} | {16,45,46} | {16,45,47} | {16,45,48} | {16,45,49} | {16,45,50} | {16,45,51} | {16,45,52} |
| {16,45,53} | {16,45,54} | {16,45,55} | {16,45,56} | {16,45,57} | {16,45,58} | {16,45,59} | {16,45,60} | {16,45,61} |
| {16,45,62} | {16,45,63} | {16,45,64} | {16,45,65} | {16,45,66} | {16,46,47} | {16,46,48} | {16,46,49} | {16,46,50} |
| {16,46,51} | {16,46,52} | {16,46,53} | {16,46,54} | {16,46,55} | {16,46,56} | {16,46,57} | {16,46,58} | {16,46,59} |
| {16,46,60} | {16,46,61} | {16,46,62} | {16,46,63} | {16,46,64} | {16,46,65} | {16,46,66} | {16,47,48} | {16,47,49} |
| {16,47,50} | {16,47,51} | {16,47,52} | {16,47,53} | {16,47,54} | {16,47,55} | {16,47,56} | {16,47,57} | {16,47,58} |
| {16,47,59} | {16,47,60} | {16,47,61} | {16,47,62} | {16,47,63} | {16,47,64} | {16,47,65} | {16,47,66} | {16,48,49} |
| {16,48,50} | {16,48,51} | {16,48,52} | {16,48,53} | {16,48,54} | {16,48,55} | {16,48,56} | {16,48,57} | {16,48,58} |
| {16,48,59} | {16,48,60} | {16,48,61} | {16,48,62} | {16,48,63} | {16,48,64} | {16,48,65} | {16,48,66} | {16,49,50} |
| {16,49,51} | {16,49,52} | {16,49,53} | {16,49,54} | {16,49,55} | {16,49,56} | {16,49,57} | {16,49,58} | {16,49,59} |
| {16,49,60} | {16,49,61} | {16,49,62} | {16,49,63} | {16,49,64} | {16,49,65} | {16,49,66} | {16,50,51} | {16,50,52} |
| {16,50,53} | {16,50,54} | {16,50,55} | {16,50,56} | {16,50,57} | {16,50,58} | {16,50,59} | {16,50,60} | {16,50,61} |
| {16,50,62} | {16,50,63} | {16,50,64} | {16,50,65} | {16,50,66} | {16,51,52} | {16,51,53} | {16,51,54} | {16,51,55} |
| {16,51,56} | {16,51,57} | {16,51,58} | {16,51,59} | {16,51,60} | {16,51,61} | {16,51,62} | {16,51,63} | {16,51,64} |
| {16,51,65} | {16,51,66} | {16,52,53} | {16,52,54} | {16,52,55} | {16,52,56} | {16,52,57} | {16,52,58} | {16,52,59} |
| {16,52,60} | {16,52,61} | {16,52,62} | {16,52,63} | {16,52,64} | {16,52,65} | {16,52,66} | {16,53,54} | {16,53,55} |
| {16,53,56} | {16,53,57} | {16,53,58} | {16,53,59} | {16,53,60} | {16,53,61} | {16,53,62} | {16,53,63} | {16,53,64} |
| {16,53,65} | {16,53,66} | {16,54,55} | {16,54,56} | {16,54,57} | {16,54,58} | {16,54,59} | {16,54,60} | {16,54,61} |
| {16,54,62} | {16,54,63} | {16,54,64} | {16,54,65} | {16,54,66} | {16,55,56} | {16,55,57} | {16,55,58} | {16,55,59} |

TABLE 3A-continued

{16,55,60} {16,55,61} {16,55,62} {16,55,63} {16,55,64} {16,55,65} {16,55,66} {16,56,57} {16,56,58}
{16,56,59} {16,56,60} {16,56,61} {16,56,62} {16,56,63} {16,56,64} {16,56,65} {16,56,66} {16,57,58}
{16,57,59} {16,57,60} {16,57,61} {16,57,62} {16,57,63} {16,57,64} {16,57,65} {16,57,66} {16,58,59}
{16,58,60} {16,58,61} {16,58,62} {16,58,63} {16,58,64} {16,58,65} {16,58,66} {16,59,60} {16,59,61}
{16,59,62} {16,59,63} {16,59,64} {16,59,65} {16,59,66} {16,60,61} {16,60,62} {16,60,63} {16,60,64}
{16,60,65} {16,60,66} {16,61,62} {16,61,63} {16,61,64} {16,61,65} {16,61,66} {16,62,63} {16,62,64}
{16,62,65} {16,62,66} {16,63,64} {16,63,65} {16,63,66} {16,64,65} {16,64,66} {16,65,66} {17,18,19}
{17,18,20} {17,18,21} {17,18,22} {17,18,23} {17,18,24} {17,18,25} {17,18,26} {17,18,27} {17,18,28}
{17,18,29} {17,18,30} {17,18,31} {17,18,32} {17,18,33} {17,18,34} {17,18,35} {17,18,36} {17,18,37}
{17,18,38} {17,18,39} {17,18,40} {17,18,41} {17,18,42} {17,18,43} {17,18,44} {17,18,45} {17,18,46}
{17,18,47} {17,18,48} {17,18,49} {17,18,50} {17,18,51} {17,18,52} {17,18,53} {17,18,54} {17,18,55}
{17,18,56} {17,18,57} {17,18,58} {17,18,59} {17,18,60} {17,18,61} {17,18,62} {17,18,63} {17,18,64}
{17,18,65} {17,18,66} {17,19,20} {17,19,21} {17,19,22} {17,19,23} {17,19,24} {17,19,25} {17,19,26}
{17,19,27} {17,19,28} {17,19,29} {17,19,30} {17,19,31} {17,19,32} {17,19,33} {17,19,34} {17,19,35}
{17,19,36} {17,19,37} {17,19,38} {17,19,39} {17,19,40} {17,19,41} {17,19,42} {17,19,43} {17,19,44}
{17,19,45} {17,19,46} {17,19,47} {17,19,48} {17,19,49} {17,19,50} {17,19,51} {17,19,52} {17,19,53}
{17,19,54} {17,19,55} {17,19,56} {17,19,57} {17,19,58} {17,19,59} {17,19,60} {17,19,61} {17,19,62}
{17,19,63} {17,19,64} {17,19,65} {17,19,66} {17,20,21} {17,20,22} {17,20,23} {17,20,24} {17,20,25}
{17,20,26} {17,20,27} {17,20,28} {17,20,29} {17,20,30} {17,20,31} {17,20,32} {17,20,33} {17,20,34}
{17,20,35} {17,20,36} {17,20,37} {17,20,38} {17,20,39} {17,20,40} {17,20,41} {17,20,42} {17,20,43}
{17,20,44} {17,20,45} {17,20,46} {17,20,47} {17,20,48} {17,20,49} {17,20,50} {17,20,51} {17,20,52}
{17,20,53} {17,20,54} {17,20,55} {17,20,56} {17,20,57} {17,20,58} {17,20,59} {17,20,60} {17,20,61}
{17,20,62} {17,20,63} {17,20,64} {17,20,65} {17,20,66} {17,21,22} {17,21,23} {17,21,24} {17,21,25}
{17,21,26} {17,21,27} {17,21,28} {17,21,29} {17,21,30} {17,21,31} {17,21,32} {17,21,33} {17,21,34}
{17,21,35} {17,21,36} {17,21,37} {17,21,38} {17,21,39} {17,21,40} {17,21,41} {17,21,42} {17,21,43}
{17,21,44} {17,21,45} {17,21,46} {17,21,47} {17,21,48} {17,21,49} {17,21,50} {17,21,51} {17,21,52}
{17,21,53} {17,21,54} {17,21,55} {17,21,56} {17,21,57} {17,21,58} {17,21,59} {17,21,60} {17,21,61}
{17,21,62} {17,21,63} {17,21,64} {17,21,65} {17,21,66} {17,22,23} {17,22,24} {17,22,25} {17,22,26}
{17,22,27} {17,22,28} {17,22,29} {17,22,30} {17,22,31} {17,22,32} {17,22,33} {17,22,34} {17,22,35}
{17,22,36} {17,22,37} {17,22,38} {17,22,39} {17,22,40} {17,22,41} {17,22,42} {17,22,43} {17,22,44}
{17,22,45} {17,22,46} {17,22,47} {17,22,48} {17,22,49} {17,22,50} {17,22,51} {17,22,52} {17,22,53}
{17,22,54} {17,22,55} {17,22,56} {17,22,57} {17,22,58} {17,22,59} {17,22,60} {17,22,61} {17,22,62}
{17,22,63} {17,22,64} {17,22,65} {17,22,66} {17,23,24} {17,23,25} {17,23,26} {17,23,27} {17,23,28}
{17,23,29} {17,23,30} {17,23,31} {17,23,32} {17,23,33} {17,23,34} {17,23,35} {17,23,36} {17,23,37}
{17,23,38} {17,23,39} {17,23,40} {17,23,41} {17,23,42} {17,23,43} {17,23,44} {17,23,45} {17,23,46}
{17,23,47} {17,23,48} {17,23,49} {17,23,50} {17,23,51} {17,23,52} {17,23,53} {17,23,54} {17,23,55}
{17,23,56} {17,23,57} {17,23,58} {17,23,59} {17,23,60} {17,23,61} {17,23,62} {17,23,63} {17,23,64}
{17,23,65} {17,23,66} {17,24,25} {17,24,26} {17,24,27} {17,24,28} {17,24,29} {17,24,30} {17,24,31}
{17,24,32} {17,24,33} {17,24,34} {17,24,35} {17,24,36} {17,24,37} {17,24,38} {17,24,39} {17,24,40}
{17,24,41} {17,24,42} {17,24,43} {17,24,44} {17,24,45} {17,24,46} {17,24,47} {17,24,48} {17,24,49}
{17,24,50} {17,24,51} {17,24,52} {17,24,53} {17,24,54} {17,24,55} {17,24,56} {17,24,57} {17,24,58}
{17,24,59} {17,24,60} {17,24,61} {17,24,62} {17,24,63} {17,24,64} {17,24,65} {17,24,66} {17,25,26}
{17,25,27} {17,25,28} {17,25,29} {17,25,30} {17,25,31} {17,25,32} {17,25,33} {17,25,34} {17,25,35}
{17,25,36} {17,25,37} {17,25,38} {17,25,39} {17,25,40} {17,25,41} {17,25,42} {17,25,43} {17,25,44}
{17,25,45} {17,25,46} {17,25,47} {17,25,48} {17,25,49} {17,25,50} {17,25,51} {17,25,52} {17,25,53}
{17,25,54} {17,25,55} {17,25,56} {17,25,57} {17,25,58} {17,25,59} {17,25,60} {17,25,61} {17,25,62}
{17,25,63} {17,25,64} {17,25,65} {17,25,66} {17,26,27} {17,26,28} {17,26,29} {17,26,30} {17,26,31}
{17,26,32} {17,26,33} {17,26,34} {17,26,35} {17,26,36} {17,26,37} {17,26,38} {17,26,39} {17,26,40}
{17,26,41} {17,26,42} {17,26,43} {17,26,44} {17,26,45} {17,26,46} {17,26,47} {17,26,48} {17,26,49}
{17,26,50} {17,26,51} {17,26,52} {17,26,53} {17,26,54} {17,26,55} {17,26,56} {17,26,57} {17,26,58}
{17,26,59} {17,26,60} {17,26,61} {17,26,62} {17,26,63} {17,26,64} {17,26,65} {17,26,66} {17,27,28}
{17,27,29} {17,27,30} {17,27,31} {17,27,32} {17,27,33} {17,27,34} {17,27,35} {17,27,36} {17,27,37}
{17,27,38} {17,27,39} {17,27,40} {17,27,41} {17,27,42} {17,27,43} {17,27,44} {17,27,45} {17,27,46}
{17,27,47} {17,27,48} {17,27,49} {17,27,50} {17,27,51} {17,27,52} {17,27,53} {17,27,54} {17,27,55}
{17,27,56} {17,27,57} {17,27,58} {17,27,59} {17,27,60} {17,27,61} {17,27,62} {17,27,63} {17,27,64}
{17,27,65} {17,27,66} {17,28,29} {17,28,30} {17,28,31} {17,28,32} {17,28,33} {17,28,34} {17,28,35}
{17,28,36} {17,28,37} {17,28,38} {17,28,39} {17,28,40} {17,28,41} {17,28,42} {17,28,43} {17,28,44}
{17,28,45} {17,28,46} {17,28,47} {17,28,48} {17,28,49} {17,28,50} {17,28,51} {17,28,52} {17,28,53}
{17,28,54} {17,28,55} {17,28,56} {17,28,57} {17,28,58} {17,28,59} {17,28,60} {17,28,61} {17,28,62}
{17,28,63} {17,28,64} {17,28,65} {17,28,66} {17,29,30} {17,29,31} {17,29,32} {17,29,33} {17,29,34}
{17,29,35} {17,29,36} {17,29,37} {17,29,38} {17,29,39} {17,29,40} {17,29,41} {17,29,42} {17,29,43}
{17,29,44} {17,29,45} {17,29,46} {17,29,47} {17,29,48} {17,29,49} {17,29,50} {17,29,51} {17,29,52}
{17,29,53} {17,29,54} {17,29,55} {17,29,56} {17,29,57} {17,29,58} {17,29,59} {17,29,60} {17,29,61}
{17,29,62} {17,29,63} {17,29,64} {17,29,65} {17,29,66} {17,30,31} {17,30,32} {17,30,33} {17,30,34}
{17,30,35} {17,30,36} {17,30,37} {17,30,38} {17,30,39} {17,30,40} {17,30,41} {17,30,42} {17,30,43}
{17,30,44} {17,30,45} {17,30,46} {17,30,47} {17,30,48} {17,30,49} {17,30,50} {17,30,51} {17,30,52}
{17,30,53} {17,30,54} {17,30,55} {17,30,56} {17,30,57} {17,30,58} {17,30,59} {17,30,60} {17,30,61}
{17,30,62} {17,30,63} {17,30,64} {17,30,65} {17,30,66} {17,31,32} {17,31,33} {17,31,34} {17,31,35}
{17,31,36} {17,31,37} {17,31,38} {17,31,39} {17,31,40} {17,31,41} {17,31,42} {17,31,43} {17,31,44}
{17,31,45} {17,31,46} {17,31,47} {17,31,48} {17,31,49} {17,31,50} {17,31,51} {17,31,52} {17,31,53}
{17,31,54} {17,31,55} {17,31,56} {17,31,57} {17,31,58} {17,31,59} {17,31,60} {17,31,61} {17,31,62}
{17,31,63} {17,31,64} {17,31,65} {17,31,66} {17,32,33} {17,32,34} {17,32,35} {17,32,36} {17,32,37}
{17,32,38} {17,32,39} {17,32,40} {17,32,41} {17,32,42} {17,32,43} {17,32,44} {17,32,45} {17,32,46}
{17,32,47} {17,32,48} {17,32,49} {17,32,50} {17,32,51} {17,32,52} {17,32,53} {17,32,54} {17,32,55}
{17,32,56} {17,32,57} {17,32,58} {17,32,59} {17,32,60} {17,32,61} {17,32,62} {17,32,63} {17,32,64}
{17,32,65} {17,32,66} {17,33,34} {17,33,35} {17,33,36} {17,33,37} {17,33,38} {17,33,39} {17,33,40}
{17,33,41} {17,33,42} {17,33,43} {17,33,44} {17,33,45} {17,33,46} {17,33,47} {17,33,48} {17,33,49}
{17,33,50} {17,32,51} {17,33,52} {17,33,53} {17,33,54} {17,33,55} {17,33,56} {17,33,57} {17,33,58}
{17,33,59} {17,33,60} {17,33,61} {17,33,62} {17,33,63} {17,33,64} {17,33,65} {17,33,66} {17,34,35}
{17,34,36} {17,34,37} {17,34,38} {17,34,39} {17,34,40} {17,34,41} {17,34,42} {17,34,43} {17,34,44}

TABLE 3A-continued

{17,34,45} {17,34,46} {17,34,47} {17,34,48} {17,34,49} {17,34,50} {17,34,51} {17,34,52} {17,34,53}
{17,34,54} {17,34,55} {17,34,56} {17,34,57} {17,34,58} {17,34,59} {17,34,60} {17,34,61} {17,34,62}
{17,34,63} {17,34,64} {17,34,65} {17,34,66} {17,35,36} {17,35,37} {17,35,38} {17,35,39} {17,35,40}
{17,35,41} {17,35,42} {17,35,43} {17,35,44} {17,35,45} {17,35,46} {17,35,47} {17,35,48} {17,35,49}
{17,35,50} {17,35,51} {17,35,52} {17,35,53} {17,35,54} {17,35,55} {17,35,56} {17,35,57} {17,35,58}
{17,35,59} {17,35,60} {17,35,61} {17,35,62} {17,35,63} {17,35,64} {17,35,65} {17,35,66} {17,36,37}
{17,36,38} {17,36,39} {17,36,40} {17,36,41} {17,36,42} {17,36,43} {17,36,44} {17,36,45} {17,36,46}
{17,36,47} {17,36,48} {17,36,49} {17,36,50} {17,36,51} {17,36,52} {17,36,53} {17,36,54} {17,36,55}
{17,36,56} {17,36,57} {17,36,58} {17,36,59} {17,36,60} {17,36,61} {17,36,62} {17,36,63} {17,36,64}
{17,36,65} {17,36,66} {17,37,38} {17,37,39} {17,37,40} {17,37,41} {17,37,42} {17,37,43} {17,37,44}
{17,37,45} {17,37,46} {17,37,47} {17,37,48} {17,37,49} {17,37,50} {17,37,51} {17,37,52} {17,37,53}
{17,37,54} {17,37,55} {17,37,56} {17,37,57} {17,37,58} {17,37,59} {17,37,60} {17,37,61} {17,37,62}
{17,37,63} {17,37,64} {17,37,65} {17,37,66} {17,38,39} {17,38,40} {17,38,41} {17,38,42} {17,38,43}
{17,38,44} {17,38,45} {17,38,46} {17,38,47} {17,38,48} {17,38,49} {17,38,50} {17,38,51} {17,38,52}
{17,38,53} {17,38,54} {17,38,55} {17,38,56} {17,38,57} {17,38,58} {17,38,59} {17,38,60} {17,38,61}
{17,38,62} {17,38,63} {17,38,64} {17,38,65} {17,38,66} {17,39,40} {17,39,41} {17,39,42} {17,39,43}
{17,39,44} {17,39,45} {17,39,46} {17,39,47} {17,39,48} {17,39,49} {17,39,50} {17,39,51} {17,39,52}
{17,39,53} {17,39,54} {17,39,55} {17,39,56} {17,39,57} {17,39,58} {17,39,59} {17,39,60} {17,39,61}
{17,39,62} {17,39,63} {17,39,64} {17,39,65} {17,39,66} {17,40,41} {17,40,42} {17,40,43} {17,40,44}
{17,40,45} {17,40,46} {17,40,47} {17,40,48} {17,40,49} {17,40,50} {17,40,51} {17,40,52} {17,40,53}
{17,40,54} {17,40,55} {17,40,56} {17,40,57} {17,40,58} {17,40,59} {17,40,60} {17,40,61} {17,40,62}
{17,40,63} {17,40,64} {17,40,65} {17,40,66} {17,41,42} {17,41,43} {17,41,44} {17,41,45} {17,41,46}
{17,41,47} {17,41,48} {17,41,49} {17,41,50} {17,41,51} {17,41,52} {17,41,53} {17,41,54} {17,41,55}
{17,41,56} {17,41,57} {17,41,58} {17,41,59} {17,41,60} {17,41,61} {17,41,62} {17,41,63} {17,41,64}
{17,41,65} {17,41,66} {17,42,43} {17,42,44} {17,42,45} {17,42,46} {17,42,47} {17,42,48} {17,42,49}
{17,42,50} {17,42,51} {17,42,52} {17,42,53} {17,42,54} {17,42,55} {17,42,56} {17,42,57} {17,42,58}
{17,42,59} {17,42,60} {17,42,61} {17,42,62} {17,42,63} {17,42,64} {17,42,65} {17,42,66} {17,43,44}
{17,43,45} {17,43,46} {17,43,47} {17,43,48} {17,43,49} {17,43,50} {17,43,51} {17,43,52} {17,43,53}
{17,43,54} {17,43,55} {17,43,56} {17,43,57} {17,43,58} {17,43,59} {17,43,60} {17,43,61} {17,43,62}
{17,43,63} {17,43,64} {17,43,65} {17,43,66} {17,44,45} {17,44,46} {17,44,47} {17,44,48} {17,44,49}
{17,44,50} {17,44,51} {17,44,52} {17,44,53} {17,44,54} {17,44,55} {17,44,56} {17,44,57} {17,44,58}
{17,44,59} {17,44,60} {17,44,61} {17,44,62} {17,44,63} {17,44,64} {17,44,65} {17,44,66} {17,45,46}
{17,45,47} {17,45,48} {17,45,49} {17,45,50} {17,45,51} {17,45,52} {17,45,53} {17,45,54} {17,45,55}
{17,45,56} {17,45,57} {17,45,58} {17,45,59} {17,45,60} {17,45,61} {17,45,62} {17,45,63} {17,45,64}
{17,45,65} {17,45,66} {17,46,47} {17,46,48} {17,46,49} {17,46,50} {17,46,51} {17,46,52} {17,46,53}
{17,46,54} {17,46,55} {17,46,56} {17,46,57} {17,46,58} {17,46,59} {17,46,60} {17,46,61} {17,46,62}
{17,46,63} {17,46,64} {17,46,65} {17,46,66} {17,47,48} {17,47,49} {17,47,50} {17,47,51} {17,47,52}
{17,47,53} {17,47,54} {17,47,55} {17,47,56} {17,47,57} {17,47,58} {17,47,59} {17,47,60} {17,47,61}
{17,47,62} {17,47,63} {17,47,64} {17,47,65} {17,47,66} {17,48,49} {17,48,50} {17,48,51} {17,48,52}
{17,48,53} {17,48,54} {17,48,55} {17,48,56} {17,48,57} {17,48,58} {17,48,59} {17,48,60} {17,48,61}
{17,48,62} {17,48,63} {17,48,64} {17,48,65} {17,48,66} {17,49,50} {17,49,51} {17,49,52} {17,49,53}
{17,49,54} {17,49,55} {17,49,56} {17,49,57} {17,49,58} {17,49,59} {17,49,60} {17,49,61} {17,49,62}
{17,49,63} {17,49,64} {17,49,65} {17,49,66} {17,50,51} {17,50,52} {17,50,53} {17,50,54} {17,50,55}
{17,50,56} {17,50,57} {17,50,58} {17,50,59} {17,50,60} {17,50,61} {17,50,62} {17,50,63} {17,50,64}
{17,50,65} {17,50,66} {17,51,52} {17,51,53} {17,51,54} {17,51,55} {17,51,56} {17,51,57} {17,51,58}
{17,51,59} {17,51,60} {17,51,61} {17,51,62} {17,51,63} {17,51,64} {17,51,65} {17,51,66} {17,52,53}
{17,52,54} {17,52,55} {17,52,56} {17,52,57} {17,52,58} {17,52,59} {17,52,60} {17,52,61} {17,52,62}
{17,52,63} {17,52,64} {17,52,65} {17,52,66} {17,53,54} {17,53,55} {17,53,56} {17,53,57} {17,53,58}
{17,53,59} {17,53,60} {17,53,61} {17,53,62} {17,53,63} {17,53,64} {17,53,65} {17,53,66} {17,54,55}
{17,54,56} {17,54,57} {17,54,58} {17,54,59} {17,54,60} {17,54,61} {17,54,62} {17,54,63} {17,54,64}
{17,54,65} {17,54,66} {17,55,56} {17,55,57} {17,55,58} {17,55,59} {17,55,60} {17,55,61} {17,55,62}
{17,55,63} {17,55,64} {17,55,65} {17,55,66} {17,56,57} {17,56,58} {17,56,59} {17,56,60} {17,56,61}
{17,56,62} {17,56,63} {17,56,64} {17,56,65} {17,56,66} {17,57,58} {17,57,59} {17,57,60} {17,57,61}
{17,57,62} {17,57,63} {17,57,64} {17,57,65} {17,57,66} {17,58,59} {17,58,60} {17,58,61} {17,58,62}
{17,58,63} {17,58,64} {17,58,65} {17,58,66} {17,59,60} {17,59,61} {17,59,62} {17,59,63} {17,59,64}
{17,59,65} {17,59,66} {17,60,61} {17,60,62} {17,60,63} {17,60,64} {17,60,65} {17,60,66} {17,61,62}
{17,61,63} {17,61,64} {17,61,65} {17,61,66} {17,62,63} {17,62,64} {17,62,65} {17,62,66} {17,63,64}
{17,63,65} {17,63,66} {17,64,65} {17,64,66} {17,65,66} {18,19,20} {18,19,21} {18,19,22} {18,19,23}
{18,19,24} {18,19,25} {18,19,26} {18,19,27} {18,19,28} {18,19,29} {18,19,30} {18,19,31} {18,19,32}
{18,19,33} {18,19,34} {18,19,35} {18,19,36} {18,19,37} {18,19,38} {18,19,39} {18,19,40} {18,19,41}
{18,19,42} {18,19,43} {18,19,44} {18,19,45} {18,19,46} {18,19,47} {18,19,48} {18,19,49} {18,19,50}
{18,19,51} {18,19,52} {18,19,53} {18,19,54} {18,19,55} {18,19,56} {18,19,57} {18,19,58} {18,19,59}
{18,19,60} {18,19,61} {18,19,62} {18,19,63} {18,19,64} {18,19,65} {18,19,66} {18,20,21} {18,20,22}
{18,20,23} {18,20,24} {18,20,25} {18,20,26} {18,20,27} {18,20,28} {18,20,29} {18,20,30} {18,20,31}
{18,20,32} {18,20,33} {18,20,34} {18,20,35} {18,20,36} {18,20,37} {18,20,38} {18,20,39} {18,20,40}
{18,20,41} {18,20,42} {18,20,43} {18,20,44} {18,20,45} {18,20,46} {18,20,47} {18,20,48} {18,20,49}
{18,20,50} {18,20,51} {18,20,52} {18,20,53} {18,20,54} {18,20,55} {18,20,56} {18,20,57} {18,20,58}
{18,20,59} {18,20,60} {18,20,61} {18,20,62} {18,20,63} {18,20,64} {18,20,65} {18,20,66} {18,21,22}
{18,21,23} {18,21,24} {18,21,25} {18,21,26} {18,21,27} {18,21,28} {18,21,29} {18,21,30} {18,21,31}
{18,21,32} {18,21,33} {18,21,34} {18,21,35} {18,21,36} {18,21,37} {18,21,38} {18,21,39} {18,21,40}
{18,21,41} {18,21,42} {18,21,43} {18,21,44} {18,21,45} {18,21,46} {18,21,47} {18,21,48} {18,21,49}
{18,21,50} {18,21,51} {18,21,52} {18,21,53} {18,21,54} {18,21,55} {18,21,56} {18,21,57} {18,21,58}
{18,21,59} {18,21,60} {18,21,61} {18,21,62} {18,21,63} {18,21,64} {18,21,65} {18,21,66} {18,22,23}
{18,22,24} {18,22,25} {18,22,26} {18,22,27} {18,22,28} {18,22,29} {18,22,30} {18,22,31} {18,22,32}
{18,22,33} {18,22,34} {18,22,35} {18,22,36} {18,22,37} {18,22,38} {18,22,39} {18,22,40} {18,22,41}
{18,22,42} {18,22,43} {18,22,44} {18,22,45} {18,22,46} {18,22,47} {18,22,48} {18,22,49} {18,22,50}
{18,22,51} {18,22,52} {18,22,53} {18,22,54} {18,22,55} {18,22,56} {18,22,57} {18,22,58} {18,22,59}
{18,22,60} {18,22,61} {18,22,62} {18,22,63} {18,22,64} {18,22,65} {18,22,66} {18,23,24} {18,23,25}
{18,23,26} {18,23,27} {18,23,28} {18,23,29} {18,23,30} {18,23,31} {18,23,32} {18,23,33} {18,23,34}
{18,23,35} {18,23,36} {18,23,37} {18,23,38} {18,23,39} {18,23,40} {18,23,41} {18,23,42} {18,23,43}

TABLE 3A-continued

{18,23,44} {18,23,45} {18,23,46} {18,23,47} {18,23,48} {18,23,49} {18,23,50} {18,23,51} {18,23,52}
{18,23,53} {18,23,54} {18,23,55} {18,23,56} {18,23,57} {18,23,58} {18,23,59} {18,23,60} {18,23,61}
{18,23,62} {18,23,63} {18,23,64} {18,23,65} {18,23,66} {18,24,25} {18,24,26} {18,24,27} {18,24,28}
{18,24,29} {18,24,30} {18,24,31} {18,24,32} {18,24,33} {18,24,34} {18,24,35} {18,24,36} {18,24,37}
{18,24,38} {18,24,39} {18,24,40} {18,24,41} {18,24,42} {18,24,43} {18,24,44} {18,24,45} {18,24,46}
{18,24,47} {18,24,48} {18,24,49} {18,24,50} {18,24,51} {18,24,52} {18,24,53} {18,24,54} {18,24,55}
{18,24,56} {18,24,57} {18,24,58} {18,24,59} {18,24,60} {18,24,61} {18,24,62} {18,24,63} {18,24,64}
{18,24,65} {18,24,66} {18,25,26} {18,25,27} {18,25,28} {18,25,29} {18,25,30} {18,25,31} {18,25,32}
{18,25,33} {18,25,34} {18,25,35} {18,25,36} {18,25,37} {18,25,38} {18,25,39} {18,25,40} {18,25,41}
{18,25,42} {18,25,43} {18,25,44} {18,25,45} {18,25,46} {18,25,47} {18,25,48} {18,25,49} {18,25,50}
{18,25,51} {18,25,52} {18,25,53} {18,25,54} {18,25,55} {18,25,56} {18,25,57} {18,25,58} {18,25,59}
{18,25,60} {18,25,61} {18,25,62} {18,25,63} {18,25,64} {18,25,65} {18,25,66} {18,26,27} {18,26,28}
{18,26,29} {18,26,30} {18,26,31} {18,26,32} {18,26,33} {18,26,34} {18,26,35} {18,26,36} {18,26,37}
{18,26,38} {18,26,39} {18,26,40} {18,26,41} {18,26,42} {18,26,43} {18,26,44} {18,26,45} {18,26,46}
{18,26,47} {18,26,48} {18,26,49} {18,26,50} {18,26,51} {18,26,52} {18,26,53} {18,26,54} {18,26,55}
{18,26,56} {18,26,57} {18,26,58} {18,26,59} {18,26,60} {18,26,61} {18,26,62} {18,26,63} {18,26,64}
{18,26,65} {18,26,66} {18,27,28} {18,27,29} {18,27,30} {18,27,31} {18,27,32} {18,27,33} {18,27,34}
{18,27,35} {18,27,36} {18,27,37} {18,27,38} {18,27,39} {18,27,40} {18,27,41} {18,27,42} {18,27,43}
{18,27,44} {18,27,45} {18,27,46} {18,27,47} {18,27,48} {18,27,49} {18,27,50} {18,27,51} {18,27,52}
{18,27,53} {18,27,54} {18,27,55} {18,27,56} {18,27,57} {18,27,58} {18,27,59} {18,27,60} {18,27,61}
{18,27,62} {18,27,63} {18,27,64} {18,27,65} {18,27,66} {18,28,29} {18,28,30} {18,28,31} {18,28,32}
{18,28,33} {18,28,34} {18,28,35} {18,28,36} {18,28,37} {18,28,38} {18,28,39} {18,28,40} {18,28,41}
{18,28,42} {18,28,43} {18,28,44} {18,28,45} {18,28,46} {18,28,47} {18,28,48} {18,28,49} {18,28,50}
{18,28,51} {18,28,52} {18,28,53} {18,28,54} {18,28,55} {18,28,56} {18,28,57} {18,28,58} {18,28,59}
{18,28,60} {18,28,61} {18,28,62} {18,28,63} {18,28,64} {18,28,65} {18,28,66} {18,29,30} {18,29,31}
{18,29,32} {18,29,33} {18,29,34} {18,29,35} {18,29,36} {18,29,37} {18,29,38} {18,29,39} {18,29,40}
{18,29,41} {18,29,42} {18,29,43} {18,29,44} {18,29,45} {18,29,46} {18,29,47} {18,29,48} {18,29,49}
{18,29,50} {18,29,51} {18,29,52} {18,29,53} {18,29,54} {18,29,55} {18,29,56} {18,29,57} {18,29,58}
{18,29,59} {18,29,60} {18,29,61} {18,29,62} {18,29,63} {18,29,64} {18,29,65} {18,29,66} {18,30,31}
{18,30,32} {18,30,33} {18,30,34} {18,30,35} {18,30,36} {18,30,37} {18,30,38} {18,30,39} {18,30,40}
{18,30,41} {18,30,42} {18,30,43} {18,30,44} {18,30,45} {18,30,46} {18,30,47} {18,30,48} {18,30,49}
{18,30,50} {18,30,51} {18,30,52} {18,30,53} {18,30,54} {18,30,55} {18,30,56} {18,30,57} {18,30,58}
{18,30,59} {18,30,60} {18,30,61} {18,30,62} {18,30,63} {18,30,64} {18,30,65} {18,30,66} {18,31,32}
{18,31,33} {18,31,34} {18,31,35} {18,31,36} {18,31,37} {18,31,38} {18,31,39} {18,31,40} {18,31,41}
{18,31,42} {18,31,43} {18,31,44} {18,31,45} {18,31,46} {18,31,47} {18,31,48} {18,31,49} {18,31,50}
{18,31,51} {18,31,52} {18,31,53} {18,31,54} {18,31,55} {18,31,56} {18,31,57} {18,31,58} {18,31,59}
{18,31,60} {18,31,61} {18,31,62} {18,31,63} {18,31,64} {18,31,65} {18,31,66} {18,32,33} {18,32,34}
{18,32,35} {18,32,36} {18,32,37} {18,32,38} {18,32,39} {18,32,40} {18,32,41} {18,32,42} {18,32,43}
{18,32,44} {18,32,45} {18,32,46} {18,32,47} {18,32,48} {18,32,49} {18,32,50} {18,32,51} {18,32,52}
{18,32,53} {18,32,54} {18,32,55} {18,32,56} {18,32,57} {18,32,58} {18,32,59} {18,32,60} {18,32,61}
{18,32,62} {18,32,63} {18,32,64} {18,32,65} {18,32,66} {18,33,34} {18,33,35} {18,33,36} {18,33,37}
{18,33,38} {18,33,39} {18,33,40} {18,33,41} {18,33,42} {18,33,43} {18,33,44} {18,33,45} {18,33,46}
{18,33,47} {18,33,48} {18,33,49} {18,33,50} {18,33,51} {18,33,52} {18,33,53} {18,33,54} {18,33,55}
{18,33,56} {18,33,57} {18,33,58} {18,33,59} {18,33,60} {18,33,61} {18,33,62} {18,33,63} {18,33,64}
{18,33,65} {18,33,66} {18,34,35} {18,34,36} {18,34,37} {18,34,38} {18,34,39} {18,34,40} {18,34,41}
{18,34,42} {18,34,43} {18,34,44} {18,34,45} {18,34,46} {18,34,47} {18,34,48} {18,34,49} {18,34,50}
{18,34,51} {18,34,52} {18,34,53} {18,34,54} {18,34,55} {18,34,56} {18,34,57} {18,34,58} {18,34,59}
{18,34,60} {18,34,61} {18,34,62} {18,34,63} {18,34,64} {18,34,65} {18,34,66} {18,35,36} {18,35,37}
{18,35,38} {18,35,39} {18,35,40} {18,35,41} {18,35,42} {18,35,43} {18,35,44} {18,35,45} {18,35,46}
{18,35,47} {18,35,48} {18,35,49} {18,35,50} {18,35,51} {18,35,52} {18,35,53} {18,35,54} {18,35,55}
{18,35,56} {18,35,57} {18,35,58} {18,35,59} {18,35,60} {18,35,61} {18,35,62} {18,35,63} {18,35,64}
{18,35,65} {18,35,66} {18,36,37} {18,36,38} {18,36,39} {18,36,40} {18,36,41} {18,36,42} {18,36,43}
{18,36,44} {18,36,45} {18,36,46} {18,36,47} {18,36,48} {18,36,49} {18,36,50} {18,36,51} {18,36,52}
{18,36,53} {18,36,54} {18,36,55} {18,36,56} {18,36,57} {18,36,58} {18,36,59} {18,36,60} {18,36,61}
{18,36,62} {18,36,63} {18,36,64} {18,36,65} {18,36,66} {18,37,38} {18,37,39} {18,37,40} {18,37,41}
{18,37,42} {18,37,43} {18,37,44} {18,37,45} {18,37,46} {18,37,47} {18,37,48} {18,37,49} {18,37,50}
{18,37,51} {18,37,52} {18,37,53} {18,37,54} {18,37,55} {18,37,56} {18,37,57} {18,37,58} {18,37,59}
{18,37,60} {18,37,61} {18,37,62} {18,37,63} {18,37,64} {18,37,65} {18,37,66} {18,38,39} {18,38,40}
{18,38,41} {18,38,42} {18,38,43} {18,38,44} {18,38,45} {18,38,46} {18,38,47} {18,38,48} {18,38,49}
{18,38,50} {18,38,51} {18,38,52} {18,38,53} {18,38,54} {18,38,55} {18,38,56} {18,38,57} {18,38,58}
{18,38,59} {18,38,60} {18,38,61} {18,38,62} {18,38,63} {18,38,64} {18,38,65} {18,38,66} {18,39,40}
{18,39,41} {18,39,42} {18,39,43} {18,39,44} {18,39,45} {18,39,46} {18,39,47} {18,39,48} {18,39,49}
{18,39,50} {18,39,51} {18,39,52} {18,39,53} {18,39,54} {18,39,55} {18,39,56} {18,39,57} {18,39,58}
{18,39,59} {18,39,60} {18,39,61} {18,39,62} {18,39,63} {18,39,64} {18,39,65} {18,39,66} {18,40,41}
{18,40,42} {18,40,43} {18,40,44} {18,40,45} {18,40,46} {18,40,47} {18,40,48} {18,40,49} {18,40,50}
{18,40,51} {18,40,52} {18,40,53} {18,40,54} {18,40,55} {18,40,56} {18,40,57} {18,40,58} {18,40,59}
{18,40,60} {18,40,61} {18,40,62} {18,40,63} {18,40,64} {18,40,65} {18,40,66} {18,41,42} {18,41,43}
{18,41,44} {18,41,45} {18,41,46} {18,41,47} {18,41,48} {18,41,49} {18,41,50} {18,41,51} {18,41,52}
{18,41,53} {18,41,54} {18,41,55} {18,41,56} {18,41,57} {18,41,58} {18,41,59} {18,41,60} {18,41,61}
{18,41,62} {18,41,63} {18,41,64} {18,41,65} {18,41,66} {18,42,43} {18,42,44} {18,42,45} {18,42,46}
{18,42,47} {18,42,48} {18,42,49} {18,42,50} {18,42,51} {18,42,52} {18,42,53} {18,42,54} {18,42,55}
{18,42,56} {18,42,57} {18,42,58} {18,42,59} {18,42,60} {18,42,61} {18,42,62} {18,42,63} {18,42,64}
{18,42,65} {18,42,66} {18,43,44} {18,43,45} {18,43,46} {18,43,47} {18,43,48} {18,43,49} {18,43,50}
{18,43,51} {18,43,52} {18,43,53} {18,43,54} {18,43,55} {18,43,56} {18,43,57} {18,43,58} {18,43,59}
{18,43,60} {18,43,61} {18,43,62} {18,43,63} {18,43,64} {18,43,65} {18,43,66} {18,44,45} {18,44,46}
{18,44,47} {18,44,48} {18,44,49} {18,44,50} {18,44,51} {18,44,52} {18,44,53} {18,44,54} {18,44,55}
{18,44,56} {18,44,57} {18,44,58} {18,44,59} {18,44,60} {18,44,61} {18,44,62} {18,44,63} {18,44,64}
{18,44,65} {18,44,66} {18,45,46} {18,45,47} {18,45,48} {18,45,49} {18,45,50} {18,45,51} {18,45,52}
{18,45,53} {18,45,54} {18,45,55} {18,45,56} {18,45,57} {18,45,58} {18,45,59} {18,45,60} {18,45,61}
{18,45,62} {18,45,63} {18,45,64} {18,45,65} {18,45,66} {18,46,47} {18,46,48} {18,46,49} {18,46,50}

TABLE 3A-continued

{18,46,51} {18,46,52} {18,46,53} {18,46,54} {18,46,55} {18,46,56} {18,46,57} {18,46,58} {18,46,59}
{18,46,60} {18,46,61} {18,46,62} {18,46,63} {18,46,64} {18,46,65} {18,46,66} {18,47,48} {18,47,49}
{18,47,50} {18,47,51} {18,47,52} {18,47,53} {18,47,54} {18,47,55} {18,47,56} {18,47,57} {18,47,58}
{18,47,59} {18,47,60} {18,47,61} {18,47,62} {18,47,63} {18,47,64} {18,47,65} {18,47,66} {18,48,49}
{18,48,50} {18,48,51} {18,48,52} {18,48,53} {18,48,54} {18,48,55} {18,48,56} {18,48,57} {18,48,58}
{18,48,59} {18,48,60} {18,48,61} {18,48,62} {18,48,63} {18,48,64} {18,48,65} {18,48,66} {18,49,50}
{18,49,51} {18,49,52} {18,49,53} {18,49,54} {18,49,55} {18,49,56} {18,49,57} {18,49,58} {18,49,59}
{18,49,60} {18,49,61} {18,49,62} {18,49,63} {18,49,64} {18,49,65} {18,49,66} {18,50,51} {18,50,52}
{18,50,53} {18,50,54} {18,50,55} {18,50,56} {18,50,57} {18,50,58} {18,50,59} {18,50,60} {18,50,61}
{18,50,62} {18,50,63} {18,50,64} {18,50,65} {18,50,66} {18,51,52} {18,51,53} {18,51,54} {18,51,55}
{18,51,56} {18,51,57} {18,51,58} {18,51,59} {18,51,60} {18,51,61} {18,51,62} {18,51,63} {18,51,64}
{18,51,65} {18,51,66} {18,52,53} {18,52,54} {18,52,55} {18,52,56} {18,52,57} {18,52,58} {18,52,59}
{18,52,60} {18,52,61} {18,52,62} {18,52,63} {18,52,64} {18,52,65} {18,52,66} {18,53,54} {18,53,55}
{18,53,56} {18,53,57} {18,53,58} {18,53,59} {18,53,60} {18,53,61} {18,53,62} {18,53,63} {18,53,64}
{18,53,65} {18,53,66} {18,54,55} {18,54,56} {18,54,57} {18,54,58} {18,54,59} {18,54,60} {18,54,61}
{18,54,62} {18,54,63} {18,54,64} {18,54,65} {18,54,66} {18,55,56} {18,55,57} {18,55,58} {18,55,59}
{18,55,60} {18,55,61} {18,55,62} {18,55,63} {18,55,64} {18,55,65} {18,55,66} {18,56,57} {18,56,58}
{18,56,59} {18,56,60} {18,56,61} {18,56,62} {18,56,63} {18,56,64} {18,56,65} {18,56,66} {18,57,58}
{18,57,59} {18,57,60} {18,57,61} {18,57,62} {18,57,63} {18,57,64} {18,57,65} {18,57,66} {18,58,59}
{18,58,60} {18,58,61} {18,58,62} {18,58,63} {18,58,64} {18,58,65} {18,58,66} {18,59,60} {18,59,61}
{18,59,62} {18,59,63} {18,59,64} {18,59,65} {18,59,66} {18,60,61} {18,60,62} {18,60,63} {18,60,64}
{18,60,65} {18,60,66} {18,61,62} {18,61,63} {18,61,64} {18,61,65} {18,61,66} {18,62,63} {18,62,64}
{18,62,65} {18,62,66} {18,63,64} {18,63,65} {18,63,66} {18,64,65} {18,64,66} {18,65,66} {19,20,21}
{19,20,22} {19,20,23} {19,20,24} {19,20,25} {19,20,26} {19,20,27} {19,20,28} {19,20,29} {19,20,30}
{19,20,31} {19,20,32} {19,20,33} {19,20,34} {19,20,35} {19,20,36} {19,20,37} {19,20,38} {19,20,39}
{19,20,40} {19,20,41} {19,20,42} {19,20,43} {19,20,44} {19,20,45} {19,20,46} {19,20,47} {19,20,48}
{19,20,49} {19,20,50} {19,20,51} {19,20,52} {19,20,53} {19,20,54} {19,20,55} {19,20,56} {19,20,57}
{19,20,58} {19,20,59} {19,20,60} {19,20,61} {19,20,62} {19,20,63} {19,20,64} {19,20,65} {19,20,66}
{19,21,22} {19,21,23} {19,21,24} {19,21,25} {19,21,26} {19,21,27} {19,21,28} {19,21,29} {19,21,30}
{19,21,31} {19,21,32} {19,21,33} {19,21,34} {19,21,35} {19,21,36} {19,21,37} {19,21,38} {19,21,39}
{19,21,40} {19,21,41} {19,21,42} {19,21,43} {19,21,44} {19,21,45} {19,21,46} {19,21,47} {19,21,48}
{19,21,49} {19,21,50} {19,21,51} {19,21,52} {19,21,53} {19,21,54} {19,21,55} {19,21,56} {19,21,57}
{19,21,58} {19,21,59} {19,21,60} {19,21,61} {19,21,62} {19,21,63} {19,21,64} {19,21,65} {19,21,66}
{19,22,23} {19,22,24} {19,22,25} {19,22,26} {19,22,27} {19,22,28} {19,22,29} {19,22,30} {19,22,31}
{19,22,32} {19,22,33} {19,22,34} {19,22,35} {19,22,36} {19,22,37} {19,22,38} {19,22,39} {19,22,40}
{19,22,41} {19,22,42} {19,22,43} {19,22,44} {19,22,45} {19,22,46} {19,22,47} {19,22,48} {19,22,49}
{19,22,50} {19,22,51} {19,22,52} {19,22,53} {19,22,54} {19,22,55} {19,22,56} {19,22,57} {19,22,58}
{19,22,59} {19,22,60} {19,22,61} {19,22,62} {19,22,63} {19,22,64} {19,22,65} {19,22,66} {19,23,24}
{19,23,25} {19,23,26} {19,23,27} {19,23,28} {19,23,29} {19,23,30} {19,23,31} {19,23,32} {19,23,33}
{19,23,34} {19,23,35} {19,23,36} {19,23,37} {19,23,38} {19,23,39} {19,23,40} {19,23,41} {19,23,42}
{19,23,43} {19,23,44} {19,23,45} {19,23,46} {19,23,47} {19,23,48} {19,23,49} {19,23,50} {19,23,51}
{19,23,52} {19,23,53} {19,23,54} {19,23,55} {19,23,56} {19,23,57} {19,23,58} {19,23,59} {19,23,60}
{19,23,61} {19,23,62} {19,23,63} {19,23,64} {19,23,65} {19,23,66} {19,24,25} {19,24,26} {19,24,27}
{19,24,28} {19,24,29} {19,24,30} {19,24,31} {19,24,32} {19,24,33} {19,24,34} {19,24,35} {19,24,36}
{19,24,37} {19,24,38} {19,24,39} {19,24,40} {19,24,41} {19,24,42} {19,24,43} {19,24,44} {19,24,45}
{19,24,46} {19,24,47} {19,24,48} {19,24,49} {19,24,50} {19,24,51} {19,24,52} {19,24,53} {19,24,54}
{19,24,55} {19,24,56} {19,24,57} {19,24,58} {19,24,59} {19,24,60} {19,24,61} {19,24,62} {19,24,63}
{19,24,64} {19,24,65} {19,24,66} {19,25,26} {19,25,27} {19,25,28} {19,25,29} {19,25,30} {19,25,31}
{19,25,32} {19,25,33} {19,25,34} {19,25,35} {19,25,36} {19,25,37} {19,25,38} {19,25,39} {19,25,40}
{19,25,41} {19,25,42} {19,25,43} {19,25,44} {19,25,45} {19,25,46} {19,25,47} {19,25,48} {19,25,49}
{19,25,50} {19,25,51} {19,25,52} {19,25,53} {19,25,54} {19,25,55} {19,25,56} {19,25,57} {19,25,58}
{19,25,59} {19,25,60} {19,25,61} {19,25,62} {19,25,63} {19,25,64} {19,25,65} {19,25,66} {19,26,27}
{19,26,28} {19,26,29} {19,26,30} {19,26,31} {19,26,32} {19,26,33} {19,26,34} {19,26,35} {19,26,36}
{19,26,37} {19,26,38} {19,26,39} {19,26,40} {19,26,41} {19,26,42} {19,26,43} {19,26,44} {19,26,45}
{19,26,46} {19,26,47} {19,26,48} {19,26,49} {19,26,50} {19,26,51} {19,26,52} {19,26,53} {19,26,54}
{19,26,55} {19,26,56} {19,26,57} {19,26,58} {19,26,59} {19,26,60} {19,26,61} {19,26,62} {19,26,63}
{19,26,64} {19,26,65} {19,26,66} {19,27,28} {19,27,29} {19,27,30} {19,27,31} {19,27,32} {19,27,33}
{19,27,34} {19,27,35} {19,27,36} {19,27,37} {19,27,38} {19,27,39} {19,27,40} {19,27,41} {19,27,42}
{19,27,43} {19,27,44} {19,27,45} {19,27,46} {19,27,47} {19,27,48} {19,27,49} {19,27,50} {19,27,51}
{19,27,52} {19,27,53} {19,27,54} {19,27,55} {19,27,56} {19,27,57} {19,27,58} {19,27,59} {19,27,60}
{19,27,61} {19,27,62} {19,27,63} {19,27,64} {19,27,65} {19,27,66} {19,28,29} {19,28,30} {19,28,31}
{19,28,32} {19,28,33} {19,28,34} {19,28,35} {19,28,36} {19,28,37} {19,28,38} {19,28,39} {19,28,40}
{19,28,41} {19,28,42} {19,28,43} {19,28,44} {19,28,45} {19,28,46} {19,28,47} {19,28,48} {19,28,49}
{19,28,50} {19,28,51} {19,28,52} {19,28,53} {19,28,54} {19,28,55} {19,28,56} {19,28,57} {19,28,58}
{19,28,59} {19,28,60} {19,28,61} {19,28,62} {19,28,63} {19,28,64} {19,28,65} {19,28,66} {19,29,30}
{19,29,31} {19,29,32} {19,29,33} {19,29,34} {19,29,35} {19,29,36} {19,29,37} {19,29,38} {19,29,39}
{19,29,40} {19,29,41} {19,29,42} {19,29,43} {19,29,44} {19,29,45} {19,29,46} {19,29,47} {19,29,48}
{19,29,49} {19,29,50} {19,29,51} {19,29,52} {19,29,53} {19,29,54} {19,29,55} {19,29,56} {19,29,57}
{19,29,58} {19,29,59} {19,29,60} {19,29,61} {19,29,62} {19,29,63} {19,29,64} {19,29,65} {19,29,66}
{19,30,31} {19,30,32} {19,30,33} {19,30,34} {19,30,35} {19,30,36} {19,30,37} {19,30,38} {19,30,39}
{19,30,40} {19,30,41} {19,30,42} {19,30,43} {19,30,44} {19,30,45} {19,30,46} {19,30,47} {19,30,48}
{19,30,49} {19,30,50} {19,30,51} {19,30,52} {19,30,53} {19,30,54} {19,30,55} {19,30,56} {19,30,57}
{19,30,58} {19,30,59} {19,30,60} {19,30,61} {19,30,62} {19,30,63} {19,30,64} {19,30,65} {19,30,66}
{19,31,32} {19,31,33} {19,31,34} {19,31,35} {19,31,36} {19,31,37} {19,31,38} {19,31,39} {19,31,40}
{19,31,41} {19,31,42} {19,31,43} {19,31,44} {19,31,45} {19,31,46} {19,31,47} {19,31,48} {19,31,49}
{19,31,50} {19,31,51} {19,31,52} {19,31,53} {19,31,54} {19,31,55} {19,31,56} {19,31,57} {19,31,58}
{19,31,59} {19,31,60} {19,31,61} {19,31,62} {19,31,63} {19,31,64} {19,31,65} {19,31,66} {19,32,33}
{19,32,34} {19,32,35} {19,32,36} {19,32,37} {19,32,38} {19,32,39} {19,32,40} {19,32,41} {19,32,42}
{19,32,43} {19,32,44} {19,32,45} {19,32,46} {19,32,47} {19,32,48} {19,32,49} {19,32,50} {19,32,51}
{19,32,52} {19,32,53} {19,32,54} {19,32,55} {19,32,56} {19,32,57} {19,32,58} {19,32,59} {19,32,60}

TABLE 3A-continued

{19,32,61} {19,32,62} {19,32,63} {19,32,64} {19,32,65} {19,32,66} {19,33,34} {19,33,35} {19,33,36}
{19,33,37} {19,33,38} {19,33,39} {19,33,40} {19,33,41} {19,33,42} {19,33,43} {19,33,44} {19,33,45}
{19,33,46} {19,33,47} {19,33,48} {19,33,49} {19,33,50} {19,33,51} {19,33,52} {19,33,53} {19,33,54}
{19,33,55} {19,33,56} {19,33,57} {19,33,58} {19,33,59} {19,33,60} {19,33,61} {19,33,62} {19,33,63}
{19,33,64} {19,33,65} {19,33,66} {19,34,35} {19,34,36} {19,34,37} {19,34,38} {19,34,39} {19,34,40}
{19,34,41} {19,34,42} {19,34,43} {19,34,44} {19,34,45} {19,34,46} {19,34,47} {19,34,48} {19,34,49}
{19,34,50} {19,34,51} {19,34,52} {19,34,53} {19,34,54} {19,34,55} {19,34,56} {19,34,57} {19,34,58}
{19,34,59} {19,34,60} {19,34,61} {19,34,62} {19,34,63} {19,34,64} {19,34,65} {19,34,66} {19,35,36}
{19,35,37} {19,35,38} {19,35,39} {19,35,40} {19,35,41} {19,35,42} {19,35,43} {19,35,44} {19,35,45}
{19,35,46} {19,35,47} {19,35,48} {19,35,49} {19,35,50} {19,35,51} {19,35,52} {19,35,53} {19,35,54}
{19,35,55} {19,35,56} {19,35,57} {19,35,58} {19,35,59} {19,35,60} {19,35,61} {19,35,62} {19,35,63}
{19,35,64} {19,35,65} {19,35,66} {19,36,37} {19,36,38} {19,36,39} {19,36,40} {19,36,41} {19,36,42}
{19,36,43} {19,36,44} {19,36,45} {19,36,46} {19,36,47} {19,36,48} {19,36,49} {19,36,50} {19,36,51}
{19,36,52} {19,36,53} {19,36,54} {19,36,55} {19,36,56} {19,36,57} {19,36,58} {19,36,59} {19,36,60}
{19,36,61} {19,36,62} {19,36,63} {19,36,64} {19,36,65} {19,36,66} {19,37,38} {19,37,39} {19,37,40}
{19,37,41} {19,37,42} {19,37,43} {19,37,44} {19,37,45} {19,37,46} {19,37,47} {19,37,48} {19,37,49}
{19,37,50} {19,37,51} {19,37,52} {19,37,53} {19,37,54} {19,37,55} {19,37,56} {19,37,57} {19,37,58}
{19,37,59} {19,37,60} {19,37,61} {19,37,62} {19,37,63} {19,37,64} {19,37,65} {19,37,66} {19,38,39}
{19,38,40} {19,38,41} {19,38,42} {19,38,43} {19,38,44} {19,38,45} {19,38,46} {19,38,47} {19,38,48}
{19,38,49} {19,38,50} {19,38,51} {19,38,52} {19,38,53} {19,38,54} {19,38,55} {19,38,56} {19,38,57}
{19,38,58} {19,38,59} {19,38,60} {19,38,61} {19,38,62} {19,38,63} {19,38,64} {19,38,65} {19,38,66}
{19,39,40} {19,39,41} {19,39,42} {19,39,43} {19,39,44} {19,39,45} {19,39,46} {19,39,47} {19,39,48}
{19,39,49} {19,39,50} {19,39,51} {19,39,52} {19,39,53} {19,39,54} {19,39,55} {19,39,56} {19,39,57}
{19,39,58} {19,39,59} {19,39,60} {19,39,61} {19,39,62} {19,39,63} {19,39,64} {19,39,65} {19,39,66}
{19,40,41} {19,40,42} {19,40,43} {19,40,44} {19,40,45} {19,40,46} {19,40,47} {19,40,48} {19,40,49}
{19,40,50} {19,40,51} {19,40,52} {19,40,53} {19,40,54} {19,40,55} {19,40,56} {19,40,57} {19,40,58}
{19,40,59} {19,40,60} {19,40,61} {19,40,62} {19,40,63} {19,40,64} {19,40,65} {19,40,66} {19,41,42}
{19,41,43} {19,41,44} {19,41,45} {19,41,46} {19,41,47} {19,41,48} {19,41,49} {19,41,50} {19,41,51}
{19,41,52} {19,41,53} {19,41,54} {19,41,55} {19,41,56} {19,41,57} {19,41,58} {19,41,59} {19,41,60}
{19,41,61} {19,41,62} {19,41,63} {19,41,64} {19,41,65} {19,41,66} {19,42,43} {19,42,44} {19,42,45}
{19,42,46} {19,42,47} {19,42,48} {19,42,49} {19,42,50} {19,42,51} {19,42,52} {19,42,53} {19,42,54}
{19,42,55} {19,42,56} {19,42,57} {19,42,58} {19,42,59} {19,42,60} {19,42,61} {19,42,62} {19,42,63}
{19,42,64} {19,42,65} {19,42,66} {19,43,44} {19,43,45} {19,43,46} {19,43,47} {19,43,48} {19,43,49}
{19,43,50} {19,43,51} {19,43,52} {19,43,53} {19,43,54} {19,43,55} {19,43,56} {19,43,57} {19,43,58}
{19,43,59} {19,43,60} {19,43,61} {19,43,62} {19,43,63} {19,43,64} {19,43,65} {19,43,66} {19,44,45}
{19,44,46} {19,44,47} {19,44,48} {19,44,49} {19,44,50} {19,44,51} {19,44,52} {19,44,53} {19,44,54}
{19,44,55} {19,44,56} {19,44,57} {19,44,58} {19,44,59} {19,44,60} {19,44,61} {19,44,62} {19,44,63}
{19,44,64} {19,44,65} {19,44,66} {19,45,46} {19,45,47} {19,45,48} {19,45,49} {19,45,50} {19,45,51}
{19,45,52} {19,45,53} {19,45,54} {19,45,55} {19,45,56} {19,45,57} {19,45,58} {19,45,59} {19,45,60}
{19,45,61} {19,45,62} {19,45,63} {19,45,64} {19,45,65} {19,45,66} {19,46,47} {19,46,48} {19,46,49}
{19,46,50} {19,46,51} {19,46,52} {19,46,53} {19,46,54} {19,46,55} {19,46,56} {19,46,57} {19,46,58}
{19,46,59} {19,46,60} {19,46,61} {19,46,62} {19,46,63} {19,46,64} {19,46,65} {19,46,66} {19,47,48}
{19,47,49} {19,47,50} {19,47,51} {19,47,52} {19,47,53} {19,47,54} {19,47,55} {19,47,56} {19,47,57}
{19,47,58} {19,47,59} {19,47,60} {19,47,61} {19,47,62} {19,47,63} {19,47,64} {19,47,65} {19,47,66}
{19,48,49} {19,48,50} {19,48,51} {19,48,52} {19,48,53} {19,48,54} {19,48,55} {19,48,56} {19,48,57}
{19,48,58} {19,48,59} {19,48,60} {19,48,61} {19,48,62} {19,48,63} {19,48,64} {19,48,65} {19,48,66}
{19,49,50} {19,49,51} {19,49,52} {19,49,53} {19,49,54} {19,49,55} {19,49,56} {19,49,57} {19,49,58}
{19,49,59} {19,49,60} {19,49,61} {19,49,62} {19,49,63} {19,49,64} {19,49,65} {19,49,66} {19,50,51}
{19,50,52} {19,50,53} {19,50,54} {19,50,55} {19,50,56} {19,50,57} {19,50,58} {19,50,59} {19,50,60}
{19,50,61} {19,50,62} {19,50,63} {19,50,64} {19,50,65} {19,50,66} {19,51,52} {19,51,53} {19,51,54}
{19,51,55} {19,51,56} {19,51,57} {19,51,58} {19,51,59} {19,51,60} {19,51,61} {19,51,62} {19,51,63}
{19,51,64} {19,51,65} {19,51,66} {19,52,53} {19,52,54} {19,52,55} {19,52,56} {19,52,57} {19,52,58}
{19,52,59} {19,52,60} {19,52,61} {19,52,62} {19,52,63} {19,52,64} {19,52,65} {19,52,66} {19,53,54}
{19,53,55} {19,53,56} {19,53,57} {19,53,58} {19,53,59} {19,53,60} {19,53,61} {19,53,62} {19,53,63}
{19,53,64} {19,53,65} {19,53,66} {19,54,55} {19,54,56} {19,54,57} {19,54,58} {19,54,59} {19,54,60}
{19,54,61} {19,54,62} {19,54,63} {19,54,64} {19,54,65} {19,54,66} {19,55,56} {19,55,57} {19,55,58}
{19,55,59} {19,55,60} {19,55,61} {19,55,62} {19,55,63} {19,55,64} {19,55,65} {19,55,66} {19,56,57}
{19,56,58} {19,56,59} {19,56,60} {19,56,61} {19,56,62} {19,56,63} {19,56,64} {19,56,65} {19,56,66}
{19,57,58} {19,57,59} {19,57,60} {19,57,61} {19,57,62} {19,57,63} {19,57,64} {19,57,65} {19,57,66}
{19,58,59} {19,58,60} {19,58,61} {19,58,62} {19,58,63} {19,58,64} {19,58,65} {19,58,66} {19,59,60}
{19,59,61} {19,59,62} {19,59,63} {19,59,64} {19,59,65} {19,59,66} {19,60,61} {19,60,62} {19,60,63}
{19,60,64} {19,60,65} {19,60,66} {19,61,62} {19,61,63} {19,61,64} {19,61,65} {19,61,66} {19,62,63}
{19,62,64} {19,62,65} {19,62,66} {19,63,64} {19,63,65} {19,63,66} {19,64,65} {19,64,66} {19,65,66}
{20,21,22} {20,21,23} {20,21,24} {20,21,25} {20,21,26} {20,21,27} {20,21,28} {20,21,29} {20,21,30}
{20,21,31} {20,21,32} {20,21,33} {20,21,34} {20,21,35} {20,21,36} {20,21,37} {20,21,38} {20,21,39}
{20,21,40} {20,21,41} {20,21,42} {20,21,43} {20,21,44} {20,21,45} {20,21,46} {20,21,47} {20,21,48}
{20,21,49} {20,21,50} {20,21,51} {20,21,52} {20,21,53} {20,21,54} {20,21,55} {20,21,56} {20,21,57}
{20,21,58} {20,21,59} {20,21,60} {20,21,61} {20,21,62} {20,21,63} {20,21,64} {20,21,65} {20,21,66}
{20,22,23} {20,22,24} {20,22,25} {20,22,26} {20,22,27} {20,22,28} {20,22,29} {20,22,30} {20,22,31}
{20,22,32} {20,22,33} {20,22,34} {20,22,35} {20,22,36} {20,22,37} {20,22,38} {20,22,39} {20,22,40}
{20,22,41} {20,22,42} {20,22,43} {20,22,44} {20,22,45} {20,22,46} {20,22,47} {20,22,48} {20,22,49}
{20,22,50} {20,22,51} {20,22,52} {20,22,53} {20,22,54} {20,22,55} {20,22,56} {20,22,57} {20,22,58}
{20,22,59} {20,22,60} {20,22,61} {20,22,62} {20,22,63} {20,22,64} {20,22,65} {20,22,66} {20,23,24}
{20,23,25} {20,23,26} {20,23,27} {20,23,28} {20,23,29} {20,23,30} {20,23,31} {20,23,32} {20,23,33}
{20,23,34} {20,23,35} {20,23,36} {20,23,37} {20,23,38} {20,23,39} {20,23,40} {20,23,41} {20,23,42}
{20,23,43} {20,23,44} {20,23,45} {20,23,46} {20,23,47} {20,23,48} {20,23,49} {20,23,50} {20,23,51}
{20,23,52} {20,23,53} {20,23,54} {20,23,55} {20,23,56} {20,23,57} {20,23,58} {20,23,59} {20,23,60}
{20,23,61} {20,23,62} {20,23,63} {20,23,64} {20,23,65} {20,23,66} {20,24,25} {20,24,26} {20,24,27}
{20,24,28} {20,24,29} {20,24,30} {20,24,31} {20,24,32} {20,24,33} {20,24,34} {20,24,35} {20,24,36}
{20,24,37} {20,24,38} {20,24,39} {20,24,40} {20,24,41} {20,24,42} {20,24,43} {20,24,44} {20,24,45}

TABLE 3A-continued

| | | | | | | | | |
|---|---|---|---|---|---|---|---|---|
| {20,24,46} | {20,24,47} | {20,24,48} | {20,24,49} | {20,24,50} | {20,24,51} | {20,24,52} | {20,24,53} | {20,24,54} |
| {20,24,55} | {20,24,56} | {20,24,57} | {20,24,58} | {20,24,59} | {20,24,60} | {20,24,61} | {20,24,62} | {20,24,63} |
| {20,24,64} | {20,24,65} | {20,24,66} | {20,25,26} | {20,25,27} | {20,25,28} | {20,25,29} | {20,25,30} | {20,25,31} |
| {20,25,32} | {20,25,33} | {20,25,34} | {20,25,35} | {20,25,36} | {20,25,37} | {20,25,38} | {20,25,39} | {20,25,40} |
| {20,25,41} | {20,25,42} | {20,25,43} | {20,25,44} | {20,25,45} | {20,25,46} | {20,25,47} | {20,25,48} | {20,25,49} |
| {20,25,50} | {20,25,51} | {20,25,52} | {20,25,53} | {20,25,54} | {20,25,55} | {20,25,56} | {20,25,57} | {20,25,58} |
| {20,25,59} | {20,25,60} | {20,25,61} | {20,25,62} | {20,25,63} | {20,25,64} | {20,25,65} | {20,25,66} | {20,26,27} |
| {20,26,28} | {20,26,29} | {20,26,30} | {20,26,31} | {20,26,32} | {20,26,33} | {20,26,34} | {20,26,35} | {20,26,36} |
| {20,26,37} | {20,26,38} | {20,26,39} | {20,26,40} | {20,26,41} | {20,26,42} | {20,26,43} | {20,26,44} | {20,26,45} |
| {20,26,46} | {20,26,47} | {20,26,48} | {20,26,49} | {20,26,50} | {20,26,51} | {20,26,52} | {20,26,53} | {20,26,54} |
| {20,26,55} | {20,26,56} | {20,26,57} | {20,26,58} | {20,26,59} | {20,26,60} | {20,26,61} | {20,26,62} | {20,26,63} |
| {20,26,64} | {20,26,65} | {20,26,66} | {20,27,28} | {20,27,29} | {20,27,30} | {20,27,31} | {20,27,32} | {20,27,33} |
| {20,27,34} | {20,27,35} | {20,27,36} | {20,27,37} | {20,27,38} | {20,27,39} | {20,27,40} | {20,27,41} | {20,27,42} |
| {20,27,43} | {20,27,44} | {20,27,45} | {20,27,46} | {20,27,47} | {20,27,48} | {20,27,49} | {20,27,50} | {20,27,51} |
| {20,27,52} | {20,27,53} | {20,27,54} | {20,27,55} | {20,27,56} | {20,27,57} | {20,27,58} | {20,27,59} | {20,27,60} |
| {20,27,61} | {20,27,62} | {20,27,63} | {20,27,64} | {20,27,65} | {20,27,66} | {20,28,29} | {20,28,30} | {20,28,31} |
| {20,28,32} | {20,28,33} | {20,28,34} | {20,28,35} | {20,28,36} | {20,28,37} | {20,28,38} | {20,28,39} | {20,28,40} |
| {20,28,41} | {20,28,42} | {20,28,43} | {20,28,44} | {20,28,45} | {20,28,46} | {20,28,47} | {20,28,48} | {20,28,49} |
| {20,28,50} | {20,28,51} | {20,28,52} | {20,28,53} | {20,28,54} | {20,28,55} | {20,28,56} | {20,28,57} | {20,28,58} |
| {20,28,59} | {20,28,60} | {20,28,61} | {20,28,62} | {20,28,63} | {20,28,64} | {20,28,65} | {20,28,66} | {20,29,30} |
| {20,29,31} | {20,29,32} | {20,29,33} | {20,29,34} | {20,29,35} | {20,29,36} | {20,29,37} | {20,29,38} | {20,29,39} |
| {20,29,40} | {20,29,41} | {20,29,42} | {20,29,43} | {20,29,44} | {20,29,45} | {20,29,46} | {20,29,47} | {20,29,48} |
| {20,29,49} | {20,29,50} | {20,29,51} | {20,29,52} | {20,29,53} | {20,29,54} | {20,29,55} | {20,29,56} | {20,29,57} |
| {20,29,58} | {20,29,59} | {20,29,60} | {20,29,61} | {20,29,62} | {20,29,63} | {20,29,64} | {20,29,65} | {20,29,66} |
| {20,30,31} | {20,30,32} | {20,30,33} | {20,30,34} | {20,30,35} | {20,30,36} | {20,30,37} | {20,30,38} | {20,30,39} |
| {20,30,40} | {20,30,41} | {20,30,42} | {20,30,43} | {20,30,44} | {20,30,45} | {20,30,46} | {20,30,47} | {20,30,48} |
| {20,30,49} | {20,30,50} | {20,30,51} | {20,30,52} | {20,30,53} | {20,30,54} | {20,30,55} | {20,30,56} | {20,30,57} |
| {20,30,58} | {20,30,59} | {20,30,60} | {20,30,61} | {20,30,62} | {20,30,63} | {20,30,64} | {20,30,65} | {20,30,66} |
| {20,31,32} | {20,31,33} | {20,31,34} | {20,31,35} | {20,31,36} | {20,31,37} | {20,31,38} | {20,31,39} | {20,31,40} |
| {20,31,41} | {20,31,42} | {20,31,43} | {20,31,44} | {20,31,45} | {20,31,46} | {20,31,47} | {20,31,48} | {20,31,49} |
| {20,31,50} | {20,31,51} | {20,31,52} | {20,31,53} | {20,31,54} | {20,31,55} | {20,31,56} | {20,31,57} | {20,31,58} |
| {20,31,59} | {20,31,60} | {20,31,61} | {20,31,62} | {20,31,63} | {20,31,64} | {20,31,65} | {20,31,66} | {20,32,33} |
| {20,32,34} | {20,32,35} | {20,32,36} | {20,32,37} | {20,32,38} | {20,32,39} | {20,32,40} | {20,32,41} | {20,32,42} |
| {20,32,43} | {20,32,44} | {20,32,45} | {20,32,46} | {20,32,47} | {20,32,48} | {20,32,49} | {20,32,50} | {20,32,51} |
| {20,32,52} | {20,32,53} | {20,32,54} | {20,32,55} | {20,32,56} | {20,32,57} | {20,32,58} | {20,32,59} | {20,32,60} |
| {20,32,61} | {20,32,62} | {20,32,63} | {20,32,64} | {20,32,65} | {20,32,66} | {20,33,34} | {20,33,35} | {20,33,36} |
| {20,33,37} | {20,33,38} | {20,33,39} | {20,33,40} | {20,33,41} | {20,33,42} | {20,33,43} | {20,33,44} | {20,33,45} |
| {20,33,46} | {20,33,47} | {20,33,48} | {20,33,49} | {20,33,50} | {20,33,51} | {20,33,52} | {20,33,53} | {20,33,54} |
| {20,33,55} | {20,33,56} | {20,33,57} | {20,33,58} | {20,33,59} | {20,33,60} | {20,33,61} | {20,33,62} | {20,33,63} |
| {20,33,64} | {20,33,65} | {20,33,66} | {20,34,35} | {20,34,36} | {20,34,37} | {20,34,38} | {20,34,39} | {20,34,40} |
| {20,34,41} | {20,34,42} | {20,34,43} | {20,34,44} | {20,34,45} | {20,34,46} | {20,34,47} | {20,34,48} | {20,34,49} |
| {20,34,50} | {20,34,51} | {20,34,52} | {20,34,53} | {20,34,54} | {20,34,55} | {20,34,56} | {20,34,57} | {20,34,58} |
| {20,34,59} | {20,34,60} | {20,34,61} | {20,34,62} | {20,34,63} | {20,34,64} | {20,34,65} | {20,34,66} | {20,35,36} |
| {20,35,37} | {20,35,38} | {20,35,39} | {20,35,40} | {20,35,41} | {20,35,42} | {20,35,43} | {20,35,44} | {20,35,45} |
| {20,35,46} | {20,35,47} | {20,35,48} | {20,35,49} | {20,35,50} | {20,35,51} | {20,35,52} | {20,35,53} | {20,35,54} |
| {20,35,55} | {20,35,56} | {20,35,57} | {20,35,58} | {20,35,59} | {20,35,60} | {20,35,61} | {20,35,62} | {20,35,63} |
| {20,35,64} | {20,35,65} | {20,35,66} | {20,36,37} | {20,36,38} | {20,36,39} | {20,36,40} | {20,36,41} | {20,36,42} |
| {20,36,43} | {20,36,44} | {20,36,45} | {20,36,46} | {20,36,47} | {20,36,48} | {20,36,49} | {20,36,50} | {20,36,51} |
| {20,36,52} | {20,36,53} | {20,36,54} | {20,36,55} | {20,36,56} | {20,36,57} | {20,36,58} | {20,36,59} | {20,36,60} |
| {20,36,61} | {20,36,62} | {20,36,63} | {20,36,64} | {20,36,65} | {20,36,66} | {20,37,38} | {20,37,39} | {20,37,40} |
| {20,37,41} | {20,37,42} | {20,37,43} | {20,37,44} | {20,37,45} | {20,37,46} | {20,37,47} | {20,37,48} | {20,37,49} |
| {20,37,50} | {20,37,51} | {20,37,52} | {20,37,53} | {20,37,54} | {20,37,55} | {20,37,56} | {20,37,57} | {20,37,58} |
| {20,37,59} | {20,37,60} | {20,37,61} | {20,37,62} | {20,37,63} | {20,37,64} | {20,37,65} | {20,37,66} | {20,38,39} |
| {20,38,40} | {20,38,41} | {20,38,42} | {20,38,43} | {20,38,44} | {20,38,45} | {20,38,46} | {20,38,47} | {20,38,48} |
| {20,38,49} | {20,38,50} | {20,38,51} | {20,38,52} | {20,38,53} | {20,38,54} | {20,38,55} | {20,38,56} | {20,38,57} |
| {20,38,58} | {20,38,59} | {20,38,60} | {20,38,61} | {20,38,62} | {20,38,63} | {20,38,64} | {20,38,65} | {20,38,66} |
| {20,39,40} | {20,39,41} | {20,39,42} | {20,39,43} | {20,39,44} | {20,39,45} | {20,39,46} | {20,39,47} | {20,39,48} |
| {20,39,49} | {20,39,50} | {20,39,51} | {20,39,52} | {20,39,53} | {20,39,54} | {20,39,55} | {20,39,56} | {20,39,57} |
| {20,39,58} | {20,39,59} | {20,39,60} | {20,39,61} | {20,39,62} | {20,39,63} | {20,39,64} | {20,39,65} | {20,39,66} |
| {20,40,41} | {20,40,42} | {20,40,43} | {20,40,44} | {20,40,45} | {20,40,46} | {20,40,47} | {20,40,48} | {20,40,49} |
| {20,40,50} | {20,40,51} | {20,40,52} | {20,40,53} | {20,40,54} | {20,40,55} | {20,40,56} | {20,40,57} | {20,40,58} |
| {20,40,59} | {20,40,60} | {20,40,61} | {20,40,62} | {20,40,63} | {20,40,64} | {20,40,65} | {20,40,66} | {20,41,42} |
| {20,41,43} | {20,41,44} | {20,41,45} | {20,41,46} | {20,41,47} | {20,41,48} | {20,41,49} | {20,41,50} | {20,41,51} |
| {20,41,52} | {20,41,53} | {20,41,54} | {20,41,55} | {20,41,56} | {20,41,57} | {20,41,58} | {20,41,59} | {20,41,60} |
| {20,41,61} | {20,41,62} | {20,41,63} | {20,41,64} | {20,41,65} | {20,41,66} | {20,42,43} | {20,42,44} | {20,42,45} |
| {20,42,46} | {20,42,47} | {20,42,48} | {20,42,49} | {20,42,50} | {20,42,51} | {20,42,52} | {20,42,53} | {20,42,54} |
| {20,42,55} | {20,42,56} | {20,42,57} | {20,42,58} | {20,42,59} | {20,42,60} | {20,42,61} | {20,42,62} | {20,42,63} |
| {20,42,64} | {20,42,65} | {20,42,66} | {20,43,44} | {20,43,45} | {20,43,46} | {20,43,47} | {20,43,48} | {20,43,49} |
| {20,43,50} | {20,43,51} | {20,43,52} | {20,43,53} | {20,43,54} | {20,43,55} | {20,43,56} | {20,43,57} | {20,43,58} |
| {20,43,59} | {20,43,60} | {20,43,61} | {20,43,62} | {20,43,63} | {20,43,64} | {20,43,65} | {20,43,66} | {20,44,45} |
| {20,44,46} | {20,44,47} | {20,44,48} | {20,44,49} | {20,44,50} | {20,44,51} | {20,44,52} | {20,44,53} | {20,44,54} |
| {20,44,55} | {20,44,56} | {20,44,57} | {20,44,58} | {20,44,59} | {20,44,60} | {20,44,61} | {20,44,62} | {20,44,63} |
| {20,44,64} | {20,44,65} | {20,44,66} | {20,45,46} | {20,45,47} | {20,45,48} | {20,45,49} | {20,45,50} | {20,45,51} |
| {20,45,52} | {20,45,53} | {20,45,54} | {20,45,55} | {20,45,56} | {20,45,57} | {20,45,58} | {20,45,59} | {20,45,60} |
| {20,45,61} | {20,45,62} | {20,45,63} | {20,45,64} | {20,45,65} | {20,45,66} | {20,46,47} | {20,46,48} | {20,46,49} |
| {20,46,50} | {20,46,51} | {20,46,52} | {20,46,53} | {20,46,54} | {20,46,55} | {20,46,56} | {20,46,57} | {20,46,58} |
| {20,46,59} | {20,46,60} | {20,46,61} | {20,46,62} | {20,46,63} | {20,46,64} | {20,46,65} | {20,46,66} | {20,47,48} |
| {20,47,49} | {20,47,50} | {20,47,51} | {20,47,52} | {20,47,53} | {20,47,54} | {20,47,55} | {20,47,56} | {20,47,57} |
| {20,47,58} | {20,47,59} | {20,47,60} | {20,47,61} | {20,47,62} | {20,47,63} | {20,47,64} | {20,47,65} | {20,47,66} |
| {20,48,49} | {20,48,50} | {20,48,51} | {20,48,52} | {20,48,53} | {20,48,54} | {20,48,55} | {20,48,56} | {20,48,57} |

TABLE 3A-continued

| | | | | | | | |
|---|---|---|---|---|---|---|---|
| {20,48,58} | {20,48,59} | {20,48,60} | {20,48,61} | {20,48,62} | {20,48,63} | {20,48,64} | {20,48,65} | {20,48,66} |
| {20,49,50} | {20,49,51} | {20,49,52} | {20,49,53} | {20,49,54} | {20,49,55} | {20,49,56} | {20,49,57} | {20,49,58} |
| {20,49,59} | {20,49,60} | {20,49,61} | {20,49,62} | {20,49,63} | {20,49,64} | {20,49,65} | {20,49,66} | {20,50,51} |
| {20,50,52} | {20,50,53} | {20,50,54} | {20,50,55} | {20,50,56} | {20,50,57} | {20,50,58} | {20,50,59} | {20,50,60} |
| {20,50,61} | {20,50,62} | {20,50,63} | {20,50,64} | {20,50,65} | {20,50,66} | {20,51,52} | {20,51,53} | {20,51,54} |
| {20,51,55} | {20,51,56} | {20,51,57} | {20,51,58} | {20,51,59} | {20,51,60} | {20,51,61} | {20,51,62} | {20,51,63} |
| {20,51,64} | {20,51,65} | {20,51,66} | {20,52,53} | {20,52,54} | {20,52,55} | {20,52,56} | {20,52,57} | {20,52,58} |
| {20,52,59} | {20,52,60} | {20,52,61} | {20,52,62} | {20,52,63} | {20,52,64} | {20,52,65} | {20,52,66} | {20,53,54} |
| {20,53,55} | {20,53,56} | {20,53,57} | {20,53,58} | {20,53,59} | {20,53,60} | {20,53,61} | {20,53,62} | {20,53,63} |
| {20,53,64} | {20,53,65} | {20,53,66} | {20,54,55} | {20,54,56} | {20,54,57} | {20,54,58} | {20,54,59} | {20,54,60} |
| {20,54,61} | {20,54,62} | {20,54,63} | {20,54,64} | {20,54,65} | {20,54,66} | {20,55,56} | {20,55,57} | {20,55,58} |
| {20,55,59} | {20,55,60} | {20,55,61} | {20,55,62} | {20,55,63} | {20,55,64} | {20,55,65} | {20,55,66} | {20,56,57} |
| {20,56,58} | {20,56,59} | {20,56,60} | {20,56,61} | {20,56,62} | {20,56,63} | {20,56,64} | {20,56,65} | {20,56,66} |
| {20,57,58} | {20,57,59} | {20,57,60} | {20,57,61} | {20,57,62} | {20,57,63} | {20,57,64} | {20,57,65} | {20,57,66} |
| {20,58,59} | {20,58,60} | {20,58,61} | {20,58,62} | {20,58,63} | {20,58,64} | {20,58,65} | {20,58,66} | {20,59,60} |
| {20,59,61} | {20,59,62} | {20,59,63} | {20,59,64} | {20,59,65} | {20,59,66} | {20,60,61} | {20,60,62} | {20,60,63} |
| {20,60,64} | {20,60,65} | {20,60,66} | {20,61,62} | {20,61,63} | {20,61,64} | {20,61,65} | {20,61,66} | {20,62,63} |
| {20,62,64} | {20,62,65} | {20,62,66} | {20,63,64} | {20,63,65} | {20,63,66} | {20,64,65} | {20,64,66} | {20,65,66} |
| {21,22,23} | {21,22,24} | {21,22,25} | {21,22,26} | {21,22,27} | {21,22,28} | {21,22,29} | {21,22,30} | {21,22,31} |
| {21,22,32} | {21,22,33} | {21,22,34} | {21,22,35} | {21,22,36} | {21,22,37} | {21,22,38} | {21,22,39} | {21,22,40} |
| {21,22,41} | {21,22,42} | {21,22,43} | {21,22,44} | {21,22,45} | {21,22,46} | {21,22,47} | {21,22,48} | {21,22,49} |
| {21,22,50} | {21,22,51} | {21,22,52} | {21,22,53} | {21,22,54} | {21,22,55} | {21,22,56} | {21,22,57} | {21,22,58} |
| {21,22,59} | {21,22,60} | {21,22,61} | {21,22,62} | {21,22,63} | {21,22,64} | {21,22,65} | {21,22,66} | {21,23,24} |
| {21,23,25} | {21,23,26} | {21,23,27} | {21,23,28} | {21,23,29} | {21,23,30} | {21,23,31} | {21,23,32} | {21,23,33} |
| {21,23,34} | {21,23,35} | {21,23,36} | {21,23,37} | {21,23,38} | {21,23,39} | {21,23,40} | {21,23,41} | {21,23,42} |
| {21,23,43} | {21,23,44} | {21,23,45} | {21,23,46} | {21,23,47} | {21,23,48} | {21,23,49} | {21,23,50} | {21,23,51} |
| {21,23,52} | {21,23,53} | {21,23,54} | {21,23,55} | {21,23,56} | {21,23,57} | {21,23,58} | {21,23,59} | {21,23,60} |
| {21,23,61} | {21,23,62} | {21,23,63} | {21,23,64} | {21,23,65} | {21,23,66} | {21,24,25} | {21,24,26} | {21,24,27} |
| {21,24,28} | {21,24,29} | {21,24,30} | {21,24,31} | {21,24,32} | {21,24,33} | {21,24,34} | {21,24,35} | {21,24,36} |
| {21,24,37} | {21,24,38} | {21,24,39} | {21,24,40} | {21,24,41} | {21,24,42} | {21,24,43} | {21,24,44} | {21,24,45} |
| {21,24,46} | {21,24,47} | {21,24,48} | {21,24,49} | {21,24,50} | {21,24,51} | {21,24,52} | {21,24,53} | {21,24,54} |
| {21,24,55} | {21,24,56} | {21,24,57} | {21,24,58} | {21,24,59} | {21,24,60} | {21,24,61} | {21,24,62} | {21,24,63} |
| {21,24,64} | {21,24,65} | {21,24,66} | {21,25,26} | {21,25,27} | {21,25,28} | {21,25,29} | {21,25,30} | {21,25,31} |
| {21,25,32} | {21,25,33} | {21,25,34} | {21,25,35} | {21,25,36} | {21,25,37} | {21,25,38} | {21,25,39} | {21,25,40} |
| {21,25,41} | {21,25,42} | {21,25,43} | {21,25,44} | {21,25,45} | {21,25,46} | {21,25,47} | {21,25,48} | {21,25,49} |
| {21,25,50} | {21,25,51} | {21,25,52} | {21,25,53} | {21,25,54} | {21,25,55} | {21,25,56} | {21,25,57} | {21,25,58} |
| {21,25,59} | {21,25,60} | {21,25,61} | {21,25,62} | {21,25,63} | {21,25,64} | {21,25,65} | {21,25,66} | {21,26,27} |
| {21,26,28} | {21,26,29} | {21,26,30} | {21,26,31} | {21,26,32} | {21,26,33} | {21,26,34} | {21,26,35} | {21,26,36} |
| {21,26,37} | {21,26,38} | {21,26,39} | {21,26,40} | {21,26,41} | {21,26,42} | {21,26,43} | {21,26,44} | {21,26,45} |
| {21,26,46} | {21,26,47} | {21,26,48} | {21,26,49} | {21,26,50} | {21,26,51} | {21,26,52} | {21,26,53} | {21,26,54} |
| {21,26,55} | {21,26,56} | {21,26,57} | {21,26,58} | {21,26,59} | {21,26,60} | {21,26,61} | {21,26,62} | {21,26,63} |
| {21,26,64} | {21,26,65} | {21,26,66} | {21,27,28} | {21,27,29} | {21,27,30} | {21,27,31} | {21,27,32} | {21,27,33} |
| {21,27,34} | {21,27,35} | {21,27,36} | {21,27,37} | {21,27,38} | {21,27,39} | {21,27,40} | {21,27,41} | {21,27,42} |
| {21,27,43} | {21,27,44} | {21,27,45} | {21,27,46} | {21,27,47} | {21,27,48} | {21,27,49} | {21,27,50} | {21,27,51} |
| {21,27,52} | {21,27,53} | {21,27,54} | {21,27,55} | {21,27,56} | {21,27,57} | {21,27,58} | {21,27,59} | {21,27,60} |
| {21,27,61} | {21,27,62} | {21,27,63} | {21,27,64} | {21,27,65} | {21,27,66} | {21,28,29} | {21,28,30} | {21,28,31} |
| {21,28,32} | {21,28,33} | {21,28,34} | {21,28,35} | {21,28,36} | {21,28,37} | {21,28,38} | {21,28,39} | {21,28,40} |
| {21,28,41} | {21,28,42} | {21,28,43} | {21,28,44} | {21,28,45} | {21,28,46} | {21,28,47} | {21,28,48} | {21,28,49} |
| {21,28,50} | {21,28,51} | {21,28,52} | {21,28,53} | {21,28,54} | {21,28,55} | {21,28,56} | {21,28,57} | {21,28,58} |
| {21,28,59} | {21,28,60} | {21,28,61} | {21,28,62} | {21,28,63} | {21,28,64} | {21,28,65} | {21,28,66} | {21,29,30} |
| {21,29,31} | {21,29,32} | {21,29,33} | {21,29,34} | {21,29,35} | {21,29,36} | {21,29,37} | {21,29,38} | {21,29,39} |
| {21,29,40} | {21,29,41} | {21,29,42} | {21,29,43} | {21,29,44} | {21,29,45} | {21,29,46} | {21,29,47} | {21,29,48} |
| {21,29,49} | {21,29,50} | {21,29,51} | {21,29,52} | {21,29,53} | {21,29,54} | {21,29,55} | {21,29,56} | {21,29,57} |
| {21,29,58} | {21,29,59} | {21,29,60} | {21,29,61} | {21,29,62} | {21,29,63} | {21,29,64} | {21,29,65} | {21,29,66} |
| {21,30,31} | {21,30,32} | {21,30,33} | {21,30,34} | {21,30,35} | {21,30,36} | {21,30,37} | {21,30,38} | {21,30,39} |
| {21,30,40} | {21,30,41} | {21,30,42} | {21,30,43} | {21,30,44} | {21,30,45} | {21,30,46} | {21,30,47} | {21,30,48} |
| {21,30,49} | {21,30,50} | {21,30,51} | {21,30,52} | {21,30,53} | {21,30,54} | {21,30,55} | {21,30,56} | {21,30,57} |
| {21,30,58} | {21,30,59} | {21,30,60} | {21,30,61} | {21,30,62} | {21,30,63} | {21,30,64} | {21,30,65} | {21,30,66} |
| {21,31,32} | {21,31,33} | {21,31,34} | {21,31,35} | {21,31,36} | {21,31,37} | {21,31,38} | {21,31,39} | {21,31,40} |
| {21,31,41} | {21,31,42} | {21,31,43} | {21,31,44} | {21,31,45} | {21,31,46} | {21,31,47} | {21,31,48} | {21,31,49} |
| {21,31,50} | {21,31,51} | {21,31,52} | {21,31,53} | {21,31,54} | {21,31,55} | {21,31,56} | {21,31,57} | {21,31,58} |
| {21,31,59} | {21,31,60} | {21,31,61} | {21,31,62} | {21,31,63} | {21,31,64} | {21,31,65} | {21,31,66} | {21,32,33} |
| {21,32,34} | {21,32,35} | {21,32,36} | {21,32,37} | {21,32,38} | {21,32,39} | {21,32,40} | {21,32,41} | {21,32,42} |
| {21,32,43} | {21,32,44} | {21,32,45} | {21,32,46} | {21,32,47} | {21,32,48} | {21,32,49} | {21,32,50} | {21,32,51} |
| {21,32,52} | {21,32,53} | {21,32,54} | {21,32,55} | {21,32,56} | {21,32,57} | {21,32,58} | {21,32,59} | {21,32,60} |
| {21,32,61} | {21,32,62} | {21,32,63} | {21,32,64} | {21,32,65} | {21,32,66} | {21,33,34} | {21,33,35} | {21,33,36} |
| {21,33,37} | {21,33,38} | {21,33,39} | {21,33,40} | {21,33,41} | {21,33,42} | {21,33,43} | {21,33,44} | {21,33,45} |
| {21,33,46} | {21,33,47} | {21,33,48} | {21,33,49} | {21,33,50} | {21,33,51} | {21,33,52} | {21,33,53} | {21,33,54} |
| {21,33,55} | {21,33,56} | {21,33,57} | {21,33,58} | {21,33,59} | {21,33,60} | {21,33,61} | {21,33,62} | {21,33,63} |
| {21,33,64} | {21,33,65} | {21,33,66} | {21,34,35} | {21,34,36} | {21,34,37} | {21,34,38} | {21,34,39} | {21,34,40} |
| {21,34,41} | {21,34,42} | {21,34,43} | {21,34,44} | {21,34,45} | {21,34,46} | {21,34,47} | {21,34,48} | {21,34,49} |
| {21,34,50} | {21,34,51} | {21,34,52} | {21,34,53} | {21,34,54} | {21,34,55} | {21,34,56} | {21,34,57} | {21,34,58} |
| {21,34,59} | {21,34,60} | {21,34,61} | {21,34,62} | {21,34,63} | {21,34,64} | {21,34,65} | {21,34,66} | {21,35,36} |
| {21,35,37} | {21,35,38} | {21,35,39} | {21,35,40} | {21,35,41} | {21,35,42} | {21,35,43} | {21,35,44} | {21,35,45} |
| {21,35,46} | {21,35,47} | {21,35,48} | {21,35,49} | {21,35,50} | {21,35,51} | {21,35,52} | {21,35,53} | {21,35,54} |
| {21,35,55} | {21,35,56} | {21,35,57} | {21,35,58} | {21,35,59} | {21,35,60} | {21,35,61} | {21,35,62} | {21,35,63} |
| {21,35,64} | {21,35,65} | {21,35,66} | {21,36,37} | {21,36,38} | {21,36,39} | {21,36,40} | {21,36,41} | {21,36,42} |
| {21,36,43} | {21,36,44} | {21,36,45} | {21,36,46} | {21,36,47} | {21,36,48} | {21,36,49} | {21,36,50} | {21,36,51} |
| {21,36,52} | {21,36,53} | {21,36,54} | {21,36,55} | {21,36,56} | {21,36,57} | {21,36,58} | {21,36,59} | {21,36,60} |
| {21,36,61} | {21,36,62} | {21,36,63} | {21,36,64} | {21,36,65} | {21,36,66} | {21,37,38} | {21,37,39} | {21,37,40} |

TABLE 3A-continued

{21,37,41} {21,37,42} {21,37,43} {21,37,44} {21,37,45} {21,37,46} {21,37,47} {21,37,48} {21,37,49}
{21,37,50} {21,37,51} {21,37,52} {21,37,53} {21,37,54} {21,37,55} {21,37,56} {21,37,57} {21,37,58}
{21,37,59} {21,37,60} {21,37,61} {21,37,62} {21,37,63} {21,37,64} {21,37,65} {21,37,66} {21,38,39}
{21,38,40} {21,38,41} {21,38,42} {21,38,43} {21,38,44} {21,38,45} {21,38,46} {21,38,47} {21,38,48}
{21,38,49} {21,38,50} {21,38,51} {21,38,52} {21,38,53} {21,38,54} {21,38,55} {21,38,56} {21,38,57}
{21,38,58} {21,38,59} {21,38,60} {21,38,61} {21,38,62} {21,38,63} {21,38,64} {21,38,65} {21,38,66}
{21,39,40} {21,39,41} {21,39,42} {21,39,43} {21,39,44} {21,39,45} {21,39,46} {21,39,47} {21,39,48}
{21,39,49} {21,39,50} {21,39,51} {21,39,52} {21,39,53} {21,39,54} {21,39,55} {21,39,56} {21,39,57}
{21,39,58} {21,39,59} {21,39,60} {21,39,61} {21,39,62} {21,39,63} {21,39,64} {21,39,65} {21,39,66}
{21,40,41} {21,40,42} {21,40,43} {21,40,44} {21,40,45} {21,40,46} {21,40,47} {21,40,48} {21,40,49}
{21,40,50} {21,40,51} {21,40,52} {21,40,53} {21,40,54} {21,40,55} {21,40,56} {21,40,57} {21,40,58}
{21,40,59} {21,40,60} {21,40,61} {21,40,62} {21,40,63} {21,40,64} {21,40,65} {21,40,66} {21,41,42}
{21,41,43} {21,41,44} {21,41,45} {21,41,46} {21,41,47} {21,41,48} {21,41,49} {21,41,50} {21,41,51}
{21,41,52} {21,41,53} {21,41,54} {21,41,55} {21,41,56} {21,41,57} {21,41,58} {21,41,59} {21,41,60}
{21,41,61} {21,41,62} {21,41,63} {21,41,64} {21,41,65} {21,41,66} {21,42,43} {21,42,44} {21,42,45}
{21,42,46} {21,42,47} {21,42,48} {21,42,49} {21,42,50} {21,42,51} {21,42,52} {21,42,53} {21,42,54}
{21,42,55} {21,42,56} {21,42,57} {21,42,58} {21,42,59} {21,42,60} {21,42,61} {21,42,62} {21,42,63}
{21,42,64} {21,42,65} {21,42,66} {21,43,44} {21,43,45} {21,43,46} {21,43,47} {21,43,48} {21,43,49}
{21,43,50} {21,43,51} {21,43,52} {21,43,53} {21,43,54} {21,43,55} {21,43,56} {21,43,57} {21,43,58}
{21,43,59} {21,43,60} {21,43,61} {21,43,62} {21,43,63} {21,43,64} {21,43,65} {21,43,66} {21,44,45}
{21,44,46} {21,44,47} {21,44,48} {21,44,49} {21,44,50} {21,44,51} {21,44,52} {21,44,53} {21,44,54}
{21,44,55} {21,44,56} {21,44,57} {21,44,58} {21,44,59} {21,44,60} {21,44,61} {21,44,62} {21,44,63}
{21,44,64} {21,44,65} {21,44,66} {21,45,46} {21,45,47} {21,45,48} {21,45,49} {21,45,50} {21,45,51}
{21,45,52} {21,45,53} {21,45,54} {21,45,55} {21,45,56} {21,45,57} {21,45,58} {21,45,59} {21,45,60}
{21,45,61} {21,45,62} {21,45,63} {21,45,64} {21,45,65} {21,45,66} {21,46,47} {21,46,48} {21,46,49}
{21,46,50} {21,46,51} {21,46,52} {21,46,53} {21,46,54} {21,46,55} {21,46,56} {21,46,57} {21,46,58}
{21,46,59} {21,46,60} {21,46,61} {21,46,62} {21,46,63} {21,46,64} {21,46,65} {21,46,66} {21,47,48}
{21,47,49} {21,47,50} {21,47,51} {21,47,52} {21,47,53} {21,47,54} {21,47,55} {21,47,56} {21,47,57}
{21,47,58} {21,47,59} {21,47,60} {21,47,61} {21,47,62} {21,47,63} {21,47,64} {21,47,65} {21,47,66}
{21,48,49} {21,48,50} {21,48,51} {21,48,52} {21,48,53} {21,48,54} {21,48,55} {21,48,56} {21,48,57}
{21,48,58} {21,48,59} {21,48,60} {21,48,61} {21,48,62} {21,48,63} {21,48,64} {21,48,65} {21,48,66}
{21,49,50} {21,49,51} {21,49,52} {21,49,53} {21,49,54} {21,49,55} {21,49,56} {21,49,57} {21,49,58}
{21,49,59} {21,49,60} {21,49,61} {21,49,62} {21,49,63} {21,49,64} {21,49,65} {21,49,66} {21,50,51}
{21,50,52} {21,50,53} {21,50,54} {21,50,55} {21,50,56} {21,50,57} {21,50,58} {21,50,59} {21,50,60}
{21,50,61} {21,50,62} {21,50,63} {21,50,64} {21,50,65} {21,50,66} {21,51,52} {21,51,53} {21,51,54}
{21,51,55} {21,51,56} {21,51,57} {21,51,58} {21,51,59} {21,51,60} {21,51,61} {21,51,62} {21,51,63}
{21,51,64} {21,51,65} {21,51,66} {21,52,53} {21,52,54} {21,52,55} {21,52,56} {21,52,57} {21,52,58}
{21,52,59} {21,52,60} {21,52,61} {21,52,62} {21,52,63} {21,52,64} {21,52,65} {21,52,66} {21,53,54}
{21,53,55} {21,53,56} {21,53,57} {21,53,58} {21,53,59} {21,53,60} {21,53,61} {21,53,62} {21,53,63}
{21,53,64} {21,53,65} {21,53,66} {21,54,55} {21,54,56} {21,54,57} {21,54,58} {21,54,59} {21,54,60}
{21,54,61} {21,54,62} {21,54,63} {21,54,64} {21,54,65} {21,54,66} {21,55,56} {21,55,57} {21,55,58}
{21,55,59} {21,55,60} {21,55,61} {21,55,62} {21,55,63} {21,55,64} {21,55,65} {21,55,66} {21,56,57}
{21,56,58} {21,56,59} {21,56,60} {21,56,61} {21,56,62} {21,56,63} {21,56,64} {21,56,65} {21,56,66}
{21,57,58} {21,57,59} {21,57,60} {21,57,61} {21,57,62} {21,57,63} {21,57,64} {21,57,65} {21,57,66}
{21,58,59} {21,58,60} {21,58,61} {21,58,62} {21,58,63} {21,58,64} {21,58,65} {21,58,66} {21,59,60}
{21,59,61} {21,59,62} {21,59,63} {21,59,64} {21,59,65} {21,59,66} {21,60,61} {21,60,62} {21,60,63}
{21,60,64} {21,60,65} {21,60,66} {21,61,62} {21,61,63} {21,61,64} {21,61,65} {21,61,66} {21,62,63}
{21,62,64} {21,62,65} {21,62,66} {21,63,64} {21,63,65} {21,63,66} {21,64,65} {21,64,66} {21,65,66}
{22,23,24} {22,23,25} {22,23,26} {22,23,27} {22,23,28} {22,23,29} {22,23,30} {22,23,31} {22,23,32}
{22,23,33} {22,23,34} {22,23,35} {22,23,36} {22,23,37} {22,23,38} {22,23,39} {22,23,40} {22,23,41}
{22,23,42} {22,23,43} {22,23,44} {22,23,45} {22,23,46} {22,23,47} {22,23,48} {22,23,49} {22,23,50}
{22,23,51} {22,23,52} {22,23,53} {22,23,54} {22,23,55} {22,23,56} {22,23,57} {22,23,58} {22,23,59}
{22,23,60} {22,23,61} {22,23,62} {22,23,63} {22,23,64} {22,23,65} {22,23,66} {22,24,25} {22,24,26}
{22,24,27} {22,24,28} {22,24,29} {22,24,30} {22,24,31} {22,24,32} {22,24,33} {22,24,34} {22,24,35}
{22,24,36} {22,24,37} {22,24,38} {22,24,39} {22,24,40} {22,24,41} {22,24,42} {22,24,43} {22,24,44}
{22,24,45} {22,24,46} {22,24,47} {22,24,48} {22,24,49} {22,24,50} {22,24,51} {22,24,52} {22,24,53}
{22,24,54} {22,24,55} {22,24,56} {22,24,57} {22,24,58} {22,24,59} {22,24,60} {22,24,61} {22,24,62}
{22,24,63} {22,24,64} {22,24,65} {22,24,66} {22,25,26} {22,25,27} {22,25,28} {22,25,29} {22,25,30}
{22,25,31} {22,25,32} {22,25,33} {22,25,34} {22,25,35} {22,25,36} {22,25,37} {22,25,38} {22,25,39}
{22,25,40} {22,25,41} {22,25,42} {22,25,43} {22,25,44} {22,25,45} {22,25,46} {22,25,47} {22,25,48}
{22,25,49} {22,25,50} {22,25,51} {22,25,52} {22,25,53} {22,25,54} {22,25,55} {22,25,56} {22,25,57}
{22,25,58} {22,25,59} {22,25,60} {22,25,61} {22,25,62} {22,25,63} {22,25,64} {22,25,65} {22,25,66}
{22,26,27} {22,26,28} {22,26,29} {22,26,30} {22,26,31} {22,26,32} {22,26,33} {22,26,34} {22,26,35}
{22,26,36} {22,26,37} {22,26,38} {22,26,39} {22,26,40} {22,26,41} {22,26,42} {22,26,43} {22,26,44}
{22,26,45} {22,26,46} {22,26,47} {22,26,48} {22,26,49} {22,26,50} {22,26,51} {22,26,52} {22,26,53}
{22,26,54} {22,26,55} {22,26,56} {22,26,57} {22,26,58} {22,26,59} {22,26,60} {22,26,61} {22,26,62}
{22,26,63} {22,26,64} {22,26,65} {22,26,66} {22,27,28} {22,27,29} {22,27,30} {22,27,31} {22,27,32}
{22,27,33} {22,27,34} {22,27,35} {22,27,36} {22,27,37} {22,27,38} {22,27,39} {22,27,40} {22,27,41}
{22,27,42} {22,27,43} {22,27,44} {22,27,45} {22,27,46} {22,27,47} {22,27,48} {22,27,49} {22,27,50}
{22,27,51} {22,27,52} {22,27,53} {22,27,54} {22,27,55} {22,27,56} {22,27,57} {22,27,58} {22,27,59}
{22,27,60} {22,27,61} {22,27,62} {22,27,63} {22,27,64} {22,27,65} {22,27,66} {22,28,29} {22,28,30}
{22,28,31} {22,28,32} {22,28,33} {22,28,34} {22,28,35} {22,28,36} {22,28,37} {22,28,38} {22,28,39}
{22,28,40} {22,28,41} {22,28,42} {22,28,43} {22,28,44} {22,28,45} {22,28,46} {22,28,47} {22,28,48}
{22,28,49} {22,28,50} {22,28,51} {22,28,52} {22,28,53} {22,28,54} {22,28,55} {22,28,56} {22,28,57}
{22,28,58} {22,28,59} {22,28,60} {22,28,61} {22,28,62} {22,28,63} {22,28,64} {22,28,65} {22,28,66}
{22,29,30} {22,29,31} {22,29,32} {22,29,33} {22,29,34} {22,29,35} {22,29,36} {22,29,37} {22,29,38}
{22,29,39} {22,29,40} {22,29,41} {22,29,42} {22,29,43} {22,29,44} {22,29,45} {22,29,46} {22,29,47}
{22,29,48} {22,29,49} {22,29,50} {22,29,51} {22,29,52} {22,29,53} {22,29,54} {22,29,55} {22,29,56}
{22,29,57} {22,29,58} {22,29,59} {22,29,60} {22,29,61} {22,29,62} {22,29,63} {22,29,64} {22,29,65}
{22,29,66} {22,30,31} {22,30,32} {22,30,33} {22,30,34} {22,30,35} {22,30,36} {22,30,37} {22,30,38}

TABLE 3A-continued

| | | | | | | | |
|---|---|---|---|---|---|---|---|
| {22,30,39} | {22,30,40} | {22,30,41} | {22,30,42} | {22,30,43} | {22,30,44} | {22,30,45} | {22,30,46} | {22,30,47} |
| {22,30,48} | {22,30,49} | {22,30,50} | {22,30,51} | {22,30,52} | {22,30,53} | {22,30,54} | {22,30,55} | {22,30,56} |
| {22,30,57} | {22,30,58} | {22,30,59} | {22,30,60} | {22,30,61} | {22,30,62} | {22,30,63} | {22,30,64} | {22,30,65} |
| {22,30,66} | {22,31,32} | {22,31,33} | {22,31,34} | {22,31,35} | {22,31,36} | {22,31,37} | {22,31,38} | {22,31,39} |
| {22,31,40} | {22,31,41} | {22,31,42} | {22,31,43} | {22,31,44} | {22,31,45} | {22,31,46} | {22,31,47} | {22,31,48} |
| {22,31,49} | {22,31,50} | {22,31,51} | {22,31,52} | {22,31,53} | {22,31,54} | {22,31,55} | {22,31,56} | {22,31,57} |
| {22,31,58} | {22,31,59} | {22,31,60} | {22,31,61} | {22,31,62} | {22,31,63} | {22,31,64} | {22,31,65} | {22,31,66} |
| {22,32,33} | {22,32,34} | {22,32,35} | {22,32,36} | {22,32,37} | {22,32,38} | {22,32,39} | {22,32,40} | {22,32,41} |
| {22,32,42} | {22,32,43} | {22,32,44} | {22,32,45} | {22,32,46} | {22,32,47} | {22,32,48} | {22,32,49} | {22,32,50} |
| {22,32,51} | {22,32,52} | {22,32,53} | {22,32,54} | {22,32,55} | {22,32,56} | {22,32,57} | {22,32,58} | {22,32,59} |
| {22,32,60} | {22,32,61} | {22,32,62} | {22,32,63} | {22,32,64} | {22,32,65} | {22,32,66} | {22,33,34} | {22,33,35} |
| {22,33,36} | {22,33,37} | {22,33,38} | {22,33,39} | {22,33,40} | {22,33,41} | {22,33,42} | {22,33,43} | {22,33,44} |
| {22,33,45} | {22,33,46} | {22,33,47} | {22,33,48} | {22,33,49} | {22,33,50} | {22,33,51} | {22,33,52} | {22,33,53} |
| {22,33,54} | {22,33,55} | {22,33,56} | {22,33,57} | {22,33,58} | {22,33,59} | {22,33,60} | {22,33,61} | {22,33,62} |
| {22,33,63} | {22,33,64} | {22,33,65} | {22,33,66} | {22,34,35} | {22,34,36} | {22,34,37} | {22,34,38} | {22,34,39} |
| {22,34,40} | {22,34,41} | {22,34,42} | {22,34,43} | {22,34,44} | {22,34,45} | {22,34,46} | {22,34,47} | {22,34,48} |
| {22,34,49} | {22,34,50} | {22,34,51} | {22,34,52} | {22,34,53} | {22,34,54} | {22,34,55} | {22,34,56} | {22,34,57} |
| {22,34,58} | {22,34,59} | {22,34,60} | {22,34,61} | {22,34,62} | {22,34,63} | {22,34,64} | {22,34,65} | {22,34,66} |
| {22,35,36} | {22,35,37} | {22,35,38} | {22,35,39} | {22,35,40} | {22,35,41} | {22,35,42} | {22,35,43} | {22,35,44} |
| {22,35,45} | {22,35,46} | {22,35,47} | {22,35,48} | {22,35,49} | {22,35,50} | {22,35,51} | {22,35,52} | {22,35,53} |
| {22,35,54} | {22,35,55} | {22,35,56} | {22,35,57} | {22,35,58} | {22,35,59} | {22,35,60} | {22,35,61} | {22,35,62} |
| {22,35,63} | {22,35,64} | {22,35,65} | {22,35,66} | {22,36,37} | {22,36,38} | {22,36,39} | {22,36,40} | {22,36,41} |
| {22,36,42} | {22,36,43} | {22,36,44} | {22,36,45} | {22,36,46} | {22,36,47} | {22,36,48} | {22,36,49} | {22,36,50} |
| {22,36,51} | {22,36,52} | {22,36,53} | {22,36,54} | {22,36,55} | {22,36,56} | {22,36,57} | {22,36,58} | {22,36,59} |
| {22,36,60} | {22,36,61} | {22,36,62} | {22,36,63} | {22,36,64} | {22,36,65} | {22,36,66} | {22,37,38} | {22,37,39} |
| {22,37,40} | {22,37,41} | {22,37,42} | {22,37,43} | {22,37,44} | {22,37,45} | {22,37,46} | {22,37,47} | {22,37,48} |
| {22,37,49} | {22,37,50} | {22,37,51} | {22,37,52} | {22,37,53} | {22,37,54} | {22,37,55} | {22,37,56} | {22,37,57} |
| {22,37,58} | {22,37,59} | {22,37,60} | {22,37,61} | {22,37,62} | {22,37,63} | {22,37,64} | {22,37,65} | {22,37,66} |
| {22,38,39} | {22,38,40} | {22,38,41} | {22,38,42} | {22,38,43} | {22,38,44} | {22,38,45} | {22,38,46} | {22,38,47} |
| {22,38,48} | {22,38,49} | {22,38,50} | {22,38,51} | {22,38,52} | {22,38,53} | {22,38,54} | {22,38,55} | {22,38,56} |
| {22,38,57} | {22,38,58} | {22,38,59} | {22,38,60} | {22,38,61} | {22,38,62} | {22,38,63} | {22,38,64} | {22,38,65} |
| {22,38,66} | {22,39,40} | {22,39,41} | {22,39,42} | {22,39,43} | {22,39,44} | {22,39,45} | {22,39,46} | {22,39,47} |
| {22,39,48} | {22,39,49} | {22,39,50} | {22,39,51} | {22,39,52} | {22,39,53} | {22,39,54} | {22,39,55} | {22,39,56} |
| {22,39,57} | {22,39,58} | {22,39,59} | {22,39,60} | {22,39,61} | {22,39,62} | {22,39,63} | {22,39,64} | {22,39,65} |
| {22,39,66} | {22,40,41} | {22,40,42} | {22,40,43} | {22,40,44} | {22,40,45} | {22,40,46} | {22,40,47} | {22,40,48} |
| {22,40,49} | {22,40,50} | {22,40,51} | {22,40,52} | {22,40,53} | {22,40,54} | {22,40,55} | {22,40,56} | {22,40,57} |
| {22,40,58} | {22,40,59} | {22,40,60} | {22,40,61} | {22,40,62} | {22,40,63} | {22,40,64} | {22,40,65} | {22,40,66} |
| {22,41,42} | {22,41,43} | {22,41,44} | {22,41,45} | {22,41,46} | {22,41,47} | {22,41,48} | {22,41,49} | {22,41,50} |
| {22,41,51} | {22,41,52} | {22,41,53} | {22,41,54} | {22,41,55} | {22,41,56} | {22,41,57} | {22,41,58} | {22,41,59} |
| {22,41,60} | {22,41,61} | {22,41,62} | {22,41,63} | {22,41,64} | {22,41,65} | {22,41,66} | {22,42,43} | {22,42,44} |
| {22,42,45} | {22,42,46} | {22,42,47} | {22,42,48} | {22,42,49} | {22,42,50} | {22,42,51} | {22,42,52} | {22,42,53} |
| {22,42,54} | {22,42,55} | {22,42,56} | {22,42,57} | {22,42,58} | {22,42,59} | {22,42,60} | {22,42,61} | {22,42,62} |
| {22,42,63} | {22,42,64} | {22,42,65} | {22,42,66} | {22,43,44} | {22,43,45} | {22,43,46} | {22,43,47} | {22,43,48} |
| {22,43,49} | {22,43,50} | {22,43,51} | {22,43,52} | {22,43,53} | {22,43,54} | {22,43,55} | {22,43,56} | {22,43,57} |
| {22,43,58} | {22,43,59} | {22,43,60} | {22,43,61} | {22,43,62} | {22,43,63} | {22,43,64} | {22,43,65} | {22,43,66} |
| {22,44,45} | {22,44,46} | {22,44,47} | {22,44,48} | {22,44,49} | {22,44,50} | {22,44,51} | {22,44,52} | {22,44,53} |
| {22,44,54} | {22,44,55} | {22,44,56} | {22,44,57} | {22,44,58} | {22,44,59} | {22,44,60} | {22,44,61} | {22,44,62} |
| {22,44,63} | {22,44,64} | {22,44,65} | {22,44,66} | {22,45,46} | {22,45,47} | {22,45,48} | {22,45,49} | {22,45,50} |
| {22,45,51} | {22,45,52} | {22,45,53} | {22,45,54} | {22,45,55} | {22,45,56} | {22,45,57} | {22,45,58} | {22,45,59} |
| {22,45,60} | {22,45,61} | {22,45,62} | {22,45,63} | {22,45,64} | {22,45,65} | {22,45,66} | {22,46,47} | {22,46,48} |
| {22,46,49} | {22,46,50} | {22,46,51} | {22,46,52} | {22,46,53} | {22,46,54} | {22,46,55} | {22,46,56} | {22,46,57} |
| {22,46,58} | {22,46,59} | {22,46,60} | {22,46,61} | {22,46,62} | {22,46,63} | {22,46,64} | {22,46,65} | {22,46,66} |
| {22,47,48} | {22,47,49} | {22,47,50} | {22,47,51} | {22,47,52} | {22,47,53} | {22,47,54} | {22,47,55} | {22,47,56} |
| {22,47,57} | {22,47,58} | {22,47,59} | {22,47,60} | {22,47,61} | {22,47,62} | {22,47,63} | {22,47,64} | {22,47,65} |
| {22,47,66} | {22,48,49} | {22,48,50} | {22,48,51} | {22,48,52} | {22,48,53} | {22,48,54} | {22,48,55} | {22,48,56} |
| {22,48,57} | {22,48,58} | {22,48,59} | {22,48,60} | {22,48,61} | {22,48,62} | {22,48,63} | {22,48,64} | {22,48,65} |
| {22,48,66} | {22,49,50} | {22,49,51} | {22,49,52} | {22,49,53} | {22,49,54} | {22,49,55} | {22,49,56} | {22,49,57} |
| {22,49,58} | {22,49,59} | {22,49,60} | {22,49,61} | {22,49,62} | {22,49,63} | {22,49,64} | {22,49,65} | {22,49,66} |
| {22,50,51} | {22,50,52} | {22,50,53} | {22,50,54} | {22,50,55} | {22,50,56} | {22,50,57} | {22,50,58} | {22,50,59} |
| {22,50,60} | {22,50,61} | {22,50,62} | {22,50,63} | {22,50,64} | {22,50,65} | {22,50,66} | {22,51,52} | {22,51,53} |
| {22,51,54} | {22,51,55} | {22,51,56} | {22,51,57} | {22,51,58} | {22,51,59} | {22,51,60} | {22,51,61} | {22,51,62} |
| {22,51,63} | {22,51,64} | {22,51,65} | {22,51,66} | {22,52,53} | {22,52,54} | {22,52,55} | {22,52,56} | {22,52,57} |
| {22,52,58} | {22,52,59} | {22,52,60} | {22,52,61} | {22,52,62} | {22,52,63} | {22,52,64} | {22,52,65} | {22,52,66} |
| {22,53,54} | {22,53,55} | {22,53,56} | {22,53,57} | {22,53,58} | {22,53,59} | {22,53,60} | {22,53,61} | {22,53,62} |
| {22,53,63} | {22,53,64} | {22,53,65} | {22,53,66} | {22,54,55} | {22,54,56} | {22,54,57} | {22,54,58} | {22,54,59} |
| {22,54,60} | {22,54,61} | {22,54,62} | {22,54,63} | {22,54,64} | {22,54,65} | {22,54,66} | {22,55,56} | {22,55,57} |
| {22,55,58} | {22,55,59} | {22,55,60} | {22,55,61} | {22,55,62} | {22,55,63} | {22,55,64} | {22,55,65} | {22,55,66} |
| {22,56,57} | {22,56,58} | {22,56,59} | {22,56,60} | {22,56,61} | {22,56,62} | {22,56,63} | {22,56,64} | {22,56,65} |
| {22,56,66} | {22,57,58} | {22,57,59} | {22,57,60} | {22,57,61} | {22,57,62} | {22,57,63} | {22,57,64} | {22,57,65} |
| {22,57,66} | {22,58,59} | {22,58,60} | {22,58,61} | {22,58,62} | {22,58,63} | {22,58,64} | {22,58,65} | {22,58,66} |
| {22,59,60} | {22,59,61} | {22,59,62} | {22,59,63} | {22,59,64} | {22,59,65} | {22,59,66} | {22,60,61} | {22,60,62} |
| {22,60,63} | {22,60,64} | {22,60,65} | {22,60,66} | {22,61,62} | {22,61,63} | {22,61,64} | {22,61,65} | {22,61,66} |
| {22,62,63} | {22,62,64} | {22,62,65} | {22,62,66} | {22,63,64} | {22,63,65} | {22,63,66} | {22,64,65} | {22,64,66} |
| {22,65,66} | {23,24,25} | {23,24,26} | {23,24,27} | {23,24,28} | {23,24,29} | {23,24,30} | {23,24,31} | {23,24,32} |
| {23,24,33} | {23,24,34} | {23,24,35} | {23,24,36} | {23,24,37} | {23,24,38} | {23,24,39} | {23,24,40} | {23,24,41} |
| {23,24,42} | {23,24,43} | {23,24,44} | {23,24,45} | {23,24,46} | {23,24,47} | {23,24,48} | {23,24,49} | {23,24,50} |
| {23,24,51} | {23,24,52} | {23,24,53} | {23,24,54} | {23,24,55} | {23,24,56} | {23,24,57} | {23,24,58} | {23,24,59} |
| {23,24,60} | {23,24,61} | {23,24,62} | {23,24,63} | {23,24,64} | {23,24,65} | {23,24,66} | {23,25,26} | {23,25,27} |
| {23,25,28} | {23,25,29} | {23,25,30} | {23,25,31} | {23,25,32} | {23,25,33} | {23,25,34} | {23,25,35} | {23,25,36} |
| {23,25,37} | {23,25,38} | {23,25,39} | {23,25,40} | {23,25,41} | {23,25,42} | {23,25,43} | {23,25,44} | {23,25,45} |

TABLE 3A-continued

| | | | | | | | |
|---|---|---|---|---|---|---|---|
| {23,25,46} | {23,25,47} | {23,25,48} | {23,25,49} | {23,25,50} | {23,25,51} | {23,25,52} | {23,25,53} | {23,25,54} |
| {23,25,55} | {23,25,56} | {23,25,57} | {23,25,58} | {23,25,59} | {23,25,60} | {23,25,61} | {23,25,62} | {23,25,63} |
| {23,25,64} | {23,25,65} | {23,25,66} | {23,26,27} | {23,26,28} | {23,26,29} | {23,26,30} | {23,26,31} | {23,26,32} |
| {23,26,33} | {23,26,34} | {23,26,35} | {23,26,36} | {23,26,37} | {23,26,38} | {23,26,39} | {23,26,40} | {23,26,41} |
| {23,26,42} | {23,26,43} | {23,26,44} | {23,26,45} | {23,26,46} | {23,26,47} | {23,26,48} | {23,26,49} | {23,26,50} |
| {23,26,51} | {23,26,52} | {23,26,53} | {23,26,54} | {23,26,55} | {23,26,56} | {23,26,57} | {23,26,58} | {23,26,59} |
| {23,26,60} | {23,26,61} | {23,26,62} | {23,26,63} | {23,26,64} | {23,26,65} | {23,26,66} | {23,27,28} | {23,27,29} |
| {23,27,30} | {23,27,31} | {23,27,32} | {23,27,33} | {23,27,34} | {23,27,35} | {23,27,36} | {23,27,37} | {23,27,38} |
| {23,27,39} | {23,27,40} | {23,27,41} | {23,27,42} | {23,27,43} | {23,27,44} | {23,27,45} | {23,27,46} | {23,27,47} |
| {23,27,48} | {23,27,49} | {23,27,50} | {23,27,51} | {23,27,52} | {23,27,53} | {23,27,54} | {23,27,55} | {23,27,56} |
| {23,27,57} | {23,27,58} | {23,27,59} | {23,27,60} | {23,27,61} | {23,27,62} | {23,27,63} | {23,27,64} | {23,27,65} |
| {23,27,66} | {23,28,29} | {23,28,30} | {23,28,31} | {23,28,32} | {23,28,33} | {23,28,34} | {23,28,35} | {23,28,36} |
| {23,28,37} | {23,28,38} | {23,28,39} | {23,28,40} | {23,28,41} | {23,28,42} | {23,28,43} | {23,28,44} | {23,28,45} |
| {23,28,46} | {23,28,47} | {23,28,48} | {23,28,49} | {23,28,50} | {23,28,51} | {23,28,52} | {23,28,53} | {23,28,54} |
| {23,28,55} | {23,28,56} | {23,28,57} | {23,28,58} | {23,28,59} | {23,28,60} | {23,28,61} | {23,28,62} | {23,28,63} |
| {23,28,64} | {23,28,65} | {23,28,66} | {23,29,30} | {23,29,31} | {23,29,32} | {23,29,33} | {23,29,34} | {23,29,35} |
| {23,29,36} | {23,29,37} | {23,29,38} | {23,29,39} | {23,29,40} | {23,29,41} | {23,29,42} | {23,29,43} | {23,29,44} |
| {23,29,45} | {23,29,46} | {23,29,47} | {23,29,48} | {23,29,49} | {23,29,50} | {23,29,51} | {23,29,52} | {23,29,53} |
| {23,29,54} | {23,29,55} | {23,29,56} | {23,29,57} | {23,29,58} | {23,29,59} | {23,29,60} | {23,29,61} | {23,29,62} |
| {23,29,63} | {23,29,64} | {23,29,65} | {23,29,66} | {23,30,31} | {23,30,32} | {23,30,33} | {23,30,34} | {23,30,35} |
| {23,30,36} | {23,30,37} | {23,30,38} | {23,30,39} | {23,30,40} | {23,30,41} | {23,30,42} | {23,30,43} | {23,30,44} |
| {23,30,45} | {23,30,46} | {23,30,47} | {23,30,48} | {23,30,49} | {23,30,50} | {23,30,51} | {23,30,52} | {23,30,53} |
| {23,30,54} | {23,30,55} | {23,30,56} | {23,30,57} | {23,30,58} | {23,30,59} | {23,30,60} | {23,30,61} | {23,30,62} |
| {23,30,63} | {23,30,64} | {23,30,65} | {23,30,66} | {23,31,32} | {23,31,33} | {23,31,34} | {23,31,35} | {23,31,36} |
| {23,31,37} | {23,31,38} | {23,31,39} | {23,31,40} | {23,31,41} | {23,31,42} | {23,31,43} | {23,31,44} | {23,31,45} |
| {23,31,46} | {23,31,47} | {23,31,48} | {23,31,49} | {23,31,50} | {23,31,51} | {23,31,52} | {23,31,53} | {23,31,54} |
| {23,31,55} | {23,31,56} | {23,31,57} | {23,31,58} | {23,31,59} | {23,31,60} | {23,31,61} | {23,31,62} | {23,31,63} |
| {23,31,64} | {23,31,65} | {23,31,66} | {23,32,33} | {23,32,34} | {23,32,35} | {23,32,36} | {23,32,37} | {23,32,38} |
| {23,32,39} | {23,32,40} | {23,32,41} | {23,32,42} | {23,32,43} | {23,32,44} | {23,32,45} | {23,32,46} | {23,32,47} |
| {23,32,48} | {23,32,49} | {23,32,50} | {23,32,51} | {23,32,52} | {23,32,53} | {23,32,54} | {23,32,55} | {23,32,56} |
| {23,32,57} | {23,32,58} | {23,32,59} | {23,32,60} | {23,32,61} | {23,32,62} | {23,32,63} | {23,32,64} | {23,32,65} |
| {23,32,66} | {23,33,34} | {23,33,35} | {23,33,36} | {23,33,37} | {23,33,38} | {23,33,39} | {23,33,40} | {23,33,41} |
| {23,33,42} | {23,33,43} | {23,33,44} | {23,33,45} | {23,33,46} | {23,33,47} | {23,33,48} | {23,33,49} | {23,33,50} |
| {23,33,51} | {23,33,52} | {23,33,53} | {23,33,54} | {23,33,55} | {23,33,56} | {23,33,57} | {23,33,58} | {23,33,59} |
| {23,33,60} | {23,33,61} | {23,33,62} | {23,33,63} | {23,33,64} | {23,33,65} | {23,33,66} | {23,34,35} | {23,34,36} |
| {23,34,37} | {23,34,38} | {23,34,39} | {23,34,40} | {23,34,41} | {23,34,42} | {23,34,43} | {23,34,44} | {23,34,45} |
| {23,34,46} | {23,34,47} | {23,34,48} | {23,34,49} | {23,34,50} | {23,34,51} | {23,34,52} | {23,34,53} | {23,34,54} |
| {23,34,55} | {23,34,56} | {23,34,57} | {23,34,58} | {23,34,59} | {23,34,60} | {23,34,61} | {23,34,62} | {23,34,63} |
| {23,34,64} | {23,34,65} | {23,34,66} | {23,35,36} | {23,35,37} | {23,35,38} | {23,35,39} | {23,35,40} | {23,35,41} |
| {23,35,42} | {23,35,43} | {23,35,44} | {23,35,45} | {23,35,46} | {23,35,47} | {23,35,48} | {23,35,49} | {23,35,50} |
| {23,35,51} | {23,35,52} | {23,35,53} | {23,35,54} | {23,35,55} | {23,35,56} | {23,35,57} | {23,35,58} | {23,35,59} |
| {23,35,60} | {23,35,61} | {23,35,62} | {23,35,63} | {23,35,64} | {23,35,65} | {23,35,66} | {23,36,37} | {23,36,38} |
| {23,36,39} | {23,36,40} | {23,36,41} | {23,36,42} | {23,36,43} | {23,36,44} | {23,36,45} | {23,36,46} | {23,36,47} |
| {23,36,48} | {23,36,49} | {23,36,50} | {23,36,51} | {23,36,52} | {23,36,53} | {23,36,54} | {23,36,55} | {23,36,56} |
| {23,36,57} | {23,36,58} | {23,36,59} | {23,36,60} | {23,36,61} | {23,36,62} | {23,36,63} | {23,36,64} | {23,36,65} |
| {23,36,66} | {23,37,38} | {23,37,39} | {23,37,40} | {23,37,41} | {23,37,42} | {23,37,43} | {23,37,44} | {23,37,45} |
| {23,37,46} | {23,37,47} | {23,37,48} | {23,37,49} | {23,37,50} | {23,37,51} | {23,37,52} | {23,37,53} | {23,37,54} |
| {23,37,55} | {23,37,56} | {23,37,57} | {23,37,58} | {23,37,59} | {23,37,60} | {23,37,61} | {23,37,62} | {23,37,63} |
| {23,37,64} | {23,37,65} | {23,37,66} | {23,38,39} | {23,38,40} | {23,38,41} | {23,38,42} | {23,38,43} | {23,38,44} |
| {23,38,45} | {23,38,46} | {23,38,47} | {23,38,48} | {23,38,49} | {23,38,50} | {23,38,51} | {23,38,52} | {23,38,53} |
| {23,38,54} | {23,38,55} | {23,38,56} | {23,38,57} | {23,38,58} | {23,38,59} | {23,38,60} | {23,38,61} | {23,38,62} |
| {23,38,63} | {23,38,64} | {23,38,65} | {23,38,66} | {23,39,40} | {23,39,41} | {23,39,42} | {23,39,43} | {23,39,44} |
| {23,39,45} | {23,39,46} | {23,39,47} | {23,39,48} | {23,39,49} | {23,39,50} | {23,39,51} | {23,39,52} | {23,39,53} |
| {23,39,54} | {23,39,55} | {23,39,56} | {23,39,57} | {23,39,58} | {23,39,59} | {23,39,60} | {23,39,61} | {23,39,62} |
| {23,39,63} | {23,39,64} | {23,39,65} | {23,39,66} | {23,40,41} | {23,40,42} | {23,40,43} | {23,40,44} | {23,40,45} |
| {23,40,46} | {23,40,47} | {23,40,48} | {23,40,49} | {23,40,50} | {23,40,51} | {23,40,52} | {23,40,53} | {23,40,54} |
| {23,40,55} | {23,40,56} | {23,40,57} | {23,40,58} | {23,40,59} | {23,40,60} | {23,40,61} | {23,40,62} | {23,40,63} |
| {23,40,64} | {23,40,65} | {23,40,66} | {23,41,42} | {23,41,43} | {23,41,44} | {23,41,45} | {23,41,46} | {23,41,47} |
| {23,41,48} | {23,41,49} | {23,41,50} | {23,41,51} | {23,41,52} | {23,41,53} | {23,41,54} | {23,41,55} | {23,41,56} |
| {23,41,57} | {23,41,58} | {23,41,59} | {23,41,60} | {23,41,61} | {23,41,62} | {23,41,63} | {23,41,64} | {23,41,65} |
| {23,41,66} | {23,42,43} | {23,42,44} | {23,42,45} | {23,42,46} | {23,42,47} | {23,42,48} | {23,42,49} | {23,42,50} |
| {23,42,51} | {23,42,52} | {23,42,53} | {23,42,54} | {23,42,55} | {23,42,56} | {23,42,57} | {23,42,58} | {23,42,59} |
| {23,42,60} | {23,42,61} | {23,42,62} | {23,42,63} | {23,42,64} | {23,42,65} | {23,42,66} | {23,43,44} | {23,43,45} |
| {23,43,46} | {23,43,47} | {23,43,48} | {23,43,49} | {23,43,50} | {23,43,51} | {23,43,52} | {23,43,53} | {23,43,54} |
| {23,43,55} | {23,43,56} | {23,43,57} | {23,43,58} | {23,43,59} | {23,43,60} | {23,43,61} | {23,43,62} | {23,43,63} |
| {23,43,64} | {23,43,65} | {23,43,66} | {23,44,45} | {23,44,46} | {23,44,47} | {23,44,48} | {23,44,49} | {23,44,50} |
| {23,44,51} | {23,44,52} | {23,44,53} | {23,44,54} | {23,44,55} | {23,44,56} | {23,44,57} | {23,44,58} | {23,44,59} |
| {23,44,60} | {23,44,61} | {23,44,62} | {23,44,63} | {23,44,64} | {23,44,65} | {23,44,66} | {23,45,46} | {23,45,47} |
| {23,45,48} | {23,45,49} | {23,45,50} | {23,45,51} | {23,45,52} | {23,45,53} | {23,45,54} | {23,45,55} | {23,45,56} |
| {23,45,57} | {23,45,58} | {23,45,59} | {23,45,60} | {23,45,61} | {23,45,62} | {23,45,63} | {23,45,64} | {23,45,65} |
| {23,45,66} | {23,46,47} | {23,46,48} | {23,46,49} | {23,46,50} | {23,46,51} | {23,46,52} | {23,46,53} | {23,46,54} |
| {23,46,55} | {23,46,56} | {23,46,57} | {23,46,58} | {23,46,59} | {23,46,60} | {23,46,61} | {23,46,62} | {23,46,63} |
| {23,46,64} | {23,46,65} | {23,46,66} | {23,47,48} | {23,47,49} | {23,47,50} | {23,47,51} | {23,47,52} | {23,47,53} |
| {23,47,54} | {23,47,55} | {23,47,56} | {23,47,57} | {23,47,58} | {23,47,59} | {23,47,60} | {23,47,61} | {23,47,62} |
| {23,47,63} | {23,47,64} | {23,47,65} | {23,47,66} | {23,48,49} | {23,48,50} | {23,48,51} | {23,48,52} | {23,48,53} |
| {23,48,54} | {23,48,55} | {23,48,56} | {23,48,57} | {23,48,58} | {23,48,59} | {23,48,60} | {23,48,61} | {23,48,62} |
| {23,48,63} | {23,48,64} | {23,48,65} | {23,48,66} | {23,49,50} | {23,49,51} | {23,49,52} | {23,49,53} | {23,49,54} |
| {23,49,55} | {23,49,56} | {23,49,57} | {23,49,58} | {23,49,59} | {23,49,60} | {23,49,61} | {23,49,62} | {23,49,63} |
| {23,49,64} | {23,49,65} | {23,49,66} | {23,50,51} | {23,50,52} | {23,50,53} | {23,50,54} | {23,50,55} | {23,50,56} |
| {23,50,57} | {23,50,58} | {23,50,59} | {23,50,60} | {23,50,61} | {23,50,62} | {23,50,63} | {23,50,64} | {23,50,65} |

TABLE 3A-continued

{23,50,66} {23,51,52} {23,51,53} {23,51,54} {23,51,55} {23,51,56} {23,51,57} {23,51,58} {23,51,59}
{23,51,60} {23,51,61} {23,51,62} {23,51,63} {23,51,64} {23,51,65} {23,51,66} {23,52,53} {23,52,54}
{23,52,55} {23,52,56} {23,52,57} {23,52,58} {23,52,59} {23,52,60} {23,52,61} {23,52,62} {23,52,63}
{23,52,64} {23,52,65} {23,52,66} {23,53,54} {23,53,55} {23,53,56} {23,53,57} {23,53,58} {23,53,59}
{23,53,60} {23,53,61} {23,53,62} {23,53,63} {23,53,64} {23,53,65} {23,53,66} {23,54,55} {23,54,56}
{23,54,57} {23,54,58} {23,54,59} {23,54,60} {23,54,61} {23,54,62} {23,54,63} {23,54,64} {23,54,65}
{23,54,66} {23,55,56} {23,55,57} {23,55,58} {23,55,59} {23,55,60} {23,55,61} {23,55,62} {23,55,63}
{23,55,64} {23,55,65} {23,55,66} {23,56,57} {23,56,58} {23,56,59} {23,56,60} {23,56,61} {23,56,62}
{23,56,63} {23,56,64} {23,56,65} {23,56,66} {23,57,58} {23,57,59} {23,57,60} {23,57,61} {23,57,62}
{23,57,63} {23,57,64} {23,57,65} {23,57,66} {23,58,59} {23,58,60} {23,58,61} {23,58,62} {23,58,63}
{23,58,64} {23,58,65} {23,58,66} {23,59,60} {23,59,61} {23,59,62} {23,59,63} {23,59,64} {23,59,65}
{23,59,66} {23,60,61} {23,60,62} {23,60,63} {23,60,64} {23,60,65} {23,60,66} {23,61,62} {23,61,63}
{23,61,64} {23,61,65} {23,61,66} {23,62,63} {23,62,64} {23,62,65} {23,62,66} {23,63,64} {23,63,65}
{23,63,66} {23,64,65} {23,64,66} {23,65,66} {24,25,26} {24,25,27} {24,25,28} {24,25,29} {24,25,30}
{24,25,31} {24,25,32} {24,25,33} {24,25,34} {24,25,35} {24,25,36} {24,25,37} {24,25,38} {24,25,39}
{24,25,40} {24,25,41} {24,25,42} {24,25,43} {24,25,44} {24,25,45} {24,25,46} {24,25,47} {24,25,48}
{24,25,49} {24,25,50} {24,25,51} {24,25,52} {24,25,53} {24,25,54} {24,25,55} {24,25,56} {24,25,57}
{24,25,58} {24,25,59} {24,25,60} {24,25,61} {24,25,62} {24,25,63} {24,25,64} {24,25,65} {24,25,66}
{24,26,27} {24,26,28} {24,26,29} {24,26,30} {24,26,31} {24,26,32} {24,26,33} {24,26,34} {24,26,35}
{24,26,36} {24,26,37} {24,26,38} {24,26,39} {24,26,40} {24,26,41} {24,26,42} {24,26,43} {24,26,44}
{24,26,45} {24,26,46} {24,26,47} {24,26,48} {24,26,49} {24,26,50} {24,26,51} {24,26,52} {24,26,53}
{24,26,54} {24,26,55} {24,26,56} {24,26,57} {24,26,58} {24,26,59} {24,26,60} {24,26,61} {24,26,62}
{24,26,63} {24,26,64} {24,26,65} {24,26,66} {24,27,28} {24,27,29} {24,27,30} {24,27,31} {24,27,32}
{24,27,33} {24,27,34} {24,27,35} {24,27,36} {24,27,37} {24,27,38} {24,27,39} {24,27,40} {24,27,41}
{24,27,42} {24,27,43} {24,27,44} {24,27,45} {24,27,46} {24,27,47} {24,27,48} {24,27,49} {24,27,50}
{24,27,51} {24,27,52} {24,27,53} {24,27,54} {24,27,55} {24,27,56} {24,27,57} {24,27,58} {24,27,59}
{24,27,60} {24,27,61} {24,27,62} {24,27,63} {24,27,64} {24,27,65} {24,27,66} {24,28,29} {24,28,30}
{24,28,31} {24,28,32} {24,28,33} {24,28,34} {24,28,35} {24,28,36} {24,28,37} {24,28,38} {24,28,39}
{24,28,40} {24,28,41} {24,28,42} {24,28,43} {24,28,44} {24,28,45} {24,28,46} {24,28,47} {24,28,48}
{24,28,49} {24,28,50} {24,28,51} {24,28,52} {24,28,53} {24,28,54} {24,28,55} {24,28,56} {24,28,57}
{24,28,58} {24,28,59} {24,28,60} {24,28,61} {24,28,62} {24,28,63} {24,28,64} {24,28,65} {24,28,66}
{24,29,30} {24,29,31} {24,29,32} {24,29,33} {24,29,34} {24,29,35} {24,29,36} {24,29,37} {24,29,38}
{24,29,39} {24,29,40} {24,29,41} {24,29,42} {24,29,43} {24,29,44} {24,29,45} {24,29,46} {24,29,47}
{24,29,48} {24,29,49} {24,29,50} {24,29,51} {24,29,52} {24,29,53} {24,29,54} {24,29,55} {24,29,56}
{24,29,57} {24,29,58} {24,29,59} {24,29,60} {24,29,61} {24,29,62} {24,29,63} {24,29,64} {24,29,65}
{24,29,66} {24,30,31} {24,30,32} {24,30,33} {24,30,34} {24,30,35} {24,30,36} {24,30,37} {24,30,38}
{24,30,39} {24,30,40} {24,30,41} {24,30,42} {24,30,43} {24,30,44} {24,30,45} {24,30,46} {24,30,47}
{24,30,48} {24,30,49} {24,30,50} {24,30,51} {24,30,52} {24,30,53} {24,30,54} {24,30,55} {24,30,56}
{24,30,57} {24,30,58} {24,30,59} {24,30,60} {24,30,61} {24,30,62} {24,30,63} {24,30,64} {24,30,65}
{24,30,66} {24,31,32} {24,31,33} {24,31,34} {24,31,35} {24,31,36} {24,31,37} {24,31,38} {24,31,39}
{24,31,40} {24,31,41} {24,31,42} {24,31,43} {24,31,44} {24,31,45} {24,31,46} {24,31,47} {24,31,48}
{24,31,49} {24,31,50} {24,31,51} {24,31,52} {24,31,53} {24,31,54} {24,31,55} {24,31,56} {24,31,57}
{24,31,58} {24,31,59} {24,31,60} {24,31,61} {24,31,62} {24,31,63} {24,31,64} {24,31,65} {24,31,66}
{24,32,33} {24,32,34} {24,32,35} {24,32,36} {24,32,37} {24,32,38} {24,32,39} {24,32,40} {24,32,41}
{24,32,42} {24,32,43} {24,32,44} {24,32,45} {24,32,46} {24,32,47} {24,32,48} {24,32,49} {24,32,50}
{24,32,51} {24,32,52} {24,32,53} {24,32,54} {24,32,55} {24,32,56} {24,32,57} {24,32,58} {24,32,59}
{24,32,60} {24,32,61} {24,32,62} {24,32,63} {24,32,64} {24,32,65} {24,32,66} {24,33,34} {24,33,35}
{24,33,36} {24,33,37} {24,33,38} {24,33,39} {24,33,40} {24,33,41} {24,33,42} {24,33,43} {24,33,44}
{24,33,45} {24,33,46} {24,33,47} {24,33,48} {24,33,49} {24,33,50} {24,33,51} {24,33,52} {24,33,53}
{24,33,54} {24,33,55} {24,33,56} {24,33,57} {24,33,58} {24,33,59} {24,33,60} {24,33,61} {24,33,62}
{24,33,63} {24,33,64} {24,33,65} {24,33,66} {24,34,35} {24,34,36} {24,34,37} {24,34,38} {24,34,39}
{24,34,40} {24,34,41} {24,34,42} {24,34,43} {24,34,44} {24,34,45} {24,34,46} {24,34,47} {24,34,48}
{24,34,49} {24,34,50} {24,34,51} {24,34,52} {24,34,53} {24,34,54} {24,34,55} {24,34,56} {24,34,57}
{24,34,58} {24,34,59} {24,34,60} {24,34,61} {24,34,62} {24,34,63} {24,34,64} {24,34,65} {24,34,66}
{24,35,36} {24,35,37} {24,35,38} {24,35,39} {24,35,40} {24,35,41} {24,35,42} {24,35,43} {24,35,44}
{24,35,45} {24,35,46} {24,35,47} {24,35,48} {24,35,49} {24,35,50} {24,35,51} {24,35,52} {24,35,53}
{24,35,54} {24,35,55} {24,35,56} {24,35,57} {24,35,58} {24,35,59} {24,35,60} {24,35,61} {24,35,62}
{24,35,63} {24,35,64} {24,35,65} {24,35,66} {24,36,37} {24,36,38} {24,36,39} {24,36,40} {24,36,41}
{24,36,42} {24,36,43} {24,36,44} {24,36,45} {24,36,46} {24,36,47} {24,36,48} {24,36,49} {24,36,50}
{24,36,51} {24,36,52} {24,36,53} {24,36,54} {24,36,55} {24,36,56} {24,36,57} {24,36,58} {24,36,59}
{24,36,60} {24,36,61} {24,36,62} {24,36,63} {24,36,64} {24,36,65} {24,36,66} {24,37,38} {24,37,39}
{24,37,40} {24,37,41} {24,37,42} {24,37,43} {24,37,44} {24,37,45} {24,37,46} {24,37,47} {24,37,48}
{24,37,49} {24,37,50} {24,37,51} {24,37,52} {24,37,53} {24,37,54} {24,37,55} {24,37,56} {24,37,57}
{24,37,58} {24,37,59} {24,37,60} {24,37,61} {24,37,62} {24,37,63} {24,37,64} {24,37,65} {24,37,66}
{24,38,39} {24,38,40} {24,38,41} {24,38,42} {24,38,43} {24,38,44} {24,38,45} {24,38,46} {24,38,47}
{24,38,48} {24,38,49} {24,38,50} {24,38,51} {24,38,52} {24,38,53} {24,38,54} {24,38,55} {24,38,56}
{24,38,57} {24,38,58} {24,38,59} {24,38,60} {24,38,61} {24,38,62} {24,38,63} {24,38,64} {24,38,65}
{24,38,66} {24,39,40} {24,39,41} {24,39,42} {24,39,43} {24,39,44} {24,39,45} {24,39,46} {24,39,47}
{24,39,48} {24,39,49} {24,39,50} {24,39,51} {24,39,52} {24,39,53} {24,39,54} {24,39,55} {24,39,56}
{24,39,57} {24,39,58} {24,39,59} {24,39,60} {24,39,61} {24,39,62} {24,39,63} {24,39,64} {24,39,65}
{24,39,66} {24,40,41} {24,40,42} {24,40,43} {24,40,44} {24,40,45} {24,40,46} {24,40,47} {24,40,48}
{24,40,49} {24,40,50} {24,40,51} {24,40,52} {24,40,53} {24,40,54} {24,40,55} {24,40,56} {24,40,57}
{24,40,58} {24,40,59} {24,40,60} {24,40,61} {24,40,62} {24,40,63} {24,40,64} {24,40,65} {24,40,66}
{24,41,42} {24,41,43} {24,41,44} {24,41,45} {24,41,46} {24,41,47} {24,41,48} {24,41,49} {24,41,50}
{24,41,51} {24,41,52} {24,41,53} {24,41,54} {24,41,55} {24,41,56} {24,41,57} {24,41,58} {24,41,59}
{24,41,60} {24,41,61} {24,41,62} {24,41,63} {24,41,64} {24,41,65} {24,41,66} {24,42,43} {24,42,44}
{24,42,45} {24,42,46} {24,42,47} {24,42,48} {24,42,49} {24,42,50} {24,42,51} {24,42,52} {24,42,53}
{24,42,54} {24,42,55} {24,42,56} {24,42,57} {24,42,58} {24,42,59} {24,42,60} {24,42,61} {24,42,62}
{24,42,63} {24,42,64} {24,42,65} {24,42,66} {24,43,44} {24,43,45} {24,43,46} {24,43,47} {24,43,48}
{24,43,49} {24,43,50} {24,43,51} {24,43,52} {24,43,53} {24,43,54} {24,43,55} {24,43,56} {24,43,57}

TABLE 3A-continued

{24,43,58} {24,43,59} {24,43,60} {24,43,61} {24,43,62} {24,43,63} {24,43,64} {24,43,65} {24,43,66}
{24,44,45} {24,44,46} {24,44,47} {24,44,48} {24,44,49} {24,44,50} {24,44,51} {24,44,52} {24,44,53}
{24,44,54} {24,44,55} {24,44,56} {24,44,57} {24,44,58} {24,44,59} {24,44,60} {24,44,61} {24,44,62}
{24,44,63} {24,44,64} {24,44,65} {24,44,66} {24,45,46} {24,45,47} {24,45,48} {24,45,49} {24,45,50}
{24,45,51} {24,45,52} {24,45,53} {24,45,54} {24,45,55} {24,45,56} {24,45,57} {24,45,58} {24,45,59}
{24,45,60} {24,45,61} {24,45,62} {24,45,63} {24,45,64} {24,45,65} {24,45,66} {24,46,47} {24,46,48}
{24,46,49} {24,46,50} {24,46,51} {24,46,52} {24,46,53} {24,46,54} {24,46,55} {24,46,56} {24,46,57}
{24,46,58} {24,46,59} {24,46,60} {24,46,61} {24,46,62} {24,46,63} {24,46,64} {24,46,65} {24,46,66}
{24,47,48} {24,47,49} {24,47,50} {24,47,51} {24,47,52} {24,47,53} {24,47,54} {24,47,55} {24,47,56}
{24,47,57} {24,47,58} {24,47,59} {24,47,60} {24,47,61} {24,47,62} {24,47,63} {24,47,64} {24,47,65}
{24,47,66} {24,48,49} {24,48,50} {24,48,51} {24,48,52} {24,48,53} {24,48,54} {24,48,55} {24,48,56}
{24,48,57} {24,48,58} {24,48,59} {24,48,60} {24,48,61} {24,48,62} {24,48,63} {24,48,64} {24,48,65}
{24,48,66} {24,49,50} {24,49,51} {24,49,52} {24,49,53} {24,49,54} {24,49,55} {24,49,56} {24,49,57}
{24,49,58} {24,49,59} {24,49,60} {24,49,61} {24,49,62} {24,49,63} {24,49,64} {24,49,65} {24,49,66}
{24,50,51} {24,50,52} {24,50,53} {24,50,54} {24,50,55} {24,50,56} {24,50,57} {24,50,58} {24,50,59}
{24,50,60} {24,50,61} {24,50,62} {24,50,63} {24,50,64} {24,50,65} {24,50,66} {24,51,52} {24,51,53}
{24,51,54} {24,51,55} {24,51,56} {24,51,57} {24,51,58} {24,51,59} {24,51,60} {24,51,61} {24,51,62}
{24,51,63} {24,51,64} {24,51,65} {24,51,66} {24,52,53} {24,52,54} {24,52,55} {24,52,56} {24,52,57}
{24,52,58} {24,52,59} {24,52,60} {24,52,61} {24,52,62} {24,52,63} {24,52,64} {24,52,65} {24,52,66}
{24,53,54} {24,53,55} {24,53,56} {24,53,57} {24,53,58} {24,53,59} {24,53,60} {24,53,61} {24,53,62}
{24,53,63} {24,53,64} {24,53,65} {24,53,66} {24,54,55} {24,54,56} {24,54,57} {24,54,58} {24,54,59}
{24,54,60} {24,54,61} {24,54,62} {24,54,63} {24,54,64} {24,54,65} {24,54,66} {24,55,56} {24,55,57}
{24,55,58} {24,55,59} {24,55,60} {24,55,61} {24,55,62} {24,55,63} {24,55,64} {24,55,65} {24,55,66}
{24,56,57} {24,56,58} {24,56,59} {24,56,60} {24,56,61} {24,56,62} {24,56,63} {24,56,64} {24,56,65}
{24,56,66} {24,57,58} {24,57,59} {24,57,60} {24,57,61} {24,57,62} {24,57,63} {24,57,64} {24,57,65}
{24,57,66} {24,58,59} {24,58,60} {24,58,61} {24,58,62} {24,58,63} {24,58,64} {24,58,65} {24,58,66}
{24,59,60} {24,59,61} {24,59,62} {24,59,63} {24,59,64} {24,59,65} {24,59,66} {24,60,61} {24,60,62}
{24,60,63} {24,60,64} {24,60,65} {24,60,66} {24,61,62} {24,61,63} {24,61,64} {24,61,65} {24,61,66}
{24,62,63} {24,62,64} {24,62,65} {24,62,66} {24,63,64} {24,63,65} {24,63,66} {24,64,65} {24,64,66}
{24,65,66} {25,26,27} {25,26,28} {25,26,29} {25,26,30} {25,26,31} {25,26,32} {25,26,33} {25,26,34}
{25,26,35} {25,26,36} {25,26,37} {25,26,38} {25,26,39} {25,26,40} {25,26,41} {25,26,42} {25,26,43}
{25,26,44} {25,26,45} {25,26,46} {25,26,47} {25,26,48} {25,26,49} {25,26,50} {25,26,51} {25,26,52}
{25,26,53} {25,26,54} {25,26,55} {25,26,56} {25,26,57} {25,26,58} {25,26,59} {25,26,60} {25,26,61}
{25,26,62} {25,26,63} {25,26,64} {25,26,65} {25,26,66} {25,27,28} {25,27,29} {25,27,30} {25,27,31}
{25,27,32} {25,27,33} {25,27,34} {25,27,35} {25,27,36} {25,27,37} {25,27,38} {25,27,39} {25,27,40}
{25,27,41} {25,27,42} {25,27,43} {25,27,44} {25,27,45} {25,27,46} {25,27,47} {25,27,48} {25,27,49}
{25,27,50} {25,27,51} {25,27,52} {25,27,53} {25,27,54} {25,27,55} {25,27,56} {25,27,57} {25,27,58}
{25,27,59} {25,27,60} {25,27,61} {25,27,62} {25,27,63} {25,27,64} {25,27,65} {25,27,66} {25,28,29}
{25,28,30} {25,28,31} {25,28,32} {25,28,33} {25,28,34} {25,28,35} {25,28,36} {25,28,37} {25,28,38}
{25,28,39} {25,28,40} {25,28,41} {25,28,42} {25,28,43} {25,28,44} {25,28,45} {25,28,46} {25,28,47}
{25,28,48} {25,28,49} {25,28,50} {25,28,51} {25,28,52} {25,28,53} {25,28,54} {25,28,55} {25,28,56}
{25,28,57} {25,28,58} {25,28,59} {25,28,60} {25,28,61} {25,28,62} {25,28,63} {25,28,64} {25,28,65}
{25,28,66} {25,29,30} {25,29,31} {25,29,32} {25,29,33} {25,29,34} {25,29,35} {25,29,36} {25,29,37}
{25,29,38} {25,29,39} {25,29,40} {25,29,41} {25,29,42} {25,29,43} {25,29,44} {25,29,45} {25,29,46}
{25,29,47} {25,29,48} {25,29,49} {25,29,50} {25,29,51} {25,29,52} {25,29,53} {25,29,54} {25,29,55}
{25,29,56} {25,29,57} {25,29,58} {25,29,59} {25,29,60} {25,29,61} {25,29,62} {25,29,63} {25,29,64}
{25,29,65} {25,29,66} {25,30,31} {25,30,32} {25,30,33} {25,30,34} {25,30,35} {25,30,36} {25,30,37}
{25,30,38} {25,30,39} {25,30,40} {25,30,41} {25,30,42} {25,30,43} {25,30,44} {25,30,45} {25,30,46}
{25,30,47} {25,30,48} {25,30,49} {25,30,50} {25,30,51} {25,30,52} {25,30,53} {25,30,54} {25,30,55}
{25,30,56} {25,30,57} {25,30,58} {25,30,59} {25,30,60} {25,30,61} {25,30,62} {25,30,63} {25,30,64}
{25,30,65} {25,30,66} {25,31,32} {25,31,33} {25,31,34} {25,31,35} {25,31,36} {25,31,37} {25,31,38}
{25,31,39} {25,31,40} {25,31,41} {25,31,42} {25,31,43} {25,31,44} {25,31,45} {25,31,46} {25,31,47}
{25,31,48} {25,31,49} {25,31,50} {25,31,51} {25,31,52} {25,31,53} {25,31,54} {25,31,55} {25,31,56}
{25,31,57} {25,31,58} {25,31,59} {25,31,60} {25,31,61} {25,31,62} {25,31,63} {25,31,64} {25,31,65}
{25,31,66} {25,32,33} {25,32,34} {25,32,35} {25,32,36} {25,32,37} {25,32,38} {25,32,39} {25,32,40}
{25,32,41} {25,32,42} {25,32,43} {25,32,44} {25,32,45} {25,32,46} {25,32,47} {25,32,48} {25,32,49}
{25,32,50} {25,32,51} {25,32,52} {25,32,53} {25,32,54} {25,32,55} {25,32,56} {25,32,57} {25,32,58}
{25,32,59} {25,32,60} {25,32,61} {25,32,62} {25,32,63} {25,32,64} {25,32,65} {25,32,66} {25,33,34}
{25,33,35} {25,33,36} {25,33,37} {25,33,38} {25,33,39} {25,33,40} {25,33,41} {25,33,42} {25,33,43}
{25,33,44} {25,33,45} {25,33,46} {25,33,47} {25,33,48} {25,33,49} {25,33,50} {25,33,51} {25,33,52}
{25,33,53} {25,33,54} {25,33,55} {25,33,56} {25,33,57} {25,33,58} {25,33,59} {25,33,60} {25,33,61}
{25,33,62} {25,33,63} {25,33,64} {25,33,65} {25,33,66} {25,34,35} {25,34,36} {25,34,37} {25,34,38}
{25,34,39} {25,34,40} {25,34,41} {25,34,42} {25,34,43} {25,34,44} {25,34,45} {25,34,46} {25,34,47}
{25,34,48} {25,34,49} {25,34,50} {25,34,51} {25,34,52} {25,34,53} {25,34,54} {25,34,55} {25,34,56}
{25,34,57} {25,34,58} {25,34,59} {25,34,60} {25,34,61} {25,34,62} {25,34,63} {25,34,64} {25,34,65}
{25,34,66} {25,35,36} {25,35,37} {25,35,38} {25,35,39} {25,35,40} {25,35,41} {25,35,42} {25,35,43}
{25,35,44} {25,35,45} {25,35,46} {25,35,47} {25,35,48} {25,35,49} {25,35,50} {25,35,51} {25,35,52}
{25,35,53} {25,35,54} {25,35,55} {25,35,56} {25,35,57} {25,35,58} {25,35,59} {25,35,60} {25,35,61}
{25,35,62} {25,35,63} {25,35,64} {25,35,65} {25,35,66} {25,36,37} {25,36,38} {25,36,39} {25,36,40}
{25,36,41} {25,36,42} {25,36,43} {25,36,44} {25,36,45} {25,36,46} {25,36,47} {25,36,48} {25,36,49}
{25,36,50} {25,36,51} {25,36,52} {25,36,53} {25,36,54} {25,36,55} {25,36,56} {25,36,57} {25,36,58}
{25,36,59} {25,36,60} {25,36,61} {25,36,62} {25,36,63} {25,36,64} {25,36,65} {25,36,66} {25,37,38}
{25,37,39} {25,37,40} {25,37,41} {25,37,42} {25,37,43} {25,37,44} {25,37,45} {25,37,46} {25,37,47}
{25,37,48} {25,37,49} {25,37,50} {25,37,51} {25,37,52} {25,37,53} {25,37,54} {25,37,55} {25,37,56}
{25,37,57} {25,37,58} {25,37,59} {25,37,60} {25,37,61} {25,37,62} {25,37,63} {25,37,64} {25,37,65}
{25,37,66} {25,38,39} {25,38,40} {25,38,41} {25,38,42} {25,38,43} {25,38,44} {25,38,45} {25,38,46}
{25,38,47} {25,38,48} {25,38,49} {25,38,50} {25,38,51} {25,38,52} {25,38,53} {25,38,54} {25,38,55}
{25,38,56} {25,38,57} {25,38,58} {25,38,59} {25,38,60} {25,38,61} {25,38,62} {25,38,63} {25,38,64}
{25,38,65} {25,38,66} {25,39,40} {25,39,41} {25,39,42} {25,39,43} {25,39,44} {25,39,45} {25,39,46}
{25,39,47} {25,39,48} {25,39,49} {25,39,50} {25,39,51} {25,39,52} {25,39,53} {25,39,54} {25,39,55}

TABLE 3A-continued

{25,39,56} {25,39,57} {25,39,58} {25,39,59} {25,39,60} {25,39,61} {25,39,62} {25,39,63} {25,39,64}
{25,39,65} {25,39,66} {25,40,41} {25,40,42} {25,40,43} {25,40,44} {25,40,45} {25,40,46} {25,40,47}
{25,40,48} {25,40,49} {25,40,50} {25,40,51} {25,40,52} {25,40,53} {25,40,54} {25,40,55} {25,40,56}
{25,40,57} {25,40,58} {25,40,59} {25,40,60} {25,40,61} {25,40,62} {25,40,63} {25,40,64} {25,40,65}
{25,40,66} {25,41,42} {25,41,43} {25,41,44} {25,41,45} {25,41,46} {25,41,47} {25,41,48} {25,41,49}
{25,41,50} {25,41,51} {25,41,52} {25,41,53} {25,41,54} {25,41,55} {25,41,56} {25,41,57} {25,41,58}
{25,41,59} {25,41,60} {25,41,61} {25,41,62} {25,41,63} {25,41,64} {25,41,65} {25,41,66} {25,42,43}
{25,42,44} {25,42,45} {25,42,46} {25,42,47} {25,42,48} {25,42,49} {25,42,50} {25,42,51} {25,42,52}
{25,42,53} {25,42,54} {25,42,55} {25,42,56} {25,42,57} {25,42,58} {25,42,59} {25,42,60} {25,42,61}
{25,42,62} {25,42,63} {25,42,64} {25,42,65} {25,42,66} {25,43,44} {25,43,45} {25,43,46} {25,43,47}
{25,43,48} {25,43,49} {25,43,50} {25,43,51} {25,43,52} {25,43,53} {25,43,54} {25,43,55} {25,43,56}
{25,43,57} {25,43,58} {25,43,59} {25,43,60} {25,43,61} {25,43,62} {25,43,63} {25,43,64} {25,43,65}
{25,43,66} {25,44,45} {25,44,46} {25,44,47} {25,44,48} {25,44,49} {25,44,50} {25,44,51} {25,44,52}
{25,44,53} {25,44,54} {25,44,55} {25,44,56} {25,44,57} {25,44,58} {25,44,59} {25,44,60} {25,44,61}
{25,44,62} {25,44,63} {25,44,64} {25,44,65} {25,44,66} {25,45,46} {25,45,47} {25,45,48} {25,45,49}
{25,45,50} {25,45,51} {25,45,52} {25,45,53} {25,45,54} {25,45,55} {25,45,56} {25,45,57} {25,45,58}
{25,45,59} {25,45,60} {25,45,61} {25,45,62} {25,45,63} {25,45,64} {25,45,65} {25,45,66} {25,46,47}
{25,46,48} {25,46,49} {25,46,50} {25,46,51} {25,46,52} {25,46,53} {25,46,54} {25,46,55} {25,46,56}
{25,46,57} {25,46,58} {25,46,59} {25,46,60} {25,46,61} {25,46,62} {25,46,63} {25,46,64} {25,46,65}
{25,46,66} {25,47,48} {25,47,49} {25,47,50} {25,47,51} {25,47,52} {25,47,53} {25,47,54} {25,47,55}
{25,47,56} {25,47,57} {25,47,58} {25,47,59} {25,47,60} {25,47,61} {25,47,62} {25,47,63} {25,47,64}
{25,47,65} {25,47,66} {25,48,49} {25,48,50} {25,48,51} {25,48,52} {25,48,53} {25,48,54} {25,48,55}
{25,48,56} {25,48,57} {25,48,58} {25,48,59} {25,48,60} {25,48,61} {25,48,62} {25,48,63} {25,48,64}
{25,48,65} {25,48,66} {25,49,50} {25,49,51} {25,49,52} {25,49,53} {25,49,54} {25,49,55} {25,49,56}
{25,49,57} {25,49,58} {25,49,59} {25,49,60} {25,49,61} {25,49,62} {25,49,63} {25,49,64} {25,49,65}
{25,49,66} {25,50,51} {25,50,52} {25,50,53} {25,50,54} {25,50,55} {25,50,56} {25,50,57} {25,50,58}
{25,50,59} {25,50,60} {25,50,61} {25,50,62} {25,50,63} {25,50,64} {25,50,65} {25,50,66} {25,51,52}
{25,51,53} {25,51,54} {25,51,55} {25,51,56} {25,51,57} {25,51,58} {25,51,59} {25,51,60} {25,51,61}
{25,51,62} {25,51,63} {25,51,64} {25,51,65} {25,51,66} {25,52,53} {25,52,54} {25,52,55} {25,52,56}
{25,52,57} {25,52,58} {25,52,59} {25,52,60} {25,52,61} {25,52,62} {25,52,63} {25,52,64} {25,52,65}
{25,52,66} {25,53,54} {25,53,55} {25,53,56} {25,53,57} {25,53,58} {25,53,59} {25,53,60} {25,53,61}
{25,53,62} {25,53,63} {25,53,64} {25,53,65} {25,53,66} {25,54,55} {25,54,56} {25,54,57} {25,54,58}
{25,54,59} {25,54,60} {25,54,61} {25,54,62} {25,54,63} {25,54,64} {25,54,65} {25,54,66} {25,55,56}
{25,55,57} {25,55,58} {25,55,59} {25,55,60} {25,55,61} {25,55,62} {25,55,63} {25,55,64} {25,55,65}
{25,55,66} {25,56,57} {25,56,58} {25,56,59} {25,56,60} {25,56,61} {25,56,62} {25,56,63} {25,56,64}
{25,56,65} {25,56,66} {25,57,58} {25,57,59} {25,57,60} {25,57,61} {25,57,62} {25,57,63} {25,57,64}
{25,57,65} {25,57,66} {25,58,59} {25,58,60} {25,58,61} {25,58,62} {25,58,63} {25,58,64} {25,58,65}
{25,58,66} {25,59,60} {25,59,61} {25,59,62} {25,59,63} {25,59,64} {25,59,65} {25,59,66} {25,60,61}
{25,60,62} {25,60,63} {25,60,64} {25,60,65} {25,60,66} {25,61,62} {25,61,63} {25,61,64} {25,61,65}
{25,61,66} {25,62,63} {25,62,64} {25,62,65} {25,62,66} {25,63,64} {25,63,65} {25,63,66} {25,64,65}
{25,64,66} {25,65,66} {26,27,28} {26,27,29} {26,27,30} {26,27,31} {26,27,32} {26,27,33} {26,27,34}
{26,27,35} {26,27,36} {26,27,37} {26,27,38} {26,27,39} {26,27,40} {26,27,41} {26,27,42} {26,27,43}
{26,27,44} {26,27,45} {26,27,46} {26,27,47} {26,27,48} {26,27,49} {26,27,50} {26,27,51} {26,27,52}
{26,27,53} {26,27,54} {26,27,55} {26,27,56} {26,27,57} {26,27,58} {26,27,59} {26,27,60} {26,27,61}
{26,27,62} {26,27,63} {26,27,64} {26,27,65} {26,27,66} {26,28,29} {26,28,30} {26,28,31} {26,28,32}
{26,28,33} {26,28,34} {26,28,35} {26,28,36} {26,28,37} {26,28,38} {26,28,39} {26,28,40} {26,28,41}
{26,28,42} {26,28,43} {26,28,44} {26,28,45} {26,28,46} {26,28,47} {26,28,48} {26,28,49} {26,28,50}
{26,28,51} {26,28,52} {26,28,53} {26,28,54} {26,28,55} {26,28,56} {26,28,57} {26,28,58} {26,28,59}
{26,28,60} {26,28,61} {26,28,62} {26,28,63} {26,28,64} {26,28,65} {26,28,66} {26,29,30} {26,29,31}
{26,29,32} {26,29,33} {26,29,34} {26,29,35} {26,29,36} {26,29,37} {26,29,38} {26,29,39} {26,29,40}
{26,29,41} {26,29,42} {26,29,43} {26,29,44} {26,29,45} {26,29,46} {26,29,47} {26,29,48} {26,29,49}
{26,29,50} {26,29,51} {26,29,52} {26,29,53} {26,29,54} {26,29,55} {26,29,56} {26,29,57} {26,29,58}
{26,29,59} {26,29,60} {26,29,61} {26,29,62} {26,29,63} {26,29,64} {26,29,65} {26,29,66} {26,30,31}
{26,30,32} {26,30,33} {26,30,34} {26,30,35} {26,30,36} {26,30,37} {26,30,38} {26,30,39} {26,30,40}
{26,30,41} {26,30,42} {26,30,43} {26,30,44} {26,30,45} {26,30,46} {26,30,47} {26,30,48} {26,30,49}
{26,30,50} {26,30,51} {26,30,52} {26,30,53} {26,30,54} {26,30,55} {26,30,56} {26,30,57} {26,30,58}
{26,30,59} {26,30,60} {26,30,61} {26,30,62} {26,30,63} {26,30,64} {26,30,65} {26,30,66} {26,31,32}
{26,31,33} {26,31,34} {26,31,35} {26,31,36} {26,31,37} {26,31,38} {26,31,39} {26,31,40} {26,31,41}
{26,31,42} {26,31,43} {26,31,44} {26,31,45} {26,31,46} {26,31,47} {26,31,48} {26,31,49} {26,31,50}
{26,31,51} {26,31,52} {26,31,53} {26,31,54} {26,31,55} {26,31,56} {26,31,57} {26,31,58} {26,31,59}
{26,31,60} {26,31,61} {26,31,62} {26,31,63} {26,31,64} {26,31,65} {26,31,66} {26,32,33} {26,32,34}
{26,32,35} {26,32,36} {26,32,37} {26,32,38} {26,32,39} {26,32,40} {26,32,41} {26,32,42} {26,32,43}
{26,32,44} {26,32,45} {26,32,46} {26,32,47} {26,32,48} {26,32,49} {26,32,50} {26,32,51} {26,32,52}
{26,32,53} {26,32,54} {26,32,55} {26,32,56} {26,32,57} {26,32,58} {26,32,59} {26,32,60} {26,32,61}
{26,32,62} {26,32,63} {26,32,64} {26,32,65} {26,32,66} {26,33,34} {26,33,35} {26,33,36} {26,33,37}
{26,33,38} {26,33,39} {26,33,40} {26,33,41} {26,33,42} {26,33,43} {26,33,44} {26,33,45} {26,33,46}
{26,33,47} {26,33,48} {26,33,49} {26,33,50} {26,33,51} {26,33,52} {26,33,53} {26,33,54} {26,33,55}
{26,33,56} {26,33,57} {26,33,58} {26,33,59} {26,33,60} {26,33,61} {26,33,62} {26,33,63} {26,33,64}
{26,33,65} {26,33,66} {26,34,35} {26,34,36} {26,34,37} {26,34,38} {26,34,39} {26,34,40} {26,34,41}
{26,34,42} {26,34,43} {26,34,44} {26,34,45} {26,34,46} {26,34,47} {26,34,48} {26,34,49} {26,34,50}
{26,34,51} {26,34,52} {26,34,53} {26,34,54} {26,34,55} {26,34,56} {26,34,57} {26,34,58} {26,34,59}
{26,34,60} {26,34,61} {26,34,62} {26,34,63} {26,34,64} {26,34,65} {26,34,66} {26,35,36} {26,35,37}
{26,35,38} {26,35,39} {26,35,40} {26,35,41} {26,35,42} {26,35,43} {26,35,44} {26,35,45} {26,35,46}
{26,35,47} {26,35,48} {26,35,49} {26,35,50} {26,35,51} {26,35,52} {26,35,53} {26,35,54} {26,35,55}
{26,35,56} {26,35,57} {26,35,58} {26,35,59} {26,35,60} {26,35,61} {26,35,62} {26,35,63} {26,35,64}
{26,35,65} {26,35,66} {26,36,37} {26,36,38} {26,36,39} {26,36,40} {26,36,41} {26,36,42} {26,36,43}
{26,36,44} {26,36,45} {26,36,46} {26,36,47} {26,36,48} {26,36,49} {26,36,50} {26,36,51} {26,36,52}
{26,36,53} {26,36,54} {26,36,55} {26,36,56} {26,36,57} {26,36,58} {26,36,59} {26,36,60} {26,36,61}
{26,36,62} {26,36,63} {26,36,64} {26,36,65} {26,36,66} {26,37,38} {26,37,39} {26,37,40} {26,37,41}
{26,37,42} {26,37,43} {26,37,44} {26,37,45} {26,37,46} {26,37,47} {26,37,48} {26,37,49} {26,37,50}

TABLE 3A-continued

{26,37,51} {26,37,52} {26,37,53} {26,37,54} {26,37,55} {26,37,56} {26,37,57} {26,37,58} {26,37,59}
{26,37,60} {26,37,61} {26,37,62} {26,37,63} {26,37,64} {26,37,65} {26,37,66} {26,38,39} {26,38,40}
{26,38,41} {26,38,42} {26,38,43} {26,38,44} {26,38,45} {26,38,46} {26,38,47} {26,38,48} {26,38,49}
{26,38,50} {26,38,51} {26,38,52} {26,38,53} {26,38,54} {26,38,55} {26,38,56} {26,38,57} {26,38,58}
{26,38,59} {26,38,60} {26,38,61} {26,38,62} {26,38,63} {26,38,64} {26,38,65} {26,38,66} {26,39,40}
{26,39,41} {26,39,42} {26,39,43} {26,39,44} {26,39,45} {26,39,46} {26,39,47} {26,39,48} {26,39,49}
{26,39,50} {26,39,51} {26,39,52} {26,39,53} {26,39,54} {26,39,55} {26,39,56} {26,39,57} {26,39,58}
{26,39,59} {26,39,60} {26,39,61} {26,39,62} {26,39,63} {26,39,64} {26,39,65} {26,39,66} {26,40,41}
{26,40,42} {26,40,43} {26,40,44} {26,40,45} {26,40,46} {26,40,47} {26,40,48} {26,40,49} {26,40,50}
{26,40,51} {26,40,52} {26,40,53} {26,40,54} {26,40,55} {26,40,56} {26,40,57} {26,40,58} {26,40,59}
{26,40,60} {26,40,61} {26,40,62} {26,40,63} {26,40,64} {26,40,65} {26,40,66} {26,41,42} {26,41,43}
{26,41,44} {26,41,45} {26,41,46} {26,41,47} {26,41,48} {26,41,49} {26,41,50} {26,41,51} {26,41,52}
{26,41,53} {26,41,54} {26,41,55} {26,41,56} {26,41,57} {26,41,58} {26,41,59} {26,41,60} {26,41,61}
{26,41,62} {26,41,63} {26,41,64} {26,41,65} {26,41,66} {26,42,43} {26,42,44} {26,42,45} {26,42,46}
{26,42,47} {26,42,48} {26,42,49} {26,42,50} {26,42,51} {26,42,52} {26,42,53} {26,42,54} {26,42,55}
{26,42,56} {26,42,57} {26,42,58} {26,42,59} {26,42,60} {26,42,61} {26,42,62} {26,42,63} {26,42,64}
{26,42,65} {26,42,66} {26,43,44} {26,43,45} {26,43,46} {26,43,47} {26,43,48} {26,43,49} {26,43,50}
{26,43,51} {26,43,52} {26,43,53} {26,43,54} {26,43,55} {26,43,56} {26,43,57} {26,43,58} {26,43,59}
{26,43,60} {26,43,61} {26,43,62} {26,43,63} {26,43,64} {26,43,65} {26,43,66} {26,44,45} {26,44,46}
{26,44,47} {26,44,48} {26,44,49} {26,44,50} {26,44,51} {26,44,52} {26,44,53} {26,44,54} {26,44,55}
{26,44,56} {26,44,57} {26,44,58} {26,44,59} {26,44,60} {26,44,61} {26,44,62} {26,44,63} {26,44,64}
{26,44,65} {26,44,66} {26,45,46} {26,45,47} {26,45,48} {26,45,49} {26,45,50} {26,45,51} {26,45,52}
{26,45,53} {26,45,54} {26,45,55} {26,45,56} {26,45,57} {26,45,58} {26,45,59} {26,45,60} {26,45,61}
{26,45,62} {26,45,63} {26,45,64} {26,45,65} {26,45,66} {26,46,47} {26,46,48} {26,46,49} {26,46,50}
{26,46,51} {26,46,52} {26,46,53} {26,46,54} {26,46,55} {26,46,56} {26,46,57} {26,46,58} {26,46,59}
{26,46,60} {26,46,61} {26,46,62} {26,46,63} {26,46,64} {26,46,65} {26,46,66} {26,47,48} {26,47,49}
{26,47,50} {26,47,51} {26,47,52} {26,47,53} {26,47,54} {26,47,55} {26,47,56} {26,47,57} {26,47,58}
{26,47,59} {26,47,60} {26,47,61} {26,47,62} {26,47,63} {26,47,64} {26,47,65} {26,47,66} {26,48,49}
{26,48,50} {26,48,51} {26,48,52} {26,48,53} {26,48,54} {26,48,55} {26,48,56} {26,48,57} {26,48,58}
{26,48,59} {26,48,60} {26,48,61} {26,48,62} {26,48,63} {26,48,64} {26,48,65} {26,48,66} {26,49,50}
{26,49,51} {26,49,52} {26,49,53} {26,49,54} {26,49,55} {26,49,56} {26,49,57} {26,49,58} {26,49,59}
{26,49,60} {26,49,61} {26,49,62} {26,49,63} {26,49,64} {26,49,65} {26,49,66} {26,50,51} {26,50,52}
{26,50,53} {26,50,54} {26,50,55} {26,50,56} {26,50,57} {26,50,58} {26,50,59} {26,50,60} {26,50,61}
{26,50,62} {26,50,63} {26,50,64} {26,50,65} {26,50,66} {26,51,52} {26,51,53} {26,51,54} {26,51,55}
{26,51,56} {26,51,57} {26,51,58} {26,51,59} {26,51,60} {26,51,61} {26,51,62} {26,51,63} {26,51,64}
{26,51,65} {26,51,66} {26,52,53} {26,52,54} {26,52,55} {26,52,56} {26,52,57} {26,52,58} {26,52,59}
{26,52,60} {26,52,61} {26,52,62} {26,52,63} {26,52,64} {26,52,65} {26,52,66} {26,53,54} {26,53,55}
{26,53,56} {26,53,57} {26,53,58} {26,53,59} {26,53,60} {26,53,61} {26,53,62} {26,53,63} {26,53,64}
{26,53,65} {26,53,66} {26,54,55} {26,54,56} {26,54,57} {26,54,58} {26,54,59} {26,54,60} {26,54,61}
{26,54,62} {26,54,63} {26,54,64} {26,54,65} {26,54,66} {26,55,56} {26,55,57} {26,55,58} {26,55,59}
{26,55,60} {26,55,61} {26,55,62} {26,55,63} {26,55,64} {26,55,65} {26,55,66} {26,56,57} {26,56,58}
{26,56,59} {26,56,60} {26,56,61} {26,56,62} {26,56,63} {26,56,64} {26,56,65} {26,56,66} {26,57,58}
{26,57,59} {26,57,60} {26,57,61} {26,57,62} {26,57,63} {26,57,64} {26,57,65} {26,57,66} {26,58,59}
{26,58,60} {26,58,61} {26,58,62} {26,58,63} {26,58,64} {26,58,65} {26,58,66} {26,59,60} {26,59,61}
{26,59,62} {26,59,63} {26,59,64} {26,59,65} {26,59,66} {26,60,61} {26,60,62} {26,60,63} {26,60,64}
{26,60,65} {26,60,66} {26,61,62} {26,61,63} {26,61,64} {26,61,65} {26,61,66} {26,62,63} {26,62,64}
{26,62,65} {26,62,66} {26,63,64} {26,63,65} {26,63,66} {26,64,65} {26,64,66} {26,65,66} {27,28,29}
{27,28,30} {27,28,31} {27,28,32} {27,28,33} {27,28,34} {27,28,35} {27,28,36} {27,28,37} {27,28,38}
{27,28,39} {27,28,40} {27,28,41} {27,28,42} {27,28,43} {27,28,44} {27,28,45} {27,28,46} {27,28,47}
{27,28,48} {27,28,49} {27,28,50} {27,28,51} {27,28,52} {27,28,53} {27,28,54} {27,28,55} {27,28,56}
{27,28,57} {27,28,58} {27,28,59} {27,28,60} {27,28,61} {27,28,62} {27,28,63} {27,28,64} {27,28,65}
{27,28,66} {27,29,30} {27,29,31} {27,29,32} {27,29,33} {27,29,34} {27,29,35} {27,29,36} {27,29,37}
{27,29,38} {27,29,39} {27,29,40} {27,29,41} {27,29,42} {27,29,43} {27,29,44} {27,29,45} {27,29,46}
{27,29,47} {27,29,48} {27,29,49} {27,29,50} {27,29,51} {27,29,52} {27,29,53} {27,29,54} {27,29,55}
{27,29,56} {27,29,57} {27,29,58} {27,29,59} {27,29,60} {27,29,61} {27,29,62} {27,29,63} {27,29,64}
{27,29,65} {27,29,66} {27,30,31} {27,30,32} {27,30,33} {27,30,34} {27,30,35} {27,30,36} {27,30,37}
{27,30,38} {27,30,39} {27,30,40} {27,30,41} {27,30,42} {27,30,43} {27,30,44} {27,30,45} {27,30,46}
{27,30,47} {27,30,48} {27,30,49} {27,30,50} {27,30,51} {27,30,52} {27,30,53} {27,30,54} {27,30,55}
{27,30,56} {27,30,57} {27,30,58} {27,30,59} {27,30,60} {27,30,61} {27,30,62} {27,30,63} {27,30,64}
{27,30,65} {27,30,66} {27,31,32} {27,31,33} {27,31,34} {27,31,35} {27,31,36} {27,31,37} {27,31,38}
{27,31,39} {27,31,40} {27,31,41} {27,31,42} {27,31,43} {27,31,44} {27,31,45} {27,31,46} {27,31,47}
{27,31,48} {27,31,49} {27,31,50} {27,31,51} {27,31,52} {27,31,53} {27,31,54} {27,31,55} {27,31,56}
{27,31,57} {27,31,58} {27,31,59} {27,31,60} {27,31,61} {27,31,62} {27,31,63} {27,31,64} {27,31,65}
{27,31,66} {27,32,33} {27,32,34} {27,32,35} {27,32,36} {27,32,37} {27,32,38} {27,32,39} {27,32,40}
{27,32,41} {27,32,42} {27,32,43} {27,32,44} {27,32,45} {27,32,46} {27,32,47} {27,32,48} {27,32,49}
{27,32,50} {27,32,51} {27,32,52} {27,32,53} {27,32,54} {27,32,55} {27,32,56} {27,32,57} {27,32,58}
{27,32,59} {27,32,60} {27,32,61} {27,32,62} {27,32,63} {27,32,64} {27,32,65} {27,32,66} {27,33,34}
{27,33,35} {27,33,36} {27,33,37} {27,33,38} {27,33,39} {27,33,40} {27,33,41} {27,33,42} {27,33,43}
{27,33,44} {27,33,45} {27,33,46} {27,33,47} {27,33,48} {27,33,49} {27,33,50} {27,33,51} {27,33,52}
{27,33,53} {27,33,54} {27,33,55} {27,33,56} {27,33,57} {27,33,58} {27,33,59} {27,33,60} {27,33,61}
{27,33,62} {27,33,63} {27,33,64} {27,33,65} {27,33,66} {27,34,35} {27,34,36} {27,34,37} {27,34,38}
{27,34,39} {27,34,40} {27,34,41} {27,34,42} {27,34,43} {27,34,44} {27,34,45} {27,34,46} {27,34,47}
{27,34,48} {27,34,49} {27,34,50} {27,34,51} {27,34,52} {27,34,53} {27,34,54} {27,34,55} {27,34,56}
{27,34,57} {27,34,58} {27,34,59} {27,34,60} {27,34,61} {27,34,62} {27,34,63} {27,34,64} {27,34,65}
{27,34,66} {27,35,36} {27,35,37} {27,35,38} {27,35,39} {27,35,40} {27,35,41} {27,35,42} {27,35,43}
{27,35,44} {27,35,45} {27,35,46} {27,35,47} {27,35,48} {27,35,49} {27,35,50} {27,35,51} {27,35,52}
{27,35,53} {27,35,54} {27,35,55} {27,35,56} {27,35,57} {27,35,58} {27,35,59} {27,35,60} {27,35,61}
{27,35,62} {27,35,63} {27,35,64} {27,35,65} {27,35,66} {27,36,37} {27,36,38} {27,36,39} {27,36,40}
{27,36,41} {27,36,42} {27,36,43} {27,36,44} {27,36,45} {27,36,46} {27,36,47} {27,36,48} {27,36,49}
{27,36,50} {27,36,51} {27,36,52} {27,36,53} {27,36,54} {27,36,55} {27,36,56} {27,36,57} {27,36,58}

TABLE 3A-continued

| | | | | | | | |
|---|---|---|---|---|---|---|---|
| {27,36,59} | {27,36,60} | {27,36,61} | {27,36,62} | {27,36,63} | {27,36,64} | {27,36,65} | {27,36,66} | {27,37,38} |
| {27,37,39} | {27,37,40} | {27,37,41} | {27,37,42} | {27,37,43} | {27,37,44} | {27,37,45} | {27,37,46} | {27,37,47} |
| {27,37,48} | {27,37,49} | {27,37,50} | {27,37,51} | {27,37,52} | {27,37,53} | {27,37,54} | {27,37,55} | {27,37,56} |
| {27,37,57} | {27,37,58} | {27,37,59} | {27,37,60} | {27,37,61} | {27,37,62} | {27,37,63} | {27,37,64} | {27,37,65} |
| {27,37,66} | {27,38,39} | {27,38,40} | {27,38,41} | {27,38,42} | {27,38,43} | {27,38,44} | {27,38,45} | {27,38,46} |
| {27,38,47} | {27,38,48} | {27,38,49} | {27,38,50} | {27,38,51} | {27,38,52} | {27,38,53} | {27,38,54} | {27,38,55} |
| {27,38,56} | {27,38,57} | {27,38,58} | {27,38,59} | {27,38,60} | {27,38,61} | {27,38,62} | {27,38,63} | {27,38,64} |
| {27,38,65} | {27,38,66} | {27,39,40} | {27,39,41} | {27,39,42} | {27,39,43} | {27,39,44} | {27,39,45} | {27,39,46} |
| {27,39,47} | {27,39,48} | {27,39,49} | {27,39,50} | {27,39,51} | {27,39,52} | {27,39,53} | {27,39,54} | {27,39,55} |
| {27,39,56} | {27,39,57} | {27,39,58} | {27,39,59} | {27,39,60} | {27,39,61} | {27,39,62} | {27,39,63} | {27,39,64} |
| {27,39,65} | {27,39,66} | {27,40,41} | {27,40,42} | {27,40,43} | {27,40,44} | {27,40,45} | {27,40,46} | {27,40,47} |
| {27,40,48} | {27,40,49} | {27,40,50} | {27,40,51} | {27,40,52} | {27,40,53} | {27,40,54} | {27,40,55} | {27,40,56} |
| {27,40,57} | {27,40,58} | {27,40,59} | {27,40,60} | {27,40,61} | {27,40,62} | {27,40,63} | {27,40,64} | {27,40,65} |
| {27,40,66} | {27,41,42} | {27,41,43} | {27,41,44} | {27,41,45} | {27,41,46} | {27,41,47} | {27,41,48} | {27,41,49} |
| {27,41,50} | {27,41,51} | {27,41,52} | {27,41,53} | {27,41,54} | {27,41,55} | {27,41,56} | {27,41,57} | {27,41,58} |
| {27,41,59} | {27,41,60} | {27,41,61} | {27,41,62} | {27,41,63} | {27,41,64} | {27,41,65} | {27,41,66} | {27,42,43} |
| {27,42,44} | {27,42,45} | {27,42,46} | {27,42,47} | {27,42,48} | {27,42,49} | {27,42,50} | {27,42,51} | {27,42,52} |
| {27,42,53} | {27,42,54} | {27,42,55} | {27,42,56} | {27,42,57} | {27,42,58} | {27,42,59} | {27,42,60} | {27,42,61} |
| {27,42,62} | {27,42,63} | {27,42,64} | {27,42,65} | {27,42,66} | {27,43,44} | {27,43,45} | {27,43,46} | {27,43,47} |
| {27,43,48} | {27,43,49} | {27,43,50} | {27,43,51} | {27,43,52} | {27,43,53} | {27,43,54} | {27,43,55} | {27,43,56} |
| {27,43,57} | {27,43,58} | {27,43,59} | {27,43,60} | {27,43,61} | {27,43,62} | {27,43,63} | {27,43,64} | {27,43,65} |
| {27,43,66} | {27,44,45} | {27,44,46} | {27,44,47} | {27,44,48} | {27,44,49} | {27,44,50} | {27,44,51} | {27,44,52} |
| {27,44,53} | {27,44,54} | {27,44,55} | {27,44,56} | {27,44,57} | {27,44,58} | {27,44,59} | {27,44,60} | {27,44,61} |
| {27,44,62} | {27,44,63} | {27,44,64} | {27,44,65} | {27,44,66} | {27,45,46} | {27,45,47} | {27,45,48} | {27,45,49} |
| {27,45,50} | {27,45,51} | {27,45,52} | {27,45,53} | {27,45,54} | {27,45,55} | {27,45,56} | {27,45,57} | {27,45,58} |
| {27,45,59} | {27,45,60} | {27,45,61} | {27,45,62} | {27,45,63} | {27,45,64} | {27,45,65} | {27,45,66} | {27,46,47} |
| {27,46,48} | {27,46,49} | {27,46,50} | {27,46,51} | {27,46,52} | {27,46,53} | {27,46,54} | {27,46,55} | {27,46,56} |
| {27,46,57} | {27,46,58} | {27,46,59} | {27,46,60} | {27,46,61} | {27,46,62} | {27,46,63} | {27,46,64} | {27,46,65} |
| {27,46,66} | {27,47,48} | {27,47,49} | {27,47,50} | {27,47,51} | {27,47,52} | {27,47,53} | {27,47,54} | {27,47,55} |
| {27,47,56} | {27,47,57} | {27,47,58} | {27,47,59} | {27,47,60} | {27,47,61} | {27,47,62} | {27,47,63} | {27,47,64} |
| {27,47,65} | {27,47,66} | {27,48,49} | {27,48,50} | {27,48,51} | {27,48,52} | {27,48,53} | {27,48,54} | {27,48,55} |
| {27,48,56} | {27,48,57} | {27,48,58} | {27,48,59} | {27,48,60} | {27,48,61} | {27,48,62} | {27,48,63} | {27,48,64} |
| {27,48,65} | {27,48,66} | {27,49,50} | {27,49,51} | {27,49,52} | {27,49,53} | {27,49,54} | {27,49,55} | {27,49,56} |
| {27,49,57} | {27,49,58} | {27,49,59} | {27,49,60} | {27,49,61} | {27,49,62} | {27,49,63} | {27,49,64} | {27,49,65} |
| {27,49,66} | {27,50,51} | {27,50,52} | {27,50,53} | {27,50,54} | {27,50,55} | {27,50,56} | {27,50,57} | {27,50,58} |
| {27,50,59} | {27,50,60} | {27,50,61} | {27,50,62} | {27,50,63} | {27,50,64} | {27,50,65} | {27,50,66} | {27,51,52} |
| {27,51,53} | {27,51,54} | {27,51,55} | {27,51,56} | {27,51,57} | {27,51,58} | {27,51,59} | {27,51,60} | {27,51,61} |
| {27,51,62} | {27,51,63} | {27,51,64} | {27,51,65} | {27,51,66} | {27,52,53} | {27,52,54} | {27,52,55} | {27,52,56} |
| {27,52,57} | {27,52,58} | {27,52,59} | {27,52,60} | {27,52,61} | {27,52,62} | {27,52,63} | {27,52,64} | {27,52,65} |
| {27,52,66} | {27,53,54} | {27,53,55} | {27,53,56} | {27,53,57} | {27,53,58} | {27,53,59} | {27,53,60} | {27,53,61} |
| {27,53,62} | {27,53,63} | {27,53,64} | {27,53,65} | {27,53,66} | {27,54,55} | {27,54,56} | {27,54,57} | {27,54,58} |
| {27,54,59} | {27,54,60} | {27,54,61} | {27,54,62} | {27,54,63} | {27,54,64} | {27,54,65} | {27,54,66} | {27,55,56} |
| {27,55,57} | {27,55,58} | {27,55,59} | {27,55,60} | {27,55,61} | {27,55,62} | {27,55,63} | {27,55,64} | {27,55,65} |
| {27,55,66} | {27,56,57} | {27,56,58} | {27,56,59} | {27,56,60} | {27,56,61} | {27,56,62} | {27,56,63} | {27,56,64} |
| {27,56,65} | {27,56,66} | {27,57,58} | {27,57,59} | {27,57,60} | {27,57,61} | {27,57,62} | {27,57,63} | {27,57,64} |
| {27,57,65} | {27,57,66} | {27,58,59} | {27,58,60} | {27,58,61} | {27,58,62} | {27,58,63} | {27,58,64} | {27,58,65} |
| {27,58,66} | {27,59,60} | {27,59,61} | {27,59,62} | {27,59,63} | {27,59,64} | {27,59,65} | {27,59,66} | {27,60,61} |
| {27,60,62} | {27,60,63} | {27,60,64} | {27,60,65} | {27,60,66} | {27,61,62} | {27,61,63} | {27,61,64} | {27,61,65} |
| {27,61,66} | {27,62,63} | {27,62,64} | {27,62,65} | {27,62,66} | {27,63,64} | {27,63,65} | {27,63,66} | {27,64,65} |
| {27,64,66} | {27,65,66} | {28,29,30} | {28,29,31} | {28,29,32} | {28,29,33} | {28,29,34} | {28,29,35} | {28,29,36} |
| {28,29,37} | {28,29,38} | {28,29,39} | {28,29,40} | {28,29,41} | {28,29,42} | {28,29,43} | {28,29,44} | {28,29,45} |
| {28,29,46} | {28,29,47} | {28,29,48} | {28,29,49} | {28,29,50} | {28,29,51} | {28,29,52} | {28,29,53} | {28,29,54} |
| {28,29,55} | {28,29,56} | {28,29,57} | {28,29,58} | {28,29,59} | {28,29,60} | {28,29,61} | {28,29,62} | {28,29,63} |
| {28,29,64} | {28,29,65} | {28,29,66} | {28,30,31} | {28,30,32} | {28,30,33} | {28,30,34} | {28,30,35} | {28,30,36} |
| {28,30,37} | {28,30,38} | {28,30,39} | {28,30,40} | {28,30,41} | {28,30,42} | {28,30,43} | {28,30,44} | {28,30,45} |
| {28,30,46} | {28,30,47} | {28,30,48} | {28,30,49} | {28,30,50} | {28,30,51} | {28,30,52} | {28,30,53} | {28,30,54} |
| {28,30,55} | {28,30,56} | {28,30,57} | {28,30,58} | {28,30,59} | {28,30,60} | {28,30,61} | {28,30,62} | {28,30,63} |
| {28,30,64} | {28,30,65} | {28,30,66} | {28,31,32} | {28,31,33} | {28,31,34} | {28,31,35} | {28,31,36} | {28,31,37} |
| {28,31,38} | {28,31,39} | {28,31,40} | {28,31,41} | {28,31,42} | {28,31,43} | {28,31,44} | {28,31,45} | {28,31,46} |
| {28,31,47} | {28,31,48} | {28,31,49} | {28,31,50} | {28,31,51} | {28,31,52} | {28,31,53} | {28,31,54} | {28,31,55} |
| {28,31,56} | {28,31,57} | {28,31,58} | {28,31,59} | {28,31,60} | {28,31,61} | {28,31,62} | {28,31,63} | {28,31,64} |
| {28,31,65} | {28,31,66} | {28,32,33} | {28,32,34} | {28,32,35} | {28,32,36} | {28,32,37} | {28,32,38} | {28,32,39} |
| {28,32,40} | {28,32,41} | {28,32,42} | {28,32,43} | {28,32,44} | {28,32,45} | {28,32,46} | {28,32,47} | {28,32,48} |
| {28,32,49} | {28,32,50} | {28,32,51} | {28,32,52} | {28,32,53} | {28,32,54} | {28,32,55} | {28,32,56} | {28,32,57} |
| {28,32,58} | {28,32,59} | {28,32,60} | {28,32,61} | {28,32,62} | {28,32,63} | {28,32,64} | {28,32,65} | {28,32,66} |
| {28,33,34} | {28,33,35} | {28,33,36} | {28,33,37} | {28,33,38} | {28,33,39} | {28,33,40} | {28,33,41} | {28,33,42} |
| {28,33,43} | {28,33,44} | {28,33,45} | {28,33,46} | {28,33,47} | {28,33,48} | {28,33,49} | {28,33,50} | {28,33,51} |
| {28,33,52} | {28,33,53} | {28,33,54} | {28,33,55} | {28,33,56} | {28,33,57} | {28,33,58} | {28,33,59} | {28,33,60} |
| {28,33,61} | {28,33,62} | {28,33,63} | {28,33,64} | {28,33,65} | {28,33,66} | {28,34,35} | {28,34,36} | {28,34,37} |
| {28,34,38} | {28,34,39} | {28,34,40} | {28,34,41} | {28,34,42} | {28,34,43} | {28,34,44} | {28,34,45} | {28,34,46} |
| {28,34,47} | {28,34,48} | {28,34,49} | {28,34,50} | {28,34,51} | {28,34,52} | {28,34,53} | {28,34,54} | {28,34,55} |
| {28,34,56} | {28,34,57} | {28,34,58} | {28,34,59} | {28,34,60} | {28,34,61} | {28,34,62} | {28,34,63} | {28,34,64} |
| {28,34,65} | {28,34,66} | {28,35,36} | {28,35,37} | {28,35,38} | {28,35,39} | {28,35,40} | {28,35,41} | {28,35,42} |
| {28,35,43} | {28,35,44} | {28,35,45} | {28,35,46} | {28,35,47} | {28,35,48} | {28,35,49} | {28,35,50} | {28,35,51} |
| {28,35,52} | {28,35,53} | {28,35,54} | {28,35,55} | {28,35,56} | {28,35,57} | {28,35,58} | {28,35,59} | {28,35,60} |
| {28,35,61} | {28,35,62} | {28,35,63} | {28,35,64} | {28,35,65} | {28,35,66} | {28,36,37} | {28,36,38} | {28,36,39} |
| {28,36,40} | {28,36,41} | {28,36,42} | {28,36,43} | {28,36,44} | {28,36,45} | {28,36,46} | {28,36,47} | {28,36,48} |
| {28,36,49} | {28,36,50} | {28,36,51} | {28,36,52} | {28,36,53} | {28,36,54} | {28,36,55} | {28,36,56} | {28,36,57} |
| {28,36,58} | {28,36,59} | {28,36,60} | {28,36,61} | {28,36,62} | {28,36,63} | {28,36,64} | {28,36,65} | {28,36,66} |
| {28,37,38} | {28,37,39} | {28,37,40} | {28,37,41} | {28,37,42} | {28,37,43} | {28,37,44} | {28,37,45} | {28,37,46} |

TABLE 3A-continued

| | | | | | | | |
|---|---|---|---|---|---|---|---|
| {28,37,47} | {28,37,48} | {28,37,49} | {28,37,50} | {28,37,51} | {28,37,52} | {28,37,53} | {28,37,54} | {28,37,55} |
| {28,37,56} | {28,37,57} | {28,37,58} | {28,37,59} | {28,37,60} | {28,37,61} | {28,37,62} | {28,37,63} | {28,37,64} |
| {28,37,65} | {28,37,66} | {28,38,39} | {28,38,40} | {28,38,41} | {28,38,42} | {28,38,43} | {28,38,44} | {28,38,45} |
| {28,38,46} | {28,38,47} | {28,38,48} | {28,38,49} | {28,38,50} | {28,38,51} | {28,38,52} | {28,38,53} | {28,38,54} |
| {28,38,55} | {28,38,56} | {28,38,57} | {28,38,58} | {28,38,59} | {28,38,60} | {28,38,61} | {28,38,62} | {28,38,63} |
| {28,38,64} | {28,38,65} | {28,38,66} | {28,39,40} | {28,39,41} | {28,39,42} | {28,39,43} | {28,39,44} | {28,39,45} |
| {28,39,46} | {28,39,47} | {28,39,48} | {28,39,49} | {28,39,50} | {28,39,51} | {28,39,52} | {28,39,53} | {28,39,54} |
| {28,39,55} | {28,39,56} | {28,39,57} | {28,39,58} | {28,39,59} | {28,39,60} | {28,39,61} | {28,39,62} | {28,39,63} |
| {28,39,64} | {28,39,65} | {28,39,66} | {28,40,41} | {28,40,42} | {28,40,43} | {28,40,44} | {28,40,45} | {28,40,46} |
| {28,40,47} | {28,40,48} | {28,40,49} | {28,40,50} | {28,40,51} | {28,40,52} | {28,40,53} | {28,40,54} | {28,40,55} |
| {28,40,56} | {28,40,57} | {28,40,58} | {28,40,59} | {28,40,60} | {28,40,61} | {28,40,62} | {28,40,63} | {28,40,64} |
| {28,40,65} | {28,40,66} | {28,41,42} | {28,41,43} | {28,41,44} | {28,41,45} | {28,41,46} | {28,41,47} | {28,41,48} |
| {28,41,49} | {28,41,50} | {28,41,51} | {28,41,52} | {28,41,53} | {28,41,54} | {28,41,55} | {28,41,56} | {28,41,57} |
| {28,41,58} | {28,41,59} | {28,41,60} | {28,41,61} | {28,41,62} | {28,41,63} | {28,41,64} | {28,41,65} | {28,41,66} |
| {28,42,43} | {28,42,44} | {28,42,45} | {28,42,46} | {28,42,47} | {28,42,48} | {28,42,49} | {28,42,50} | {28,42,51} |
| {28,42,52} | {28,42,53} | {28,42,54} | {28,42,55} | {28,42,56} | {28,42,57} | {28,42,58} | {28,42,59} | {28,42,60} |
| {28,42,61} | {28,42,62} | {28,42,63} | {28,42,64} | {28,42,65} | {28,42,66} | {28,43,44} | {28,43,45} | {28,43,46} |
| {28,43,47} | {28,43,48} | {28,43,49} | {28,43,50} | {28,43,51} | {28,43,52} | {28,43,53} | {28,43,54} | {28,43,55} |
| {28,43,56} | {28,43,57} | {28,43,58} | {28,43,59} | {28,43,60} | {28,43,61} | {28,43,62} | {28,43,63} | {28,43,64} |
| {28,43,65} | {28,43,66} | {28,44,45} | {28,44,46} | {28,44,47} | {28,44,48} | {28,44,49} | {28,44,50} | {28,44,51} |
| {28,44,52} | {28,44,53} | {28,44,54} | {28,44,55} | {28,44,56} | {28,44,57} | {28,44,58} | {28,44,59} | {28,44,60} |
| {28,44,61} | {28,44,62} | {28,44,63} | {28,44,64} | {28,44,65} | {28,44,66} | {28,45,46} | {28,45,47} | {28,45,48} |
| {28,45,49} | {28,45,50} | {28,45,51} | {28,45,52} | {28,45,53} | {28,45,54} | {28,45,55} | {28,45,56} | {28,45,57} |
| {28,45,58} | {28,45,59} | {28,45,60} | {28,45,61} | {28,45,62} | {28,45,63} | {28,45,64} | {28,45,65} | {28,45,66} |
| {28,46,47} | {28,46,48} | {28,46,49} | {28,46,50} | {28,46,51} | {28,46,52} | {28,46,53} | {28,46,54} | {28,46,55} |
| {28,46,56} | {28,46,57} | {28,46,58} | {28,46,59} | {28,46,60} | {28,46,61} | {28,46,62} | {28,46,63} | {28,46,64} |
| {28,46,65} | {28,46,66} | {28,47,48} | {28,47,49} | {28,47,50} | {28,47,51} | {28,47,52} | {28,47,53} | {28,47,54} |
| {28,47,55} | {28,47,56} | {28,47,57} | {28,47,58} | {28,47,59} | {28,47,60} | {28,47,61} | {28,47,62} | {28,47,63} |
| {28,47,64} | {28,47,65} | {28,47,66} | {28,48,49} | {28,48,50} | {28,48,51} | {28,48,52} | {28,48,53} | {28,48,54} |
| {28,48,55} | {28,48,56} | {28,48,57} | {28,48,58} | {28,48,59} | {28,48,60} | {28,48,61} | {28,48,62} | {28,48,63} |
| {28,48,64} | {28,48,65} | {28,48,66} | {28,49,50} | {28,49,51} | {28,49,52} | {28,49,53} | {28,49,54} | {28,49,55} |
| {28,49,56} | {28,49,57} | {28,49,58} | {28,49,59} | {28,49,60} | {28,49,61} | {28,49,62} | {28,49,63} | {28,49,64} |
| {28,49,65} | {28,49,66} | {28,50,51} | {28,50,52} | {28,50,53} | {28,50,54} | {28,50,55} | {28,50,56} | {28,50,57} |
| {28,50,58} | {28,50,59} | {28,50,60} | {28,50,61} | {28,50,62} | {28,50,63} | {28,50,64} | {28,50,65} | {28,50,66} |
| {28,51,52} | {28,51,53} | {28,51,54} | {28,51,55} | {28,51,56} | {28,51,57} | {28,51,58} | {28,51,59} | {28,51,60} |
| {28,51,61} | {28,51,62} | {28,51,63} | {28,51,64} | {28,51,65} | {28,51,66} | {28,52,53} | {28,52,54} | {28,52,55} |
| {28,52,56} | {28,52,57} | {28,52,58} | {28,52,59} | {28,52,60} | {28,52,61} | {28,52,62} | {28,52,63} | {28,52,64} |
| {28,52,65} | {28,52,66} | {28,53,54} | {28,53,55} | {28,53,56} | {28,53,57} | {28,53,58} | {28,53,59} | {28,53,60} |
| {28,53,61} | {28,53,62} | {28,53,63} | {28,53,64} | {28,53,65} | {28,53,66} | {28,54,55} | {28,54,56} | {28,54,57} |
| {28,54,58} | {28,54,59} | {28,54,60} | {28,54,61} | {28,54,62} | {28,54,63} | {28,54,64} | {28,54,65} | {28,54,66} |
| {28,55,56} | {28,55,57} | {28,55,58} | {28,55,59} | {28,55,60} | {28,55,61} | {28,55,62} | {28,55,63} | {28,55,64} |
| {28,55,65} | {28,55,66} | {28,56,57} | {28,56,58} | {28,56,59} | {28,56,60} | {28,56,61} | {28,56,62} | {28,56,63} |
| {28,56,64} | {28,56,65} | {28,56,66} | {28,57,58} | {28,57,59} | {28,57,60} | {28,57,61} | {28,57,62} | {28,57,63} |
| {28,57,64} | {28,57,65} | {28,57,66} | {28,58,59} | {28,58,60} | {28,58,61} | {28,58,62} | {28,58,63} | {28,58,64} |
| {28,58,65} | {28,58,66} | {28,59,60} | {28,59,61} | {28,59,62} | {28,59,63} | {28,59,64} | {28,59,65} | {28,59,66} |
| {28,60,61} | {28,60,62} | {28,60,63} | {28,60,64} | {28,60,65} | {28,60,66} | {28,61,62} | {28,61,63} | {28,61,64} |
| {28,61,65} | {28,61,66} | {28,62,63} | {28,62,64} | {28,62,65} | {28,62,66} | {28,63,64} | {28,63,65} | {28,63,66} |
| {28,64,65} | {28,64,66} | {28,65,66} | {29,30,31} | {29,30,32} | {29,30,33} | {29,30,34} | {29,30,35} | {29,30,36} |
| {29,30,37} | {29,30,38} | {29,30,39} | {29,30,40} | {29,30,41} | {29,30,42} | {29,30,43} | {29,30,44} | {29,30,45} |
| {29,30,46} | {29,30,47} | {29,30,48} | {29,30,49} | {29,30,50} | {29,30,51} | {29,30,52} | {29,30,53} | {29,30,54} |
| {29,30,55} | {29,30,56} | {29,30,57} | {29,30,58} | {29,30,59} | {29,30,60} | {29,30,61} | {29,30,62} | {29,30,63} |
| {29,30,64} | {29,30,65} | {29,30,66} | {29,31,32} | {29,31,33} | {29,31,34} | {29,31,35} | {29,31,36} | {29,31,37} |
| {29,31,38} | {29,31,39} | {29,31,40} | {29,31,41} | {29,31,42} | {29,31,43} | {29,31,44} | {29,31,45} | {29,31,46} |
| {29,31,47} | {29,31,48} | {29,31,49} | {29,31,50} | {29,31,51} | {29,31,52} | {29,31,53} | {29,31,54} | {29,31,55} |
| {29,31,56} | {29,31,57} | {29,31,58} | {29,31,59} | {29,31,60} | {29,31,61} | {29,31,62} | {29,31,63} | {29,31,64} |
| {29,31,65} | {29,31,66} | {29,32,33} | {29,32,34} | {29,32,35} | {29,32,36} | {29,32,37} | {29,32,38} | {29,32,39} |
| {29,32,40} | {29,32,41} | {29,32,42} | {29,32,43} | {29,32,44} | {29,32,45} | {29,32,46} | {29,32,47} | {29,32,48} |
| {29,32,49} | {29,32,50} | {29,32,51} | {29,32,52} | {29,32,53} | {29,32,54} | {29,32,55} | {29,32,56} | {29,32,57} |
| {29,32,58} | {29,32,59} | {29,32,60} | {29,32,61} | {29,32,62} | {29,32,63} | {29,32,64} | {29,32,65} | {29,32,66} |
| {29,33,34} | {29,33,35} | {29,33,36} | {29,33,37} | {29,33,38} | {29,33,39} | {29,33,40} | {29,33,41} | {29,33,42} |
| {29,33,43} | {29,33,44} | {29,33,45} | {29,33,46} | {29,33,47} | {29,33,48} | {29,33,49} | {29,33,50} | {29,33,51} |
| {29,33,52} | {29,33,53} | {29,33,54} | {29,33,55} | {29,33,56} | {29,33,57} | {29,33,58} | {29,33,59} | {29,33,60} |
| {29,33,61} | {29,33,62} | {29,33,63} | {29,33,64} | {29,33,65} | {29,33,66} | {29,34,35} | {29,34,36} | {29,34,37} |
| {29,34,38} | {29,34,39} | {29,34,40} | {29,34,41} | {29,34,42} | {29,34,43} | {29,34,44} | {29,34,45} | {29,34,46} |
| {29,34,47} | {29,34,48} | {29,34,49} | {29,34,50} | {29,34,51} | {29,34,52} | {29,34,53} | {29,34,54} | {29,34,55} |
| {29,34,56} | {29,34,57} | {29,34,58} | {29,34,59} | {29,34,60} | {29,34,61} | {29,34,62} | {29,34,63} | {29,34,64} |
| {29,34,65} | {29,34,66} | {29,35,36} | {29,35,37} | {29,35,38} | {29,35,39} | {29,35,40} | {29,35,41} | {29,35,42} |
| {29,35,43} | {29,35,44} | {29,35,45} | {29,35,46} | {29,35,47} | {29,35,48} | {29,35,49} | {29,35,50} | {29,35,51} |
| {29,35,52} | {29,35,53} | {29,35,54} | {29,35,55} | {29,35,56} | {29,35,57} | {29,35,58} | {29,35,59} | {29,35,60} |
| {29,35,61} | {29,35,62} | {29,35,63} | {29,35,64} | {29,35,65} | {29,35,66} | {29,36,37} | {29,36,38} | {29,36,39} |
| {29,36,40} | {29,36,41} | {29,36,42} | {29,36,43} | {29,36,44} | {29,36,45} | {29,36,46} | {29,36,47} | {29,36,48} |
| {29,36,49} | {29,36,50} | {29,36,51} | {29,36,52} | {29,36,53} | {29,36,54} | {29,36,55} | {29,36,56} | {29,36,57} |
| {29,36,58} | {29,36,59} | {29,36,60} | {29,36,61} | {29,36,62} | {29,36,63} | {29,36,64} | {29,36,65} | {29,36,66} |
| {29,37,38} | {29,37,39} | {29,37,40} | {29,37,41} | {29,37,42} | {29,37,43} | {29,37,44} | {29,37,45} | {29,37,46} |
| {29,37,47} | {29,37,48} | {29,37,49} | {29,37,50} | {29,37,51} | {29,37,52} | {29,37,53} | {29,37,54} | {29,37,55} |
| {29,37,56} | {29,37,57} | {29,37,58} | {29,37,59} | {29,37,60} | {29,37,61} | {29,37,62} | {29,37,63} | {29,37,64} |
| {29,37,65} | {29,37,66} | {29,38,39} | {29,38,40} | {29,38,41} | {29,38,42} | {29,38,43} | {29,38,44} | {29,38,45} |
| {29,38,46} | {29,38,47} | {29,38,48} | {29,38,49} | {29,38,50} | {29,38,51} | {29,38,52} | {29,38,53} | {29,38,54} |
| {29,38,55} | {29,38,56} | {29,38,57} | {29,38,58} | {29,38,59} | {29,38,60} | {29,38,61} | {29,38,62} | {29,38,63} |
| {29,38,64} | {29,38,65} | {29,38,66} | {29,39,40} | {29,39,41} | {29,39,42} | {29,39,43} | {29,39,44} | {29,39,45} |

TABLE 3A-continued

| | | | | | | | |
|---|---|---|---|---|---|---|---|
| {29,39,46} | {29,39,47} | {29,39,48} | {29,39,49} | {29,39,50} | {29,39,51} | {29,39,52} | {29,39,53} | {29,39,54} |
| {29,39,55} | {29,39,56} | {29,39,57} | {29,39,58} | {29,39,59} | {29,39,60} | {29,39,61} | {29,39,62} | {29,39,63} |
| {29,39,64} | {29,39,65} | {29,39,66} | {29,40,41} | {29,40,42} | {29,40,43} | {29,40,44} | {29,40,45} | {29,40,46} |
| {29,40,47} | {29,40,48} | {29,40,49} | {29,40,50} | {29,40,51} | {29,40,52} | {29,40,53} | {29,40,54} | {29,40,55} |
| {29,40,56} | {29,40,57} | {29,40,58} | {29,40,59} | {29,40,60} | {29,40,61} | {29,40,62} | {29,40,63} | {29,40,64} |
| {29,40,65} | {29,40,66} | {29,41,42} | {29,41,43} | {29,41,44} | {29,41,45} | {29,41,46} | {29,41,47} | {29,41,48} |
| {29,41,49} | {29,41,50} | {29,41,51} | {29,41,52} | {29,41,53} | {29,41,54} | {29,41,55} | {29,41,56} | {29,41,57} |
| {29,41,58} | {29,41,59} | {29,41,60} | {29,41,61} | {29,41,62} | {29,41,63} | {29,41,64} | {29,41,65} | {29,41,66} |
| {29,42,43} | {29,42,44} | {29,42,45} | {29,42,46} | {29,42,47} | {29,42,48} | {29,42,49} | {29,42,50} | {29,42,51} |
| {29,42,52} | {29,42,53} | {29,42,54} | {29,42,55} | {29,42,56} | {29,42,57} | {29,42,58} | {29,42,59} | {29,42,60} |
| {29,42,61} | {29,42,62} | {29,42,63} | {29,42,64} | {29,42,65} | {29,42,66} | {29,43,44} | {29,43,45} | {29,43,46} |
| {29,43,47} | {29,43,48} | {29,43,49} | {29,43,50} | {29,43,51} | {29,43,52} | {29,43,53} | {29,43,54} | {29,43,55} |
| {29,43,56} | {29,43,57} | {29,43,58} | {29,43,59} | {29,43,60} | {29,43,61} | {29,43,62} | {29,43,63} | {29,43,64} |
| {29,43,65} | {29,43,66} | {29,44,45} | {29,44,46} | {29,44,47} | {29,44,48} | {29,44,49} | {29,44,50} | {29,44,51} |
| {29,44,52} | {29,44,53} | {29,44,54} | {29,44,55} | {29,44,56} | {29,44,57} | {29,44,58} | {29,44,59} | {29,44,60} |
| {29,44,61} | {29,44,62} | {29,44,63} | {29,44,64} | {29,44,65} | {29,44,66} | {29,45,46} | {29,45,47} | {29,45,48} |
| {29,45,49} | {29,45,50} | {29,45,51} | {29,45,52} | {29,45,53} | {29,45,54} | {29,45,55} | {29,45,56} | {29,45,57} |
| {29,45,58} | {29,45,59} | {29,45,60} | {29,45,61} | {29,45,62} | {29,45,63} | {29,45,64} | {29,45,65} | {29,45,66} |
| {29,46,47} | {29,46,48} | {29,46,49} | {29,46,50} | {29,46,51} | {29,46,52} | {29,46,53} | {29,46,54} | {29,46,55} |
| {29,46,56} | {29,46,57} | {29,46,58} | {29,46,59} | {29,46,60} | {29,46,61} | {29,46,62} | {29,46,63} | {29,46,64} |
| {29,46,65} | {29,46,66} | {29,47,48} | {29,47,49} | {29,47,50} | {29,47,51} | {29,47,52} | {29,47,53} | {29,47,54} |
| {29,47,55} | {29,47,56} | {29,47,57} | {29,47,58} | {29,47,59} | {29,47,60} | {29,47,61} | {29,47,62} | {29,47,63} |
| {29,47,64} | {29,47,65} | {29,47,66} | {29,48,49} | {29,48,50} | {29,48,51} | {29,48,52} | {29,48,53} | {29,48,54} |
| {29,48,55} | {29,48,56} | {29,48,57} | {29,48,58} | {29,48,59} | {29,48,60} | {29,48,61} | {29,48,62} | {29,48,63} |
| {29,48,64} | {29,48,65} | {29,48,66} | {29,49,50} | {29,49,51} | {29,49,52} | {29,49,53} | {29,49,54} | {29,49,55} |
| {29,49,56} | {29,49,57} | {29,49,58} | {29,49,59} | {29,49,60} | {29,49,61} | {29,49,62} | {29,49,63} | {29,49,64} |
| {29,49,65} | {29,49,66} | {29,50,51} | {29,50,52} | {29,50,53} | {29,50,54} | {29,50,55} | {29,50,56} | {29,50,57} |
| {29,50,58} | {29,50,59} | {29,50,60} | {29,50,61} | {29,50,62} | {29,50,63} | {29,50,64} | {29,50,65} | {29,50,66} |
| {29,51,52} | {29,51,53} | {29,51,54} | {29,51,55} | {29,51,56} | {29,51,57} | {29,51,58} | {29,51,59} | {29,51,60} |
| {29,51,61} | {29,51,62} | {29,51,63} | {29,51,64} | {29,51,65} | {29,51,66} | {29,52,53} | {29,52,54} | {29,52,55} |
| {29,52,56} | {29,52,57} | {29,52,58} | {29,52,59} | {29,52,60} | {29,52,61} | {29,52,62} | {29,52,63} | {29,52,64} |
| {29,52,65} | {29,52,66} | {29,53,54} | {29,53,55} | {29,53,56} | {29,53,57} | {29,53,58} | {29,53,59} | {29,53,60} |
| {29,53,61} | {29,53,62} | {29,53,63} | {29,53,64} | {29,53,65} | {29,53,66} | {29,54,55} | {29,54,56} | {29,54,57} |
| {29,54,58} | {29,54,59} | {29,54,60} | {29,54,61} | {29,54,62} | {29,54,63} | {29,54,64} | {29,54,65} | {29,54,66} |
| {29,55,56} | {29,55,57} | {29,55,58} | {29,55,59} | {29,55,60} | {29,55,61} | {29,55,62} | {29,55,63} | {29,55,64} |
| {29,55,65} | {29,55,66} | {29,56,57} | {29,56,58} | {29,56,59} | {29,56,60} | {29,56,61} | {29,56,62} | {29,56,63} |
| {29,56,64} | {29,56,65} | {29,56,66} | {29,57,58} | {29,57,59} | {29,57,60} | {29,57,61} | {29,57,62} | {29,57,63} |
| {29,57,64} | {29,57,65} | {29,57,66} | {29,58,59} | {29,58,60} | {29,58,61} | {29,58,62} | {29,58,63} | {29,58,64} |
| {29,58,65} | {29,58,66} | {29,59,60} | {29,59,61} | {29,59,62} | {29,59,63} | {29,59,64} | {29,59,65} | {29,59,66} |
| {29,60,61} | {29,60,62} | {29,60,63} | {29,60,64} | {29,60,65} | {29,60,66} | {29,61,62} | {29,61,63} | {29,61,64} |
| {29,61,65} | {29,61,66} | {29,62,63} | {29,62,64} | {29,62,65} | {29,62,66} | {29,63,64} | {29,63,65} | {29,63,66} |
| {29,64,65} | {29,64,66} | {29,65,66} | {30,31,32} | {30,31,33} | {30,31,34} | {30,31,35} | {30,31,36} | {30,31,37} |
| {30,31,38} | {30,31,39} | {30,31,40} | {30,31,41} | {30,31,42} | {30,31,43} | {30,31,44} | {30,31,45} | {30,31,46} |
| {30,31,47} | {30,31,48} | {30,31,49} | {30,31,50} | {30,31,51} | {30,31,52} | {30,31,53} | {30,31,54} | {30,31,55} |
| {30,31,56} | {30,31,57} | {30,31,58} | {30,31,59} | {30,31,60} | {30,31,61} | {30,31,62} | {30,31,63} | {30,31,64} |
| {30,31,65} | {30,31,66} | {30,32,33} | {30,32,34} | {30,32,35} | {30,32,36} | {30,32,37} | {30,32,38} | {30,32,39} |
| {30,32,40} | {30,32,41} | {30,32,42} | {30,32,43} | {30,32,44} | {30,32,45} | {30,32,46} | {30,32,47} | {30,32,48} |
| {30,32,49} | {30,32,50} | {30,32,51} | {30,32,52} | {30,32,53} | {30,32,54} | {30,32,55} | {30,32,56} | {30,32,57} |
| {30,32,58} | {30,32,59} | {30,32,60} | {30,32,61} | {30,32,62} | {30,32,63} | {30,32,64} | {30,32,65} | {30,32,66} |
| {30,33,34} | {30,33,35} | {30,33,36} | {30,33,37} | {30,33,38} | {30,33,39} | {30,33,40} | {30,33,41} | {30,33,42} |
| {30,33,43} | {30,33,44} | {30,33,45} | {30,33,46} | {30,33,47} | {30,33,48} | {30,33,49} | {30,33,50} | {30,33,51} |
| {30,33,52} | {30,33,53} | {30,33,54} | {30,33,55} | {30,33,56} | {30,33,57} | {30,33,58} | {30,33,59} | {30,33,60} |
| {30,33,61} | {30,33,62} | {30,33,63} | {30,33,64} | {30,33,65} | {30,33,66} | {30,34,35} | {30,34,36} | {30,34,37} |
| {30,34,38} | {30,34,39} | {30,34,40} | {30,34,41} | {30,34,42} | {30,34,43} | {30,34,44} | {30,34,45} | {30,34,46} |
| {30,34,47} | {30,34,48} | {30,34,49} | {30,34,50} | {30,34,51} | {30,34,52} | {30,34,53} | {30,34,54} | {30,34,55} |
| {30,34,56} | {30,34,57} | {30,34,58} | {30,34,59} | {30,34,60} | {30,34,61} | {30,34,62} | {30,34,63} | {30,34,64} |
| {30,34,65} | {30,34,66} | {30,35,36} | {30,35,37} | {30,35,38} | {30,35,39} | {30,35,40} | {30,35,41} | {30,35,42} |
| {30,35,43} | {30,35,44} | {30,35,45} | {30,35,46} | {30,35,47} | {30,35,48} | {30,35,49} | {30,35,50} | {30,35,51} |
| {30,35,52} | {30,35,53} | {30,35,54} | {30,35,55} | {30,35,56} | {30,35,57} | {30,35,58} | {30,35,59} | {30,35,60} |
| {30,35,61} | {30,35,62} | {30,35,63} | {30,35,64} | {30,35,65} | {30,35,66} | {30,36,37} | {30,36,38} | {30,36,39} |
| {30,36,40} | {30,36,41} | {30,36,42} | {30,36,43} | {30,36,44} | {30,36,45} | {30,36,46} | {30,36,47} | {30,36,48} |
| {30,36,49} | {30,36,50} | {30,36,51} | {30,36,52} | {30,36,53} | {30,36,54} | {30,36,55} | {30,36,56} | {30,36,57} |
| {30,36,58} | {30,36,59} | {30,36,60} | {30,36,61} | {30,36,62} | {30,36,63} | {30,36,64} | {30,36,65} | {30,36,66} |
| {30,37,38} | {30,37,39} | {30,37,40} | {30,37,41} | {30,37,42} | {30,37,43} | {30,37,44} | {30,37,45} | {30,37,46} |
| {30,37,47} | {30,37,48} | {30,37,49} | {30,37,50} | {30,37,51} | {30,37,52} | {30,37,53} | {30,37,54} | {30,37,55} |
| {30,37,56} | {30,37,57} | {30,37,58} | {30,37,59} | {30,37,60} | {30,37,61} | {30,37,62} | {30,37,63} | {30,37,64} |
| {30,37,65} | {30,37,66} | {30,38,39} | {30,38,40} | {30,38,41} | {30,38,42} | {30,38,43} | {30,38,44} | {30,38,45} |
| {30,38,46} | {30,38,47} | {30,38,48} | {30,38,49} | {30,38,50} | {30,38,51} | {30,38,52} | {30,38,53} | {30,38,54} |
| {30,38,55} | {30,38,56} | {30,38,57} | {30,38,58} | {30,38,59} | {30,38,60} | {30,38,61} | {30,38,62} | {30,38,63} |
| {30,38,64} | {30,38,65} | {30,38,66} | {30,39,40} | {30,39,41} | {30,39,42} | {30,39,43} | {30,39,44} | {30,39,45} |
| {30,39,46} | {30,39,47} | {30,39,48} | {30,39,49} | {30,39,50} | {30,39,51} | {30,39,52} | {30,39,53} | {30,39,54} |
| {30,39,55} | {30,39,56} | {30,39,57} | {30,39,58} | {30,39,59} | {30,39,60} | {30,39,61} | {30,39,62} | {30,39,63} |
| {30,39,64} | {30,39,65} | {30,39,66} | {30,40,41} | {30,40,42} | {30,40,43} | {30,40,44} | {30,40,45} | {30,40,46} |
| {30,40,47} | {30,40,48} | {30,40,49} | {30,40,50} | {30,40,51} | {30,40,52} | {30,40,53} | {30,40,54} | {30,40,55} |
| {30,40,56} | {30,40,57} | {30,40,58} | {30,40,59} | {30,40,60} | {30,40,61} | {30,40,62} | {30,40,63} | {30,40,64} |
| {30,40,65} | {30,40,66} | {30,41,42} | {30,41,43} | {30,41,44} | {30,41,45} | {30,41,46} | {30,41,47} | {30,41,48} |
| {30,41,49} | {30,41,50} | {30,41,51} | {30,41,52} | {30,41,53} | {30,41,54} | {30,41,55} | {30,41,56} | {30,41,57} |
| {30,41,58} | {30,41,59} | {30,41,60} | {30,41,61} | {30,41,62} | {30,41,63} | {30,41,64} | {30,41,65} | {30,41,66} |
| {30,42,43} | {30,42,44} | {30,42,45} | {30,42,46} | {30,42,47} | {30,42,48} | {30,42,49} | {30,42,50} | {30,42,51} |
| {30,42,52} | {30,42,53} | {30,42,54} | {30,42,55} | {30,42,56} | {30,42,57} | {30,42,58} | {30,42,59} | {30,42,60} |

TABLE 3A-continued

{30,42,61} {30,42,62} {30,42,63} {30,42,64} {30,42,65} {30,42,66} {30,43,44} {30,43,45} {30,43,46}
{30,43,47} {30,43,48} {30,43,49} {30,43,50} {30,43,51} {30,43,52} {30,43,53} {30,43,54} {30,43,55}
{30,43,56} {30,43,57} {30,43,58} {30,43,59} {30,43,60} {30,43,61} {30,43,62} {30,43,63} {30,43,64}
{30,43,65} {30,43,66} {30,44,45} {30,44,46} {30,44,47} {30,44,48} {30,44,49} {30,44,50} {30,44,51}
{30,44,52} {30,44,53} {30,44,54} {30,44,55} {30,44,56} {30,44,57} {30,44,58} {30,44,59} {30,44,60}
{30,44,61} {30,44,62} {30,44,63} {30,44,64} {30,44,65} {30,44,66} {30,45,46} {30,45,47} {30,45,48}
{30,45,49} {30,45,50} {30,45,51} {30,45,52} {30,45,53} {30,45,54} {30,45,55} {30,45,56} {30,45,57}
{30,45,58} {30,45,59} {30,45,60} {30,45,61} {30,45,62} {30,45,63} {30,45,64} {30,45,65} {30,45,66}
{30,46,47} {30,46,48} {30,46,49} {30,46,50} {30,46,51} {30,46,52} {30,46,53} {30,46,54} {30,46,55}
{30,46,56} {30,46,57} {30,46,58} {30,46,59} {30,46,60} {30,46,61} {30,46,62} {30,46,63} {30,46,64}
{30,46,65} {30,46,66} {30,47,48} {30,47,49} {30,47,50} {30,47,51} {30,47,52} {30,47,53} {30,47,54}
{30,47,55} {30,47,56} {30,47,57} {30,47,58} {30,47,59} {30,47,60} {30,47,61} {30,47,62} {30,47,63}
{30,47,64} {30,47,65} {30,47,66} {30,48,49} {30,48,50} {30,48,51} {30,48,52} {30,48,53} {30,48,54}
{30,48,55} {30,48,56} {30,48,57} {30,48,58} {30,48,59} {30,48,60} {30,48,61} {30,48,62} {30,48,63}
{30,48,64} {30,48,65} {30,48,66} {30,49,50} {30,49,51} {30,49,52} {30,49,53} {30,49,54} {30,49,55}
{30,49,56} {30,49,57} {30,49,58} {30,49,59} {30,49,60} {30,49,61} {30,49,62} {30,49,63} {30,49,64}
{30,49,65} {30,49,66} {30,50,51} {30,50,52} {30,50,53} {30,50,54} {30,50,55} {30,50,56} {30,50,57}
{30,50,58} {30,50,59} {30,50,60} {30,50,61} {30,50,62} {30,50,63} {30,50,64} {30,50,65} {30,50,66}
{30,51,52} {30,51,53} {30,51,54} {30,51,55} {30,51,56} {30,51,57} {30,51,58} {30,51,59} {30,51,60}
{30,51,61} {30,51,62} {30,51,63} {30,51,64} {30,51,65} {30,51,66} {30,52,53} {30,52,54} {30,52,55}
{30,52,56} {30,52,57} {30,52,58} {30,52,59} {30,52,60} {30,52,61} {30,52,62} {30,52,63} {30,52,64}
{30,52,65} {30,52,66} {30,53,54} {30,53,55} {30,53,56} {30,53,57} {30,53,58} {30,53,59} {30,53,60}
{30,53,61} {30,53,62} {30,53,63} {30,53,64} {30,53,65} {30,53,66} {30,54,55} {30,54,56} {30,54,57}
{30,54,58} {30,54,59} {30,54,60} {30,54,61} {30,54,62} {30,54,63} {30,54,64} {30,54,65} {30,54,66}
{30,55,56} {30,55,57} {30,55,58} {30,55,59} {30,55,60} {30,55,61} {30,55,62} {30,55,63} {30,55,64}
{30,55,65} {30,55,66} {30,56,57} {30,56,58} {30,56,59} {30,56,60} {30,56,61} {30,56,62} {30,56,63}
{30,56,64} {30,56,65} {30,56,66} {30,57,58} {30,57,59} {30,57,60} {30,57,61} {30,57,62} {30,57,63}
{30,57,64} {30,57,65} {30,57,66} {30,58,59} {30,58,60} {30,58,61} {30,58,62} {30,58,63} {30,58,64}
{30,58,65} {30,58,66} {30,59,60} {30,59,61} {30,59,62} {30,59,63} {30,59,64} {30,59,65} {30,59,66}
{30,60,61} {30,60,62} {30,60,63} {30,60,64} {30,60,65} {30,60,66} {30,61,62} {30,61,63} {30,61,64}
{30,61,65} {30,61,66} {30,62,63} {30,62,64} {30,62,65} {30,62,66} {30,63,64} {30,63,65} {30,63,66}
{30,64,65} {30,64,66} {30,65,66} {31,32,33} {31,32,34} {31,32,35} {31,32,36} {31,32,37} {31,32,38}
{31,32,39} {31,32,40} {31,32,41} {31,32,42} {31,32,43} {31,32,44} {31,32,45} {31,32,46} {31,32,47}
{31,32,48} {31,32,49} {31,32,50} {31,32,51} {31,32,52} {31,32,53} {31,32,54} {31,32,55} {31,32,56}
{31,32,57} {31,32,58} {31,32,59} {31,32,60} {31,32,61} {31,32,62} {31,32,63} {31,32,64} {31,32,65}
{31,32,66} {31,33,34} {31,33,35} {31,33,36} {31,33,37} {31,33,38} {31,33,39} {31,33,40} {31,33,41}
{31,33,42} {31,33,43} {31,33,44} {31,33,45} {31,33,46} {31,33,47} {31,33,48} {31,33,49} {31,33,50}
{31,33,51} {31,33,52} {31,33,53} {31,33,54} {31,33,55} {31,33,56} {31,33,57} {31,33,58} {31,33,59}
{31,33,60} {31,33,61} {31,33,62} {31,33,63} {31,33,64} {31,33,65} {31,33,66} {31,34,35} {31,34,36}
{31,34,37} {31,34,38} {31,34,39} {31,34,40} {31,34,41} {31,34,42} {31,34,43} {31,34,44} {31,34,45}
{31,34,46} {31,34,47} {31,34,48} {31,34,49} {31,34,50} {31,34,51} {31,34,52} {31,34,53} {31,34,54}
{31,34,55} {31,34,56} {31,34,57} {31,34,58} {31,34,59} {31,34,60} {31,34,61} {31,34,62} {31,34,63}
{31,34,64} {31,34,65} {31,34,66} {31,35,36} {31,35,37} {31,35,38} {31,35,39} {31,35,40} {31,35,41}
{31,35,42} {31,35,43} {31,35,44} {31,35,45} {31,35,46} {31,35,47} {31,35,48} {31,35,49} {31,35,50}
{31,35,51} {31,35,52} {31,35,53} {31,35,54} {31,35,55} {31,35,56} {31,35,57} {31,35,58} {31,35,59}
{31,35,60} {31,35,61} {31,35,62} {31,35,63} {31,35,64} {31,35,65} {31,35,66} {31,36,37} {31,36,38}
{31,36,39} {31,36,40} {31,36,41} {31,36,42} {31,36,43} {31,36,44} {31,36,45} {31,36,46} {31,36,47}
{31,36,48} {31,36,49} {31,36,50} {31,36,51} {31,36,52} {31,36,53} {31,36,54} {31,36,55} {31,36,56}
{31,36,57} {31,36,58} {31,36,59} {31,36,60} {31,36,61} {31,36,62} {31,36,63} {31,36,64} {31,36,65}
{31,36,66} {31,37,38} {31,37,39} {31,37,40} {31,37,41} {31,37,42} {31,37,43} {31,37,44} {31,37,45}
{31,37,46} {31,37,47} {31,37,48} {31,37,49} {31,37,50} {31,37,51} {31,37,52} {31,37,53} {31,37,54}
{31,37,55} {31,37,56} {31,37,57} {31,37,58} {31,37,59} {31,37,60} {31,37,61} {31,37,62} {31,37,63}
{31,37,64} {31,37,65} {31,37,66} {31,38,39} {31,38,40} {31,38,41} {31,38,42} {31,38,43} {31,38,44}
{31,38,45} {31,38,46} {31,38,47} {31,38,48} {31,38,49} {31,38,50} {31,38,51} {31,38,52} {31,38,53}
{31,38,54} {31,38,55} {31,38,56} {31,38,57} {31,38,58} {31,38,59} {31,38,60} {31,38,61} {31,38,62}
{31,38,63} {31,38,64} {31,38,65} {31,38,66} {31,39,40} {31,39,41} {31,39,42} {31,39,43} {31,39,44}
{31,39,45} {31,39,46} {31,39,47} {31,39,48} {31,39,49} {31,39,50} {31,39,51} {31,39,52} {31,39,53}
{31,39,54} {31,39,55} {31,39,56} {31,39,57} {31,39,58} {31,39,59} {31,39,60} {31,39,61} {31,39,62}
{31,39,63} {31,39,64} {31,39,65} {31,39,66} {31,40,41} {31,40,42} {31,40,43} {31,40,44} {31,40,45}
{31,40,46} {31,40,47} {31,40,48} {31,40,49} {31,40,50} {31,40,51} {31,40,52} {31,40,53} {31,40,54}
{31,40,55} {31,40,56} {31,40,57} {31,40,58} {31,40,59} {31,40,60} {31,40,61} {31,40,62} {31,40,63}
{31,40,64} {31,40,65} {31,40,66} {31,41,42} {31,41,43} {31,41,44} {31,41,45} {31,41,46} {31,41,47}
{31,41,48} {31,41,49} {31,41,50} {31,41,51} {31,41,52} {31,41,53} {31,41,54} {31,41,55} {31,41,56}
{31,41,57} {31,41,58} {31,41,59} {31,41,60} {31,41,61} {31,41,62} {31,41,63} {31,41,64} {31,41,65}
{31,41,66} {31,42,43} {31,42,44} {31,42,45} {31,42,46} {31,42,47} {31,42,48} {31,42,49} {31,42,50}
{31,42,51} {31,42,52} {31,42,53} {31,42,54} {31,42,55} {31,42,56} {31,42,57} {31,42,58} {31,42,59}
{31,42,60} {31,42,61} {31,42,62} {31,42,63} {31,42,64} {31,42,65} {31,42,66} {31,43,44} {31,43,45}
{31,43,46} {31,43,47} {31,43,48} {31,43,49} {31,43,50} {31,43,51} {31,43,52} {31,43,51} {31,43,51}
{31,43,55} {31,43,56} {31,43,57} {31,43,58} {31,43,59} {31,43,60} {31,43,61} {31,43,62} {31,43,63}
{31,43,64} {31,43,65} {31,43,66} {31,44,45} {31,44,46} {31,44,47} {31,44,48} {31,44,49} {31,44,50}
{31,44,51} {31,44,52} {31,44,53} {31,44,54} {31,44,55} {31,44,56} {31,44,57} {31,44,58} {31,44,59}
{31,44,60} {31,44,61} {31,44,62} {31,44,63} {31,44,64} {31,44,65} {31,44,66} {31,45,46} {31,45,47}
{31,45,48} {31,45,49} {31,45,50} {31,45,51} {31,45,52} {31,45,53} {31,45,54} {31,45,55} {31,45,56}
{31,45,57} {31,45,58} {31,45,59} {31,45,60} {31,45,61} {31,45,62} {31,45,63} {31,45,64} {31,45,65}
{31,45,66} {31,46,47} {31,46,48} {31,46,49} {31,46,50} {31,46,51} {31,46,52} {31,46,53} {31,46,54}
{31,46,55} {31,46,56} {31,46,57} {31,46,58} {31,46,59} {31,46,60} {31,46,61} {31,46,62} {31,46,63}
{31,46,64} {31,46,65} {31,46,66} {31,47,48} {31,47,49} {31,47,50} {31,47,51} {31,47,52} {31,47,53}
{31,47,54} {31,47,55} {31,47,56} {31,47,57} {31,47,58} {31,47,59} {31,47,60} {31,47,61} {31,47,62}
{31,47,63} {31,47,64} {31,47,65} {31,47,66} {31,48,49} {31,48,50} {31,48,51} {31,48,52} {31,48,53}
{31,48,54} {31,48,55} {31,48,56} {31,48,57} {31,48,58} {31,48,59} {31,48,60} {31,48,61} {31,48,62}

TABLE 3A-continued

{31,48,63} {31,48,64} {31,48,65} {31,48,66} {31,49,50} {31,49,51} {31,49,52} {31,49,53} {31,49,54}
{31,49,55} {31,49,56} {31,49,57} {31,49,58} {31,49,59} {31,49,60} {31,49,61} {31,49,62} {31,49,63}
{31,49,64} {31,49,65} {31,49,66} {31,50,51} {31,50,52} {31,50,53} {31,50,54} {31,50,55} {31,50,56}
{31,50,57} {31,50,58} {31,50,59} {31,50,60} {31,50,61} {31,50,62} {31,50,63} {31,50,64} {31,50,65}
{31,50,66} {31,51,52} {31,51,53} {31,51,54} {31,51,55} {31,51,56} {31,51,57} {31,51,58} {31,51,59}
{31,51,60} {31,51,61} {31,51,62} {31,51,63} {31,51,64} {31,51,65} {31,51,66} {31,52,53} {31,52,54}
{31,52,55} {31,52,56} {31,52,57} {31,52,58} {31,52,59} {31,52,60} {31,52,61} {31,52,62} {31,52,63}
{31,52,64} {31,52,65} {31,52,66} {31,53,54} {31,53,55} {31,53,56} {31,53,57} {31,53,58} {31,53,59}
{31,53,60} {31,53,61} {31,53,62} {31,53,63} {31,53,64} {31,53,65} {31,53,66} {31,54,55} {31,54,56}
{31,54,57} {31,54,58} {31,54,59} {31,54,60} {31,54,61} {31,54,62} {31,54,63} {31,54,64} {31,54,65}
{31,54,66} {31,55,56} {31,55,57} {31,55,58} {31,55,59} {31,55,60} {31,55,61} {31,55,62} {31,55,63}
{31,55,64} {31,55,65} {31,55,66} {31,56,57} {31,56,58} {31,56,59} {31,56,60} {31,56,61} {31,56,62}
{31,56,63} {31,56,64} {31,56,65} {31,56,66} {31,57,58} {31,57,59} {31,57,60} {31,57,61} {31,57,62}
{31,57,63} {31,57,64} {31,57,65} {31,57,66} {31,58,59} {31,58,60} {31,58,61} {31,58,62} {31,58,63}
{31,58,64} {31,58,65} {31,58,66} {31,59,60} {31,59,61} {31,59,62} {31,59,63} {31,59,64} {31,59,65}
{31,59,66} {31,60,61} {31,60,62} {31,60,63} {31,60,64} {31,60,65} {31,60,66} {31,61,62} {31,61,63}
{31,61,64} {31,61,65} {31,61,66} {31,62,63} {31,62,64} {31,62,65} {31,62,66} {31,63,64} {31,63,65}
{31,63,66} {31,64,65} {31,64,66} {31,65,66} {32,33,34} {32,33,35} {32,33,36} {32,33,37} {32,33,38}
{32,33,39} {32,33,40} {32,33,41} {32,33,42} {32,33,43} {32,33,44} {32,33,45} {32,33,46} {32,33,47}
{32,33,48} {32,33,49} {32,33,50} {32,33,51} {32,33,52} {32,33,53} {32,33,54} {32,33,55} {32,33,56}
{32,33,57} {32,33,58} {32,33,59} {32,33,60} {32,33,61} {32,33,62} {32,33,63} {32,33,64} {32,33,65}
{32,33,66} {32,34,35} {32,34,36} {32,34,37} {32,34,38} {32,34,39} {32,34,40} {32,34,41} {32,34,42}
{32,34,43} {32,34,44} {32,34,45} {32,34,46} {32,34,47} {32,34,48} {32,34,49} {32,34,50} {32,34,51}
{32,34,52} {32,34,53} {32,34,54} {32,34,55} {32,34,56} {32,34,57} {32,34,58} {32,34,59} {32,34,60}
{32,34,61} {32,34,62} {32,34,63} {32,34,64} {32,34,65} {32,34,66} {32,35,36} {32,35,37} {32,35,38}
{32,35,39} {32,35,40} {32,35,41} {32,35,42} {32,35,43} {32,35,44} {32,35,45} {32,35,46} {32,35,47}
{32,35,48} {32,35,49} {32,35,50} {32,35,51} {32,35,52} {32,35,53} {32,35,54} {32,35,55} {32,35,56}
{32,35,57} {32,35,58} {32,35,59} {32,35,60} {32,35,61} {32,35,62} {32,35,63} {32,35,64} {32,35,65}
{32,35,66} {32,36,37} {32,36,38} {32,36,39} {32,36,40} {32,36,41} {32,36,42} {32,36,43} {32,36,44}
{32,36,45} {32,36,46} {32,36,47} {32,36,48} {32,36,49} {32,36,50} {32,36,51} {32,36,52} {32,36,53}
{32,36,54} {32,36,55} {32,36,56} {32,36,57} {32,36,58} {32,36,59} {32,36,60} {32,36,61} {32,36,62}
{32,36,63} {32,36,64} {32,36,65} {32,36,66} {32,37,38} {32,37,39} {32,37,40} {32,37,41} {32,37,42}
{32,37,43} {32,37,44} {32,37,45} {32,37,46} {32,37,47} {32,37,48} {32,37,49} {32,37,50} {32,37,51}
{32,37,52} {32,37,53} {32,37,54} {32,37,55} {32,37,56} {32,37,57} {32,37,58} {32,37,59} {32,37,60}
{32,37,61} {32,37,62} {32,37,63} {32,37,64} {32,37,65} {32,37,66} {32,38,39} {32,38,40} {32,38,41}
{32,38,42} {32,38,43} {32,38,44} {32,38,45} {32,38,46} {32,38,47} {32,38,48} {32,38,49} {32,38,50}
{32,38,51} {32,38,52} {32,38,53} {32,38,54} {32,38,55} {32,38,56} {32,38,57} {32,38,58} {32,38,59}
{32,38,60} {32,38,61} {32,38,62} {32,38,63} {32,38,64} {32,38,65} {32,38,66} {32,39,40} {32,39,41}
{32,39,42} {32,39,43} {32,39,44} {32,39,45} {32,39,46} {32,39,47} {32,39,48} {32,39,49} {32,39,50}
{32,39,51} {32,39,52} {32,39,53} {32,39,54} {32,39,55} {32,39,56} {32,39,57} {32,39,58} {32,39,59}
{32,39,60} {32,39,61} {32,39,62} {32,39,63} {32,39,64} {32,39,65} {32,39,66} {32,40,41} {32,40,42}
{32,40,43} {32,40,44} {32,40,45} {32,40,46} {32,40,47} {32,40,48} {32,40,49} {32,40,50} {32,40,51}
{32,40,52} {32,40,53} {32,40,54} {32,40,55} {32,40,56} {32,40,57} {32,40,58} {32,40,59} {32,40,60}
{32,40,61} {32,40,62} {32,40,63} {32,40,64} {32,40,65} {32,40,66} {32,41,42} {32,41,43} {32,41,44}
{32,41,45} {32,41,46} {32,41,47} {32,41,48} {32,41,49} {32,41,50} {32,41,51} {32,41,52} {32,41,53}
{32,41,54} {32,41,55} {32,41,56} {32,41,57} {32,41,58} {32,41,59} {32,41,60} {32,41,61} {32,41,62}
{32,41,63} {32,41,64} {32,41,65} {32,41,66} {32,42,43} {32,42,44} {32,42,45} {32,42,46} {32,42,47}
{32,42,48} {32,42,49} {32,42,50} {32,42,51} {32,42,52} {32,42,53} {32,42,54} {32,42,55} {32,42,56}
{32,42,57} {32,42,58} {32,42,59} {32,42,60} {32,42,61} {32,42,62} {32,42,63} {32,42,64} {32,42,65}
{32,42,66} {32,43,44} {32,43,45} {32,43,46} {32,43,47} {32,43,48} {32,43,49} {32,43,50} {32,43,51}
{32,43,52} {32,43,53} {32,43,54} {32,43,55} {32,43,56} {32,43,57} {32,43,58} {32,43,59} {32,43,60}
{32,43,61} {32,43,62} {32,43,63} {32,43,64} {32,43,65} {32,43,66} {32,44,45} {32,44,46} {32,44,47}
{32,44,48} {32,44,49} {32,44,50} {32,44,51} {32,44,52} {32,44,53} {32,44,54} {32,44,55} {32,44,56}
{32,44,57} {32,44,58} {32,44,59} {32,44,60} {32,44,61} {32,44,62} {32,44,63} {32,44,64} {32,44,65}
{32,44,66} {32,45,46} {32,45,47} {32,45,48} {32,45,49} {32,45,50} {32,45,51} {32,45,52} {32,45,53}
{32,45,54} {32,45,55} {32,45,56} {32,45,57} {32,45,58} {32,45,59} {32,45,60} {32,45,61} {32,45,62}
{32,45,63} {32,45,64} {32,45,65} {32,45,66} {32,46,47} {32,46,48} {32,46,49} {32,46,50} {32,46,51}
{32,46,52} {32,46,53} {32,46,54} {32,46,55} {32,46,56} {32,46,57} {32,46,58} {32,46,59} {32,46,60}
{32,46,61} {32,46,62} {32,46,63} {32,46,64} {32,46,65} {32,46,66} {32,47,48} {32,47,49} {32,47,50}
{32,47,51} {32,47,52} {32,47,53} {32,47,54} {32,47,55} {32,47,56} {32,47,57} {32,47,58} {32,47,59}
{32,47,60} {32,47,61} {32,47,62} {32,47,63} {32,47,64} {32,47,65} {32,47,66} {32,48,49} {32,48,50}
{32,48,51} {32,48,52} {32,48,53} {32,48,54} {32,48,55} {32,48,56} {32,48,57} {32,48,58} {32,48,59}
{32,48,60} {32,48,61} {32,48,62} {32,48,63} {32,48,64} {32,48,65} {32,48,66} {32,49,50} {32,49,51}
{32,49,52} {32,49,53} {32,49,54} {32,49,55} {32,49,56} {32,49,57} {32,49,58} {32,49,59} {32,49,60}
{32,49,61} {32,49,62} {32,49,63} {32,49,64} {32,49,65} {32,49,66} {32,50,51} {32,50,52} {32,50,53}
{32,50,54} {32,50,55} {32,50,56} {32,50,57} {32,50,58} {32,50,59} {32,50,60} {32,50,61} {32,50,62}
{32,50,63} {32,50,64} {32,50,65} {32,50,66} {32,51,52} {32,51,53} {32,51,54} {32,51,55} {32,51,56}
{32,51,57} {32,51,58} {32,51,59} {32,51,60} {32,51,61} {32,51,62} {32,51,63} {32,51,64} {32,51,65}
{32,51,66} {32,52,53} {32,52,54} {32,52,55} {32,52,56} {32,52,57} {32,52,58} {32,52,59} {32,52,60}
{32,52,61} {32,52,62} {32,52,63} {32,52,64} {32,52,65} {32,52,66} {32,53,54} {32,53,55} {32,53,56}
{32,53,57} {32,53,58} {32,53,59} {32,53,60} {32,53,61} {32,53,62} {32,53,63} {32,53,64} {32,53,65}
{32,53,66} {32,54,55} {32,54,56} {32,54,57} {32,54,58} {32,54,59} {32,54,60} {32,54,61} {32,54,62}
{32,54,63} {32,54,64} {32,54,65} {32,54,66} {32,55,56} {32,55,57} {32,55,58} {32,55,59} {32,55,60}
{32,55,61} {32,55,62} {32,55,63} {32,55,64} {32,55,65} {32,55,66} {32,56,57} {32,56,58} {32,56,59}
{32,56,60} {32,56,61} {32,56,62} {32,56,63} {32,56,64} {32,56,65} {32,56,66} {32,57,58} {32,57,59}
{32,57,60} {32,57,61} {32,57,62} {32,57,63} {32,57,64} {32,57,65} {32,57,66} {32,58,59} {32,58,60}
{32,58,61} {32,58,62} {32,58,63} {32,58,64} {32,58,65} {32,58,66} {32,59,60} {32,59,61} {32,59,62}
{32,59,63} {32,59,64} {32,59,65} {32,59,66} {32,60,61} {32,60,62} {32,60,63} {32,60,64} {32,60,65}
{32,60,66} {32,61,62} {32,61,63} {32,61,64} {32,61,65} {32,61,66} {32,62,63} {32,62,64} {32,62,65}
{32,62,66} {32,63,64} {32,63,65} {32,63,66} {32,64,65} {32,64,66} {32,65,66} {33,34,35} {33,34,36}

TABLE 3A-continued

{33,34,37} {33,34,38} {33,34,39} {33,34,40} {33,34,41} {33,34,42} {33,34,43} {33,34,44} {33,34,45}
{33,34,46} {33,34,47} {33,34,48} {33,34,49} {33,34,50} {33,34,51} {33,34,52} {33,34,53} {33,34,54}
{33,34,55} {33,34,56} {33,34,57} {33,34,58} {33,34,59} {33,34,60} {33,34,61} {33,34,62} {33,34,63}
{33,34,64} {33,34,65} {33,34,66} {33,35,36} {33,35,37} {33,35,38} {33,35,39} {33,35,40} {33,35,41}
{33,35,42} {33,35,43} {33,35,44} {33,35,45} {33,35,46} {33,35,47} {33,35,48} {33,35,49} {33,35,50}
{33,35,51} {33,35,52} {33,35,53} {33,35,54} {33,35,55} {33,35,56} {33,35,57} {33,35,58} {33,35,59}
{33,35,60} {33,35,61} {33,35,62} {33,35,63} {33,35,64} {33,35,65} {33,35,66} {33,36,37} {33,36,38}
{33,36,39} {33,36,40} {33,36,41} {33,36,42} {33,36,43} {33,36,44} {33,36,45} {33,36,46} {33,36,47}
{33,36,48} {33,36,49} {33,36,50} {33,36,51} {33,36,52} {33,36,53} {33,36,54} {33,36,55} {33,36,56}
{33,36,57} {33,36,58} {33,36,59} {33,36,60} {33,36,61} {33,36,62} {33,36,63} {33,36,64} {33,36,65}
{33,36,66} {33,37,38} {33,37,39} {33,37,40} {33,37,41} {33,37,42} {33,37,43} {33,37,44} {33,37,45}
{33,37,46} {33,37,47} {33,37,48} {33,37,49} {33,37,50} {33,37,51} {33,37,52} {33,37,53} {33,37,54}
{33,37,55} {33,37,56} {33,37,57} {33,37,58} {33,37,59} {33,37,60} {33,37,61} {33,37,62} {33,37,63}
{33,37,64} {33,37,65} {33,37,66} {33,38,39} {33,38,40} {33,38,41} {33,38,42} {33,38,43} {33,38,44}
{33,38,45} {33,38,46} {33,38,47} {33,38,48} {33,38,49} {33,38,50} {33,38,51} {33,38,52} {33,38,53}
{33,38,54} {33,38,55} {33,38,56} {33,38,57} {33,38,58} {33,38,59} {33,38,60} {33,38,61} {33,38,62}
{33,38,63} {33,38,64} {33,38,65} {33,38,66} {33,39,40} {33,39,41} {33,39,42} {33,39,43} {33,39,44}
{33,39,45} {33,39,46} {33,39,47} {33,39,48} {33,39,49} {33,39,50} {33,39,51} {33,39,52} {33,39,53}
{33,39,54} {33,39,55} {33,39,56} {33,39,57} {33,39,58} {33,39,59} {33,39,60} {33,39,61} {33,39,62}
{33,39,63} {33,39,64} {33,39,65} {33,39,66} {33,40,41} {33,40,42} {33,40,43} {33,40,44} {33,40,45}
{33,40,46} {33,40,47} {33,40,48} {33,40,49} {33,40,50} {33,40,51} {33,40,52} {33,40,53} {33,40,54}
{33,40,55} {33,40,56} {33,40,57} {33,40,58} {33,40,59} {33,40,60} {33,40,61} {33,40,62} {33,40,63}
{33,40,64} {33,40,65} {33,40,66} {33,41,42} {33,41,43} {33,41,44} {33,41,45} {33,41,46} {33,41,47}
{33,41,48} {33,41,49} {33,41,50} {33,41,51} {33,41,52} {33,41,53} {33,41,54} {33,41,55} {33,41,56}
{33,41,57} {33,41,58} {33,41,59} {33,41,60} {33,41,61} {33,41,62} {33,41,63} {33,41,64} {33,41,65}
{33,41,66} {33,42,43} {33,42,44} {33,42,45} {33,42,46} {33,42,47} {33,42,48} {33,42,49} {33,42,50}
{33,42,51} {33,42,52} {33,42,53} {33,42,54} {33,42,55} {33,42,56} {33,42,57} {33,42,58} {33,42,59}
{33,42,60} {33,42,61} {33,42,62} {33,42,63} {33,42,64} {33,42,65} {33,42,66} {33,43,44} {33,43,45}
{33,43,46} {33,43,47} {33,43,48} {33,43,49} {33,43,50} {33,43,51} {33,43,52} {33,43,53} {33,43,54}
{33,43,55} {33,43,56} {33,43,57} {33,43,58} {33,43,59} {33,43,60} {33,43,61} {33,43,62} {33,43,63}
{33,43,64} {33,43,65} {33,43,66} {33,44,45} {33,44,46} {33,44,47} {33,44,48} {33,44,49} {33,44,50}
{33,44,51} {33,44,52} {33,44,53} {33,44,54} {33,44,55} {33,44,56} {33,44,57} {33,44,58} {33,44,59}
{33,44,60} {33,44,61} {33,44,62} {33,44,63} {33,44,64} {33,44,65} {33,44,66} {33,45,46} {33,45,47}
{33,45,48} {33,45,49} {33,45,50} {33,45,51} {33,45,52} {33,45,53} {33,45,54} {33,45,55} {33,45,56}
{33,45,57} {33,45,58} {33,45,59} {33,45,60} {33,45,61} {33,45,62} {33,45,63} {33,45,64} {33,45,65}
{33,45,66} {33,46,47} {33,46,48} {33,46,49} {33,46,50} {33,46,51} {33,46,52} {33,46,53} {33,46,54}
{33,46,55} {33,46,56} {33,46,57} {33,46,58} {33,46,59} {33,46,60} {33,46,61} {33,46,62} {33,46,63}
{33,46,64} {33,46,65} {33,46,66} {33,47,48} {33,47,49} {33,47,50} {33,47,51} {33,47,52} {33,47,53}
{33,47,54} {33,47,55} {33,47,56} {33,47,57} {33,47,58} {33,47,59} {33,47,60} {33,47,61} {33,47,62}
{33,47,63} {33,47,64} {33,47,65} {33,47,66} {33,48,49} {33,48,50} {33,48,51} {33,48,52} {33,48,53}
{33,48,54} {33,48,55} {33,48,56} {33,48,57} {33,48,58} {33,48,59} {33,48,60} {33,48,61} {33,48,62}
{33,48,63} {33,48,64} {33,48,65} {33,48,66} {33,49,50} {33,49,51} {33,49,52} {33,49,53} {33,49,54}
{33,49,55} {33,49,56} {33,49,57} {33,49,58} {33,49,59} {33,49,60} {33,49,61} {33,49,62} {33,49,63}
{33,49,64} {33,49,65} {33,49,66} {33,50,51} {33,50,52} {33,50,53} {33,50,54} {33,50,55} {33,50,56}
{33,50,57} {33,50,58} {33,50,59} {33,50,60} {33,50,61} {33,50,62} {33,50,63} {33,50,64} {33,50,65}
{33,50,66} {33,51,52} {33,51,53} {33,51,54} {33,51,55} {33,51,56} {33,51,57} {33,51,58} {33,51,59}
{33,51,60} {33,51,61} {33,51,62} {33,51,63} {33,51,64} {33,51,65} {33,51,66} {33,52,53} {33,52,54}
{33,52,55} {33,52,56} {33,52,57} {33,52,58} {33,52,59} {33,52,60} {33,52,61} {33,52,62} {33,52,63}
{33,52,64} {33,52,65} {33,52,66} {33,53,54} {33,53,55} {33,53,56} {33,53,57} {33,53,58} {33,53,59}
{33,53,60} {33,53,61} {33,53,62} {33,53,63} {33,53,64} {33,53,65} {33,53,66} {33,54,55} {33,54,56}
{33,54,57} {33,54,58} {33,54,59} {33,54,60} {33,54,61} {33,54,62} {33,54,63} {33,54,64} {33,54,65}
{33,54,66} {33,55,56} {33,55,57} {33,55,58} {33,55,59} {33,55,60} {33,55,61} {33,55,62} {33,55,63}
{33,55,64} {33,55,65} {33,55,66} {33,56,57} {33,56,58} {33,56,59} {33,56,60} {33,56,61} {33,56,62}
{33,56,63} {33,56,64} {33,56,65} {33,56,66} {33,57,58} {33,57,59} {33,57,60} {33,57,61} {33,57,62}
{33,57,63} {33,57,64} {33,57,65} {33,57,66} {33,58,59} {33,58,60} {33,58,61} {33,58,62} {33,58,63}
{33,58,64} {33,58,65} {33,58,66} {33,59,60} {33,59,61} {33,59,62} {33,59,63} {33,59,64} {33,59,65}
{33,59,66} {33,60,61} {33,60,62} {33,60,63} {33,60,64} {33,60,65} {33,60,66} {33,61,62} {33,61,63}
{33,61,64} {33,61,65} {33,61,66} {33,62,63} {33,62,64} {33,62,65} {33,62,66} {33,63,64} {33,63,65}
{33,63,66} {33,64,65} {33,64,66} {33,65,66} {34,35,36} {34,35,37} {34,35,38} {34,35,39} {34,35,40}
{34,35,41} {34,35,42} {34,35,43} {34,35,44} {34,35,45} {34,35,46} {34,35,47} {34,35,48} {34,35,49}
{34,35,50} {34,35,51} {34,35,52} {34,35,53} {34,35,54} {34,35,55} {34,35,56} {34,35,57} {34,35,58}
{34,35,59} {34,35,60} {34,35,61} {34,35,62} {34,35,63} {34,35,64} {34,35,65} {34,35,66} {34,36,37}
{34,36,38} {34,36,39} {34,36,40} {34,36,41} {34,36,42} {34,36,43} {34,36,44} {34,36,45} {34,36,46}
{34,36,47} {34,36,48} {34,36,49} {34,36,50} {34,36,51} {34,36,52} {34,36,53} {34,36,54} {34,36,55}
{34,36,56} {34,36,57} {34,36,58} {34,36,59} {34,36,60} {34,36,61} {34,36,62} {34,36,63} {34,36,64}
{34,36,65} {34,36,66} {34,37,38} {34,37,39} {34,37,40} {34,37,41} {34,37,42} {34,37,43} {34,37,44}
{34,37,45} {34,37,46} {34,37,47} {34,37,48} {34,37,49} {34,37,50} {34,37,51} {34,37,52} {34,37,53}
{34,37,54} {34,37,55} {34,37,56} {34,37,57} {34,37,58} {34,37,59} {34,37,60} {34,37,61} {34,37,62}
{34,37,63} {34,37,64} {34,37,65} {34,37,66} {34,38,39} {34,38,40} {34,38,41} {34,38,42} {34,38,43}
{34,38,44} {34,38,45} {34,38,46} {34,38,47} {34,38,48} {34,38,49} {34,38,50} {34,38,51} {34,38,52}
{34,38,53} {34,38,54} {34,38,55} {34,38,56} {34,38,57} {34,38,58} {34,38,59} {34,38,60} {34,38,61}
{34,38,62} {34,38,63} {34,38,64} {34,38,65} {34,38,66} {34,39,40} {34,39,41} {34,39,42} {34,39,43}
{34,39,44} {34,39,45} {34,39,46} {34,39,47} {34,39,48} {34,39,49} {34,39,50} {34,39,51} {34,39,52}
{34,39,53} {34,39,54} {34,39,55} {34,39,56} {34,39,57} {34,39,58} {34,39,59} {34,39,60} {34,39,61}
{34,39,62} {34,39,63} {34,39,64} {34,39,65} {34,39,66} {34,40,41} {34,40,42} {34,40,43} {34,40,44}
{34,40,45} {34,40,46} {34,40,47} {34,40,48} {34,40,49} {34,40,50} {34,40,51} {34,40,52} {34,40,53}
{34,40,54} {34,40,55} {34,40,56} {34,40,57} {34,40,58} {34,40,59} {34,40,60} {34,40,61} {34,40,62}
{34,40,63} {34,40,64} {34,40,65} {34,40,66} {34,41,42} {34,41,43} {34,41,44} {34,41,45} {34,41,46}
{34,41,47} {34,41,48} {34,41,49} {34,41,50} {34,41,51} {34,41,52} {34,41,53} {34,41,54} {34,41,55}
{34,41,56} {34,41,57} {34,41,58} {34,41,59} {34,41,60} {34,41,61} {34,41,62} {34,41,63} {34,41,64}

TABLE 3A-continued

| | | | | | | | |
|---|---|---|---|---|---|---|---|
| {34,41,65} | {34,41,66} | {34,42,43} | {34,42,44} | {34,42,45} | {34,42,46} | {34,42,47} | {34,42,48} | {34,42,49} |
| {34,42,50} | {34,42,51} | {34,42,52} | {34,42,53} | {34,42,54} | {34,42,55} | {34,42,56} | {34,42,57} | {34,42,58} |
| {34,42,59} | {34,42,60} | {34,42,61} | {34,42,62} | {34,42,63} | {34,42,64} | {34,42,65} | {34,42,66} | {34,43,44} |
| {34,43,45} | {34,43,46} | {34,43,47} | {34,43,48} | {34,43,49} | {34,43,50} | {34,43,51} | {34,43,52} | {34,43,53} |
| {34,43,54} | {34,43,55} | {34,43,56} | {34,43,57} | {34,43,58} | {34,43,59} | {34,43,60} | {34,43,61} | {34,43,62} |
| {34,43,63} | {34,43,64} | {34,43,65} | {34,43,66} | {34,44,45} | {34,44,46} | {34,44,47} | {34,44,48} | {34,44,49} |
| {34,44,50} | {34,44,51} | {34,44,52} | {34,44,53} | {34,44,54} | {34,44,55} | {34,44,56} | {34,44,57} | {34,44,58} |
| {34,44,59} | {34,44,60} | {34,44,61} | {34,44,62} | {34,44,63} | {34,44,64} | {34,44,65} | {34,44,66} | {34,45,46} |
| {34,45,47} | {34,45,48} | {34,45,49} | {34,45,50} | {34,45,51} | {34,45,52} | {34,45,53} | {34,45,54} | {34,45,55} |
| {34,45,56} | {34,45,57} | {34,45,58} | {34,45,59} | {34,45,60} | {34,45,61} | {34,45,62} | {34,45,63} | {34,45,64} |
| {34,45,65} | {34,45,66} | {34,46,47} | {34,46,48} | {34,46,49} | {34,46,50} | {34,46,51} | {34,46,52} | {34,46,53} |
| {34,46,54} | {34,46,55} | {34,46,56} | {34,46,57} | {34,46,58} | {34,46,59} | {34,46,60} | {34,46,61} | {34,46,62} |
| {34,46,63} | {34,46,64} | {34,46,65} | {34,46,66} | {34,47,48} | {34,47,49} | {34,47,50} | {34,47,51} | {34,47,52} |
| {34,47,53} | {34,47,54} | {34,47,55} | {34,47,56} | {34,47,57} | {34,47,58} | {34,47,59} | {34,47,60} | {34,47,61} |
| {34,47,62} | {34,47,63} | {34,47,64} | {34,47,65} | {34,47,66} | {34,48,49} | {34,48,50} | {34,48,51} | {34,48,52} |
| {34,48,53} | {34,48,54} | {34,48,55} | {34,48,56} | {34,48,57} | {34,48,58} | {34,48,59} | {34,48,60} | {34,48,61} |
| {34,48,62} | {34,48,63} | {34,48,64} | {34,48,65} | {34,48,66} | {34,49,50} | {34,49,51} | {34,49,52} | {34,49,53} |
| {34,49,54} | {34,49,55} | {34,49,56} | {34,49,57} | {34,49,58} | {34,49,59} | {34,49,60} | {34,49,61} | {34,49,62} |
| {34,49,63} | {34,49,64} | {34,49,65} | {34,49,66} | {34,50,51} | {34,50,52} | {34,50,53} | {34,50,54} | {34,50,55} |
| {34,50,56} | {34,50,57} | {34,50,58} | {34,50,59} | {34,50,60} | {34,50,61} | {34,50,62} | {34,50,63} | {34,50,64} |
| {34,50,65} | {34,50,66} | {34,51,52} | {34,51,53} | {34,51,54} | {34,51,55} | {34,51,56} | {34,51,57} | {34,51,58} |
| {34,51,59} | {34,51,60} | {34,51,61} | {34,51,62} | {34,51,63} | {34,51,64} | {34,51,65} | {34,51,66} | {34,52,53} |
| {34,52,54} | {34,52,55} | {34,52,56} | {34,52,57} | {34,52,58} | {34,52,59} | {34,52,60} | {34,52,61} | {34,52,62} |
| {34,52,63} | {34,52,64} | {34,52,65} | {34,52,66} | {34,53,54} | {34,53,55} | {34,53,56} | {34,53,57} | {34,53,58} |
| {34,53,59} | {34,53,60} | {34,53,61} | {34,53,62} | {34,53,63} | {34,53,64} | {34,53,65} | {34,53,66} | {34,54,55} |
| {34,54,56} | {34,54,57} | {34,54,58} | {34,54,59} | {34,54,60} | {34,54,61} | {34,54,62} | {34,54,63} | {34,54,64} |
| {34,54,65} | {34,54,66} | {34,55,56} | {34,55,57} | {34,55,58} | {34,55,59} | {34,55,60} | {34,55,61} | {34,55,62} |
| {34,55,63} | {34,55,64} | {34,55,65} | {34,55,66} | {34,56,57} | {34,56,58} | {34,56,59} | {34,56,60} | {34,56,61} |
| {34,56,62} | {34,56,63} | {34,56,64} | {34,56,65} | {34,56,66} | {34,57,58} | {34,57,59} | {34,57,60} | {34,57,61} |
| {34,57,62} | {34,57,63} | {34,57,64} | {34,57,65} | {34,57,66} | {34,58,59} | {34,58,60} | {34,58,61} | {34,58,62} |
| {34,58,63} | {34,58,64} | {34,58,65} | {34,58,66} | {34,59,60} | {34,59,61} | {34,59,62} | {34,59,63} | {34,59,64} |
| {34,59,65} | {34,59,66} | {34,60,61} | {34,60,62} | {34,60,63} | {34,60,64} | {34,60,65} | {34,60,66} | {34,61,62} |
| {34,61,63} | {34,61,64} | {34,61,65} | {34,61,66} | {34,62,63} | {34,62,64} | {34,62,65} | {34,62,66} | {34,63,64} |
| {34,63,65} | {34,63,66} | {34,64,65} | {34,64,66} | {34,65,66} | {35,36,37} | {35,36,38} | {35,36,39} | {35,36,40} |
| {35,36,41} | {35,36,42} | {35,36,43} | {35,36,44} | {35,36,45} | {35,36,46} | {35,36,47} | {35,36,48} | {35,36,49} |
| {35,36,50} | {35,36,51} | {35,36,52} | {35,36,53} | {35,36,54} | {35,36,55} | {35,36,56} | {35,36,57} | {35,36,58} |
| {35,36,59} | {35,36,60} | {35,36,61} | {35,36,62} | {35,36,63} | {35,36,64} | {35,36,65} | {35,36,66} | {35,37,38} |
| {35,37,39} | {35,37,40} | {35,37,41} | {35,37,42} | {35,37,43} | {35,37,44} | {35,37,45} | {35,37,46} | {35,37,47} |
| {35,37,48} | {35,37,49} | {35,37,50} | {35,37,51} | {35,37,52} | {35,37,53} | {35,37,54} | {35,37,55} | {35,37,56} |
| {35,37,57} | {35,37,58} | {35,37,59} | {35,37,60} | {35,37,61} | {35,37,62} | {35,37,63} | {35,37,64} | {35,37,65} |
| {35,37,66} | {35,38,39} | {35,38,40} | {35,38,41} | {35,38,42} | {35,38,43} | {35,38,44} | {35,38,45} | {35,38,46} |
| {35,38,47} | {35,38,48} | {35,38,49} | {35,38,50} | {35,38,51} | {35,38,52} | {35,38,53} | {35,38,54} | {35,38,55} |
| {35,38,56} | {35,38,57} | {35,38,58} | {35,38,59} | {35,38,60} | {35,38,61} | {35,38,62} | {35,38,63} | {35,38,64} |
| {35,38,65} | {35,38,66} | {35,39,40} | {35,39,41} | {35,39,42} | {35,39,43} | {35,39,44} | {35,39,45} | {35,39,46} |
| {35,39,47} | {35,39,48} | {35,39,49} | {35,39,50} | {35,39,51} | {35,39,52} | {35,39,53} | {35,39,54} | {35,39,55} |
| {35,39,56} | {35,39,57} | {35,39,58} | {35,39,59} | {35,39,60} | {35,39,61} | {35,39,62} | {35,39,63} | {35,39,64} |
| {35,39,65} | {35,39,66} | {35,40,41} | {35,40,42} | {35,40,43} | {35,40,44} | {35,40,45} | {35,40,46} | {35,40,47} |
| {35,40,48} | {35,40,49} | {35,40,50} | {35,40,51} | {35,40,52} | {35,40,53} | {35,40,54} | {35,40,55} | {35,40,56} |
| {35,40,57} | {35,40,58} | {35,40,59} | {35,40,60} | {35,40,61} | {35,40,62} | {35,40,63} | {35,40,64} | {35,40,65} |
| {35,40,66} | {35,41,42} | {35,41,43} | {35,41,44} | {35,41,45} | {35,41,46} | {35,41,47} | {35,41,48} | {35,41,49} |
| {35,41,50} | {35,41,51} | {35,41,52} | {35,41,53} | {35,41,54} | {35,41,55} | {35,41,56} | {35,41,57} | {35,41,58} |
| {35,41,59} | {35,41,60} | {35,41,61} | {35,41,62} | {35,41,63} | {35,41,64} | {35,41,65} | {35,41,66} | {35,42,43} |
| {35,42,44} | {35,42,45} | {35,42,46} | {35,42,47} | {35,42,48} | {35,42,49} | {35,42,50} | {35,42,51} | {35,42,52} |
| {35,42,53} | {35,42,54} | {35,42,55} | {35,42,56} | {35,42,57} | {35,42,58} | {35,42,59} | {35,42,60} | {35,42,61} |
| {35,42,62} | {35,42,63} | {35,42,64} | {35,42,65} | {35,42,66} | {35,43,44} | {35,43,45} | {35,43,46} | {35,43,47} |
| {35,43,48} | {35,43,49} | {35,43,50} | {35,43,51} | {35,43,52} | {35,43,53} | {35,43,54} | {35,43,55} | {35,43,56} |
| {35,43,57} | {35,43,58} | {35,43,59} | {35,43,60} | {35,43,61} | {35,43,62} | {35,43,63} | {35,43,64} | {35,43,65} |
| {35,43,66} | {35,44,45} | {35,44,46} | {35,44,47} | {35,44,48} | {35,44,49} | {35,44,50} | {35,44,51} | {35,44,52} |
| {35,44,53} | {35,44,54} | {35,44,55} | {35,44,56} | {35,44,57} | {35,44,58} | {35,44,59} | {35,44,60} | {35,44,61} |
| {35,44,62} | {35,44,63} | {35,44,64} | {35,44,65} | {35,44,66} | {35,45,46} | {35,45,47} | {35,45,48} | {35,45,49} |
| {35,45,50} | {35,45,51} | {35,45,52} | {35,45,53} | {35,45,54} | {35,45,55} | {35,45,56} | {35,45,57} | {35,45,58} |
| {35,45,59} | {35,45,60} | {35,45,61} | {35,45,62} | {35,45,63} | {35,45,64} | {35,45,65} | {35,45,66} | {35,46,47} |
| {35,46,48} | {35,46,49} | {35,46,50} | {35,46,51} | {35,46,52} | {35,46,53} | {35,46,54} | {35,46,55} | {35,46,56} |
| {35,46,57} | {35,46,58} | {35,46,59} | {35,46,60} | {35,46,61} | {35,46,62} | {35,46,63} | {35,46,64} | {35,46,65} |
| {35,46,66} | {35,47,48} | {35,47,49} | {35,47,50} | {35,47,51} | {35,47,52} | {35,47,53} | {35,47,54} | {35,47,55} |
| {35,47,56} | {35,47,57} | {35,47,58} | {35,47,59} | {35,47,60} | {35,47,61} | {35,47,62} | {35,47,63} | {35,47,64} |
| {35,47,65} | {35,47,66} | {35,48,49} | {35,48,50} | {35,48,51} | {35,48,52} | {35,48,53} | {35,48,54} | {35,48,55} |
| {35,48,56} | {35,48,57} | {35,48,58} | {35,48,59} | {35,48,60} | {35,48,61} | {35,48,62} | {35,48,63} | {35,48,64} |
| {35,48,65} | {35,48,66} | {35,49,50} | {35,49,51} | {35,49,52} | {35,49,53} | {35,49,54} | {35,49,55} | {35,49,56} |
| {35,49,57} | {35,49,58} | {35,49,59} | {35,49,60} | {35,49,61} | {35,49,62} | {35,49,63} | {35,49,64} | {35,49,65} |
| {35,49,66} | {35,50,51} | {35,50,52} | {35,50,53} | {35,50,54} | {35,50,55} | {35,50,56} | {35,50,57} | {35,50,58} |
| {35,50,59} | {35,50,60} | {35,50,61} | {35,50,62} | {35,50,63} | {35,50,64} | {35,50,65} | {35,50,66} | {35,51,52} |
| {35,51,53} | {35,51,54} | {35,51,55} | {35,51,56} | {35,51,57} | {35,51,58} | {35,51,59} | {35,51,60} | {35,51,61} |
| {35,51,62} | {35,51,63} | {35,51,64} | {35,51,65} | {35,51,66} | {35,52,53} | {35,52,54} | {35,52,55} | {35,52,56} |
| {35,52,57} | {35,52,58} | {35,52,59} | {35,52,60} | {35,52,61} | {35,52,62} | {35,52,63} | {35,52,64} | {35,52,65} |
| {35,52,66} | {35,53,54} | {35,53,55} | {35,53,56} | {35,53,57} | {35,53,58} | {35,53,59} | {35,53,60} | {35,53,61} |
| {35,53,62} | {35,53,63} | {35,53,64} | {35,53,65} | {35,53,66} | {35,54,55} | {35,54,56} | {35,54,57} | {35,54,58} |
| {35,54,59} | {35,54,60} | {35,54,61} | {35,54,62} | {35,54,63} | {35,54,64} | {35,54,65} | {35,54,66} | {35,55,56} |
| {35,55,57} | {35,55,58} | {35,55,59} | {35,55,60} | {35,55,61} | {35,55,62} | {35,55,63} | {35,55,64} | {35,55,65} |
| {35,55,66} | {35,56,57} | {35,56,58} | {35,56,59} | {35,56,60} | {35,56,61} | {35,56,62} | {35,56,63} | {35,56,64} |

TABLE 3A-continued

| | | | | | | | |
|---|---|---|---|---|---|---|---|
| {35,56,65} | {35,56,66} | {35,57,58} | {35,57,59} | {35,57,60} | {35,57,61} | {35,57,62} | {35,57,63} | {35,57,64} |
| {35,57,65} | {35,57,66} | {35,58,59} | {35,58,60} | {35,58,61} | {35,58,62} | {35,58,63} | {35,58,64} | {35,58,65} |
| {35,58,66} | {35,59,60} | {35,59,61} | {35,59,62} | {35,59,63} | {35,59,64} | {35,59,65} | {35,59,66} | {35,60,61} |
| {35,60,62} | {35,60,63} | {35,60,64} | {35,60,65} | {35,60,66} | {35,61,62} | {35,61,63} | {35,61,64} | {35,61,65} |
| {35,61,66} | {35,62,63} | {35,62,64} | {35,62,65} | {35,62,66} | {35,63,64} | {35,63,65} | {35,63,66} | {35,64,65} |
| {35,64,66} | {35,65,66} | {36,37,38} | {36,37,39} | {36,37,40} | {36,37,41} | {36,37,42} | {36,37,43} | {36,37,44} |
| {36,37,45} | {36,37,46} | {36,37,47} | {36,37,48} | {36,37,49} | {36,37,50} | {36,37,51} | {36,37,52} | {36,37,53} |
| {36,37,54} | {36,37,55} | {36,37,56} | {36,37,57} | {36,37,58} | {36,37,59} | {36,37,60} | {36,37,61} | {36,37,62} |
| {36,37,63} | {36,37,64} | {36,37,65} | {36,37,66} | {36,38,39} | {36,38,40} | {36,38,41} | {36,38,42} | {36,38,43} |
| {36,38,44} | {36,38,45} | {36,38,46} | {36,38,47} | {36,38,48} | {36,38,49} | {36,38,50} | {36,38,51} | {36,38,52} |
| {36,38,53} | {36,38,54} | {36,38,55} | {36,38,56} | {36,38,57} | {36,38,58} | {36,38,59} | {36,38,60} | {36,38,61} |
| {36,38,62} | {36,38,63} | {36,38,64} | {36,38,65} | {36,38,66} | {36,39,40} | {36,39,41} | {36,39,42} | {36,39,43} |
| {36,39,44} | {36,39,45} | {36,39,46} | {36,39,47} | {36,39,48} | {36,39,49} | {36,39,50} | {36,39,51} | {36,39,52} |
| {36,39,53} | {36,39,54} | {36,39,55} | {36,39,56} | {36,39,57} | {36,39,58} | {36,39,59} | {36,39,60} | {36,39,61} |
| {36,39,62} | {36,39,63} | {36,39,64} | {36,39,65} | {36,39,66} | {36,40,41} | {36,40,42} | {36,40,43} | {36,40,44} |
| {36,40,45} | {36,40,46} | {36,40,47} | {36,40,48} | {36,40,49} | {36,40,50} | {36,40,51} | {36,40,52} | {36,40,53} |
| {36,40,54} | {36,40,55} | {36,40,56} | {36,40,57} | {36,40,58} | {36,40,59} | {36,40,60} | {36,40,61} | {36,40,62} |
| {36,40,63} | {36,40,64} | {36,40,65} | {36,40,66} | {36,41,42} | {36,41,43} | {36,41,44} | {36,41,45} | {36,41,46} |
| {36,41,47} | {36,41,48} | {36,41,49} | {36,41,50} | {36,41,51} | {36,41,52} | {36,41,53} | {36,41,54} | {36,41,55} |
| {36,41,56} | {36,41,57} | {36,41,58} | {36,41,59} | {36,41,60} | {36,41,61} | {36,41,62} | {36,41,63} | {36,41,64} |
| {36,41,65} | {36,41,66} | {36,42,43} | {36,42,44} | {36,42,45} | {36,42,46} | {36,42,47} | {36,42,48} | {36,42,49} |
| {36,42,50} | {36,42,51} | {36,42,52} | {36,42,53} | {36,42,54} | {36,42,55} | {36,42,56} | {36,42,57} | {36,42,58} |
| {36,42,59} | {36,42,60} | {36,42,61} | {36,42,62} | {36,42,63} | {36,42,64} | {36,42,65} | {36,42,66} | {36,43,44} |
| {36,43,45} | {36,43,46} | {36,43,47} | {36,43,48} | {36,43,49} | {36,43,50} | {36,43,51} | {36,43,52} | {36,43,53} |
| {36,43,54} | {36,43,55} | {36,43,56} | {36,43,57} | {36,43,58} | {36,43,59} | {36,43,60} | {36,43,61} | {36,43,62} |
| {36,43,63} | {36,43,64} | {36,43,65} | {36,43,66} | {36,44,45} | {36,44,46} | {36,44,47} | {36,44,48} | {36,44,49} |
| {36,44,50} | {36,44,51} | {36,44,52} | {36,44,53} | {36,44,54} | {36,44,55} | {36,44,56} | {36,44,57} | {36,44,58} |
| {36,44,59} | {36,44,60} | {36,44,61} | {36,44,62} | {36,44,63} | {36,44,64} | {36,44,65} | {36,44,66} | {36,45,46} |
| {36,45,47} | {36,45,48} | {36,45,49} | {36,45,50} | {36,45,51} | {36,45,52} | {36,45,53} | {36,45,54} | {36,45,55} |
| {36,45,56} | {36,45,57} | {36,45,58} | {36,45,59} | {36,45,60} | {36,45,61} | {36,45,62} | {36,45,63} | {36,45,64} |
| {36,45,65} | {36,45,66} | {36,46,47} | {36,46,48} | {36,46,49} | {36,46,50} | {36,46,51} | {36,46,52} | {36,46,53} |
| {36,46,54} | {36,46,55} | {36,46,56} | {36,46,57} | {36,46,58} | {36,46,59} | {36,46,60} | {36,46,61} | {36,46,62} |
| {36,46,63} | {36,46,64} | {36,46,65} | {36,46,66} | {36,47,48} | {36,47,49} | {36,47,50} | {36,47,51} | {36,47,52} |
| {36,47,53} | {36,47,54} | {36,47,55} | {36,47,56} | {36,47,57} | {36,47,58} | {36,47,59} | {36,47,60} | {36,47,61} |
| {36,47,62} | {36,47,63} | {36,47,64} | {36,47,65} | {36,47,66} | {36,48,49} | {36,48,50} | {36,48,51} | {36,48,52} |
| {36,48,53} | {36,48,54} | {36,48,55} | {36,48,56} | {36,48,57} | {36,48,58} | {36,48,59} | {36,48,60} | {36,48,61} |
| {36,48,62} | {36,48,63} | {36,48,64} | {36,48,65} | {36,48,66} | {36,49,50} | {36,49,51} | {36,49,52} | {36,49,53} |
| {36,49,54} | {36,49,55} | {36,49,56} | {36,49,57} | {36,49,58} | {36,49,59} | {36,49,60} | {36,49,61} | {36,49,62} |
| {36,49,63} | {36,49,64} | {36,49,65} | {36,49,66} | {36,50,51} | {36,50,52} | {36,50,53} | {36,50,54} | {36,50,55} |
| {36,50,56} | {36,50,57} | {36,50,58} | {36,50,59} | {36,50,60} | {36,50,61} | {36,50,62} | {36,50,63} | {36,50,64} |
| {36,50,65} | {36,50,66} | {36,51,52} | {36,51,53} | {36,51,54} | {36,51,55} | {36,51,56} | {36,51,57} | {36,51,58} |
| {36,51,59} | {36,51,60} | {36,51,61} | {36,51,62} | {36,51,63} | {36,51,64} | {36,51,65} | {36,51,66} | {36,52,53} |
| {36,52,54} | {36,52,55} | {36,52,56} | {36,52,57} | {36,52,58} | {36,52,59} | {36,52,60} | {36,52,61} | {36,52,62} |
| {36,52,63} | {36,52,64} | {36,52,65} | {36,52,66} | {36,53,54} | {36,53,55} | {36,53,56} | {36,53,57} | {36,53,58} |
| {36,53,59} | {36,53,60} | {36,53,61} | {36,53,62} | {36,53,63} | {36,53,64} | {36,53,65} | {36,53,66} | {36,54,55} |
| {36,54,56} | {36,54,57} | {36,54,58} | {36,54,59} | {36,54,60} | {36,54,61} | {36,54,62} | {36,54,63} | {36,54,64} |
| {36,54,65} | {36,54,66} | {36,55,56} | {36,55,57} | {36,55,58} | {36,55,59} | {36,55,60} | {36,55,61} | {36,55,62} |
| {36,55,63} | {36,55,64} | {36,55,65} | {36,55,66} | {36,56,57} | {36,56,58} | {36,56,59} | {36,56,60} | {36,56,61} |
| {36,56,62} | {36,56,63} | {36,56,64} | {36,56,65} | {36,56,66} | {36,57,58} | {36,57,59} | {36,57,60} | {36,57,61} |
| {36,57,62} | {36,57,63} | {36,57,64} | {36,57,65} | {36,57,66} | {36,58,59} | {36,58,60} | {36,58,61} | {36,58,62} |
| {36,58,63} | {36,58,64} | {36,58,65} | {36,58,66} | {36,59,60} | {36,59,61} | {36,59,62} | {36,59,63} | {36,59,64} |
| {36,59,65} | {36,59,66} | {36,60,61} | {36,60,62} | {36,60,63} | {36,60,64} | {36,60,65} | {36,60,66} | {36,61,62} |
| {36,61,63} | {36,61,64} | {36,61,65} | {36,61,66} | {36,62,63} | {36,62,64} | {36,62,65} | {36,62,66} | {36,63,64} |
| {36,63,65} | {36,63,66} | {36,64,65} | {36,64,66} | {36,65,66} | {37,38,39} | {37,38,40} | {37,38,41} | {37,38,42} |
| {37,38,43} | {37,38,44} | {37,38,45} | {37,38,46} | {37,38,47} | {37,38,48} | {37,38,49} | {37,38,50} | {37,38,51} |
| {37,38,52} | {37,38,53} | {37,38,54} | {37,38,55} | {37,38,56} | {37,38,57} | {37,38,58} | {37,38,59} | {37,38,60} |
| {37,38,61} | {37,38,62} | {37,38,63} | {37,38,64} | {37,38,65} | {37,38,66} | {37,39,40} | {37,39,41} | {37,39,42} |
| {37,39,43} | {37,39,44} | {37,39,45} | {37,39,46} | {37,39,47} | {37,39,48} | {37,39,49} | {37,39,50} | {37,39,51} |
| {37,39,52} | {37,39,53} | {37,39,54} | {37,39,55} | {37,39,56} | {37,39,57} | {37,39,58} | {37,39,59} | {37,39,60} |
| {37,39,61} | {37,39,62} | {37,39,63} | {37,39,64} | {37,39,65} | {37,39,66} | {37,40,41} | {37,40,42} | {37,40,43} |
| {37,40,44} | {37,40,45} | {37,40,46} | {37,40,47} | {37,40,48} | {37,40,49} | {37,40,50} | {37,40,51} | {37,40,52} |
| {37,40,53} | {37,40,54} | {37,40,55} | {37,40,56} | {37,40,57} | {37,40,58} | {37,40,59} | {37,40,60} | {37,40,61} |
| {37,40,62} | {37,40,63} | {37,40,64} | {37,40,65} | {37,40,66} | {37,41,42} | {37,41,43} | {37,41,44} | {37,41,45} |
| {37,41,46} | {37,41,47} | {37,41,48} | {37,41,49} | {37,41,50} | {37,41,51} | {37,41,52} | {37,41,53} | {37,41,54} |
| {37,41,55} | {37,41,56} | {37,41,57} | {37,41,58} | {37,41,59} | {37,41,60} | {37,41,61} | {37,41,62} | {37,41,63} |
| {37,41,64} | {37,41,65} | {37,41,66} | {37,42,43} | {37,42,44} | {37,42,45} | {37,42,46} | {37,42,47} | {37,42,48} |
| {37,42,49} | {37,42,50} | {37,42,51} | {37,42,52} | {37,42,53} | {37,42,54} | {37,42,55} | {37,42,56} | {37,42,57} |
| {37,42,58} | {37,42,59} | {37,42,60} | {37,42,61} | {37,42,62} | {37,42,63} | {37,42,64} | {37,42,65} | {37,42,66} |
| {37,43,44} | {37,43,45} | {37,43,46} | {37,43,47} | {37,43,48} | {37,43,49} | {37,43,50} | {37,43,51} | {37,43,52} |
| {37,43,53} | {37,43,54} | {37,43,55} | {37,43,56} | {37,43,57} | {37,43,58} | {37,43,59} | {37,43,60} | {37,43,61} |
| {37,43,62} | {37,43,63} | {37,43,64} | {37,43,65} | {37,43,66} | {37,44,45} | {37,44,46} | {37,44,47} | {37,44,48} |
| {37,44,49} | {37,44,50} | {37,44,51} | {37,44,52} | {37,44,53} | {37,44,54} | {37,44,55} | {37,44,56} | {37,44,57} |
| {37,44,58} | {37,44,59} | {37,44,60} | {37,44,61} | {37,44,62} | {37,44,63} | {37,44,64} | {37,44,65} | {37,44,66} |
| {37,45,46} | {37,45,47} | {37,45,48} | {37,45,49} | {37,45,50} | {37,45,51} | {37,45,52} | {37,45,53} | {37,45,54} |
| {37,45,55} | {37,45,56} | {37,45,57} | {37,45,58} | {37,45,59} | {37,45,60} | {37,45,61} | {37,45,62} | {37,45,63} |
| {37,45,64} | {37,45,65} | {37,45,66} | {37,46,47} | {37,46,48} | {37,46,49} | {37,46,50} | {37,46,51} | {37,46,52} |
| {37,46,53} | {37,46,54} | {37,46,55} | {37,46,56} | {37,46,57} | {37,46,58} | {37,46,59} | {37,46,60} | {37,46,61} |
| {37,46,62} | {37,46,63} | {37,46,64} | {37,46,65} | {37,46,66} | {37,47,48} | {37,47,49} | {37,47,50} | {37,47,51} |
| {37,47,52} | {37,47,53} | {37,47,54} | {37,47,55} | {37,47,56} | {37,47,57} | {37,47,58} | {37,47,59} | {37,47,60} |
| {37,47,61} | {37,47,62} | {37,47,63} | {37,47,64} | {37,47,65} | {37,47,66} | {37,48,49} | {37,48,50} | {37,48,51} |

TABLE 3A-continued

| | | | | | | | |
|---|---|---|---|---|---|---|---|
| {37,48,52} | {37,48,53} | {37,48,54} | {37,48,55} | {37,48,56} | {37,48,57} | {37,48,58} | {37,48,59} | {37,48,60} |
| {37,48,61} | {37,48,62} | {37,48,63} | {37,48,64} | {37,48,65} | {37,48,66} | {37,49,50} | {37,49,51} | {37,49,52} |
| {37,49,53} | {37,49,54} | {37,49,55} | {37,49,56} | {37,49,57} | {37,49,58} | {37,49,59} | {37,49,60} | {37,49,61} |
| {37,49,62} | {37,49,63} | {37,49,64} | {37,49,65} | {37,49,66} | {37,50,51} | {37,50,52} | {37,50,53} | {37,50,54} |
| {37,50,55} | {37,50,56} | {37,50,57} | {37,50,58} | {37,50,59} | {37,50,60} | {37,50,61} | {37,50,62} | {37,50,63} |
| {37,50,64} | {37,50,65} | {37,50,66} | {37,51,52} | {37,51,53} | {37,51,54} | {37,51,55} | {37,51,56} | {37,51,57} |
| {37,51,58} | {37,51,59} | {37,51,60} | {37,51,61} | {37,51,62} | {37,51,63} | {37,51,64} | {37,51,65} | {37,51,66} |
| {37,52,53} | {37,52,54} | {37,52,55} | {37,52,56} | {37,52,57} | {37,52,58} | {37,52,59} | {37,52,60} | {37,52,61} |
| {37,52,62} | {37,52,63} | {37,52,64} | {37,52,65} | {37,52,66} | {37,53,54} | {37,53,55} | {37,53,56} | {37,53,57} |
| {37,53,58} | {37,53,59} | {37,53,60} | {37,53,61} | {37,53,62} | {37,53,63} | {37,53,64} | {37,53,65} | {37,53,66} |
| {37,54,55} | {37,54,56} | {37,54,57} | {37,54,58} | {37,54,59} | {37,54,60} | {37,54,61} | {37,54,62} | {37,54,63} |
| {37,54,64} | {37,54,65} | {37,54,66} | {37,55,56} | {37,55,57} | {37,55,58} | {37,55,59} | {37,55,60} | {37,55,61} |
| {37,55,62} | {37,55,63} | {37,55,64} | {37,55,65} | {37,55,66} | {37,56,57} | {37,56,58} | {37,56,59} | {37,56,60} |
| {37,56,61} | {37,56,62} | {37,56,63} | {37,56,64} | {37,56,65} | {37,56,66} | {37,57,58} | {37,57,59} | {37,57,60} |
| {37,57,61} | {37,57,62} | {37,57,63} | {37,57,64} | {37,57,65} | {37,57,66} | {37,58,59} | {37,58,60} | {37,58,61} |
| {37,58,62} | {37,58,63} | {37,58,64} | {37,58,65} | {37,58,66} | {37,59,60} | {37,59,61} | {37,59,62} | {37,59,63} |
| {37,59,64} | {37,59,65} | {37,59,66} | {37,60,61} | {37,60,62} | {37,60,63} | {37,60,64} | {37,60,65} | {37,60,66} |
| {37,61,62} | {37,61,63} | {37,61,64} | {37,61,65} | {37,61,66} | {37,62,63} | {37,62,64} | {37,62,65} | {37,62,66} |
| {37,63,64} | {37,63,65} | {37,63,66} | {37,64,65} | {37,64,66} | {37,65,66} | {38,39,40} | {38,39,41} | {38,39,42} |
| {38,39,43} | {38,39,44} | {38,39,45} | {38,39,46} | {38,39,47} | {38,39,48} | {38,39,49} | {38,39,50} | {38,39,51} |
| {38,39,52} | {38,39,53} | {38,39,54} | {38,39,55} | {38,39,56} | {38,39,57} | {38,39,58} | {38,39,59} | {38,39,60} |
| {38,39,61} | {38,39,62} | {38,39,63} | {38,39,64} | {38,39,65} | {38,39,66} | {38,40,41} | {38,40,42} | {38,40,43} |
| {38,40,44} | {38,40,45} | {38,40,46} | {38,40,47} | {38,40,48} | {38,40,49} | {38,40,50} | {38,40,51} | {38,40,52} |
| {38,40,53} | {38,40,54} | {38,40,55} | {38,40,56} | {38,40,57} | {38,40,58} | {38,40,59} | {38,40,60} | {38,40,61} |
| {38,40,62} | {38,40,63} | {38,40,64} | {38,40,65} | {38,40,66} | {38,41,42} | {38,41,43} | {38,41,44} | {38,41,45} |
| {38,41,46} | {38,41,47} | {38,41,48} | {38,41,49} | {38,41,50} | {38,41,51} | {38,41,52} | {38,41,53} | {38,41,54} |
| {38,41,55} | {38,41,56} | {38,41,57} | {38,41,58} | {38,41,59} | {38,41,60} | {38,41,61} | {38,41,62} | {38,41,63} |
| {38,41,64} | {38,41,65} | {38,41,66} | {38,42,43} | {38,42,44} | {38,42,45} | {38,42,46} | {38,42,47} | {38,42,48} |
| {38,42,49} | {38,42,50} | {38,42,51} | {38,42,52} | {38,42,53} | {38,42,54} | {38,42,55} | {38,42,56} | {38,42,57} |
| {38,42,58} | {38,42,59} | {38,42,60} | {38,42,61} | {38,42,62} | {38,42,63} | {38,42,64} | {38,42,65} | {38,42,66} |
| {38,43,44} | {38,43,45} | {38,43,46} | {38,43,47} | {38,43,48} | {38,43,49} | {38,43,50} | {38,43,51} | {38,43,52} |
| {38,43,53} | {38,43,54} | {38,43,55} | {38,43,56} | {38,43,57} | {38,43,58} | {38,43,59} | {38,43,60} | {38,43,61} |
| {38,43,62} | {38,43,63} | {38,43,64} | {38,43,65} | {38,43,66} | {38,44,45} | {38,44,46} | {38,44,47} | {38,44,48} |
| {38,44,49} | {38,44,50} | {38,44,51} | {38,44,52} | {38,44,53} | {38,44,54} | {38,44,55} | {38,44,56} | {38,44,57} |
| {38,44,58} | {38,44,59} | {38,44,60} | {38,44,61} | {38,44,62} | {38,44,63} | {38,44,64} | {38,44,65} | {38,44,66} |
| {38,45,46} | {38,45,47} | {38,45,48} | {38,45,49} | {38,45,50} | {38,45,51} | {38,45,52} | {38,45,53} | {38,45,54} |
| {38,45,55} | {38,45,56} | {38,45,57} | {38,45,58} | {38,45,59} | {38,45,60} | {38,45,61} | {38,45,62} | {38,45,63} |
| {38,45,64} | {38,45,65} | {38,45,66} | {38,46,47} | {38,46,48} | {38,46,49} | {38,46,50} | {38,46,51} | {38,46,52} |
| {38,46,53} | {38,46,54} | {38,46,55} | {38,46,56} | {38,46,57} | {38,46,58} | {38,46,59} | {38,46,60} | {38,46,61} |
| {38,46,62} | {38,46,63} | {38,46,64} | {38,46,65} | {38,46,66} | {38,47,48} | {38,47,49} | {38,47,50} | {38,47,51} |
| {38,47,52} | {38,47,53} | {38,47,54} | {38,47,55} | {38,47,56} | {38,47,57} | {38,47,58} | {38,47,59} | {38,47,60} |
| {38,47,61} | {38,47,62} | {38,47,63} | {38,47,64} | {38,47,65} | {38,47,66} | {38,48,49} | {38,48,50} | {38,48,51} |
| {38,48,52} | {38,48,53} | {38,48,54} | {38,48,55} | {38,48,56} | {38,48,57} | {38,48,58} | {38,48,59} | {38,48,60} |
| {38,48,61} | {38,48,62} | {38,48,63} | {38,48,64} | {38,48,65} | {38,48,66} | {38,49,50} | {38,49,51} | {38,49,52} |
| {38,49,53} | {38,49,54} | {38,49,55} | {38,49,56} | {38,49,57} | {38,49,58} | {38,49,59} | {38,49,60} | {38,49,61} |
| {38,49,62} | {38,49,63} | {38,49,64} | {38,49,65} | {38,49,66} | {38,50,51} | {38,50,52} | {38,50,53} | {38,50,54} |
| {38,50,55} | {38,50,56} | {38,50,57} | {38,50,58} | {38,50,59} | {38,50,60} | {38,50,61} | {38,50,62} | {38,50,63} |
| {38,50,64} | {38,50,65} | {38,50,66} | {38,51,52} | {38,51,53} | {38,51,54} | {38,51,55} | {38,51,56} | {38,51,57} |
| {38,51,58} | {38,51,59} | {38,51,60} | {38,51,61} | {38,51,62} | {38,51,63} | {38,51,64} | {38,51,65} | {38,51,66} |
| {38,52,53} | {38,52,54} | {38,52,55} | {38,52,56} | {38,52,57} | {38,52,58} | {38,52,59} | {38,52,60} | {38,52,61} |
| {38,52,62} | {38,52,63} | {38,52,64} | {38,52,65} | {38,52,66} | {38,53,54} | {38,53,55} | {38,53,56} | {38,53,57} |
| {38,53,58} | {38,53,59} | {38,53,60} | {38,53,61} | {38,53,62} | {38,53,63} | {38,53,64} | {38,53,65} | {38,53,66} |
| {38,54,55} | {38,54,56} | {38,54,57} | {38,54,58} | {38,54,59} | {38,54,60} | {38,54,61} | {38,54,62} | {38,54,63} |
| {38,54,64} | {38,54,65} | {38,54,66} | {38,55,56} | {38,55,57} | {38,55,58} | {38,55,59} | {38,55,60} | {38,55,61} |
| {38,55,62} | {38,55,63} | {38,55,64} | {38,55,65} | {38,55,66} | {38,56,57} | {38,56,58} | {38,56,59} | {38,56,60} |
| {38,56,61} | {38,56,62} | {38,56,63} | {38,56,64} | {38,56,65} | {38,56,66} | {38,57,58} | {38,57,59} | {38,57,60} |
| {38,57,61} | {38,57,62} | {38,57,63} | {38,57,64} | {38,57,65} | {38,57,66} | {38,58,59} | {38,58,60} | {38,58,61} |
| {38,58,62} | {38,58,63} | {38,58,64} | {38,58,65} | {38,58,66} | {38,59,60} | {38,59,61} | {38,59,62} | {38,59,63} |
| {38,59,64} | {38,59,65} | {38,59,66} | {38,60,61} | {38,60,62} | {38,60,63} | {38,60,64} | {38,60,65} | {38,60,66} |
| {38,61,62} | {38,61,63} | {38,61,64} | {38,61,65} | {38,61,66} | {38,62,63} | {38,62,64} | {38,62,65} | {38,62,66} |
| {38,63,64} | {38,63,65} | {38,63,66} | {38,64,65} | {38,64,66} | {38,65,66} | {39,40,41} | {39,40,42} | {39,40,43} |
| {39,40,44} | {39,40,45} | {39,40,46} | {39,40,47} | {39,40,48} | {39,40,49} | {39,40,50} | {39,40,51} | {39,40,52} |
| {39,40,53} | {39,40,54} | {39,40,55} | {39,40,56} | {39,40,57} | {39,40,58} | {39,40,59} | {39,40,60} | {39,40,61} |
| {39,40,62} | {39,40,63} | {39,40,64} | {39,40,65} | {39,40,66} | {39,41,42} | {39,41,43} | {39,41,44} | {39,41,45} |
| {39,41,46} | {39,41,47} | {39,41,48} | {39,41,49} | {39,41,50} | {39,41,51} | {39,41,52} | {39,41,53} | {39,41,54} |
| {39,41,55} | {39,41,56} | {39,41,57} | {39,41,58} | {39,41,59} | {39,41,60} | {39,41,61} | {39,41,62} | {39,41,63} |
| {39,41,64} | {39,41,65} | {39,41,66} | {39,42,43} | {39,42,44} | {39,42,45} | {39,42,46} | {39,42,47} | {39,42,48} |
| {39,42,49} | {39,42,50} | {39,42,51} | {39,42,52} | {39,42,53} | {39,42,54} | {39,42,55} | {39,42,56} | {39,42,57} |
| {39,42,58} | {39,42,59} | {39,42,60} | {39,42,61} | {39,42,62} | {39,42,63} | {39,42,64} | {39,42,65} | {39,42,66} |
| {39,43,44} | {39,43,45} | {39,43,46} | {39,43,47} | {39,43,48} | {39,43,49} | {39,43,50} | {39,43,51} | {39,43,52} |
| {39,43,53} | {39,43,54} | {39,43,55} | {39,43,56} | {39,43,57} | {39,43,58} | {39,43,59} | {39,43,60} | {39,43,61} |
| {39,43,62} | {39,43,63} | {39,43,64} | {39,43,65} | {39,43,66} | {39,44,45} | {39,44,46} | {39,44,47} | {39,44,48} |
| {39,44,49} | {39,44,50} | {39,44,51} | {39,44,52} | {39,44,53} | {39,44,54} | {39,44,55} | {39,44,56} | {39,44,57} |
| {39,44,58} | {39,44,59} | {39,44,60} | {39,44,61} | {39,44,62} | {39,44,63} | {39,44,64} | {39,44,65} | {39,44,66} |
| {39,45,46} | {39,45,47} | {39,45,48} | {39,45,49} | {39,45,50} | {39,45,51} | {39,45,52} | {39,45,53} | {39,45,54} |
| {39,45,55} | {39,45,56} | {39,45,57} | {39,45,58} | {39,45,59} | {39,45,60} | {39,45,61} | {39,45,62} | {39,45,63} |
| {39,45,64} | {39,45,65} | {39,45,66} | {39,46,47} | {39,46,48} | {39,46,49} | {39,46,50} | {39,46,51} | {39,46,52} |
| {39,46,53} | {39,46,54} | {39,46,55} | {39,46,56} | {39,46,57} | {39,46,58} | {39,46,59} | {39,46,60} | {39,46,61} |
| {39,46,62} | {39,46,63} | {39,46,64} | {39,46,65} | {39,46,66} | {39,47,48} | {39,47,49} | {39,47,50} | {39,47,51} |
| {39,47,52} | {39,47,53} | {39,47,54} | {39,47,55} | {39,47,56} | {39,47,57} | {39,47,58} | {39,47,59} | {39,47,60} |

TABLE 3A-continued

{39,47,61} {39,47,62} {39,47,63} {39,47,64} {39,47,65} {39,47,66} {39,48,49} {39,48,50} {39,48,51}
{39,48,52} {39,48,53} {39,48,54} {39,48,55} {39,48,56} {39,48,57} {39,48,58} {39,48,59} {39,48,60}
{39,48,61} {39,48,62} {39,48,63} {39,48,64} {39,48,65} {39,48,66} {39,49,50} {39,49,51} {39,49,52}
{39,49,53} {39,49,54} {39,49,55} {39,49,56} {39,49,57} {39,49,58} {39,49,59} {39,49,60} {39,49,61}
{39,49,62} {39,49,63} {39,49,64} {39,49,65} {39,49,66} {39,50,51} {39,50,52} {39,50,53} {39,50,54}
{39,50,55} {39,50,56} {39,50,57} {39,50,58} {39,50,59} {39,50,60} {39,50,61} {39,50,62} {39,50,63}
{39,50,64} {39,50,65} {39,50,66} {39,51,52} {39,51,53} {39,51,54} {39,51,55} {39,51,56} {39,51,57}
{39,51,58} {39,51,59} {39,51,60} {39,51,61} {39,51,62} {39,51,63} {39,51,64} {39,51,65} {39,51,66}
{39,52,53} {39,52,54} {39,52,55} {39,52,56} {39,52,57} {39,52,58} {39,52,59} {39,52,60} {39,52,61}
{39,52,62} {39,52,63} {39,52,64} {39,52,65} {39,52,66} {39,53,54} {39,53,55} {39,53,56} {39,53,57}
{39,53,58} {39,53,59} {39,53,60} {39,53,61} {39,53,62} {39,53,63} {39,53,64} {39,53,65} {39,53,66}
{39,54,55} {39,54,56} {39,54,57} {39,54,58} {39,54,59} {39,54,60} {39,54,61} {39,54,62} {39,54,63}
{39,54,64} {39,54,65} {39,54,66} {39,55,56} {39,55,57} {39,55,58} {39,55,59} {39,55,60} {39,55,61}
{39,55,62} {39,55,63} {39,55,64} {39,55,65} {39,55,66} {39,56,57} {39,56,58} {39,56,59} {39,56,60}
{39,56,61} {39,56,62} {39,56,63} {39,56,64} {39,56,65} {39,56,66} {39,57,58} {39,57,59} {39,57,60}
{39,57,61} {39,57,62} {39,57,63} {39,57,64} {39,57,65} {39,57,66} {39,58,59} {39,58,60} {39,58,61}
{39,58,62} {39,58,63} {39,58,64} {39,58,65} {39,58,66} {39,59,60} {39,59,61} {39,59,62} {39,59,63}
{39,59,64} {39,59,65} {39,59,66} {39,60,61} {39,60,62} {39,60,63} {39,60,64} {39,60,65} {39,60,66}
{39,61,62} {39,61,63} {39,61,64} {39,61,65} {39,61,66} {39,62,63} {39,62,64} {39,62,65} {39,62,66}
{39,63,64} {39,63,65} {39,63,66} {39,64,65} {39,64,66} {39,65,66} {40,41,42} {40,41,43} {40,41,44}
{40,41,45} {40,41,46} {40,41,47} {40,41,48} {40,41,49} {40,41,50} {40,41,51} {40,41,52} {40,41,53}
{40,41,54} {40,41,55} {40,41,56} {40,41,57} {40,41,58} {40,41,59} {40,41,60} {40,41,61} {40,41,62}
{40,41,63} {40,41,64} {40,41,65} {40,41,66} {40,42,43} {40,42,44} {40,42,45} {40,42,46} {40,42,47}
{40,42,48} {40,42,49} {40,42,50} {40,42,51} {40,42,52} {40,42,53} {40,42,54} {40,42,55} {40,42,56}
{40,42,57} {40,42,58} {40,42,59} {40,42,60} {40,42,61} {40,42,62} {40,42,63} {40,42,64} {40,42,65}
{40,42,66} {40,43,44} {40,43,45} {40,43,46} {40,43,47} {40,43,48} {40,43,49} {40,43,50} {40,43,51}
{40,43,52} {40,43,53} {40,43,54} {40,43,55} {40,43,56} {40,43,57} {40,43,58} {40,43,59} {40,43,60}
{40,43,61} {40,43,62} {40,43,63} {40,43,64} {40,43,65} {40,43,66} {40,44,45} {40,44,46} {40,44,47}
{40,44,48} {40,44,49} {40,44,50} {40,44,51} {40,44,52} {40,44,53} {40,44,54} {40,44,55} {40,44,56}
{40,44,57} {40,44,58} {40,44,59} {40,44,60} {40,44,61} {40,44,62} {40,44,63} {40,44,64} {40,44,65}
{40,44,66} {40,45,46} {40,45,47} {40,45,48} {40,45,49} {40,45,50} {40,45,51} {40,45,52} {40,45,53}
{40,45,54} {40,45,55} {40,45,56} {40,45,57} {40,45,58} {40,45,59} {40,45,60} {40,45,61} {40,45,62}
{40,45,63} {40,45,64} {40,45,65} {40,45,66} {40,46,47} {40,46,48} {40,46,49} {40,46,50} {40,46,51}
{40,46,52} {40,46,53} {40,46,54} {40,46,55} {40,46,56} {40,46,57} {40,46,58} {40,46,59} {40,46,60}
{40,46,61} {40,46,62} {40,46,63} {40,46,64} {40,46,65} {40,46,66} {40,47,48} {40,47,49} {40,47,50}
{40,47,51} {40,47,52} {40,47,53} {40,47,54} {40,47,55} {40,47,56} {40,47,57} {40,47,58} {40,47,59}
{40,47,60} {40,47,61} {40,47,62} {40,47,63} {40,47,64} {40,47,65} {40,47,66} {40,48,49} {40,48,50}
{40,48,51} {40,48,52} {40,48,53} {40,48,54} {40,48,55} {40,48,56} {40,48,57} {40,48,58} {40,48,59}
{40,48,60} {40,48,61} {40,48,62} {40,48,63} {40,48,64} {40,48,65} {40,48,66} {40,49,50} {40,49,51}
{40,49,52} {40,49,53} {40,49,54} {40,49,55} {40,49,56} {40,49,57} {40,49,58} {40,49,59} {40,49,60}
{40,49,61} {40,49,62} {40,49,63} {40,49,64} {40,49,65} {40,49,66} {40,50,51} {40,50,52} {40,50,53}
{40,50,54} {40,50,55} {40,50,56} {40,50,57} {40,50,58} {40,50,59} {40,50,60} {40,50,61} {40,50,62}
{40,50,63} {40,50,64} {40,50,65} {40,50,66} {40,51,52} {40,51,53} {40,51,54} {40,51,55} {40,51,56}
{40,51,57} {40,51,58} {40,51,59} {40,51,60} {40,51,61} {40,51,62} {40,51,63} {40,51,64} {40,51,65}
{40,51,66} {40,52,53} {40,52,54} {40,52,55} {40,52,56} {40,52,57} {40,52,58} {40,52,59} {40,52,60}
{40,52,61} {40,52,62} {40,52,63} {40,52,64} {40,52,65} {40,52,66} {40,53,54} {40,53,55} {40,53,56}
{40,53,57} {40,53,58} {40,53,59} {40,53,60} {40,53,61} {40,53,62} {40,53,63} {40,53,64} {40,53,65}
{40,53,66} {40,54,55} {40,54,56} {40,54,57} {40,54,58} {40,54,59} {40,54,60} {40,54,61} {40,54,62}
{40,54,63} {40,54,64} {40,54,65} {40,54,66} {40,55,56} {40,55,57} {40,55,58} {40,55,59} {40,55,60}
{40,55,61} {40,55,62} {40,55,63} {40,55,64} {40,55,65} {40,55,66} {40,56,57} {40,56,58} {40,56,59}
{40,56,60} {40,56,61} {40,56,62} {40,56,63} {40,56,64} {40,56,65} {40,56,66} {40,57,58} {40,57,59}
{40,57,60} {40,57,61} {40,57,62} {40,57,63} {40,57,64} {40,57,65} {40,57,66} {40,58,59} {40,58,60}
{40,58,61} {40,58,62} {40,58,63} {40,58,64} {40,58,65} {40,58,66} {40,59,60} {40,59,61} {40,59,62}
{40,59,63} {40,59,64} {40,59,65} {40,59,66} {40,60,61} {40,60,62} {40,60,63} {40,60,64} {40,60,65}
{40,60,66} {40,61,62} {40,61,63} {40,61,64} {40,61,65} {40,61,66} {40,62,63} {40,62,64} {40,62,65}
{40,62,66} {40,63,64} {40,63,65} {40,63,66} {40,64,65} {40,64,66} {40,65,66} {41,42,43} {41,42,44}
{41,42,45} {41,42,46} {41,42,47} {41,42,48} {41,42,49} {41,42,50} {41,42,51} {41,42,52} {41,42,53}
{41,42,54} {41,42,55} {41,42,56} {41,42,57} {41,42,58} {41,42,59} {41,42,60} {41,42,61} {41,42,62}
{41,42,63} {41,42,64} {41,42,65} {41,42,66} {41,43,44} {41,43,45} {41,43,46} {41,43,47} {41,43,48}
{41,43,49} {41,43,50} {41,43,51} {41,43,52} {41,43,53} {41,43,54} {41,43,55} {41,43,56} {41,43,57}
{41,43,58} {41,43,59} {41,43,60} {41,43,61} {41,43,62} {41,43,63} {41,43,64} {41,43,65} {41,43,66}
{41,44,45} {41,44,46} {41,44,47} {41,44,48} {41,44,49} {41,44,50} {41,44,51} {41,44,52} {41,44,53}
{41,44,54} {41,44,55} {41,44,56} {41,44,57} {41,44,58} {41,44,59} {41,44,60} {41,44,61} {41,44,62}
{41,44,63} {41,44,64} {41,44,65} {41,44,66} {41,45,46} {41,45,47} {41,45,48} {41,45,49} {41,45,50}
{41,45,51} {41,45,52} {41,45,53} {41,45,54} {41,45,55} {41,45,56} {41,45,57} {41,45,58} {41,45,59}
{41,45,60} {41,45,61} {41,45,62} {41,45,63} {41,45,64} {41,45,65} {41,45,66} {41,46,47} {41,46,48}
{41,46,49} {41,46,50} {41,46,51} {41,46,52} {41,46,53} {41,46,54} {41,46,55} {41,46,56} {41,46,57}
{41,46,58} {41,46,59} {41,46,60} {41,46,61} {41,46,62} {41,46,63} {41,46,64} {41,46,65} {41,46,66}
{41,47,48} {41,47,49} {41,47,50} {41,47,51} {41,47,52} {41,47,53} {41,47,54} {41,47,55} {41,47,56}
{41,47,57} {41,47,58} {41,47,59} {41,47,60} {41,47,61} {41,47,62} {41,47,63} {41,47,64} {41,47,65}
{41,47,66} {41,48,49} {41,48,50} {41,48,51} {41,48,52} {41,48,53} {41,48,54} {41,48,55} {41,48,56}
{41,48,57} {41,48,58} {41,48,59} {41,48,60} {41,48,61} {41,48,62} {41,48,63} {41,48,64} {41,48,65}
{41,48,66} {41,49,50} {41,49,51} {41,49,52} {41,49,53} {41,49,54} {41,49,55} {41,49,56} {41,49,57}
{41,49,58} {41,49,59} {41,49,60} {41,49,61} {41,49,62} {41,49,63} {41,49,64} {41,49,65} {41,49,66}
{41,50,51} {41,50,52} {41,50,53} {41,50,54} {41,50,55} {41,50,56} {41,50,57} {41,50,58} {41,50,59}
{41,50,60} {41,50,61} {41,50,62} {41,50,63} {41,50,64} {41,50,65} {41,50,66} {41,51,52} {41,51,53}
{41,51,54} {41,51,55} {41,51,56} {41,51,57} {41,51,58} {41,51,59} {41,51,60} {41,51,61} {41,51,62}
{41,51,63} {41,51,64} {41,51,65} {41,51,66} {41,52,53} {41,52,54} {41,52,55} {41,52,56} {41,52,57}
{41,52,58} {41,52,59} {41,52,60} {41,52,61} {41,52,62} {41,52,63} {41,52,64} {41,52,65} {41,52,66}
{41,53,54} {41,53,55} {41,53,56} {41,53,57} {41,53,58} {41,53,59} {41,53,60} {41,53,61} {41,53,62}

TABLE 3A-continued

{41,53,63} {41,53,64} {41,53,65} {41,53,66} {41,54,55} {41,54,56} {41,54,57} {41,54,58} {41,54,59}
{41,54,60} {41,54,61} {41,54,62} {41,54,63} {41,54,64} {41,54,65} {41,54,66} {41,55,56} {41,55,57}
{41,55,58} {41,55,59} {41,55,60} {41,55,61} {41,55,62} {41,55,63} {41,55,64} {41,55,65} {41,55,66}
{41,56,57} {41,56,58} {41,56,59} {41,56,60} {41,56,61} {41,56,62} {41,56,63} {41,56,64} {41,56,65}
{41,56,66} {41,57,58} {41,57,59} {41,57,60} {41,57,61} {41,57,62} {41,57,63} {41,57,64} {41,57,65}
{41,57,66} {41,58,59} {41,58,60} {41,58,61} {41,58,62} {41,58,63} {41,58,64} {41,58,65} {41,58,66}
{41,59,60} {41,59,61} {41,59,62} {41,59,63} {41,59,64} {41,59,65} {41,59,66} {41,60,61} {41,60,62}
{41,60,63} {41,60,64} {41,60,65} {41,60,66} {41,61,62} {41,61,63} {41,61,64} {41,61,65} {41,61,66}
{41,62,63} {41,62,64} {41,62,65} {41,62,66} {41,63,64} {41,63,65} {41,63,66} {41,64,65} {41,64,66}
{41,65,66} {42,43,44} {42,43,45} {42,43,46} {42,43,47} {42,43,48} {42,43,49} {42,43,50} {42,43,51}
{42,43,52} {42,43,53} {42,43,54} {42,43,55} {42,43,56} {42,43,57} {42,43,58} {42,43,59} {42,43,60}
{42,43,61} {42,43,62} {42,43,63} {42,43,64} {42,43,65} {42,43,66} {42,44,45} {42,44,46} {42,44,47}
{42,44,48} {42,44,49} {42,44,50} {42,44,51} {42,44,52} {42,44,53} {42,44,54} {42,44,55} {42,44,56}
{42,44,57} {42,44,58} {42,44,59} {42,44,60} {42,44,61} {42,44,62} {42,44,63} {42,44,64} {42,44,65}
{42,44,66} {42,45,46} {42,45,47} {42,45,48} {42,45,49} {42,45,50} {42,45,51} {42,45,52} {42,45,53}
{42,45,54} {42,45,55} {42,45,56} {42,45,57} {42,45,58} {42,45,59} {42,45,60} {42,45,61} {42,45,62}
{42,45,63} {42,45,64} {42,45,65} {42,45,66} {42,46,47} {42,46,48} {42,46,49} {42,46,50} {42,46,51}
{42,46,52} {42,46,53} {42,46,54} {42,46,55} {42,46,56} {42,46,57} {42,46,58} {42,46,59} {42,46,60}
{42,46,61} {42,46,62} {42,46,63} {42,46,64} {42,46,65} {42,46,66} {42,47,48} {42,47,49} {42,47,50}
{42,47,51} {42,47,52} {42,47,53} {42,47,54} {42,47,55} {42,47,56} {42,47,57} {42,47,58} {42,47,59}
{42,47,60} {42,47,61} {42,47,62} {42,47,63} {42,47,64} {42,47,65} {42,47,66} {42,48,49} {42,48,50}
{42,48,51} {42,48,52} {42,48,53} {42,48,54} {42,48,55} {42,48,56} {42,48,57} {42,48,58} {42,48,59}
{42,48,60} {42,48,61} {42,48,62} {42,48,63} {42,48,64} {42,48,65} {42,48,66} {42,49,50} {42,49,51}
{42,49,52} {42,49,53} {42,49,54} {42,49,55} {42,49,56} {42,49,57} {42,49,58} {42,49,59} {42,49,60}
{42,49,61} {42,49,62} {42,49,63} {42,49,64} {42,49,65} {42,49,66} {42,50,51} {42,50,52} {42,50,53}
{42,50,54} {42,50,55} {42,50,56} {42,50,57} {42,50,58} {42,50,59} {42,50,60} {42,50,61} {42,50,62}
{42,50,63} {42,50,64} {42,50,65} {42,50,66} {42,51,52} {42,51,53} {42,51,54} {42,51,55} {42,51,56}
{42,51,57} {42,51,58} {42,51,59} {42,51,60} {42,51,61} {42,51,62} {42,51,63} {42,51,64} {42,51,65}
{42,51,66} {42,52,53} {42,52,54} {42,52,55} {42,52,56} {42,52,57} {42,52,58} {42,52,59} {42,52,60}
{42,52,61} {42,52,62} {42,52,63} {42,52,64} {42,52,65} {42,52,66} {42,53,54} {42,53,55} {42,53,56}
{42,53,57} {42,53,58} {42,53,59} {42,53,60} {42,53,61} {42,53,62} {42,53,63} {42,53,64} {42,53,65}
{42,53,66} {42,54,55} {42,54,56} {42,54,57} {42,54,58} {42,54,59} {42,54,60} {42,54,61} {42,54,62}
{42,54,63} {42,54,64} {42,54,65} {42,54,66} {42,55,56} {42,55,57} {42,55,58} {42,55,59} {42,55,60}
{42,55,61} {42,55,62} {42,55,63} {42,55,64} {42,55,65} {42,55,66} {42,56,57} {42,56,58} {42,56,59}
{42,56,60} {42,56,61} {42,56,62} {42,56,63} {42,56,64} {42,56,65} {42,56,66} {42,57,58} {42,57,59}
{42,57,60} {42,57,61} {42,57,62} {42,57,63} {42,57,64} {42,57,65} {42,57,66} {42,58,59} {42,58,60}
{42,58,61} {42,58,62} {42,58,63} {42,58,64} {42,58,65} {42,58,66} {42,59,60} {42,59,61} {42,59,62}
{42,59,63} {42,59,64} {42,59,65} {42,59,66} {42,60,61} {42,60,62} {42,60,63} {42,60,64} {42,60,65}
{42,60,66} {42,61,62} {42,61,63} {42,61,64} {42,61,65} {42,61,66} {42,62,63} {42,62,64} {42,62,65}
{42,62,66} {42,63,64} {42,63,65} {42,63,66} {42,64,65} {42,64,66} {42,65,66} {43,44,45} {43,44,46}
{43,44,47} {43,44,48} {43,44,49} {43,44,50} {43,44,51} {43,44,52} {43,44,53} {43,44,54} {43,44,55}
{43,44,56} {43,44,57} {43,44,58} {43,44,59} {43,44,60} {43,44,61} {43,44,62} {43,44,63} {43,44,64}
{43,44,65} {43,44,66} {43,45,46} {43,45,47} {43,45,48} {43,45,49} {43,45,50} {43,45,51} {43,45,52}
{43,45,53} {43,45,54} {43,45,55} {43,45,56} {43,45,57} {43,45,58} {43,45,59} {43,45,60} {43,45,61}
{43,45,62} {43,45,63} {43,45,64} {43,45,65} {43,45,66} {43,46,47} {43,46,48} {43,46,49} {43,46,50}
{43,46,51} {43,46,52} {43,46,53} {43,46,54} {43,46,55} {43,46,56} {43,46,57} {43,46,58} {43,46,59}
{43,46,60} {43,46,61} {43,46,62} {43,46,63} {43,46,64} {43,46,65} {43,46,66} {43,47,48} {43,47,49}
{43,47,50} {43,47,51} {43,47,52} {43,47,53} {43,47,54} {43,47,55} {43,47,56} {43,47,57} {43,47,58}
{43,47,59} {43,47,60} {43,47,61} {43,47,62} {43,47,63} {43,47,64} {43,47,65} {43,47,66} {43,48,49}
{43,48,50} {43,48,51} {43,48,52} {43,48,53} {43,48,54} {43,48,55} {43,48,56} {43,48,57} {43,48,58}
{43,48,59} {43,48,60} {43,48,61} {43,48,62} {43,48,63} {43,48,64} {43,48,65} {43,48,66} {43,49,50}
{43,49,51} {43,49,52} {43,49,53} {43,49,54} {43,49,55} {43,49,56} {43,49,57} {43,49,58} {43,49,59}
{43,49,60} {43,49,61} {43,49,62} {43,49,63} {43,49,64} {43,49,65} {43,49,66} {43,50,51} {43,50,52}
{43,50,53} {43,50,54} {43,50,55} {43,50,56} {43,50,57} {43,50,58} {43,50,59} {43,50,60} {43,50,61}
{43,50,62} {43,50,63} {43,50,64} {43,50,65} {43,50,66} {43,51,52} {43,51,53} {43,51,54} {43,51,55}
{43,51,56} {43,51,57} {43,51,58} {43,51,59} {43,51,60} {43,51,61} {43,51,62} {43,51,63} {43,51,64}
{43,51,65} {43,51,66} {43,52,53} {43,52,54} {43,52,55} {43,52,56} {43,52,57} {43,52,58} {43,52,59}
{43,52,60} {43,52,61} {43,52,62} {43,52,63} {43,52,64} {43,52,65} {43,52,66} {43,53,54} {43,53,55}
{43,53,56} {43,53,57} {43,53,58} {43,53,59} {43,53,60} {43,53,61} {43,53,62} {43,53,63} {43,53,64}
{43,53,65} {43,53,66} {43,54,55} {43,54,56} {43,54,57} {43,54,58} {43,54,59} {43,54,60} {43,54,61}
{43,54,62} {43,54,63} {43,54,64} {43,54,65} {43,54,66} {43,55,56} {43,55,57} {43,55,58} {43,55,59}
{43,55,60} {43,55,61} {43,55,62} {43,55,63} {43,55,64} {43,55,65} {43,55,66} {43,56,57} {43,56,58}
{43,56,59} {43,56,60} {43,56,61} {43,56,62} {43,56,63} {43,56,64} {43,56,65} {43,56,66} {43,57,58}
{43,57,59} {43,57,60} {43,57,61} {43,57,62} {43,57,63} {43,57,64} {43,57,65} {43,57,66} {43,58,59}
{43,58,60} {43,58,61} {43,58,62} {43,58,63} {43,58,64} {43,58,65} {43,58,66} {43,59,60} {43,59,61}
{43,59,62} {43,59,63} {43,59,64} {43,59,65} {43,59,66} {43,60,61} {43,60,62} {43,60,63} {43,60,64}
{43,60,65} {43,60,66} {43,61,62} {43,61,63} {43,61,64} {43,61,65} {43,61,66} {43,62,63} {43,62,64}
{43,62,65} {43,62,66} {43,63,64} {43,63,65} {43,63,66} {43,64,65} {43,64,66} {43,65,66} {44,45,46}
{44,45,47} {44,45,48} {44,45,49} {44,45,50} {44,45,51} {44,45,52} {44,45,53} {44,45,54} {44,45,55}
{44,45,56} {44,45,57} {44,45,58} {44,45,59} {44,45,60} {44,45,61} {44,45,62} {44,45,63} {44,45,64}
{44,45,65} {44,45,66} {44,46,47} {44,46,48} {44,46,49} {44,46,50} {44,46,51} {44,46,52} {44,46,53}
{44,46,54} {44,46,55} {44,46,56} {44,46,57} {44,46,58} {44,46,59} {44,46,60} {44,46,61} {44,46,62}
{44,46,63} {44,46,64} {44,46,65} {44,46,66} {44,47,48} {44,47,49} {44,47,50} {44,47,51} {44,47,52}
{44,47,53} {44,47,54} {44,47,55} {44,47,56} {44,47,57} {44,47,58} {44,47,59} {44,47,60} {44,47,61}
{44,47,62} {44,47,63} {44,47,64} {44,47,65} {44,47,66} {44,48,49} {44,48,50} {44,48,51} {44,48,52}
{44,48,53} {44,48,54} {44,48,55} {44,48,56} {44,48,57} {44,48,58} {44,48,59} {44,48,60} {44,48,61}
{44,48,62} {44,48,63} {44,48,64} {44,48,65} {44,48,66} {44,49,50} {44,49,51} {44,49,52} {44,49,53}
{44,49,54} {44,49,55} {44,49,56} {44,49,57} {44,49,58} {44,49,59} {44,49,60} {44,49,61} {44,49,62}
{44,49,63} {44,49,64} {44,49,65} {44,49,66} {44,50,51} {44,50,52} {44,50,53} {44,50,54} {44,50,55}
{44,50,56} {44,50,57} {44,50,58} {44,50,59} {44,50,60} {44,50,61} {44,50,62} {44,50,63} {44,50,64}

TABLE 3A-continued

{44,50,65} {44,50,66} {44,51,52} {44,51,53} {44,51,54} {44,51,55} {44,51,56} {44,51,57} {44,51,58}
{44,51,59} {44,51,60} {44,51,61} {44,51,62} {44,51,63} {44,51,64} {44,51,65} {44,51,66} {44,52,53}
{44,52,54} {44,52,55} {44,52,56} {44,52,57} {44,52,58} {44,52,59} {44,52,60} {44,52,61} {44,52,62}
{44,52,63} {44,52,64} {44,52,65} {44,52,66} {44,53,54} {44,53,55} {44,53,56} {44,53,57} {44,53,58}
{44,53,59} {44,53,60} {44,53,61} {44,53,62} {44,53,63} {44,53,64} {44,53,65} {44,53,66} {44,54,55}
{44,54,56} {44,54,57} {44,54,58} {44,54,59} {44,54,60} {44,54,61} {44,54,62} {44,54,63} {44,54,64}
{44,54,65} {44,54,66} {44,55,56} {44,55,57} {44,55,58} {44,55,59} {44,55,60} {44,55,61} {44,55,62}
{44,55,63} {44,55,64} {44,55,65} {44,55,66} {44,56,57} {44,56,58} {44,56,59} {44,56,60} {44,56,61}
{44,56,62} {44,56,63} {44,56,64} {44,56,65} {44,56,66} {44,57,58} {44,57,59} {44,57,60} {44,57,61}
{44,57,62} {44,57,63} {44,57,64} {44,57,65} {44,57,66} {44,58,59} {44,58,60} {44,58,61} {44,58,62}
{44,58,63} {44,58,64} {44,58,65} {44,58,66} {44,59,60} {44,59,61} {44,59,62} {44,59,63} {44,59,64}
{44,59,65} {44,59,66} {44,60,61} {44,60,62} {44,60,63} {44,60,64} {44,60,65} {44,60,66} {44,61,62}
{44,61,63} {44,61,64} {44,61,65} {44,61,66} {44,62,63} {44,62,64} {44,62,65} {44,62,66} {44,63,64}
{44,63,65} {44,63,66} {44,64,65} {44,64,66} {44,65,66} {45,46,47} {45,46,48} {45,46,49} {45,46,50}
{45,46,51} {45,46,52} {45,46,53} {45,46,54} {45,46,55} {45,46,56} {45,46,57} {45,46,58} {45,46,59}
{45,46,60} {45,46,61} {45,46,62} {45,46,63} {45,46,64} {45,46,65} {45,46,66} {45,47,48} {45,47,49}
{45,47,50} {45,47,51} {45,47,52} {45,47,53} {45,47,54} {45,47,55} {45,47,56} {45,47,57} {45,47,58}
{45,47,59} {45,47,60} {45,47,61} {45,47,62} {45,47,63} {45,47,64} {45,47,65} {45,47,66} {45,48,49}
{45,48,50} {45,48,51} {45,48,52} {45,48,53} {45,48,54} {45,48,55} {45,48,56} {45,48,57} {45,48,58}
{45,48,59} {45,48,60} {45,48,61} {45,48,62} {45,48,63} {45,48,64} {45,48,65} {45,48,66} {45,49,50}
{45,49,51} {45,49,52} {45,49,53} {45,49,54} {45,49,55} {45,49,56} {45,49,57} {45,49,58} {45,49,59}
{45,49,60} {45,49,61} {45,49,62} {45,49,63} {45,49,64} {45,49,65} {45,49,66} {45,50,51} {45,50,52}
{45,50,53} {45,50,54} {45,50,55} {45,50,56} {45,50,57} {45,50,58} {45,50,59} {45,50,60} {45,50,61}
{45,50,62} {45,50,63} {45,50,64} {45,50,65} {45,50,66} {45,51,52} {45,51,53} {45,51,54} {45,51,55}
{45,51,56} {45,51,57} {45,51,58} {45,51,59} {45,51,60} {45,51,61} {45,51,62} {45,51,63} {45,51,64}
{45,51,65} {45,51,66} {45,52,53} {45,52,54} {45,52,55} {45,52,56} {45,52,57} {45,52,58} {45,52,59}
{45,52,60} {45,52,61} {45,52,62} {45,52,63} {45,52,64} {45,52,65} {45,52,66} {45,53,54} {45,53,55}
{45,53,56} {45,53,57} {45,53,58} {45,53,59} {45,53,60} {45,53,61} {45,53,62} {45,53,63} {45,53,64}
{45,53,65} {45,53,66} {45,54,55} {45,54,56} {45,54,57} {45,54,58} {45,54,59} {45,54,60} {45,54,61}
{45,54,62} {45,54,63} {45,54,64} {45,54,65} {45,54,66} {45,55,56} {45,55,57} {45,55,58} {45,55,59}
{45,55,60} {45,55,61} {45,55,62} {45,55,63} {45,55,64} {45,55,65} {45,55,66} {45,56,57} {45,56,58}
{45,56,59} {45,56,60} {45,56,61} {45,56,62} {45,56,63} {45,56,64} {45,56,65} {45,56,66} {45,57,58}
{45,57,59} {45,57,60} {45,57,61} {45,57,62} {45,57,63} {45,57,64} {45,57,65} {45,57,66} {45,58,59}
{45,58,60} {45,58,61} {45,58,62} {45,58,63} {45,58,64} {45,58,65} {45,58,66} {45,59,60} {45,59,61}
{45,59,62} {45,59,63} {45,59,64} {45,59,65} {45,59,66} {45,60,61} {45,60,62} {45,60,63} {45,60,64}
{45,60,65} {45,60,66} {45,61,62} {45,61,63} {45,61,64} {45,61,65} {45,61,66} {45,62,63} {45,62,64}
{45,62,65} {45,62,66} {45,63,64} {45,63,65} {45,63,66} {45,64,65} {45,64,66} {45,65,66} {46,47,48}
{46,47,49} {46,47,50} {46,47,51} {46,47,52} {46,47,53} {46,47,54} {46,47,55} {46,47,56} {46,47,57}
{46,47,58} {46,47,59} {46,47,60} {46,47,61} {46,47,62} {46,47,63} {46,47,64} {46,47,65} {46,47,66}
{46,48,49} {46,48,50} {46,48,51} {46,48,52} {46,48,53} {46,48,54} {46,48,55} {46,48,56} {46,48,57}
{46,48,58} {46,48,59} {46,48,60} {46,48,61} {46,48,62} {46,48,63} {46,48,64} {46,48,65} {46,48,66}
{46,49,50} {46,49,51} {46,49,52} {46,49,53} {46,49,54} {46,49,55} {46,49,56} {46,49,57} {46,49,58}
{46,49,59} {46,49,60} {46,49,61} {46,49,62} {46,49,63} {46,49,64} {46,49,65} {46,49,66} {46,50,51}
{46,50,52} {46,50,53} {46,50,54} {46,50,55} {46,50,56} {46,50,57} {46,50,58} {46,50,59} {46,50,60}
{46,50,61} {46,50,62} {46,50,63} {46,50,64} {46,50,65} {46,50,66} {46,51,52} {46,51,53} {46,51,54}
{46,51,55} {46,51,56} {46,51,57} {46,51,58} {46,51,59} {46,51,60} {46,51,61} {46,51,62} {46,51,63}
{46,51,64} {46,51,65} {46,51,66} {46,52,53} {46,52,54} {46,52,55} {46,52,56} {46,52,57} {46,52,58}
{46,52,59} {46,52,60} {46,52,61} {46,52,62} {46,52,63} {46,52,64} {46,52,65} {46,52,66} {46,53,54}
{46,53,55} {46,53,56} {46,53,57} {46,53,58} {46,53,59} {46,53,60} {46,53,61} {46,53,62} {46,53,63}
{46,53,64} {46,53,65} {46,53,66} {46,54,55} {46,54,56} {46,54,57} {46,54,58} {46,54,59} {46,54,60}
{46,54,61} {46,54,62} {46,54,63} {46,54,64} {46,54,65} {46,54,66} {46,55,56} {46,55,57} {46,55,58}
{46,55,59} {46,55,60} {46,55,61} {46,55,62} {46,55,63} {46,55,64} {46,55,65} {46,55,66} {46,56,57}
{46,56,58} {46,56,59} {46,56,60} {46,56,61} {46,56,62} {46,56,63} {46,56,64} {46,56,65} {46,56,66}
{46,57,58} {46,57,59} {46,57,60} {46,57,61} {46,57,62} {46,57,63} {46,57,64} {46,57,65} {46,57,66}
{46,58,59} {46,58,60} {46,58,61} {46,58,62} {46,58,63} {46,58,64} {46,58,65} {46,58,66} {46,59,60}
{46,59,61} {46,59,62} {46,59,63} {46,59,64} {46,59,65} {46,59,66} {46,60,61} {46,60,62} {46,60,63}
{46,60,64} {46,60,65} {46,60,66} {46,61,62} {46,61,63} {46,61,64} {46,61,65} {46,61,66} {46,62,63}
{46,62,64} {46,62,65} {46,62,66} {46,63,64} {46,63,65} {46,63,66} {46,64,65} {46,64,66} {46,65,66}
{47,48,49} {47,48,50} {47,48,51} {47,48,52} {47,48,53} {47,48,54} {47,48,55} {47,48,56} {47,48,57}
{47,48,58} {47,48,59} {47,48,60} {47,48,61} {47,48,62} {47,48,63} {47,48,64} {47,48,65} {47,48,66}
{47,49,50} {47,49,51} {47,49,52} {47,49,53} {47,49,54} {47,49,55} {47,49,56} {47,49,57} {47,49,58}
{47,49,59} {47,49,60} {47,49,61} {47,49,62} {47,49,63} {47,49,64} {47,49,65} {47,49,66} {47,50,51}
{47,50,52} {47,50,53} {47,50,54} {47,50,55} {47,50,56} {47,50,57} {47,50,58} {47,50,59} {47,50,60}
{47,50,61} {47,50,62} {47,50,63} {47,50,64} {47,50,65} {47,50,66} {47,51,52} {47,51,53} {47,51,54}
{47,51,55} {47,51,56} {47,51,57} {47,51,58} {47,51,59} {47,51,60} {47,51,61} {47,51,62} {47,51,63}
{47,51,64} {47,51,65} {47,51,66} {47,52,53} {47,52,54} {47,52,55} {47,52,56} {47,52,57} {47,52,58}
{47,52,59} {47,52,60} {47,52,61} {47,52,62} {47,52,63} {47,52,64} {47,52,65} {47,52,66} {47,53,54}
{47,53,55} {47,53,56} {47,53,57} {47,53,58} {47,53,59} {47,53,60} {47,53,61} {47,53,62} {47,53,63}
{47,53,64} {47,53,65} {47,53,66} {47,54,55} {47,54,56} {47,54,57} {47,54,58} {47,54,59} {47,54,60}
{47,54,61} {47,54,62} {47,54,63} {47,54,64} {47,54,65} {47,54,66} {47,55,56} {47,55,57} {47,55,58}
{47,55,59} {47,55,60} {47,55,61} {47,55,62} {47,55,63} {47,55,64} {47,55,65} {47,55,66} {47,56,57}
{47,56,58} {47,56,59} {47,56,60} {47,56,61} {47,56,62} {47,56,63} {47,56,64} {47,56,65} {47,56,66}
{47,57,58} {47,57,59} {47,57,60} {47,57,61} {47,57,62} {47,57,63} {47,57,64} {47,57,65} {47,57,66}
{47,58,59} {47,58,60} {47,58,61} {47,58,62} {47,58,63} {47,58,64} {47,58,65} {47,58,66} {47,59,60}
{47,59,61} {47,59,62} {47,59,63} {47,59,64} {47,59,65} {47,59,66} {47,60,61} {47,60,62} {47,60,63}
{47,60,64} {47,60,65} {47,60,66} {47,61,62} {47,61,63} {47,61,64} {47,61,65} {47,61,66} {47,62,63}
{47,62,64} {47,62,65} {47,62,66} {47,63,64} {47,63,65} {47,63,66} {47,64,65} {47,64,66} {47,65,66}
{48,49,50} {48,49,51} {48,49,52} {48,49,53} {48,49,54} {48,49,55} {48,49,56} {48,49,57} {48,49,58}
{48,49,59} {48,49,60} {48,49,61} {48,49,62} {48,49,63} {48,49,64} {48,49,65} {48,49,66} {48,50,51}
{48,50,52} {48,50,53} {48,50,54} {48,50,55} {48,50,56} {48,50,57} {48,50,58} {48,50,59} {48,50,60}

TABLE 3A-continued

{48,50,61} {48,50,62} {48,50,63} {48,50,64} {48,50,65} {48,50,66} {48,51,52} {48,51,53} {48,51,54}
{48,51,55} {48,51,56} {48,51,57} {48,51,58} {48,51,59} {48,51,60} {48,51,61} {48,51,62} {48,51,63}
{48,51,64} {48,51,65} {48,51,66} {48,52,53} {48,52,54} {48,52,55} {48,52,56} {48,52,57} {48,52,58}
{48,52,59} {48,52,60} {48,52,61} {48,52,62} {48,52,63} {48,52,64} {48,52,65} {48,52,66} {48,53,54}
{48,53,55} {48,53,56} {48,53,57} {48,53,58} {48,53,59} {48,53,60} {48,53,61} {48,53,62} {48,53,63}
{48,53,64} {48,53,65} {48,53,66} {48,54,55} {48,54,56} {48,54,57} {48,54,58} {48,54,59} {48,54,60}
{48,54,61} {48,54,62} {48,54,63} {48,54,64} {48,54,65} {48,54,66} {48,55,56} {48,55,57} {48,55,58}
{48,55,59} {48,55,60} {48,55,61} {48,55,62} {48,55,63} {48,55,64} {48,55,65} {48,55,66} {48,56,57}
{48,56,58} {48,56,59} {48,56,60} {48,56,61} {48,56,62} {48,56,63} {48,56,64} {48,56,65} {48,56,66}
{48,57,58} {48,57,59} {48,57,60} {48,57,61} {48,57,62} {48,57,63} {48,57,64} {48,57,65} {48,57,66}
{48,58,59} {48,58,60} {48,58,61} {48,58,62} {48,58,63} {48,58,64} {48,58,65} {48,58,66} {48,59,60}
{48,59,61} {48,59,62} {48,59,63} {48,59,64} {48,59,65} {48,59,66} {48,60,61} {48,60,62} {48,60,63}
{48,60,64} {48,60,65} {48,60,66} {48,61,62} {48,61,63} {48,61,64} {48,61,65} {48,61,66} {48,62,63}
{48,62,64} {48,62,65} {48,62,66} {48,63,64} {48,63,65} {48,63,66} {48,64,65} {48,64,66} {48,65,66}
{49,50,51} {49,50,52} {49,50,53} {49,50,54} {49,50,55} {49,50,56} {49,50,57} {49,50,58} {49,50,59}
{49,50,60} {49,50,61} {49,50,62} {49,50,63} {49,50,64} {49,50,65} {49,50,66} {49,51,52} {49,51,53}
{49,51,54} {49,51,55} {49,51,56} {49,51,57} {49,51,58} {49,51,59} {49,51,60} {49,51,61} {49,51,62}
{49,51,63} {49,51,64} {49,51,65} {49,51,66} {49,52,53} {49,52,54} {49,52,55} {49,52,56} {49,52,57}
{49,52,58} {49,52,59} {49,52,60} {49,52,61} {49,52,62} {49,52,63} {49,52,64} {49,52,65} {49,52,66}
{49,53,54} {49,53,55} {49,53,56} {49,53,57} {49,53,58} {49,53,59} {49,53,60} {49,53,61} {49,53,62}
{49,53,63} {49,53,64} {49,53,65} {49,53,66} {49,54,55} {49,54,56} {49,54,57} {49,54,58} {49,54,59}
{49,54,60} {49,54,61} {49,54,62} {49,54,63} {49,54,64} {49,54,65} {49,54,66} {49,55,56} {49,55,57}
{49,55,58} {49,55,59} {49,55,60} {49,55,61} {49,55,62} {49,55,63} {49,55,64} {49,55,65} {49,55,66}
{49,56,57} {49,56,58} {49,56,59} {49,56,60} {49,56,61} {49,56,62} {49,56,63} {49,56,64} {49,56,65}
{49,56,66} {49,57,58} {49,57,59} {49,57,60} {49,57,61} {49,57,62} {49,57,63} {49,57,64} {49,57,65}
{49,57,66} {49,58,59} {49,58,60} {49,58,61} {49,58,62} {49,58,63} {49,58,64} {49,58,65} {49,58,66}
{49,59,60} {49,59,61} {49,59,62} {49,59,63} {49,59,64} {49,59,65} {49,59,66} {49,60,61} {49,60,62}
{49,60,63} {49,60,64} {49,60,65} {49,60,66} {49,61,62} {49,61,63} {49,61,64} {49,61,65} {49,61,66}
{49,62,63} {49,62,64} {49,62,65} {49,62,66} {49,63,64} {49,63,65} {49,63,66} {49,64,65} {49,64,66}
{49,65,66} {50,51,52} {50,51,53} {50,51,54} {50,51,55} {50,51,56} {50,51,57} {50,51,58} {50,51,59}
{50,51,60} {50,51,61} {50,51,62} {50,51,63} {50,51,64} {50,51,65} {50,51,66} {50,52,53} {50,52,54}
{50,52,55} {50,52,56} {50,52,57} {50,52,58} {50,52,59} {50,52,60} {50,52,61} {50,52,62} {50,52,63}
{50,52,64} {50,52,65} {50,52,66} {50,53,54} {50,53,55} {50,53,56} {50,53,57} {50,53,58} {50,53,59}
{50,53,60} {50,53,61} {50,53,62} {50,53,63} {50,53,64} {50,53,65} {50,53,66} {50,54,55} {50,54,56}
{50,54,57} {50,54,58} {50,54,59} {50,54,60} {50,54,61} {50,54,62} {50,54,63} {50,54,64} {50,54,65}
{50,54,66} {50,55,56} {50,55,57} {50,55,58} {50,55,59} {50,55,60} {50,55,61} {50,55,62} {50,55,63}
{50,55,64} {50,55,65} {50,55,66} {50,56,57} {50,56,58} {50,56,59} {50,56,60} {50,56,61} {50,56,62}
{50,56,63} {50,56,64} {50,56,65} {50,56,66} {50,57,58} {50,57,59} {50,57,60} {50,57,61} {50,57,62}
{50,57,63} {50,57,64} {50,57,65} {50,57,66} {50,58,59} {50,58,60} {50,58,61} {50,58,62} {50,58,63}
{50,58,64} {50,58,65} {50,58,66} {50,59,60} {50,59,61} {50,59,62} {50,59,63} {50,59,64} {50,59,65}
{50,59,66} {50,60,61} {50,60,62} {50,60,63} {50,60,64} {50,60,65} {50,60,66} {50,61,62} {50,61,63}
{50,61,64} {50,61,65} {50,61,66} {50,62,63} {50,62,64} {50,62,65} {50,62,66} {50,63,64} {50,63,65}
{50,63,66} {50,64,65} {50,64,66} {50,65,66} {51,52,53} {51,52,54} {51,52,55} {51,52,56} {51,52,57}
{51,52,58} {51,52,59} {51,52,60} {51,52,61} {51,52,62} {51,52,63} {51,52,64} {51,52,65} {51,52,66}
{51,53,54} {51,53,55} {51,53,56} {51,53,57} {51,53,58} {51,53,59} {51,53,60} {51,53,61} {51,53,62}
{51,53,63} {51,53,64} {51,53,65} {51,53,66} {51,54,55} {51,54,56} {51,54,57} {51,54,58} {51,54,59}
{51,54,60} {51,54,61} {51,54,62} {51,54,63} {51,54,64} {51,54,65} {51,54,66} {51,55,56} {51,55,57}
{51,55,58} {51,55,59} {51,55,60} {51,55,61} {51,55,62} {51,55,63} {51,55,64} {51,55,65} {51,55,66}
{51,56,57} {51,56,58} {51,56,59} {51,56,60} {51,56,61} {51,56,62} {51,56,63} {51,56,64} {51,56,65}
{51,56,66} {51,57,58} {51,57,59} {51,57,60} {51,57,61} {51,57,62} {51,57,63} {51,57,64} {51,57,65}
{51,57,66} {51,58,59} {51,58,60} {51,58,61} {51,58,62} {51,58,63} {51,58,64} {51,58,65} {51,58,66}
{51,59,60} {51,59,61} {51,59,62} {51,59,63} {51,59,64} {51,59,65} {51,59,66} {51,60,61} {51,60,62}
{51,60,63} {51,60,64} {51,60,65} {51,60,66} {51,61,62} {51,61,63} {51,61,64} {51,61,65} {51,61,66}
{51,62,63} {51,62,64} {51,62,65} {51,62,66} {51,63,64} {51,63,65} {51,63,66} {51,64,65} {51,64,66}
{51,65,66} {52,53,54} {52,53,55} {52,53,56} {52,53,57} {52,53,58} {52,53,59} {52,53,60} {52,53,61}
{52,53,62} {52,53,63} {52,53,64} {52,53,65} {52,53,66} {52,54,55} {52,54,56} {52,54,57} {52,54,58}
{52,54,59} {52,54,60} {52,54,61} {52,54,62} {52,54,63} {52,54,64} {52,54,65} {52,54,66} {52,55,56}
{52,55,57} {52,55,58} {52,55,59} {52,55,60} {52,55,61} {52,55,62} {52,55,63} {52,55,64} {52,55,65}
{52,55,66} {52,56,57} {52,56,58} {52,56,59} {52,56,60} {52,56,61} {52,56,62} {52,56,63} {52,56,64}
{52,56,65} {52,56,66} {52,57,58} {52,57,59} {52,57,60} {52,57,61} {52,57,62} {52,57,63} {52,57,64}
{52,57,65} {52,57,66} {52,58,59} {52,58,60} {52,58,61} {52,58,62} {52,58,63} {52,58,64} {52,58,65}
{52,58,66} {52,59,60} {52,59,61} {52,59,62} {52,59,63} {52,59,64} {52,59,65} {52,59,66} {52,60,61}
{52,60,62} {52,60,63} {52,60,64} {52,60,65} {52,60,66} {52,61,62} {52,61,63} {52,61,64} {52,61,65}
{52,61,66} {52,62,63} {52,62,64} {52,62,65} {52,62,66} {52,63,64} {52,63,65} {52,63,66} {52,64,65}
{52,64,66} {52,65,66} {53,54,55} {53,54,56} {53,54,57} {53,54,58} {53,54,59} {53,54,60} {53,54,61}
{53,54,62} {53,54,63} {53,54,64} {53,54,65} {53,54,66} {53,55,56} {53,55,57} {53,55,58} {53,55,59}
{53,55,60} {53,55,61} {53,55,62} {53,55,63} {53,55,64} {53,55,65} {53,55,66} {53,56,57} {53,56,58}
{53,56,59} {53,56,60} {53,56,61} {53,56,62} {53,56,63} {53,56,64} {53,56,65} {53,56,66} {53,57,58}
{53,57,59} {53,57,60} {53,57,61} {53,57,62} {53,57,63} {53,57,64} {53,57,65} {53,57,66} {53,58,59}
{53,58,60} {53,58,61} {53,58,62} {53,58,63} {53,58,64} {53,58,65} {53,58,66} {53,59,60} {53,59,61}
{53,59,62} {53,59,63} {53,59,64} {53,59,65} {53,59,66} {53,60,61} {53,60,62} {53,60,63} {53,60,64}
{53,60,65} {53,60,66} {53,61,62} {53,61,63} {53,61,64} {53,61,65} {53,62,63} {53,62,64}
{53,62,65} {53,62,66} {53,63,64} {53,63,65} {53,63,66} {53,64,65} {53,64,66} {53,65,66} {54,55,56}
{54,55,57} {54,55,58} {54,55,59} {54,55,60} {54,55,61} {54,55,62} {54,55,63} {54,55,64} {54,55,65}
{54,55,66} {54,56,57} {54,56,58} {54,56,59} {54,56,60} {54,56,61} {54,56,62} {54,56,63} {54,56,64}
{54,56,65} {54,56,66} {54,57,58} {54,57,59} {54,57,60} {54,57,61} {54,57,62} {54,57,63} {54,57,64}
{54,57,65} {54,57,66} {54,58,59} {54,58,60} {54,58,61} {54,58,62} {54,58,63} {54,58,64} {54,58,65}
{54,58,66} {54,59,60} {54,59,61} {54,59,62} {54,59,63} {54,59,64} {54,59,65} {54,59,66} {54,60,61}
{54,60,62} {54,60,63} {54,60,64} {54,60,65} {54,60,66} {54,61,62} {54,61,63} {54,61,64} {54,61,65}
{54,61,66} {54,62,63} {54,62,64} {54,62,65} {54,62,66} {54,63,64} {54,63,65} {54,63,66} {54,64,65}

TABLE 3A-continued

{54,64,66} {54,65,66} {55,56,57} {55,56,58} {55,56,59} {55,56,60} {55,56,61} {55,56,62} {55,56,63}
{55,56,64} {55,56,65} {55,56,66} {55,57,58} {55,57,59} {55,57,60} {55,57,61} {55,57,62} {55,57,63}
{55,57,64} {55,57,65} {55,57,66} {55,58,59} {55,58,60} {55,58,61} {55,58,62} {55,58,63} {55,58,64}
{55,58,65} {55,58,66} {55,59,60} {55,59,61} {55,59,62} {55,59,63} {55,59,64} {55,59,65} {55,59,66}
{55,60,61} {55,60,62} {55,60,63} {55,60,64} {55,60,65} {55,60,66} {55,61,62} {55,61,63} {55,61,64}
{55,61,65} {55,61,66} {55,62,63} {55,62,64} {55,62,65} {55,62,66} {55,63,64} {55,63,65} {55,63,66}
{55,64,65} {55,64,66} {55,65,66} {56,57,58} {56,57,59} {56,57,60} {56,57,61} {56,57,62} {56,57,63}
{56,57,64} {56,57,65} {56,57,66} {56,58,59} {56,58,60} {56,58,61} {56,58,62} {56,58,63} {56,58,64}
{56,58,65} {56,58,66} {56,59,60} {56,59,61} {56,59,62} {56,59,63} {56,59,64} {56,59,65} {56,59,66}
{56,60,61} {56,60,62} {56,60,63} {56,60,64} {56,60,65} {56,60,66} {56,61,62} {56,61,63} {56,61,64}
{56,61,65} {56,61,66} {56,62,63} {56,62,64} {56,62,65} {56,62,66} {56,63,64} {56,63,65} {56,63,66}
{56,64,65} {56,64,66} {56,65,66} {57,58,59} {57,58,60} {57,58,61} {57,58,62} {57,58,63} {57,58,64}
{57,58,65} {57,58,66} {57,59,60} {57,59,61} {57,59,62} {57,59,63} {57,59,64} {57,59,65} {57,59,66}
{57,60,61} {57,60,62} {57,60,63} {57,60,64} {57,60,65} {57,60,66} {57,61,62} {57,61,63} {57,61,64}
{57,61,65} {57,61,66} {57,62,63} {57,62,64} {57,62,65} {57,62,66} {57,63,64} {57,63,65} {57,63,66}
{57,64,65} {57,64,66} {57,65,66} {58,59,60} {58,59,61} {58,59,62} {58,59,63} {58,59,64} {58,59,65}
{58,59,66} {58,60,61} {58,60,62} {58,60,63} {58,60,64} {58,60,65} {58,60,66} {58,61,62} {58,61,63}
{58,61,64} {58,61,65} {58,61,66} {58,62,63} {58,62,64} {58,62,65} {58,62,66} {58,63,64} {58,63,65}
{58,63,66} {58,64,65} {58,64,66} {58,65,66} {59,60,61} {59,60,62} {59,60,63} {59,60,64} {59,60,65}
{59,60,66} {59,61,62} {59,61,63} {59,61,64} {59,61,65} {59,61,66} {59,62,63} {59,62,64} {59,62,65}
{59,62,66} {59,63,64} {59,63,65} {59,63,66} {59,64,65} {59,64,66} {59,65,66} {60,61,62} {60,61,63}
{60,61,64} {60,61,65} {60,61,66} {60,62,63} {60,62,64} {60,62,65} {60,62,66} {60,63,64} {60,63,65}
{60,63,66} {60,64,65} {60,64,66} {60,65,66} {61,62,63} {61,62,64} {61,62,65} {61,62,66} {61,63,64}
{61,63,65} {61,63,66} {61,64,65} {61,64,66} {61,65,66} {62,63,64} {62,63,65} {62,63,66} {62,64,65}
{62,64,66} {62,65,66} {63,64,65} {63,64,66} {63,65,66} {64,65,66}

TABLE 3B

{93,96,100} {93,96,106} {93,96,111} {93,96,112} {93,96,113} {93,96,114} {93,96,115} {93,96,116}
{93,96,121} {93,96,122} {93,96,123} {93,96,124} {93,96,125} {93,96,126} {93,96,127} {93,96,128}
{93,96,129} {93,96,130} {93,96,131} {93,96,132} {93,96,133} {93,96,134} {93,96,135} {93,96,136}
{93,96,137} {93,96,138} {93,96,139} {93,100,106} {93,100,111} {93,100,112} {93,100,113} {93,100,114}
{93,100,115} {93,100,116} {93,100,121} {93,100,122} {93,100,123} {93,100,124} {93,100,125}
{93,100,126} {93,100,127} {93,100,128} {93,100,129} {93,100,130} {93,100,131} {93,100,132}
{93,100,133} {93,100,134} {93,100,135} {93,100,136} {93,100,137} {93,100,138} {93,100,139}
{93,106,111} {93,106,112} {93,106,113} {93,106,114} {93,106,115} {93,106,116} {93,106,121}
{93,106,122} {93,106,123} {93,106,124} {93,106,125} {93,106,126} {93,106,127} {93,106,128}
{93,106,129} {93,106,130} {93,106,131} {93,106,132} {93,106,133} {93,106,134} {93,106,135}
{93,106,136} {93,106,137} {93,106,138} {93,106,139} {93,111,112} {93,111,113} {93,111,114}
{93,111,115} {93,111,116} {93,111,121} {93,111,122} {93,111,123} {93,111,124} {93,111,125}
{93,111,126} {93,111,127} {93,111,128} {93,111,129} {93,111,130} {93,111,131} {93,111,132}
{93,111,133} {93,111,134} {93,111,135} {93,111,136} {93,111,137} {93,111,138} {93,111,139}
{93,112,113} {93,112,114} {93,112,115} {93,112,116} {93,112,121} {93,112,122} {93,112,123}
{93,112,124} {93,112,125} {93,112,126} {93,112,127} {93,112,128} {93,112,129} {93,112,130}
{93,112,131} {93,112,132} {93,112,133} {93,112,134} {93,112,135} {93,112,136} {93,112,137}
{93,112,138} {93,112,139} {93,113,114} {93,113,115} {93,113,116} {93,113,121} {93,113,122}
{93,113,123} {93,113,124} {93,113,125} {93,113,126} {93,113,127} {93,113,128} {93,113,129}
{93,113,130} {93,113,131} {93,113,132} {93,113,133} {93,113,134} {93,113,135} {93,113,136}
{93,113,137} {93,113,138} {93,113,139} {93,114,115} {93,114,116} {93,114,121} {93,114,122}
{93,114,123} {93,114,124} {93,114,125} {93,114,126} {93,114,127} {93,114,128} {93,114,129}
{93,114,130} {93,114,131} {93,114,132} {93,114,133} {93,114,134} {93,114,135} {93,114,136}
{93,114,137} {93,114,138} {93,114,139} {93,115,116} {93,115,121} {93,115,122} {93,115,123}
{93,115,124} {93,115,125} {93,115,126} {93,115,127} {93,115,128} {93,115,129} {93,115,130}
{93,115,131} {93,115,132} {93,115,133} {93,115,134} {93,115,135} {93,115,136} {93,115,137}
{93,115,138} {93,115,139} {93,116,121} {93,116,122} {93,116,123} {93,116,124} {93,116,125}
{93,116,126} {93,116,127} {93,116,128} {93,116,129} {93,116,130} {93,116,131} {93,116,132}
{93,116,133} {93,116,134} {93,116,135} {93,116,136} {93,116,137} {93,116,138} {93,116,139}
{93,121,122} {93,121,123} {93,121,124} {93,121,125} {93,121,126} {93,121,127} {93,121,128}
{93,121,129} {93,121,130} {93,121,131} {93,121,132} {93,121,133} {93,121,134} {93,121,135}
{93,121,136} {93,121,137} {93,121,138} {93,121,139} {93,122,123} {93,122,124} {93,122,125}
{93,122,126} {93,122,127} {93,122,128} {93,122,129} {93,122,130} {93,122,131} {93,122,132}
{93,122,133} {93,122,134} {93,122,135} {93,122,136} {93,122,137} {93,122,138} {93,122,139}
{93,123,124} {93,123,125} {93,123,126} {93,123,127} {93,123,128} {93,123,129} {93,123,130}
{93,123,131} {93,123,132} {93,123,133} {93,123,134} {93,123,135} {93,123,136} {93,123,137}
{93,123,138} {93,123,139} {93,124,125} {93,124,126} {93,124,127} {93,124,128} {93,124,129}
{93,124,130} {93,124,131} {93,124,132} {93,124,133} {93,124,134} {93,124,135} {93,124,136}
{93,124,137} {93,124,138} {93,124,139} {93,125,126} {93,125,127} {93,125,128} {93,125,129}
{93,125,130} {93,125,131} {93,125,132} {93,125,133} {93,125,134} {93,125,135} {93,125,136}
{93,125,137} {93,125,138} {93,125,139} {93,126,127} {93,126,128} {93,126,129} {93,126,130}
{93,126,131} {93,126,132} {93,126,133} {93,126,134} {93,126,135} {93,126,136} {93,126,137}
{93,126,138} {93,126,139} {93,127,128} {93,127,129} {93,127,130} {93,127,131} {93,127,132}
{93,127,133} {93,127,134} {93,127,135} {93,127,136} {93,127,137} {93,127,138} {93,127,139}
{93,128,129} {93,128,130} {93,128,131} {93,128,132} {93,128,133} {93,128,134} {93,128,135}
{93,128,136} {93,128,137} {93,128,138} {93,128,139} {93,129,130} {93,129,131} {93,129,132}
{93,129,133} {93,129,134} {93,129,135} {93,129,136} {93,129,137} {93,129,138} {93,129,139}
{93,130,131} {93,130,132} {93,130,133} {93,130,134} {93,130,135} {93,130,136} {93,130,137}
{93,130,138} {93,130,139} {93,131,132} {93,131,133} {93,131,134} {93,131,135} {93,131,136}

TABLE 3B-continued

{93,131,137} {93,131,138} {93,131,139} {93,132,133} {93,132,134} {93,132,135} {93,132,136}
{93,132,137} {93,132,138} {93,132,139} {93,133,134} {93,133,135} {93,133,136} {93,133,137}
{93,133,138} {93,133,139} {93,134,135} {93,134,136} {93,134,137} {93,134,138} {93,134,139}
{93,135,136} {93,135,137} {93,135,138} {93,135,139} {93,136,137} {93,136,138} {93,136,139}
{93,137,138} {93,137,139} {93,138,139} {96,100,106} {96,100,111} {96,100,112} {96,100,113}
{96,100,114} {96,100,115} {96,100,116} {96,100,121} {96,100,122} {96,100,123} {96,100,124}
{96,100,125} {96,100,126} {96,100,127} {96,100,128} {96,100,129} {96,100,130} {96,100,131}
{96,100,132} {96,100,133} {96,100,134} {96,100,135} {96,100,136} {96,100,137} {96,100,138}
{96,100,139} {96,106,111} {96,106,112} {96,106,113} {96,106,114} {96,106,115} {96,106,116}
{96,106,121} {96,106,122} {96,106,123} {96,106,124} {96,106,125} {96,106,126} {96,106,127}
{96,106,128} {96,106,129} {96,106,130} {96,106,131} {96,106,132} {96,106,133} {96,106,134}
{96,106,135} {96,106,136} {96,106,137} {96,106,138} {96,106,139} {96,111,112} {96,111,113}
{96,111,114} {96,111,115} {96,111,116} {96,111,121} {96,111,122} {96,111,123} {96,111,124}
{96,111,125} {96,111,126} {96,111,127} {96,111,128} {96,111,129} {96,111,130} {96,111,131}
{96,111,132} {96,111,133} {96,111,134} {96,111,135} {96,111,136} {96,111,137} {96,111,138}
{96,111,139} {96,112,113} {96,112,114} {96,112,115} {96,112,116} {96,112,121} {96,112,122}
{96,112,123} {96,112,124} {96,112,125} {96,112,126} {96,112,127} {96,112,128} {96,112,129}
{96,112,130} {96,112,131} {96,112,132} {96,112,133} {96,112,134} {96,112,135} {96,112,136}
{96,112,137} {96,112,138} {96,112,139} {96,113,114} {96,113,115} {96,113,116} {96,113,121}
{96,113,122} {96,113,123} {96,113,124} {96,113,125} {96,113,126} {96,113,127} {96,113,128}
{96,113,129} {96,113,130} {96,113,131} {96,113,132} {96,113,133} {96,113,134} {96,113,135}
{96,113,136} {96,113,137} {96,113,138} {96,113,139} {96,114,115} {96,114,116} {96,114,121}
{96,114,122} {96,114,123} {96,114,124} {96,114,125} {96,114,126} {96,114,127} {96,114,128}
{96,114,129} {96,114,130} {96,114,131} {96,114,132} {96,114,133} {96,114,134} {96,114,135}
{96,114,136} {96,114,137} {96,114,138} {96,114,139} {96,115,116} {96,115,121} {96,115,122}
{96,115,123} {96,115,124} {96,115,125} {96,115,126} {96,115,127} {96,115,128} {96,115,129}
{96,115,130} {96,115,131} {96,115,132} {96,115,133} {96,115,134} {96,115,135} {96,115,136}
{96,115,137} {96,115,138} {96,115,139} {96,116,121} {96,116,122} {96,116,123} {96,116,124}
{96,116,125} {96,116,126} {96,116,127} {96,116,128} {96,116,129} {96,116,130} {96,116,131}
{96,116,132} {96,116,133} {96,116,134} {96,116,135} {96,116,136} {96,116,137} {96,116,138}
{96,116,139} {96,121,122} {96,121,123} {96,121,124} {96,121,125} {96,121,126} {96,121,127}
{96,121,128} {96,121,129} {96,121,130} {96,121,131} {96,121,132} {96,121,133} {96,121,134}
{96,121,135} {96,121,136} {96,121,137} {96,121,138} {96,121,139} {96,122,123} {96,122,124}
{96,122,125} {96,122,126} {96,122,127} {96,122,128} {96,122,129} {96,122,130} {96,122,131}
{96,122,132} {96,122,133} {96,122,134} {96,122,135} {96,122,136} {96,122,137} {96,122,138}
{96,122,139} {96,123,124} {96,123,125} {96,123,126} {96,123,127} {96,123,128} {96,123,129}
{96,123,130} {96,123,131} {96,123,132} {96,123,133} {96,123,134} {96,123,135} {96,123,136}
{96,123,137} {96,123,138} {96,123,139} {96,124,125} {96,124,126} {96,124,127} {96,124,128}
{96,124,129} {96,124,130} {96,124,131} {96,124,132} {96,124,133} {96,124,134} {96,124,135}
{96,124,136} {96,124,137} {96,124,138} {96,124,139} {96,125,126} {96,125,127} {96,125,128}
{96,125,129} {96,125,130} {96,125,131} {96,125,132} {96,125,133} {96,125,134} {96,125,135}
{96,125,136} {96,125,137} {96,125,138} {96,125,139} {96,126,127} {96,126,128} {96,126,129}
{96,126,130} {96,126,131} {96,126,132} {96,126,133} {96,126,134} {96,126,135} {96,126,136}
{96,126,137} {96,126,138} {96,126,139} {96,127,128} {96,127,129} {96,127,130} {96,127,131}
{96,127,132} {96,127,133} {96,127,134} {96,127,135} {96,127,136} {96,127,137} {96,127,138}
{96,127,139} {96,128,129} {96,128,130} {96,128,131} {96,128,132} {96,128,133} {96,128,134}
{96,128,135} {96,128,136} {96,128,137} {96,128,138} {96,128,139} {96,129,130} {96,129,131}
{96,129,132} {96,129,133} {96,129,134} {96,129,135} {96,129,136} {96,129,137} {96,129,138}
{96,129,139} {96,130,131} {96,130,132} {96,130,133} {96,130,134} {96,130,135} {96,130,136}
{96,130,137} {96,130,138} {96,130,139} {96,131,132} {96,131,133} {96,131,134} {96,131,135}
{96,131,136} {96,131,137} {96,131,138} {96,131,139} {96,132,133} {96,132,134} {96,132,135}
{96,132,136} {96,132,137} {96,132,138} {96,132,139} {96,133,134} {96,133,135} {96,133,136}
{96,133,137} {96,133,138} {96,133,139} {96,134,135} {96,134,136} {96,134,137} {96,134,138}
{96,134,139} {96,135,136} {96,135,137} {96,135,138} {96,135,139} {96,136,137} {96,136,138}
{96,136,139} {96,137,138} {96,137,139} {96,138,139} {100,106,111} {100,106,112} {100,106,113}
{100,106,114} {100,106,115} {100,106,116} {100,106,121} {100,106,122} {100,106,123} {100,106,124}
{100,106,125} {100,106,126} {100,106,127} {100,106,128} {100,106,129} {100,106,130} {100,106,131}
{100,106,132} {100,106,133} {100,106,134} {100,106,135} {100,106,136} {100,106,137} {100,106,138}
{100,106,139} {100,111,112} {100,111,113} {100,111,114} {100,111,115} {100,111,116} {100,111,121}
{100,111,122} {100,111,123} {100,111,124} {100,111,125} {100,111,126} {100,111,127} {100,111,128}
{100,111,129} {100,111,130} {100,111,131} {100,111,132} {100,111,133} {100,111,134} {100,111,135}
{100,111,136} {100,111,137} {100,111,138} {100,111,139} {100,112,113} {100,112,114} {100,112,115}
{100,112,116} {100,112,121} {100,112,122} {100,112,123} {100,112,124} {100,112,125} {100,112,126}
{100,112,127} {100,112,128} {100,112,129} {100,112,130} {100,112,131} {100,112,132} {100,112,133}
{100,112,134} {100,112,135} {100,112,136} {100,112,137} {100,112,138} {100,112,139} {100,113,114}
{100,113,115} {100,113,116} {100,113,121} {100,113,122} {100,113,123} {100,113,124} {100,113,125}
{100,113,126} {100,113,127} {100,113,128} {100,113,129} {100,113,130} {100,113,131} {100,113,132}
{100,113,133} {100,113,134} {100,113,135} {100,113,136} {100,113,137} {100,113,138} {100,113,139}
{100,114,115} {100,114,116} {100,114,121} {100,114,122} {100,114,123} {100,114,124} {100,114,125}
{100,114,126} {100,114,127} {100,114,128} {100,114,129} {100,114,130} {100,114,131} {100,114,132}
{100,114,133} {100,114,134} {100,114,135} {100,114,136} {100,114,137} {100,114,138} {100,114,139}
{100,115,116} {100,115,121} {100,115,122} {100,115,123} {100,115,124} {100,115,125} {100,115,126}
{100,115,127} {100,115,128} {100,115,129} {100,115,130} {100,115,131} {100,115,132} {100,115,133}
{100,115,134} {100,115,135} {100,115,136} {100,115,137} {100,115,138} {100,115,139} {100,116,121}
{100,116,122} {100,116,123} {100,116,124} {100,116,125} {100,116,126} {100,116,127} {100,116,128}
{100,116,129} {100,116,130} {100,116,131} {100,116,132} {100,116,133} {100,116,134} {100,116,135}
{100,116,136} {100,116,137} {100,116,138} {100,116,139} {100,121,122} {100,121,123} {100,121,124}
{100,121,125} {100,121,126} {100,121,127} {100,121,128} {100,121,129} {100,121,130} {100,121,131}
{100,121,132} {100,121,133} {100,121,134} {100,121,135} {100,121,136} {100,121,137} {100,121,138}
{100,121,139} {100,122,123} {100,122,124} {100,122,125} {100,122,126} {100,122,127} {100,122,128}

TABLE 3B-continued

{100,122,129} {100,122,130} {100,122,131} {100,122,132} {100,122,133} {100,122,134} {100,122,135}
{100,122,136} {100,122,137} {100,122,138} {100,122,139} {100,123,124} {100,123,125} {100,123,126}
{100,123,127} {100,123,128} {100,123,129} {100,123,130} {100,123,131} {100,123,132} {100,123,133}
{100,123,134} {100,123,135} {100,123,136} {100,123,137} {100,123,138} {100,123,139} {100,124,125}
{100,124,126} {100,124,127} {100,124,128} {100,124,129} {100,124,130} {100,124,131} {100,124,132}
{100,124,133} {100,124,134} {100,124,135} {100,124,136} {100,124,137} {100,124,138} {100,124,139}
{100,125,126} {100,125,127} {100,125,128} {100,125,129} {100,125,130} {100,125,131} {100,125,132}
{100,125,133} {100,125,134} {100,125,135} {100,125,136} {100,125,137} {100,125,138} {100,125,139}
{100,126,127} {100,126,128} {100,126,129} {100,126,130} {100,126,131} {100,126,132} {100,126,133}
{100,126,134} {100,126,135} {100,126,136} {100,126,137} {100,126,138} {100,126,139} {100,127,128}
{100,127,129} {100,127,130} {100,127,131} {100,127,132} {100,127,133} {100,127,134} {100,127,135}
{100,127,136} {100,127,137} {100,127,138} {100,127,139} {100,128,129} {100,128,130} {100,128,131}
{100,128,132} {100,128,133} {100,128,134} {100,128,135} {100,128,136} {100,128,137} {100,128,138}
{100,128,139} {100,129,130} {100,129,131} {100,129,132} {100,129,133} {100,129,134} {100,129,135}
{100,129,136} {100,129,137} {100,129,138} {100,129,139} {100,130,131} {100,130,132} {100,130,133}
{100,130,134} {100,130,135} {100,130,136} {100,130,137} {100,130,138} {100,130,139} {100,131,132}
{100,131,133} {100,131,134} {100,131,135} {100,131,136} {100,131,137} {100,131,138} {100,131,139}
{100,132,133} {100,132,134} {100,132,135} {100,132,136} {100,132,137} {100,132,138} {100,132,139}
{100,133,134} {100,133,135} {100,133,136} {100,133,137} {100,133,138} {100,133,139} {100,134,135}
{100,134,136} {100,134,137} {100,134,138} {100,134,139} {100,135,136} {100,135,137} {100,135,138}
{100,135,139} {100,136,137} {100,136,138} {100,136,139} {100,137,138} {100,137,139} {100,138,139}
{106,111,112} {106,111,113} {106,111,114} {106,111,115} {106,111,116} {106,111,121} {106,111,122}
{106,111,123} {106,111,124} {106,111,125} {106,111,126} {106,111,127} {106,111,128} {106,111,129}
{106,111,130} {106,111,131} {106,111,132} {106,111,133} {106,111,134} {106,111,135} {106,111,136}
{106,111,137} {106,111,138} {106,111,139} {106,112,113} {106,112,114} {106,112,115} {106,112,116}
{106,112,121} {106,112,122} {106,112,123} {106,112,124} {106,112,125} {106,112,126} {106,112,127}
{106,112,128} {106,112,129} {106,112,130} {106,112,131} {106,112,132} {106,112,133} {106,112,134}
{106,112,135} {106,112,136} {106,112,137} {106,112,138} {106,112,139} {106,113,114} {106,113,115}
{106,113,116} {106,113,121} {106,113,122} {106,113,123} {106,113,124} {106,113,125} {106,113,126}
{106,113,127} {106,113,128} {106,113,129} {106,113,130} {106,113,131} {106,113,132} {106,113,133}
{106,113,134} {106,113,135} {106,113,136} {106,113,137} {106,113,138} {106,113,139} {106,114,115}
{106,114,116} {106,114,121} {106,114,122} {106,114,123} {106,114,124} {106,114,125} {106,114,126}
{106,114,127} {106,114,128} {106,114,129} {106,114,130} {106,114,131} {106,114,132} {106,114,133}
{106,114,134} {106,114,135} {106,114,136} {106,114,137} {106,114,138} {106,114,139} {106,115,116}
{106,115,121} {106,115,122} {106,115,123} {106,115,124} {106,115,125} {106,115,126} {106,115,127}
{106,115,128} {106,115,129} {106,115,130} {106,115,131} {106,115,132} {106,115,133} {106,115,134}
{106,115,135} {106,115,136} {106,115,137} {106,115,138} {106,115,139} {106,116,121} {106,116,122}
{106,116,123} {106,116,124} {106,116,125} {106,116,126} {106,116,127} {106,116,128} {106,116,129}
{106,116,130} {106,116,131} {106,116,132} {106,116,133} {106,116,134} {106,116,135} {106,116,136}
{106,116,137} {106,116,138} {106,116,139} {106,121,122} {106,121,123} {106,121,124} {106,121,125}
{106,121,126} {106,121,127} {106,121,128} {106,121,129} {106,121,130} {106,121,131} {106,121,132}
{106,121,133} {106,121,134} {106,121,135} {106,121,136} {106,121,137} {106,121,138} {106,121,139}
{106,122,123} {106,122,124} {106,122,125} {106,122,126} {106,122,127} {106,122,128} {106,122,129}
{106,122,130} {106,122,131} {106,122,132} {106,122,133} {106,122,134} {106,122,135} {106,122,136}
{106,122,137} {106,122,138} {106,122,139} {106,123,124} {106,123,125} {106,123,126} {106,123,127}
{106,123,128} {106,123,129} {106,123,130} {106,123,131} {106,123,132} {106,123,133} {106,123,134}
{106,123,135} {106,123,136} {106,123,137} {106,123,138} {106,123,139} {106,124,125} {106,124,126}
{106,124,127} {106,124,128} {106,124,129} {106,124,130} {106,124,131} {106,124,132} {106,124,133}
{106,124,134} {106,124,135} {106,124,136} {106,124,137} {106,124,138} {106,124,139} {106,125,126}
{106,125,127} {106,125,128} {106,125,129} {106,125,130} {106,125,131} {106,125,132} {106,125,133}
{106,125,134} {106,125,135} {106,125,136} {106,125,137} {106,125,138} {106,125,139} {106,126,127}
{106,126,128} {106,126,129} {106,126,130} {106,126,131} {106,126,132} {106,126,133} {106,126,134}
{106,126,135} {106,126,136} {106,126,137} {106,126,138} {106,126,139} {106,127,128} {106,127,129}
{106,127,130} {106,127,131} {106,127,132} {106,127,133} {106,127,134} {106,127,135} {106,127,136}
{106,127,137} {106,127,138} {106,127,139} {106,128,129} {106,128,130} {106,128,131} {106,128,132}
{106,128,133} {106,128,134} {106,128,135} {106,128,136} {106,128,137} {106,128,138} {106,128,139}
{106,129,130} {106,129,131} {106,129,132} {106,129,133} {106,129,134} {106,129,135} {106,129,136}
{106,129,137} {106,129,138} {106,129,139} {106,130,131} {106,130,132} {106,130,133} {106,130,134}
{106,130,135} {106,130,136} {106,130,137} {106,130,138} {106,130,139} {106,131,132} {106,131,133}
{106,131,134} {106,131,135} {106,131,136} {106,131,137} {106,131,138} {106,131,139} {106,132,133}
{106,132,134} {106,132,135} {106,132,136} {106,132,137} {106,132,138} {106,132,139} {106,133,134}
{106,133,135} {106,133,136} {106,133,137} {106,133,138} {106,133,139} {106,134,135} {106,134,136}
{106,134,137} {106,134,138} {106,134,139} {106,135,136} {106,135,137} {106,135,138} {106,135,139}
{106,136,137} {106,136,138} {106,136,139} {106,137,138} {106,137,139} {106,138,139} {111,112,113}
{111,112,114} {111,112,115} {111,112,116} {111,112,121} {111,112,122} {111,112,123} {111,112,124}
{111,112,125} {111,112,126} {111,112,127} {111,112,128} {111,112,129} {111,112,130} {111,112,131}
{111,112,132} {111,112,133} {111,112,134} {111,112,135} {111,112,136} {111,112,137} {111,112,138}
{111,112,139} {111,113,114} {111,113,115} {111,113,116} {111,113,121} {111,113,122} {111,113,123}
{111,113,124} {111,113,125} {111,113,126} {111,113,127} {111,113,128} {111,113,129} {111,113,130}
{111,113,131} {111,113,132} {111,113,133} {111,113,134} {111,113,135} {111,113,136} {111,113,137}
{111,113,138} {111,113,139} {111,114,115} {111,114,116} {111,114,121} {111,114,122} {111,114,123}
{111,114,124} {111,114,125} {111,114,126} {111,114,127} {111,114,128} {111,114,129} {111,114,130}
{111,114,131} {111,114,132} {111,114,133} {111,114,134} {111,114,135} {111,114,136} {111,114,137}
{111,114,138} {111,114,139} {111,115,116} {111,115,121} {111,115,122} {111,115,123} {111,115,124}
{111,115,125} {111,115,126} {111,115,127} {111,115,128} {111,115,129} {111,115,130} {111,115,131}
{111,115,132} {111,115,133} {111,115,134} {111,115,135} {111,115,136} {111,115,137} {111,115,138}
{111,115,139} {111,116,121} {111,116,122} {111,116,123} {111,116,124} {111,116,125} {111,116,126}
{111,116,127} {111,116,128} {111,116,129} {111,116,130} {111,116,131} {111,116,132} {111,116,133}
{111,116,134} {111,116,135} {111,116,136} {111,116,137} {111,116,138} {111,116,139} {111,121,122}
{111,121,123} {111,121,124} {111,121,125} {111,121,126} {111,121,127} {111,121,128} {111,121,129}

TABLE 3B-continued

{111,121,130} {111,121,131} {111,121,132} {111,121,133} {111,121,134} {111,121,135} {111,121,136}
{111,121,137} {111,121,138} {111,121,139} {111,122,123} {111,122,124} {111,122,125} {111,122,126}
{111,122,127} {111,122,128} {111,122,129} {111,122,130} {111,122,131} {111,122,132} {111,122,133}
{111,122,134} {111,122,135} {111,122,136} {111,122,137} {111,122,138} {111,122,139} {111,123,124}
{111,123,125} {111,123,126} {111,123,127} {111,123,128} {111,123,129} {111,123,130} {111,123,131}
{111,123,132} {111,123,133} {111,123,134} {111,123,135} {111,123,136} {111,123,137} {111,123,138}
{111,123,139} {111,124,125} {111,124,126} {111,124,127} {111,124,128} {111,124,129} {111,124,130}
{111,124,131} {111,124,132} {111,124,133} {111,124,134} {111,124,135} {111,124,136} {111,124,137}
{111,124,138} {111,124,139} {111,125,126} {111,125,127} {111,125,128} {111,125,129} {111,125,130}
{111,125,131} {111,125,132} {111,125,133} {111,125,134} {111,125,135} {111,125,136} {111,125,137}
{111,125,138} {111,125,139} {111,126,127} {111,126,128} {111,126,129} {111,126,130} {111,126,131}
{111,126,132} {111,126,133} {111,126,134} {111,126,135} {111,126,136} {111,126,137} {111,126,138}
{111,126,139} {111,127,128} {111,127,129} {111,127,130} {111,127,131} {111,127,132} {111,127,133}
{111,127,134} {111,127,135} {111,127,136} {111,127,137} {111,127,138} {111,127,139} {111,128,129}
{111,128,130} {111,128,131} {111,128,132} {111,128,133} {111,128,134} {111,128,135} {111,128,136}
{111,128,137} {111,128,138} {111,128,139} {111,129,130} {111,129,131} {111,129,132} {111,129,133}
{111,129,134} {111,129,135} {111,129,136} {111,129,137} {111,129,138} {111,129,139} {111,130,131}
{111,130,132} {111,130,133} {111,130,134} {111,130,135} {111,130,136} {111,130,137} {111,130,138}
{111,130,139} {111,131,132} {111,131,133} {111,131,134} {111,131,135} {111,131,136} {111,131,137}
{111,131,138} {111,131,139} {111,132,133} {111,132,134} {111,132,135} {111,132,136} {111,132,137}
{111,132,138} {111,132,139} {111,133,134} {111,133,135} {111,133,136} {111,133,137} {111,133,138}
{111,133,139} {111,134,135} {111,134,136} {111,134,137} {111,134,138} {111,134,139} {111,135,136}
{111,135,137} {111,135,138} {111,135,139} {111,136,137} {111,136,138} {111,136,139} {111,137,138}
{111,137,139} {111,138,139} {112,113,114} {112,113,115} {112,113,116} {112,113,121} {112,113,122}
{112,113,123} {112,113,124} {112,113,125} {112,113,126} {112,113,127} {112,113,128} {112,113,129}
{112,113,130} {112,113,131} {112,113,132} {112,113,133} {112,113,134} {112,113,135} {112,113,136}
{112,113,137} {112,113,138} {112,113,139} {112,114,115} {112,114,116} {112,114,121} {112,114,122}
{112,114,123} {112,114,124} {112,114,125} {112,114,126} {112,114,127} {112,114,128} {112,114,129}
{112,114,130} {112,114,131} {112,114,132} {112,114,133} {112,114,134} {112,114,135} {112,114,136}
{112,114,137} {112,114,138} {112,114,139} {112,115,116} {112,115,121} {112,115,122} {112,115,123}
{112,115,124} {112,115,125} {112,115,126} {112,115,127} {112,115,128} {112,115,129} {112,115,130}
{112,115,131} {112,115,132} {112,115,133} {112,115,134} {112,115,135} {112,115,136} {112,115,137}
{112,115,138} {112,115,139} {112,116,121} {112,116,122} {112,116,123} {112,116,124} {112,116,125}
{112,116,126} {112,116,127} {112,116,128} {112,116,129} {112,116,130} {112,116,131} {112,116,132}
{112,116,133} {112,116,134} {112,116,135} {112,116,136} {112,116,137} {112,116,138} {112,116,139}
{112,121,122} {112,121,123} {112,121,124} {112,121,125} {112,121,126} {112,121,127} {112,121,128}
{112,121,129} {112,121,130} {112,121,131} {112,121,132} {112,121,133} {112,121,134} {112,121,135}
{112,121,136} {112,121,137} {112,121,138} {112,121,139} {112,122,123} {112,122,124} {112,122,125}
{112,122,126} {112,122,127} {112,122,128} {112,122,129} {112,122,130} {112,122,131} {112,122,132}
{112,122,133} {112,122,134} {112,122,135} {112,122,136} {112,122,137} {112,122,138} {112,122,139}
{112,123,124} {112,123,125} {112,123,126} {112,123,127} {112,123,128} {112,123,129} {112,123,130}
{112,123,131} {112,123,132} {112,123,133} {112,123,134} {112,123,135} {112,123,136} {112,123,137}
{112,123,138} {112,123,139} {112,124,125} {112,124,126} {112,124,127} {112,124,128} {112,124,129}
{112,124,130} {112,124,131} {112,124,132} {112,124,133} {112,124,134} {112,124,135} {112,124,136}
{112,124,137} {112,124,138} {112,124,139} {112,125,126} {112,125,127} {112,125,128} {112,125,129}
{112,125,130} {112,125,131} {112,125,132} {112,125,133} {112,125,134} {112,125,135} {112,125,136}
{112,125,137} {112,125,138} {112,125,139} {112,126,127} {112,126,128} {112,126,129} {112,126,130}
{112,126,131} {112,126,132} {112,126,133} {112,126,134} {112,126,135} {112,126,136} {112,126,137}
{112,126,138} {112,126,139} {112,127,128} {112,127,129} {112,127,130} {112,127,131} {112,127,132}
{112,127,133} {112,127,134} {112,127,135} {112,127,136} {112,127,137} {112,127,138} {112,127,139}
{112,128,129} {112,128,130} {112,128,131} {112,128,132} {112,128,133} {112,128,134} {112,128,135}
{112,128,136} {112,128,137} {112,128,138} {112,128,139} {112,129,130} {112,129,131} {112,129,132}
{112,129,133} {112,129,134} {112,129,135} {112,129,136} {112,129,137} {112,129,138} {112,129,139}
{112,130,131} {112,130,132} {112,130,133} {112,130,134} {112,130,135} {112,130,136} {112,130,137}
{112,130,138} {112,130,139} {112,131,132} {112,131,133} {112,131,134} {112,131,135} {112,131,136}
{112,131,137} {112,131,138} {112,131,139} {112,132,133} {112,132,134} {112,132,135} {112,132,136}
{112,132,137} {112,132,138} {112,132,139} {112,133,134} {112,133,135} {112,133,136} {112,133,137}
{112,133,138} {112,133,139} {112,134,135} {112,134,136} {112,134,137} {112,134,138} {112,134,139}
{112,135,136} {112,135,137} {112,135,138} {112,135,139} {112,136,137} {112,136,138} {112,136,139}
{112,137,138} {112,137,139} {112,138,139} {113,114,115} {113,114,116} {113,114,121} {113,114,122}
{113,114,123} {113,114,124} {113,114,125} {113,114,126} {113,114,127} {113,114,128} {113,114,129}
{113,114,130} {113,114,131} {113,114,132} {113,114,133} {113,114,134} {113,114,135} {113,114,136}
{113,114,137} {113,114,138} {113,114,139} {113,115,116} {113,115,121} {113,115,122} {113,115,123}
{113,115,124} {113,115,125} {113,115,126} {113,115,127} {113,115,128} {113,115,129} {113,115,130}
{113,115,131} {113,115,132} {113,115,133} {113,115,134} {113,115,135} {113,115,136} {113,115,137}
{113,115,138} {113,115,139} {113,116,121} {113,116,122} {113,116,123} {113,116,124} {113,116,125}
{113,116,126} {113,116,127} {113,116,128} {113,116,129} {113,116,130} {113,116,131} {113,116,132}
{113,116,133} {113,116,134} {113,116,135} {113,116,136} {113,116,137} {113,116,138} {113,116,139}
{113,121,122} {113,121,123} {113,121,124} {113,121,125} {113,121,126} {113,121,127} {113,121,128}
{113,121,129} {113,121,130} {113,121,131} {113,121,132} {113,121,133} {113,121,134} {113,121,135}
{113,121,136} {113,121,137} {113,121,138} {113,121,139} {113,122,123} {113,122,124} {113,122,125}
{113,122,126} {113,122,127} {113,122,128} {113,122,129} {113,122,130} {113,122,131} {113,122,132}
{113,122,133} {113,122,134} {113,122,135} {113,122,136} {113,122,137} {113,122,138} {113,122,139}
{113,123,124} {113,123,125} {113,123,126} {113,123,127} {113,123,128} {113,123,129} {113,123,130}
{113,123,131} {113,123,132} {113,123,133} {113,123,134} {113,123,135} {113,123,136} {113,123,137}
{113,123,138} {113,123,139} {113,124,125} {113,124,126} {113,124,127} {113,124,128} {113,124,129}
{113,124,130} {113,124,131} {113,124,132} {113,124,133} {113,124,134} {113,124,135} {113,124,136}
{113,124,137} {113,124,138} {113,124,139} {113,125,126} {113,125,127} {113,125,128} {113,125,129}
{113,125,130} {113,125,131} {113,125,132} {113,125,133} {113,125,134} {113,125,135} {113,125,136}
{113,125,137} {113,125,138} {113,125,139} {113,126,127} {113,126,128} {113,126,129} {113,126,130}

TABLE 3B-continued

{113,126,131} {113,126,132} {113,126,133} {113,126,134} {113,126,135} {113,126,136} {113,126,137}
{113,126,138} {113,126,139} {113,127,128} {113,127,129} {113,127,130} {113,127,131} {113,127,132}
{113,127,133} {113,127,134} {113,127,135} {113,127,136} {113,127,137} {113,127,138} {113,127,139}
{113,128,129} {113,128,130} {113,128,131} {113,128,132} {113,128,133} {113,128,134} {113,128,135}
{113,128,136} {113,128,137} {113,128,138} {113,128,139} {113,129,130} {113,129,131} {113,129,132}
{113,129,133} {113,129,134} {113,129,135} {113,129,136} {113,129,137} {113,129,138} {113,129,139}
{113,130,131} {113,130,132} {113,130,133} {113,130,134} {113,130,135} {113,130,136} {113,130,137}
{113,130,138} {113,130,139} {113,131,132} {113,131,133} {113,131,134} {113,131,135} {113,131,136}
{113,131,137} {113,131,138} {113,131,139} {113,132,133} {113,132,134} {113,132,135} {113,132,136}
{113,132,137} {113,132,138} {113,132,139} {113,133,134} {113,133,135} {113,133,136} {113,133,137}
{113,133,138} {113,133,139} {113,134,135} {113,134,136} {113,134,137} {113,134,138} {113,134,139}
{113,135,136} {113,135,137} {113,135,138} {113,135,139} {113,136,137} {113,136,138} {113,136,139}
{113,137,138} {113,137,139} {113,138,139} {114,115,116} {114,115,121} {114,115,122} {114,115,123}
{114,115,124} {114,115,125} {114,115,126} {114,115,127} {114,115,128} {114,115,129} {114,115,130}
{114,115,131} {114,115,132} {114,115,133} {114,115,134} {114,115,135} {114,115,136} {114,115,137}
{114,115,138} {114,115,139} {114,116,121} {114,116,122} {114,116,123} {114,116,124} {114,116,125}
{114,116,126} {114,116,127} {114,116,128} {114,116,129} {114,116,130} {114,116,131} {114,116,132}
{114,116,133} {114,116,134} {114,116,135} {114,116,136} {114,116,137} {114,116,138} {114,116,139}
{114,121,122} {114,121,123} {114,121,124} {114,121,125} {114,121,126} {114,121,127} {114,121,128}
{114,121,129} {114,121,130} {114,121,131} {114,121,132} {114,121,133} {114,121,134} {114,121,135}
{114,121,136} {114,121,137} {114,121,138} {114,121,139} {114,122,123} {114,122,124} {114,122,125}
{114,122,126} {114,122,127} {114,122,128} {114,122,129} {114,122,130} {114,122,131} {114,122,132}
{114,122,133} {114,122,134} {114,122,135} {114,122,136} {114,122,137} {114,122,138} {114,122,139}
{114,123,124} {114,123,125} {114,123,126} {114,123,127} {114,123,128} {114,123,129} {114,123,130}
{114,123,131} {114,123,132} {114,123,133} {114,123,134} {114,123,135} {114,123,136} {114,123,137}
{114,123,138} {114,123,139} {114,124,125} {114,124,126} {114,124,127} {114,124,128} {114,124,129}
{114,124,130} {114,124,131} {114,124,132} {114,124,133} {114,124,134} {114,124,135} {114,124,136}
{114,124,137} {114,124,138} {114,124,139} {114,125,126} {114,125,127} {114,125,128} {114,125,129}
{114,125,130} {114,125,131} {114,125,132} {114,125,133} {114,125,134} {114,125,135} {114,125,136}
{114,125,137} {114,125,138} {114,125,139} {114,126,127} {114,126,128} {114,126,129} {114,126,130}
{114,126,131} {114,126,132} {114,126,133} {114,126,134} {114,126,135} {114,126,136} {114,126,137}
{114,126,138} {114,126,139} {114,127,128} {114,127,129} {114,127,130} {114,127,131} {114,127,132}
{114,127,133} {114,127,134} {114,127,135} {114,127,136} {114,127,137} {114,127,138} {114,127,139}
{114,128,129} {114,128,130} {114,128,131} {114,128,132} {114,128,133} {114,128,134} {114,128,135}
{114,128,136} {114,128,137} {114,128,138} {114,128,139} {114,129,130} {114,129,131} {114,129,132}
{114,129,133} {114,129,134} {114,129,135} {114,129,136} {114,129,137} {114,129,138} {114,129,139}
{114,130,131} {114,130,132} {114,130,133} {114,130,134} {114,130,135} {114,130,136} {114,130,137}
{114,130,138} {114,130,139} {114,131,132} {114,131,133} {114,131,134} {114,131,135} {114,131,136}
{114,131,137} {114,131,138} {114,131,139} {114,132,133} {114,132,134} {114,132,135} {114,132,136}
{114,132,137} {114,132,138} {114,132,139} {114,133,134} {114,133,135} {114,133,136} {114,133,137}
{114,133,138} {114,133,139} {114,134,135} {114,134,136} {114,134,137} {114,134,138} {114,134,139}
{114,135,136} {114,135,137} {114,135,138} {114,135,139} {114,136,137} {114,136,138} {114,136,139}
{114,137,138} {114,137,139} {114,138,139} {115,116,121} {115,116,122} {115,116,123} {115,116,124}
{115,116,125} {115,116,126} {115,116,127} {115,116,128} {115,116,129} {115,116,130} {115,116,131}
{115,116,132} {115,116,133} {115,116,134} {115,116,135} {115,116,136} {115,116,137} {115,116,138}
{115,116,139} {115,121,122} {115,121,123} {115,121,124} {115,121,125} {115,121,126} {115,121,127}
{115,121,128} {115,121,129} {115,121,130} {115,121,131} {115,121,132} {115,121,133} {115,121,134}
{115,121,135} {115,121,136} {115,121,137} {115,121,138} {115,121,139} {115,122,123} {115,122,124}
{115,122,125} {115,122,126} {115,122,127} {115,122,128} {115,122,129} {115,122,130} {115,122,131}
{115,122,132} {115,122,133} {115,122,134} {115,122,135} {115,122,136} {115,122,137} {115,122,138}
{115,122,139} {115,123,124} {115,123,125} {115,123,126} {115,123,127} {115,123,128} {115,123,129}
{115,123,130} {115,123,131} {115,123,132} {115,123,133} {115,123,134} {115,123,135} {115,123,136}
{115,123,137} {115,123,138} {115,123,139} {115,124,125} {115,124,126} {115,124,127} {115,124,128}
{115,124,129} {115,124,130} {115,124,131} {115,124,132} {115,124,133} {115,124,134} {115,124,135}
{115,124,136} {115,124,137} {115,124,138} {115,124,139} {115,125,126} {115,125,127} {115,125,128}
{115,125,129} {115,125,130} {115,125,131} {115,125,132} {115,125,133} {115,125,134} {115,125,135}
{115,125,136} {115,125,137} {115,125,138} {115,125,139} {115,126,127} {115,126,128} {115,126,129}
{115,126,130} {115,126,131} {115,126,132} {115,126,133} {115,126,134} {115,126,135} {115,126,136}
{115,126,137} {115,126,138} {115,126,139} {115,127,128} {115,127,129} {115,127,130} {115,127,131}
{115,127,132} {115,127,133} {115,127,134} {115,127,135} {115,127,136} {115,127,137} {115,127,138}
{115,127,139} {115,128,129} {115,128,130} {115,128,131} {115,128,132} {115,128,133} {115,128,134}
{115,128,135} {115,128,136} {115,128,137} {115,128,138} {115,128,139} {115,129,130} {115,129,131}
{115,129,132} {115,129,133} {115,129,134} {115,129,135} {115,129,136} {115,129,137} {115,129,138}
{115,129,139} {115,130,131} {115,130,132} {115,130,133} {115,130,134} {115,130,135} {115,130,136}
{115,130,137} {115,130,138} {115,130,139} {115,131,132} {115,131,133} {115,131,134} {115,131,135}
{115,131,136} {115,131,137} {115,131,138} {115,131,139} {115,132,133} {115,132,134} {115,132,135}
{115,132,136} {115,132,137} {115,132,138} {115,132,139} {115,133,134} {115,133,135} {115,133,136}
{115,133,137} {115,133,138} {115,133,139} {115,134,135} {115,134,136} {115,134,137} {115,134,138}
{115,134,139} {115,135,136} {115,135,137} {115,135,138} {115,135,139} {115,136,137} {115,136,138}
{115,136,139} {115,137,138} {115,137,139} {115,138,139} {116,121,122} {116,121,123} {116,121,124}
{116,121,125} {116,121,126} {116,121,127} {116,121,128} {116,121,129} {116,121,130} {116,121,131}
{116,121,132} {116,121,133} {116,121,134} {116,121,135} {116,121,136} {116,121,137} {116,121,138}
{116,121,139} {116,122,123} {116,122,124} {116,122,125} {116,122,126} {116,122,127} {116,122,128}
{116,122,129} {116,122,130} {116,122,131} {116,122,132} {116,122,133} {116,122,134} {116,122,135}
{116,122,136} {116,122,137} {116,122,138} {116,122,139} {116,123,124} {116,123,125} {116,123,126}
{116,123,127} {116,123,128} {116,123,129} {116,123,130} {116,123,131} {116,123,132} {116,123,133}
{116,123,134} {116,123,135} {116,123,136} {116,123,137} {116,123,138} {116,123,139} {116,124,125}
{116,124,126} {116,124,127} {116,124,128} {116,124,129} {116,124,130} {116,124,131} {116,124,132}
{116,124,133} {116,124,134} {116,124,135} {116,124,136} {116,124,137} {116,124,138} {116,124,139}
{116,125,126} {116,125,127} {116,125,128} {116,125,129} {116,125,130} {116,125,131} {116,125,132}

TABLE 3B-continued

{116,125,133} {116,125,134} {116,125,135} {116,125,136} {116,125,137} {116,125,138} {116,125,139}
{116,126,127} {116,126,128} {116,126,129} {116,126,130} {116,126,131} {116,126,132} {116,126,133}
{116,126,134} {116,126,135} {116,126,136} {116,126,137} {116,126,138} {116,126,139} {116,127,128}
{116,127,129} {116,127,130} {116,127,131} {116,127,132} {116,127,133} {116,127,134} {116,127,135}
{116,127,136} {116,127,137} {116,127,138} {116,127,139} {116,128,129} {116,128,130} {116,128,131}
{116,128,132} {116,128,133} {116,128,134} {116,128,135} {116,128,136} {116,128,137} {116,128,138}
{116,128,139} {116,129,130} {116,129,131} {116,129,132} {116,129,133} {116,129,134} {116,129,135}
{116,129,136} {116,129,137} {116,129,138} {116,129,139} {116,130,131} {116,130,132} {116,130,133}
{116,130,134} {116,130,135} {116,130,136} {116,130,137} {116,130,138} {116,130,139} {116,131,132}
{116,131,133} {116,131,134} {116,131,135} {116,131,136} {116,131,137} {116,131,138} {116,131,139}
{116,132,133} {116,132,134} {116,132,135} {116,132,136} {116,132,137} {116,132,138} {116,132,139}
{116,133,134} {116,133,135} {116,133,136} {116,133,137} {116,133,138} {116,133,139} {116,134,135}
{116,134,136} {116,134,137} {116,134,138} {116,134,139} {116,135,136} {116,135,137} {116,135,138}
{116,135,139} {116,136,137} {116,136,138} {116,136,139} {116,137,138} {116,137,139} {116,138,139}
{121,122,123} {121,122,124} {121,122,125} {121,122,126} {121,122,127} {121,122,128} {121,122,129}
{121,122,130} {121,122,131} {121,122,132} {121,122,133} {121,122,134} {121,122,135} {121,122,136}
{121,122,137} {121,122,138} {121,122,139} {121,123,124} {121,123,125} {121,123,126} {121,123,127}
{121,123,128} {121,123,129} {121,123,130} {121,123,131} {121,123,132} {121,123,133} {121,123,134}
{121,123,135} {121,123,136} {121,123,137} {121,123,138} {121,123,139} {121,124,125} {121,124,126}
{121,124,127} {121,124,128} {121,124,129} {121,124,130} {121,124,131} {121,124,132} {121,124,133}
{121,124,134} {121,124,135} {121,124,136} {121,124,137} {121,124,138} {121,124,139} {121,125,126}
{121,125,127} {121,125,128} {121,125,129} {121,125,130} {121,125,131} {121,125,132} {121,125,133}
{121,125,134} {121,125,135} {121,125,136} {121,125,137} {121,125,138} {121,125,139} {121,126,127}
{121,126,128} {121,126,129} {121,126,130} {121,126,131} {121,126,132} {121,126,133} {121,126,134}
{121,126,135} {121,126,136} {121,126,137} {121,126,138} {121,126,139} {121,127,128} {121,127,129}
{121,127,130} {121,127,131} {121,127,132} {121,127,133} {121,127,134} {121,127,135} {121,127,136}
{121,127,137} {121,127,138} {121,127,139} {121,128,129} {121,128,130} {121,128,131} {121,128,132}
{121,128,133} {121,128,134} {121,128,135} {121,128,136} {121,128,137} {121,128,138} {121,128,139}
{121,129,130} {121,129,131} {121,129,132} {121,129,133} {121,129,134} {121,129,135} {121,129,136}
{121,129,137} {121,129,138} {121,129,139} {121,130,131} {121,130,132} {121,130,133} {121,130,134}
{121,130,135} {121,130,136} {121,130,137} {121,130,138} {121,130,139} {121,131,132} {121,131,133}
{121,131,134} {121,131,135} {121,131,136} {121,131,137} {121,131,138} {121,131,139} {121,132,133}
{121,132,134} {121,132,135} {121,132,136} {121,132,137} {121,132,138} {121,132,139} {121,133,134}
{121,133,135} {121,133,136} {121,133,137} {121,133,138} {121,133,139} {121,134,135} {121,134,136}
{121,134,137} {121,134,138} {121,134,139} {121,135,136} {121,135,137} {121,135,138} {121,135,139}
{121,136,137} {121,136,138} {121,136,139} {121,137,138} {121,137,139} {121,138,139} {122,123,124}
{122,123,125} {122,123,126} {122,123,127} {122,123,128} {122,123,129} {122,123,130} {122,123,131}
{122,123,132} {122,123,133} {122,123,134} {122,123,135} {122,123,136} {122,123,137} {122,123,138}
{122,123,139} {122,124,125} {122,124,126} {122,124,127} {122,124,128} {122,124,129} {122,124,130}
{122,124,131} {122,124,132} {122,124,133} {122,124,134} {122,124,135} {122,124,136} {122,124,137}
{122,124,138} {122,124,139} {122,125,126} {122,125,127} {122,125,128} {122,125,129} {122,125,130}
{122,125,131} {122,125,132} {122,125,133} {122,125,134} {122,125,135} {122,125,136} {122,125,137}
{122,125,138} {122,125,139} {122,126,127} {122,126,128} {122,126,129} {122,126,130} {122,126,131}
{122,126,132} {122,126,133} {122,126,134} {122,126,135} {122,126,136} {122,126,137} {122,126,138}
{122,126,139} {122,127,128} {122,127,129} {122,127,130} {122,127,131} {122,127,132} {122,127,133}
{122,127,134} {122,127,135} {122,127,136} {122,127,137} {122,127,138} {122,127,139} {122,128,129}
{122,128,130} {122,128,131} {122,128,132} {122,128,133} {122,128,134} {122,128,135} {122,128,136}
{122,128,137} {122,128,138} {122,128,139} {122,129,130} {122,129,131} {122,129,132} {122,129,133}
{122,129,134} {122,129,135} {122,129,136} {122,129,137} {122,129,138} {122,129,139} {122,130,131}
{122,130,132} {122,130,133} {122,130,134} {122,130,135} {122,130,136} {122,130,137} {122,130,138}
{122,130,139} {122,131,132} {122,131,133} {122,131,134} {122,131,135} {122,131,136} {122,131,137}
{122,131,138} {122,131,139} {122,132,133} {122,132,134} {122,132,135} {122,132,136} {122,132,137}
{122,132,138} {122,132,139} {122,133,134} {122,133,135} {122,133,136} {122,133,137} {122,133,138}
{122,133,139} {122,134,135} {122,134,136} {122,134,137} {122,134,138} {122,134,139} {122,135,136}
{122,135,137} {122,135,138} {122,135,139} {122,136,137} {122,136,138} {122,136,139} {122,137,138}
{122,137,139} {122,138,139} {123,124,125} {123,124,126} {123,124,127} {123,124,128} {123,124,129}
{123,124,130} {123,124,131} {123,124,132} {123,124,133} {123,124,134} {123,124,135} {123,124,136}
{123,124,137} {123,124,138} {123,124,139} {123,125,126} {123,125,127} {123,125,128} {123,125,129}
{123,125,130} {123,125,131} {123,125,132} {123,125,133} {123,125,134} {123,125,135} {123,125,136}
{123,125,137} {123,125,138} {123,125,139} {123,126,127} {123,126,128} {123,126,129} {123,126,130}
{123,126,131} {123,126,132} {123,126,133} {123,126,134} {123,126,135} {123,126,136} {123,126,137}
{123,126,138} {123,126,139} {123,127,128} {123,127,129} {123,127,130} {123,127,131} {123,127,132}
{123,127,133} {123,127,134} {123,127,135} {123,127,136} {123,127,137} {123,127,138} {123,127,139}
{123,128,129} {123,128,130} {123,128,131} {123,128,132} {123,128,133} {123,128,134} {123,128,135}
{123,128,136} {123,128,137} {123,128,138} {123,128,139} {123,129,130} {123,129,131} {123,129,132}
{123,129,133} {123,129,134} {123,129,135} {123,129,136} {123,129,137} {123,129,138} {123,129,139}
{123,130,131} {123,130,132} {123,130,133} {123,130,134} {123,130,135} {123,130,136} {123,130,137}
{123,130,138} {123,130,139} {123,131,132} {123,131,133} {123,131,134} {123,131,135} {123,131,136}
{123,131,137} {123,131,138} {123,131,139} {123,132,133} {123,132,134} {123,132,135} {123,132,136}
{123,132,137} {123,132,138} {123,132,139} {123,133,134} {123,133,135} {123,133,136} {123,133,137}
{123,133,138} {123,133,139} {123,134,135} {123,134,136} {123,134,137} {123,134,138} {123,134,139}
{123,135,136} {123,135,137} {123,135,138} {123,135,139} {123,136,137} {123,136,138} {123,136,139}
{123,137,138} {123,137,139} {123,138,139} {124,125,126} {124,125,127} {124,125,128} {124,125,129}
{124,125,130} {124,125,131} {124,125,132} {124,125,133} {124,125,134} {124,125,135} {124,125,136}
{124,125,137} {124,125,138} {124,125,139} {124,126,127} {124,126,128} {124,126,129} {124,126,130}
{124,126,131} {124,126,132} {124,126,133} {124,126,134} {124,126,135} {124,126,136} {124,126,137}
{124,126,138} {124,126,139} {124,127,128} {124,127,129} {124,127,130} {124,127,131} {124,127,132}
{124,127,133} {124,127,134} {124,127,135} {124,127,136} {124,127,137} {124,127,138} {124,127,139}
{124,128,129} {124,128,130} {124,128,131} {124,128,132} {124,128,133} {124,128,134} {124,128,135}
{124,128,136} {124,128,137} {124,128,138} {124,128,139} {124,129,130} {124,129,131} {124,129,132}

TABLE 3B-continued

{124,129,133} {124,129,134} {124,129,135} {124,129,136} {124,129,137} {124,129,138} {124,129,139}
{124,130,131} {124,130,132} {124,130,133} {124,130,134} {124,130,135} {124,130,136} {124,130,137}
{124,130,138} {124,130,139} {124,131,132} {124,131,133} {124,131,134} {124,131,135} {124,131,136}
{124,131,137} {124,131,138} {124,131,139} {124,132,133} {124,132,134} {124,132,135} {124,132,136}
{124,132,137} {124,132,138} {124,132,139} {124,133,134} {124,133,135} {124,133,136} {124,133,137}
{124,133,138} {124,133,139} {124,134,135} {124,134,136} {124,134,137} {124,134,138} {124,134,139}
{124,135,136} {124,135,137} {124,135,138} {124,135,139} {124,136,137} {124,136,138} {124,136,139}
{124,137,138} {124,137,139} {124,138,139} {125,126,127} {125,126,128} {125,126,129} {125,126,130}
{125,126,131} {125,126,132} {125,126,133} {125,126,134} {125,126,135} {125,126,136} {125,126,137}
{125,126,138} {125,126,139} {125,127,128} {125,127,129} {125,127,130} {125,127,131} {125,127,132}
{125,127,133} {125,127,134} {125,127,135} {125,127,136} {125,127,137} {125,127,138} {125,127,139}
{125,128,129} {125,128,130} {125,128,131} {125,128,132} {125,128,133} {125,128,134} {125,128,135}
{125,128,136} {125,128,137} {125,128,138} {125,128,139} {125,129,130} {125,129,131} {125,129,132}
{125,129,133} {125,129,134} {125,129,135} {125,129,136} {125,129,137} {125,129,138} {125,129,139}
{125,130,131} {125,130,132} {125,130,133} {125,130,134} {125,130,135} {125,130,136} {125,130,137}
{125,130,138} {125,130,139} {125,131,132} {125,131,133} {125,131,134} {125,131,135} {125,131,136}
{125,131,137} {125,131,138} {125,131,139} {125,132,133} {125,132,134} {125,132,135} {125,132,136}
{125,132,137} {125,132,138} {125,132,139} {125,133,134} {125,133,135} {125,133,136} {125,133,137}
{125,133,138} {125,133,139} {125,134,135} {125,134,136} {125,134,137} {125,134,138} {125,134,139}
{125,135,136} {125,135,137} {125,135,138} {125,135,139} {125,136,137} {125,136,138} {125,136,139}
{125,137,138} {125,137,139} {125,138,139} {126,127,128} {126,127,129} {126,127,130} {126,127,131}
{126,127,132} {126,127,133} {126,127,134} {126,127,135} {126,127,136} {126,127,137} {126,127,138}
{126,127,139} {126,128,129} {126,128,130} {126,128,131} {126,128,132} {126,128,133} {126,128,134}
{126,128,135} {126,128,136} {126,128,137} {126,128,138} {126,128,139} {126,129,130} {126,129,131}
{126,129,132} {126,129,133} {126,129,134} {126,129,135} {126,129,136} {126,129,137} {126,129,138}
{126,129,139} {126,130,131} {126,130,132} {126,130,133} {126,130,134} {126,130,135} {126,130,136}
{126,130,137} {126,130,138} {126,130,139} {126,131,132} {126,131,133} {126,131,134} {126,131,135}
{126,131,136} {126,131,137} {126,131,138} {126,131,139} {126,132,133} {126,132,134} {126,132,135}
{126,132,136} {126,132,137} {126,132,138} {126,132,139} {126,133,134} {126,133,135} {126,133,136}
{126,133,137} {126,133,138} {126,133,139} {126,134,135} {126,134,136} {126,134,137} {126,134,138}
{126,134,139} {126,135,136} {126,135,137} {126,135,138} {126,135,139} {126,136,137} {126,136,138}
{126,136,139} {126,137,138} {126,137,139} {126,138,139} {127,128,129} {127,128,130} {127,128,131}
{127,128,132} {127,128,133} {127,128,134} {127,128,135} {127,128,136} {127,128,137} {127,128,138}
{127,128,139} {127,129,130} {127,129,131} {127,129,132} {127,129,133} {127,129,134} {127,129,135}
{127,129,136} {127,129,137} {127,129,138} {127,129,139} {127,130,131} {127,130,132} {127,130,133}
{127,130,134} {127,130,135} {127,130,136} {127,130,137} {127,130,138} {127,130,139} {127,131,132}
{127,131,133} {127,131,134} {127,131,135} {127,131,136} {127,131,137} {127,131,138} {127,131,139}
{127,132,133} {127,132,134} {127,132,135} {127,132,136} {127,132,137} {127,132,138} {127,132,139}
{127,133,134} {127,133,135} {127,133,136} {127,133,137} {127,133,138} {127,133,139} {127,134,135}
{127,134,136} {127,134,137} {127,134,138} {127,134,139} {127,135,136} {127,135,137} {127,135,138}
{127,135,139} {127,136,137} {127,136,138} {127,136,139} {127,137,138} {127,137,139} {127,138,139}
{128,129,130} {128,129,131} {128,129,132} {128,129,133} {128,129,134} {128,129,135} {128,129,136}
{128,129,137} {128,129,138} {128,129,139} {128,130,131} {128,130,132} {128,130,133} {128,130,134}
{128,130,135} {128,130,136} {128,130,137} {128,130,138} {128,130,139} {128,131,132} {128,131,133}
{128,131,134} {128,131,135} {128,131,136} {128,131,137} {128,131,138} {128,131,139} {128,132,133}
{128,132,134} {128,132,135} {128,132,136} {128,132,137} {128,132,138} {128,132,139} {128,133,134}
{128,133,135} {128,133,136} {128,133,137} {128,133,138} {128,133,139} {128,134,135} {128,134,136}
{128,134,137} {128,134,138} {128,134,139} {128,135,136} {128,135,137} {128,135,138} {128,135,139}
{128,136,137} {128,136,138} {128,136,139} {128,137,138} {128,137,139} {128,138,139} {129,130,131}
{129,130,132} {129,130,133} {129,130,134} {129,130,135} {129,130,136} {129,130,137} {129,130,138}
{129,130,139} {129,131,132} {129,131,133} {129,131,134} {129,131,135} {129,131,136} {129,131,137}
{129,131,138} {129,131,139} {129,132,133} {129,132,134} {129,132,135} {129,132,136} {129,132,137}
{129,132,138} {129,132,139} {129,133,134} {129,133,135} {129,133,136} {129,133,137} {129,133,138}
{129,133,139} {129,134,135} {129,134,136} {129,134,137} {129,134,138} {129,134,139} {129,135,136}
{129,135,137} {129,135,138} {129,135,139} {129,136,137} {129,136,138} {129,136,139} {129,137,138}
{129,137,139} {129,138,139} {130,131,132} {130,131,133} {130,131,134} {130,131,135} {130,131,136}
{130,131,137} {130,131,138} {130,131,139} {130,132,133} {130,132,134} {130,132,135} {130,132,136}
{130,132,137} {130,132,138} {130,132,139} {130,133,134} {130,133,135} {130,133,136} {130,133,137}
{130,133,138} {130,133,139} {130,134,135} {130,134,136} {130,134,137} {130,134,138} {130,134,139}
{130,135,136} {130,135,137} {130,135,138} {130,135,139} {130,136,137} {130,136,138} {130,136,139}
{130,137,138} {130,137,139} {130,138,139} {131,132,133} {131,132,134} {131,132,135} {131,132,136}
{131,132,137} {131,132,138} {131,132,139} {131,133,134} {131,133,135} {131,133,136} {131,133,137}
{131,133,138} {131,133,139} {131,134,135} {131,134,136} {131,134,137} {131,134,138} {131,134,139}
{131,135,136} {131,135,137} {131,135,138} {131,135,139} {131,136,137} {131,136,138} {131,136,139}
{131,137,138} {131,137,139} {131,138,139} {132,133,134} {132,133,135} {132,133,136} {132,133,137}
{132,133,138} {132,133,139} {132,134,135} {132,134,136} {132,134,137} {132,134,138} {132,134,139}
{132,135,136} {132,135,137} {132,135,138} {132,135,139} {132,136,137} {132,136,138} {132,136,139}
{132,137,138} {132,137,139} {132,138,139} {133,134,135} {133,134,136} {133,134,137} {133,134,138}
{133,134,139} {133,135,136} {133,135,137} {133,135,138} {133,135,139} {133,136,137} {133,136,138}
{133,136,139} {133,137,138} {133,137,139} {133,138,139} {134,135,136} {134,135,137} {134,135,138}
{134,135,139} {134,136,137} {134,136,138} {134,136,139} {134,137,138} {134,137,139} {134,138,139}
{135,136,137} {135,136,138} {135,136,139} {135,137,138} {135,137,139} {135,138,139} {136,137,138}
{136,137,139} {136,138,139} {137,138,139}

In some embodiments, when an ALK polypeptide includes a first sequence and a second sequence, or a first sequence, a second sequence, and a third sequence, as described above, a linker is placed between adjacent sequences. A linker is a linkage or connection between two adjacent sequences in an ALK polypeptide, for which the linker connects the C-terminus of the first sequence to the N-terminus of the second sequence, such that the two sequences are joined to each other in tandem series in an ALK polypeptide. A linker can be a simple covalent bond, e.g., a peptide bond, an amino acid spacer, a synthetic polymer, e.g., a polyethylene glycol (PEG) polymer, or any kind of bond created from a chemical reaction, e.g. chemical conjugation. The peptide bond can be formed from synthetic means through a conventional organic chemistry reaction well-known in the art, or by natural production from a host cell, wherein a polynucleotide sequence encoding the first and second sequences in tandem series in an ALK polypeptide can be directly transcribed and translated into a contiguous polypeptide by the necessary molecular machineries, e.g., DNA polymerase and ribosome, in the host cell. In some embodiments, a linker is an amino acid spacer including 1-200 amino acids. Suitable peptide spacers are known in the art, and include, for example, peptide linkers containing flexible amino acid residues such as glycine and serine. In certain embodiments, a spacer can contain motifs, e.g., multiple or repeating motifs, of GS, GGS, GGGGS (SEQ ID NO: 71), GGSG (SEQ ID NO: 72), or SGGG (SEQ ID NO: 73). In certain embodiments, a spacer can contain 2 to 12 amino acids including motifs of GS, e.g., GS, GSGS (SEQ ID NO: 74), GSGSGS (SEQ ID NO: 75), GSGSGSGS (SEQ ID NO: 76), GSGSGSGSGS (SEQ ID NO: 77), or GSGSGSGSGSGS (SEQ ID NO: 78). In certain other embodiments, a spacer can contain 3 to 12 amino acids including motifs of GGS, e.g., GGS, GGSGGS (SEQ ID NO: 79), GGSGGSGGS (SEQ ID NO: 80), and GGSGGSGGSGGS (SEQ ID NO: 81). In yet other embodiments, a spacer can contain 4 to 12 amino acids including motifs of GGSG (SEQ ID NO: 72), e.g., GGSG (SEQ ID NO: 72), GGSGGGSG (SEQ ID NO: 82), or GGSGGGSGGGSG (SEQ ID NO: 83). In other embodiments, a spacer can contain motifs of GGGGS (SEQ ID NO: 71), e.g., GGGGSGGGGSGGGGS (SEQ ID NO: 84). In other embodiments, a spacer can also contain amino acids other than glycine and serine, e.g., GENLYFQSGG (SEQ ID NO: 85), SACYCELS (SEQ ID NO: 86), RSIAT (SEQ ID NO: 87), RPACKIPNDLKQKVMNH (SEQ ID NO: 88), GGSAGGSGSGSSGGSSGASGTGTAGGTGSGSGTGSG (SEQ ID NO: 89), AAANSSIDLISVPVDSR (SEQ ID NO: 90), or GGSGGGSEGGGSEGGGSEGGGSEGGGSEGGGSGGGS (SEQ ID NO: 91).

In the case that a linker is a synthetic polymer, e.g., a PEG polymer, the polymer can be functionalized with reactive chemical functional groups at each end to react with the terminal amino acids at the connecting ends of the sequences in an ALK polypeptide. In the case that a linker (except peptide bond mentioned above) is made from a chemical reaction, chemical functional groups, e.g., amine, carboxylic acid, ester, azide, or other functional groups commonly used in the art, can be attached synthetically to the C-terminus of one sequence and the N-terminus of another sequence, respectively. The two functional groups can then react to through synthetic chemistry means to form a chemical bond, thus connecting the two sequences together. Such chemical conjugation procedures are routine for those skilled in the art.

In some embodiments, an ALK polypeptide described herein may be covalently linked to one or more moieties or conjugates which enhance the activity, cellular distribution, and/or cellular uptake of the resulting ALK polypeptide. Typical conjugate groups include, but are not limited to, cholesterol moieties, lipid moieties, carbohydrate moieties, peptides, antibodies, biotin, phenazine, folate, phenanthridine, anthraquinone, acridine, and other small molecules.

In some embodiments, an immunogenic composition described herein may further include one or more immunomodulators, adjuvants, and/or anti-cancer agents (e.g., tyrosine kinase inhibitors, e.g., Crizotinib, Ceritinib, Alectinib, or Brigatinib). In some embodiments, an immunogenic composition described herein may be free of immunomodulators, adjuvants, and/or anti-cancer agents.

Interbilayer Crosslinked Multilamellar Lipid Vesicles

In some embodiments, an immunogenic composition includes (a) a multilamellar lipid vesicle having crosslinks between lipid bilayers; and (b) one or more ALK polypeptides described herein. Stabilized multilamellar lipid vesicles having crosslinks between lipid bilayers (i.e., interbilayer-crosslinked multilamellar vesicles or ICMVs) can be used to deliver one or more ALK polypeptides. Multilamellar lipid vesicles are stabilized by linking adjacent (or apposed) lipid bilayers to one another and may include ALK polypeptides covalently conjugated to a lipid in the vesicle. As used herein, a multilamellar vesicle is a nano- or microsphere having a shell that includes two or more concentrically arranged lipid bilayers. As used herein, adjacent or apposed lipid bilayers (or lipid bilayer surfaces) refer to bilayers or surfaces that are in close proximity to each other but that are otherwise distinct and typically physically separate. This term does not typically mean the relationship between the two monolayers of a single bilayer. The present invention also incorporates by reference herein the disclosures of U.S. Pat. No. 8,747,869 (see, e.g., column 1, line 43 through column 5, line 40, and column 8, line 9 through column 35, line 69) and 9,149,432 (see, e.g., column 11, line 32 through column 35, line 32), which are directed to compositions, methods of synthesis, and methods of use of stabilized multilamellar vesicles.

The ICMVs are formed by crosslinking headgroups of adjacent lipid bilayers within multilamellar vesicles in which one or more ALK polypeptides have been covalently conjugated. In some embodiments, the ALK polypeptides may be conjugated to a lipid in the vesicle, e.g., within the vesicle core, within the vesicle walls, or on an outer surface of the vesicle. The stabilized nature of these vesicles and the covalent conjugation of one or more ALK polypeptides allow them to incorporate higher amounts of the ALK polypeptides and to retain such protein over a longer time period, as compared to simple liposomes or lipid coated nanoparticles or microparticles. Their sustained release kinetics, particularly in the presence of serum, make them useful in in vivo delivery of ALK polypeptides for which a slow, steady and prolonged release is desirable or for which slow release in the extracellular environment but rapid release within cells is desirable. In some embodiments, the ICMVs including one or more conjugated ALK polypeptides also include immunomodulators. The ICMVs exhibit rapid release in the presence of endolysosomal lipases.

The amount of an ALK polypeptide in the vesicles may vary and may depend on the nature of the protein. In some embodiments, 10-500 µg of the ALK polypeptide per mg of lipid may be incorporated into the vesicles of the invention. In some embodiments, the vesicles may include about 10 µg of the ALK polypeptide, or about 20 µg of the ALK polypeptide, or about 50 μg of the ALK polypeptide, or about 100 μg of the ALK polypeptide, or about 150 μg of the ALK polypeptide, or about 200 μg of the ALK polypeptide, or about 250 μg of the ALK polypeptide, or about 300 μg of the ALK polypeptide, or about 325 μg of the ALK polypeptide, or about 350 μg of the ALK polypeptide, or about 375 μg of the ALK polypeptide, or about 400 μg of the ALK polypeptide, or about 500 μg of the ALK polypeptide, per mg of lipid. In other embodiments, the vesicles may include 10-20 μg of the ALK polypeptide per mg of lipid, or 15-60 μg of the ALK polypeptide per mg of lipid, or 50-200 μg of the ALK polypeptide per mg of lipid, or 100-300 μg of the ALK polypeptide per mg of lipid, or 200-400 μg of the ALK polypeptide per mg of lipid, or 300-500 μg of the ALK polypeptide per mg of lipid.

The number of lipid bilayers in the ICMVs may vary from about 2-30 (e.g., 2-15, 5-20, 10-30). Accordingly, in various embodiments, the number of layers may be 2, 3, 4, 5, 6, 7, 8, 9, 10, 11, 12, 13, 14, 15 or more. The bilayers are typically composed of lipids having hydrophilic heads and hydrophobic tails that are arranged in a manner similar to a cell membrane (i.e., with the hydrophilic heads exposed to typically an aqueous environment and the hydrophobic tails buried in the bilayer). The ICMVs are stabilized via crosslinks between their lipid bilayers. As used herein, this means that at least two lipid bilayers in the shell of the vesicle are crosslinked to each other. The crosslinked bilayers are typically those that are apposed or adjacent to each other. Most or all of the lipid bilayers in the shell may be crosslinked to their apposing lipid bilayer in the shell. There may be one or more crosslinks between lipid bilayers. Typically, there will be numerous crosslinks between lipid bilayers. The arrangement and positioning of such crosslinks may be random or non-random. The degree of crosslinks (and thus the resultant stability of the vesicles) will depend upon the proportion of functionalized lipids (or other lipid bilayer components) used to make the vesicles and the crosslinking conditions (including, for example, time of incubation of the vesicles with a crosslinker). It will be understood that the higher the proportion of functionalized lipids (or other lipid bilayer components) in the vesicles, the more crosslinks that will be formed, all other factors and parameters being equal. Similarly, the more favorable the conditions towards crosslinking, the greater degree of crosslinking that will be achieved.

One or more of the lipids used in the synthesis of the vesicles may be functionalized lipids. As used herein, a functionalized lipid is a lipid having a reactive group that can be used to crosslink adjacent bilayers of the multilamellar vesicle (e.g., an ICMV). The bilayer component may be modified to include the reactive group. In some embodiments, the reactive group is one that will react with a crosslinker (or other moiety) to form crosslinks between such functionalized lipids (and thus between lipid bilayers in the vesicle). The reactive group may be located anywhere on the lipid that allows it to contact a crosslinker and be crosslinked to another lipid in an adjacent apposed bilayer. In some embodiments, it is in the head group of the lipid, including for example a phospholipid. An example of a reactive group is a maleimide group. Maleimide groups may be crosslinked to each other in the presence of dithiol crosslinkers such as but not limited to dithiolthrietol (DTT). An example of a functionalized lipid is 1,2-dioleoyl-sn-glycero-3-phosphoethanolamine-N-[4-(p-maleimidophenyl) butyramide, referred to herein as MPB. Another example of a functionalized lipid is 1,2-distearoyl-sn-glycero-3-phosphoethanolamine-N-[maleimide(polyethylene glycol)2000] (also referred to as maleimide-PEG 2k-PE). Another example of a functionalized lipid is dioleoyl-phosphatidylethanolamine 4-(N-maleimidomethyl)-cyclohexane-1-carboxylate (DOPE-mal). It is to be understood that the invention contemplates the use of other functionalized lipids, other functionalized lipid bilayer components, other reactive groups, and other crosslinkers. In addition to the maleimide groups, other examples of reactive groups include, but are not limited, to other thiol reactive groups, amino groups such as primary and secondary amines, carboxyl groups, hydroxyl groups, aldehyde groups, alkyne groups, azide groups, carbonyls, haloacetyl (e.g., iodoacetyl) groups, imidoester groups, N-hydroxysuccinimide esters, sulfhydryl groups, and pyridyl disulfide groups.

The stabilized multilamellar lipid vesicles having crosslinks between lipid bilayers (i.e., interbilayer-crosslinked multilamellar vesicles or ICMVs) include one or more ALK polypeptides conjugated to a lipid of the vesicle. As used herein, "conjugated" refers to covalent attachment or crosslink of the ALK polypeptide to the lipid of the stabilized multilamellar lipid vesicle (e.g., ICMV). The ALK polypeptide may be covalently attached to the lipid by reaction of complementary reactive groups on the ALK polypeptide and the lipid. The ALK polypeptide and/or lipid may be functionalized to contain the complementary reactive groups or the reactive groups may be a group already present in the ALK polypeptide or lipid. For example, the ALK polypeptide may include or be functionalized to include a thiol group and a covalent linkage may be formed by reaction with a lipid functionalized to include a maleimide group. Alternatively, the reactive group on the ALK polypeptide may be an amine or carboxylic acid and the covalent attachment to the lipid could be an amide bond formed by reaction with an amine or carboxylic acid of the lipid. The ALK polypeptide may be conjugated to the lipid prior to vesicle (e.g., ICMV) synthesis, and therefore may be encapsulated within the vesicle, between the lipid bilayers of the vesicle, or present on the outer surface of the vesicle.

Reactive groups to be used to conjugate the ALK polypeptide to the lipid may be the same as those used to crosslink the bilayers, in which case no additional functionalized lipids (or other functionalized components) are required. As an example, if the vesicles (e.g., ICMVs) include maleimide functionalized lipids, then the functionalized ALK polypeptide may be thiol-functionalized ALK polypeptide. Alternatively, the reactive groups used to stabilize the vesicles may be different from those used to conjugate the ALK polypeptide to the lipid. Those of ordinary skill in the art will appreciate that other modified versions of ALK polypeptide may be used depending on the nature of the reactive group in the functionalized lipid (or component) in the lipid bilayer of the vesicles. Suitable reactive groups include without limitation amino groups such as primary and secondary amines, carboxyl groups, sulfhydryl groups, hydroxyl groups, aldehyde groups, azide groups, carbonyls, maleimide groups, haloacetyl (e.g., iodoacetyl) groups, imidoester groups, N-hydroxysuccinimide ester groups, and pyridyl disulfide groups.

An ALK polypeptide may be functionalized or reactive. As used herein, a functionalized ALK polypeptide is an ALK polypeptide that includes a reactive group that can be used to conjugate the ALK polypeptide to a lipid (e.g., a functionalized lipid). The ALK polypeptide may be modified to include the reactive group. An ALK polypeptide used in the synthesis of the stabilized multilamellar lipid vesicles (e.g., ICMVs) including one or more ALK polypeptides may be functionalized ALK polypeptide. In some embodiments, the reactive group in an ALK polypeptide is one that will react to form a covalent attachment to a lipid of the stabilized multilamellar lipid vesicle (e.g., ICMV). The reactive group may be located anywhere on the ALK polypeptide that allows it to be conjugated to a lipid. An example of a reactive group is a thiol group. Other functionalized ALK polypeptides and other reactive groups may also be used. In addition to the thiol group, other examples of reactive groups include, but are not limited to, other thiol reactive groups, amino groups such as primary and secondary amines, carboxyl groups, hydroxyl groups, aldehyde groups, alkyne groups, azide groups, carbonyls, haloacetyl (e.g., iodoacetyl) groups, imidoester groups, N-hydroxysuccinimide ester groups, sulfhydryl groups, and pyridyl disulfide groups.

In some embodiments, an stabilized multilamellar lipid vesicle (e.g., ICMV) is functionalized with a maleimide reactive group, which can react with a cysteine in an ALK polypeptide to form a covalent attachment between the ALK polypeptide and the multilamellar lipid vesicle. In some embodiments, the cysteine in the ALK polypeptide is a naturally occurring cysteine or a non-naturally occurring cysteine (i.e., a cysteine that is introduced into the ALK polypeptide using conventional techniques in the art, e.g., PCR or site-directed mutagenesis). In some embodiments, the cysteine in the ALK polypeptide is a terminal-cysteine. A terminal-cysteine refers to a cysteine that is located near the N- or C-terminus of the ALK polypeptide. In some embodiments, for an ALK polypeptide that is 40-230 amino acids in length, a terminal-cysteine refers to a cysteine that is located within 10 amino acid residues of the amino terminus (i.e., at amino acid positions 1 through 10) and/or within 10 amino acid residues of the carboxy terminus (i.e., at amino acids (n-10) through n, where n represents the number of amino acid residues in the ALK polypeptide). Thus, a terminal-cysteine may occupy positions 1, 2, 3, 4, 5, 6, 7, 8, 9, 10, n-10, n-9, n-8, n-7, n-6, n-5, n-4, n-3, n-2, n-1 and/or n, where 1 represents the residue at the amino terminus and n represents the residue at the carboxy terminus. In some embodiments, for an ALK polypeptide that is 20-39 amino acids in length, a terminal-cysteine refers a cysteine that is located within 5 amino acid residues of the amino terminus (i.e., at amino acid positions 1 through 5) and/or within 5 amino acid residues of the carboxy terminus (i.e., at amino acids (n-5) through n, where n represents the number of amino acid residues in the ALK polypeptide). In some embodiments, for an ALK polypeptide that is 8-19 amino acids in length, a terminal-cysteine refers a cysteine that is located within 2 amino acid residues of the amino terminus (i.e., at amino acid positions 1 or 2) and/or within 2 amino acid residues of the carboxy terminus (i.e., at amino acids (n-2) through n, where n represents the number of amino acid residues in the ALK polypeptide).

An average of 1-2 molecules of added reactive group (e.g., a thiol) per ALK polypeptide molecule is desirable for efficient conjugation of the ALK polypeptide to the lipid. However, for some ALK polypeptides, addition of more reactive groups (e.g., a thiol molecule) per ALK polypeptide molecule may result in increased conjugation. As such, addition of 2, 3, 4, 5, or more reactive groups (e.g., thiols) per ALK polypeptide molecule is encompassed by the invention. As an example, ALK polypeptides may be conjugated to lipids by reacting a thiol-functionalized ALK polypeptide with a maleimide functionalized lipid. Thiol-functionalized ALK polypeptides may be prepared using methods known in the art, e.g., 2-iminothiolane-HCl (Traut's reagent), N-succinimidyl S-acetylthioacetate hydrochloride (SATA), or N-Succinimidyl S-acetyl(thiotetraethylene glycol). For example, treatment of an ALK polypeptide containing a primary amine with 10, 20, 30, 40, 50, 60, 70, 80, or more molar equivalents of Traut's reagent at room temperature (e.g., for 1 hour) provides thiol-functionalized ALK polypeptides. An average of 1-2 molecules of added thiol per ALK polypeptide molecule is desirable for efficient conjugation. However, for some ALK polypeptides, addition of more thiol molecules per ALK polypeptide molecule may result in increased conjugation. As such, addition of 2, 3, 4, 5, or more thiol molecules per ALK polypeptide molecule is encompassed by the invention.

Amphiphilic Conjugates

In some embodiments, an immunogenic composition includes an amphiphilic conjugate. An amphiphilic conjugate refers to a conjugate that includes an ALK polypeptide covalently linked to an albumin-binding domain (e.g., a lipid). In some embodiments, an amphiphilic conjugate includes an ALK polypeptide that is covalently linked to an albumin-binding domain (e.g., a lipid) directly. In some embodiments, an amphiphilic conjugate includes an ALK polypeptide that is covalently linked to an albumin-binding domain (e.g., a lipid) through a linker. For amphiphilic conjugates that include an ALK polypeptide conjugated to an albumin-binding domain either directly or through a linker, the albumin-binding domain binds to endogenous albumin, which prevents the amphiphilic conjugate from rapidly flushing into the bloodstream and instead re-targets them to lymphatics and draining lymph nodes where they accumulate due to filtering of albumin by antigen presenting cells. In some embodiments, an amphiphilic conjugate may spontaneously insert itself into lipid bilayers of a multilamellar lipid vesicle having crosslinks between lipid bilayers (e.g., an ICMV). In some embodiments, an amphiphilic conjugate may be further linked to a targeting agent. A targeting agent may be a therapeutic, prophylactic, or diagnostic agent. For example, a targeting agent may be an antibody, a protein, a peptide, or a small molecule drug that can target the amphiphilic conjugate to a specific cell or tissue. For example, a targeting agent may be a tumor-specific targeting agent (e.g., a tumor-specific antibody or chemotherapeutic agent) that targets the amphiphilic conjugate to a tumor (e.g., a tumor that expresses ALK or a portion thereof (e.g., an ALK$^+$ tumor).

In some embodiments, for amphiphilic conjugates that include an ALK polypeptide conjugated to an albumin-binding domain either directly or through a linker, the albumin-binding domain may be linear, branched, or cyclic. In some embodiments, the albumin-binding domain may be a lipid. In some embodiments, the albumin-binding domain may be a diacyl lipid (e.g., a diacyl lipid including 5-30 carbon units, which may be saturated, unsaturated, or combinations thereof). In some embodiments, the albumin-binding domain may be a fatty acid lipid (e.g., a fatty acid lipid including 5-30 carbon units, which may be saturated, unsaturated, or combinations thereof). In some embodiments, the albumin-binding domain (e.g., a lipid) may be a fatty acid derivative, e.g., a fatty acid ester, a fatty acid amide, a fatty acid thioester, cholesterol, a cholesterol derivative, or a steroid acid. In some embodiments, the albumin-binding domain (e.g., a lipid) contains at least 8 or more carbon units. In some embodiments, the albumin-binding domain is a peptide, e.g., a peptide having the sequence DICLPRWGCLW (SEQ ID NO: 92), which is described in U.S. Pat. No. 7,635,749 and US Patent Publication No. US20050287153.

In some embodiments, for amphiphilic conjugates that include an ALK polypeptide conjugated to an albumin-binding domain (e.g., a lipid) through a linker, the linker may be selected from the group consisting of polymers, a string of amino acids (e.g., a string of hydrophilic amino acids, such as serine, threonine, cysteine, tyrosine, asparagine, glutamine, aspartic acid, glutamic acid, lysine, arginine, histidine, or combinations thereof), nucleic acids (e.g., an oligonucleotide, e.g., an oligonucleotide including "n" guanines, wherein n is 1-10), polysaccharides (e.g., dextran), or a combination thereof. In some embodiments, the linker includes consecutive polyethylene glycol units. In some embodiments, the linker includes "N" consecutive polyethylene glycol units, wherein N is between 20 and 80, between 30 and 80, between 40 and 60, or between 45 and 55 (e.g., 48 polyethylene glycol units).

In some embodiments, an ALK polypeptide in an amphiphilic conjugate includes at least 6 contiguous amino acids from a sequence of any one of SEQ ID NOs: 1-66 and 93-139 and does not include a sequence of any one of SEQ ID NOs: 67-70 and 140-145, In some embodiments, an ALK polypeptide in an amphiphilic conjugate includes a first sequence selected from any one of SEQ ID NOs: 1-66 and a second sequence selected from any one of SEQ ID NOs: 1-66, wherein the first and second sequences are different, wherein the first and second sequences include a pair of sequences of SEQ ID NOs recited in Table 2A, and wherein the ALK polypeptide does not include a sequence of any one of SEQ ID NOs: 67-70 and 140-145. In some embodiments, an ALK polypeptide in an amphiphilic conjugate includes a first sequence selected from any one of SEQ ID NOs: 1-66, a second sequence selected from any one of SEQ ID NOs: 1-66, and a third sequence selected from any one of SEQ ID NOs: 1-66, wherein the first, second, and third sequences are different, wherein the first, second, and third sequences include a set of sequences of SEQ ID NOs recited in Table 3A, and wherein the ALK polypeptide does not include a sequence of any one of SEQ ID NOs: 67-70 and 140-145.

In some embodiments, an ALK polypeptide in an amphiphilic conjugate includes at least 6 contiguous amino acids from a sequence of any one of SEQ ID NOs: 93, 96, 100, 106, 111-116, and 121-139 and does not include a sequence of any one of SEQ ID NOs: 67-70 and 140-145, In some embodiments, an ALK polypeptide in an amphiphilic conjugate includes a first sequence selected from any one of SEQ ID NOs: 93, 96, 100, 106, 111-116, and 121-139 and a second sequence selected from any one of SEQ ID NOs: 93, 96, 100, 106, 111-116, and 121-139, wherein the first and second sequences are different, wherein the first and second sequences include a pair of sequences of SEQ ID NOs recited in Table 2B, and wherein the ALK polypeptide does not include a sequence of any one of SEQ ID NOs: 67-70 and 140-145. In some embodiments, an ALK polypeptide in an amphiphilic conjugate includes a first sequence selected from any one of SEQ ID NOs: 93, 96, 100, 106, 111-116, and 121-139, a second sequence selected from any one of SEQ ID NOs: 93, 96, 100, 106, 111-116, and 121-139, and a third sequence selected from any one of SEQ ID NOs: 93, 96, 100, 106, 111-116, and 121-139, wherein the first, second, and third sequences are different, wherein the first, second, and third sequences include a set of sequences of SEQ ID NOs recited in Table 3B, and wherein the ALK polypeptide does not include a sequence of any one of SEQ ID NOs: 67-70 and 140-145.

Partner Proteins

In some embodiments, an ALK polypeptide described herein may be fused to a partner protein, or a fragment thereof (i.e., an extracellular domain or a fragment thereof). A partner protein refers to a protein that ALK translocates next to in a chromosomal translocation. For example, within anaplastic large cell lymphomas (ALCLs), nearly 70% of the cases carry the t(2;5)(p23;q35) chromosomal translocation that juxtaposes ALK locus to nucleophosmin (NPM) gene locus, generating a fusion protein of NPM and the cytoplasmic domain of ALK. Examples of partner proteins include, but are not limited to, a nucleophosmin (NPM) protein, a tropomyosin 3 (TPM3) protein, a tropomyosin 4 (TPM4) protein, a TRK-fused gene (TFG) protein, a 5-Aminoimidazole-4-carboxamide ribonucleotide formyltransferase/IMP cyclohydrolase (ATIC) protein, a clathrin heavy chain-like 1 (CLTC1) protein, a moesin (MSN) protein, an ALK lymphoma oligomerization partner on chromosome 17 (ALO17) protein, a RAN binding protein 2 (RANBP2), a non-muscle myosin heavy chain (MYH9) protein, a cysteinyl-tRNA synthetase (CARS) protein, a SEC31 homologue A (SEC31 L1) protein, a transforming growth factor (TGF) protein, and an echinoderm microtubule-associated protein-like 4 (EML4) protein, and a fragment thereof, such as an extracellular domain or a fragment of the extracellular domain thereof. A partner protein may be fused to the N- or C-terminus of an ALK polypeptide described herein.

Immunomodulators

In some embodiments, an immunogenic composition described herein may include one or more immunomodulators. An immunomodulator is an agent that stimulates (i.e., an immunostimulator) or inhibits (i.e., an immunoinhibitor) an immune response in a subject to whom it is administered, whether alone or in combination with another agent. In some embodiments, immunomodulators as described herein specifically exclude CureTech's anti-PD-1 antibody CT-011 as described in Patent and Patent Application Publication Nos.: U.S. Pat. No. 8,686,119, WO 2013014668, and WO 2009101611.

Examples of immunomodulators include, but are not limited to, an anti-CTLA-4 antibody, an anti-CD40 antibody, a cyclophosphamide (CPM), an AMD3100, an anti-LAG-3/CD223 antibody, an anti-B7-H5 antibody, an anti-OX40 antibody, an anti-CD28 antibody, an anti-GITR antibody, an anti-4-1BB/CD137 antibody, a 4-1 BB ligand, an anti-BTLA antibody, an anti-TIM-3/HAVCR2 antibody, an anti-KIR antibody, an anti-Flt3/CD135 antibody, an anti-FasL antibody, an anti-CD25 antibody, an GM-CSF, an anti-GM-CSF-receptor (R) antibody, an IL-2, an anti-IL-2-R antibody, an IL-7, an anti-IL-7-R antibody, an IL-21, an anti-IL-21-R antibody, an IL-12, an anti-IL-12-R antibody, an IL-15, an anti-IL-15-R antibody, an IL-18, an anti-IL-18-R antibody, an anti-IDO antibody, an ipilimumab, a crizotinib, a ceritinib, an alectinib, a brigatinib, a celecoxib, a SOCS-1 inhibitor, a heat shock protein (HSP), a HSP inhibitor, a polyinosinic:polycytidylic acid (poly I:C), and an anti-galectin-1 antibody. In some embodiments, one or more immunomodulators are selected from the group consisting of an anti-CTLA-4 antibody, an anti-CD40 antibody, a cyclophosphamide (CPM), and an AMD3100.

Immunostimulators

As used herein, an immunostimulator is an agent that stimulates an immune response (including enhancing a pre-existing immune response) in a subject to whom it is administered, whether alone or in combination with another agent. Examples include antigens, adjuvants (e.g., TLR ligands such as imiquimod and resiquimod, imidazoquinolines, nucleic acids including an unmethylated CpG dinucleotide, monophosphoryl lipid A (MPLA) or other lipopolysaccharide derivatives, single-stranded or double-stranded RNA, flagellin, muramyl dipeptide), cytokines including interleukins (e.g., IL-2, IL-7, IL-15 (or superagonist/mutant forms of these cytokines), IL-12, IFN-gamma, IFN-alpha, GM-CSF, FLT3-ligand, etc.), AMD3100, immunostimulatory antibodies (e.g., anti-CD40 antibody, anti-CTLA-4 antibody, anti-CD28 antibody, anti-CD3 antibody, or single chain/antibody fragments of these molecules), and PD-1 inhibitors.

The term "PD-1 inhibitor" refers to any agent that inhibits the molecular pathway of PD-1. For example, a PD-1 inhibitor can be an antibody that binds to the PD-1 to block ligand binding to PD-1 (e.g., an anti-PD-1 antibody, nivolumab, and pembrolizumab). A PD-1 inhibitor can also be an antibody that binds to PD-L1 or PD-L2, each of which is a ligand of PD-1, to prevent it from binding to PD-1 (e.g., an anti-PD-L1 antibody (e.g., BMS-936559 and MPDL3280A) and an anti-PD-L2 antibody (see, e.g., Patent Application Publication No.: WO 2010036959 (see, e.g., p. 79, ¶ [0253] through p. 101, ¶ [0296]))).

Examples of anti-PD-1 antibodies include nivolumab, pembrolizumab, as well as antibodies described in the following Patent and Patent Application Publication Nos.: WO 2013173223 (see, e.g., p. 3, lines 19-21, p. 8, line 25 through p. 9, line 30, p. 40, line 9 through p. 50, line 24), U.S. Pat. No. 8,008,449 (see, e.g., column 69, Table 2, column 63, line 55 through column 86, line 15), U.S. Pat. No. 8,552,154 (see, e.g., column 67, Table 4, column 57, line 35 through column 74, line 43), U.S. Pat. No. 8,735,553 (see, e.g., column 35, Table 22, column 31, Table 20, column 13, line 9 through column 36, line 62), WO 2004056875 (see, e.g., p. 37, Table 6, p. 33, ¶ [0106] through p. 43, ¶ [0137]), U.S. Pat. No. 7,488,802 (see, e.g., column 22, Tables 6 and 7, column 19, line 62 through column 25, line 4), US 20140294852 (see, e.g., p. 37, Table 2, p. 34, ¶ [0525] through p. 40, ¶[0585]), U.S. Pat. No. 8,779,105 (see, e.g., column 69, Table 2, column 63, line 55 through column 86, line 11), U.S. Pat. No. 8,741,295 (see, e.g., column 18, line 1 through column 24, line 60), EP 2535354 (see, e.g., p. 23, Table IV, p. 23, line 1 through p. 28, line 35), U.S. Pat. No. 8,168,757 (see, e.g., column 34, line 36 through column 48, line 2), US 20130095098 (see, e.g., p. 12, ¶ [0165] through p. 14, ¶ [0188]), WO 2010029435 (see, e.g., p. 14, Example 1, p. 17, Example 2, pp. 26-28), WO 2014100079 (see, e.g., p. 39, ¶ [00155] through p. 45, ¶ [00174]), U.S. Pat. No. 7,943,743 (see, e.g., column 67, Tables 2 and 3, column 61, line 7 through column 74, line 51), EP 2170959 (see, e.g., p. 26, Table V, p. 16, line 39 through p. 28, line 2), WO 2008156712 (see, e.g., p. 56, Table V, pp. 40-57), and U.S. Pat. No. 8,217,149 (see, e.g., column 99, line 6 through column 118, line 15), each of which is incorporated herein by reference in its entirety. In certain embodiments, the anti-PD-1 antibody has the sequence of nivolumab (see, e.g., FIGS. 4a, 4b, and 9 of U.S. Pat. No. 8,008,449) or pembrolizumab (see, e.g., Patent Application Publication No.: US 2011/0008369). Anti-PD-1 antibodies as described herein specifically exclude CureTech's anti-PD-1 antibody CT-011 as described in Patent and Patent Publication Nos.: U.S. Pat. No. 8,686,119, WO 2013014668, and WO 2009101611.

Examples of anti-PD-L1 antibodies include BMS-936559, MPDL3280A, as well as antibodies described in the following Patent and Patent Application Publication Nos.: U.S. Pat. No. 8,552,154 (see, e.g., column 57, line 35 through column 69, line 16), WO 2014055897 (see, e.g., p. 50, ¶ [00190] through p. 58, ¶ [00219]), WO 2013079174 (see, e.g., p. 48, line 15 through p. 68, line 31), U.S. Pat. No. 8,217,149 (see, e.g., column 99, line 5 through column 118, line 15), U.S. Pat. No. 7,943,743 (see, e.g., column 61, line 9 through column 76, line 45), WO 2014100079 (see, e.g., p. 39, ¶ [00155] through p. 45, ¶ [00175]), U.S. Pat. No. 8,552,154 (see, e.g., column 57, line 35 through column 75, line 13), and U.S. Pat. No. 8,741,295 (see, e.g., column 18, line 32 through column 24, line 60), each of which is incorporated herein by reference in its entirety.

Examples of anti-CD40 antibodies include antibodies described in the following Patent and Patent Application Publication Nos.: US 20030059427 (see, e.g., p. 15, ¶ [0157] through p. 20, ¶ [0212]), WO 2013034904 (see, e.g., p. 58, line 4 through p. 102, line 20), WO 2003029296 (see, e.g., p. 30, line 20 through p. 34, line 16), U.S. Pat. No. 8,637,032 (see, e.g., column 252, line 55 through column 254, line 37), WO 2002028905 (see, e.g., p. 20, line 18 through p. 32, line 30), U.S. Pat. No. 8,778,345 (see, e.g., column 48, line 31 through column 54, line 38), WO 1997031025 (see, e.g., p. 14, line 6 through p. 31, line 26), WO 2012125569 (see, e.g., p. 25, line 33 through p. 27, line 14), WO 2011123489 (see, e.g., p. 93, ¶ [00339] through p. 109, ¶ [00145]), CA 2544949 (see, e.g., p. 78, line 26 through p. 122, line 21), WO 2014070934 (see, e.g., p. 86, line 4 through p. 103, line 4), US 20140093497 (see, e.g., p. 12, ¶ [0112] through p. 13, ¶ [0118]), WO 2010104761 (see, e.g., p. 37, line 3 through p. 66, line 29), U.S. Pat. No. 8,591,900 (see, e.g., column 60, line 14 through column 80, line 29), WO 2007124299 (see, e.g., 68, line 29 through p. p. 88, line 17), U.S. Pat. No. 7,445,780 (see, e.g., column 22, line 29 through column 36, line 39), WO 2006073443 (see, e.g., p. 82, line 6 through p. 89, line 12), WO 2005044294 (see, e.g., p. 137, line 19 through p. 158, line 15), U.S. Pat. No. 5,677,165 (see, e.g., column 11, line 45 through column 18, line 6), WO 2001083755 (see, e.g., p. 39, line 4 through p. 47, line 2), US 20080057070 (see, e.g., p. 26, ¶ [0176] through p. 47, ¶ [0296]), U.S. Pat. No. 7,172,759 (see, e.g., column 9, line 5 through column 12, line 58), WO 2006128103 (see, e.g., p. 75, ¶ [00244] through p. 84, ¶ [000255]), WO 2001016180 (see, e.g., p. 79, line 21 through p. 89, line 14), WO 2003040170 (see, e.g., p. 76, ¶ [0248] through p. 141, ¶ [0239]), U.S. Pat. No. 6,312,693 (see, e.g., column 8, line 51 through column 34, line 45), U.S. Pat. No. 8,492,531 (see, e.g., column 47, line 46 through column 58, line 31), U.S. Pat. No. 8,551,485 (see, e.g., column 78, line 15 through column 85, line 7), U.S. Pat. No. 6,838,261 (see, e.g., column 26, line 10 through column 34, line 26), EP 2243492 (see, e.g., p. 26, ¶ [0144] through p. 37, ¶ [0219]), and EP 2011802 (see, e.g., p. 12, ¶ [0047] through p. 40, ¶ [0127]), each of which is incorporated herein by reference in its entirety.

Examples of anti-CD40 antibodies include antibodies described in the following Patent and Patent Application Publication Nos.: US 20030059427 (see, e.g., p. 15, ¶ [0157] through p. 20, ¶ [0212]), WO 2013034904 (see, e.g., p. 58, line 4 through p. 102, line 20), WO 2003029296 (see, e.g., p. 30, line 20 through p. 34, line 16), U.S. Pat. No. 8,637,032 (see, e.g., column 252, line 55 through column 254, line 37), WO 2002028905 (see, e.g., p. 20, line 18 through p. 32, line 30), U.S. Pat. No. 8,778,345 (see, e.g., column 48, line 31 through column 54, line 38), WO 1997031025 (see, e.g., p. 14, line 6 through p. 31, line 26), WO 2012125569 (see, e.g., p. 25, line 33 through p. 27, line 14), WO 2011123489 (see, e.g., p. 93, ¶ [00339] through p. 109, ¶ [00145]), CA 2544949 (see, e.g., p. 78, line 26 through p. 122, line 21), WO 2014070934 (see, e.g., p. 86, line 4 through p. 103, line 4), US 20140093497 (see, e.g., p. 12, ¶ [0112] through p. 13, ¶ [0118]), WO 2010104761 (see, e.g., p. 37, line 3 through p. 66, line 29), U.S. Pat. No. 8,591,900 (see, e.g., column 60, line 14 through column 80, line 29), WO 2007124299 (see, e.g., 68, line 29 through p. p. 88, line 17), U.S. Pat. No.

7,445,780 (see, e.g., column 22, line 29 through column 36, line 39), WO 2006073443 (see, e.g., p. 82, line 6 through p. 89, line 12), WO 2005044294 (see, e.g., p. 137, line 19 through p. 158, line 15), U.S. Pat. No. 5,677,165 (see, e.g., column 11, line 45 through column 18, line 6), WO 2001083755 (see, e.g., p. 39, line 4 through p. 47, line 2), US 20080057070 (see, e.g., p. 26, ¶ [0176] through p. 47, ¶ [0296]), U.S. Pat. No. 7,172,759 (see, e.g., column 9, line 5 through column 12, line 58), WO 2006128103 (see, e.g., p. 75, ¶ [00244] through p. 84, ¶ [000555]), WO 2001016180 (see, e.g., p. 79, line 21 through p. 89, line 14), WO 2003040170 (see, e.g., p. 76, ¶ [0248] through p. 141, ¶ [0239]), U.S. Pat. No. 6,312,693 (see, e.g., column 8, line 51 through column 34, line 45), U.S. Pat. No. 8,492,531 (see, e.g., column 47, line 46 through column 58, line 31), U.S. Pat. No. 8,551,485 (see, e.g., column 78, line 15 through column 85, line 7), U.S. Pat. No. 6,838,261 (see, e.g., column 26, line 10 through column 34, line 26), EP 2243492 (see, e.g., p. 26, ¶ [0144] through p. 37, ¶ [0219]), and EP 2011802 (see, e.g., p. 12, ¶ [0047] through p. 40, ¶ [0127]), each of which is incorporated herein by reference in its entirety.

Examples of anti-CTLA-4 antibodies include ipilimumab (see, e.g., Patent No.: U.S. Pat. No. 6,682,736 (see, e.g., column 34, line 40 through collum 48, line 6)) and antibodies described in the following Patent and Patent Application Publication Nos.: WO 2012120125 (see, e.g., p. 13, line 1 through p. 27, line 18), U.S. Pat. No. 8,017,114 (see, e.g., column 46, line 40 through column 74, line 12), WO 2001014424 (see, e.g., p. 65, line 21 through p. 96, line 15), and WO 2000037504 (see, e.g., p. 56, line 25 through p. 86, line 31), each of which is incorporated herein by reference in its entirety.

Immunoinhibitory

As used herein, an immunoinhibitor is an agent that inhibits an immune response in a subject to whom it is administered, whether alone or in combination with another agent. Examples include steroids, retinoic acid, dexamethasone, cyclophosphamide, anti-CD3 antibody or antibody fragment, and other immunosuppressants. Examples include immunoinhibitory antibodies (e.g., anti-CD3 antibody, or single chain/antibody fragments of this molecule), steroids, retinoic acid, dexamethasone, cyclophosphamide (CPM) (such as those described in the Patent Nos.: U.S. Pat. No. 4,537,883 (see, e.g., column 9, line 62 through column 13, line 6), U.S. Pat. No. 3,808,297 (see, e.g., column 7, line 5 through column 9, line 75), and U.S. Pat. No. 5,036,060 (see, e.g., column 5, line 60 through column 14, line 19), each of which is incorporate herein by reference in its entirety), and other immunosuppressants.

Other immunomodulators include cell-surface makers and antibodies that target cell-surface makers. Examples of immunomodulators such as cell-surface makers and antibodies that target cell-surface makers include anti-LAG-3/CD223 antibodies (such as C9B7W (UniProt ID No. P18627) and those described in the Patent and Patent Application Publication Nos.: WO 2010019570 (see, p. 73, line 4 through e.g., p. 97, line 10), WO 2014008218 (see, e.g., p. 57, line 20 through p. 65, line 17), and WO 2008132601 (see, e.g., p. 15, line 13 through p. 28, line 17)), anti-VISTA/PD-L3 antibodies (such as those described in the Patent and Patent Application Publication Nos.: US 20140105912 (see, e.g., p. 71, ¶ [0601] through p. 87, ¶ [0755]), U.S. Pat. No. 8,236,304 (see, e.g., column 17, line 7 through column 18, line 48), and US 20110027278 (see, e.g., p. 39, ¶ [0302] through p. 43, ¶ [0333])), anti-B7-H5 antibodies (such as those described in the Patent Application Publication No.: US 20080248007 (see, e.g., p. 9, ¶ [0087] through p. 10, ¶ [0094])), anti-OX40 antibodies (such as those described in the Patent Application Publication No.: WO 2013130102 (see, e.g., p. 31, ¶ [0101] through p. 41, ¶ [0124])), anti-CD28 antibodies (such as those described in the Patent Application Publication No.: EP0440373 (see, e.g., p. 4, line 45 through p. 8, line 37)), anti-GITR antibodies (such as those described in the Patent and Patent Application Publication Nos.: WO 2007133822 (see, e.g., p. 48, line 16 through p. 52, line 18), WO 2009009116 (see, e.g., p. 52, line 30 through p. 56, line 6), WO 2004107618 (see, e.g., p. 78, ¶ [0199] through p. 105, ¶ [0261]), WO 2006105021 (see, e.g., p. 70, line 21 through p. 80, line 31), U.S. Pat. No. 7,812,135 (see, e.g., column 55, line 52 through column 66, line 38), and U.S. Pat. No. 8,591,886 (see, e.g., column 41, line 15 through column 44, line 20)), anti-4-1BB/CD137 antibodies (such as those described in the Patent No: U.S. Pat. No. 8,716,452 (see, e.g., column 13, line 55 through column 20, line 62)), 4-1BB ligands (such as those described in the Patent Application Publication Nos.: WO 1994026290 (see, e.g., 21, line 23 through p. 32, line 33), US 200601.10802 (see, e.g., p. 9, ¶ [0098] through p. 16, ¶ [0167]), WO 1999036093 (see, e.g., p. 18, line 5 through p. 56, line 17), WO 2010132389 (see, e.g., p. 30, ¶ [00134] through p. 41, ¶ [00166]), WO 2012145183 (see, e.g., p. 43, line 26 through p. 64, line 12), US 20080008716 (see, e.g., p. 3, ¶ [0042] through p. 7, ¶ [0070]), WO 2004010947 (see, e.g., p. 13, line 12 through p. 23, line 19), and US 20070286860 (see, e.g., p. 27, ¶ [0172] through p. 31, ¶ [200])), anti-BTLA antibodies (such as those described in the Patent and Patent Application Publication Nos.: WO 2010106051 (see, e.g., p. 35, line through p. 35, line 8), WO 2008076560 (see, e.g., p. 85, line 2 through p. 97, line 11), U.S. Pat. No. 8,349,320 (see, e.g., column 47, line 62 through column 72, line 26), and U.S. Pat. No. 8,563,694 (see, e.g., column 56, line 25 through column 65, line 45)), anti-TIM-3/HAVCR2 antibodies (such as those described in the Patent and Patent Application Publication Nos.: U.S. Pat. No. 8,841,418 (see, e.g., column 36, line 45 through column 46, line 47), EP 2417984 (see, e.g., p. 19, ¶ [0137] through p. 28, ¶ [0206]), WO 2014022332 (see, e.g., p. 51, ¶ [00191] through p. 54, ¶ [00202]), and U.S. Pat. No. 8,697,069 (see, e.g., p. 40, line 26 through p. 50, line 37)), anti-KIR antibodies (such as those described in the Patent and Patent Application Publication Nos.: WO 2014066532 (see, e.g., p. 25, line 30 through p. 57, line 17), EP 2446897 (see, e.g., p. 45, ¶ [0294] through p. 47, ¶ [0309]), WO 2014055648 (see, e.g., pp. 24-49), and US 20140302052 (see, e.g., p. 2, ¶ [0021] through p. 4, ¶ [0044])), anti-Flt3/CD135 antibodies (such as those described in the Patent and Patent Application Publication Nos.: U.S. Pat. No. 6,291,661 (see, e.g., column 23, line 36 through column 38, line 23), EP 0754230 (see, e.g., p. 13, ¶ [0099] through p. 20, ¶ [0138]), EP 0992584 (see, e.g., p. 25, line 28 through p. 30, line 45), and WO 2011076922 (see, e.g., p. 95, ¶ [000269] through p. 82, ¶ [000233])), anti-FasL antibodies (such as those described in the Patent and Patent Application Publication Nos.: US 20100266577 (see, e.g., p. 7, through p. 10, ¶ [0122]), US 20070142456 (see, e.g., p. 6, ¶ [0054] through p. 8, ¶ [0066]), WO 2011066211 (see, e.g., pp. 38-97), US 20020187534 (see, e.g., p. 5, ¶ [0061] through p. 10, ¶ [0112]), WO 1999036079 (see, e.g., p. 53, line 15 through p. 60, line 19), and WO 1997033617 (see, e.g., p. 18, line 1 through p. 25, line 17)), and anti-CD25 antibodies (such as those described in the Patent and Patent Application Publication Nos.: WO 2006108670 (see, e.g., pp. 4-8), U.S. Pat.

No. 8,182,812 (see, e.g., column 43, line 6 through column 54, line 15), and CA 2585776 (see, e.g., p. 31, ¶ [00100] through p. 52, ¶ [00163])).

Other immunomodulators include cytokines or antibodies that target cytokine receptors. Examples of immunomodulators such as cytokines and antibodies that target cytokine receptors include GM-CSF (such as those described in the Patent and Patent Application Publication Nos.: WO 2013074489 (see, e.g., p. 52, line 29 through p. 61, line 26), U.S. Pat. No. 5,891,429 (see, e.g., column 12, line 1 through column 28, line 21), and WO 1989010403 (see, e.g., p. 5, line 35 through p. 13, line 21)), anti-GM-CSF-receptor (R) antibodies (such as those described in the Patent and Patent Application Publication Nos.: WO 1994011404 (see, e.g., pp. 9-28), U.S. Pat. No. 8,263,075 (see, e.g., column 29, line 25 through column 49, line 26), and U.S. Pat. No. 5,932,704 (see, e.g., column 2, line 55 through column 12, line 67)), IL-2 (such as those described in the Patent and Patent Application Publication Nos.: WO 2013130102 (see, e.g., p. 31, ¶ [0101] through p. 41, ¶ [0124]), U.S. Pat. No. 8,349,311 (see, e.g., column 21, line 31 through column 31, line 9), WO 2005007121 (see, e.g., p. 30, line 29 through p. 43, line 31), and WO 1991002000 (see, e.g., pp. 2-7)), anti-IL-2-R antibodies (such as those described in the Patent Application Publication No.: WO 1989009622 (see, e.g., p. 18, line 4 through p. 33, line 12)), IL-7 (such as those described in the Patent and Patent Application Publication Nos.: WO 2012031115 (see, e.g., p. 77, ¶ [00240] through p. 102, ¶ [00347]), WO 2013074489 (see, e.g., p. 52, line 30 through p. 61, line 26), U.S. Pat. No. 7,323,549 (see, e.g., column 12, line 14 through column 24, line 37), and U.S. Pat. No. 8,338,575 (see, e.g., column 11, line 60 through column 24, line 18)), anti-IL-7-R antibodies, IL-21 (as those described in the Patent Application Publication No.: WO 2013169693 (see, e.g., p. 44, line 3 through p. 73, line 15)), anti-IL-21-R antibodies, IL-12 (as those described in the Patent No.: U.S. Pat. No. 8,765,462 (see, e.g., column 27, line 15 through column 50, line 16)), anti-IL-12-R antibodies, IL-15, anti-IL-15-R antibodies, IL-18, anti-IL-8-R antibodies, and anti-IDO antibodies.

Yet other immunomodulators include kinase inhibitors such as crizotinib (see, e.g., Patent Application Publication No.: WO 2013017989 (see, e.g., pp. 54-69)), ceritinib (see, e.g., Patent Application Publication Nos.: WO 2012082972 (see, e.g., p. 11, line 6 through p. 14, line 17) and WO 2008073687 (see, e.g., p. 34, ¶ [0089] through p. 144, ¶ [0151])), alectinib, and brigatinib, COX-2 inhibitors such as celecoxib (such as those described in the Patent and Patent Application Publication Nos.: WO 2000032189 (see, e.g., p. 38, line 17 through p. 61, line 20), U.S. Pat. No. 6,127,545 (see, e.g., column 7, line 30 through column 17, line 67), WO 2002028270 (see, e.g., p. 37, line 27 through p. 45, line 28), U.S. Pat. No. 6,403,630 (see, e.g., column 16, line 29 through column 17, line 7), and U.S. Pat. No. 5,972,986 (see, e.g., column 5, line 9 through column 16, line 44)), SOCS-1 inhibitors (e.g., PI3K or Jak inhibitors), heat shock proteins (HSP) (such as those described in the Patent and Patent Application Publication Nos.: U.S. Pat. No. 7,678,803 (see, e.g., column 79, line 20 through column 158, line 55), U.S. Pat. No. 7,608,635 (see, e.g., column 93, line 55 through column 108, line 40), U.S. Pat. No. 8,318,790 (see, e.g., column 158, line 51 through column 196, line 20), and US 20130184336 (see, e.g., p. 5, ¶ [0075] through p. 6, [0093])), HSP inhibitors (such as those described in the Patent No.: U.S. Pat. No. 7,776,849 (see, e.g., column 32, line 47 through column 50, line 67)), and anti-galectin-1 antibodies (such as those described in the Patent Application Publication Nos.: WO 2012131079 (see, e.g., pp. 24-35), WO 2014070214 (see, e.g., p. 42, line 15 through p. 53, line 13), and WO 2014043708 (see, e.g., p. 27, ¶ [00140] through p. 36, ¶ [00199])).

The disclosures of the aforementioned Patent and Patent Application Publication Nos. are incorporated herein by reference in their entireties.

Adjuvants

In some embodiments, an immunogenic composition described herein may include one or more adjuvants. An adjuvant refers to a substance that causes stimulation of the immune system. In this context, an adjuvant is used to enhance an immune response to one or more antigens (e.g., an ALK polypeptide). An adjuvant may be administered to a subject before, in combination with, or after administration of the antigens (e.g., an ALK polypeptide). In some embodiments, an adjuvant may be conjugated to a lipid in the ICMV.

The adjuvant may be without limitation a lipid (e.g., monophosphoryl lipid A (MPLA)), alum (e.g., aluminum hydroxide, aluminum phosphate); Freund's adjuvant; saponins purified from the bark of the *Q. saponaria* tree such as QS21 (a glycolipid that elutes in the 21st peak with HPLC fractionation; Antigenics, Inc., Worcester, Mass.); poly[di (carboxylatophenoxy)phosphazene (PCPP polymer; Virus Research Institute, USA), Flt3 ligand, *Leishmania* elongation factor (a purified *Leishmania* protein; Corixa Corporation, Seattle, Wash.), ISCOMS (immunostimulating complexes which contain mixed saponins, lipids and form virus-sized particles with pores that can hold antigen; CSL, Melbourne, Australia), Pam3Cys, SB-AS4 (SmithKline Beecham adjuvant system #4 which contains alum and MPL; SBB, Belgium), non-ionic block copolymers that form micelles such as CRL 1005 (these contain a linear chain of hydrophobic polyoxypropylene flanked by chains of polyoxyethylene, Vaxcel, Inc., Norcross, Ga.), and Montanide IMS (e.g., IMS1312, water-based nanoparticles combined with a soluble immunostimulant, Seppic), and CDNs (cyclic di-nucleotides).

Adjuvants may be toll-like receptor (TLR) ligands. Adjuvants that act through TLR3 include without limitation double-stranded RNA. Adjuvants that act through TLR4 include without limitation derivatives of lipopolysaccharides such as monophosphoryl lipid A (MPLA; Ribi ImmunoChem Research, Inc., Hamilton, Mont.) and muramyl dipeptide (MDP; Ribi) andthreonyl-muramyl dipeptide (t-MDP; Ribi); OM-174 (a glucosamine disaccharide related to lipid A; OM Pharma SA, Meyrin, Switzerland). Adjuvants that act through TLR5 include without limitation flagellin. Adjuvants that act through TLR7 and/or TLR8 include single-stranded RNA, oligoribonucleotides (ORN), synthetic low molecular weight compounds such as imidazoquinolinamines (e.g., imiquimod (R-837), resiquimod (R-848)). Adjuvants acting through TLR9 include DNA of viral or bacterial origin, or synthetic oligodeoxynucleotides (ODN), such as CpG ODN. Another adjuvant class is phosphorothioate containing molecules such as phosphorothioate nucleotide analogs and nucleic acids containing phosphorothioate backbone linkages.

Anti-Cancer Agents

In some embodiments, an immunogenic composition described herein may include one or more anti-cancer agents. An anti-cancer agent is an agent that at least partially inhibits the development or progression of a cancer, including inhibiting in whole or in part symptoms associated with the cancer even if only for the short term. Several anti-cancer agents can be categorized as DNA damaging agents and these include topoisomerase inhibitors (e.g., etoposide, ramptothecin, topotecan, teniposide, mitoxantrone), DNA alkylating agents (e.g., cisplatin, mechlorethamine, cyclophosphamide, ifosfamide, melphalan, chorambucil, busulfan, thiotepa, carmustine, lomustine, carboplatin, dacarbazine, procarbazine), DNA strand break inducing agents (e.g., bleomycin, doxorubicin, daunorubicin, idarubicin, mitomycin C), anti-microtubule agents (e.g., vincristine, vinblastine), anti-metabolic agents (e.g., cytarabine, methotrexate, hydroxyurea, 5-fluorouracil, floxuridine, 6-thioguanine, 6-mercaptopurine, fludarabine, pentostatin, chlorodeoxyadenosine), anthracyclines, vinca alkaloids, or epipodophyllotoxins.

Examples of anti-cancer agents include without limitation Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Bortezomib (VELCADE); Brequinar Sodium; Bropirimine; Busulfan; Cactinomycin; Calusterone; Caracemide; Carbetimer; Carboplatin (a platinum-containing regimen); Carmustine; Carubicin Hydrochloride; Carzelesin; Cedefingol; Chlorambucil; Cirolemycin; Cisplatin (a platinum-containing regimen); Cladribine; Crisnatol Mesylate; Cyclophosphamide; Cytarabine; Dacarbazine; Dactinomycin; Daunorubicin; Decitabine; Dexormaplatin; Dezaguanine; Diaziquone; Docetaxel (TAXOTERE); Doxorubicin; Droloxifene; Dromostanolone; Duazomycin; Edatrexate; Eflornithine; Elsamitrucin; Enloplatin; Enpromate; Epipropidine; Epirubicin; Erbulozole; Erlotinib (TARCEVA); Esorubicin; Estramustine; Etanidazole; Etoposide; Etoprine; Fadrozole; Fazarabine; Fenretinide; Floxuridine; Fludarabine; 5-Fluorouracil; Fluorocitabine; Fosquidone; Fostriecin; Gefitinib (IRESSA), Gemcitabine; Hydroxyurea; Idarubicin; Ifosfamide; Ilmofosine; Imatinib mesylate (GLEEVAC); Interferon alpha-2a; Interferon alpha-2b; Interferon alpha-n1; Interferon alpha-n3; Interferon beta-I a; Interferon gamma-I b; Iproplatin; Irinotecan; Lanreotide; Lenalidomide (REVLIMID, REVIMID); Letrozole; Leuprolide; Liarozole; Lometerxol; Lomustine; Losoxantrone; Masoprocol; Maytansine; Mechlorethamine; Megestrol; Melengestrol; Melphalan; Menogaril; Mercaptopurine; Methotrexate; Metoprine; Meturedepa; Mitindomide; Mitocarcin; Mitocromin; Mitogillin; Mitomalcin; Mitomycin; Mitosper; Mitotane; Mitoxantrone; Mycophenolic Acid; Nocodazole; Nogalamycin; Ormaplatin; Oxisuran; Paclitaxel; Pemeterxed (ALIMTA), Pegaspargase; Peliomycin; Pentamustine; Pentomone; Peplomycin; Perfosfamide; Pipobroman; Piposulfan; Piritrexim Isethionate; Piroxantrone; Plicamycin; Plomestane; Porfimer; Porfiromycin; Prednimustine; Procarbazine; Puromycin; Pyrazofurin; Riboprine; Rogletimide; Safingol; Semustine; Simtrazene; Sitogluside; Sparfosate; Sparsomycin; Spirogermanium; Spiromustine; Spiroplatin; Streptonigrin; Streptozocin; Sulofenur; Talisomycin; Tamsulosin; Taxol; Taxotere; Tecogalan; Tegafur; Teloxantrone; Temoporfin; Temozolomide (TEMODAR); Teniposide; Teroxirone; Testolactone; Thalidomide (THALOMID) and derivatives thereof; Thiamiprine; Thioguanine; Thiotepa; Tiazofurin; Tirapazamine; Topotecan; Toremifene; Trestolone; Triciribine; Trimeterxate; Triptorelin; Tubulozole; Uracil Mustard; Uredepa; Vapreotide; Verteporfin; Vinblastine; Vincristine; Vindesine; Vinepidine; Vinglycinate; Vinleurosine; Vinorelbine; Vinrosidine; Vinzolidine; Vorozole; Zeniplatin; Zinostatin; Zorubicin.

The anti-cancer agent may be an enzyme inhibitor including without limitation a tyrosine kinase inhibitor, a cyclin-dependent kinase (CDK) inhibitor, a mitogen-activated protein (MAP) kinase inhibitor, or an epidermal growth factor receptor (EGFR) inhibitor. The tyrosine kinase inhibitor may be without limitation Genistein (4',5,7-trihydroxyisoflavone), Tyrphostin 25 (3,4,5-trihydroxyphenyl), methylene]-propanedinitrile, Herbimycin A, Daidzein (4',7-dihydroxyisoflavone), AG-126, trans-1-(3'-carboxy-4'-hydroxyphenyl)-2-(2",5"-dihydroxy-phenyl)ethane, or HDBA (2-Hydroxy-5-(2,5-Dihydroxybenzylamino)-2-hydroxybenzoic acid. The CDK inhibitor may be without limitation p21, p27, p57, p15, p16, p18, or p19. The MAP kinase inhibitor may be without limitation KY12420 (C.sub.23H.sub.240.sub.8), CNI-1493, PD98059, or 4-(4-Fluorophenyl)-2-(4-methylsulfinyl phenyl)-5-(4-pyridyl) 1H-imidazole. The EGFR inhibitor may be without limitation erlotinib (TARCEVA), gefitinib (IRESSA), WH1-P97 (quinazoline derivative), LFM-A12 (leflunomide metabolite analog), ABX-EGF, lapatinib, canertinib, ZD-6474 (ZACTIMA), AEE788, and AG1458.

The anti-cancer agent may be a vascular endothelial growth factor (VEGF) inhibitor including without limitation bevacizumab (AVASTIN), ranibizumab (LUCENTIS), pegaptanib (MACUGEN), sorafenib, sunitinib (SUTENT), vatalanib, ZD-6474 (ZACTIMA), anecortave (RETAANE), squalamine lactate, and semaphorin.

The anti-cancer agent may be an antibody or an antibody fragment including without limitation an antibody or an antibody fragment including but not limited to bevacizumab (AVASTIN), trastuzumab (HERCEPTIN), alemtuzumab (CAMPATH, indicated for B cell chronic lymphocytic leukemia,), gemtuzumab (MYLOTARG, hP67.6, anti-CD33, indicated for leukemia such as acute myeloid leukemia), rituximab (RITUXAN), tositumomab (BEXXAR, anti-CD20, indicated for B cell malignancy), MDX-210 (bispecific antibody that binds simultaneously to HER-2/neu oncogene protein product and type I Fc receptors for immunoglobulin G (IgG) (Fc gamma RI)), oregovomab (OVAREX, indicated for ovarian cancer), edrecolomab (PANOREX), daclizumab (ZENAPAX), palivizumab (SYNAGIS, indicated for respiratory conditions such as RSV infection), ibritumomab tiuxetan (ZEVALIN, indicated for Non-Hodgkin's lymphoma), cetuximab (ERBITUX), MDX-447, MDX-22, MDX-220 (anti-TAG-72), IOR-05, IOR-T6 (anti-CD1), IOR EGF/R3, celogovab (ONCOSCINT OV103), epratuzumab (LYMPHOCIDE), pemtumomab (THERAGYN), and Gliomab-H (indicated for brain cancer, melanoma).

Methods of Constructing a Library of ALK Polypeptides

Figure 2A:
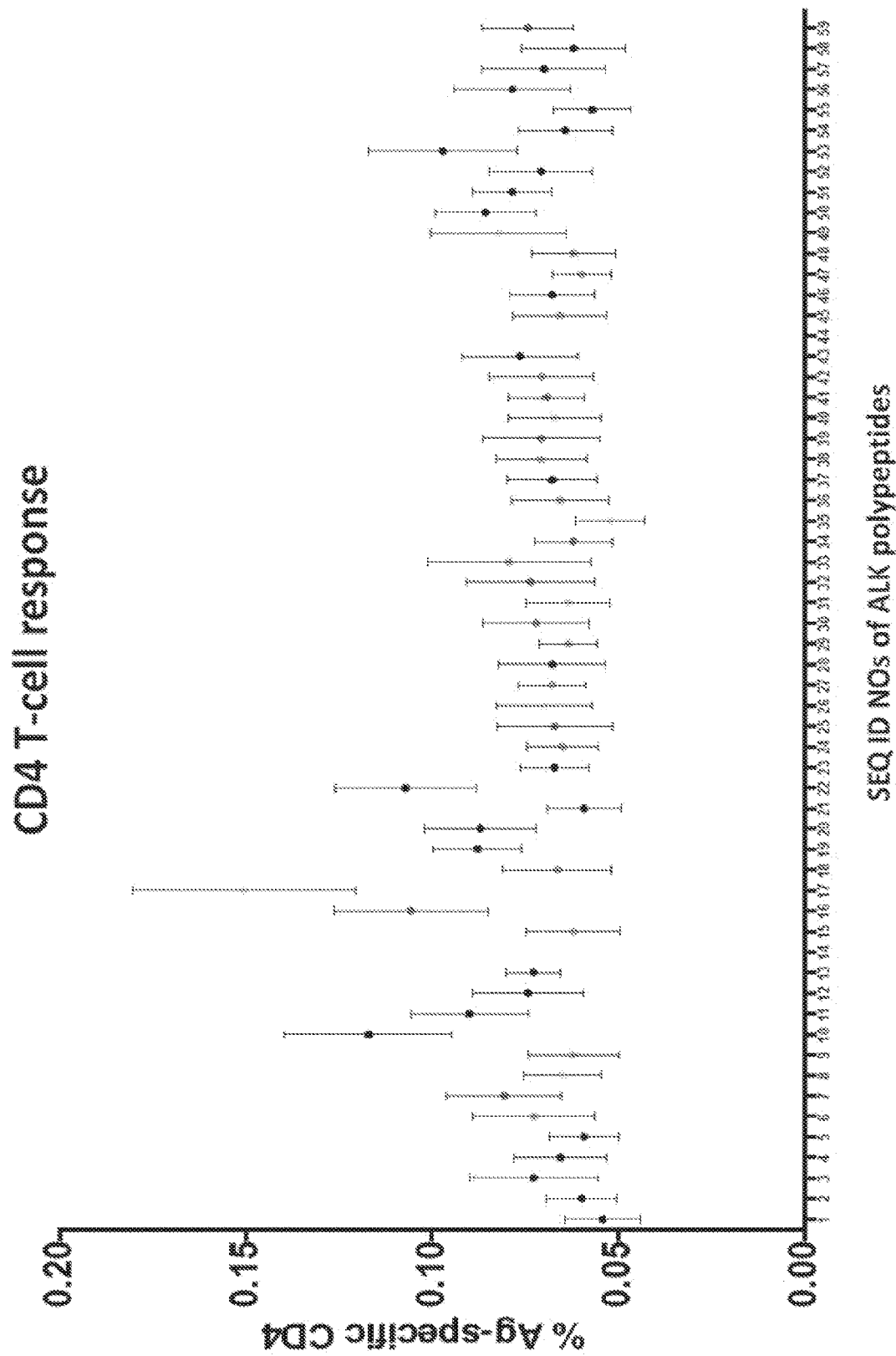
FIGS. 2A and 2B show the CD4 T-cell response stimulated by ALK polypeptides each having the sequence of any one of SEQ ID NOs: 1-59 listed in Table 1A.
Figure 2B:
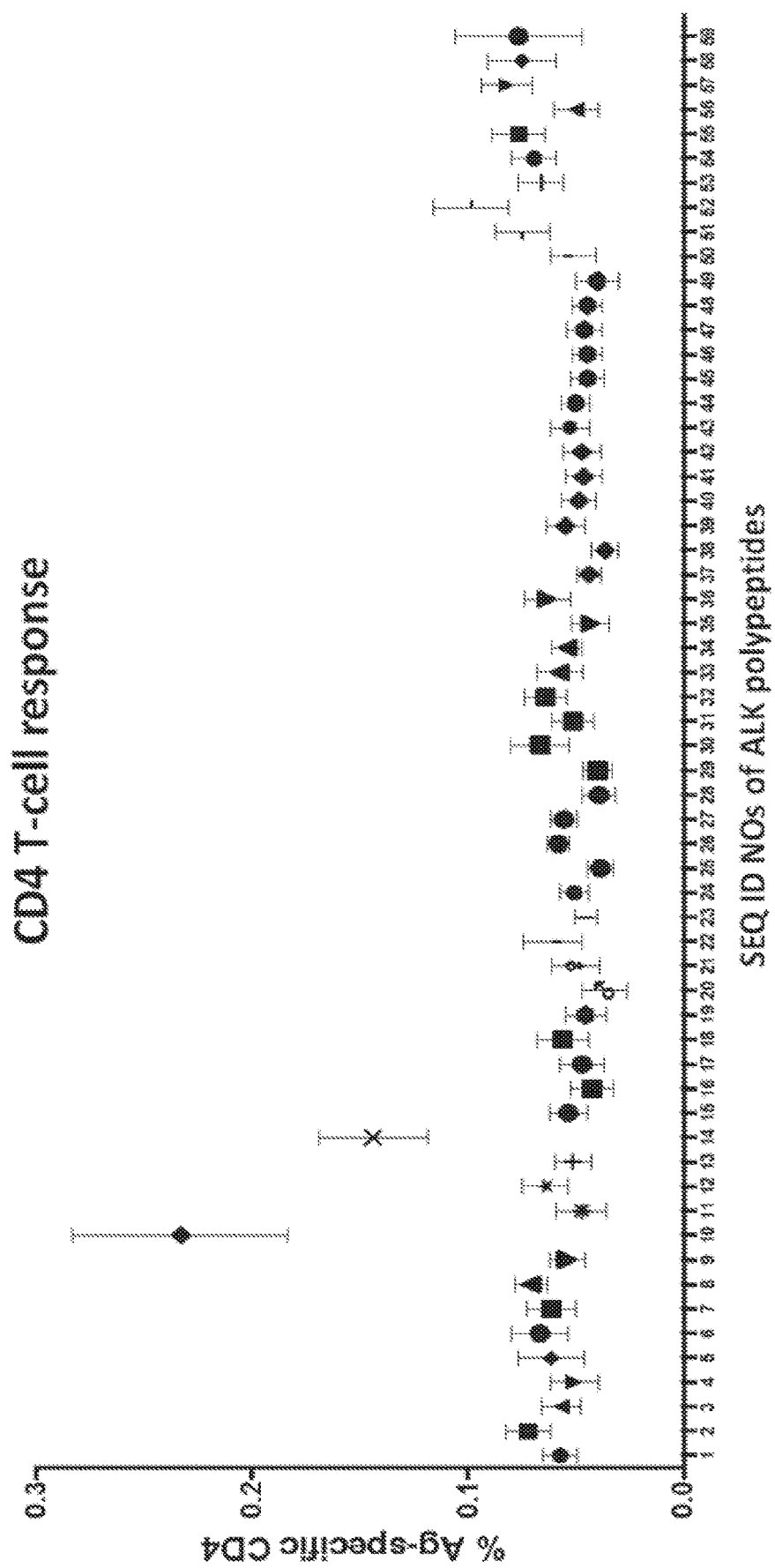
Figure 2C:
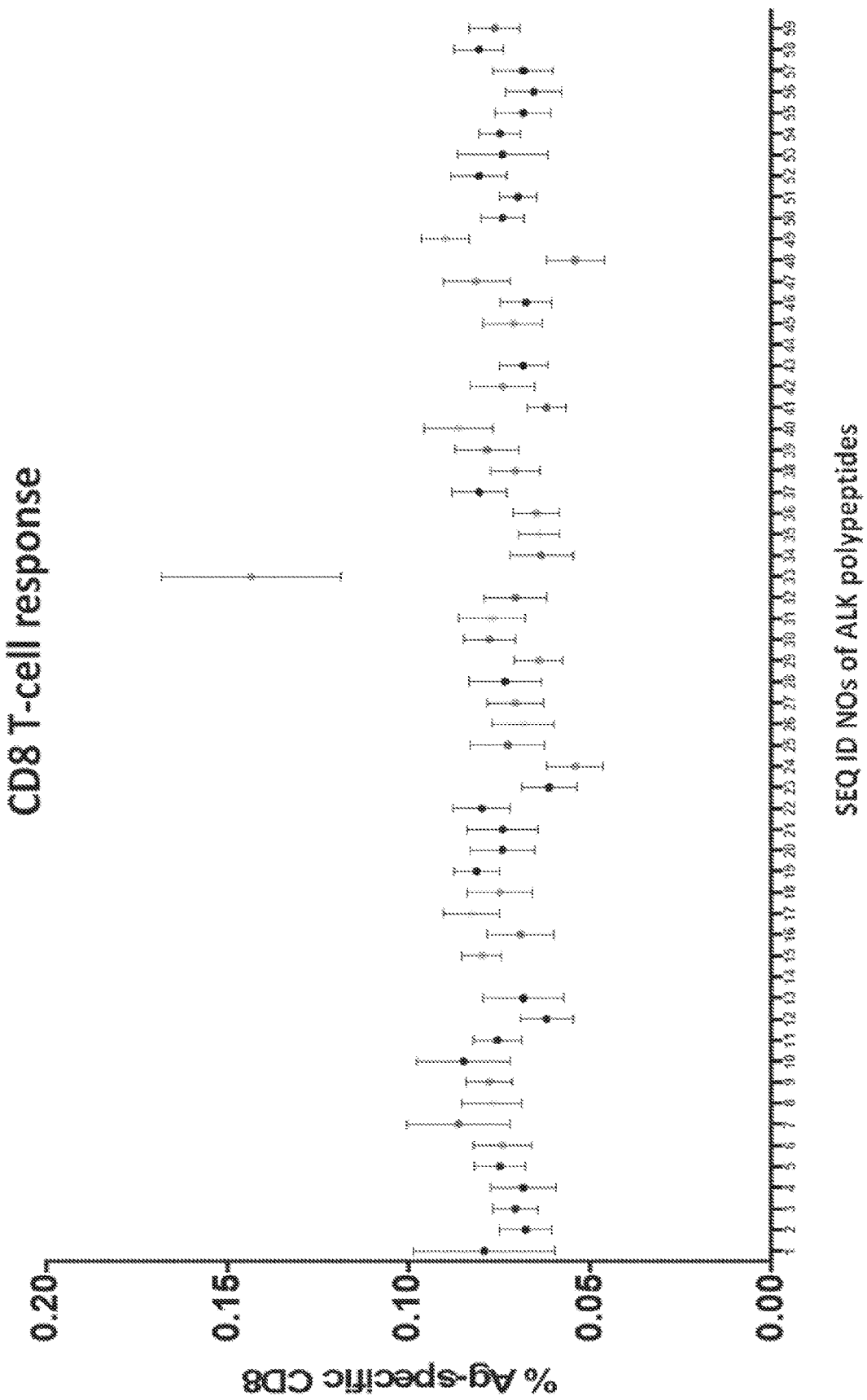
FIGS. 2C and 2D show the CD8 T-cell response stimulated by ALK polypeptides each having the sequence of any one of SEQ ID NOs: 1-59 listed in Table 1A.
Figure 2D:
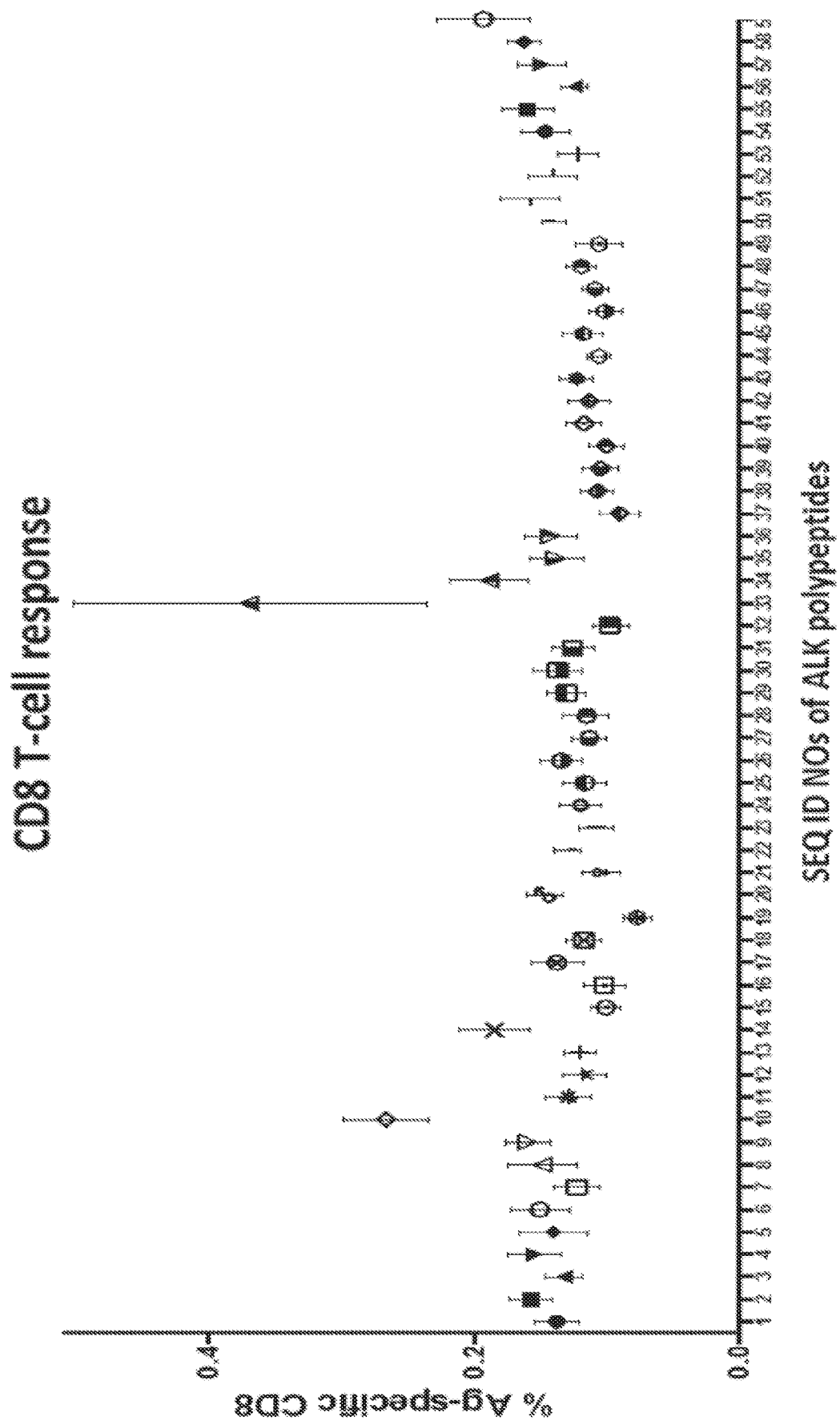

A library of ALK polypeptides may be constructed in a random or semi-random fashion. For example, ALK polypeptides each having 15 amino acids (e.g., SEQ ID NOs: 1-58) may be constructed from the sequence of any one of SEQ ID NOs: 67-70 (e.g., SEQ ID NO: 70). The 15-mer ALK polypeptides (e.g., SEQ ID NOs: 1-58) overlap each other by 10 amino acids. After initial screening of the 15-mer ALK polypeptides, ALK polypeptides that demonstrate desirable immunogenic properties may be selected for further screening. For example, intracellular cytokine staining (ICS) results in FIGS. 2A and 2B show that the strongest CD4 T-cell responses were found in cells re-stimulated with ALK polypeptides having the sequences of SEQ ID NOs: 10, 14, 17, 22, 52, and 53, and ICS results in FIGS. 2C and 2D show that the strongest CD8 T-cell response was found in cells re-stimulated with ALK polypeptide having the sequence of SEQ ID NOs: 10, 14, and 33. Thus, ALK polypeptides having sequences of SEQ ID NOs: 10, 14, 17, 22, 33, 52, and 53 may be further tested. Other ALK polypeptides may be constructed from ALK polypeptides having sequences of SEQ ID NOs: 10, 14, 17, 22, 33, 52, and 53. For example, 9-mer ALK polypeptides may be constructed from the sequence of any one of SEQ ID NOs: 10, 14, 17, 22, 33, 52, and 53. ALK polypeptides each having 9 amino acids (e.g., SEQ ID NOs: 60-66) are constructed from the sequence of SEQ ID NO: 33. The 9-mer ALK polypeptides having sequences of SEQ ID NOs: 60-66 overlap each other by one amino acid and cover the entire sequence of SEQ ID NO: 33.

In another example, ALK polypeptides each having 31 amino acids (e.g., SEQ ID NOs: 93-121) may be constructed from the sequence of any one of SEQ ID NOs: 67-70 (e.g., SEQ ID NO: 70). The 31-mer ALK polypeptides (e.g., SEQ ID NOs: 93-121) overlap each other by 12 amino acids.

In some embodiments, a Cys in an ALK polypeptide described herein (e.g., any one of the ALK polypeptides in Tables 1A and 1B) may be replaced by an Ala. In some embodiments, a Cys in an ALK polypeptide of any one of SEQ ID NOs: 94, 95, 97-99, 101-105, 107-110, and 117-120 may be replaced with an Ala, generating the ALK polypeptides of SEQ ID NOs:122-139 in Table 1C.

A library of ALK polypeptides may also be constructed using computer-aided design. Computer programs that help to design polypeptides are available in the art and are described in, e.g., U.S. Pat. Nos. 8,575,070 and 8,275,595, US Patent Publication No. 2015/0205911, and International Patent Publication No. WO 2001047541. Computer programs may combine methods used in biological sequence analysis and bioinformatics data mining. In some embodiments, computer programs may scan ALK polypeptides and identify the motifs or specific amino acids that may be important in conferring the immunogenic properties of potentially active ALK polypeptides. In some embodiments, computer programs may select and combine certain fragments from individual ALK polypeptides and construct new ALK polypeptides based on the most active ALK polypeptides. Examples of computer programs that may be used to construct a library of ALK polypeptides include, but are not limited to, Rosetta and Panorama.

Depending on how much is known about the immunogenic property of the potentially active ALK polypeptides, certain residues in the library may be kept constant, while other positions varied. For example, if certain properties of the ALK polypeptides are known (e.g., having a positively charged amino acid, such as lysine or arginine at or near a particular position), the variable positions can be built around the pre-determined residue position.

In some embodiments, one or more amino acid substitutions in an ALK polypeptide may improve its immunogenic property. In some embodiments, an amino acid in a wild-type ALK may be replaced by a different amino acid (e.g., a naturally occurring amino acid (e.g., Ala, Arg, Asn, Asp, Cys, Gln, Glu, Gly, His, Ile, Leu, Lys, Met, Phe, Pro, Ser, Thr, Trp, Tyr, or Val) or a non-naturally occurring amino acid). In some embodiments, a Cys in an ALK polypeptide described herein (e.g., any one of the ALK polypeptides in Tables 1A and 1B) may be replaced by an Ala. A "non-naturally occurring amino acid" is an amino acid which is not naturally produced or found in a mammal. Examples of non-naturally occurring amino acids include D-amino acids; an amino acid having an acetylaminomethyl group attached to a sulfur atom of a cysteine; a pegylated amino acid; the omega amino acids of the formula $NH_2(CH_2)_n COOH$ where n is 2-6, neutral nonpolar amino acids, such as sarcosine, t-butyl alanine, t-butyl glycine, N-methyl isoleucine, and norleucine; oxymethionine; phenylglycine; citrulline; methionine sulfoxide; cysteic acid; ornithine; diaminobutyric acid; diaminopropionic acid; and hydroxyproline.. Other amino acids are a-aminobutyric acid, a-amino-a-methylbutyrate, aminocyclopropane-carboxylate, aminoisobutyric acid, aminonorbornyl-carboxylate, L-cyclohexylalanine, cyclopentylalanine, L-N-methylleucine, L-N-methylmethionine, L-N-methylnorvaline, L-N-methylphenylalanine, L-N-methylproline, L-N-methylserine, L-N-methyltryptophan, D-ornithine, L-N-methylethylglycine, L-norleucine, α-methyl-aminoisobutyrate, α-methylcyclohexylalanine, D-α-methylalanine, D-α-methylarginine, D-α-methylasparagine, D-α-methylaspartate, D-α-methylcysteine, D-α-methylglutamine, D-α-methylhistidine, D-α-methylisoleucine, D-α-methylleucine, D-α-methyllysine, D-α-methylmethionine, D-α-methylornithine, D-α-methylphenylalanine, D-α-methylproline, D-α-methylserine, D-N-methylserine, D-α-methylthreonine, D-α-methyltryptophan, D-α-methyltyrosine, D-α-methylvaline, D-N-methylalanine, D-N-methylarginine, D-N-methylasparagine, D-N-methylaspartate, D-N-methylcysteine, D-N-methylglutamine, D-N-methylglutamate, D-N-methylhistidine, D-N-methylisoleucine, D-N-methylleucine, D-N-methyllysine, N-methylcyclohexylalanine, D-N-methylornithine, N-methylglycine, N-methylaminoisobutyrate, N-(1-methylpropyl) glycine, N-(2-methylpropyl)glycine, D-N-methyltryptophan, D-N-methyltyrosine, D-N-methylvaline, γ-aminobutyric acid, L-t-butylglycine, L-ethylglycine, L-homophenylalanine, L-α-methylarginine, L-α-methylaspartate, L-α-methylcysteine, L-α-methylglutamine, L-α-methylhistidine, L-α-methylisoleucine, L-α-methylleucine, L-α-methylmethionine, L-α-methylnorvaline, L-α-methylphenylalanine, L-α-methylserine, L-α-methyltryptophan, L-α-methylvaline, N—(N-(2,2-diphenylethyl) carbamylmethylglycine, 1-carboxy-1-(2,2-diphenyl-ethylamino) cyclopropane, 4-hydroxyproline, ornithine, 2-aminobenzoyl (anthraniloyl), D-cyclohexylalanine, 4-phenyl-phenylalanine, L-citrulline, α-cyclohexylglycine, L-1,2,3,4-tetrahydroisoquinoline-3-carboxylic acid, L-thiazolidine-4-carboxylic acid, L-homotyrosine, L-2-furylalanine, L-histidine (3-methyl), N-(3-guanidinopropyl)glycine, O-methyl-L-tyrosine, O-glycan-serine, meta-tyrosine, nor-tyrosine, L-N, N',N"-trimethyllysine, homolysine, norlysine, N-glycan asparagine, 7-hydroxy-1,2,3,4-tetrahydro-4-fluorophenylalanine, 4-methylphenylalanine, bis-(2-picolyl)amine, pentafluorophenylalanine, indoline-2-carboxylic acid, 2-aminobenzoic acid, 3-amino-2-naphthoic acid, asymmetric dimethylarginine, L-tetrahydroisoquinoline-1-carboxylic acid, D-tetrahydroisoquinoline-1-carboxylic acid, 1-aminocyclohexane acetic acid, D/L-allylglycine, 4-aminobenzoic acid, 1-amino-cyclobutane carboxylic acid, 2 or 3 or 4-aminocyclohexane carboxylic acid, 1-amino-1-cyclopentane carboxylic acid, 1-aminoindane-1-carboxylic acid, 4-amino-pyrrolidine-2-carboxylic acid, 2-aminotetraline-2-carboxylic acid, azetidine-3-carboxylic acid, 4-benzyl-pyrolidine-2-carboxylic acid, tert-butylglycine, b-(benzothiazolyl-2-yl)-alanine, b-cyclopropyl alanine, 5,5-dimethyl-1,3-thiazolidine-4-carboxylic acid, (2R,4S)$_4$-hydroxypiperidine-2-carboxylic acid, (2S,4S) and (2S,4R)-4-(2-naphthylmethoxy)-pyrrolidine-2-carboxylic acid, (2S,4S) and (2S,4R)4-phenoxy-pyrrolidine-2-carboxylic acid, (2R, 5S)and(2S,5R)-5-phenyl-pyrrolidine-2-carboxylic acid, (2S, 4S)-4-amino-1-benzoyl-pyrrolidine-2-carboxylic acid, t-butylalanine, (2S,5R)-5-phenyl-pyrrolidine-2-carboxylic acid, 1-aminomethyl-cyclohexane-acetic acid, 3,5-bis-(2-amino)ethoxy-benzoic acid, 3,5-diamino-benzoic acid, 2-methylamino-benzoic acid, N-methylanthranylic acid, L-N-methylalanine, L-N-methylarginine, L-N-methyl-asparagine, L-N-methylaspartic acid, L-N-methylcysteine, L-N-methylglutamine, L-N-methylglutamic acid, L-N-methylhistidine, L-N-methylisoleucine, L-N-methyllysine, L-N-methylnorleucine, L-N-methylornithine, L-N-methyl-threonine, L-N-methyltyrosine, L-N-methylvaline, L-N-methyl-t-butylglycine, L-norvaline, α-methyl-γ-aminobu-tyrate, 4,4'-biphenylalanine, α-methylcylcopentylalanine, α-methyl-α-napthylalanine, α-methylpenicillamine, N-(4-aminobutyl)glycine, N-(2-aminoethyl)glycine, N-(3-amino-propyl)glycine, N-amino-α-methylbutyrate, α-napthylala-nine, N-benzylglycine, N-(2-carbamylethyl)glycine, N-(carbamylmethyl)glycine, N-(2-carboxyethyl)glycine, N-(carboxymethyl)glycine, N-cyclobutylglycine, N-cyclo-decylglycine, N-cycloheptylglycine, N-cyclohexylglycine, N-cyclodecylglycine, N-cylcododecylglycine, N-cyclooc-tylglycine, N-cyclopropylglycine, N-cycloundecylglycine, N-(2,2-diphenylethyl)glycine, N-(3,3-diphenylpropyl)gly-cine, N-(3-guanidinopropyl)glycine, N-(1-hydroxyethyl) glycine, N-(hydroxyethyl))glycine, N-(imidazolylethyl)) glycine, N-(3-indolylyethyl)glycine, N-methyl-γ-aminobutyrate, D-N-methylmethionine, N-methylcyclopentylalanine, D-N-methylphenylalanine, D-N-methylproline, D-N-methylthreonine, N-(1-methyl-ethyl)glycine, N-methyl-napthylalanine, N-methylpenicil-lamine, N-(p-hydroxyphenyl)glycine, N-(thiomethyl)gly-cine, penicillamine, L-α-methylalanine, L-α-methylasparagine, L-α-methyl-t-butylglycine, L-methylethylglycine, L-α-methylglutamate, L-α-methyl-homophenylalanine, N-(2-methylthioethyl)glycine, L-α-methyllysine, L-α-methylnorleucine, L-α-methylornithine, L-α-methylproline, L-α-methylthreonine, L-α-methyltyro-sine, L-N-methyl-homophenylalanine, N—(N-(3,3-diphe-nylpropyl) carbamylmethylglycine, L-pyroglutamic acid, D-pyroglutamic acid, O-methyl-L-serine, O-methyl-L-ho-moserine, 5-hydroxylysine, α-carboxyglutamate, phe-nylglycine, L-pipecolic acid (homoproline), L-homoleucine, L-lysine (dimethyl), L-2-naphthylalanine, L-dimethyldopa or L-dimethoxy-phenylalanine, L-3-pyridylalanine, L-histi-dine (benzoyloxymethyl), N-cycloheptylglycine, L-diphe-nylalanine, O-methyl-L-homotyrosine, L-β-homolysine, O-glycan-threoine, Ortho-tyrosine, L-N,N'-dimethyllysine, L-homoarginine, neotryptophan, 3-benzothienylalanine, iso-quinoline-3-carboxylic acid, diaminopropionic acid, homo-cysteine, 3,4-dimethoxyphenylalanine, 4-chlorophenylala-nine, L-1,2,3,4-tetrahydronorharman carboxylic acid, adamantylalanine, symmetrical dimethylarginine, 3-car-boxythiomorpholine, D-1,2,3,4-tetrahydronorharman-3-car-boxylic acid, 3-aminobenzoic acid, 3-amino-1-carboxym-ethyl-pyridin-2-one, 1-amino-1-cyclohexane carboxylic acid, 2-aminocyclopentane carboxylic acid, 1-amino-1-cy-clopropane carboxylic acid, 2-aminoindane-2-carboxylic acid, 4-amino-tetrahydrothiopyran-4-carboxylic acid, azeti-dine-2-carboxylic acid, b-(benzothiazol-2-yl)-alanine, neo-pentylglycine, 2-carboxymethyl piperidine, b-cyclobutyl alanine, allylglycine, diaminopropionic acid, homo-cyclo-hexyl alanine, (2S,4R)-4-hydroxypiperidine-2-carboxylic acid, octahydroindole-2-carboxylic acid, (2S,4R) and (2S, 4R)-4-(2-naphthyl), pyrrolidine-2-carboxylic acid, nipecotic acid, (2S,4R)and (2S,4S)-4-(4-phenylbenzyl) pyrrolidine-2-carboxylic acid, (3S)-1-pyrrolidine-3-carboxylic acid, (2S, 4S)-4-tritylmercapto-pyrrolidine-2-carboxylic acid, (2S, 4S)-4-mercaptoproline, t-butylglycine, N,N-bis(3-aminopropyl)glycine, 1-amino-cyclohexane-1-carboxylic acid, N-mercaptoethylglycine, and selenocysteine.

Methods of Producing ALK Polypeptides

ALK polypeptides described herein can be produced from a host cell. A host cell refers to a vehicle that includes the necessary cellular components, e.g., organelles, needed to express the polypeptides and constructs described herein from their corresponding nucleic acids. The nucleic acids may be included in nucleic acid vectors that can be introduced into the host cell by conventional techniques known in the art (e.g., transformation, transfection, electroporation, calcium phosphate precipitation, direct microinjection, infection, etc). The choice of nucleic acid vectors depends in part on the host cells to be used. Generally, preferred host cells are of either prokaryotic (e.g., bacterial) or eukaryotic (e.g., mammalian) origin. ALK polypeptides described herein can be also produced by the solid phase method of Merrifield (J. Am. Chem. Soc. 85:2149-2154, 1963) or other well-known procedures using conventional automated peptide synthesizers.

Nucleic Acid Vector Construction and Host Cells

A polynucleotide sequence encoding the amino acid sequence of an ALK polypeptide described herein may be prepared by a variety of methods known in the art. These methods include, but are not limited to, oligonucleotide-mediated (or site-directed) mutagenesis and PCR mutagenesis. A polynucleotide molecule encoding an ALK polypeptide described herein may be obtained using standard techniques, e.g., gene synthesis. Alternatively, a polynucleotide molecule encoding a wild-type ALK may be mutated to contain specific substitutions using standard techniques in the art, e.g., QuikChange™ mutagenesis. Polynucleotides can be synthesized using nucleotide synthesizer or PCR techniques.

Polynucleotide sequences encoding ALK polypeptides described herein may be inserted into a vector capable of replicating and expressing the polynucleotides in prokaryotic or eukaryotic host cells. Many vectors are available in the art and can be used for the purpose of the invention. Each vector may contain various components that may be adjusted and optimized for compatibility with the particular host cell. For example, the vector components may include, but are not limited to, an origin of replication, a selection marker gene, a promoter, a ribosome binding site, a signal sequence, a polynucleotide sequence encoding an ALK polypeptide described herein, and a transcription termination sequence. In some embodiments, a vector can include internal ribosome entry site (IRES) that allows the expression of multiple ALK polypeptides. Some examples of bacterial expression vectors include, but are not limited to, pGEX series of vectors (e.g., pGEX-2T, pGEX-3X, pGEX-4T, pGEX-5X, pGEX-6P), pET series of vectors (e.g., pET-21, pET-21a, pET-21b, pET-23, pET-24), pACYC series of vectors (e.g., pACYDuet-1), pDEST series of vectors (e.g., pDEST14, pDEST15, pDEST24, pDEST42), and pBR322 and its derivatives (see, e.g., U.S. Pat. No. 5,648,237). Some examples of mammalian expression vectors include, but are not limited to, pCDNA3, pCDNA4, pNICE, pSELECT, and pFLAG-CMV. Other types of nucleic acid vectors include viral vectors for expressing a protein in a cell (e.g., a cell of a subject). Such viral vectors include, but are not limited to, retroviral vectors, adenoviral vectors, poxviral vectors (e.g., vaccinia viral vectors, such as Modified Vaccinia Ankara (MVA)), adeno-associated viral vectors, and alphaviral vectors.

In some embodiments, E. coli cells are used as host cells for the invention. Examples of E co/i strains include, but are not limited to, *E. coli* 294 (ATCC® 31,446), *E. coli* A 1776 (ATCC® 31,537, *E. coli* BL21 (DE3) (ATCC® BAA-1025), and *E. coli* RV308 (ATCC® 31,608). In other embodiments, mammalian cells are used as host cells for the invention. Examples of mammalian cell types include, but are not limited to, human embryonic kidney (HEK) cells, Chinese hamster ovary (CHO) cells, HeLa cells, PC3 cells, Vero cells, and MC3T3 cells. Different host cells have characteristic and specific mechanisms for the posttranslational processing and modification of protein products. Appropriate cell lines or host systems may be chosen to ensure the correct modification and processing of the protein expressed. The above-described expression vectors may be introduced into appropriate host cells using conventional techniques in the art, e.g., transformation, transfection, electroporation, calcium phosphate precipitation, and direct microinjection. Once the vectors are introduced into host cells for protein production, host cells are cultured in conventional nutrient media modified as appropriate for inducing promoters, selecting transformants, or amplifying the genes encoding the desired sequences.

Protein Production, Recovery, and Purification

Host cells used to produce the ALK polypeptides described herein may be grown in media known in the art and suitable for culturing of the selected host cells. Examples of suitable media for bacterial host cells include Luria broth (LB) plus necessary supplements, such as a selection agent, e.g., ampicillin. Examples of suitable media for mammalian host cells include Minimal Essential Medium (MEM), Dulbecco's Modified Eagle's Medium (DMEM), DMEM with supplemented fetal bovine serum (FBS), and RPMI-1640.

Host cells are cultured at suitable temperatures, such as from about 20° C. to about 39° C., e.g., from 25° C. to about 37° C. The pH of the medium is generally from about 6.8 to 7.4, e.g., 7.0, depending mainly on the host organism. If an inducible promoter is used in the expression vector of the invention, protein expression is induced under conditions suitable for the activation of the promoter.

Protein recovery typically involves disrupting the host cell, generally by such means as osmotic shock, sonication, or lysis. Once the cells are disrupted, cell debris may be removed by centrifugation or filtration. The proteins may be further purified, for example, by affinity resin chromatography. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin, SDS-PAGE, and gel filtration.

Alternatively, ALK polypeptides described herein can be produced by the cells of a subject (e.g., a human), e.g., in the context of therapy, by administrating a vector (e.g., a retroviral vector, adenoviral vector, poxviral vector (e.g., vaccinia viral vector, such as Modified Vaccinia Ankara (MVA)), adeno-associated viral vector, and alphaviral vector) containing a nucleic acid molecule encoding the ALK polypeptide described herein. The vector, once inside a cell of the subject (e.g., by transformation, transfection, electroporation, calcium phosphate precipitation, direct microinjection, infection, etc) will promote expression of the ALK polypeptide described herein, which is then secreted from the cell.

Pharmaceutical Compositions and Preparations

In some embodiments, pharmaceutical compositions of the invention may contain one or more ALK polypeptides described herein as the therapeutic proteins. In addition to a therapeutic amount of the protein, the pharmaceutical compositions may contain a pharmaceutically acceptable carrier or excipient, which can be formulated by methods known to those skilled in the art. In other embodiments, pharmaceutical compositions of the invention may contain nucleic acid molecules encoding one or more ALK polypeptides described herein (e.g., in a vector, such as a viral vector). The nucleic acid molecule encoding an ALK polypeptide described herein may be cloned into an appropriate expression vector, which may be delivered via well-known methods in gene therapy.

Acceptable carriers and excipients in the pharmaceutical compositions are nontoxic to recipients at the dosages and concentrations employed. Acceptable carriers and excipients may include buffers such as phosphate, citrate, HEPES, and TAE, antioxidants such as ascorbic acid and methionine, preservatives such as hexamethonium chloride, octadecyldimethylbenzyl ammonium chloride, resorcinol, and benzalkonium chloride, proteins such as human serum albumin, gelatin, dextran, and immunoglobulins, hydrophilic polymers such as polyvinylpyrrolidone, amino acids such as glycine, glutamine, histidine, and lysine, and carbohydrates such as glucose, mannose, sucrose, and sorbitol. Pharmaceutical compositions of the invention can be administered parenterally in the form of an injectable formulation. Pharmaceutical compositions for injection can be formulated using a sterile solution or any pharmaceutically acceptable liquid as a vehicle. Pharmaceutically acceptable vehicles include, but are not limited to, sterile water, physiological saline, and cell culture media (e.g., Dulbecco's Modified Eagle Medium (DMEM), α-Modified Eagles Medium (α-MEM), F-12 medium).

The pharmaceutical compositions of the invention may be prepared in microcapsules, such as hydroxylmethylcellulose or gelatin-microcapsule and poly-(methylmethacrylate) microcapsule. The pharmaceutical compositions of the invention may also be prepared in other drug delivery systems such as liposomes, albumin microspheres, microemulsions, nano-particles, and nanocapsules. Such techniques are described in Remington: The Science and Practice of Pharmacy $22^{nd}$ edition (2012). The pharmaceutical compositions to be used for in vivo administration must be sterile. This is readily accomplished by filtration through sterile filtration membranes.

The pharmaceutical compositions of the invention may also be prepared as a sustained-release formulation. Suitable examples of sustained-release preparations include semipermeable matrices of solid hydrophobic polymers containing the ALK polypeptides described herein. Examples of sustained release matrices include polyesters, hydrogels, polyactides (U.S. Pat. No. 3,773,919), copolymers of L-glutamic acid and γ ethyl-L-glutamate, non-degradable ethylene-vinyl acetate, degradable lactic acid-glycolic acid copolymers such as LUPRON DEPOT™, and poly-D-(−)-3-hydroxybutyric acid. Some sustained-release formulations enable release of molecules over a few months, e.g., one to six months, while other formulations release pharmaceutical compositions of the invention for shorter time periods, e.g., days to weeks.

The pharmaceutical composition may be formed in a unit dose form as needed. The amount of an active component, e.g., an ALK polypeptide of the invention, included in the pharmaceutical preparations is such that a suitable dose within the designated range is provided (e.g., a dose within the range of 0.01-100 mg/kg of body weight).

The pharmaceutical composition for gene therapy can be in an acceptable diluent, or can include a slow release matrix in which the gene delivery vehicle is imbedded. Vectors that may be used as in vivo gene delivery vehicle include, but are not limited to, retroviral vectors, adenoviral vectors, poxviral vectors (e.g., vaccinia viral vectors, such as Modified Vaccinia Ankara (MVA)), adeno-associated viral vectors, and alphaviral vectors. In some embodiments, a vector can include internal ribosome entry site (IRES) that allows the expression of multiple ALK polypeptides described herein. Other vehicles and methods for gene delivery are described in U.S. Pat. Nos. 5,972,707, 5,697,901, and 6,261,554, each of which is incorporated by reference herein in its entirety.

Other methods of producing pharmaceutical compositions are described in, e.g., U.S. Pat. Nos. 5,478,925, 8,603,778, 7,662,367, and 7,892,558, all of which are incorporated by reference herein in their entireties.

Routes, Dosage, and Timing of Administration

Pharmaceutical compositions of the invention that contain one or more ALK polypeptides described herein as the therapeutic proteins may be formulated for parenteral administration, subcutaneous administration, intravenous administration, intramuscular administration, intra-arterial administration, intrathecal administration, or intraperitoneal administration. The pharmaceutical composition may also be formulated for, or administered via, nasal, spray, oral, aerosol, rectal, or vaginal administration. Methods of administering therapeutic proteins are known in the art. See, for example, U.S. Pat. Nos. 6,174,529, 6,613,332, 8,518,869, 7,402,155, and 6,591,129, and US Patent Application Publication Nos. US20140051634, WO1993000077, and US20110184145, the disclosures of which are incorporated by reference in their entireties. One or more of these methods may be used to administer a pharmaceutical composition of the invention that contains one or more ALK polypeptides described herein. For injectable formulations, various effective pharmaceutical carriers are known in the art. See, e.g., Pharmaceutics and Pharmacy Practice, J. B. Lippincott Company, Philadelphia, Pa., Banker and Chalmers, eds., pages 238-250 (1982), and ASHP Handbook on Injectable Drugs, Toissel, 4th ed., pages 622-630 (1986).

The dosage of the pharmaceutical compositions of the invention depends on factors including the route of administration, the disease to be treated, and physical characteristics, e.g., age, weight, general health, of the subject. Typically, the amount of an ALK polypeptide described herein contained within a single dose may be an amount that effectively treats the disease without inducing significant toxicity. A pharmaceutical composition of the invention may include a dosage of an ALK polypeptide described herein ranging from 0.001 to 500 mg (e.g., 0.05, 0.01, 0.1, 0.2, 0.3, 0.5, 0.7, 0.8, 1 mg, 2 mg, 3 mg, 4 mg, 5 mg, 10 mg, 15 mg, 20 mg, 30 mg, 50 mg, 100 mg, 250 mg, or 500 mg) and, in a more specific embodiment, about 0.1 to about 100 mg and, in a more specific embodiment, about 0.2 to about 20 mg. The dosage may be adapted by the clinician in accordance with conventional factors such as the extent of the disease and different parameters of the subject.

A pharmaceutical composition of the invention can be administered in an amount from about 0.001 mg up to about 500 mg/kg/day (e.g., 0.05, 0.01, 0.1, 0.2, 0.3, 0.5, 0.7, 0.8, 1 mg, 2 mg, 3 mg, 4 mg, 5 mg, 10 mg, 15 mg, 20 mg, 30 mg, 50 mg, 100 mg, 250 mg, or 500 mg/kg/day). Pharmaceutical compositions of the invention that contain an ALK polypeptide described herein may be administered to a subject in need thereof, for example, one or more times (e.g., 1-10 times or more) daily, weekly, monthly, biannually, annually, or as medically necessary. Dosages may be provided in either a single or multiple dosage regimens. For example, in some embodiments, the effective amount is a dose that ranges from about 0.1 to about 100 mg/kg/day, from about 0.2 mg to about 20 mg of the ALK polypeptide described herein per day, about 1 mg to about 10 mg of the ALK polypeptide described herein per day, from about 0.7 mg to about 210 mg of the ALK polypeptide described herein per week, 1.4 mg to about 140 mg of the ALK polypeptide described herein per week, about 0.3 mg to about 300 mg of the ALK polypeptide described herein every three days, about 0.4 mg to about 40 mg of the ALK polypeptide described herein every other day, and about 2 mg to about 20 mg of the ALK polypeptide described herein every other day. The timing between administrations may decrease as the medical condition improves or increase as the health of the patient declines.

Methods of Treatment

The invention provides methods of treating a disease associated with ALK in a subject (e.g., a mammal, e.g., a human) by administering to the subject a therapeutically effective amount of an immunogenic composition or pharmaceutical composition described herein. In some embodiments, the immunogenic composition or pharmaceutical composition includes one or more ALK polypeptides described herein, as well as one or more immunomodulators, adjuvants, and/or anti-cancer agents. In some embodiments, the immunogenic composition or pharmaceutical composition is administered without an immunomodulator, an adjuvant, and/or an anti-cancer agent.

In some embodiments, the method includes administering to the subject 1) a therapeutically effective amount of an immunogenic composition or pharmaceutical composition described herein, and 2) one or more immunomodulators.

In some embodiments, the method includes administering to the subject 1) a therapeutically effective amount of an immunogenic composition or pharmaceutical composition described herein, and 2) one or more tyrosine kinase inhibitors.

In some embodiments, 1) and 2) are administered substantially simultaneously (e.g., in two separate pharmaceutical compositions administered at the same time). In some embodiments, 1) and 2) are administered separately (e.g., in two separate pharmaceutical compositions administered at different times). In some embodiments, 1) is administered first, followed by administering of 2). In some embodiments, 2) is administered first, followed by administering of 1).

In some embodiments, the methods described herein are used in combination with a radiation therapy. Radiation therapy uses high-energy particles or waves, such as x-rays, gamma rays, electron beams, or protons, to destroy or damage cancer cells. For example, a subject may be treated with radiation therapy before or after being administered a therapeutically effective amount of an immunogenic composition or pharmaceutical composition described herein. In some embodiments, a subject may be treated with radiation therapy before or after being administered a therapeutically effective amount of an immunogenic composition or pharmaceutical composition described herein and one or more immunomodulators. In some embodiments, a subject may be treated with radiation therapy before or after being administered a therapeutically effective amount of an immunogenic composition or pharmaceutical composition described herein and one or more tyrosine kinase inhibitors.

In some embodiments, the immunomodulator used in the methods of the invention is selected from the group consisting of a PD-1 inhibitor, an anti-CTLA-4 antibody, an anti-CD40 antibody, a cyclophosphamide (CPM), an AMD3100, an anti-LAG-3/CD223 antibody, an anti-B7-H5 antibody, an anti-OX40 antibody, an anti-CD28 antibody, an anti-GITR antibody, an anti-4-1BB/CD137 antibody, a 4-1 BB ligand, an anti-BTLA antibody, an anti-TIM-3/HAVCR2 antibody, an anti-KIR antibody, an anti-Flt3/CD135 antibody, an anti-FasL antibody, an anti-CD25 antibody, an GM-CSF, an anti-GM-CSF-receptor (R) antibody, an IL-2, an anti-IL-2-R antibody, an IL-7, an anti-IL-7-R antibody, an IL-21, an anti-IL-21-R antibody, an IL-12, an anti-IL-12-R antibody, an IL-15, an anti-IL-15-R antibody, an IL-18, an anti-IL-18-R antibody, an anti-IDO antibody, an ipilimumab, a crizotinib, a ceritinib, an alectinib, a brigatinib, a celecoxib, a SOCS-1 inhibitor, a heat shock protein (HSP), a HSP inhibitor, and an anti-galectin-1 antibody.

In some embodiments, the tyrosine kinase inhibitor used in the methods of the invention is Crizotinib. In some embodiments, the tyrosine kinase inhibitor is Ceritinib. In some embodiments, the tyrosine kinase inhibitor is Alectinib. In some embodiments, the tyrosine kinase inhibitor is Brigatinib.

In some embodiments, a disease associated with ALK that can be treated by methods of the invention is cancer, such as a solid tumor cancer or an ALK$^+$ cancer. In some embodiments, an immunogenic composition or pharmaceutical composition described herein is administered before or after surgery to remove at least some of a solid tumor in the solid tumor cancer. In some embodiments, the cancer is anaplastic large cell lymphoma, non-small-cell lung cancer, neuroblastoma, rhabdomyosarcoma, neuroectodermal cancer, glioblastoma, breast carcinoma, melanoma, inflammatory myofibroblastic tumor, soft tissue tumor, ALK expressing lymphoma, or ALK expressing lung, colon, or prostate carcinoma.

Other cancers that may be treated with methods of the invention include, but are not limited to, bladder cancer, pancreatic cancer, lung cancer, liver cancer, ovarian cancer, colon cancer, stomach cancer, breast cancer, prostate cancer, renal cancer, testicular cancer, thyroid cancer, uterine cancer, rectal cancer, a cancer of the respiratory system, a cancer of the urinary system, oral cavity cancer, skin cancer, leukemia, sarcoma, carcinoma, basal cell carcinoma, non-Hodgkin's lymphoma, acute myeloid leukemia (AML), chronic lymphocytic leukemia (CLL), B-cells chronic lymphocytic leukemia (B-CLL), multiple myeloma (MM), erythroleukemia, renal cell carcinoma, astrocytoma, oligoastrocytoma, biliary tract cancer, choriocarcinoma, CNS cancer, larynx cancer, small cell lung cancer, adenocarcinoma, giant (or oat) cell carcinoma, and squamous cell carcinoma.

EXAMPLES

Example 1— Overall T-Cell Response Stimulated by ALK Polypeptides Having the Sequences of SEQ ID NOs: 1-59 in Table 1A To identify the immunodominant ALK polypeptides, mice were immunized with ALK polypeptides having the sequences of SEQ ID NOs: 1-59 listed in Table 1A mixed with Freund's adjuvant. Spleens and lymph nodes were removed from immunized mice and assayed by Enzyme-Linked ImmunoSpot (ELISPOT). Cells were separately re-stimulated with ALK polypeptide pools each containing five ALK polypeptides. For example, as shown in FIG. 1, "1-5" indicates an ALK polypeptide pool containing five ALK polypeptides having the sequences of SEQ ID NOs: 1-5 (Table 1A). ELISPOT results in FIG. 1 show that the strongest T cell responses were found in cells re-stimulated with ALK polypeptide pools 6-10, 26-20, and 31-35.

Example 2— CD4 and CD8 T-Cell Responses Stimulated by ALK Polypeptides

To identify the immunodominant ALK polypeptides, mice were immunized with ALK polypeptides having the sequences of SEQ ID NOs: 1-59 listed in Table 1A mixed with Freund's adjuvant. Spleens and lymph nodes were then removed from immunized mice and assayed by intracellular cytokine staining (ICS). Cells were re-stimulated with individual ALK polypeptides listed in Table 1A. ICS results in FIGS. 2A and 2B show that the strongest CD4 T-cell responses were found in cells re-stimulated with ALK polypeptides having the sequences of SEQ ID NOs: 10, 14, 17, 22, 52, and 53. Similarly, ICS results in FIGS. 2C and 2D show that the strongest CD8 T-cell response was found in cells re-stimulated with ALK polypeptide having the sequence of SEQ ID NOs: 10, 14, and 33.

Example 3— Overall T-Cell Response Stimulated by ALK Polypeptides Having the Sequences of SEQ ID NOs: 60-66 in Table 1A To identify the immunodominant ALK polypeptides, mice were immunized with ALK polypeptides having the sequences of SEQ ID NOs: 60-66 listed in Table 1A (10 μg) mixed with polyinosinic:polycytidylic acid (poly I:C) (50 μg). Three doses were administered on Day 0, 25, and 56. One week after immunization, 170 μl of blood was collected from each mouse for detection of T-cell response using ELISPOT. An ALK polypeptide pool containing 7 overlapping 9-mer ALK polypeptides (SEQ ID NOs: 60-66; see Table 1A) covering the sequence LTCPGPGRVAKIGDF (SEQ ID NO: 33) was incubated with the cells. The sequence LTCPGPGRVAKIGDF (SEQ ID NO: 33) was previously identified as a CD8 T-cell (CD8) stimulating sequence in Example 2. As shown in FIG. 3, T-cell response were detected in cells re-stimulated with the ALK polypeptide pool containing the 7 overlapping 9-mer ALK polypeptides.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

All publications, patents, and patent applications are herein incorporated by reference in their entirety to the same extent as if each individual publication, patent or patent application was specifically and individually indicated to be incorporated by reference in its entirety.

SEQUENCE LISTING

Sequence total quantity: 145

SEQ ID NO: 1  moltype = AA  length = 15
FEATURE       Location/Qualifiers
source        1..15
              mol_type = protein
              organism = synthetic construct
SEQUENCE: 1
CFAGKTSSIS DLKEV                                                 15

SEQ ID NO: 2  moltype = AA  length = 15
FEATURE       Location/Qualifiers
source        1..15
              mol_type = protein
              organism = synthetic construct
SEQUENCE: 2
TSSISDLKEV PRKNI                                                 15

SEQ ID NO: 3  moltype = AA  length = 15
FEATURE       Location/Qualifiers
source        1..15
              mol_type = protein
              organism = synthetic construct
SEQUENCE: 3
DLKEVPRKNI TLIRG                                                 15

SEQ ID NO: 4  moltype = AA  length = 15
FEATURE       Location/Qualifiers
source        1..15
              mol_type = protein
              organism = synthetic construct
SEQUENCE: 4
PRKNITLIRG LGHGA                                                 15

SEQ ID NO: 5  moltype = AA  length = 15
FEATURE       Location/Qualifiers
source        1..15
              mol_type = protein
              organism = synthetic construct
SEQUENCE: 5
TLIRGLGHGA FGEVY                                                 15

SEQ ID NO: 6  moltype = AA  length = 15
FEATURE       Location/Qualifiers
source        1..15
              mol_type = protein
              organism = synthetic construct
SEQUENCE: 6
LGHGAFGEVY EGQVS                                                 15

SEQ ID NO: 7  moltype = AA  length = 15
FEATURE       Location/Qualifiers
source        1..15
              mol_type = protein
              organism = synthetic construct
SEQUENCE: 7
FGEVYEGQVS GMPND                                                 15

SEQ ID NO: 8  moltype = AA  length = 15
FEATURE       Location/Qualifiers
source        1..15
              mol_type = protein
              organism = synthetic construct
SEQUENCE: 8
EGQVSGMPND PSPLQ                                                 15

SEQ ID NO: 9  moltype = AA  length = 15
FEATURE       Location/Qualifiers
source        1..15
              mol_type = protein
              organism = synthetic construct
SEQUENCE: 9
GMPNDPSPLQ VAVRT                                                 15

SEQ ID NO: 10  moltype = AA  length = 15
FEATURE        Location/Qualifiers
source         1..15
               mol_type = protein
               organism = synthetic construct

```
SEQUENCE: 10
PSPLQVAVRT LPEVC                                                         15

SEQ ID NO: 11           moltype = AA  length = 15
FEATURE                 Location/Qualifiers
source                  1..15
                        mol_type = protein
                        organism = synthetic construct
SEQUENCE: 11
VAVRTLPEVC SEQDE                                                         15

SEQ ID NO: 12           moltype = AA  length = 15
FEATURE                 Location/Qualifiers
source                  1..15
                        mol_type = protein
                        organism = synthetic construct
SEQUENCE: 12
LPEVCSEQDE LDFLM                                                         15

SEQ ID NO: 13           moltype = AA  length = 15
FEATURE                 Location/Qualifiers
source                  1..15
                        mol_type = protein
                        organism = synthetic construct
SEQUENCE: 13
SEQDELDFLM EALII                                                         15

SEQ ID NO: 14           moltype = AA  length = 15
FEATURE                 Location/Qualifiers
source                  1..15
                        mol_type = protein
                        organism = synthetic construct
SEQUENCE: 14
LDFLMEALII SKFNH                                                         15

SEQ ID NO: 15           moltype = AA  length = 15
FEATURE                 Location/Qualifiers
source                  1..15
                        mol_type = protein
                        organism = synthetic construct
SEQUENCE: 15
EALIISKFNH QNIVR                                                         15

SEQ ID NO: 16           moltype = AA  length = 15
FEATURE                 Location/Qualifiers
source                  1..15
                        mol_type = protein
                        organism = synthetic construct
SEQUENCE: 16
SKFNHQNIVR CIGVS                                                         15

SEQ ID NO: 17           moltype = AA  length = 15
FEATURE                 Location/Qualifiers
source                  1..15
                        mol_type = protein
                        organism = synthetic construct
SEQUENCE: 17
QNIVRCIGVS LQSLP                                                         15

SEQ ID NO: 18           moltype = AA  length = 15
FEATURE                 Location/Qualifiers
source                  1..15
                        mol_type = protein
                        organism = synthetic construct
SEQUENCE: 18
CIGVSLQSLP RFILL                                                         15

SEQ ID NO: 19           moltype = AA  length = 15
FEATURE                 Location/Qualifiers
source                  1..15
                        mol_type = protein
                        organism = synthetic construct
SEQUENCE: 19
LQSLPRFILL ELMAG                                                         15

SEQ ID NO: 20           moltype = AA  length = 15
FEATURE                 Location/Qualifiers
source                  1..15
                        mol_type = protein
```

```
                        -continued
SEQUENCE: 20
RFILLELMAG GDLKS                                                15

SEQ ID NO: 21           moltype = AA   length = 15
FEATURE                 Location/Qualifiers
source                  1..15
                        mol_type = protein
                        organism = synthetic construct
SEQUENCE: 21
ELMAGGDLKS FLRET                                                15

SEQ ID NO: 22           moltype = AA   length = 15
FEATURE                 Location/Qualifiers
source                  1..15
                        mol_type = protein
                        organism = synthetic construct
SEQUENCE: 22
GDLKSFLRET RPRPS                                                15

SEQ ID NO: 23           moltype = AA   length = 15
FEATURE                 Location/Qualifiers
source                  1..15
                        mol_type = protein
                        organism = synthetic construct
SEQUENCE: 23
FLRETRPRPS QPSSL                                                15

SEQ ID NO: 24           moltype = AA   length = 15
FEATURE                 Location/Qualifiers
source                  1..15
                        mol_type = protein
                        organism = synthetic construct
SEQUENCE: 24
RPRPSQPSSL AMLDL                                                15

SEQ ID NO: 25           moltype = AA   length = 15
FEATURE                 Location/Qualifiers
source                  1..15
                        mol_type = protein
                        organism = synthetic construct
SEQUENCE: 25
QPSSLAMLDL LHVAR                                                15

SEQ ID NO: 26           moltype = AA   length = 15
FEATURE                 Location/Qualifiers
source                  1..15
                        mol_type = protein
                        organism = synthetic construct
SEQUENCE: 26
AMLDLLHVAR DIACG                                                15

SEQ ID NO: 27           moltype = AA   length = 15
FEATURE                 Location/Qualifiers
source                  1..15
                        mol_type = protein
                        organism = synthetic construct
SEQUENCE: 27
LHVARDIACG CQYLE                                                15

SEQ ID NO: 28           moltype = AA   length = 15
FEATURE                 Location/Qualifiers
source                  1..15
                        mol_type = protein
                        organism = synthetic construct
SEQUENCE: 28
DIACGCQYLE ENHFI                                                15

SEQ ID NO: 29           moltype = AA   length = 15
FEATURE                 Location/Qualifiers
source                  1..15
                        mol_type = protein
                        organism = synthetic construct
SEQUENCE: 29
CQYLEENHFI HRDIA                                                15

SEQ ID NO: 30           moltype = AA   length = 15
FEATURE                 Location/Qualifiers
source                  1..15
```

```
                        mol_type = protein
                        organism = synthetic construct
SEQUENCE: 30
ENHFIHRDIA ARNCL                                                        15

SEQ ID NO: 31           moltype = AA  length = 15
FEATURE                 Location/Qualifiers
source                  1..15
                        mol_type = protein
                        organism = synthetic construct
SEQUENCE: 31
HRDIAARNCL LTCPG                                                        15

SEQ ID NO: 32           moltype = AA  length = 15
FEATURE                 Location/Qualifiers
source                  1..15
                        mol_type = protein
                        organism = synthetic construct
SEQUENCE: 32
ARNCLLTCPG PGRVA                                                        15

SEQ ID NO: 33           moltype = AA  length = 15
FEATURE                 Location/Qualifiers
source                  1..15
                        mol_type = protein
                        organism = synthetic construct
SEQUENCE: 33
LTCPGPGRVA KIGDF                                                        15

SEQ ID NO: 34           moltype = AA  length = 15
FEATURE                 Location/Qualifiers
source                  1..15
                        mol_type = protein
                        organism = synthetic construct
SEQUENCE: 34
PGRVAKIGDF GMARD                                                        15

SEQ ID NO: 35           moltype = AA  length = 15
FEATURE                 Location/Qualifiers
source                  1..15
                        mol_type = protein
                        organism = synthetic construct
SEQUENCE: 35
KIGDFGMARD IYRAS                                                        15

SEQ ID NO: 36           moltype = AA  length = 15
FEATURE                 Location/Qualifiers
source                  1..15
                        mol_type = protein
                        organism = synthetic construct
SEQUENCE: 36
GMARDIYRAS YYRKG                                                        15

SEQ ID NO: 37           moltype = AA  length = 15
FEATURE                 Location/Qualifiers
source                  1..15
                        mol_type = protein
                        organism = synthetic construct
SEQUENCE: 37
IYRASYYRKG GCAML                                                        15

SEQ ID NO: 38           moltype = AA  length = 15
FEATURE                 Location/Qualifiers
source                  1..15
                        mol_type = protein
                        organism = synthetic construct
SEQUENCE: 38
YYRKGGCAML PVKWM                                                        15

SEQ ID NO: 39           moltype = AA  length = 15
FEATURE                 Location/Qualifiers
source                  1..15
                        mol_type = protein
                        organism = synthetic construct
SEQUENCE: 39
GCAMLPVKWM PPEAF                                                        15

SEQ ID NO: 40           moltype = AA  length = 15
FEATURE                 Location/Qualifiers
```

```
source                    1..15
                          mol_type = protein
                          organism = synthetic construct
SEQUENCE: 40
PVKWMPPEAF MEGIF                                                            15

SEQ ID NO: 41             moltype = AA  length = 15
FEATURE                   Location/Qualifiers
source                    1..15
                          mol_type = protein
                          organism = synthetic construct
SEQUENCE: 41
PPEAFMEGIF TSKTD                                                            15

SEQ ID NO: 42             moltype = AA  length = 15
FEATURE                   Location/Qualifiers
source                    1..15
                          mol_type = protein
                          organism = synthetic construct
SEQUENCE: 42
MEGIFTSKTD TWSFG                                                            15

SEQ ID NO: 43             moltype = AA  length = 15
FEATURE                   Location/Qualifiers
source                    1..15
                          mol_type = protein
                          organism = synthetic construct
SEQUENCE: 43
TSKTDTWSFG VLLWE                                                            15

SEQ ID NO: 44             moltype = AA  length = 15
FEATURE                   Location/Qualifiers
source                    1..15
                          mol_type = protein
                          organism = synthetic construct
SEQUENCE: 44
TWSFGVLLWE IFSLG                                                            15

SEQ ID NO: 45             moltype = AA  length = 15
FEATURE                   Location/Qualifiers
source                    1..15
                          mol_type = protein
                          organism = synthetic construct
SEQUENCE: 45
VLLWEIFSLG YMPYP                                                            15

SEQ ID NO: 46             moltype = AA  length = 15
FEATURE                   Location/Qualifiers
source                    1..15
                          mol_type = protein
                          organism = synthetic construct
SEQUENCE: 46
IFSLGYMPYP SKSNQ                                                            15

SEQ ID NO: 47             moltype = AA  length = 15
FEATURE                   Location/Qualifiers
source                    1..15
                          mol_type = protein
                          organism = synthetic construct
SEQUENCE: 47
YMPYPSKSNQ EVLEF                                                            15

SEQ ID NO: 48             moltype = AA  length = 15
FEATURE                   Location/Qualifiers
source                    1..15
                          mol_type = protein
                          organism = synthetic construct
SEQUENCE: 48
SKSNQEVLEF VTSGG                                                            15

SEQ ID NO: 49             moltype = AA  length = 15
FEATURE                   Location/Qualifiers
source                    1..15
                          mol_type = protein
                          organism = synthetic construct
SEQUENCE: 49
EVLEFVTSGG RMDPP                                                            15

SEQ ID NO: 50             moltype = AA  length = 15
```

```
FEATURE                 Location/Qualifiers
source                  1..15
                        mol_type = protein
                        organism = synthetic construct
SEQUENCE: 50
VTSGGRMDPP KNCPG                                                         15

SEQ ID NO: 51           moltype = AA  length = 15
FEATURE                 Location/Qualifiers
source                  1..15
                        mol_type = protein
                        organism = synthetic construct
SEQUENCE: 51
RMDPPKNCPG PVYRI                                                         15

SEQ ID NO: 52           moltype = AA  length = 15
FEATURE                 Location/Qualifiers
source                  1..15
                        mol_type = protein
                        organism = synthetic construct
SEQUENCE: 52
KNCPGPVYRI MTQCW                                                         15

SEQ ID NO: 53           moltype = AA  length = 15
FEATURE                 Location/Qualifiers
source                  1..15
                        mol_type = protein
                        organism = synthetic construct
SEQUENCE: 53
PVYRIMTQCW QHQPE                                                         15

SEQ ID NO: 54           moltype = AA  length = 15
FEATURE                 Location/Qualifiers
source                  1..15
                        mol_type = protein
                        organism = synthetic construct
SEQUENCE: 54
MTQCWQHQPE DRPNF                                                         15

SEQ ID NO: 55           moltype = AA  length = 15
FEATURE                 Location/Qualifiers
source                  1..15
                        mol_type = protein
                        organism = synthetic construct
SEQUENCE: 55
QHQPEDRPNF AIILE                                                         15

SEQ ID NO: 56           moltype = AA  length = 15
FEATURE                 Location/Qualifiers
source                  1..15
                        mol_type = protein
                        organism = synthetic construct
SEQUENCE: 56
DRPNFAIILE RIEYC                                                         15

SEQ ID NO: 57           moltype = AA  length = 15
FEATURE                 Location/Qualifiers
source                  1..15
                        mol_type = protein
                        organism = synthetic construct
SEQUENCE: 57
AIILERIEYC TQDPD                                                         15

SEQ ID NO: 58           moltype = AA  length = 15
FEATURE                 Location/Qualifiers
source                  1..15
                        mol_type = protein
                        organism = synthetic construct
SEQUENCE: 58
RIEYCTQDPD VINTA                                                         15

SEQ ID NO: 59           moltype = AA  length = 12
FEATURE                 Location/Qualifiers
source                  1..12
                        mol_type = protein
                        organism = synthetic construct
SEQUENCE: 59
TQDPDVINTA LP                                                            12
```

-continued

```
SEQ ID NO: 60            moltype = AA   length = 9
FEATURE                  Location/Qualifiers
source                   1..9
                         mol_type = protein
                         organism = synthetic construct
SEQUENCE: 60
LTCPGPGRV                                                                  9

SEQ ID NO: 61            moltype = AA   length = 9
FEATURE                  Location/Qualifiers
source                   1..9
                         mol_type = protein
                         organism = synthetic construct
SEQUENCE: 61
TCPGPGRVA                                                                  9

SEQ ID NO: 62            moltype = AA   length = 9
FEATURE                  Location/Qualifiers
source                   1..9
                         mol_type = protein
                         organism = synthetic construct
SEQUENCE: 62
CPGPGRVAK                                                                  9

SEQ ID NO: 63            moltype = AA   length = 9
FEATURE                  Location/Qualifiers
source                   1..9
                         mol_type = protein
                         organism = synthetic construct
SEQUENCE: 63
PGPGRVAKI                                                                  9

SEQ ID NO: 64            moltype = AA   length = 9
FEATURE                  Location/Qualifiers
source                   1..9
                         mol_type = protein
                         organism = synthetic construct
SEQUENCE: 64
GPGRVAKIG                                                                  9

SEQ ID NO: 65            moltype = AA   length = 9
FEATURE                  Location/Qualifiers
source                   1..9
                         mol_type = protein
                         organism = synthetic construct
SEQUENCE: 65
PGRVAKIGD                                                                  9

SEQ ID NO: 66            moltype = AA   length = 9
FEATURE                  Location/Qualifiers
source                   1..9
                         mol_type = protein
                         organism = synthetic construct
SEQUENCE: 66
GRVAKIGDF                                                                  9

SEQ ID NO: 67            moltype = AA   length = 1620
FEATURE                  Location/Qualifiers
source                   1..1620
                         mol_type = protein
                         organism = Homo sapiens
SEQUENCE: 67
MGAIGLLWLL  PLLLSTAAVG  SGMGTGQRAG  SPAAGPPLQP  REPLSYSRLQ  RKSLAVDFVV    60
PSLFRVYARD  LLLPPSSSEL  KAGRPEARGS  LALDCAPLLR  LLGPAPGVSW  TAGSPAPAEA   120
RTLSRVLKGG  SVRKLRRAKQ  LVLELGEEAI  LEGCVGPPGE  AAVGLLQFNL  SELFSWWIRQ   180
GEGRLRIRLM  PEKKASEVGR  EGRLSAAIRA  SQPRLLFQIF  GTGHSSLESP  TNMPSPSPDY   240
FTWNLTWIMK  DSFPFLSHRS  RYGLECSFDF  PCELEYSPPL  HDLRNQSWSW  RRIPSEEASQ   300
MDLLDGPGAE  RSKEMPRGSF  LLLNTSADSK  HTILSPWMRS  SSEHCTLAVS  VHRHLQPSGR   360
YIAQLLPHNE  AAREILLMPT  PGKHGWTVLQ  GRIGRPDNPF  RVALEYISSG  NRSLSAVDFF   420
ALKNCSEGTS  PGSKMALQSS  FTCWNGTVLQ  LGQACDFHQD  CAQGEDESQM  CRKLPVGFYC   480
NFEDGFCGWT  QGTLSPHTPQ  WQVRTLKDAR  FQDHQDHALL  LSTTDVPASE  SATVTSATFP   540
APIKSSPCEL  RMSWLIRGVL  RGNVSLVLVE  NKTGKEQGRM  VWHVAAYEGL  SLWQWMVLPL   600
LDVSDRFWLQ  MVAWWGQGSR  AIVAFDNISI  SLDCYLTISG  EDKILQNTAP  KSRNLFERNP   660
NKELKPGENS  PRQTPIFDPT  VHWLFTTCGA  SGPHGPTQAQ  CNNAYQNSNL  SVEVGSEGPL   720
KGIQIWKVPA  TDTYSISGYG  AAGGKGGKNT  MMRSHGVSVL  GIFNLEKDDM  LYILVGQQGE   780
DACPSTNQLI  QKVCIGENNV  IEEEIRVNRS  VHEWAGGGGG  GGGATYVFKM  KDGVPVPLII   840
AAGGGGRAYG  AKTDTFHPER  LENNSSVLGL  NGNSGAAGGG  GGWNDNTSLL  WAGKSLQEGA   900
TGGHSCPQAM  KKWGWETRGG  FGGGGGGCSS  GGGGGGYIGG  NAASNNDPEM  DGEDGVSFIS   960
PLGILYTPAL  KVMEGHGEVN  IKHYLNCSHC  EVDECHMDPE  SHKVICFCDH  GTVLAEDGVS  1020
```

```
CIVSPTPEPH LPLSLILSVV TSALVAALVL AFSGIMIVYR RKHQELQAMQ MELQSPEYKL    1080
SKLRTSIIMT DYNPNYCFAG KTSSISDLKE VPRKNITLIR GLGHGAFGEV YEGQVSGMPN    1140
DPSPLQVAVK TLPEVCSEQD ELDFLMEALI ISKFNHQNIV RCIGVSLQSL PRFILLELMA    1200
GGDLKSFLRE TRPRPSQPSS LAMLDLLHVA RDIACGCQYL EENHFIHRDI AARNCLLTCP    1260
GPGRVAKIGD FGMARDIYRA SYYRKGGCAM LPVKWMPPEA FMEGIFTSKT DTWSFGVLLW    1320
EIFSLGYMPY PSKSNQEVLE FVTSGGRMDP PKNCPGPVYR IMTQCWQHQP EDRPNFAIIL    1380
ERIEYCTQDP DVINTALPIE YGPLVEEEEK VPVRPKDPEG VPPLLSQQA KREEERSPAA     1440
PPPLPTTSSG KAAKKPTAAE ISVRVPRGPA VEGGHVNMAF SQSNPPSELH KVHGSRNKPT    1500
SLWNPTYGSW FTEKPTKKNN PIAKKEPHDR GNLGLEGSCT VPPNVATGRL PGASLLLEPS    1560
SLTANMKEVP LFRLRHFPCG NVNYGYQQQG LPLEAATAPG AGHYEDTILK SKNSMNQPGP    1620

SEQ ID NO: 68              moltype = AA   length = 1620
FEATURE                    Location/Qualifiers
source                     1..1620
                           mol_type = protein
                           organism = synthetic construct
SEQUENCE: 68
MGAIGLLWLL PLLLSTAAVG SGMGTGQRAG SPAAGPPLQP REPLSYSRLQ RKSLAVDFVV     60
PSLFRVYARD LLLPPSSSEL KAGRPEARGS LALDCAPLLR LLGPAPGVSW TAGSPAPAEA    120
RTLSRVLKGG SVRKLRRAKQ LVLELGEEAI LEGCVGPPGE AAVGLLQFNL SELFSWWIRQ    180
GEGRLRIRLM PEKKASEVGR EGRLSAAIRA SQPRLLFQIF GTGHSSLESP TNMPSPSPDY    240
FTWNLTWIMK DSFPFLSHRS RYGLECSFDP PCELEYSPPL HDLRNQSWSW RRIPSEEASQ    300
MDLLDGPGAE RSKEMPRGSF LLLNTSADSK HTILSPWMRS SSEHCTLAVS VHRHLQPSGR    360
YIAQLLPHNE AAREILLMPT PGKHGWTVLQ GRIGRPDNPF RVALEYISSG NRSLSAVDFF    420
ALKNCSEGTS PGSKMALQSS FTCWNGTVLQ LGQACDFHQD CAQGEDESQM CRKLPVGFYC    480
NFEDGFCGWT QGTLSPHTPQ WQVRTLKDAR FQDHQDHALL LSTTDVPASE SATVTSATFP    540
APIKSSPCEL RMSWLIRGVL RGNVSLVLVE NKTGKEQGRM VWHVAAYEGL SLWQWMVLPL    600
LDVSDRFWLQ MVAWWGQGSR AIVAFDNISI SLDCYLTISG EDKILQNTAP KSRNLFERNP    660
NKELKPGENS PRQTPIFDPT VHWLFTTCGA SGPHGPTQAQ CNNAYQNSNL SVEVGSEGPL    720
KGIQIWKVPA TDTYSISGYG AAGGKGGKNT MMRSHGVSVL GIFNLEKDDM LYILVGQQGE    780
DACPSTNQLI QKVCIGENNV IEEEIRVNRS VHEWAGGGGG GGGATYVFKM KDGVPVPLII    840
AAGGGGRAYG AKTDTFHPER LENNSSVLGL NGNSGAAGGG GGWNDNTSLL WAGKSLQEGA    900
TGGHSCPQAM KKWGWETRGG FGGGGGGCSS GGGGGGYIGG NAASNNDPEM DGEDGVSFIS    960
PLGILYTPAL KVMEGHGEVN IKHYLNCSHC EVDECHMDPE SHKVICFCDH GTVLAEDGVS   1020
CIVSPTPEPH LPLSLILSVV TSALVAALVL AFSGIMIVYR RKHQELQAMQ MELQSPEYKL   1080
SKLRTSIIMT DYNPNYCFAG KTSSISDLKE VPRKNITLIR GLGHGAFGEV YEGQVSGMPN   1140
DPSPLQVAVR TLPEVCSEQD ELDFLMEALI ISKFNHQNIV RCIGVSLQSL PRFILLELMA   1200
GGDLKSFLRE TRPRPSQPSS LAMLDLLHVA RDIACGCQYL EENHFIHRDI AARNCLLTCP   1260
GPGRVAKIGD FGMARDIYRA SYYRKGGCAM LPVKWMPPEA FMEGIFTSKT DTWSFGVLLW   1320
EIFSLGYMPY PSKSNQEVLE FVTSGGRMDP PKNCPGPVYR IMTQCWQHQP EDRPNFAIIL   1380
ERIEYCTQDP DVINTALPIE YGPLVEEEEK VPVRPKDPEG VPPLLSQQA KREEERSPAA    1440
PPPLPTTSSG KAAKKPTAAE ISVRVPRGPA VEGGHVNMAF SQSNPPSELH KVHGSRNKPT   1500
SLWNPTYGSW FTEKPTKKNN PIAKKEPHDR GNLGLEGSCT VPPNVATGRL PGASLLLEPS   1560
SLTANMKEVP LFRLRHFPCG NVNYGYQQQG LPLEAATAPG AGHYEDTILK SKNSMNQPGP   1620

SEQ ID NO: 69              moltype = AA   length = 563
FEATURE                    Location/Qualifiers
source                     1..563
                           mol_type = protein
                           organism = Homo sapiens
SEQUENCE: 69
VYRRKHQELQ AMQMELQSPE YKLSKLRTST IMTDYNPNYC FAGKTSSISD LKEVPRKNIT     60
LIRGLGHGAF GEVYEGQVSG MPNDPSPLQV AVKTLPEVCS EQDELDFLME ALIISKFNHQ    120
NIVRCIGVSL QSLPRFILLE LMAGGDLKSF LRETRPRPSQ PSSLAMLDLL HVARDIACGC    180
QYLEENHFIH RDIAARNCLL TCPGPGRVAK IGDFGMARDI YRASYYRKGG CAMLPVKWMP    240
PEAFMEGIFT SKTDTWSFGV LLWEIFSLGY MPYPSKSNQE VLEFVTSGGR MDPPKNCPGP    300
VYRIMTQCWQ HQPEDRPNFA IILERIEYCT QDPDVINTAL PIEYGPLVEE EKVPVRPKD    360
PEGVPPLLVS QQAKREEERS PAAPPPLPTT SSGKAAKKPT AAEVSVRVPR GPAVEGGHVN    420
MAFSQSNPPS ELHRVHGSRN KPTSLWNPTY GSWFTEKPTK KNNPIAKKEP HERGNLGLEG    480
SCTVPPNVAT GRLPGASLLL EPSSLTANMK EVPLFRLRHF PCGNVNYGYQ QQGLPLEAAT    540
APGAGHYEDT ILKSKNSMNQ PGP                                            563

SEQ ID NO: 70              moltype = AA   length = 563
FEATURE                    Location/Qualifiers
source                     1..563
                           mol_type = protein
                           organism = synthetic construct
SEQUENCE: 70
VYRRKHQELQ AMQMELQSPE YKLSKLRTST IMTDYNPNYC FAGKTSSISD LKEVPRKNIT     60
LIRGLGHGAF GEVYEGQVSG MPNDPSPLQV AVRTLPEVCS EQDELDFLME ALIISKFNHQ    120
NIVRCIGVSL QSLPRFILLE LMAGGDLKSF LRETRPRPSQ PSSLAMLDLL HVARDIACGC    180
QYLEENHFIH RDIAARNCLL TCPGPGRVAK IGDFGMARDI YRASYYRKGG CAMLPVKWMP    240
PEAFMEGIFT SKTDTWSFGV LLWEIFSLGY MPYPSKSNQE VLEFVTSGGR MDPPKNCPGP    300
VYRIMTQCWQ HQPEDRPNFA IILERIEYCT QDPDVINTAL PIEYGPLVEE EKVPVRPKD    360
PEGVPPLLVS QQAKREEERS PAAPPPLPTT SSGKAAKKPT AAEVSVRVPR GPAVEGGHVN    420
MAFSQSNPPS ELHRVHGSRN KPTSLWNPTY GSWFTEKPTK KNNPIAKKEP HERGNLGLEG    480
SCTVPPNVAT GRLPGASLLL EPSSLTANMK EVPLFRLRHF PCGNVNYGYQ QQGLPLEAAT    540
APGAGHYEDT ILKSKNSMNQ PGP                                            563
```

```
SEQ ID NO: 71              moltype = AA   length = 5
FEATURE                    Location/Qualifiers
source                     1..5
                           mol_type = protein
                           organism = synthetic construct
SEQUENCE: 71
GGGGS                                                                         5

SEQ ID NO: 72              moltype = AA   length = 4
FEATURE                    Location/Qualifiers
source                     1..4
                           mol_type = protein
                           organism = synthetic construct
SEQUENCE: 72
GGSG                                                                          4

SEQ ID NO: 73              moltype = AA   length = 4
FEATURE                    Location/Qualifiers
source                     1..4
                           mol_type = protein
                           organism = synthetic construct
SEQUENCE: 73
SGGG                                                                          4

SEQ ID NO: 74              moltype = AA   length = 4
FEATURE                    Location/Qualifiers
source                     1..4
                           mol_type = protein
                           organism = synthetic construct
SEQUENCE: 74
GSGS                                                                          4

SEQ ID NO: 75              moltype = AA   length = 6
FEATURE                    Location/Qualifiers
source                     1..6
                           mol_type = protein
                           organism = synthetic construct
SEQUENCE: 75
GSGSGS                                                                        6

SEQ ID NO: 76              moltype = AA   length = 8
FEATURE                    Location/Qualifiers
source                     1..8
                           mol_type = protein
                           organism = synthetic construct
SEQUENCE: 76
GSGSGSGS                                                                      8

SEQ ID NO: 77              moltype = AA   length = 10
FEATURE                    Location/Qualifiers
source                     1..10
                           mol_type = protein
                           organism = synthetic construct
SEQUENCE: 77
GSGSGSGSGS                                                                   10

SEQ ID NO: 78              moltype = AA   length = 12
FEATURE                    Location/Qualifiers
source                     1..12
                           mol_type = protein
                           organism = synthetic construct
SEQUENCE: 78
GSGSGSGSGS GS                                                                12

SEQ ID NO: 79              moltype = AA   length = 6
FEATURE                    Location/Qualifiers
source                     1..6
                           mol_type = protein
                           organism = synthetic construct
SEQUENCE: 79
GGSGGS                                                                        6

SEQ ID NO: 80              moltype = AA   length = 9
FEATURE                    Location/Qualifiers
source                     1..9
                           mol_type = protein
                           organism = synthetic construct
SEQUENCE: 80
GGSGGSGGS                                                                     9
```

| | | |
|---|---|---|
| SEQ ID NO: 81<br>FEATURE<br>source<br><br>SEQUENCE: 81<br>GGSGGSGGSG GS | moltype = AA   length = 12<br>Location/Qualifiers<br>1..12<br>mol_type = protein<br>organism = synthetic construct | <br><br><br><br><br>12 |
| SEQ ID NO: 82<br>FEATURE<br>source<br><br>SEQUENCE: 82<br>GGSGGGSG | moltype = AA   length = 8<br>Location/Qualifiers<br>1..8<br>mol_type = protein<br>organism = synthetic construct | <br><br><br><br><br>8 |
| SEQ ID NO: 83<br>FEATURE<br>source<br><br>SEQUENCE: 83<br>GGSGGGSGGG SG | moltype = AA   length = 12<br>Location/Qualifiers<br>1..12<br>mol_type = protein<br>organism = synthetic construct | <br><br><br><br><br>12 |
| SEQ ID NO: 84<br>FEATURE<br>source<br><br>SEQUENCE: 84<br>GGGGSGGGGS GGGGS | moltype = AA   length = 15<br>Location/Qualifiers<br>1..15<br>mol_type = protein<br>organism = synthetic construct | <br><br><br><br><br>15 |
| SEQ ID NO: 85<br>FEATURE<br>source<br><br>SEQUENCE: 85<br>GENLYFQSGG | moltype = AA   length = 10<br>Location/Qualifiers<br>1..10<br>mol_type = protein<br>organism = synthetic construct | <br><br><br><br><br>10 |
| SEQ ID NO: 86<br>FEATURE<br>source<br><br>SEQUENCE: 86<br>SACYCELS | moltype = AA   length = 8<br>Location/Qualifiers<br>1..8<br>mol_type = protein<br>organism = synthetic construct | <br><br><br><br><br>8 |
| SEQ ID NO: 87<br>FEATURE<br>source<br><br>SEQUENCE: 87<br>RSIAT | moltype = AA   length = 5<br>Location/Qualifiers<br>1..5<br>mol_type = protein<br>organism = synthetic construct | <br><br><br><br><br>5 |
| SEQ ID NO: 88<br>FEATURE<br>source<br><br>SEQUENCE: 88<br>RPACKIPNDL KQKVMNH | moltype = AA   length = 17<br>Location/Qualifiers<br>1..17<br>mol_type = protein<br>organism = synthetic construct | <br><br><br><br><br>17 |
| SEQ ID NO: 89<br>FEATURE<br>source<br><br>SEQUENCE: 89<br>GGSAGGSGSG SSGGSSGASG TGTAGGTGSG SGTGSG | moltype = AA   length = 36<br>Location/Qualifiers<br>1..36<br>mol_type = protein<br>organism = synthetic construct | <br><br><br><br><br>36 |
| SEQ ID NO: 90<br>FEATURE<br>source<br><br>SEQUENCE: 90 | moltype = AA   length = 17<br>Location/Qualifiers<br>1..17<br>mol_type = protein<br>organism = synthetic construct | |

```
AAANSSIDLI SVPVDSR                                                              17

SEQ ID NO: 91           moltype = AA   length = 36
FEATURE                 Location/Qualifiers
source                  1..36
                        mol_type = protein
                        organism = synthetic construct
SEQUENCE: 91
GGSGGGSEGG GSEGGGSEGG GSEGGGSEGG GSGGGS                                          36

SEQ ID NO: 92           moltype = AA   length = 11
FEATURE                 Location/Qualifiers
source                  1..11
                        mol_type = protein
                        organism = synthetic construct
SEQUENCE: 92
DICLPRWGCL W                                                                    11

SEQ ID NO: 93           moltype = AA   length = 31
FEATURE                 Location/Qualifiers
source                  1..31
                        mol_type = protein
                        organism = synthetic construct
SEQUENCE: 93
VYRRKHQELQ AMQMELQSPE YKLSKLRTST I                                              31

SEQ ID NO: 94           moltype = AA   length = 31
FEATURE                 Location/Qualifiers
source                  1..31
                        mol_type = protein
                        organism = synthetic construct
SEQUENCE: 94
EYKLSKLRTS TIMTDYNPNY CFAGKTSSIS D                                              31

SEQ ID NO: 95           moltype = AA   length = 31
FEATURE                 Location/Qualifiers
source                  1..31
                        mol_type = protein
                        organism = synthetic construct
SEQUENCE: 95
YCFAGKTSSI SDLKEVPRKN ITLIRGLGHG A                                              31

SEQ ID NO: 96           moltype = AA   length = 31
FEATURE                 Location/Qualifiers
source                  1..31
                        mol_type = protein
                        organism = synthetic construct
SEQUENCE: 96
NITLIRGLGH GAFGEVYEGQ VSGMPNDPSP L                                              31

SEQ ID NO: 97           moltype = AA   length = 31
FEATURE                 Location/Qualifiers
source                  1..31
                        mol_type = protein
                        organism = synthetic construct
SEQUENCE: 97
QVSGMPNDPS PLQVAVKTLP EVCSEQDELD F                                              31

SEQ ID NO: 98           moltype = AA   length = 31
FEATURE                 Location/Qualifiers
source                  1..31
                        mol_type = protein
                        organism = synthetic construct
SEQUENCE: 98
PEVCSEQDEL DFLMEALIIS KFNHQNIVRC I                                              31

SEQ ID NO: 99           moltype = AA   length = 31
FEATURE                 Location/Qualifiers
source                  1..31
                        mol_type = protein
                        organism = synthetic construct
SEQUENCE: 99
SKFNHQNIVR CIGVSLQSLP RFILLELMAG G                                              31

SEQ ID NO: 100          moltype = AA   length = 31
FEATURE                 Location/Qualifiers
source                  1..31
                        mol_type = protein
                        organism = synthetic construct
```

```
SEQUENCE: 100
PRFILLELMA GGDLKSFLRE TRPRPSQPSS L                              31

SEQ ID NO: 101          moltype = AA  length = 31
FEATURE                 Location/Qualifiers
source                  1..31
                        mol_type = protein
                        organism = synthetic construct
SEQUENCE: 101
ETRPRPSQPS SLAMLDLLHV ARDIACGCQY L                              31

SEQ ID NO: 102          moltype = AA  length = 31
FEATURE                 Location/Qualifiers
source                  1..31
                        mol_type = protein
                        organism = synthetic construct
SEQUENCE: 102
VARDIACGCQ YLEENHFIHR DIAARNCLLT C                              31

SEQ ID NO: 103          moltype = AA  length = 31
FEATURE                 Location/Qualifiers
source                  1..31
                        mol_type = protein
                        organism = synthetic construct
SEQUENCE: 103
RDIAARNCLL TCPGPGRVAK IGDFGMARDI Y                              31

SEQ ID NO: 104          moltype = AA  length = 31
FEATURE                 Location/Qualifiers
source                  1..31
                        mol_type = protein
                        organism = synthetic construct
SEQUENCE: 104
KIGDFGMARD IYRASYYRKG GCAMLPVKWM P                              31

SEQ ID NO: 105          moltype = AA  length = 31
FEATURE                 Location/Qualifiers
source                  1..31
                        mol_type = protein
                        organism = synthetic construct
SEQUENCE: 105
GGCAMLPVKW MPPEAFMEGI FTSKTDTWSF G                              31

SEQ ID NO: 106          moltype = AA  length = 31
FEATURE                 Location/Qualifiers
source                  1..31
                        mol_type = protein
                        organism = synthetic construct
SEQUENCE: 106
IFTSKTDTWS FGVLLWEIFS LGYMPYPSKS N                              31

SEQ ID NO: 107          moltype = AA  length = 31
FEATURE                 Location/Qualifiers
source                  1..31
                        mol_type = protein
                        organism = synthetic construct
SEQUENCE: 107
SLGYMPYPSK SNQEVLEFVT SGGRMDPPKN C                              31

SEQ ID NO: 108          moltype = AA  length = 31
FEATURE                 Location/Qualifiers
source                  1..31
                        mol_type = protein
                        organism = synthetic construct
SEQUENCE: 108
TSGGRMDPPK NCPGPVYRIM TQCWQHQPED R                              31

SEQ ID NO: 109          moltype = AA  length = 31
FEATURE                 Location/Qualifiers
source                  1..31
                        mol_type = protein
                        organism = synthetic construct
SEQUENCE: 109
MTQCWQHQPE DRPNFAIILE RIEYCTQDPD V                              31

SEQ ID NO: 110          moltype = AA  length = 31
FEATURE                 Location/Qualifiers
source                  1..31
                        mol_type = protein
```

```
                              organism = synthetic construct
SEQUENCE: 110
ERIEYCTQDP DVINTALPIE YGPLVEEEEK V                                  31

SEQ ID NO: 111           moltype = AA  length = 31
FEATURE                  Location/Qualifiers
source                   1..31
                         mol_type = protein
                         organism = synthetic construct
SEQUENCE: 111
EYGPLVEEEE KVPVRPKDPE GVPPLLVSQQ A                                  31

SEQ ID NO: 112           moltype = AA  length = 31
FEATURE                  Location/Qualifiers
source                   1..31
                         mol_type = protein
                         organism = synthetic construct
SEQUENCE: 112
EGVPPLLVSQ QAKREEERSP AAPPPLPTTS S                                  31

SEQ ID NO: 113           moltype = AA  length = 31
FEATURE                  Location/Qualifiers
source                   1..31
                         mol_type = protein
                         organism = synthetic construct
SEQUENCE: 113
PAAPPPLPTT SSGKAAKKPT AAEISVRVPR G                                  31

SEQ ID NO: 114           moltype = AA  length = 31
FEATURE                  Location/Qualifiers
source                   1..31
                         mol_type = protein
                         organism = synthetic construct
SEQUENCE: 114
TAAEISVRVP RGPAVEGGHV NMAFSQSNPP S                                  31

SEQ ID NO: 115           moltype = AA  length = 31
FEATURE                  Location/Qualifiers
source                   1..31
                         mol_type = protein
                         organism = synthetic construct
SEQUENCE: 115
VNMAFSQSNP PSELHKVHGS RNKPTSLWNP T                                  31

SEQ ID NO: 116           moltype = AA  length = 31
FEATURE                  Location/Qualifiers
source                   1..31
                         mol_type = protein
                         organism = synthetic construct
SEQUENCE: 116
SRNKPTSLWN PTYGSWFTEK PTKKNNPIAK K                                  31

SEQ ID NO: 117           moltype = AA  length = 31
FEATURE                  Location/Qualifiers
source                   1..31
                         mol_type = protein
                         organism = synthetic construct
SEQUENCE: 117
KPTKKNNPIA KKEPHDRGNL GLEGSCTVPP N                                  31

SEQ ID NO: 118           moltype = AA  length = 31
FEATURE                  Location/Qualifiers
source                   1..31
                         mol_type = protein
                         organism = synthetic construct
SEQUENCE: 118
LGLEGSCTVP PNVATGRLPG ASLLLEPSSL T                                  31

SEQ ID NO: 119           moltype = AA  length = 31
FEATURE                  Location/Qualifiers
source                   1..31
                         mol_type = protein
                         organism = synthetic construct
SEQUENCE: 119
GASLLLEPSS LTANMKEVPL FRLRHFPCGN V                                  31

SEQ ID NO: 120           moltype = AA  length = 31
FEATURE                  Location/Qualifiers
source                   1..31
```

```
                        mol_type = protein
                        organism = synthetic construct
SEQUENCE: 120
LFRLRHFPCG NVNYGYQQQG LPLEAATAPG A                              31

SEQ ID NO: 121          moltype = AA   length = 31
FEATURE                 Location/Qualifiers
source                  1..31
                        mol_type = protein
                        organism = synthetic construct
SEQUENCE: 121
GLPLEAATAP GAGHYEDTIL KSKNSMNQPG P                              31

SEQ ID NO: 122          moltype = AA   length = 31
FEATURE                 Location/Qualifiers
source                  1..31
                        mol_type = protein
                        organism = synthetic construct
SEQUENCE: 122
EYKLSKLRTS TIMTDYNPNY AFAGKTSSIS D                              31

SEQ ID NO: 123          moltype = AA   length = 31
FEATURE                 Location/Qualifiers
source                  1..31
                        mol_type = protein
                        organism = synthetic construct
SEQUENCE: 123
YAFAGKTSSI SDLKEVPRKN ITLIRGLGHG A                              31

SEQ ID NO: 124          moltype = AA   length = 31
FEATURE                 Location/Qualifiers
source                  1..31
                        mol_type = protein
                        organism = synthetic construct
SEQUENCE: 124
QVSGMPNDPS PLQVAVKTLP EVASEQDELD F                              31

SEQ ID NO: 125          moltype = AA   length = 31
FEATURE                 Location/Qualifiers
source                  1..31
                        mol_type = protein
                        organism = synthetic construct
SEQUENCE: 125
PEVASEQDEL DFLMEALIIS KFNHQNIVRA I                              31

SEQ ID NO: 126          moltype = AA   length = 31
FEATURE                 Location/Qualifiers
source                  1..31
                        mol_type = protein
                        organism = synthetic construct
SEQUENCE: 126
SKFNHQNIVR AIGVSLQSLP RFILLELMAG G                              31

SEQ ID NO: 127          moltype = AA   length = 31
FEATURE                 Location/Qualifiers
source                  1..31
                        mol_type = protein
                        organism = synthetic construct
SEQUENCE: 127
ETRPRPSQPS SLAMLDLLHV ARDIAAGAQY L                              31

SEQ ID NO: 128          moltype = AA   length = 31
FEATURE                 Location/Qualifiers
source                  1..31
                        mol_type = protein
                        organism = synthetic construct
SEQUENCE: 128
VARDIAAGAQ YLEENHFIHR DIAARNALLT A                              31

SEQ ID NO: 129          moltype = AA   length = 31
FEATURE                 Location/Qualifiers
source                  1..31
                        mol_type = protein
                        organism = synthetic construct
SEQUENCE: 129
RDIAARNALL TAPGPGRVAK IGDFGMARDI Y                              31

SEQ ID NO: 130          moltype = AA   length = 31
FEATURE                 Location/Qualifiers
```

```
source                  1..31
                        mol_type = protein
                        organism = synthetic construct
SEQUENCE: 130
KIGDFGMARD IYRASYYRKG GAAMLPVKWM P                                31

SEQ ID NO: 131          moltype = AA   length = 31
FEATURE                 Location/Qualifiers
source                  1..31
                        mol_type = protein
                        organism = synthetic construct
SEQUENCE: 131
GGAAMLPVKW MPPEAFMEGI FTSKTDTWSF G                                31

SEQ ID NO: 132          moltype = AA   length = 31
FEATURE                 Location/Qualifiers
source                  1..31
                        mol_type = protein
                        organism = synthetic construct
SEQUENCE: 132
SLGYMPYPSK SNQEVLEFVT SGGRMDPPKN A                                31

SEQ ID NO: 133          moltype = AA   length = 31
FEATURE                 Location/Qualifiers
source                  1..31
                        mol_type = protein
                        organism = synthetic construct
SEQUENCE: 133
TSGGRMDPPK NAPGPVYRIM TQAWQHQPED R                                31

SEQ ID NO: 134          moltype = AA   length = 31
FEATURE                 Location/Qualifiers
source                  1..31
                        mol_type = protein
                        organism = synthetic construct
SEQUENCE: 134
MTQAWQHQPE DRPNFAIILE RIEYATQDPD V                                31

SEQ ID NO: 135          moltype = AA   length = 31
FEATURE                 Location/Qualifiers
source                  1..31
                        mol_type = protein
                        organism = synthetic construct
SEQUENCE: 135
ERIEYATQDP DVINTALPIE YGPLVEEEEK V                                31

SEQ ID NO: 136          moltype = AA   length = 31
FEATURE                 Location/Qualifiers
source                  1..31
                        mol_type = protein
                        organism = synthetic construct
SEQUENCE: 136
KPTKKNNPIA KKEPHDRGNL GLEGSATVPP N                                31

SEQ ID NO: 137          moltype = AA   length = 31
FEATURE                 Location/Qualifiers
source                  1..31
                        mol_type = protein
                        organism = synthetic construct
SEQUENCE: 137
LGLEGSATVP PNVATGRLPG ASLLLEPSSL T                                31

SEQ ID NO: 138          moltype = AA   length = 31
FEATURE                 Location/Qualifiers
source                  1..31
                        mol_type = protein
                        organism = synthetic construct
SEQUENCE: 138
GASLLLEPSS LTANMKEVPL FRLRHFPAGN V                                31

SEQ ID NO: 139          moltype = AA   length = 31
FEATURE                 Location/Qualifiers
source                  1..31
                        mol_type = protein
                        organism = synthetic construct
SEQUENCE: 139
LFRLRHFPAG NVNYGYQQQG LPLEAATAPG A                                31

SEQ ID NO: 140          moltype = AA   length = 24
```

```
FEATURE             Location/Qualifiers
source              1..24
                    mol_type = protein
                    organism = synthetic construct
SEQUENCE: 140
PSSLAMLDLL HVARDIACGC QYLE                                              24

SEQ ID NO: 141      moltype = AA  length = 24
FEATURE             Location/Qualifiers
source              1..24
                    mol_type = protein
                    organism = synthetic construct
SEQUENCE: 141
KFNHQNIVRC IGVSLQSLPR FILL                                              24

SEQ ID NO: 142      moltype = AA  length = 24
FEATURE             Location/Qualifiers
source              1..24
                    mol_type = protein
                    organism = synthetic construct
SEQUENCE: 142
PKNCPGPVYR IMTQCWQHQP EDRP                                              24

SEQ ID NO: 143      moltype = AA  length = 10
FEATURE             Location/Qualifiers
source              1..10
                    mol_type = protein
                    organism = synthetic construct
SEQUENCE: 143
SLAMLDLLHV                                                              10

SEQ ID NO: 144      moltype = AA  length = 9
FEATURE             Location/Qualifiers
source              1..9
                    mol_type = protein
                    organism = synthetic construct
SEQUENCE: 144
AMLDLLHVA                                                               9

SEQ ID NO: 145      moltype = AA  length = 9
FEATURE             Location/Qualifiers
source              1..9
                    mol_type = protein
                    organism = synthetic construct
SEQUENCE: 145
CIGVSLQSL                                                               9
```

Other embodiments are described in the following claims:

1. An amphiphilic conjugate comprising:
   (a) an albumin-binding domain;
   (b) an ALK polypeptide; and
   (c) an optional linker,
   wherein the ALK polypeptide is 9 to 40 amino acids in length, comprises at least Z contiguous amino acids from the sequence of SEQ ID NO:23, and does not comprise a sequence of any one of SEQ ID NOs: 67-70 and 140-145, and
   wherein the ALK polypeptide is conjugated directly to the albumin-binding domain or is conjugated to the albumin-binding domain through the linker.

2. The amphiphilic conjugate of claim 1, wherein the albumin-binding domain is a lipid.

3. The amphiphilic conjugate of claim 1, wherein the linker is selected from the group consisting of polymers, a string of amino acids, nucleic acids, polysaccharides, or a combination thereof.

4. The amphiphilic conjugate of claim 3, wherein the linker comprises consecutive polyethylene glycol units.

5. The amphiphilic conjugate of claim 4, wherein the linker comprises "N" consecutive polyethylene glycol units, wherein N is between 20 and 80.

6. The amphiphilic conjugate of claim 5, wherein the linker comprises 48 consecutive polyethylene glycol units.

7. An immunogenic composition comprising an amphiphilic conjugate of claim 1.

8. The immunogenic composition of claim 7, further comprising an adjuvant.

9. A pharmaceutical composition comprising a therapeutically effective amount of an immunogenic composition of claim 7 and one or more pharmaceutically acceptable carriers or excipients.

* * * * *

UNITED STATES PATENT AND TRADEMARK OFFICE
CERTIFICATE OF CORRECTION

| | | |
|---|---|---|
| PATENT NO. | : 12,370,245 B2 | Page 1 of 1 |
| APPLICATION NO. | : 18/176013 | |
| DATED | : July 29, 2025 | |
| INVENTOR(S) | : Adrienne Li et al. | |

It is certified that error appears in the above-identified patent and that said Letters Patent is hereby corrected as shown below:

In the Claims

Column 231, Claim 1, Line 48, replace "least Z" with --least 7--.

Signed and Sealed this
Fourth Day of November, 2025

John A. Squires
*Director of the United States Patent and Trademark Office*